US012686673B2

(12) United States Patent
Hallur et al.

(10) Patent No.: US 12,686,673 B2
(45) Date of Patent: Jul. 21, 2026

(54) PYRIMIDINE COMPOUNDS, COMPOSITIONS, AND MEDICINAL APPLICATIONS THEREOF

(71) Applicant: Blueprint Medicines Corporation, Cambridge, MA (US)

(72) Inventors: Gurulingappa Hallur, Bangalore (IN); Naveena Madhyastha, Bangalore (IN); Michael Rajesh Stephen, Bangalore (IN); Bruce Roth, Menlo Park, CA (US); Anjali Pandey, Menlo Park, CA (US); Tracy Saxton, Menlo Park, CA (US); Sridharan Rajagopal, Bangalore (IN); M. Naveen Sadhu, Bangalore (IN)

(73) Assignee: Blueprint Medicines Corporation, Cambridge, MA (US)

( * ) Notice: Subject to any disclaimer, the term of this patent is extended or adjusted under 35 U.S.C. 154(b) by 484 days.

(21) Appl. No.: 18/033,954

(22) PCT Filed: Oct. 30, 2021

(86) PCT No.: PCT/US2021/057472
§ 371 (c)(1),
(2) Date: Apr. 26, 2023

(87) PCT Pub. No.: WO2022/094354
PCT Pub. Date: May 5, 2022

(65) Prior Publication Data

US 2024/0051945 A1 Feb. 15, 2024

Related U.S. Application Data

(60) Provisional application No. 63/271,991, filed on Oct. 26, 2021, provisional application No. 63/236,194, filed on Aug. 23, 2021, provisional application No. 63/108,185, filed on Oct. 30, 2020.

(51) Int. Cl.

| | |
|---|---|
| *C07D 403/12* | (2006.01) |
| *C07D 401/04* | (2006.01) |
| *C07D 401/14* | (2006.01) |
| *C07D 403/14* | (2006.01) |
| *C07D 405/14* | (2006.01) |
| *C07D 413/12* | (2006.01) |
| *C07D 417/12* | (2006.01) |
| *C07D 417/14* | (2006.01) |
| *C07D 471/04* | (2006.01) |

(52) U.S. Cl.
CPC ......... *C07D 403/12* (2013.01); *C07D 401/04* (2013.01); *C07D 401/14* (2013.01); *C07D 403/14* (2013.01); *C07D 405/14* (2013.01); *C07D 413/12* (2013.01); *C07D 417/12* (2013.01); *C07D 417/14* (2013.01); *C07D 471/04* (2013.01); *C07B 2200/05* (2013.01)

(58) Field of Classification Search
CPC .. C07D 403/12; C07D 401/04; C07D 401/14; C07D 403/14; C07D 405/14; C07D 413/12; C07D 417/12; C07D 417/14; C07D 471/04
See application file for complete search history.

(56) References Cited

U.S. PATENT DOCUMENTS

| | | | | |
|---|---|---|---|---|
| 8,541,242 | B2 | 9/2013 | Boone et al. | |
| 9,163,017 | B2 | 10/2015 | Degoey et al. | |
| 2023/0416232 | A1 * | 12/2023 | Hallur .................. | C07D 403/12 |

FOREIGN PATENT DOCUMENTS

| | | | |
|---|---|---|---|
| CN | 103153064 | A | 6/2013 |
| CN | 103269704 | A | 8/2013 |
| CN | 103501612 | A | 1/2014 |
| CN | 105188371 | A | 12/2015 |
| WO | 2009/158571 | A1 | 12/2009 |
| WO | 2010/075376 | A2 | 7/2010 |
| WO | 2012/051587 | A1 | 4/2012 |
| WO | 2012/061299 | A1 | 5/2012 |
| WO | 2012/151561 | A1 | 11/2012 |
| WO | 2014/031928 | A2 | 2/2014 |
| WO | 2014/124230 | A2 | 8/2014 |
| WO | 2015/025197 | A1 | 2/2015 |
| WO | 2015/061247 | A2 | 4/2015 |
| WO | 2019/177374 | A1 | 9/2019 |
| WO | 2020/088390 | A1 | 5/2020 |
| WO | 2020/228635 | A1 | 11/2020 |
| WO | 2021/062327 | A1 | 4/2021 |
| WO | 2021/104305 | A1 | 6/2021 |
| WO | 2021/185298 | A1 | 9/2021 |
| WO | 2022/063140 | A1 | 3/2022 |

OTHER PUBLICATIONS

Murtuza, Cancer Research, 2019, 79 (4): 689-698 (Year: 2019).*
Thomas, Frontiers in Oncology, Aug. 2019, vol. 9, Article 800 (Year: 2019).*
Hernandes, Current Drug Targets, Mar. 2010, 11 (3): 303-314 (Year: 2010).*
International Search Report and Written Opinion for Application No. PCT/US2021/057474, dated Mar. 22, 2022, 13 pages.
U.S. Appl. No. 18/033,931, filed Apr. 26, 2023, 2023-0416232, Published.
Zhou et al., Novel mutant-selective EGFR kinase inhibitors against EGFR T790M. Nature. Dec. 24, 2009;462(7276):1070-4.
International Search Report and Written Opinion for Application No. PCT/US2021/057472, dated Mar. 22, 2022, 17 pages.

* cited by examiner

*Primary Examiner* — Andrew D Kosar
*Assistant Examiner* — Phillip Matthew Rzeczycki
(74) *Attorney, Agent, or Firm* — McCarter & English, LLP; Xin Zhang; Sujatha Rochford

(57) ABSTRACT

The present disclosure relates to a class of pyrimidine compounds, their stereoisomers, tautomers, pharmaceutically acceptable salts, stereoisomers, solvates, and hydrates thereof. The present disclosure also relates to a process of preparation of these pyrimidine compounds, pharmaceutical compositions containing them, and medicinal applications thereof.

20 Claims, No Drawings

PYRIMIDINE COMPOUNDS, COMPOSITIONS, AND MEDICINAL APPLICATIONS THEREOF

CROSS-REFERENCE

This application is a 35 U.S.C. § 371 national stage filing of International Application No. PCT/US2021/057472, filed Oct. 30, 2021, which claims the benefit of U.S. Provisional Patent Application No. 63/108,185 filed Oct. 30, 2020; U.S. Provisional Patent Application No. 63/236,194 filed Aug. 23, 2021; and U.S. Provisional Patent Application No. 63/271,991 filed Oct. 26, 2021. The entire contents of each of the above-referenced applications are expressly incorporated herein by reference in their entirety.

BACKGROUND OF THE DISCLOSURE

Lung cancer accounts for the greatest number of cancer deaths, and approximately 85% of lung cancer cases are non-small cell lung cancer (NSCLC). The development of targeted therapies for lung cancer has primarily focused on tumors displaying specific oncogenic drivers, namely mutations in epidermal growth factor receptor (EGFR) and anaplastic lymphoma kinase (ALK). Three generations of tyrosine kinase inhibitors (TKIs) have been developed for cancers with the most frequently observed EGFR mutations, however, other oncogenic drivers in the EGFR family of receptor tyrosine kinases have received less research and development focus and several oncogenic drivers, including insertions in the exon 20 gene of EGFR, have no currently approved therapeutics to treat their cancers.

Given that many patients with mutations in EGFR do not derive clinical benefit from currently available therapies against these targets, there remains a significant unmet need for the development of novel therapies for the treatment of cancers associated with EGFR mutations.

SUMMARY OF THE DISCLOSURE

In one aspect, provided herein is a compound of Formula I:

Formula I

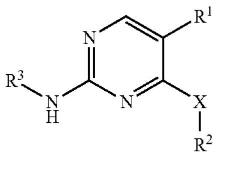

or a pharmaceutically acceptable salt or stereoisomer thereof, wherein:

X is —NH— or —O—;

$R^1$ is $—(C(R^4)_2)_nR^5$, wherein $R^5$ is unsubstituted or substituted with 1 $R^{5'}$;

n is 0, 1, 2, or 3;

each $R^4$ is independently hydrogen, alkyl, halo, haloalkyl, hydroxy, alkoxy, or heteroalkyl;

$R^5$ is $C_{4-10}$cycloalkyl, aryl, or heteroaryl;

each $R^{5'}$ is independently deuterium, aryl, heteroaryl, alkyl, $C_3$-$C_6$ cycloalkyl, 3-8 membered heterocycloalkyl, oxo, halo, heteroalkyl, haloalkyl, cyano, hydroxy, amino, $—NH_2$, $—NHR^6$, $—N(CH_3)R_6$, $—N(R^6)_2$, $—C(=O)NH_2$, $—C(=O)NHR^6$, $—C(=O)N(R^6)_2$, $—NR^6C(=O)R^6$, $—NHC(=O)R^6$, $—S(=O)_2$ alkyl, $—S(=O)_2$aryl, $—S(=O)_2NH_2$, $—S(=O)_2NHR^6$, $—S(=O)_2N(R^6)_2$, $—S(=O)_2$heteroaryl, alkoxy, or haloalkoxy;

each $R^6$ is independently alkyl, aminoalkyl, cycloalkyl, aryl, or heteroaryl;

$R^2$ is aryl, heteroaryl, cycloalkyl, or heterocycloalkyl, wherein the aryl, heteroaryl, cycloalkyl, or heterocycloalkyl is substituted with at least one $R^7$ and 0, 1, or 2 $R^8$;

each $R^7$ is independently

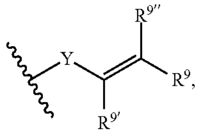, 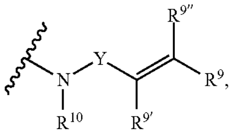, 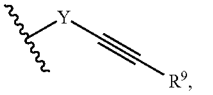, or 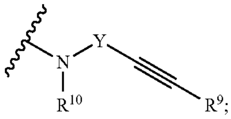;

Y is $—C(=O)—$, $—S(=O)—$, or $—S(=O)_2—$;

$R^9$, $R^{9'}$, and $R^{9''}$ are independently hydrogen, deuterium, halo, alkyl, haloalkyl, cycloalkyl, heteroalkyl, or (alkyl)heterocycloalkyl;

$R^{10}$ is hydrogen, alkyl, haloalkyl, or cycloalkyl;

each $R^3$ is independently aryl, heteroaryl, alkyl, cycloalkyl, heterocycloalkyl, halo, heteroalkyl, haloalkyl, cyano, hydroxy, amino, $—N(R^{11})_2$, $—S(=O)_2$ alkyl, $—S(=O)_2$aryl, $—S(=O)_2$heteroaryl, or alkoxy;

each $R^{11}$ is independently alkyl, cycloalkyl, aryl, or heteroaryl;

$R^3$ is heteroaryl substituted with 0, 1, 2, or 3 $R^{12}$;

each $R^{12}$ is independently aryl, heteroaryl, alkyl, heteroalkyl, haloalkyl, halo, cyano, alkoxy, heterocycloalkyl, $—N(R^{13})_2$, $—S(=O)_2NH_2$, $—S(=O)_2$ alkyl, $—S(=O)_2$aryl, $—S(=O)_2$heteroaryl, or cycloalkyl, wherein the aryl, heteroaryl, heterocycloalkyl, or cycloalkyl are each independently unsubstituted or substituted with 0, 1, or 2 $R^{14}$;

each $R^{13}$ is independently hydrogen, alkyl, cycloalkyl, aryl, or heteroaryl;

each $R^{14}$ is independently deuterium, aryl, heteroaryl, alkyl, cycloalkyl, heterocycloalkyl, halo, heteroalkyl, haloalkyl, cyano, hydroxy, amino, $—N(R^{15})_2$, $—S(=O)_2$ alkyl, $—S(=O)_2$aryl, $—S(=O)_2$heteroaryl, or alkoxy; and each $R^{15}$ is independently alkyl, cycloalkyl, aryl, or heteroaryl.

In some embodiments, X is —NH—.

In some embodiments, n is 0.

In some embodiments, $R^5$ is phenyl, naphthyl, anthracenyl, phenanthrenyl, C-linked pyridyl, C-linked pyrimidinyl, C-linked pyrazolyl, C-linked imidazolyl, or C-linked indolyl; wherein $R^5$ is substituted with 0 or 1 $R^{5'}$. In some embodiments, $R^5$ is unsubstituted. In some embodiments, $R^5$ is substituted with 1 $R^{5'}$.

In some embodiments, each $R^{5'}$ is independently alkyl, haloalkyl, 3-8 membered heterocycloalkyl, halo, cyano, hydroxy, $—N(R^6)_2$, $—N(CH_3)R_6$, $—C(=O)NHR^6$, $—NHC(=O)R^6$, $—S(=O)_2NH_2$, alkoxy, or haloalkoxy. In some embodiments, each $R^{5'}$ is independently methyl, ethyl, tert-butyl, pyrrolidinyl, piperidinyl, piperazinyl, morpholinyl, fluoro, chloro, cyano, hydroxy, $—N(R^6)_2$, $—C(=O)NHR^6$, —NHC(═O)$R^6$, —S(═O)$_2$NH$_2$, methoxy, ethoxy, fluoromethyl, difluoromethyl, trifluoromethyl, fluoromethoxy, difluoromethoxy, or trifluoromethoxy. In some embodiments, each $R^{5'}$ is independently methyl, morpholinyl, fluoro, chloro, cyano, —C(═O)NHMe, —NHC(═O)Me, —S(═O)$_2$NH$_2$, methoxy, fluoromethyl, difluoromethyl, trifluoromethyl, difluoromethoxy, or trifluoromethoxy.

In some embodiments, each $R^6$ is independently alkyl or aryl. In some embodiments, each $R^6$ is independently methyl, ethyl, iso-propyl, tert-butyl, phenyl, or naphthyl. In some embodiments, each $R^6$ is independently methyl or phenyl.

In some embodiments, $R^2$ is monocyclic. In some embodiments, $R^2$ is phenyl, cyclopropyl, cyclobutyl, cyclopentyl, cyclohexyl, pyrrolyl, imidazolyl, pyrazolyl, triazolyl, tetrazolyl, thiazolyl, isothiazolyl, oxazolyl, isoxazolyl, pyridinyl, pyrimidinyl, pyridazinyl, pyrazinyl, or triazinyl; wherein $R^2$ is substituted with at least one $R^7$ and 0, 1, or 2 $R^8$. In some embodiments, $R^2$ is phenyl, cyclohexyl, or pyrrolyl; wherein $R^2$ is substituted with at least one $R^7$ and 0, 1, or 2 $R^8$. In some embodiments, $R^2$ is aryl, heteroaryl, cycloalkyl, or heterocycloalkyl, wherein the aryl, heteroaryl, cycloalkyl, or heterocycloalkyl is substituted with 1 $R^7$ and 0, 1, or 2 $R^8$. In some embodiments, $R^2$ is substituted with 1 $R^7$ and 0, 1, or 2 $R^8$. In some embodiments, $R^2$ is substituted with 1 $R^7$ and not substituted with $R^8$. In some embodiments, $R^2$ is substituted with 1 $R^7$ and 1 $R^8$. In some embodiments, $R^2$ is substituted with 1 $R^7$ and 2 $R^8$.

In some embodiments, $R^2$ is substituted with 1 $R^7$.

In some embodiments, $R^7$ is

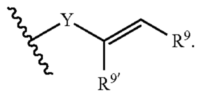

In some embodiments, $R^7$ is

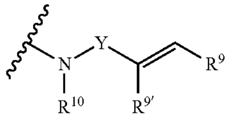

In some embodiments, $R^7$ is

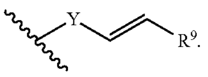

In some embodiments, $R^7$ is

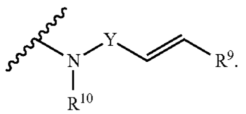

In some embodiments, Y is —C(═O)—. In some embodiments, Y is —S(═O)$_2$—.

In some embodiments, $R^9$, $R^9$, and $R^{9''}$ are independently hydrogen, halo, alkyl, heteroalkyl, haloalkyl, or (alkyl)heterocycloalkyl. In some embodiments, $R^9$, $R^9$, and $R^{9''}$ are independently hydrogen, fluoro, chloro, methyl, hydroxyethyl, methoxyethyl, methoxymethyl, dimethylaminomethyl, 1-piperidinylmethyl, 1-morpholinylmethyl, or fluoromethyl. In some embodiments, $R^9$ and $R^{9'}$ are independently hydrogen, halo, alkyl, heteroalkyl, haloalkyl, or (alkyl)heterocycloalkyl. In some embodiments, $R^9$ and $R^{9'}$ are independently hydrogen, fluoro, chloro, methyl, hydroxyethyl, methoxyethyl, methoxymethyl, dimethylaminomethyl, 1-piperidinylmethyl, 1-morpholinylmethyl, or fluoromethyl.

In some embodiments, $R^{10}$ is hydrogen, methyl, ethyl n-propyl, iso-propyl, n-butyl, sec-butyl, tert-butyl, trifluoromethyl, or cyclopropyl. In some embodiments, $R^{10}$ is hydrogen or methyl.

In some embodiments, $R^2$ is not substituted with $R^8$. In some embodiments, $R^2$ is substituted with 1 or 2 $R^8$. In some embodiments, $R^2$ is substituted with 1 $R^8$. In some embodiments, $R^2$ is substituted with 2 $R^8$. In some embodiments, each $R^8$ is independently methyl, ethyl, n-propyl, iso-propyl, n-butyl, iso-butyl, sec-butyl, tert-butyl, fluoro, chloro, heteroalkyl, cyano, hydroxy, amino, —N($R^{11}$)$_2$, methoxy, ethoxy, or trifluoromethoxy. In some embodiments, each $R^8$ is independently methyl, ethyl, iso-propyl, tert-butyl, fluoro, chloro, —N($R^{11}$)$_2$, hydroxyethyl, methoxyethyl, or cyano.

In some embodiments, each $R^{11}$ is independently alkyl or aryl. In some embodiments, each $R^{11}$ is independently methyl, ethyl, n-propyl, iso-propyl, n-butyl, iso-butyl, sec-butyl, tert-butyl, phenyl, naphthyl, anthracenyl, or phenanthrenyl. In some embodiments, each $R^{11}$ is independently methyl, ethyl, iso-propyl, tert-butyl, phenyl, or naphthyl. In some embodiments, each $R^{11}$ is independently methyl or phenyl.

In some embodiments, $R^3$ is pyrrolyl, imidazolyl, pyrazolyl, triazolyl, tetrazolyl, indolyl, indazolyl, benzimidazolyl, azaindolyl, thiazolyl, isothiazolyl, oxazolyl, isoxazolyl, pyridinyl, pyrimidinyl, pyridazinyl, pyrazinyl, triazinyl, quinolinyl, isoquinolinyl, quinoxalinyl, quinazolinyl, cinnolinyl, or naphthyridinyl; wherein $R^3$ is substituted with 0, 1, 2, or 3 $R^{12}$. In some embodiments, $R^3$ is imidazolyl, pyrazolyl, triazolyl, indolyl, indazolyl, thiazolyl, isothiazolyl, or pyridinyl; wherein $R^3$ is substituted with 0, 1, 2, or 3 $R^{12}$.

In some embodiments, $R^3$ is:

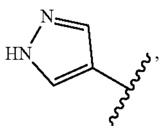, 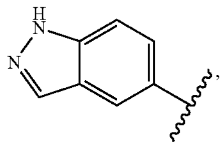,

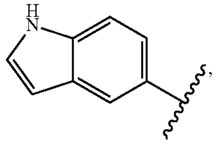, 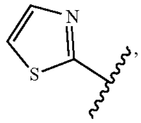, 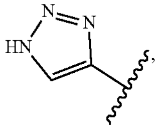,

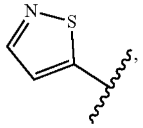, 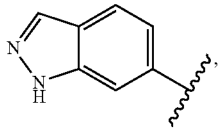, or 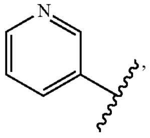, wherein $R^3$ is substituted with 0 to 3 $R^{12}$.

In some embodiments, $R^3$ is:
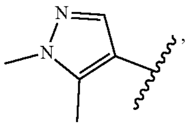 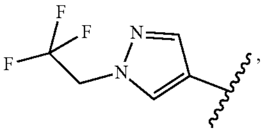
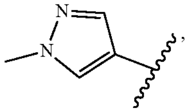 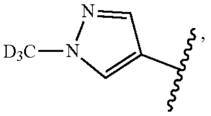
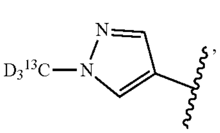 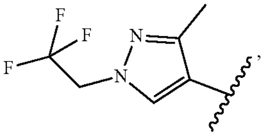
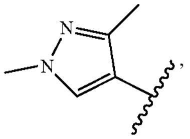 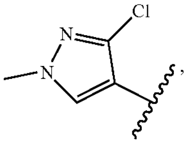
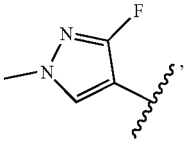 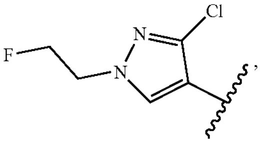
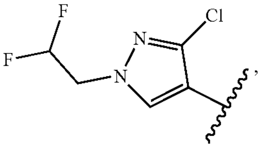 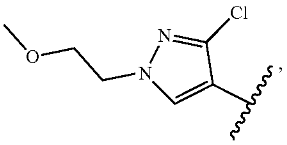
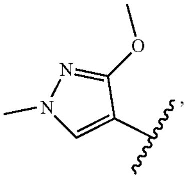 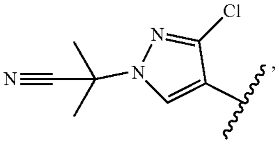
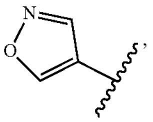 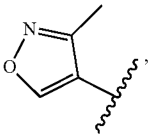 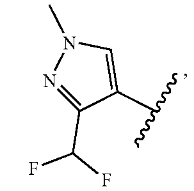
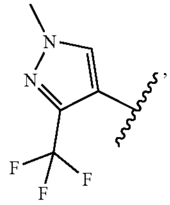 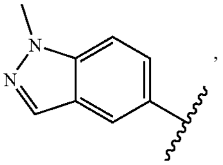
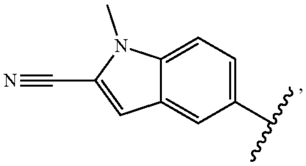 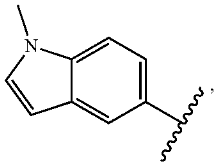
-continued
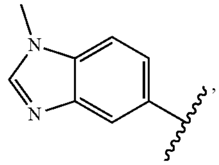 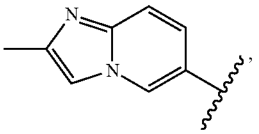
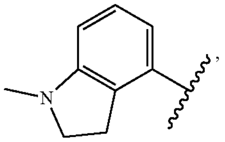
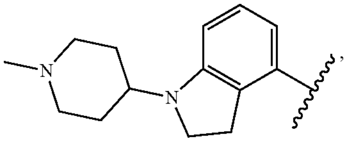
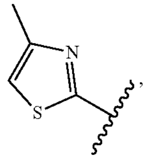 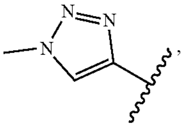 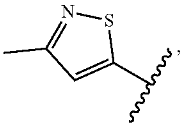
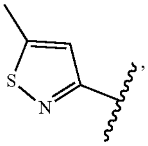 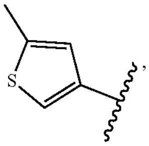 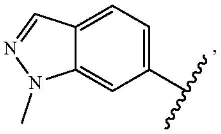
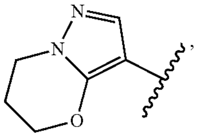 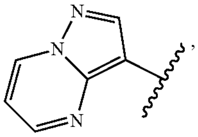
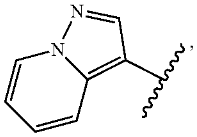 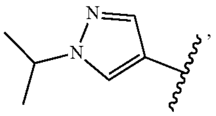
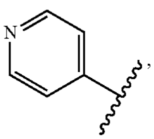 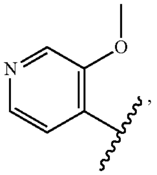 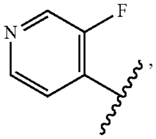
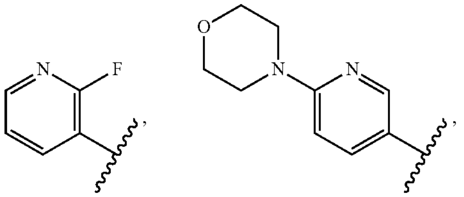
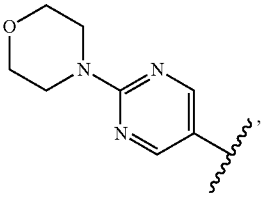

-continued

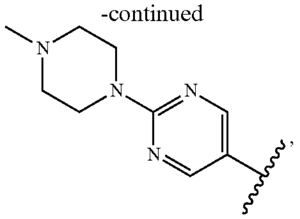

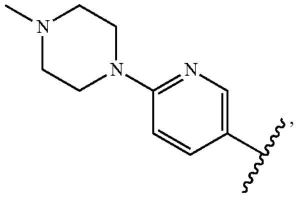

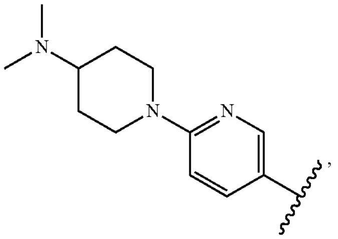

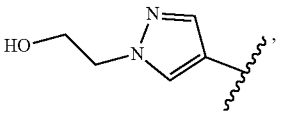

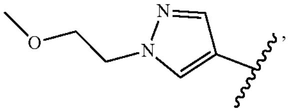

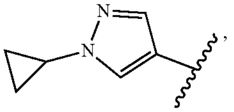

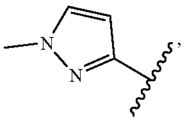

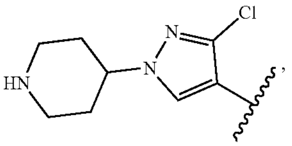

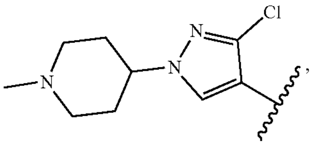

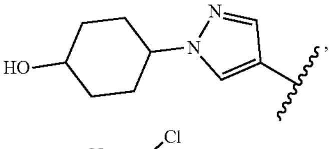

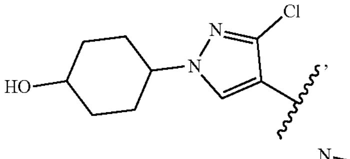

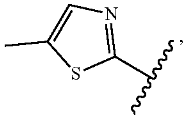

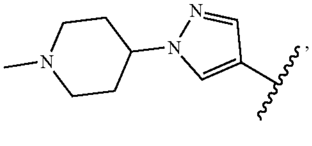

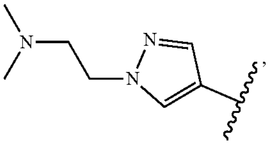

or

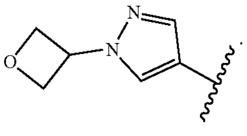

In some embodiments, $R^3$ is:

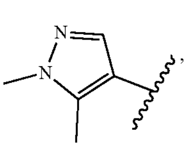

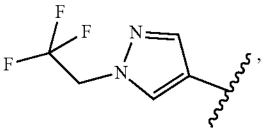

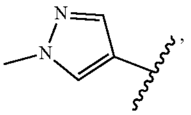

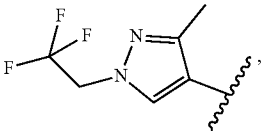

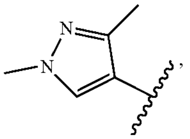

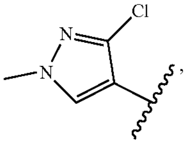

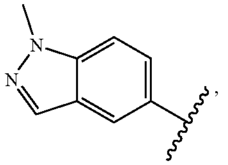

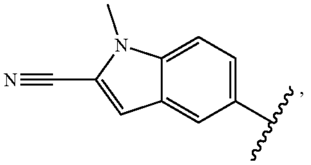

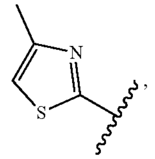

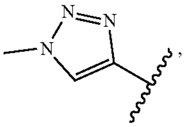

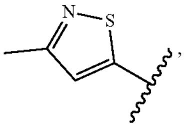

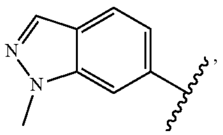

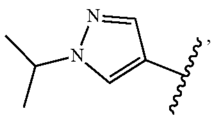

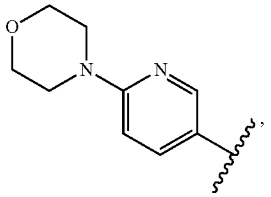

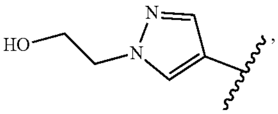

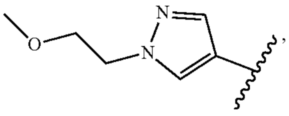

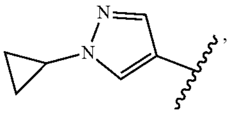

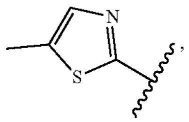

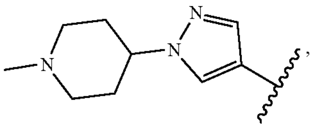

or

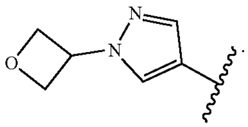

In some embodiments, $R^3$ is unsubstituted. In some embodiments, $R^3$ is substituted with at least 1 $R^{12}$. In some embodiments, $R^3$ is substituted with at least 2 $R^{12}$.

In some embodiments, each $R^{12}$ is independently aryl, heteroaryl, alkyl, heteroalkyl, haloalkyl, halo, cyano, heterocycloalkyl, $—N(R^{13})_2$, $—S(=O)_2NH_2$, or cycloalkyl. In some embodiments, each $R^{12}$ is independently methyl, ethyl, n-propyl, iso-propyl, n-butyl, iso-butyl, sec-butyl, tert-butyl, hydroxyethyl, methoxyethyl, trifluoromethyl, trifluoroethyl, pentafluoroethyl, fluoro, chloro, cyano, azetidinyl, oxetanyl, pyrrolidinyl, imidazolidinyl, tetrahydrofuranyl, piperidinyl, piperazinyl, tetrahydropyranyl, morpholinyl, —N($R^{13}$)$_2$, cyclopropyl, cyclobutyl, cyclopentyl, or cyclohexyl. In some embodiments, each $R^{12}$ is independently methyl, iso-propyl, tert-butyl, hydroxyethyl, methoxyethyl, trifluoromethyl, trifluoroethyl, chloro, cyano, morpholinyl, or cyclopropyl. In some embodiments, each $R^{12}$ is independently methyl, hydroxyethyl, methoxyethyl, trifluoroethyl, or chloro. In some embodiments, each $R^{12}$ is independently methyl or chloro.

In some embodiments, each $R^{13}$ is independently alkyl or cycloalkyl. In some embodiments, each $R^{13}$ is independently methyl, ethyl, n-propyl, iso-propyl, n-butyl, iso-butyl, sec-butyl, tert-butyl, cyclopropyl, cyclobutyl, cyclopentyl, or cyclohexyl. In some embodiments, each $R^{13}$ is independently methyl, ethyl, iso-propyl, tert-butyl, cyclopropyl, cyclopentyl, or cyclohexyl. In some embodiments, each $R^{13}$ is independently methyl, cyclopropyl, or cyclohexyl.

In some embodiments, the aryl, heteroaryl, heterocycloalkyl, or cycloalkyl of $R^{12}$ is unsubstituted. In some embodiments, aryl, heteroaryl, heterocycloalkyl, or cycloalkyl of $R^{12}$ is substituted with 1 or 2 $R^{14}$.

In some embodiments, each $R^{14}$ is independently alkyl, cycloalkyl, heterocycloalkyl, halo, cyano, —N($R^{15}$)$_2$, or alkoxy. In some embodiments, each $R^{14}$ is independently methyl, ethyl, n-propyl, iso-propyl, n-butyl, iso-butyl, sec-butyl, tert-butyl, cyclopropyl, cyclobutyl, cyclopentyl, cyclohexyl, azetidinyl, oxetanyl, pyrrolidinyl, imidazolidinyl, tetrahydrofuranyl, piperidinyl, piperazinyl, tetrahydropyranyl, morpholinyl, fluoro, chloro, cyano, —N($R^{15}$)$_2$ methoxy, ethoxy, or trifluoromethoxy. In some embodiments, each $R^{14}$ is independently methyl, ethyl, iso-propyl, tert-butyl, pyrrolidinyl, piperidinyl, morpholinyl, fluoro, chloro, —N($R^{15}$)$_2$, or methoxy.

In some embodiments, each $R^{15}$ is independently alkyl or cycloalkyl. In some embodiments, each $R^{15}$ is methyl, ethyl, n-propyl, iso-propyl, n-butyl, iso-butyl, sec-butyl, tert-butyl, cyclopropyl, cyclobutyl, cyclopentyl, or cyclohexyl.

In some embodiments, each $R^{13}$ is independently methyl, ethyl, iso-propyl, tert-butyl, cyclopropyl, cyclopentyl, or cyclohexyl. In some embodiments, each $R^{13}$ is independently methyl, cyclopropyl, or cyclohexyl.

In some embodiments:

X is —NH— or —O—;

n is 0;

$R^5$ is phenyl substituted with 0 or 1 $R^{5'}$;

$R^2$ is phenyl substituted with at least one $R^7$ and 0, 1, or 2 $R^8$; and $R^3$ is pyrazolyl substituted with 0, 1, 2, or 3 $R^{12}$.

In some embodiments, X is —NH—.

In some embodiments, $R^{5'}$ is fluoromethyl, difluoromethyl, or trifluoromethyl.

In some embodiments:

$R^7$ is

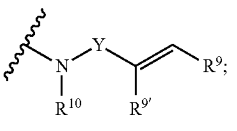

and $R^8$ is halo.

In some embodiments:

$R^8$ is fluoro;

Y is —C(=O)—;

$R^9$ and $R^{9'}$ are hydrogen; and $R^{10}$ is hydrogen.

In some embodiments, $R^{12}$ is alkyl.

In some embodiments, $R^{12}$ is methyl.

In some embodiments, the compound is of Formula I-A, Formula I-B, Formula I-C, Formula I-D, Formula I-E, Formula I-F, or Formula I-G:

Formula I-A

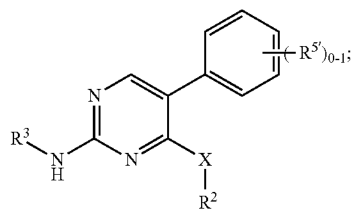

Formula I-B

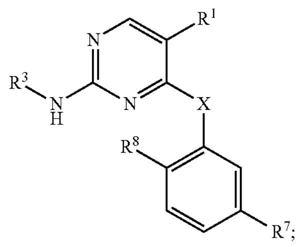

Formula I-C

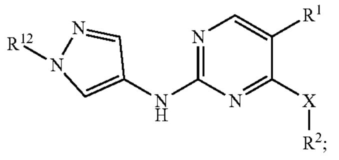

Formula I-D

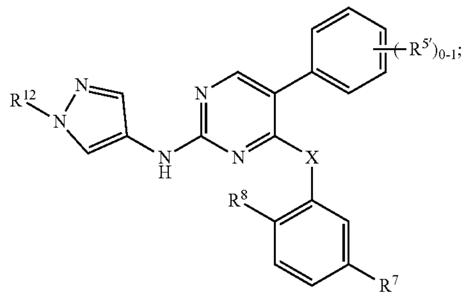

Formula I-E

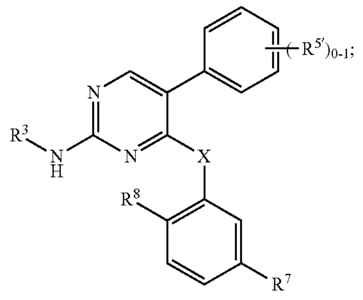

-continued

Formula I-F

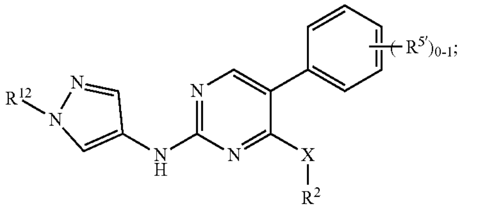

Formula I-G

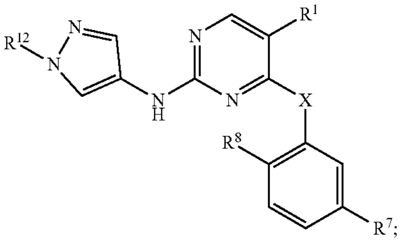

or a pharmaceutically acceptable salt or stereoisomer thereof.

In some embodiments, the compound is of Formula I-A:

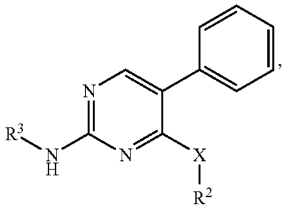

or a pharmaceutically acceptable salt or stereoisomer thereof. In some embodiments, the compound is of Formula I-A:

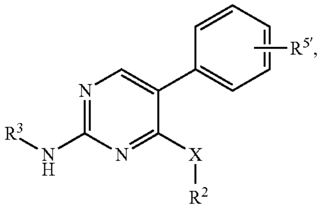

or a pharmaceutically acceptable salt or stereoisomer thereof.

In some embodiments, the compound is of Formula I-B:

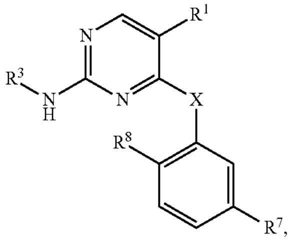

or a pharmaceutically acceptable salt or stereoisomer thereof. In some embodiments of the compound of Formula I-B, wherein $R^1$ is $R^5$. In some embodiments of the compound of Formula I-B, $R^5$ is substituted with 0 or 1 $R^{5'}$. In some embodiments of the compound of Formula I-B, $R^5$ is unsubstituted. In some embodiments of the compound of Formula I-B, $R^5$ is substituted with 1 $R^{5'}$.

In some embodiments, the compound is of Formula I-C:

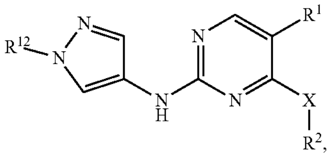

or a pharmaceutically acceptable salt or stereoisomer thereof. In some embodiments of the compound of Formula I-B, wherein $R^1$ is $R^5$. In some embodiments of the compound of Formula I-C, $R^5$ is substituted with 0 or 1 $R^{5'}$. In some embodiments of the compound of Formula I-C, $R^5$ is unsubstituted. In some embodiments of the compound of Formula I-C, $R^5$ is substituted with 1 $R^{5'}$.

In some embodiments, the compound is of Formula I-D:

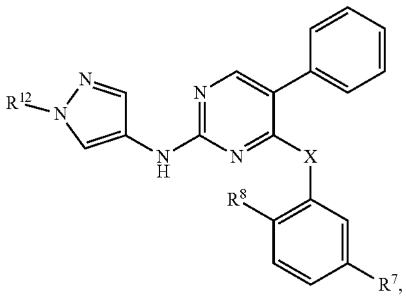

or a pharmaceutically acceptable salt or stereoisomer thereof. In some embodiments, the compound is of Formula I-D:

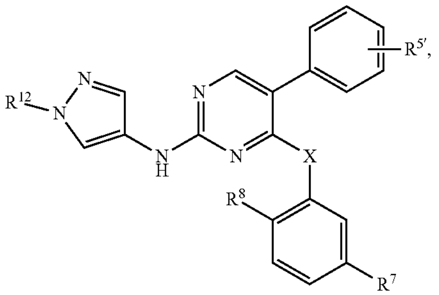

or a pharmaceutically acceptable salt or stereoisomer thereof.

In some embodiments, the compound is of Formula I-E:

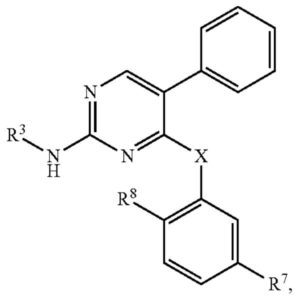

or a pharmaceutically acceptable salt or stereoisomer thereof. In some embodiments, the compound is of Formula I-E:

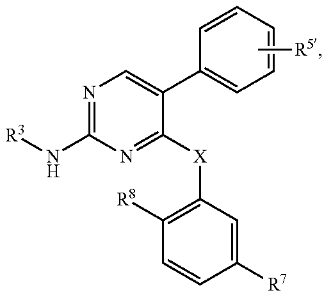

or a pharmaceutically acceptable salt or stereoisomer thereof.

In some embodiments, the compound is of Formula I-F:

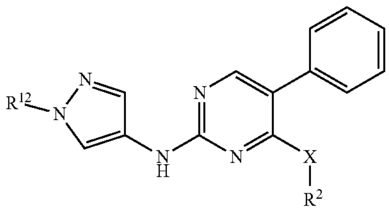

, or a pharmaceutically acceptable salt or stereoisomer thereof. In some embodiments, the compound is of Formula I-F:

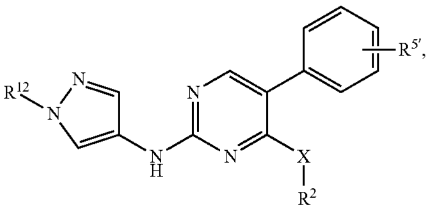

or a pharmaceutically acceptable salt or stereoisomer thereof.

In some embodiments, the compound is of Formula I-G:

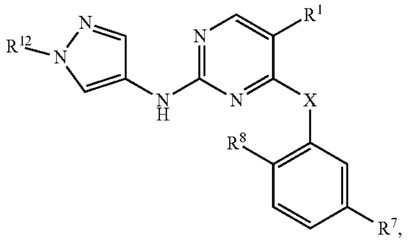

or a pharmaceutically acceptable salt or stereoisomer thereof. In some embodiments of the compound of Formula I-G, wherein $R^1$ is $R^5$. In some embodiments of the compound of Formula I-G, $R^5$ is substituted with 0 or 1 $R^{5'}$. In some embodiments of the compound of Formula I-G, $R^5$ is unsubstituted. In some embodiments of the compound of Formula I-G, $R^5$ is substituted with 1 $R^{5'}$.

In some embodiments, the compound is:

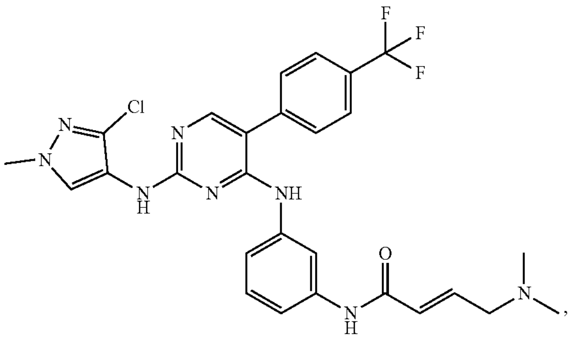

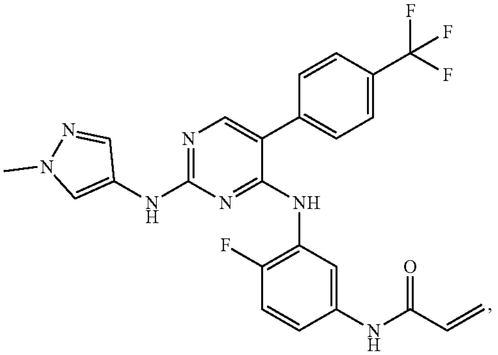

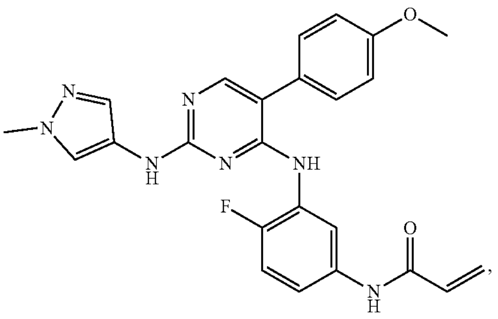

-continued
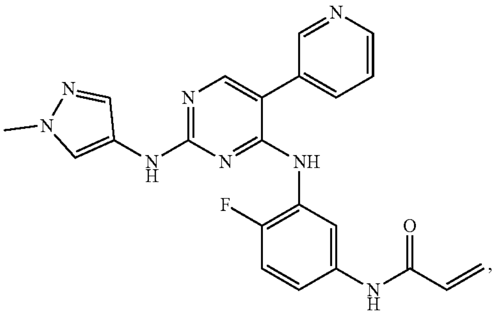,
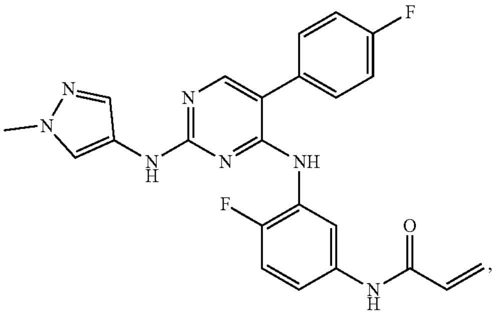,
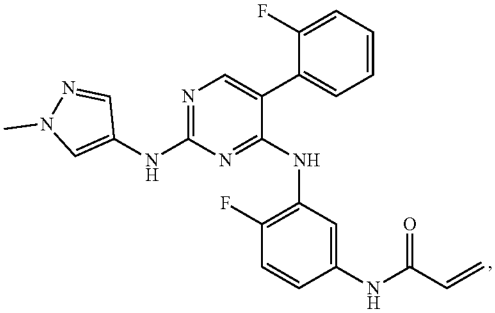,
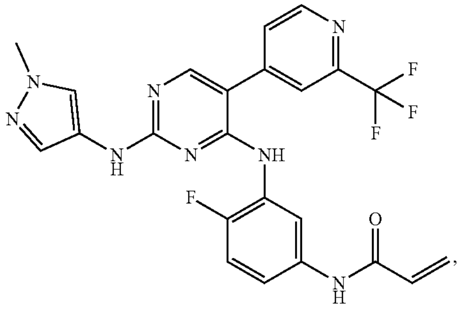,
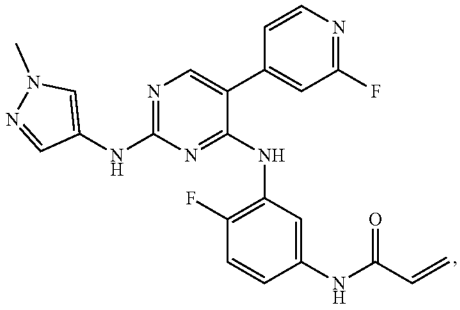,
-continued
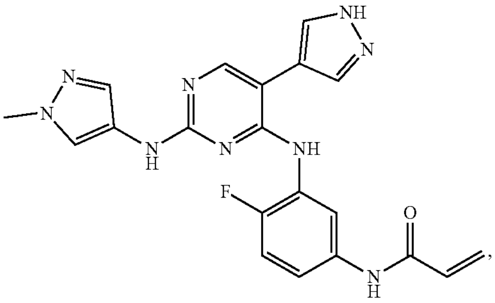,
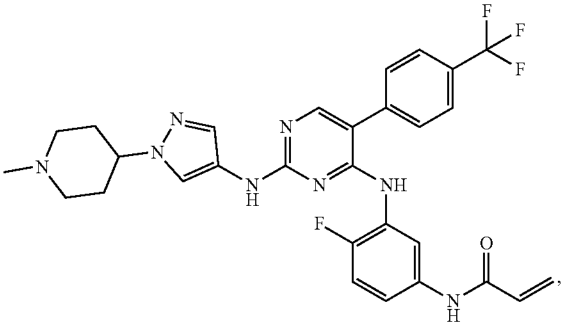,
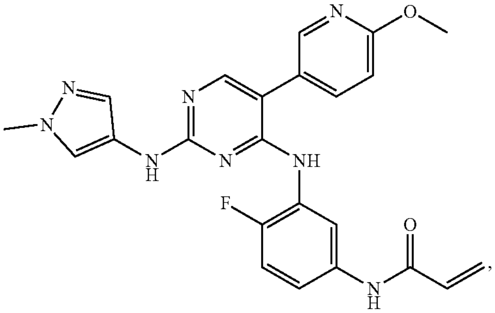,
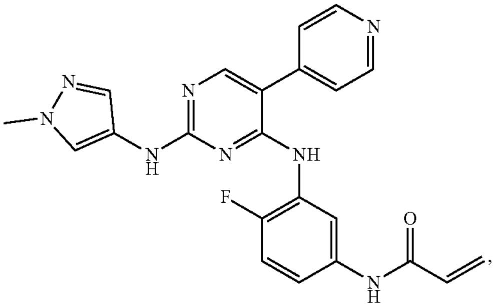,
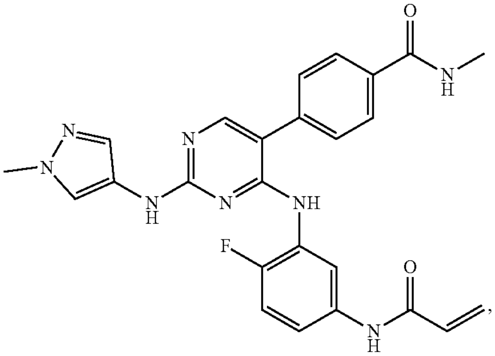, -continued
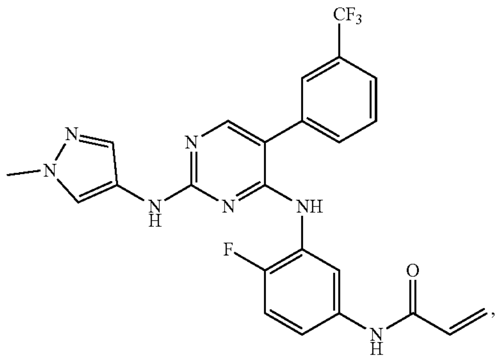
,
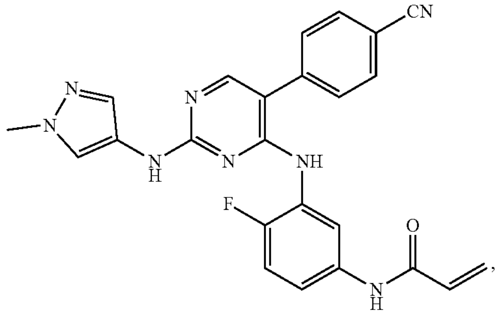
,
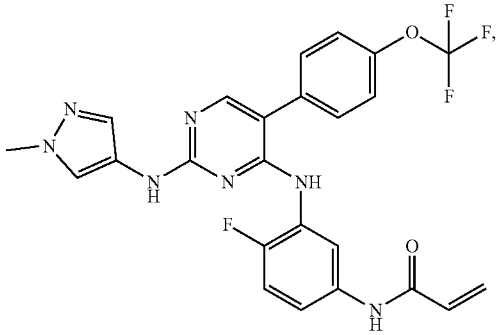
,
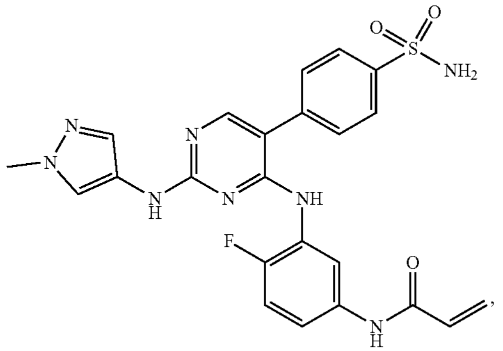
,
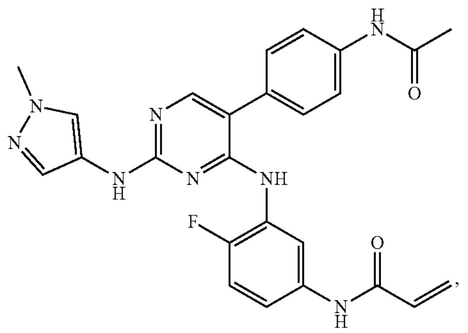
,
-continued
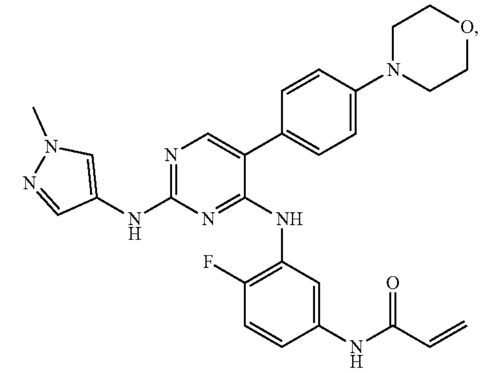
,
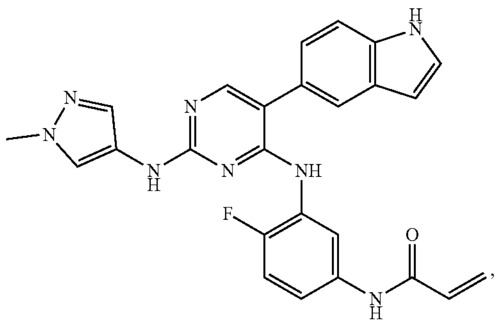
,
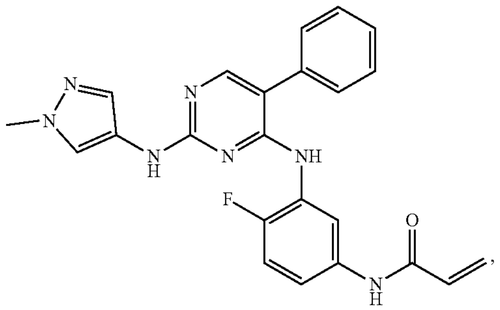
,
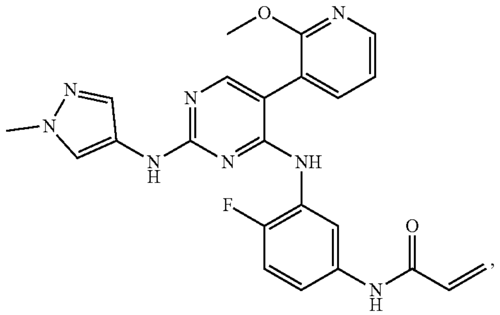
,
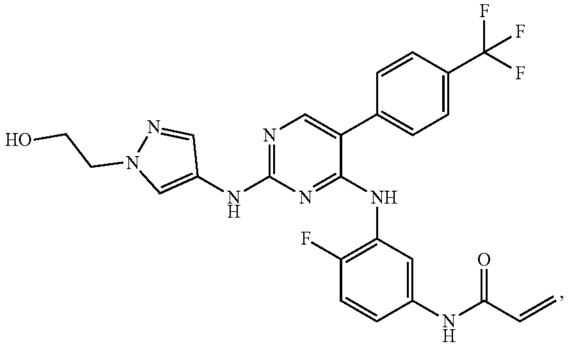
, -continued
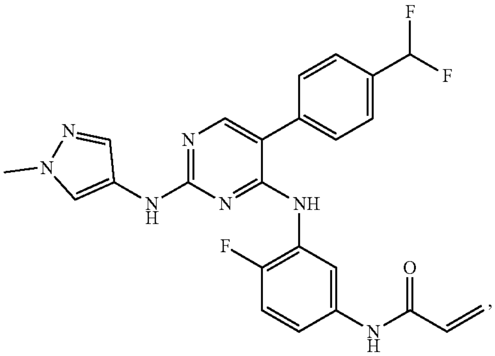
,
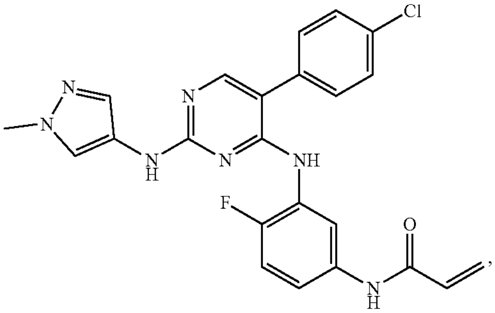
,
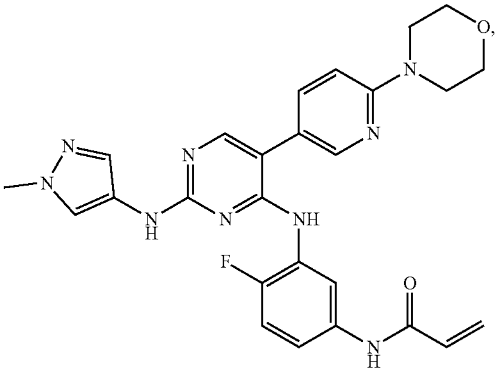
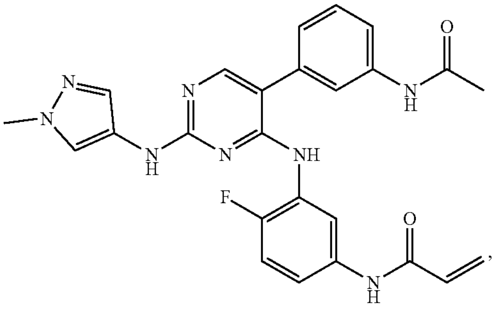
,
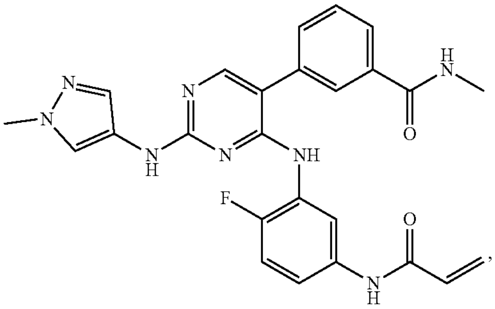
,
-continued
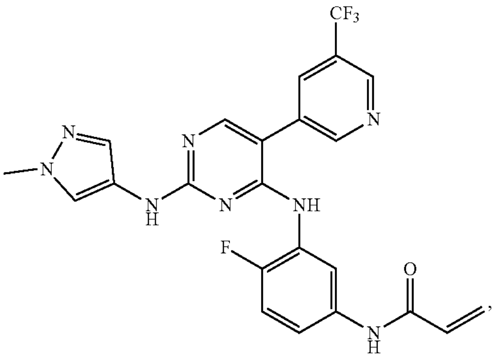
,
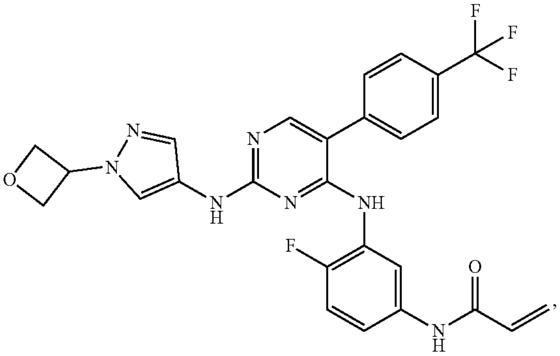
,
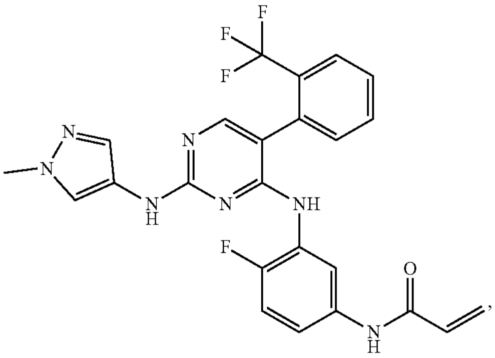
,
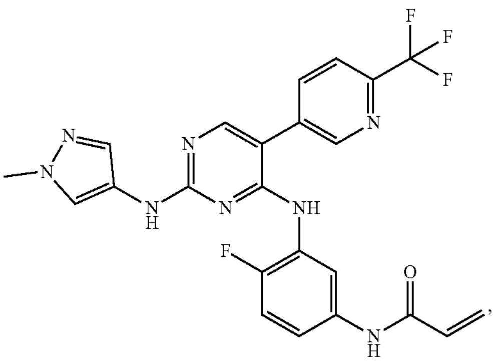
, -continued
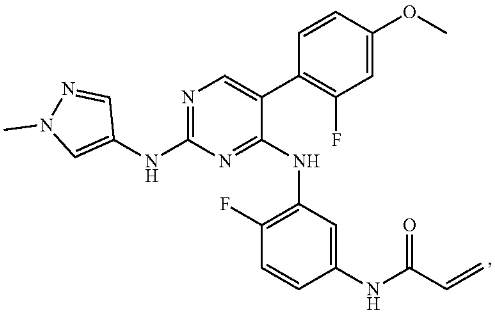
,
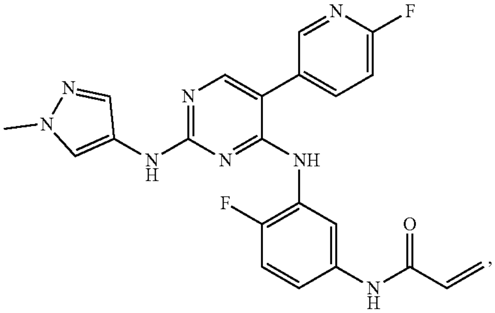
,
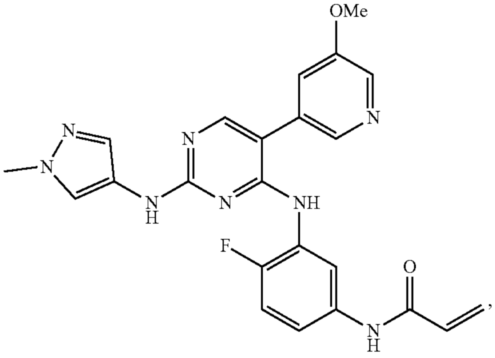
,
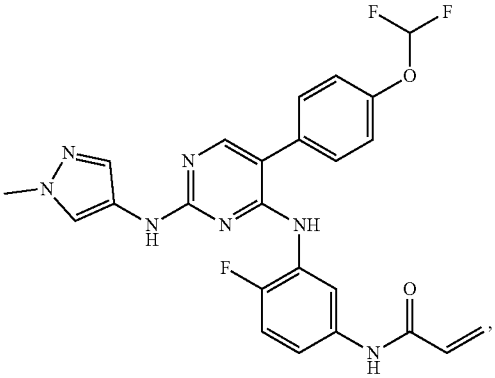
,
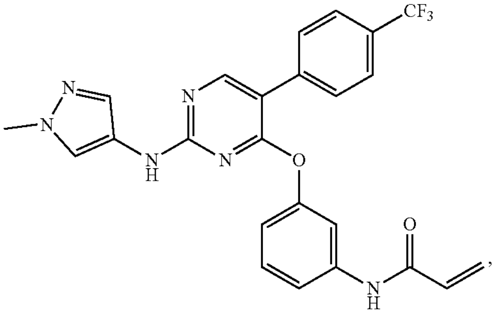
,
-continued
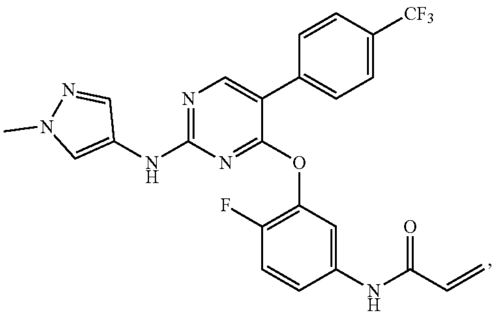
,
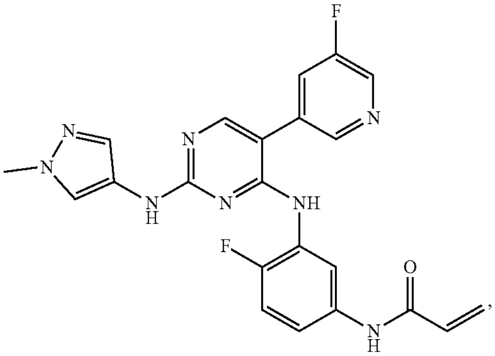
,
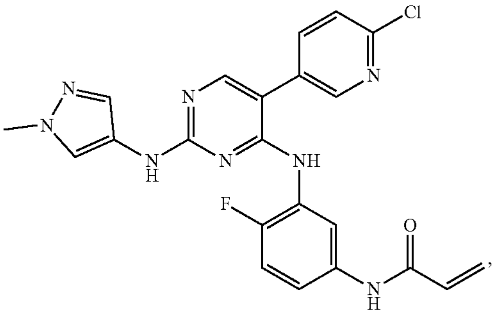
,
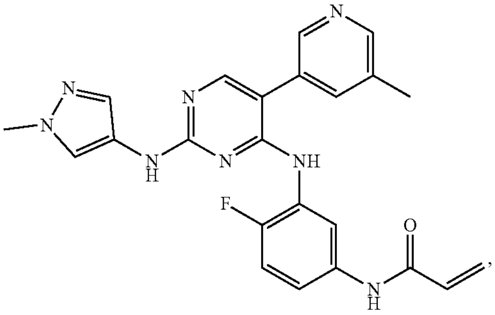
,
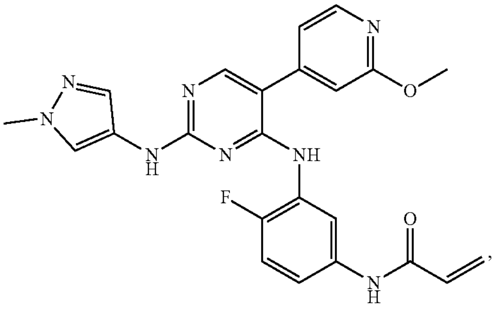
, -continued
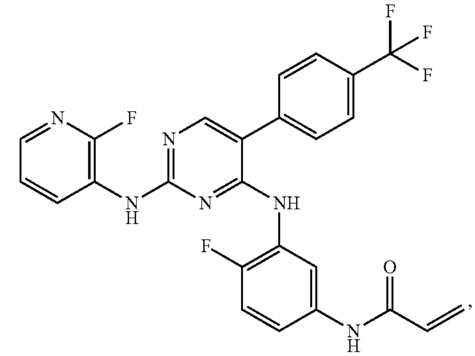
,
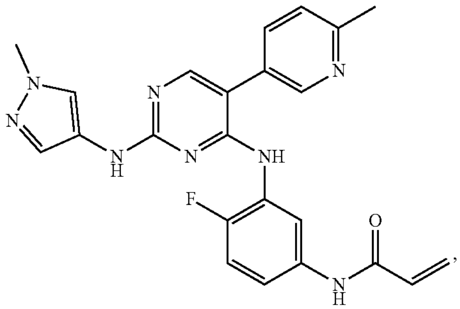
,
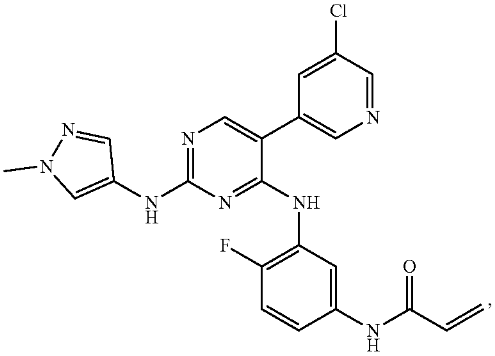
,
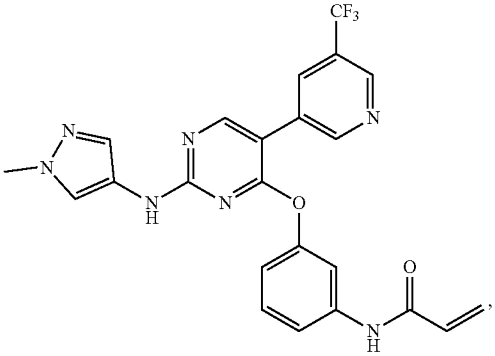
,
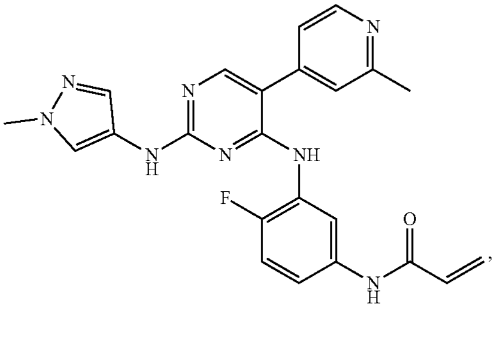
,
-continued
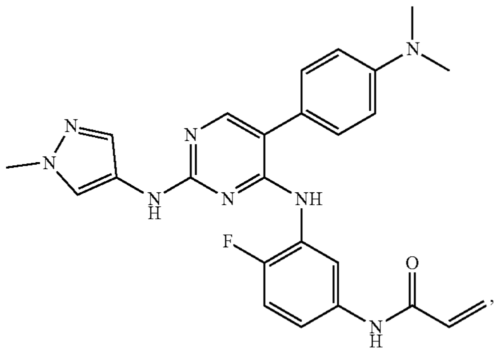
,
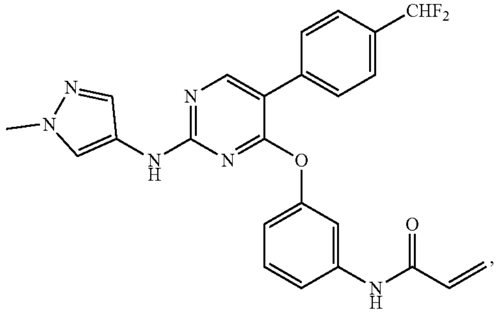
,
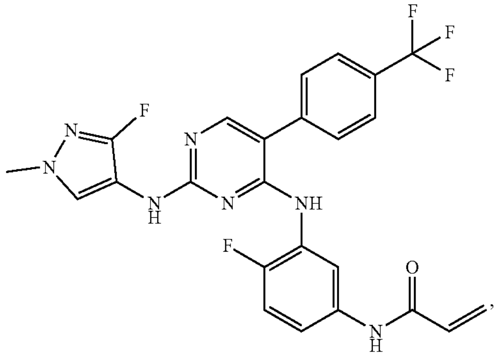
,
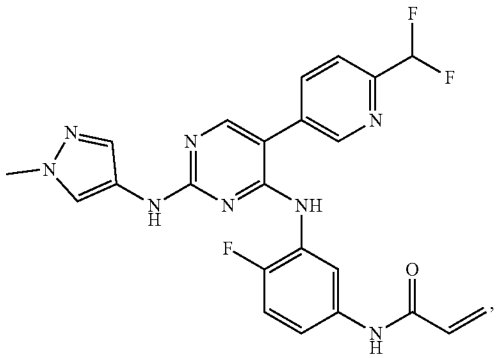
, -continued
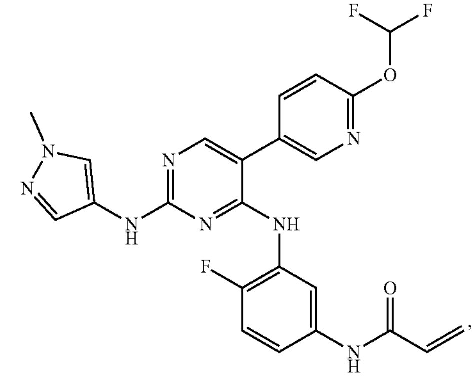
,
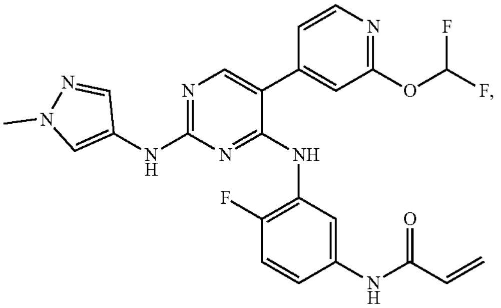
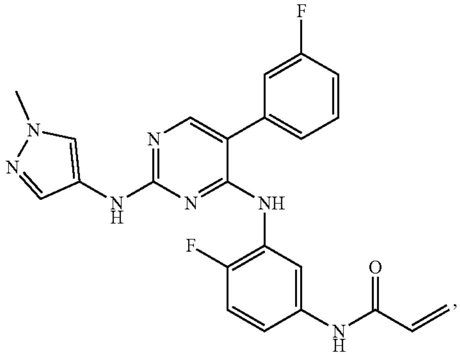
,
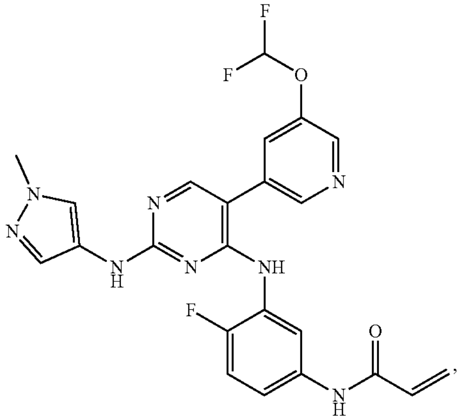
,
-continued
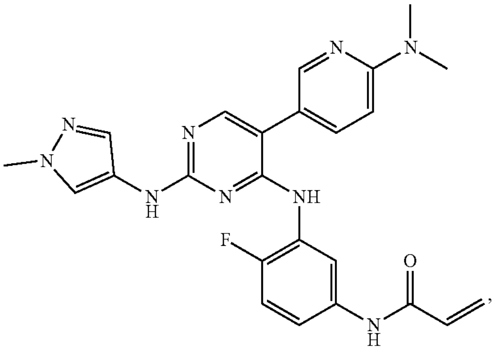
,
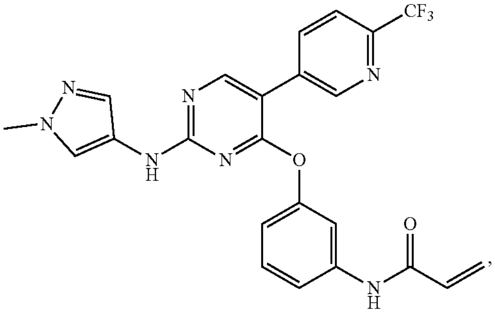
,
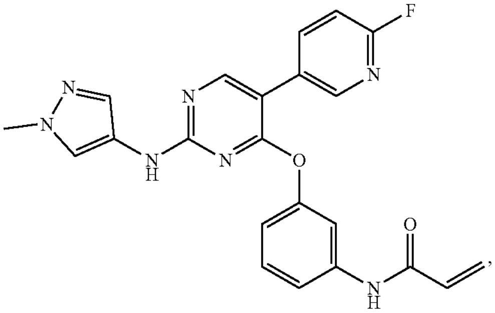
,
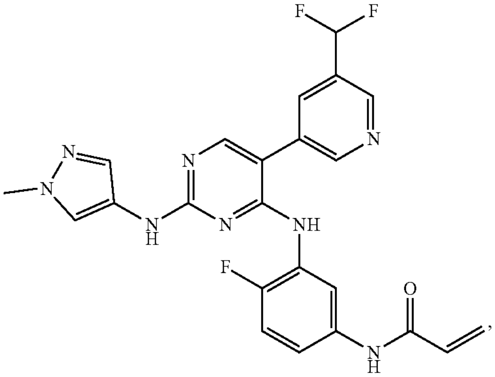
,
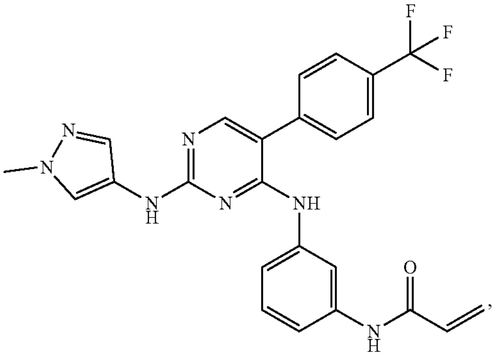
, -continued
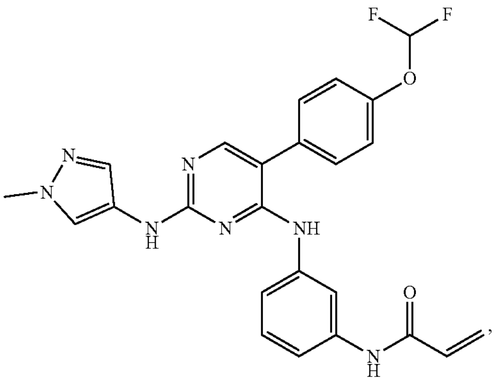
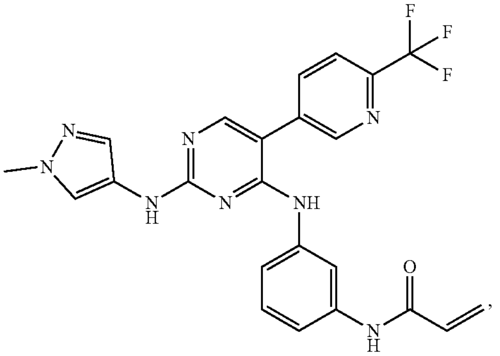
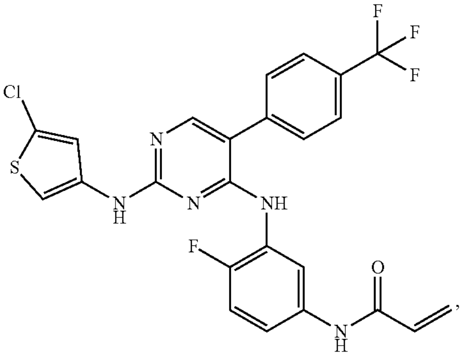
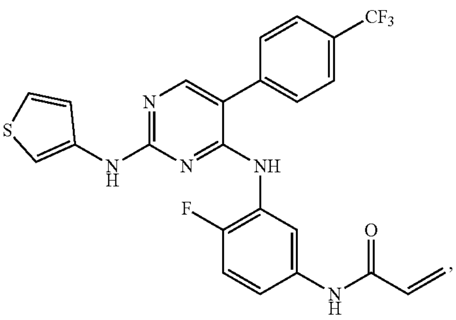
-continued
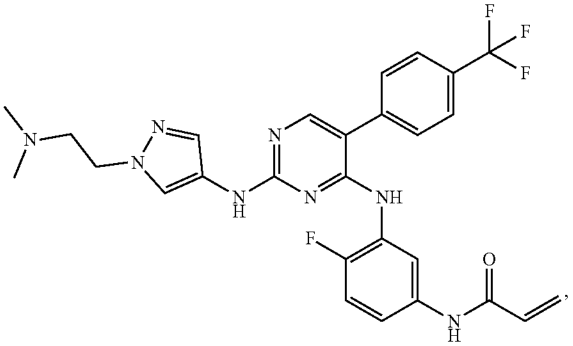
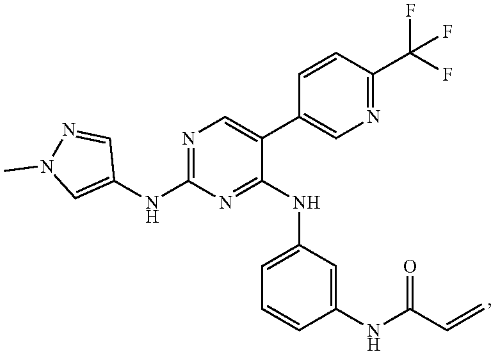
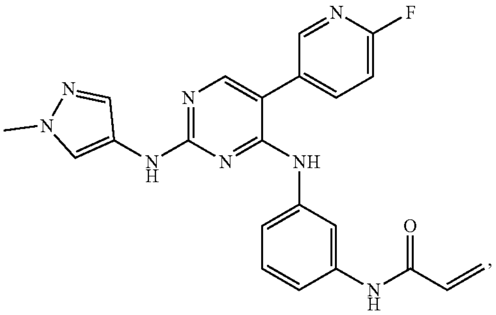
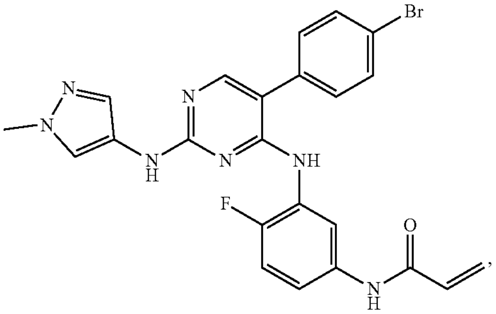
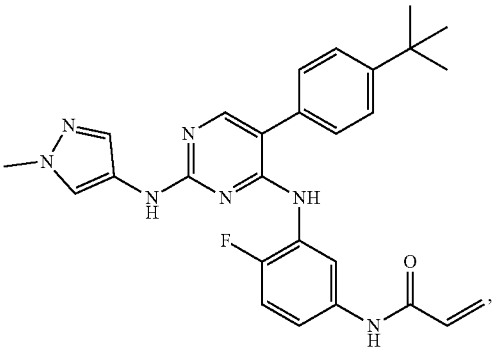

-continued
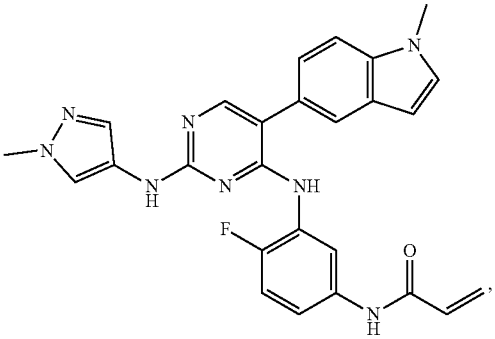
,
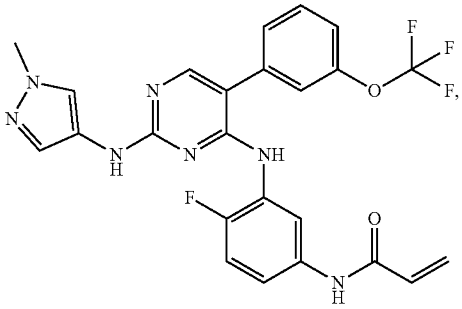
,
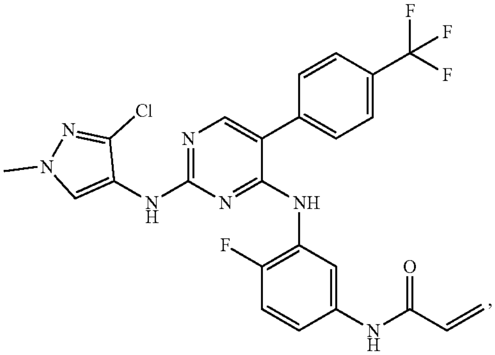
,
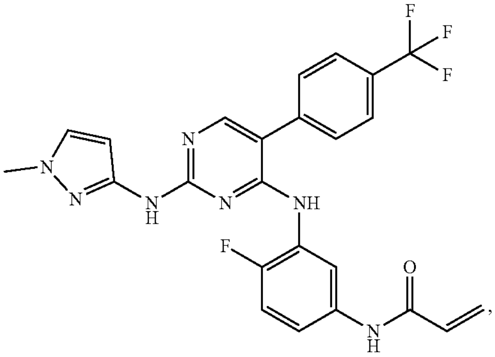
,
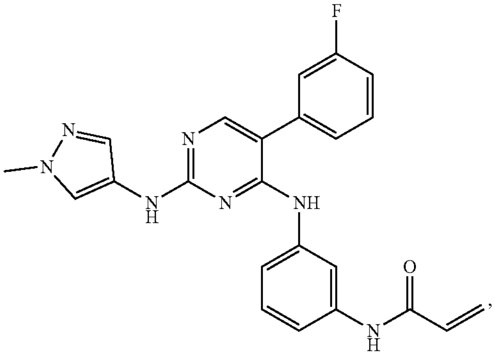
,
-continued
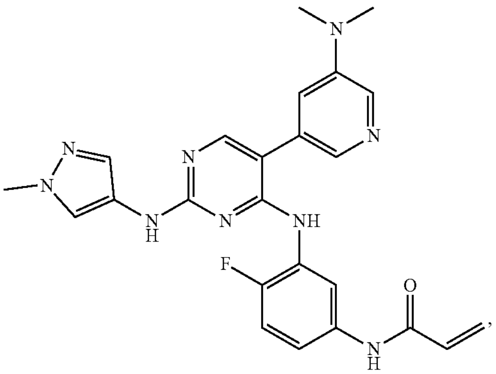
,
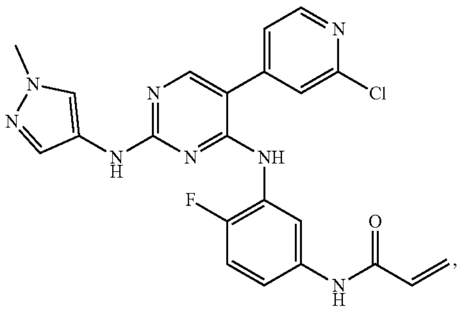
,
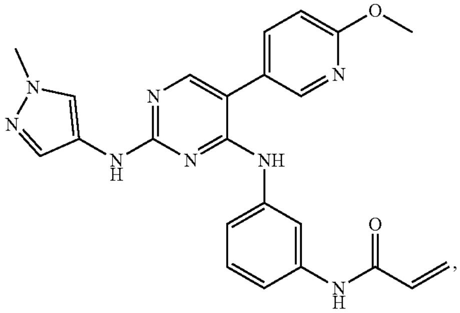
,
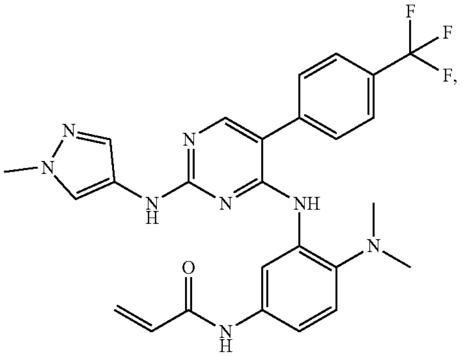
,
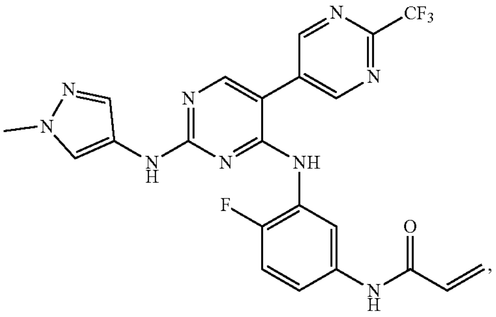
, -continued
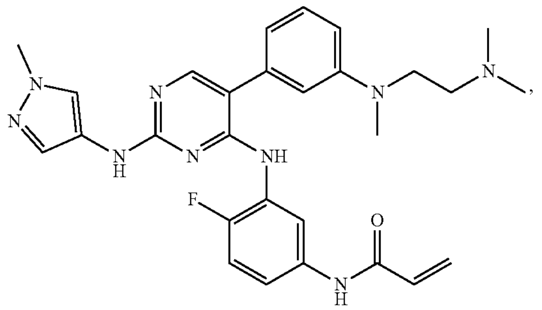
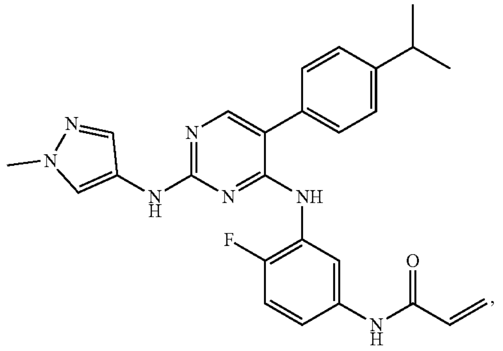
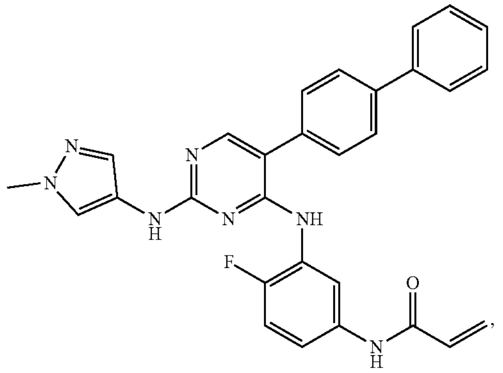
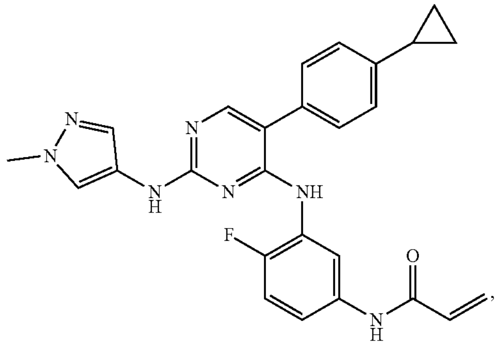
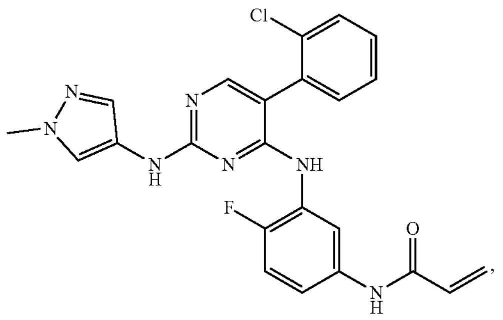
-continued
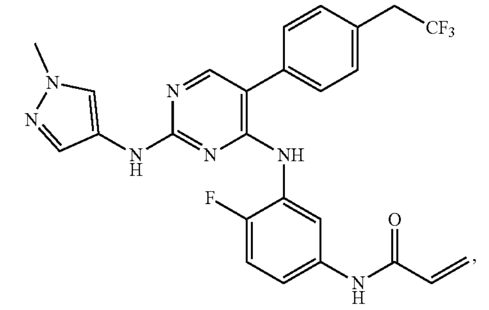
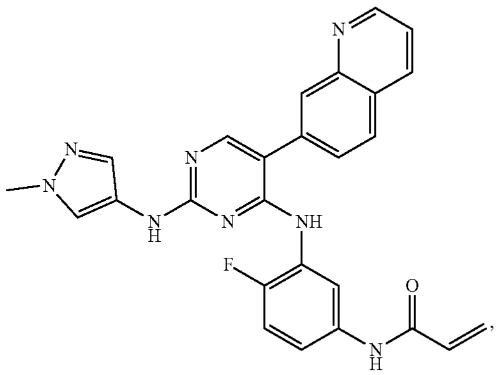
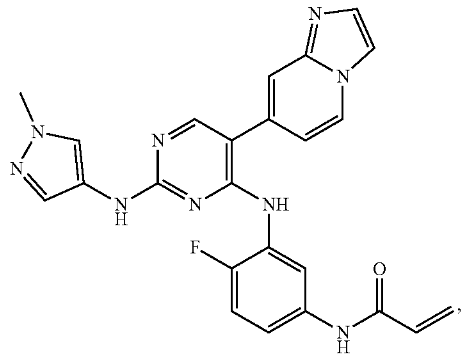
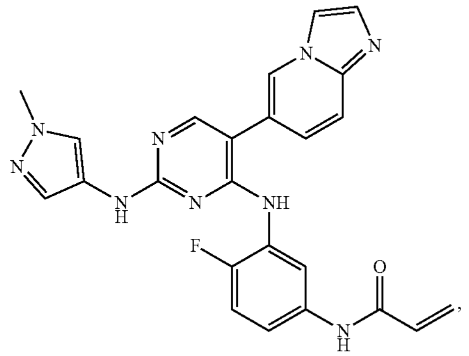
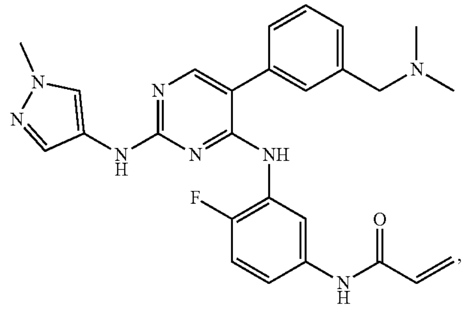

-continued
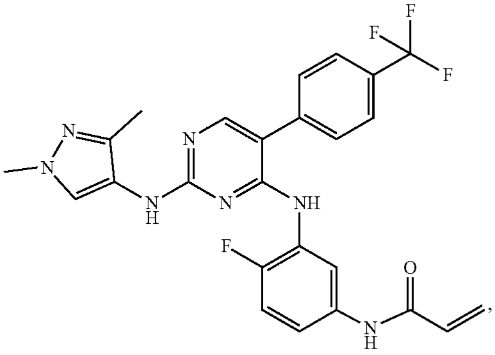
,
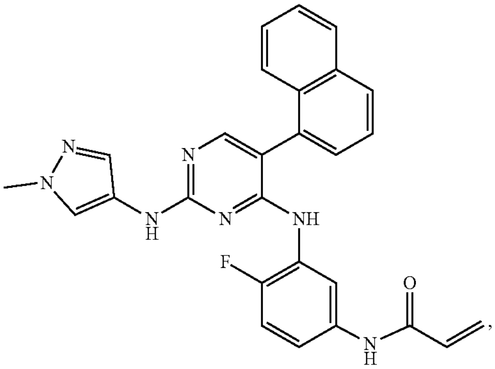
,
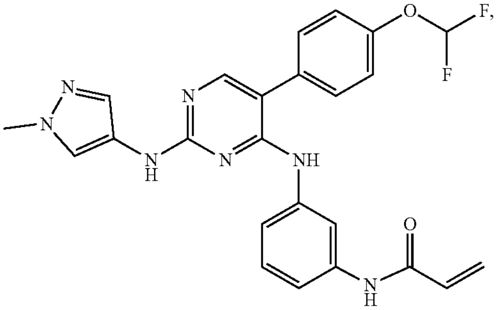
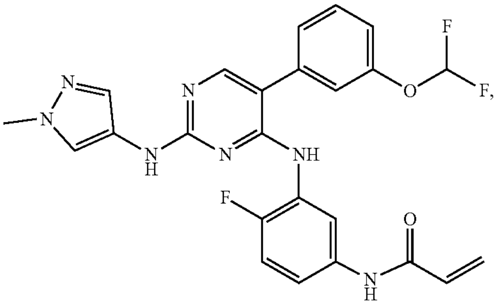
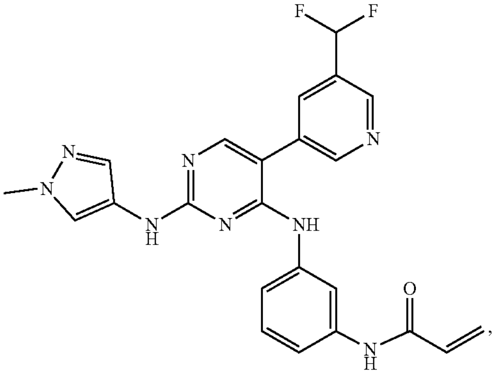
,
-continued
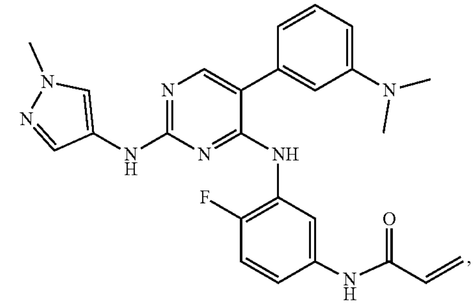
,
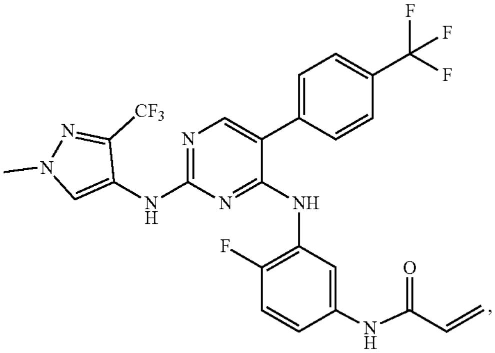
,
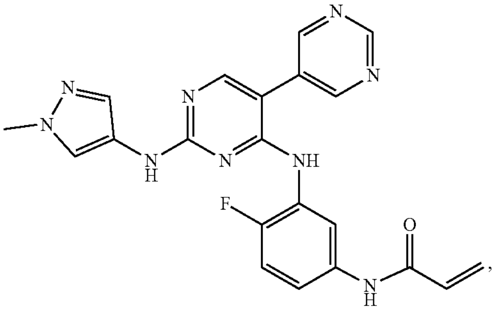
,
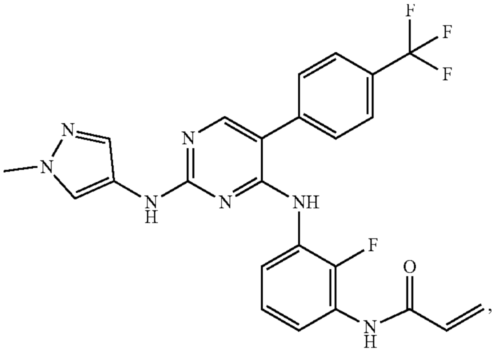
,
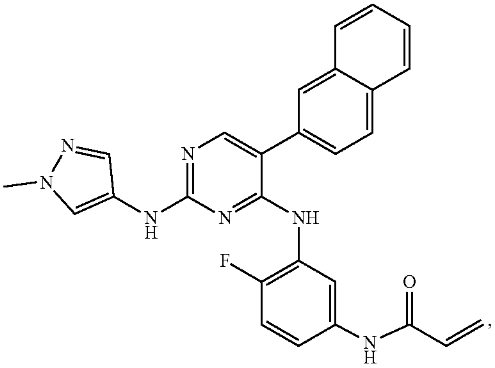
, -continued
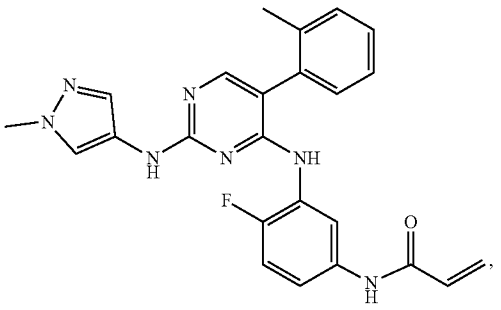
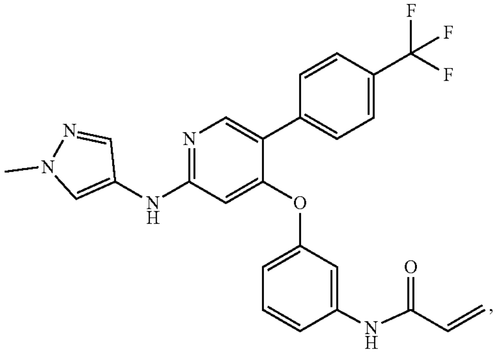
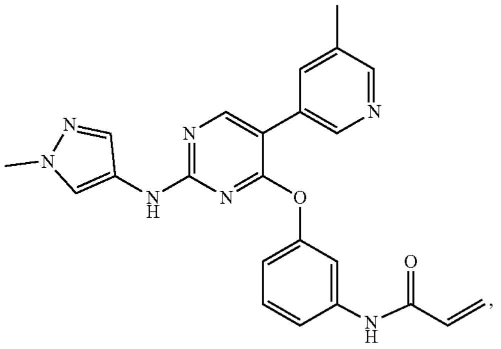
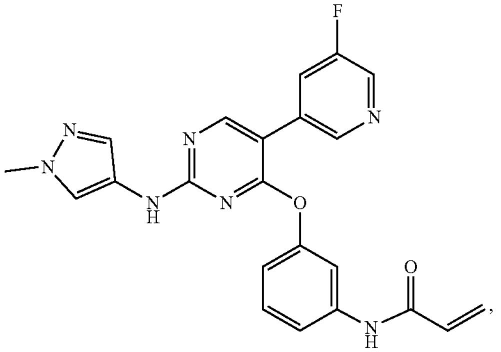
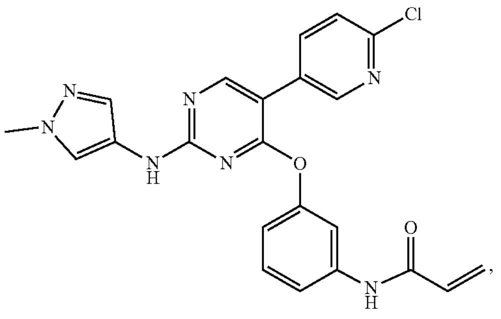
-continued
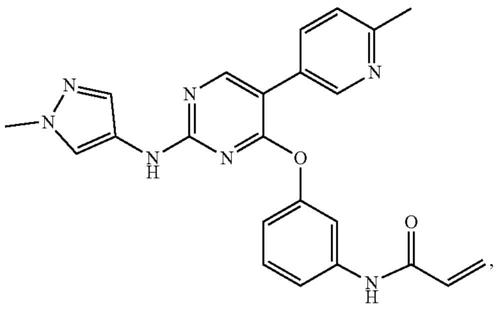
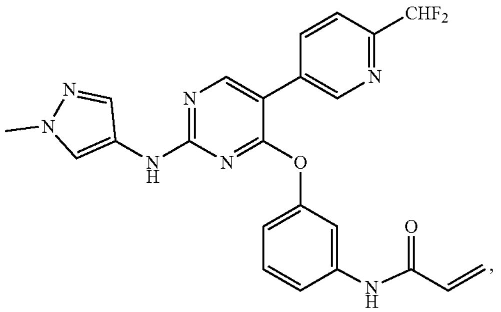
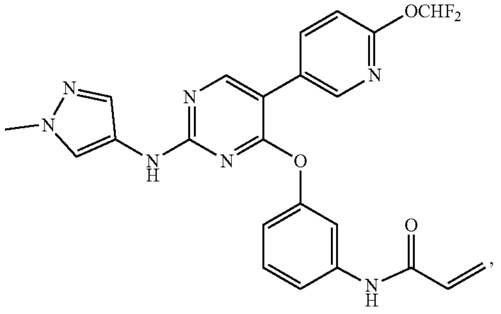
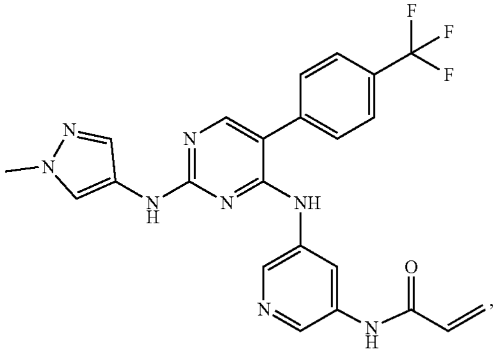
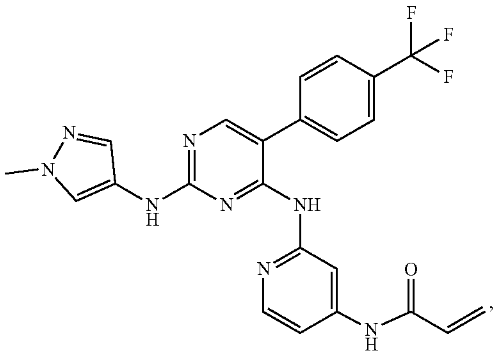

-continued
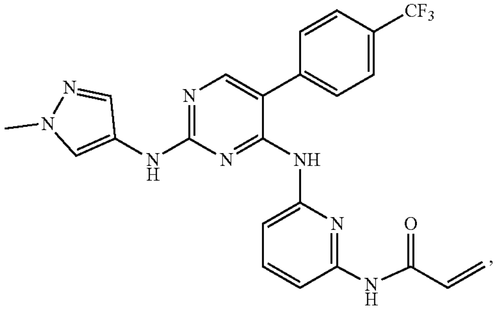
,
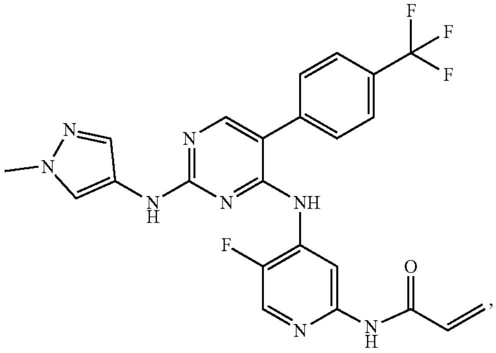
,
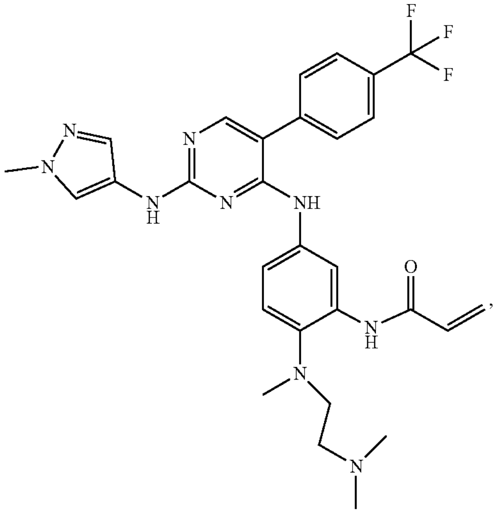
,
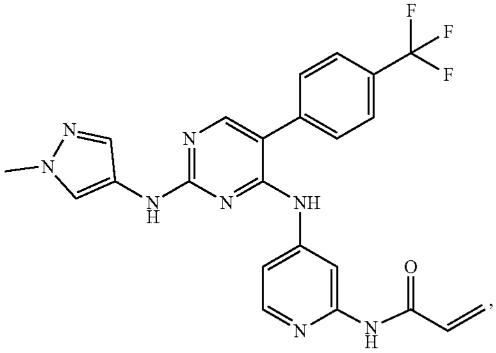
,
-continued
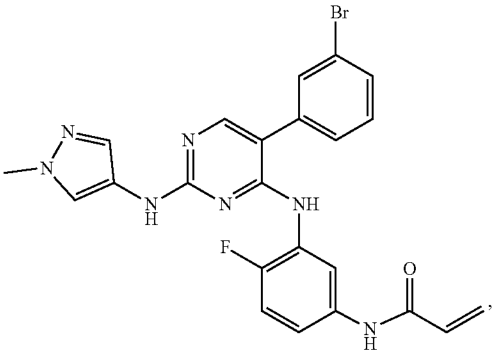
,
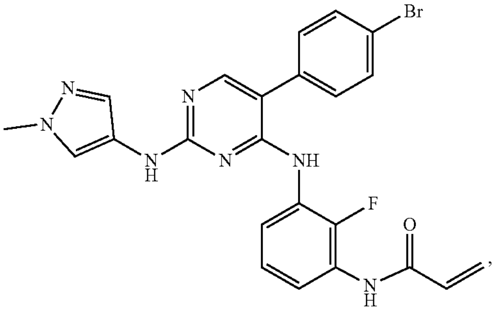
,
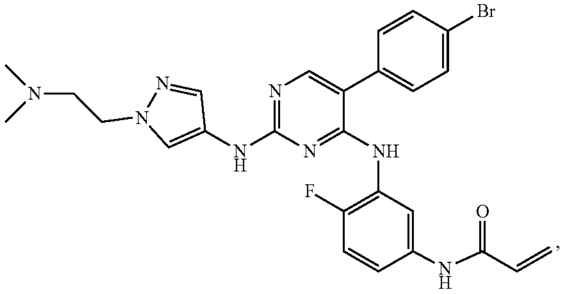
,
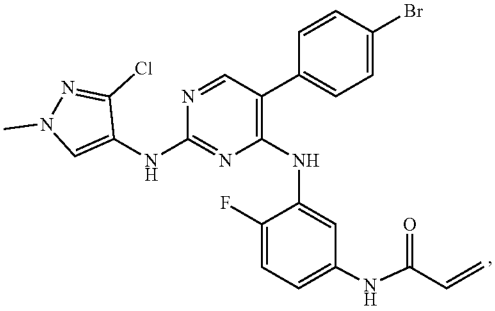
,
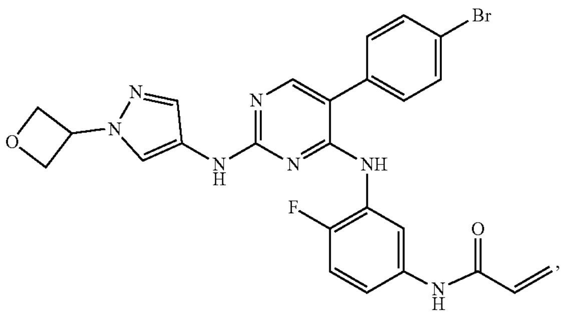
, -continued
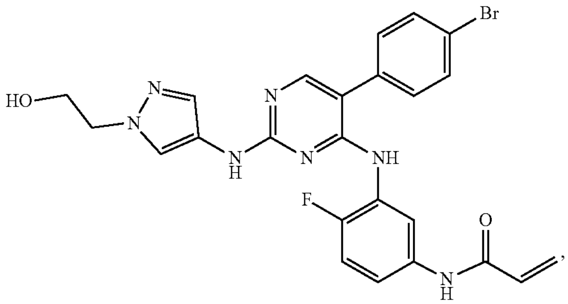
,
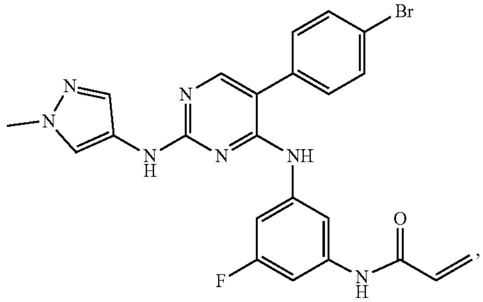
,
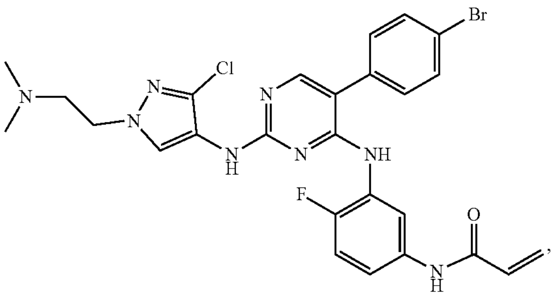
,
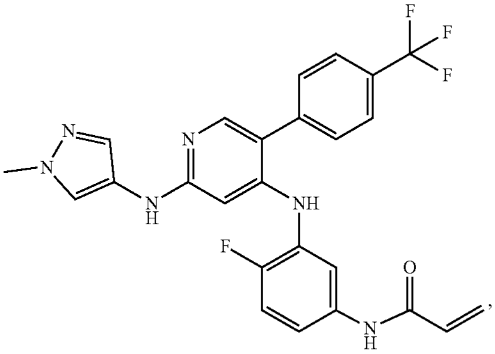
,
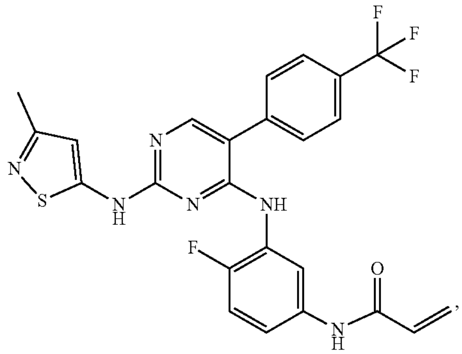
,
-continued
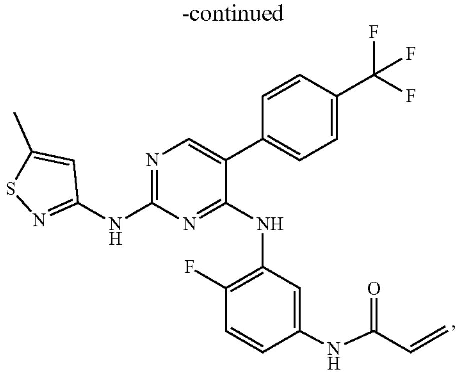
,
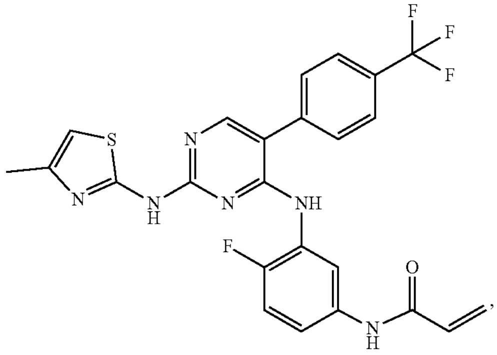
,
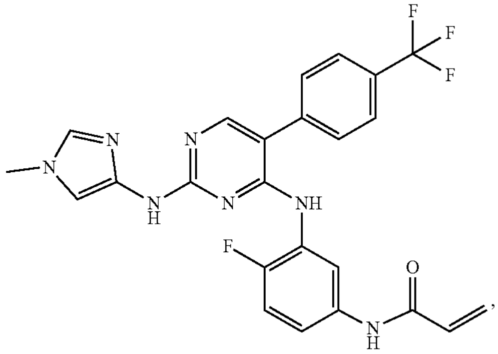
,
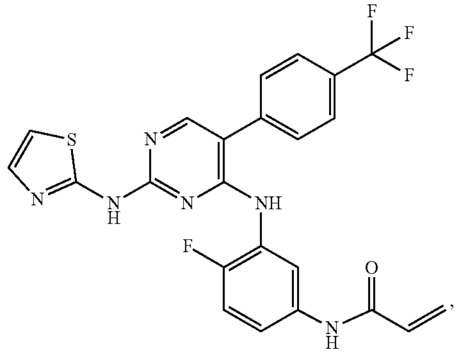
,
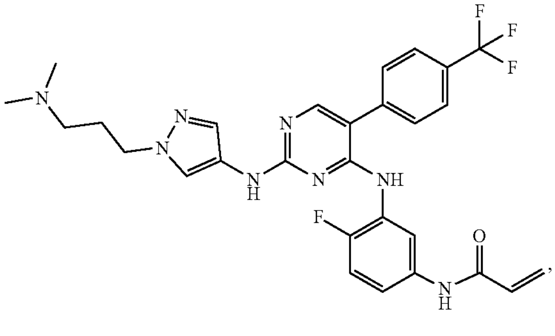
, -continued
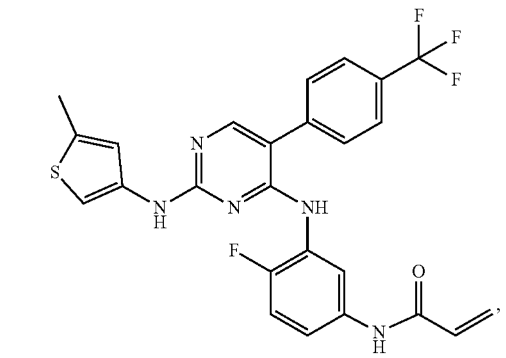
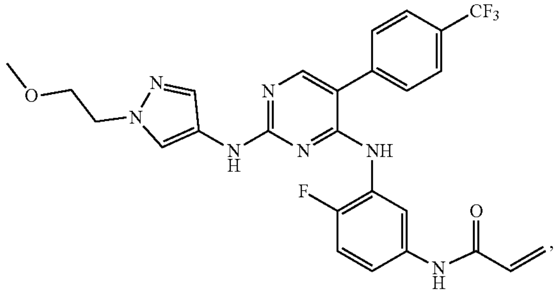
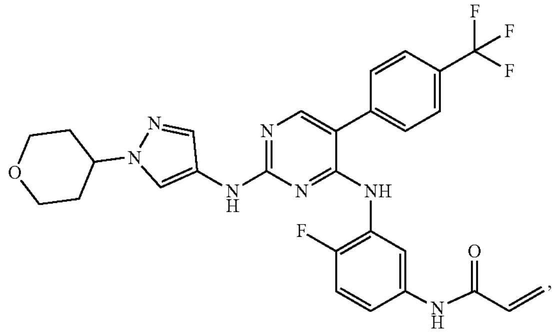
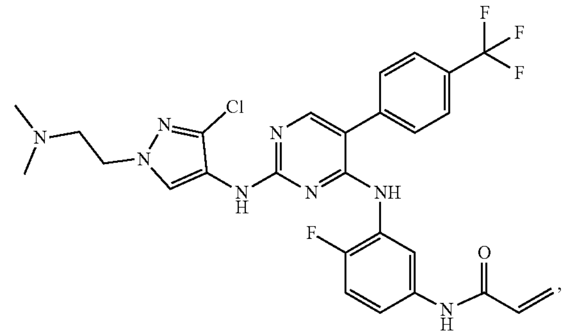
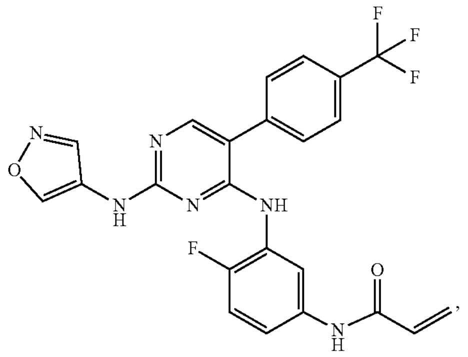
-continued
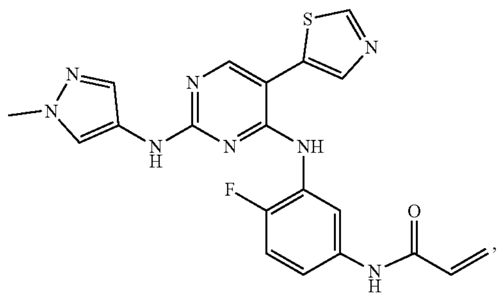
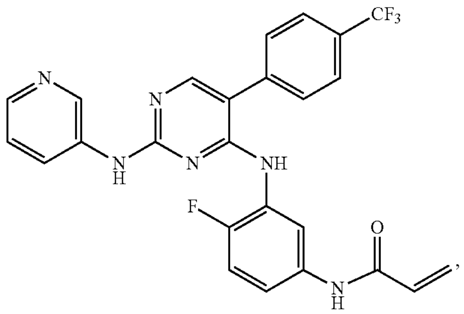
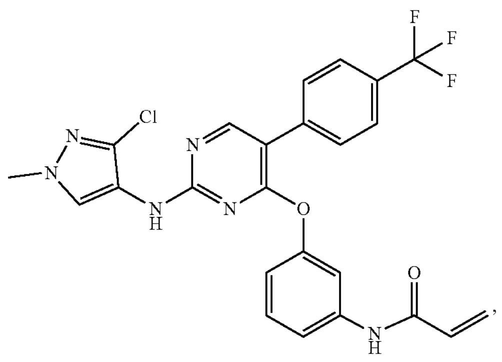
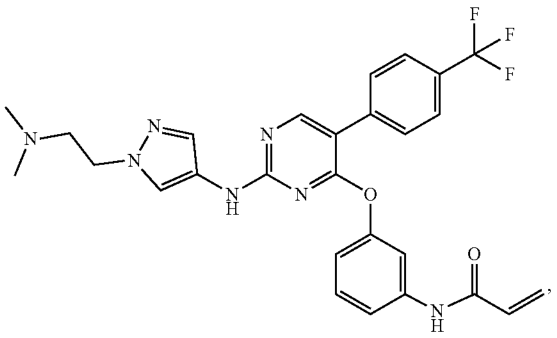
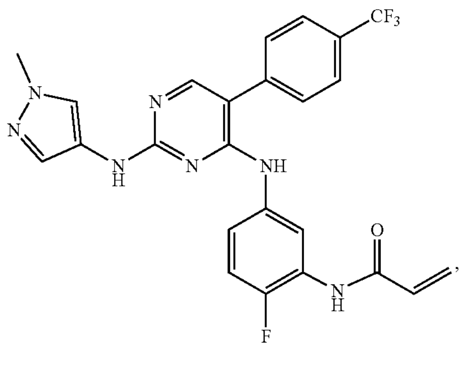

-continued
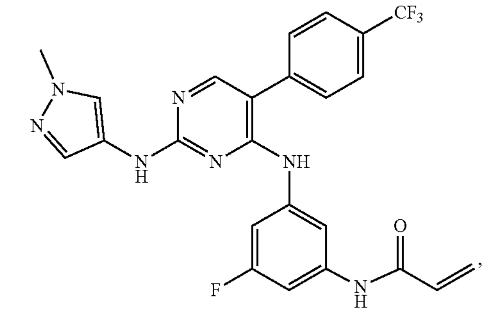
,
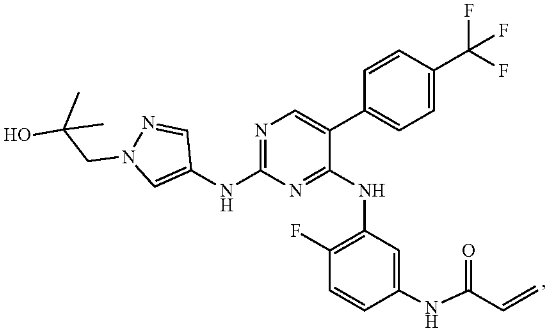
,
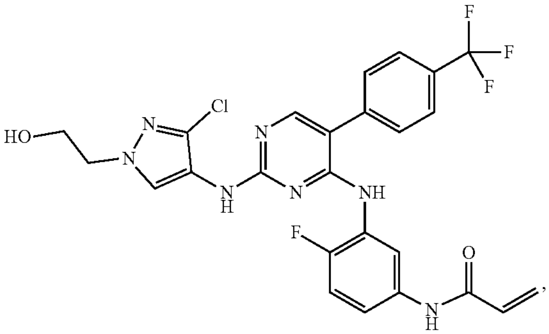
,
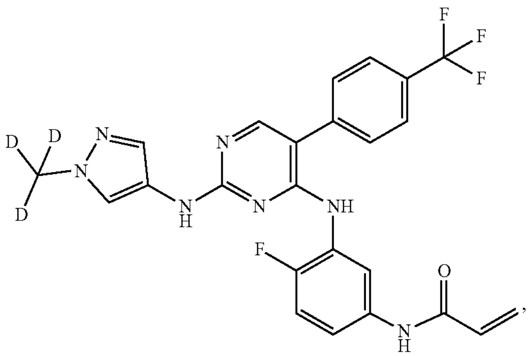
,
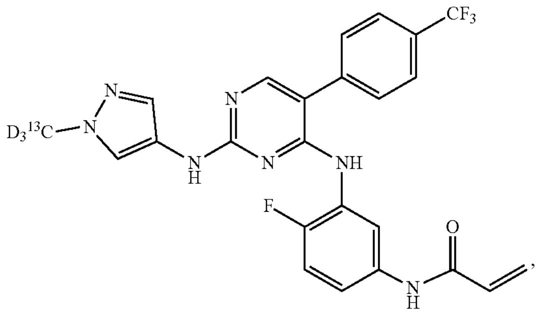
,
-continued
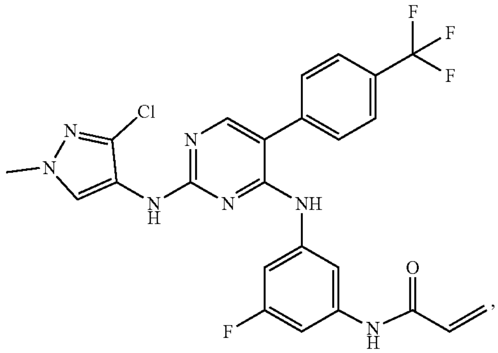
,
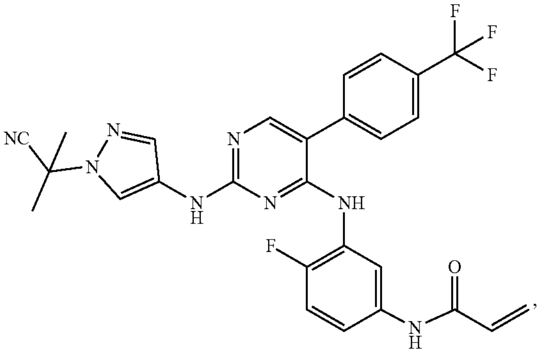
,
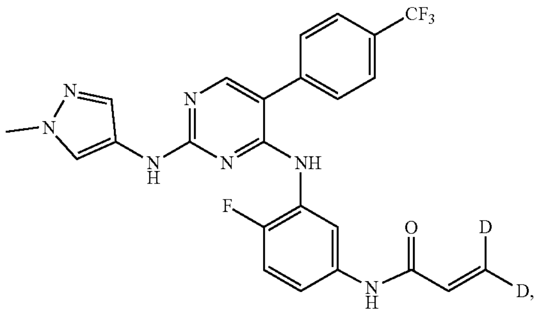
,
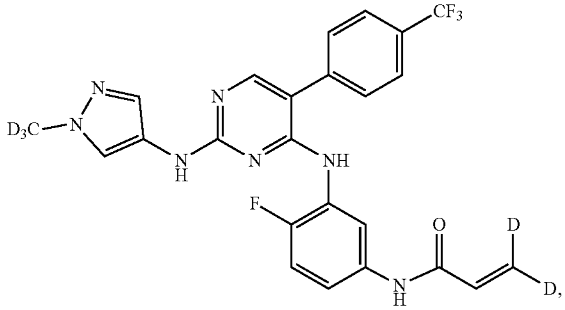
,
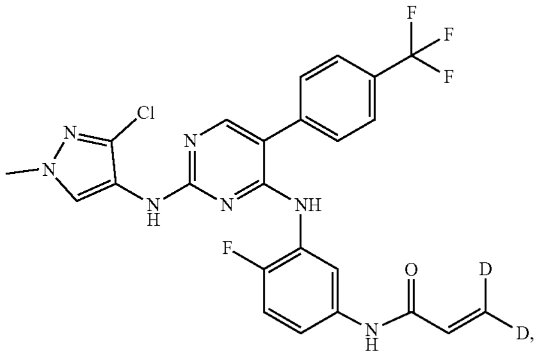
, -continued
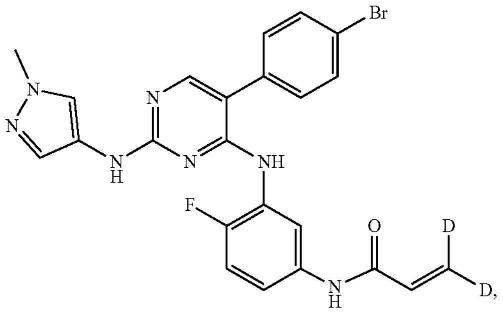
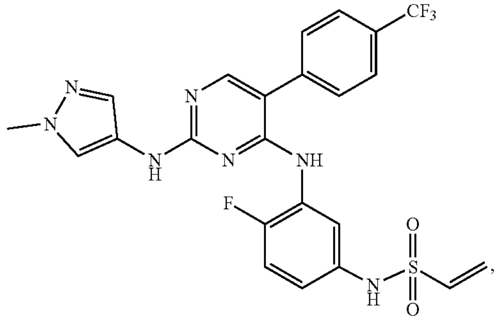
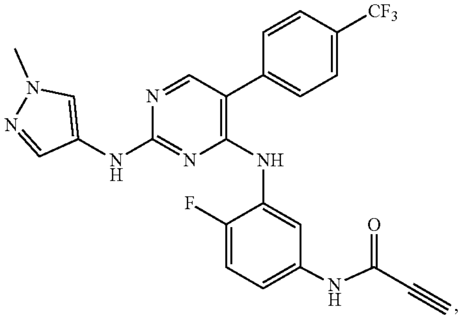
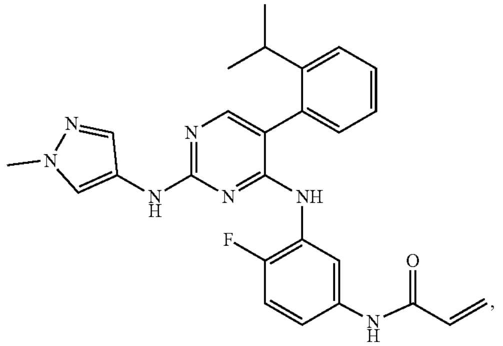
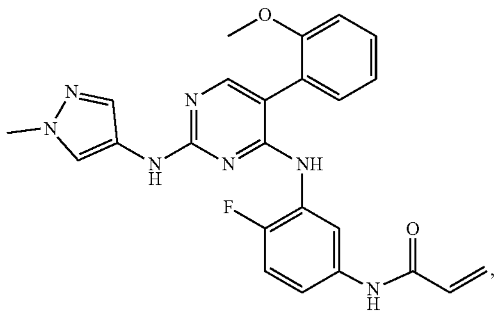
-continued
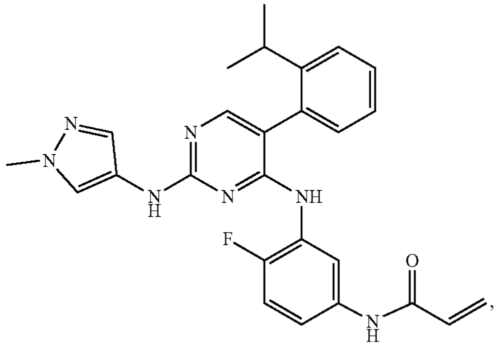
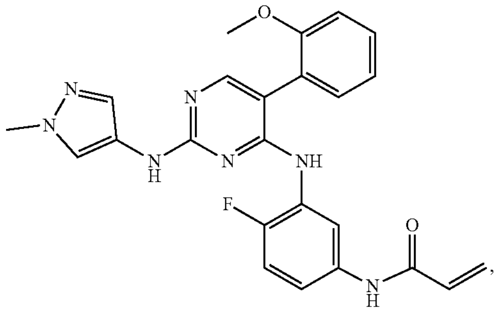
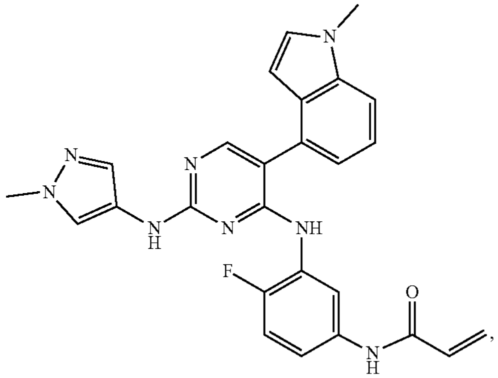
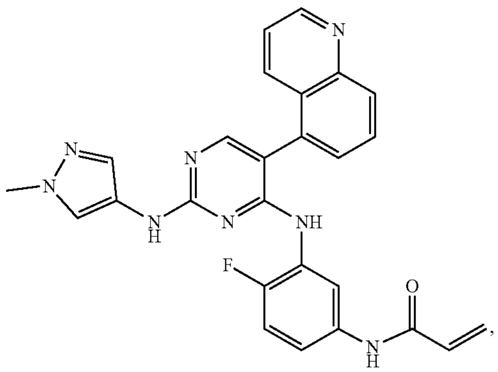

-continued
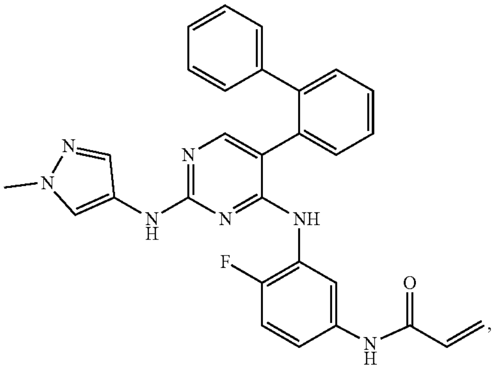
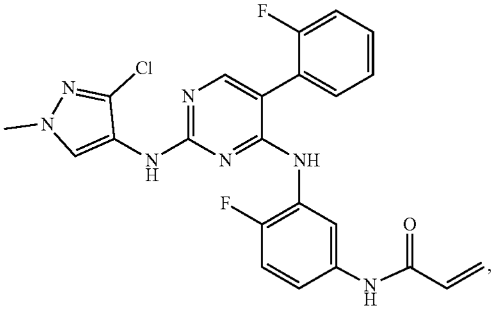
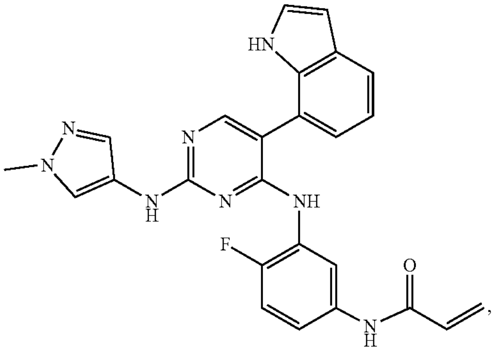
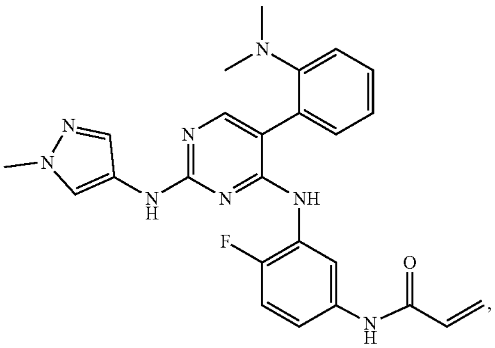
-continued
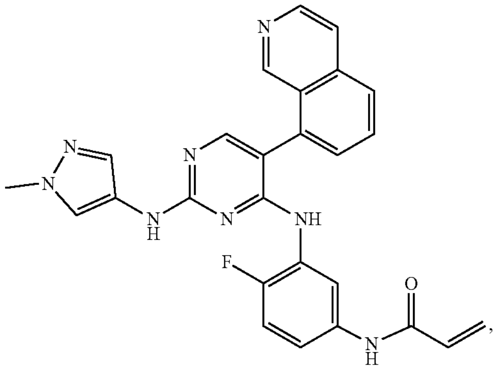
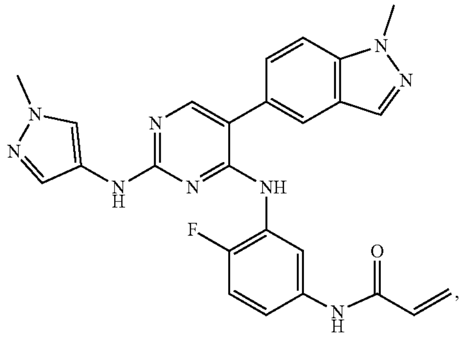
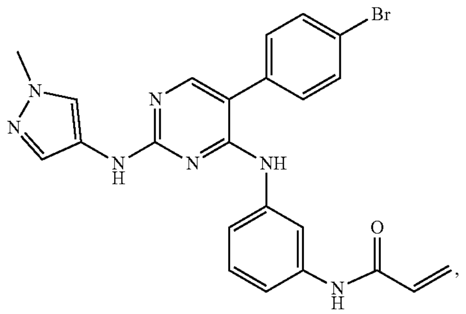
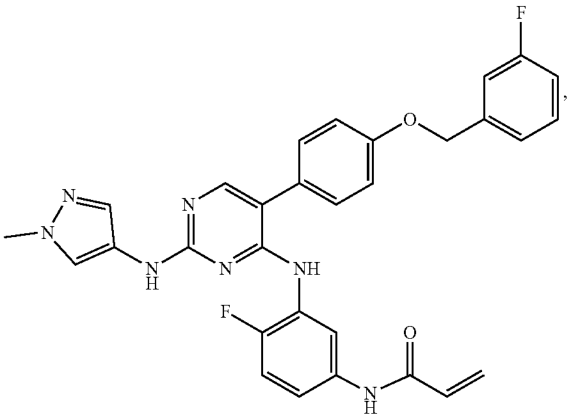

-continued
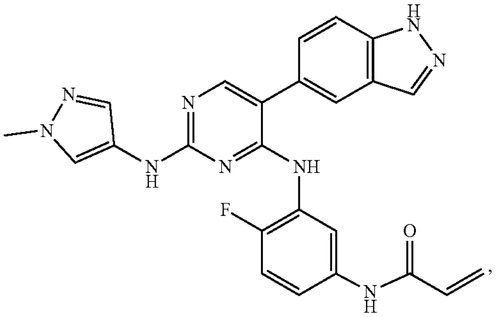
,
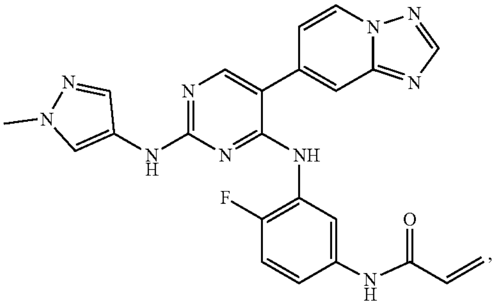
,
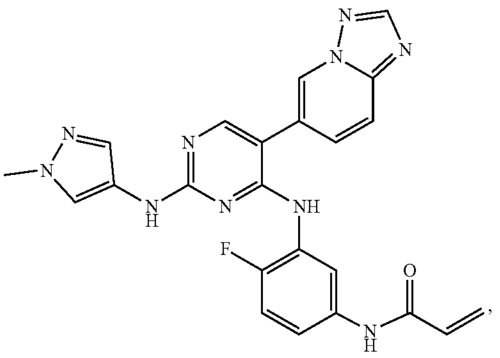
,
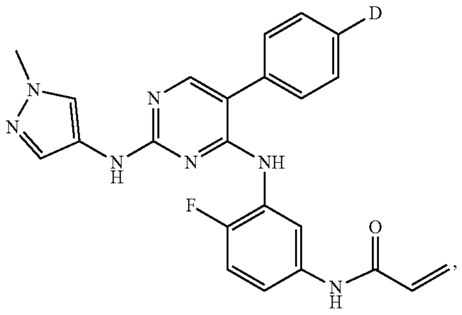
,
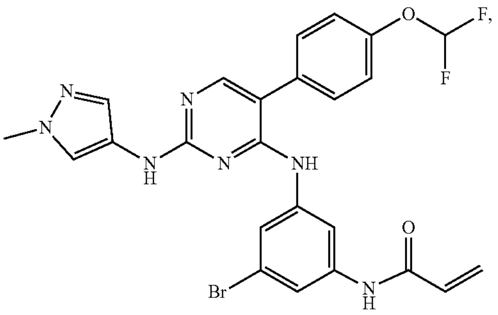
,
-continued
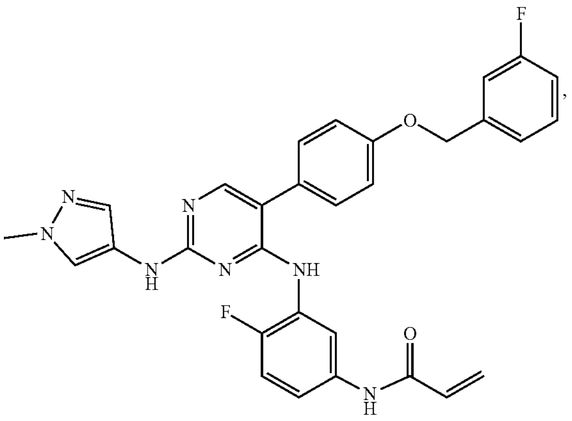
,
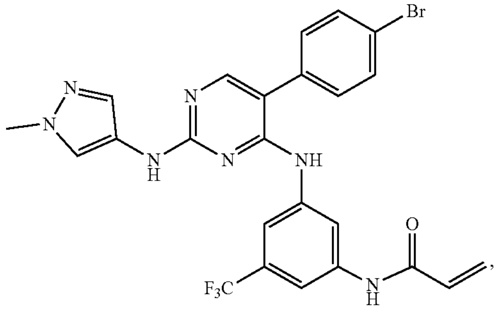
,
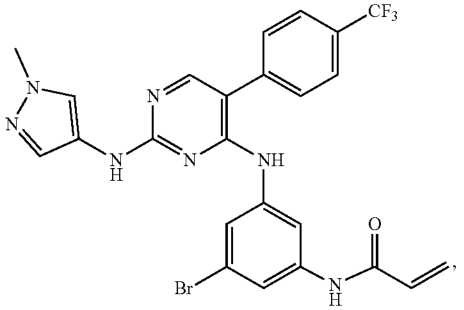
,
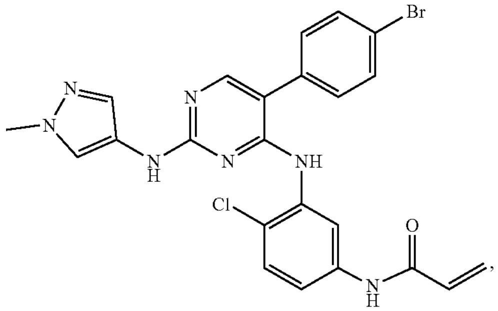
,
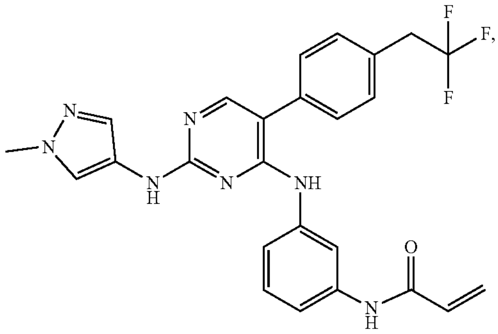
, -continued

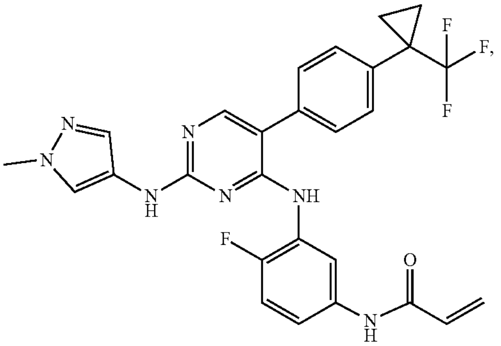

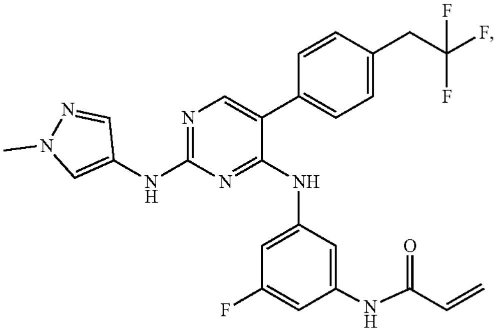

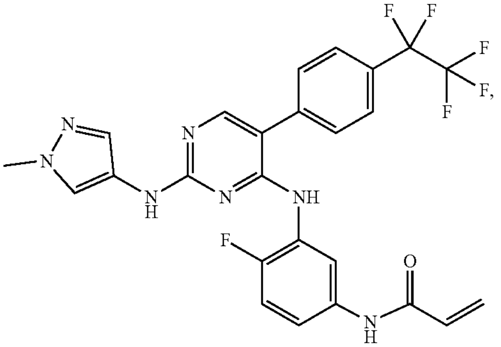

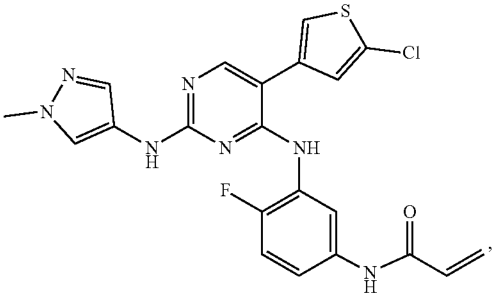

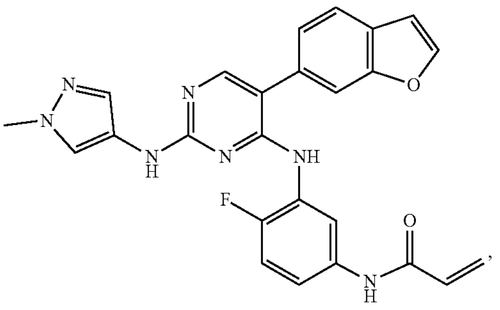

-continued

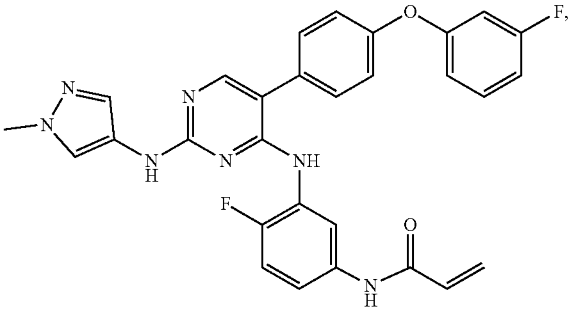

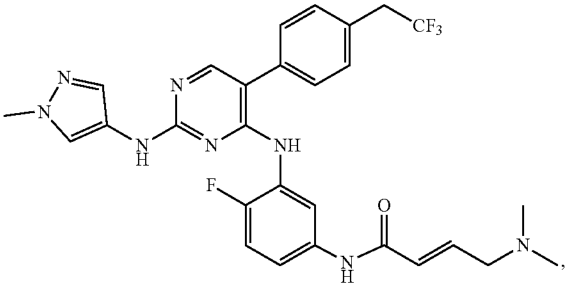

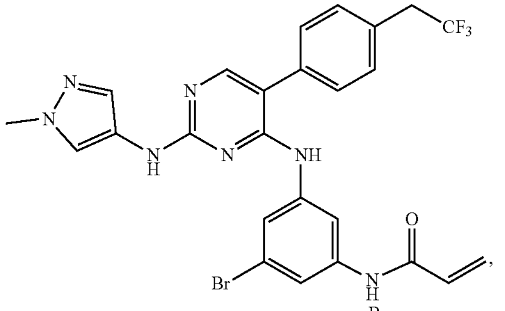

and

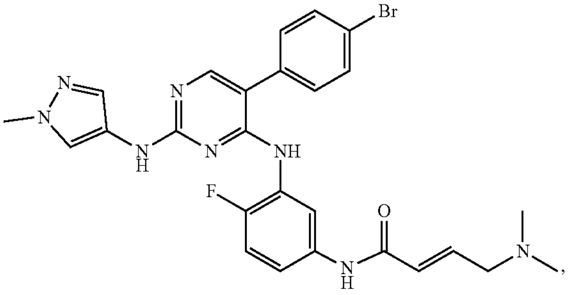

or a pharmaceutically acceptable salt thereof.

In some embodiments, the compounds described herein are selective inhibitors of EGFR over HER2.

In some embodiments, the compounds described herein have improved safety profiles. In some embodiments, the compounds described herein have improved toxicity profile. In some embodiments, the compounds described herein have improved therapeutic index.

In another aspect, provided herein is a pharmaceutical composition comprising a compound of Formula I, or a pharmaceutically acceptable salt or stereoisomer thereof, and a pharmaceutically acceptable carrier.

In another aspect, provided herein is a method of inhibiting an epidermal growth factor receptor (EGFR) family kinase mutant in a subject in need thereof, comprising administering to the subject a therapeutically effective amount of a compound of Formula I, or a pharmaceutically acceptable salt or stereoisomer thereof. In some embodiments, the EGFR family kinase mutant comprises a substitution in exon 18, a deletion in exon 19, a substitution in exon 20, an insertion in exon 20, a mutation in the extracellular domain, or a substitution in exon 21. In some embodiments, the EGFR family kinase mutant is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR, 770insNPG EGFR, 770insGT EGFR, 770insGF EGFR, 770insG EGFR, 771insH EGFR, 771insN EGFR, 772insNP EGFR, 773insNPH EGFR, 773insH EGFR, 773insPH EGFR, EGFRvii, EGFRviii, A767_dupASV EGFR, 773insAH EGFR, M766_A767insAI EGFR, and any combination thereof.

In another aspect, provided herein is a method of inhibiting an epidermal growth factor receptor (EGFR) mutant in a subject in need thereof, comprising administering to the subject a therapeutically effective amount of a compound of Formula I, or a pharmaceutically acceptable salt or stereoisomer thereof. In some embodiments, the EGFR mutant comprises a substitution in exon 18, a deletion in exon 19, a substitution in exon 20, an insertion in exon 20, a mutation in the extracellular domain, or a substitution in exon 21. In some embodiments, the EGFR mutant is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR, 770insNPG EGFR, 770insGT EGFR, 770insGF EGFR, 770insG EGFR, 771insH EGFR, 771insN EGFR, 772insNP EGFR, 773insNPH EGFR, 773insH EGFR, 773insPH EGFR, EGFRvii, EGFRviii, A767_dupASV EGFR, 773insAH EGFR, M766_A767insAI EGFR, and any combination thereof.

In another aspect, provided herein is a method of inhibiting a drug-resistant epidermal growth factor receptor (EGFR) mutant in a subject in need thereof, comprising administering to the subject a therapeutically effective amount of a compound of Formula I, or a pharmaceutically acceptable salt or stereoisomer thereof. In some embodiments, the drug-resistant EGFR mutant is del19/T790M EGFR or L858R/T790M EGFR.

In another aspect, provided herein is a method of inhibiting epidermal growth factor receptor (EGFR) in a subject in need thereof, comprising administering to the subject a therapeutically effective amount of a compound of Formula I, or a pharmaceutically acceptable salt or stereoisomer thereof, wherein the compound exhibits greater inhibition of an EGFR mutant relative to wild-type EGFR.

In some embodiments, the EGFR mutant comprises a substitution in exon 18, a deletion in exon 19, a substitution in exon 20, an insertion in exon 20, a mutation in the extracellular domain, or a substitution in exon 21. In some embodiments, the EGFR mutant is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR (or D770_N771insSVD EGFR), 770insNPG EGFR (or D770_N771insNPG EGFR), 770insGT EGFR, 770insGF EGFR, 770insG EGFR, 771insH EGFR, 771insN EGFR, 772insNP EGFR, 773insNPH EGFR (or H773insNPH EGFR), 773insH EGFR, 773insPH EGFR, EGFRvii, EGFRviii, A767_dupASV EGFR, 773insAH EGFR, M766_A767insAI EGFR, and any combination thereof. In some embodiments, the EGFR mutant is del19/T790M EGFR or L858R/T790M EGFR.

In another aspect, provided herein is a method of treating a disease or disorder associated with an epidermal growth factor receptor (EGFR) family kinase in a subject in need thereof, comprising administering to the subject a therapeutically effective amount of a compound of Formula I, or a pharmaceutically acceptable salt or stereoisomer thereof. In some embodiments, the EGFR mutant comprises a substitution in exon 18, a deletion in exon 19, a substitution in exon 20, an insertion in exon 20, a mutation in the extracellular domain, or a substitution in exon 21. In some embodiments, the EGFR mutant is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR, 770insNPG EGFR, 770insGT EGFR, 770insGF EGFR, 770insG EGFR, 771insH EGFR, 771insN EGFR, 772insNP EGFR, 773insNPH EGFR, 773insH EGFR, 773insPH EGFR, EGFRvii, EGFRviii, A767_dupASV EGFR, 773insAH EGFR, M766_A767insAI EGFR, and any combination thereof.

In some embodiments, the disease or disorder in the subject comprises an EGFR mutation. In some embodiments, the EGFR mutation comprises a substitution in exon 18, a deletion in exon 19, a substitution in exon 20, an insertion in exon 20, a mutation in the extracellular domain, or a substitution in exon 21. In some embodiments, the EGFR mutation is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR (or D770_N771insSVD EGFR), 770insNPG EGFR (or D770_N771insNPG EGFR), 770insGT EGFR, 770insGF EGFR, 770insG EGFR, 771insH EGFR, 771insN EGFR, 772insNP EGFR, 773insNPH EGFR (or H773insNPH EGFR), 773insH EGFR, 773insPH EGFR, EGFRvii, EGFRviii, A767_dupASV EGFR, 773insAH EGFR, M766_A767insAI EGFR, and any combination thereof. In some embodiments, the EGFR mutation is del19/T790M EGFR or L858R/T790M EGFR.

In another aspect, provided herein is a method of treating one or more cancer cells in a subject in need thereof, comprising administering to the subject a therapeutically effective amount of a compound of Formula I, or a pharmaceutically acceptable salt or stereoisomer thereof.

In another aspect, provided herein is a method of treating cancer in a subject in need thereof, comprising administering to the subject a therapeutically effective amount of a compound of Formula I, or a pharmaceutically acceptable salt or stereoisomer thereof.

In some embodiments, the cancer is bladder cancer, prostate cancer, breast cancer, cervical cancer, colorectal cancer, endometrial cancer, gastric cancer, glioblastoma, head and neck cancer, lung cancer, or non-small cell lung cancer. In some embodiments, the cancer is non-small cell lung cancer, prostate cancer, head and neck cancer, breast cancer, colorectal cancer, or glioblastoma.

In some embodiments, the cancer in the subject comprises an EGFR mutation. In some embodiments, the EGFR mutation comprises a substitution in exon 18, a deletion in exon 19, a substitution in exon 20, an insertion in exon 20, a mutation in the extracellular domain, or a substitution in exon 21. In some embodiments, the EGFR mutation is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR (or D770_N771insSVD EGFR), 770insNPG EGFR (or D770_N771insNPG EGFR), 770insGT EGFR, 770insGF EGFR, 770insG EGFR, 771insH EGFR, 771insN EGFR, 772insNP EGFR, 773insNPH EGFR (or H773insNPH EGFR), 773insH EGFR, 773insPH EGFR, EGFRvii, EGFRviii, A767_dupASV EGFR, 773insAH EGFR, M766_A767insAI EGFR, and any combination thereof. In some embodiments, the EGFR mutation is del19/T790M EGFR or L858R/T790M EGFR.

In another aspect, the present disclosure provides a method of treating an inflammatory disease in a subject in need thereof, comprising administering to the subject a therapeutically effective amount of a compound of Formula I, or a pharmaceutically acceptable salt or stereoisomer thereof.

In some embodiments, the inflammatory disease is psoriasis, eczema, or atherosclerosis.

In some embodiments, the inflammatory disease in the subject comprises an EGFR mutation. In some embodiments, the EGFR mutation comprises a substitution in exon 18, a deletion in exon 19, a substitution in exon 20, an insertion in exon 20, a mutation in the extracellular domain, or a substitution in exon 21. In some embodiments, the EGFR mutation is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR (or D770_N771insSVD EGFR), 770insNPG EGFR (or D770_N771insNPG EGFR), 770insGT EGFR, 770insGF EGFR, 770insG EGFR, 771insH EGFR, 771insN EGFR, 772insNP EGFR, 773insNPH EGFR (or H773insNPH EGFR), 773insH EGFR, 773insPH EGFR, EGFRvii, EGFRviii, A767_dupASV EGFR, 773insAH EGFR, M766_A767insAI EGFR, and any combination thereof. In some embodiments, the EGFR mutation is del19/T790M EGFR or L858R/T790M EGFR.

In another aspect the present disclosure provides a compound wherein the compound is:

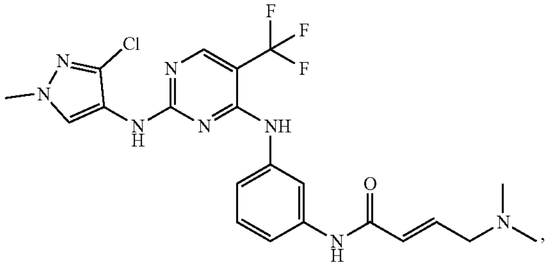

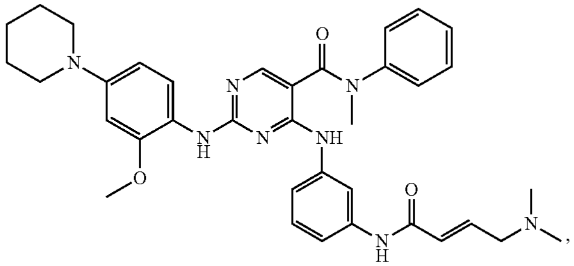

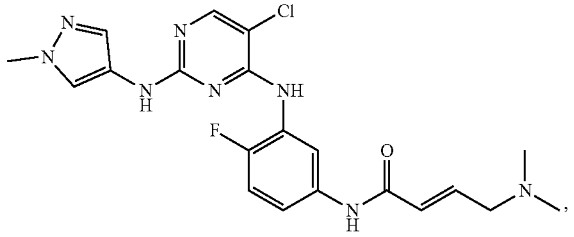

-continued

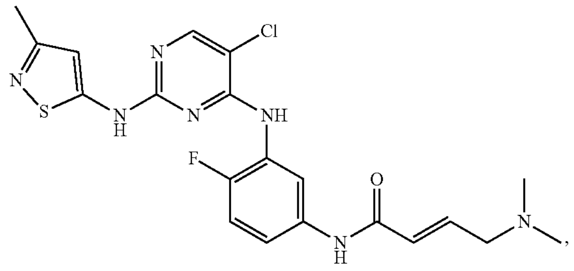

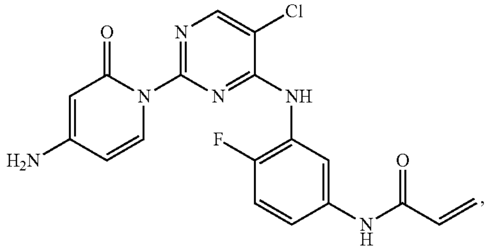

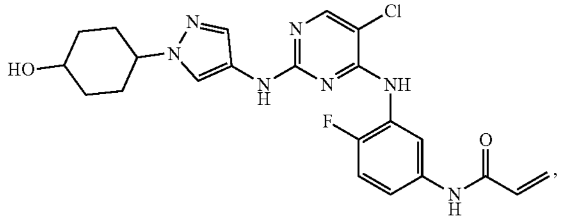

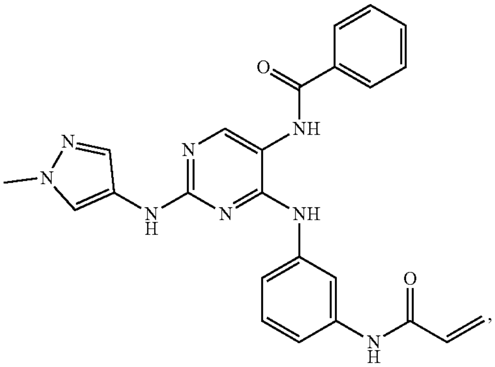

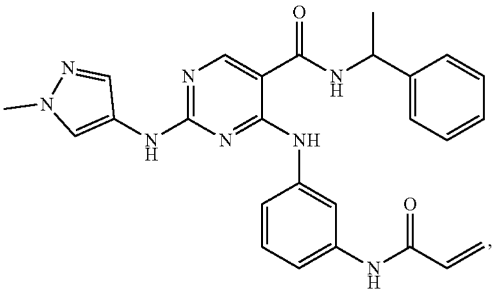

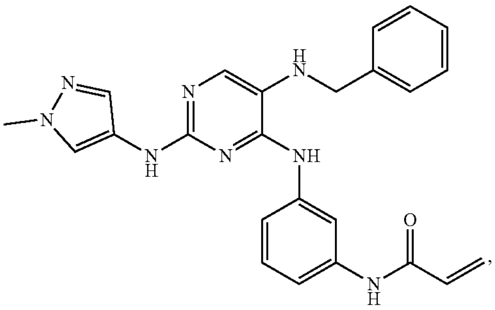

-continued
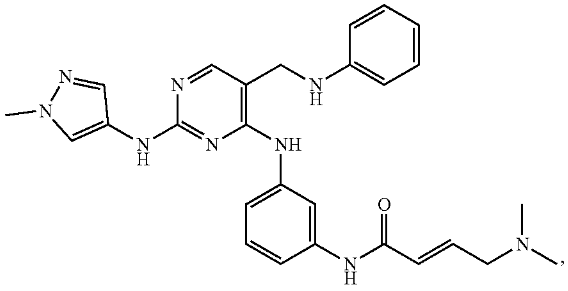
,
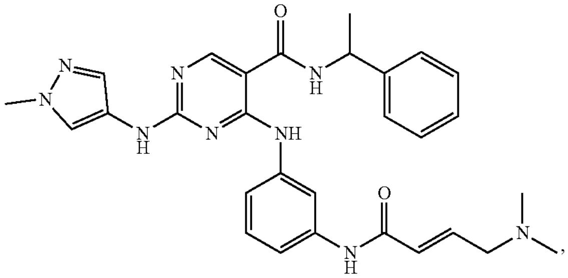
,
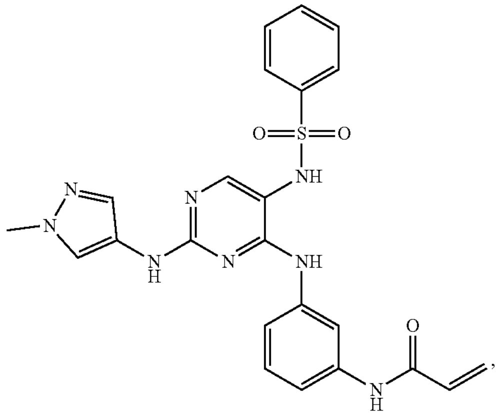
,
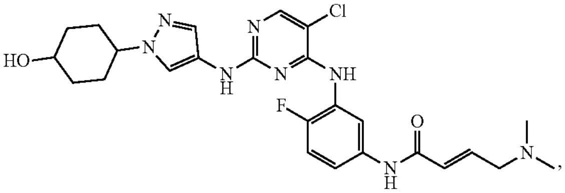
,
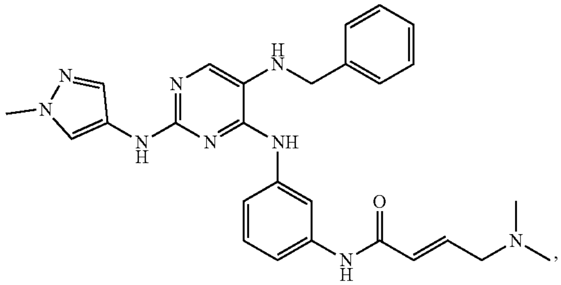
,
-continued
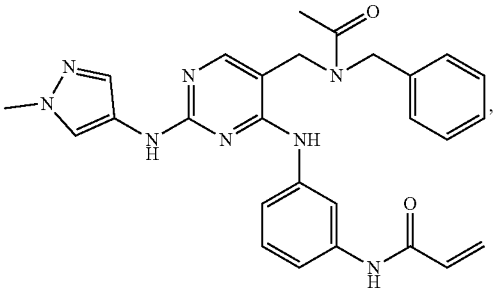
,
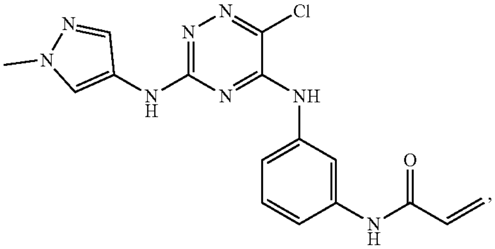
,
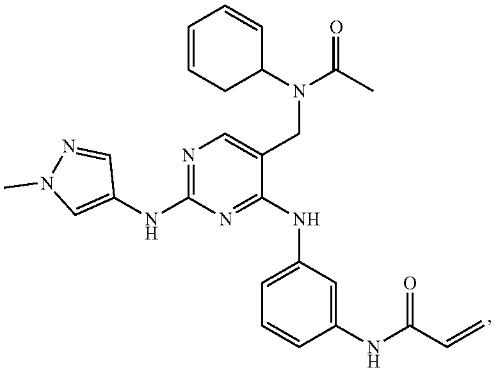
,
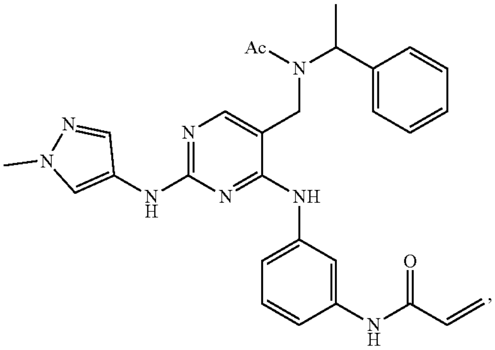
,
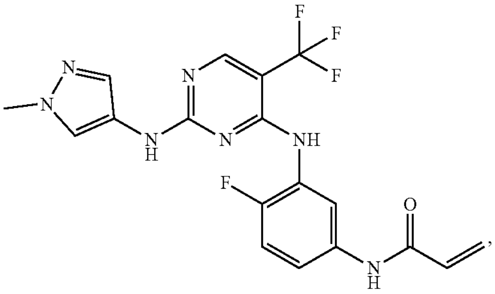
, -continued
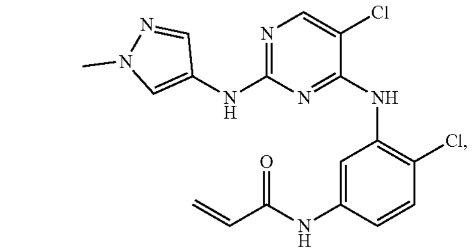
,
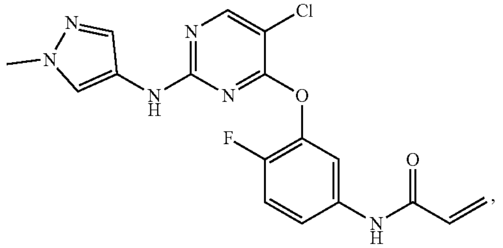
,
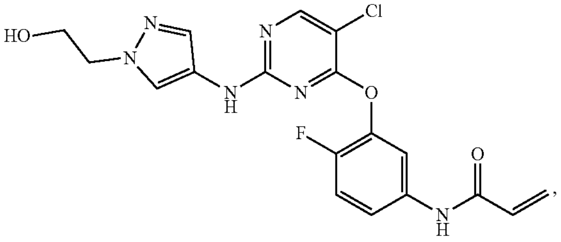
,
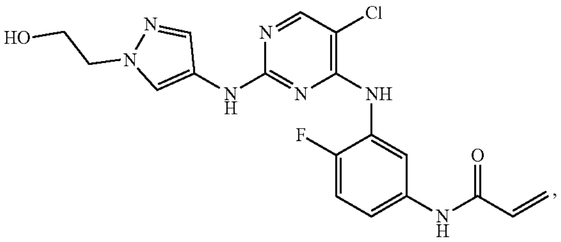
,
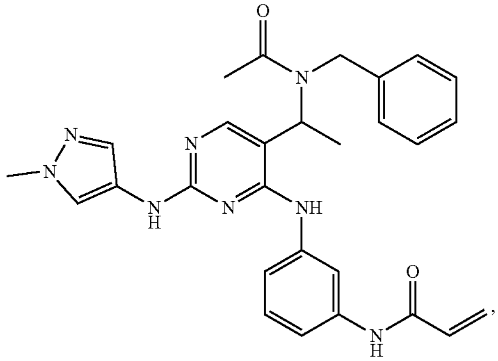
,
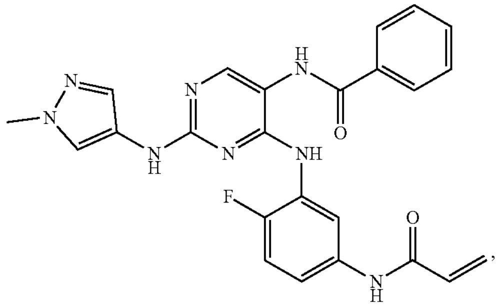
,
-continued
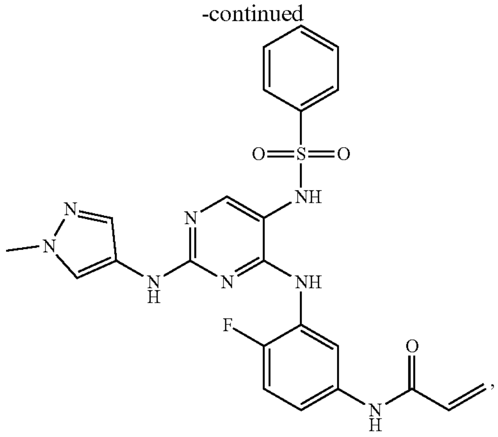
,
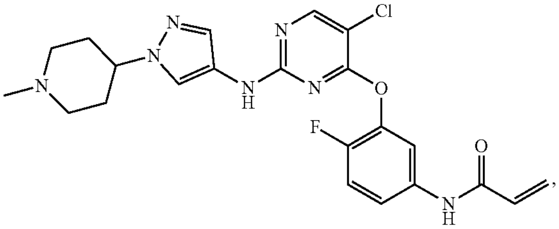
,
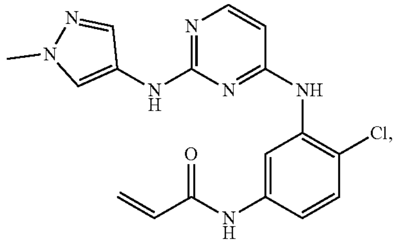
,
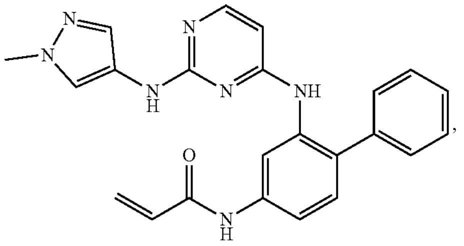
,
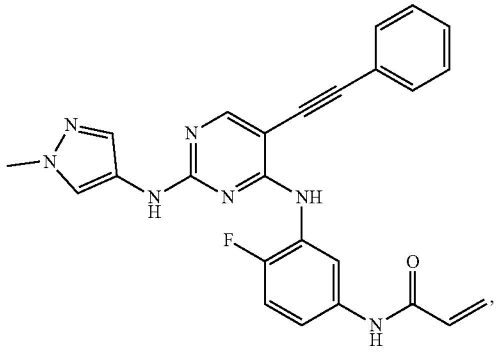
,
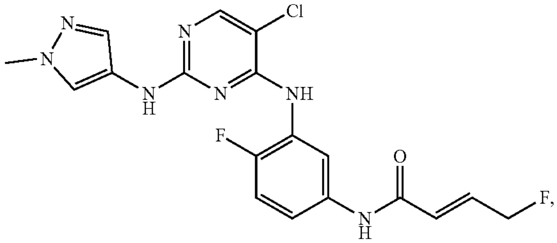
, -continued
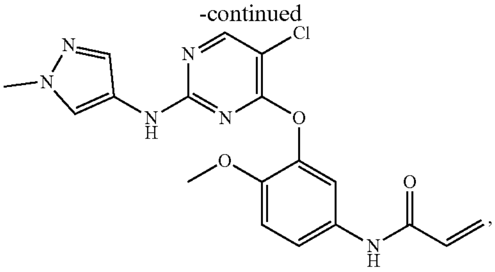
,
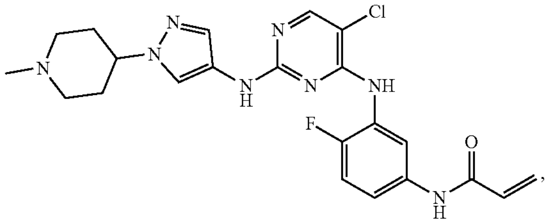
,
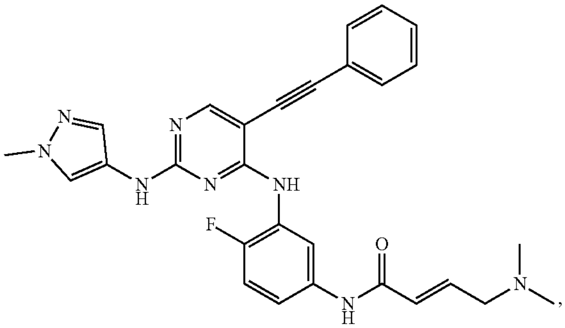
,
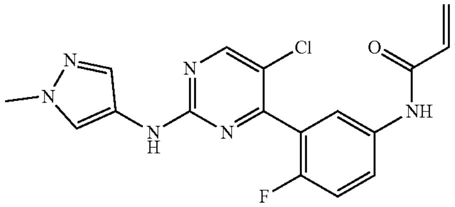
,
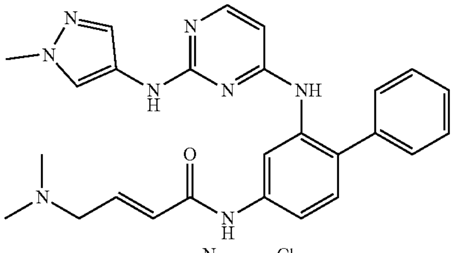
,
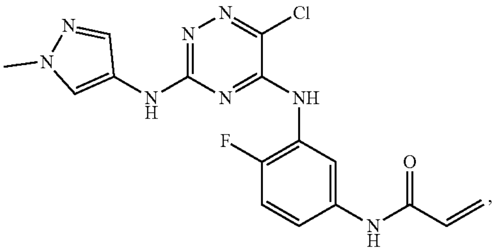
,
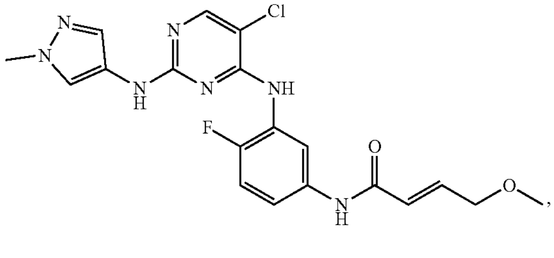
,
-continued
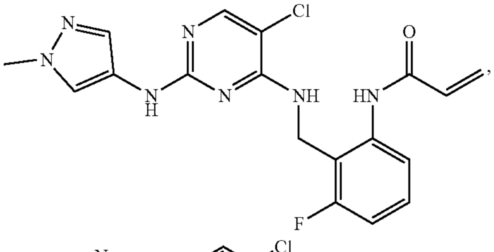
,
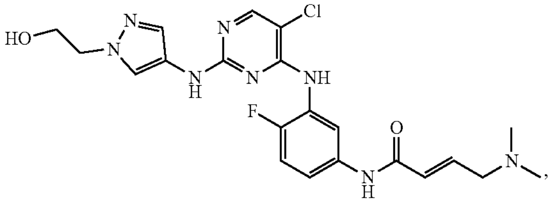
,
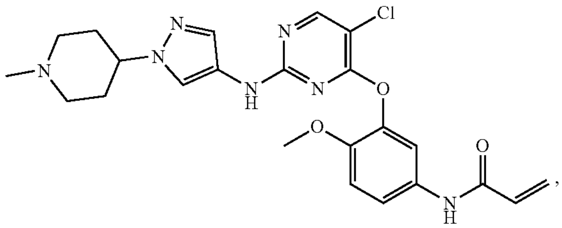
,
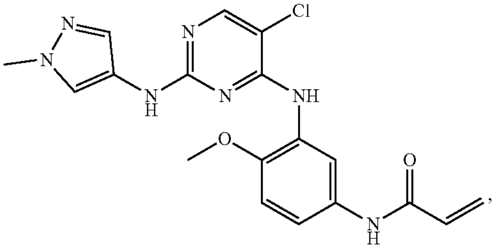
,
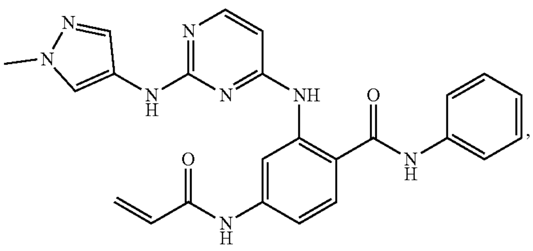
,
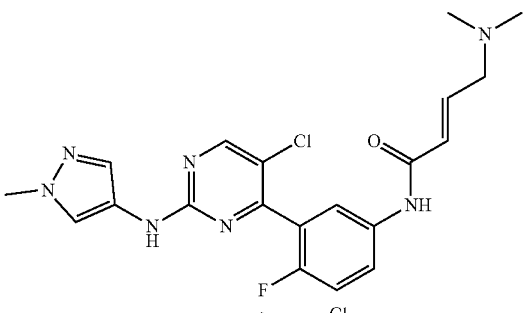
,
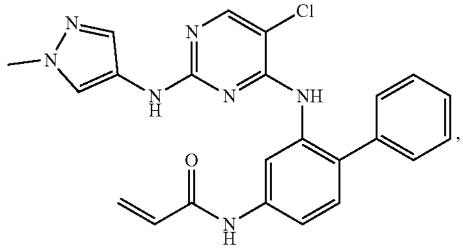
, -continued
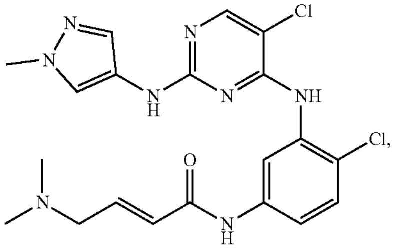
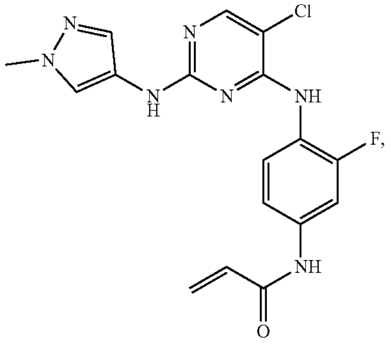
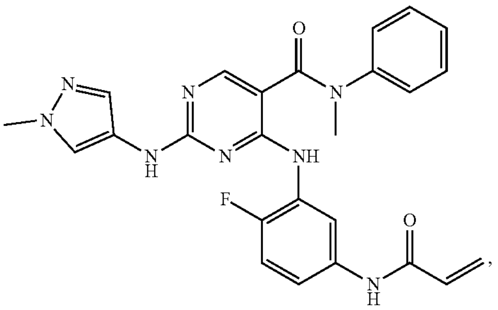
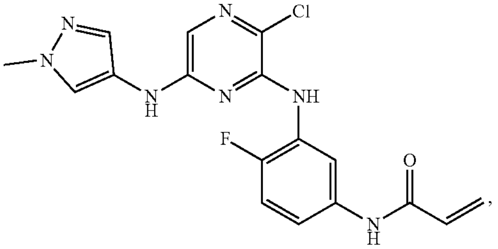
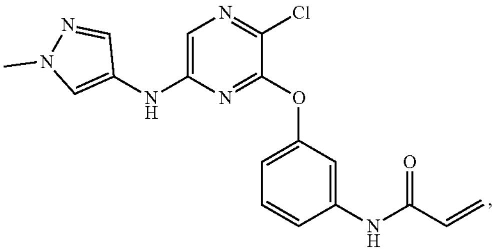
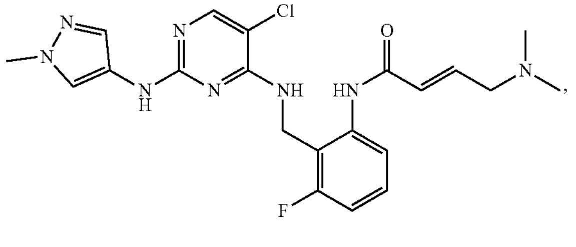
-continued
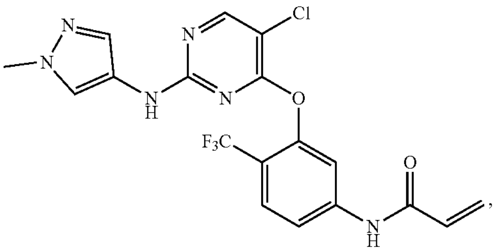
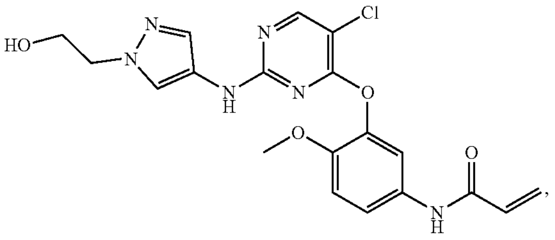
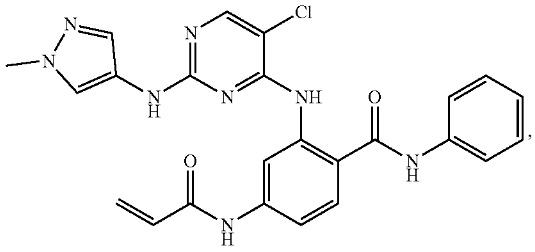
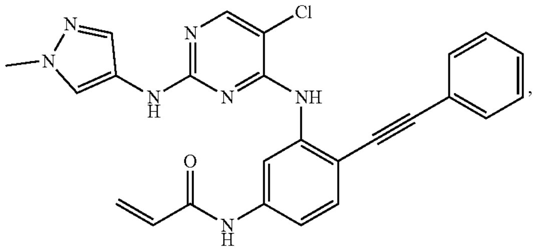
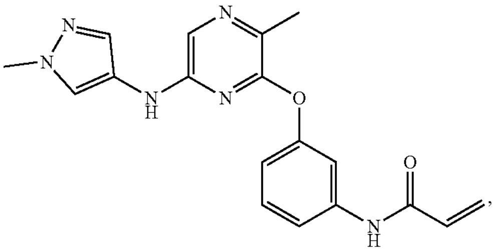
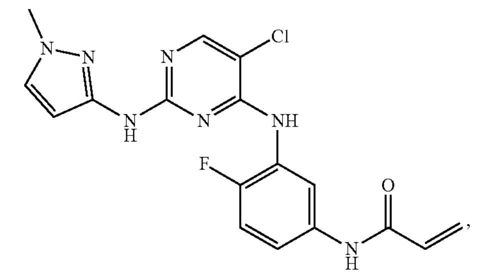

-continued
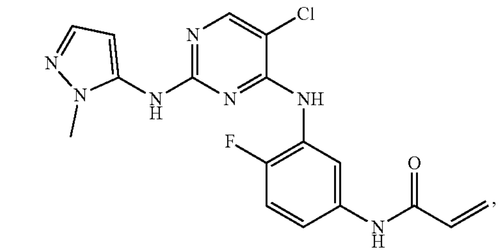
,
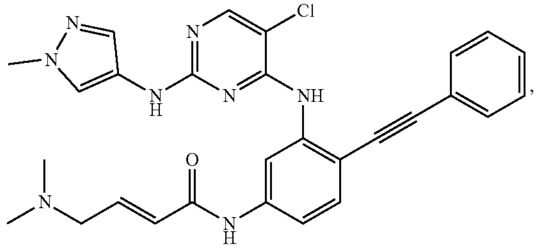
,
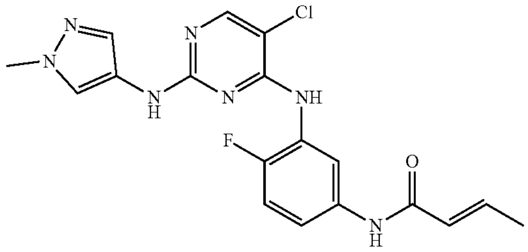
,
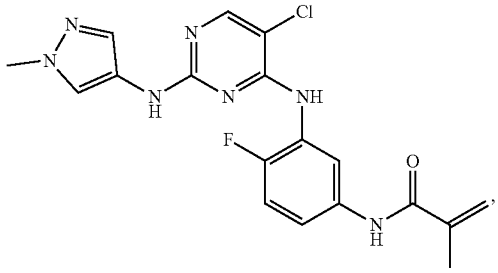
,
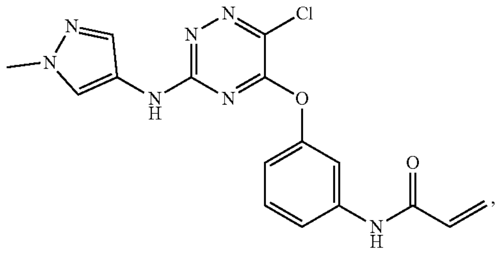
,
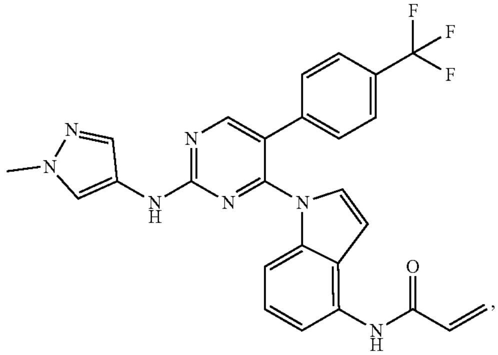
,
-continued
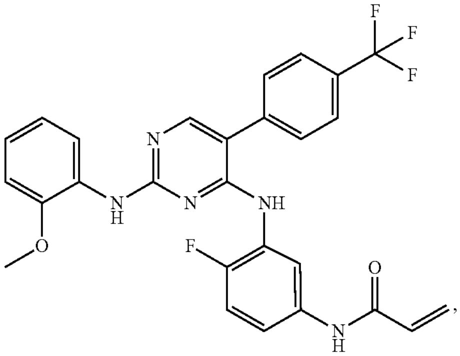
,
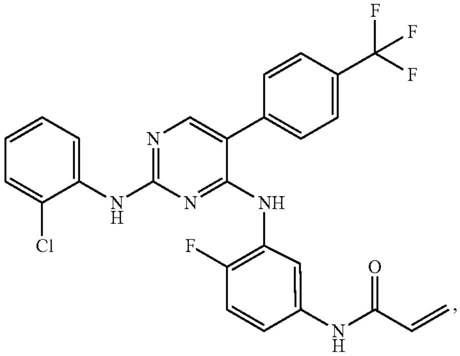
,
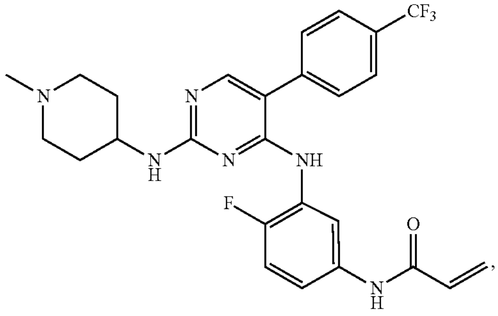
,
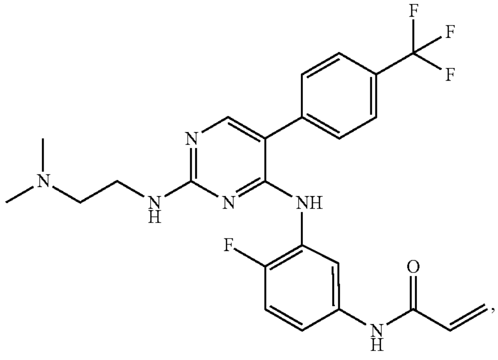 [SMILES: C=CC(=O)Nc1ccc(F)c(Nc2nc(NCCN(C)C)ncc2-c2ccc(C(F)(F)F)cc2)c1]
,
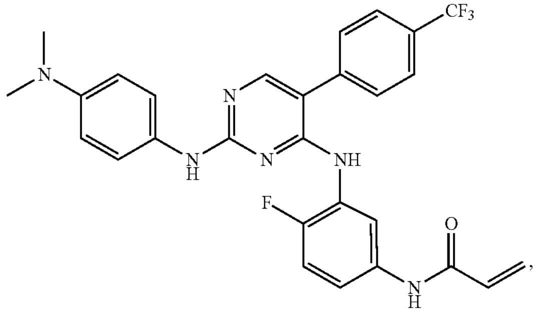
, -continued
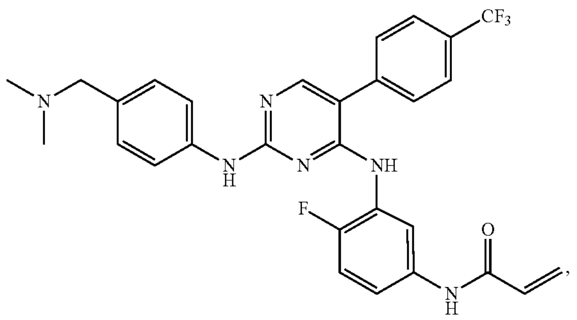
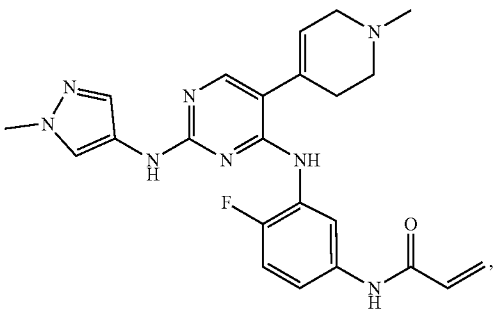
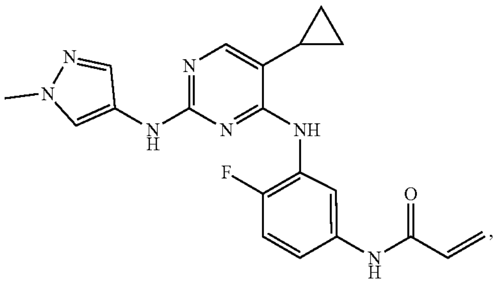
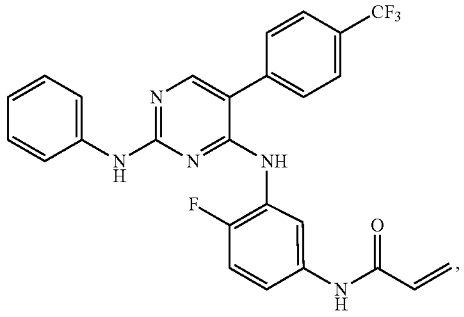
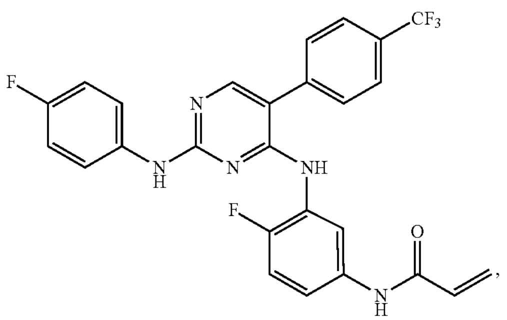
-continued
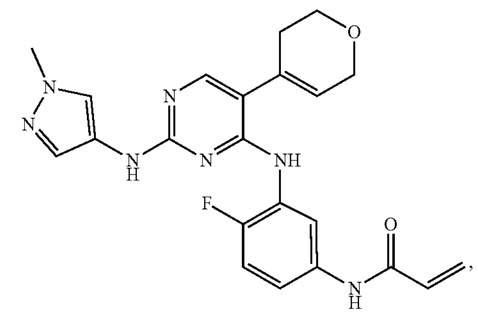
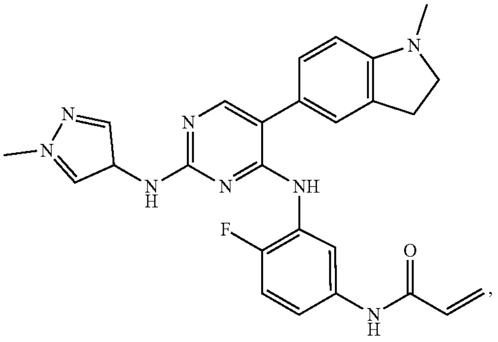
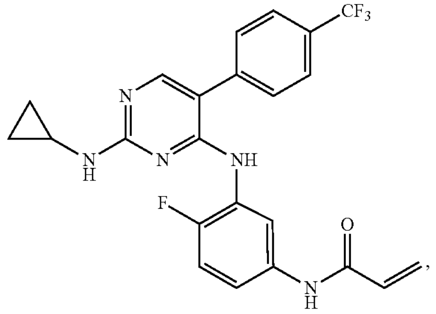
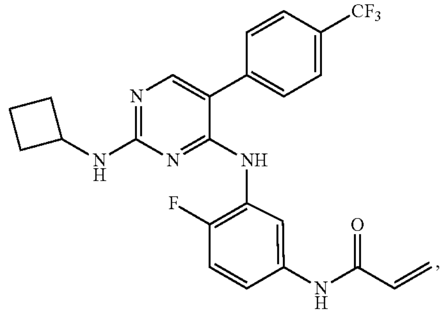
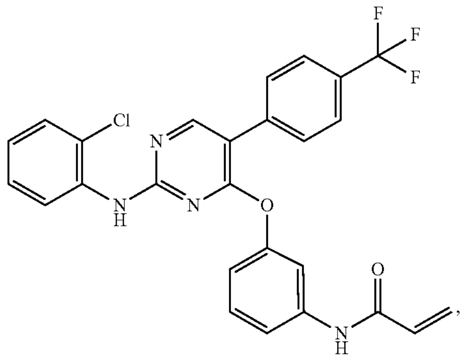

-continued
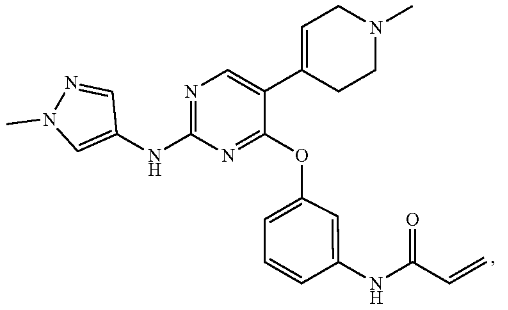
,
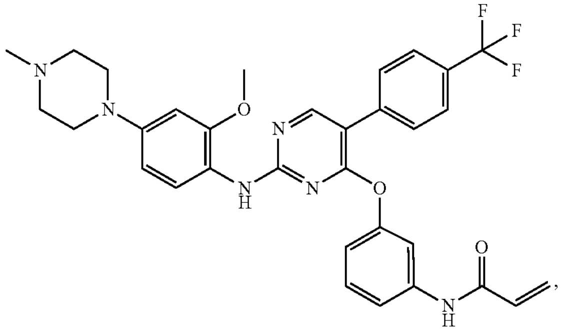
,
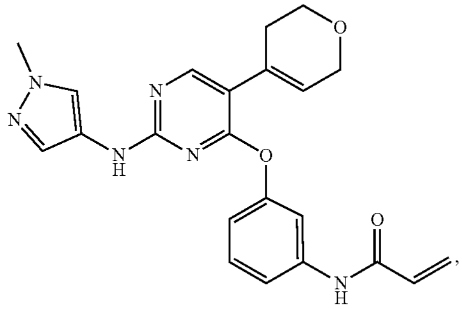
,
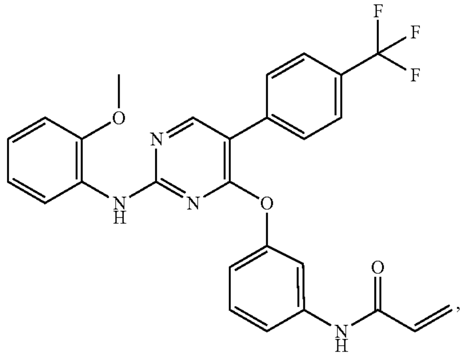
,
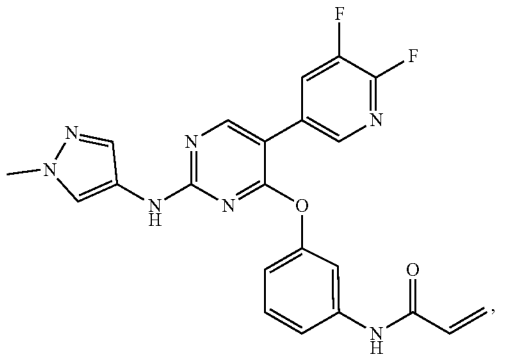
,
-continued
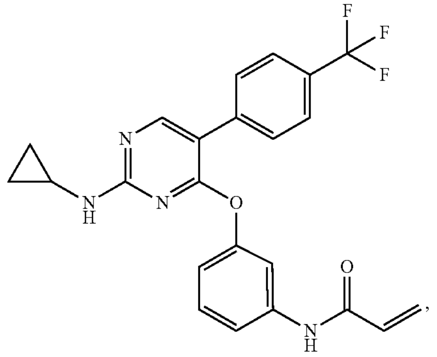
,
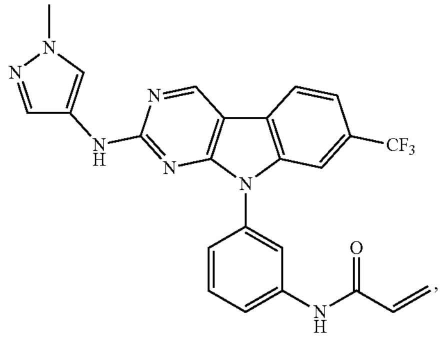
,
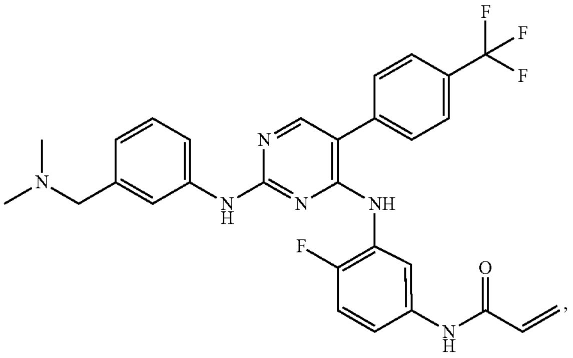
,
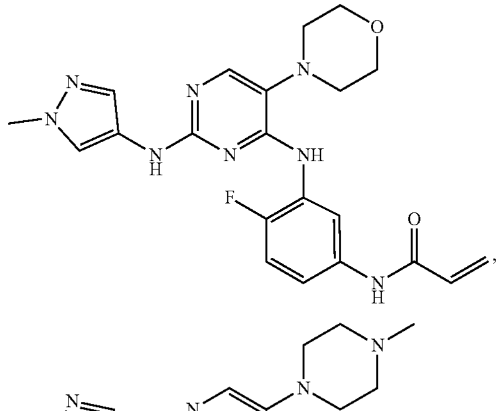
,
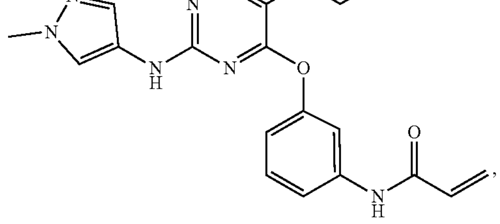
, -continued
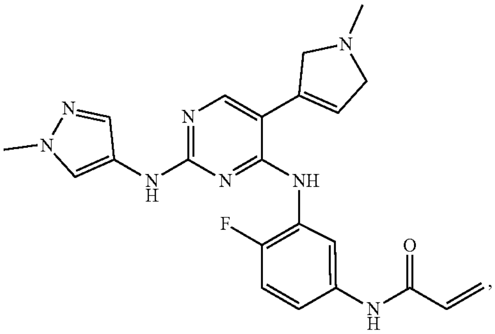
,
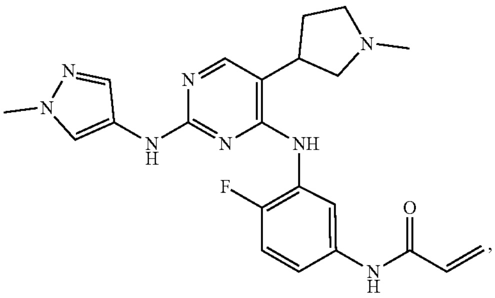
,
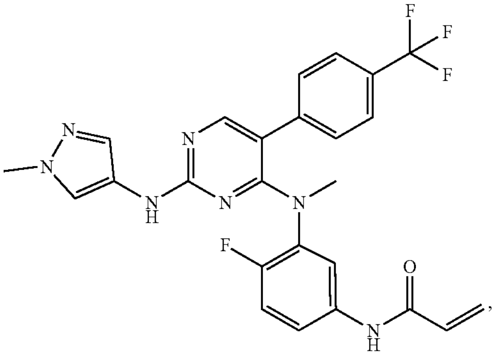
,
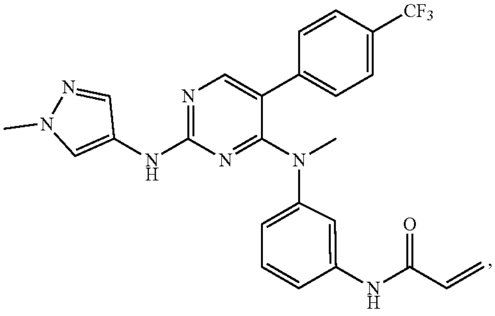
,
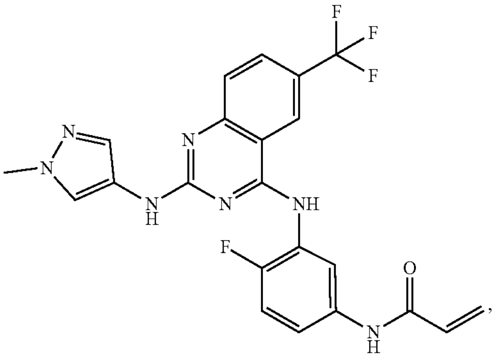
,
-continued
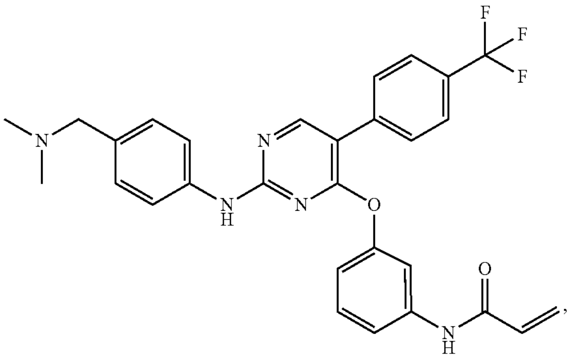
,
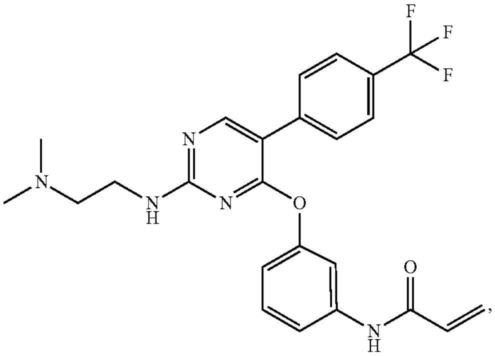
,
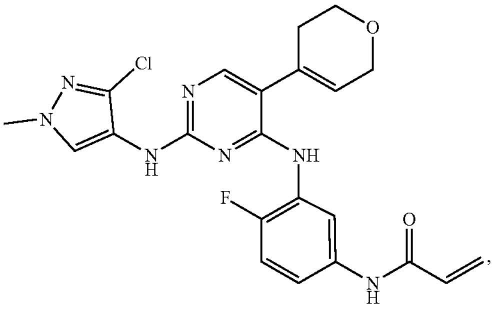
,
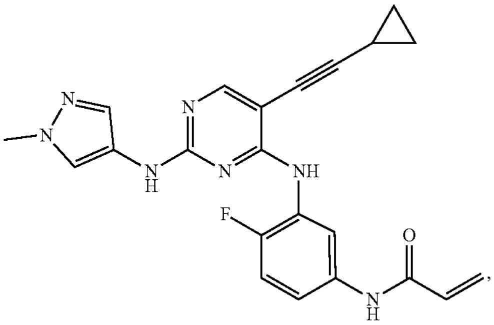
,
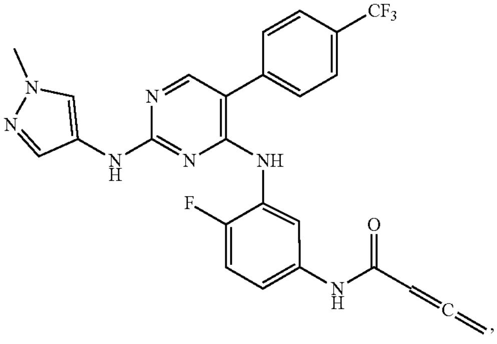
, -continued
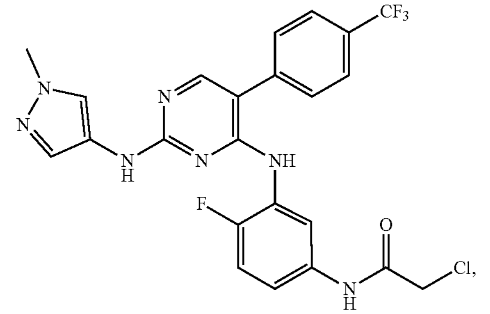
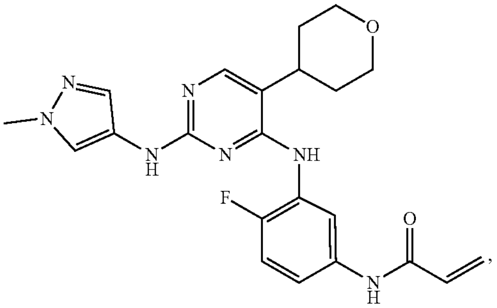
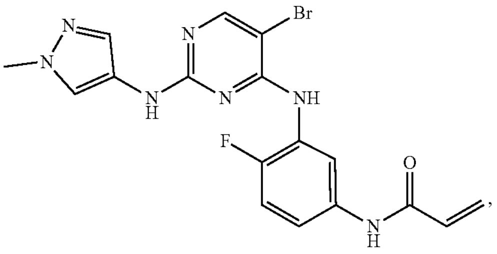
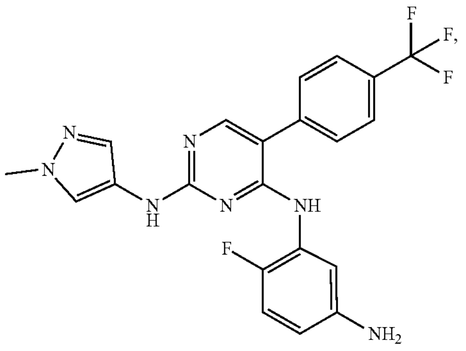
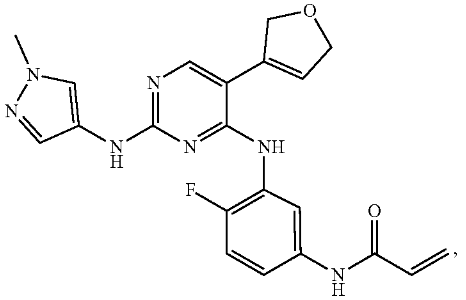
-continued
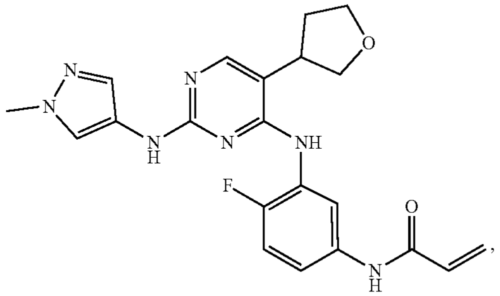
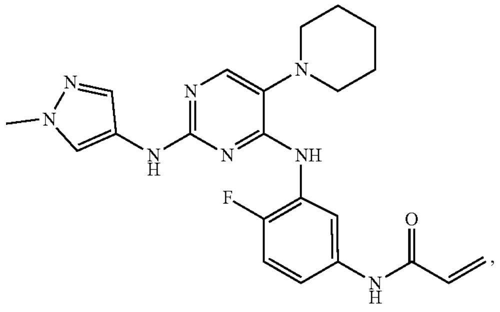
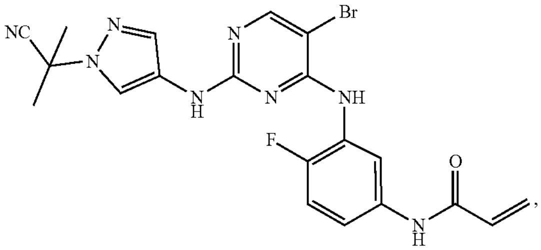
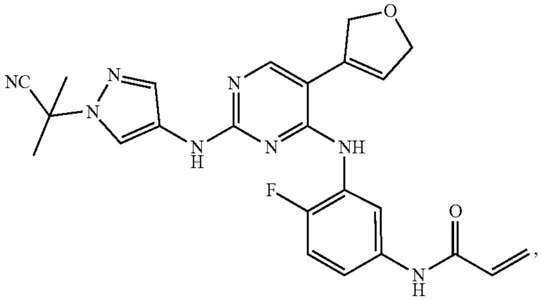
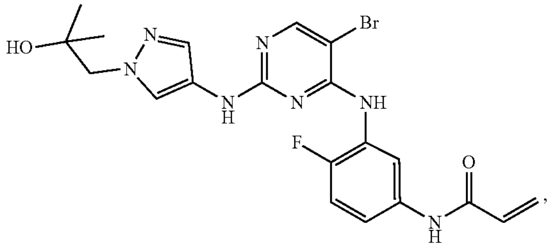
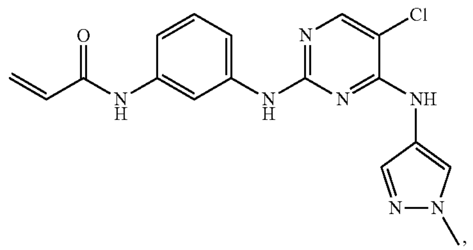 [SMILES: C=CC(=O)Nc1cccc(Nc2ncc(Cl)c(Nc3cnn(C)c3)n2)c1]

-continued

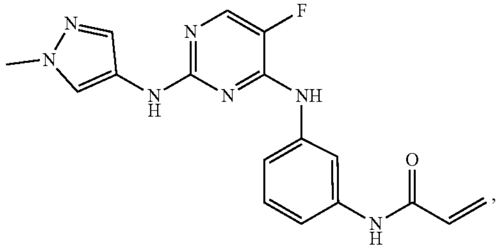,

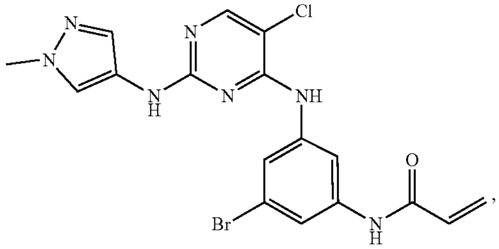,

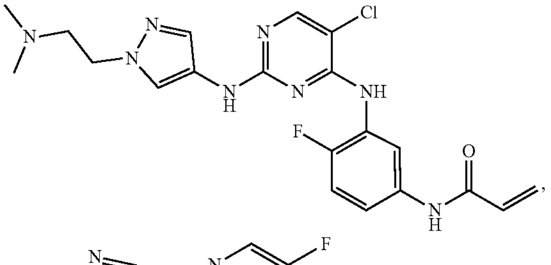,

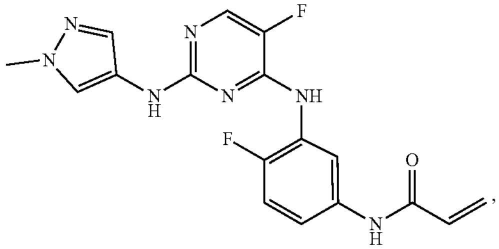,

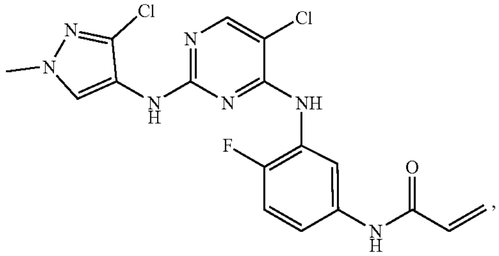,

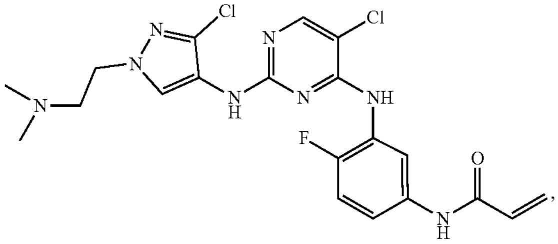,

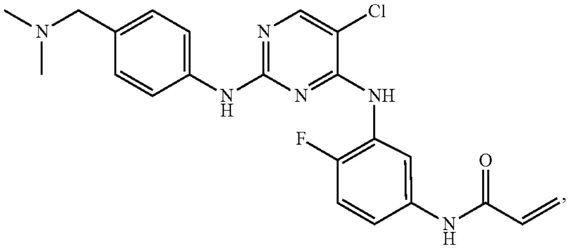,

-continued

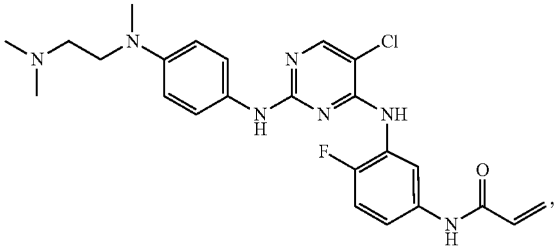,

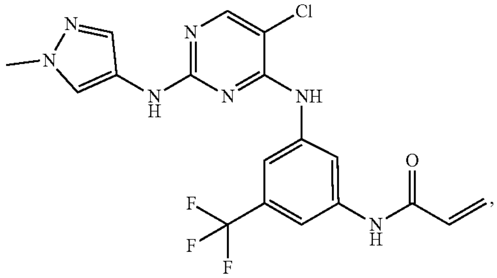,

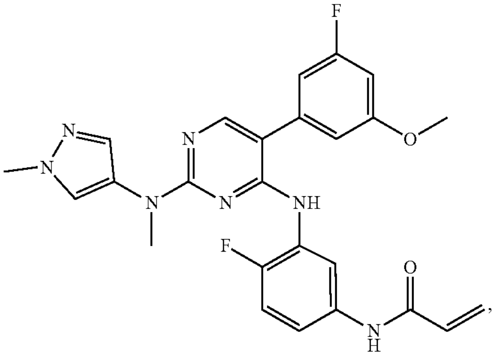, and

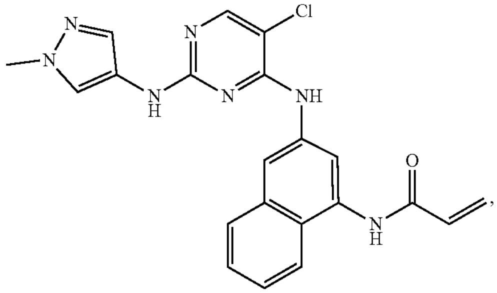, or a pharmaceutically acceptable salt or stereoisomer thereof.

The present disclosure discloses a process of preparation of compounds of Formula I, or its stereoisomers, tautomers, pharmaceutically acceptable salts, stereoisomers, solvates, and hydrates thereof, and to pharmaceutical compositions containing them.

The compounds of the present disclosure may be useful in the treatment, prevention or suppression of diseases and disorders mediated by epidermal growth factor receptor (EGFR).

These and other features, aspects, and advantages of the present disclosure will become better understood with reference to the following description. This statement is provided to introduce a selection of concepts in simplified form. This statement is not intended to identify key features or essential features of the subject matter, nor is it intended to be used to limit the scope of the subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DISCLOSURE

Definitions

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. In some embodiments, when the group in question is substituted with more than one substituent, the substituent is the same. In some embodiments, when the group in question is substituted with more than one substituent, the substituent is different. In some embodiments, the reference group is optionally substituted with one or more additional group(s) individually and independently selected from halogen, —CN, —$NH_2$, —NH(alkyl), —N$(alkyl)_2$, —OH, —$CO_2H$, —$CO_2$ alkyl, —C(═O)$NH_2$, —C(═O)NH(alkyl), —C(═O)N$(alkyl)_2$, —S$(=O)_2NH_2$, —S$(=O)_2$NH(alkyl), —S$(=O)_2$N$(alkyl)_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —$NH_2$, —NH($CH_3$), —N$(CH_3)_2$, —OH, —$CO_2H$, —$CO_2$($C_1$-$C_4$ alkyl), —C(═O)$NH_2$, —C(═O)NH($C_1$-$C_4$ alkyl), —C(═O)N($C_1$-$C_4$ alkyl)$_2$, —S$(=O)_2NH_2$, —S$(=O)_2$NH($C_1$-$C_4$ alkyl), —S$(=O)_2$N($C_1$-$C_4$ alkyl)$_2$, $C_1$-$C_4$ alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$ alkyl, —S(═O)$C_1$-$C_4$ alkyl, and —S$(=O)_2C_1$-$C_4$ alkyl. In some embodiments, optional substituents are independently selected from halogen, —CN, —$NH_2$, —OH, —NH($CH_3$), —N$(CH_3)_2$, —$CH_3$, —$CH_2CH_3$, —$CHF_2$, —$CF_3$, —$OCH_3$, —$OCHF_2$, and —$OCF_3$. In some embodiments, substituted groups are substituted with one or two of the preceding groups. In some embodiments, an optional substituent on an aliphatic carbon atom (acyclic or cyclic) includes oxo (═O)

As used herein, $C_1$-$C_x$ includes $C_1$-$C_2$, $C_1$-$C_3$ . . . $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl The term "alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "cycloalkyl" refers to unless otherwise mentioned, carbocyclic groups of from 3 to 6 carbon atoms having a single cyclic ring or multiple condensed rings or spirocyclic rings or bridged rings. This definition encompasses rings that are saturated or partially unsaturated.

Such cycloalkyl groups include, by way of example, single ring structures such as cyclopropyl, cyclobutyl, cyclopentyl, cyclopentenyl, cyclohexyl, cyclohexenyl, and the like.

"Halo" or "Halogen", alone or in combination with any other term means halogens such as chloro (Cl), fluoro (F), bromo (Br) and iodo (I).

The term "aryl" refers to a radical derived from a hydrocarbon ring system comprising hydrogen, 6 to 30 carbon atoms and at least one aromatic ring. This definition encompasses monocyclic, bicyclic, tricyclic or tetracyclic ring system, as well as fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

The term "phenyl" refers to an aromatic carbocyclic group of 6 carbon atoms having a single ring.

The term "phenyl alkyl" refers to a monoradical branched or unbranched saturated hydrocarbon chain having 1, 2, 3, 4, 5, or 6 carbon atoms substituted with an aromatic carbocyclic group of 6 carbon atoms having a single ring.

The term "heteroaryl" refers to an aromatic cyclic group having 5, or 6 carbon atoms and 1, 2, or 3 heteroatoms selected from oxygen, nitrogen and sulfur within at least one ring. An "X-linked heteroaryl" refers to a heteroaryl connected to the rest of the molecule via an X atom. For example,

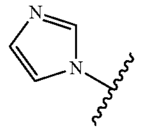 [SMILES: *n1ccnc1]

is an N-linked imidazolyl, while

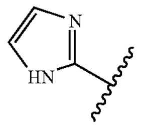 [SMILES: *c1ncc[nH]1]

is a C-linked imidazolyl.

The term "heterocycloalkyl" refers to a saturated, partially unsaturated, or unsaturated group having a single ring or multiple condensed rings or spirocyclic rings, or bridged rings unless otherwise mentioned, having from 2 to 10 carbon atoms and from 1 to 3 hetero atoms, selected from nitrogen, sulfur, phosphorus, and/or oxygen within the ring.

The term "alkenyl" refers to unsaturated aliphatic groups having at least one double bond.

The term "alkynyl" refers to unsaturated aliphatic groups having at least one triple bond.

The term "amino" refers to the —$NH_2$ radical.

The term "cyano" refers to the —CN radical.

The term "hydroxy" or "hydroxyl" refers to the —OH radical.

The term "heteroalkyl" refers to an alkyl radical as described above where one or more carbon atoms of the alkyl is replaced with an O, N or S atom. Unless stated otherwise specifically in the specification, the heteroalkyl group is optionally substituted as described below. Representative heteroalkyl groups include, but are not limited to $—OCH_2CH_2OMe$, $—OCH_2CH_2OCH_2CH_2NH_2$, and $—OCH_2CH_2OCH_2CH_2OCH_2CH_2N(Me)_2$.

A "hetercycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl is monocyclic or bicyclic. In some embodiments, a heterocycloalkyl is monocyclic and is a 3, 4, 5, 6, 7, or 8-membered ring. In some embodiments, a heterocycloalkyl is monocyclic and is a 3, 4, 5, or 6-membered ring. In some embodiments, a heterocycloalkyl is monocyclic and is a 3 or 4-membered ring. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "haloalkyl" refers to an alkyl radical as described above where one or more carbon atoms of the alkyl is replaced with a halogen atom. In some embodiments, the haloalkyl group is optionally substituted as described below. Representative haloalkyl groups include, but are not limited to, fluoromethyl, difluoromethyl, trifluoromethyl, difluoroethyl, and trifluoroethyl.

The term "aminoalkyl" refers to an alkyl group substituted with an amino (NH2) group. In some embodiments, the aminoalkyl group is unsubstituted or substituted with alkyl on the nitrogen atom.

The term "alkoxy" refers to the group R—O—, where R is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. In some embodiments, the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, the compounds described herein exist as isotopic variants. In some embodiments, an isotopic variant of a compound described herein has one or more hydrogen atoms replaced by deuterium.

In some embodiments, the compounds described herein contain one or more chiral centers and/or double bonds and therefore, exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. In some embodiments, enantiomeric and stereoisomeric mixtures are resolved into their component enantiomers or stereoisomers using separation techniques or chiral synthesis techniques well known to the person skilled in the art. In some embodiments, the compounds also exist in several tautomeric forms including the enol form, the keto form and mixtures thereof. Accordingly, the chemical structures depicted herein encompass all possible tautomeric forms of the illustrated or identified compounds.

In some embodiments, a compound disclosed herein is a free base, salt, hydrate, isomer, diastereomer, prodrug (e.g., ester), metabolite, ion pair complex, or chelate form. In some embodiments, compounds exist in unsolvated forms as well as solvated forms, including hydrated forms and as N-oxides. In some embodiments, compounds are hydrated, solvated or N-oxides. Also contemplated within the scope of the disclosure are congeners, analogs, hydrolysis products, metabolites and precursor or prodrugs of the compound. In general, unless otherwise indicated, all physical forms are equivalent for the uses contemplated herein and are intended to be within the scope of the present disclosure.

"Pharmaceutically acceptable salt" embraces salts with a pharmaceutically acceptable acid or base. Pharmaceutically acceptable acids include both inorganic acids, for example hydrochloric, sulfuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulfonic, ethanesulfonic, benzenesulfonic or p-toluenesulfonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines. In some embodiments, the compound is a pharmaceutically acceptable salt derived from acids including, but not limited to, the following: acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, or p-toluenesulfonic acid.

"Pharmaceutical composition" refers to one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition comprising a compound of the present disclosure and a pharmaceutically acceptable carrier.

"Carrier" refers to a diluent, adjuvant, excipient, or vehicle with which the therapeutic is administered. In some embodiments, such pharmaceutical carriers are sterile liquids, such as water and oils, including those of petroleum, animal, vegetable or synthetic origin, including but not limited to peanut oil, soybean oil, mineral oil, sesame oil and the like. In some embodiments, water is a carrier when the pharmaceutical composition is administered orally. In some embodiments, saline and aqueous dextrose are exemplary carriers when the pharmaceutical composition is administered intravenously. In some embodiments, saline solutions and aqueous dextrose and glycerol solutions are employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In some embodiments, the composition comprises minor amounts of wetting or emulsifying agents, or pH buffering agents. In some embodiments, these compositions take the form of solutions, suspensions, emulsions, tablets, pills, capsules, powders, sustained-release formulations and the like. In some embodiments, the composition is formulated as a suppository, with traditional binders and carriers such as triglycerides. In some embodiments, an oral formulation comprises carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, for example in purified form, together with a suitable amount of carrier so as to provide the form for proper administration to the patient. The formulation should suit the mode of administration.

"Combined" or "in combination" or "combination" should be understood as a functional coadministration, encompassing scenarios wherein compounds are administered separately, in different formulations, different modes of administration (for example subcutaneous, intravenous or oral) and different times of administration. In some embodiments, the individual compounds of such combinations are administered sequentially in separate pharmaceutical compositions. In some embodiments, the individual compounds of such combinations are administered simultaneously in combined pharmaceutical compositions.

Compounds

In one aspect, provided herein is a compound of Formula I:

Formula I

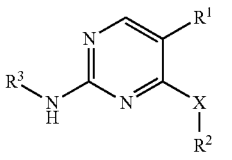

or a pharmaceutically acceptable salt or stereoisomer thereof, wherein:

X is —NH— or —O—;

$R^1$ is $—(C(R^4)_2)_nR^5$, wherein $R^5$ is substituted with 0 or 1 $R^{5'}$;

n is 0, 1, 2, or 3;

each $R^4$ is independently hydrogen, alkyl, halo, haloalkyl, hydroxy, alkoxy, or heteroalkyl; $R^5$ is $C_{4-10}$cycloalkyl, C-linked heterocycloalkyl, aryl, or heteroaryl;

each $R^{5'}$ is independently aryl, heteroaryl, alkyl, cycloalkyl, heterocycloalkyl, oxo, halo, heteroalkyl, haloalkyl, cyano, hydroxy, amino, $—NH_2$, $—NHR^6$, $—N(R^6)_2$, $—C(═O)NH_2$, $—C(═O)NR^6$, $—C(═O)N(R^6)_2$, $—NR^6C(═O)R^6$, $—NHC(═O)R^6$, $—S(═O)_2$ alkyl, $—S(═O)_2$aryl, $—S(═O)_2NH_2$, $—S(═O)_2NHR^6$, $—S(═O)_2N(R^6)_2$, $—S(═O)_2$heteroaryl, alkoxy, or haloalkoxy;

each $R^6$ is independently alkyl, cycloalkyl, aryl, or heteroaryl;

$R^2$ is aryl, heteroaryl, cycloalkyl, or heterocycloalkyl, wherein the aryl, heteroaryl, cycloalkyl, or heterocycloalkyl is substituted with at least one $R^7$ and 0, 1, or 2 $R^8$;

each $R^7$ is independently

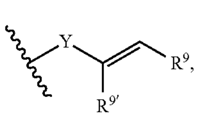,
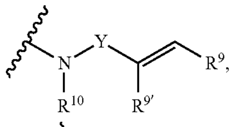,
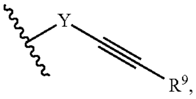
or
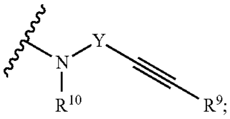;

Y is —C(═O)—, —S(═O)—, or $—S(═O)_2—$;

$R^9$ and $R^{9'}$ are independently hydrogen, halo, alkyl, haloalkyl, cycloalkyl, heteroalkyl, or (alkyl)heterocycloalkyl;

$R^{10}$ is hydrogen, alkyl, haloalkyl, or cycloalkyl;

each $R^8$ is independently aryl, heteroaryl, alkyl, cycloalkyl, heterocycloalkyl, halo, heteroalkyl, haloalkyl, cyano, hydroxy, amino, $—N(R^1)_2$, $—S(═O)_2$ alkyl, $—S(═O)_2$aryl, $—S(═O)_2$heteroaryl, or alkoxy;

each $R^{11}$ is independently alkyl, cycloalkyl, aryl, or heteroaryl;

$R^3$ is heteroaryl substituted with 0, 1, 2, or 3 $R^{12}$;

each $R^{12}$ is independently aryl, heteroaryl, alkyl, heteroalkyl, haloalkyl, halo, cyano, alkoxy, heterocycloalkyl, $—N(R^{13})_2$, $—S(═O)_2NH_2$, $—S(═O)_2$ alkyl, $—S(═O)_2$aryl, $—S(═O)_2$heteroaryl, or cycloalkyl, wherein the aryl, heteroaryl, heterocycloalkyl, or cycloalkyl are each independently substituted with 0, 1, or 2 $R^{14}$;

each $R^{13}$ is independently alkyl, cycloalkyl, aryl, or heteroaryl;

each $R^{14}$ is independently aryl, heteroaryl, alkyl, cycloalkyl, heterocycloalkyl, halo, heteroalkyl, haloalkyl, cyano, hydroxy, amino, $—N(R^{15})_2$, $—S(═O)_2$ alkyl, $—S(═O)_2$aryl, $—S(═O)_2$heteroaryl, or alkoxy; and each $R^{15}$ is independently alkyl, cycloalkyl, aryl, or heteroaryl;

provided that when X is —O—, $R^5$ is not C-linked heterocycloalkyl.

In one aspect, provided herein is a compound of Formula I:

Formula I

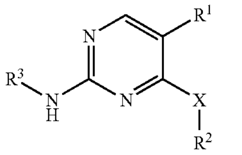

or a pharmaceutically acceptable salt or stereoisomer thereof, wherein:

X is —NH— or —O—;

$R^1$ is —$(C(R^4)_2)_n R^5$, wherein $R^5$ is unsubstituted or substituted with 1 $R^{5'}$;

n is 0, 1, 2, or 3;

each $R^4$ is independently hydrogen, alkyl, halo, haloalkyl, hydroxy, alkoxy, or heteroalkyl;

$R^5$ is $C_{4-10}$cycloalkyl, aryl, or heteroaryl;

each $R^{5'}$ is independently deuterium, aryl, heteroaryl, alkyl, $C_3$-$C_6$ cycloalkyl, 3-8 membered heterocycloalkyl, oxo, halo, heteroalkyl, haloalkyl, cyano, hydroxy, amino, —$NH_2$, —$NHR^6$, —$N(CH_3)R_6$, —$N(R^6)_2$, —C(═O)$NH_2$, —C(═O)$NHR^6$, —C(═O)$N(R^6)_2$, —$NR^6$C(═O)$R^6$, —NHC(═O)$R^6$, —S(═O)$_2$ alkyl, —S(═O)$_2$aryl, —S(═O)$_2NH_2$, —S(═O)$_2NHR^6$, —S(═O)$_2$ $N(R^6)_2$, —S(═O)$_2$heteroaryl, alkoxy, or haloalkoxy;

each $R^6$ is independently alkyl, aminoalkyl, cycloalkyl, aryl, or heteroaryl;

$R^2$ is aryl, heteroaryl, cycloalkyl, or heterocycloalkyl, wherein the aryl, heteroaryl, cycloalkyl, or heterocycloalkyl is substituted with at least one $R^7$ and 0, 1, or 2 $R^8$;

each $R^7$ is independently

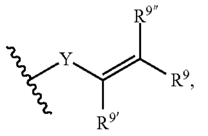
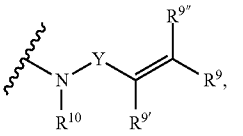
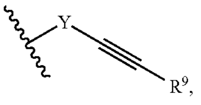
or
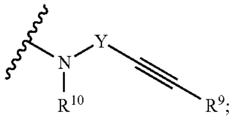

Y is —C(═O)—, —S(═O)—, or —S(═O)$_2$—;

$R^9$, $R^{9'}$, and $R^{9''}$ are independently hydrogen, deuterium, halo, alkyl, haloalkyl, cycloalkyl, heteroalkyl, or (alkyl)heterocycloalkyl;

$R^{10}$ is hydrogen, alkyl, haloalkyl, or cycloalkyl;

each $R^8$ is independently aryl, heteroaryl, alkyl, cycloalkyl, heterocycloalkyl, halo, heteroalkyl, haloalkyl, cyano, hydroxy, amino, —$N(R^{11})_2$, —S(═O)$_2$ alkyl, —S(═O)$_2$aryl, —S(═O)$_2$heteroaryl, or alkoxy;

each $R^{11}$ is independently alkyl, cycloalkyl, aryl, or heteroaryl;

$R^3$ is heteroaryl substituted with 0, 1, 2, or 3 $R^{12}$;

each $R^{12}$ is independently aryl, heteroaryl, alkyl, heteroalkyl, haloalkyl, halo, cyano, alkoxy, heterocycloalkyl, —$N(R^{13})_2$, —S(═O)$_2NH_2$, —S(═O)$_2$ alkyl, —S(═O)$_2$aryl, —S(═O)$_2$heteroaryl, or cycloalkyl, wherein the aryl, heteroaryl, heterocycloalkyl, or cycloalkyl are each independently unsubstituted or substituted with 0, 1, or 2 $R^{14}$;

each $R^{13}$ is independently hydrogen, alkyl, cycloalkyl, aryl, or heteroaryl;

each $R^{14}$ is independently deuterium, aryl, heteroaryl, alkyl, cycloalkyl, heterocycloalkyl, halo, heteroalkyl, haloalkyl, cyano, hydroxy, amino, —$N(R^{15})_2$, —S(═O)$_2$ alkyl, —S(═O)$_2$aryl, —S(═O)$_2$heteroaryl, or alkoxy; and each $R^{15}$ is independently alkyl, cycloalkyl, aryl, or heteroaryl.

For any and all of the embodiments, substituents are selected from among a subset of the listed alternatives. For example, in some embodiments, X is —NH—. In some embodiments, X is —O—.

In some embodiments, n is 0, 1, 2, or 3. In some embodiments, n is 0, 1, or 2. In some embodiments, n is 0, 1, or 3. In some embodiments, n is 0, 2, or 3. In some embodiments, n is 1, 2, or 3. In some embodiments, n is 0 or 1. In some embodiments, n is 1 or 2. In some embodiments, n is 2 or 3. In some embodiments, n is 0 or 2. In some embodiments, n is 0 or 3.

In some embodiments, n is 1 or 3. In some embodiments, n is 0. In some embodiments, n is 1. In some embodiments, n is 2. In some embodiments, n is 3.

In some embodiments, $R^5$ is phenyl, naphthyl, anthracenyl, phenanthrenyl, chrysenyl, pyrenyl, C-linked pyridyl, C-linked pyrimidinyl, C-linked pyrazolyl, C-linked imidazolyl, or C-linked indolyl; wherein $R^5$ is substituted with 0 or 1 $R^{5'}$. In some embodiments, $R^5$ is phenyl, naphthyl, anthracenyl, phenanthrenyl, C-linked pyridyl, C-linked pyrimidinyl, C-linked pyrazolyl, or C-linked imidazolyl; wherein $R^5$ is substituted with 0 or 1 $R^{5'}$. In some embodiments, $R^5$ is phenyl; wherein the phenyl is substituted with 0 or 1 $R^{5'}$. In some embodiments, $R^5$ is naphthyl; wherein the naphthyl is substituted with 0 or 1 $R^{5'}$. In some embodiments, $R^5$ is anthracenyl; wherein the anthracenyl is substituted with 0 or 1 $R^{5'}$. In some embodiments, $R^5$ is phenanthrenyl; wherein the phenanthrenyl is substituted with 0 or 1 $R^{5'}$. In some embodiments, $R^5$ is chrysenyl; wherein the chrysenyl is substituted with 0 or 1 $R^{5'}$. In some embodiments, $R^5$ is pyrenyl; wherein the pyrenyl is substituted with 0 or 1 $R^{5'}$. In some embodiments, $R^5$ is C-linked pyridyl; wherein the C-linked pyridyl is substituted with 0 or 1 $R^{5'}$. In some embodiments, $R^5$ is C-linked pyrimidinyl; wherein the C-linked pyrimidinyl is substituted with 0 or 1 $R^{5'}$. In some embodiments, $R^5$ is C-linked pyrazolyl; wherein the C-linked pyrazolyl is substituted with 0 or 1 $R^{5'}$. In some embodiments, $R^5$ is C-linked imidazolyl; wherein the C-linked imidazolyl is substituted with 0 or 1 $R^{5'}$. In some embodiments, $R^5$ is C-linked indolyl; wherein the C-linked indolyl is substituted with 0 or 1 $R^{5'}$.

In some embodiments, $R^5$ is substituted with 0 or 1 $R^{5'}$. In some embodiments, $R^5$ is unsubstituted. In some embodiments, $R^5$ is substituted with 1 $R^{5'}$.

In some embodiments, each $R^4$ is independently hydrogen, alkyl, halo, haloalkyl, hydroxy, alkoxy, or heteroalkyl. In some embodiments, each $R^4$ is independently hydrogen, alkyl, halo, haloalkyl, or alkoxy. In some embodiments, each $R^4$ is independently hydrogen, methyl, ethyl, n-propyl, isopropyl, n-butyl, iso-butyl, sec-butyl, tert-butyl, fluoro, chloro, trifluoromethyl, trifluoroethyl, pentafluoroethyl, methoxy, ethoxy, or trifluoromethoxy. In some embodiments, each $R^4$ is independently hydrogen, methyl, fluoro, trifluoromethyl, methoxy, or trifluoromethoxy. In some embodiments, each $R^4$ is hydrogen. In some embodiments, each $R^4$ is independently alkyl. In some embodiments, each $R^4$ is independently halo. In some embodiments, each $R^4$ is independently haloalkyl. In some embodiments, each $R^4$ is hydroxy. In some embodiments, each $R^4$ is independently alkoxy. In some embodiments, each $R^4$ is independently heteroalkyl. In some embodiments, each $R^4$ is methyl. In some embodiments, each $R^4$ is ethyl. In some embodiments, each $R^4$ is n-propyl. In some embodiments, each $R^4$ is iso-propyl. In some embodiments, each $R^4$ is n-butyl. In some embodiments, each $R^4$ is iso-butyl. In some embodiments, each $R^4$ is sec-butyl. In some embodiments, each $R^4$ is tert-butyl. In some embodiments, each $R^4$ is fluoro. In some embodiments, each $R^4$ is chloro. In some embodiments, each $R^4$ is trifluoromethyl. In some embodiments, each $R^4$ is trifluoroethyl. In some embodiments, each $R^4$ is pentafluoroethyl. In some embodiments, each $R^4$ is methoxy. In some embodiments, each $R^4$ is ethoxy. In some embodiments, each $R^4$ is trifluoromethoxy.

In some embodiments, each $R^{5'}$ is independently alkyl, haloalkyl, heterocycloalkyl, halo, cyano, hydroxy, —$N(R^6)_2$, —C(═O)$NHR^6$, —NHC(═O)$R^6$, —S(═O)$_2NH_2$, alkoxy, or haloalkoxy. In some embodiments, each $R^{5'}$ is independently aryl, heteroaryl, alkyl, cycloalkyl, heterocycloalkyl, halo, heteroalkyl, haloalkyl, cyano, hydroxy, amino, —$N(R^6)_2$, —S(═O)$_2$ alkyl, —S(═O)$_2$aryl, —S(═O)$_2$heteroaryl, or alkoxy. In some embodiments, each $R^{5'}$ is independently aryl, heteroaryl, alkyl, heterocycloalkyl, halo, cyano, hydroxy, —$N(R^6)_2$, or alkoxy. In some embodiments, each $R^{5'}$ is independently aryl. In some embodiments, each $R^{5'}$ is independently heteroaryl. In some embodiments, each $R^{5'}$ is independently alkyl. In some embodiments, each $R^{5'}$ is independently cycloalkyl. In some embodiments, each $R^{5'}$ is independently heterocycloalkyl. In some embodiments, each $R^{5'}$ is independently halo. In some embodiments, each $R^{5'}$ is independently heteroalkyl. In some embodiments, each $R^{5'}$ is independently haloalkyl. In some embodiments, each $R^{5'}$ is cyano. In some embodiments, each $R^{5'}$ is hydroxy. In some embodiments, each $R^{5'}$ is amino. In some embodiments, each $R^{5'}$ is independently —$N(R^6)_2$. In some embodiments, each $R^{5'}$ is independently —S(═O)$_2$ alkyl. In some embodiments, each $R^{5'}$ is independently —S(═O)$_2$aryl. In some embodiments, each $R^{5'}$ is independently-S(═O)$_2$heteroaryl. In some embodiments, each $R^{5'}$ is independently alkoxy. In some embodiments, each $R^{5'}$ is independently phenyl, naphthyl, anthracenyl, phenanthrenyl, chrysenyl, pyrenyl, pyrrolyl, imidazolyl, pyrazolyl, triazolyl, tetrazolyl, indolyl, indazolyl, benzimidazolyl, azaindolyl, thiazolyl, isothiazolyl, oxazolyl, isoxazolyl, pyridinyl, pyrimidinyl, pyridazinyl, pyrazinyl, triazinyl, quinolinyl, isoquinolinyl, quinoxalinyl, quinazolinyl, cinnolinyl, naphthyridinyl, methyl, ethyl, n-propyl, iso-propyl, n-butyl, iso-butyl, sec-butyl, tert-butyl, azetidinyl, oxetanyl, pyrrolidinyl, imidazolidinyl, tetrahydrofuranyl, piperidinyl, piperazinyl, tetrahydropyranyl, morpholinyl, fluoro, chloro, cyano, hydroxy, —$N(R^6)_2$, methoxy, ethoxy, or trifluoromethoxy. In some embodiments, each $R^{5'}$ is independently phenyl, pyrrolyl, imidazolyl, thiazolyl, isothiazolyl, oxazolyl, isoxazolyl, pyridinyl, pyrimidinyl, methyl, ethyl, tert-butyl, pyrrolidinyl, piperidinyl, piperazinyl, morpholinyl, fluoro, chloro, cyano, hydroxy, —$N(R^6)_2$, methoxy, ethoxy, or trifluoromethoxy. In some embodiments, each $R^{5'}$ is independently methyl, ethyl, tert-butyl, pyrrolidinyl, piperidinyl, piperazinyl, morpholinyl, fluoro, chloro, cyano, hydroxy, —$N(R^6)_2$, —C(═O)$NR^6$, —NHC(═O)$R^6$, —S(═O)$_2NH_2$, methoxy, ethoxy, fluoromethyl, difluoromethyl, trifluoromethyl, fluoromethoxy, difluoromethoxy, or trifluoromethoxy. In some embodiments, each $R^{5'}$ is independently methyl, morpholinyl, fluoro, chloro, cyano, —C(═O)NHMe, —NHC(═O)Me, —S(═O)$_2NH_2$, methoxy, fluoromethyl, difluoromethyl, trifluoromethyl, difluoromethoxy, or trifluoromethoxy. In some embodiments, each $R^{5'}$ is independently phenyl, imidazolyl, pyridinyl, methyl, tert-butyl, pyrrolidinyl, morpholinyl, fluoro, cyano, hydroxy, —$N(R^6)_2$, or methoxy. In some embodiments, each $R^{5'}$ is phenyl. In some embodiments, each $R^{5'}$ is naphthyl. In some embodiments, each $R^{5'}$ is anthracenyl. In some embodiments, each $R^{5'}$ is phenanthrenyl. In some embodiments, each $R^{5'}$ is chrysenyl. In some embodiments, each $R^{5'}$ is pyrenyl. In some embodiments, each $R^{5'}$ is pyrrolyl. In some embodiments, each $R^{5'}$ is imidazolyl. In some embodiments, each $R^{5'}$ is pyrazolyl. In some embodiments, each $R^{5'}$ is triazolyl. In some embodiments, each $R^{5'}$ is tetrazolyl. In some embodiments, each $R^{5'}$ is indolyl. In some embodiments, each $R^{5'}$ is indazolyl. In some embodiments, each $R^{5'}$ is benzimidazolyl. In some embodiments, each $R^{5'}$ is azaindolyl. In some embodiments, each $R^{5'}$ is thiazolyl. In some embodiments, each $R^{5'}$ is isothiazolyl. In some embodiments, each $R^{5'}$ is oxazolyl. In some embodiments, each $R^{5'}$ is isoxazolyl. In some embodiments, each $R^{5'}$ is pyridinyl. In some embodiments, each $R^{5'}$ is pyrimidinyl. In some embodiments, each $R^{5'}$ is pyridazinyl. In some embodiments, each $R^{5'}$ is pyrazinyl. In some embodiments, each $R^{5'}$ is triazinyl. In some embodiments, each $R^{5'}$ is quinolinyl. In some embodiments, each $R^{5'}$ is isoquinolinyl. In some embodiments, each $R^{5'}$ is quinoxalinyl. In some embodiments, each $R^{5'}$ is quinazolinyl. In some embodiments, each $R^{5'}$ is cinnolinyl. In some embodiments, each $R^{5'}$ is naphthyridinyl. In some embodiments, each $R^{5'}$ is methyl. In some embodiments, each $R^{5'}$ is ethyl. In some embodiments, each $R^{5'}$ is n-propyl. In some embodiments, each $R^{5'}$ is iso-propyl. In some embodiments, each $R^{5'}$ is n-butyl. In some embodiments, each $R^{5'}$ is iso-butyl. In some embodiments, each $R^{5'}$ is sec-butyl. In some embodiments, each $R^{5'}$ is tert-butyl. In some embodiments, each $R^{5'}$ is azetidinyl. In some embodiments, each $R^{5'}$ is oxetanyl. In some embodiments, each $R^{5'}$ is pyrrolidinyl. In some embodiments, each $R^{5'}$ is imidazolidinyl. In some embodiments, each $R^{5'}$ is tetrahydrofuranyl. In some embodiments, each $R^{5'}$ is piperidinyl. In some embodiments, each $R^{5'}$ is piperazinyl. In some embodiments, each $R^{5'}$ is tetrahydropyranyl. In some embodiments, each $R^{5'}$ is morpholinyl. In some embodiments, each $R^{5'}$ is fluoro. In some embodiments, each $R^{5'}$ is chloro. In some embodiments, each $R^{5'}$ is methoxy. In some embodiments, each $R^{5'}$ is ethoxy. In some embodiments, each $R^{5'}$ is trifluoromethoxy. In some embodiments, each $R^{5'}$ is —C(═O)NHMe. In some embodiments, each $R^{5'}$ is —NHC(═O)Me. In some embodiments, each $R^{5'}$ is —S(═O)$_2NH_2$. In some embodiments, each $R^{5'}$ is difluoromethoxy.

In some embodiments, each $R^6$ is independently alkyl, cycloalkyl, aryl, or heteroaryl. In some embodiments, each $R^6$ is independently alkyl or aryl. In some embodiments, each $R^6$ is independently methyl, ethyl, n-propyl, iso-propyl, n-butyl, iso-butyl, sec-butyl, tert-butyl, phenyl, naphthyl, anthracenyl, phenanthrenyl, chrysenyl, or pyrenyl. In some embodiments, each $R^6$ is independently methyl, ethyl, isopropyl, tert-butyl, phenyl, or naphthyl. In some embodiments, each $R^6$ is independently methyl or phenyl. In some embodiments, each $R^6$ is methyl. In some embodiments, each $R^6$ is ethyl. In some embodiments, each $R^6$ is n-propyl. In some embodiments, each $R^6$ is iso-propyl. In some embodiments, each $R^6$ is n-butyl. In some embodiments, each $R^6$ is iso-butyl. In some embodiments, each $R^6$ is sec-butyl. In some embodiments, each $R^6$ is tert-butyl. In some embodiments, each $R^6$ is phenyl. In some embodiments, each $R^6$ is naphthyl. In some embodiments, each $R^6$ is anthracenyl. In some embodiments, each $R^6$ is phenanthrenyl. In some embodiments, each $R^6$ is chrysenyl. In some embodiments, each $R^6$ is pyrenyl.

In some embodiments, $R^2$ is aryl, heteroaryl, cycloalkyl, or heterocycloalkyl; wherein $R^2$ is substituted with at least one $R^7$ and 0, 1, or 2 $R^8$. In some embodiments, $R^2$ is aryl, wherein $R^2$ is substituted with at least one $R^7$ and 0, 1, or 2 $R^8$. In some embodiments, $R^2$ is heteroaryl; wherein $R^2$ is substituted with at least one $R^7$ and 0, 1, or 2 $R^8$. In some embodiments, $R^2$ is cycloalkyl; wherein $R^2$ is substituted with at least one $R^7$ and 0, 1, or 2 $R^8$. In some embodiments, $R^2$ is heterocycloalkyl; wherein $R^2$ is substituted with at least one $R^7$ and 0, 1, or 2 $R^8$. In some embodiments, $R^2$ is monocyclic. In some embodiments, $R^2$ is phenyl, cyclopropyl, cyclobutyl, cyclopentyl, cyclohexyl, pyrrolyl, imidazolyl, pyrazolyl, triazolyl, tetrazolyl, thiazolyl, isothiazolyl, oxazolyl, isoxazolyl, pyridinyl, pyrimidinyl, pyridazinyl, pyrazinyl, or triazinyl; wherein $R^2$ is substituted with at least one $R^7$ and 0, 1, or 2 $R^8$. In some embodiments, $R^2$ is phenyl, cyclohexyl, or pyrrolyl; wherein $R^2$ is substituted with at least one $R^7$ and 0, 1, or 2 $R^8$. In some embodiments, $R^2$ is phenyl; wherein $R^2$ is substituted with at least one $R^7$ and 0, 1, or 2 $R^8$. In some embodiments, $R^2$ is cyclopropyl; wherein $R^2$ is substituted with at least one $R^7$ and 0, 1, or 2 $R^8$. In some embodiments, $R^2$ is cyclobutyl; wherein $R^2$ is substituted with at least one $R^7$ and 0, 1, or 2 $R^8$. In some embodiments, $R^2$ is cyclopentyl; wherein $R^2$ is substituted with at least one $R^7$ and 0, 1, or 2 $R^8$. In some embodiments, $R^2$ is cyclohexyl; wherein $R^2$ is substituted with at least one $R^7$ and 0, 1, or 2 $R^8$. In some embodiments, $R^2$ is pyrrolyl; wherein $R^2$ is substituted with at least one $R^7$ and 0, 1, or 2 $R^8$. In some embodiments, $R^2$ is imidazolyl; wherein $R^2$ is substituted with at least one $R^7$ and 0, 1, or 2 $R^8$. In some embodiments, $R^2$ is pyrazolyl; wherein $R^2$ is substituted with at least one $R^7$ and 0, 1, or 2 $R^8$. In some embodiments, $R^2$ is triazolyl; wherein $R^2$ is substituted with at least one $R^7$ and 0, 1, or 2 $R^8$. In some embodiments, $R^2$ is tetrazolyl; wherein $R^2$ is substituted with at least one $R^7$ and 0, 1, or 2 $R^8$. In some embodiments, $R^2$ is thiazolyl; wherein $R^2$ is substituted with at least one $R^7$ and 0, 1, or 2 $R^8$. In some embodiments, $R^2$ is isothiazolyl; wherein $R^2$ is substituted with at least one $R^7$ and 0, 1, or 2 $R^8$. In some embodiments, $R^2$ is oxazolyl; wherein $R^2$ is substituted with at least one $R^7$ and 0, 1, or 2 $R^8$. In some embodiments, $R^2$ is isoxazolyl; wherein $R^2$ is substituted with at least one $R^7$ and 0, 1, or 2 $R^8$. In some embodiments, $R^2$ is pyridinyl; wherein $R^2$ is substituted with at least one $R^7$ and 0, 1, or 2 $R^8$. In some embodiments, $R^2$ is pyrimidinyl; wherein $R^2$ is substituted with at least one $R^7$ and 0, 1, or 2 $R^8$. In some embodiments, $R^2$ is pyridazinyl; wherein $R^2$ is substituted with at least one $R^7$ and 0, 1, or 2 $R^8$. In some embodiments, $R^2$ is pyrazinyl; wherein $R^2$ is substituted with at least one $R^7$ and 0, 1, or 2 $R^8$. In some embodiments, $R^2$ is triazinyl; wherein $R^2$ is substituted with at least one $R^7$ and 0, 1, or 2 $R^8$. In some embodiments, $R^2$ is substituted with at least one $R^7$ and not substituted with $R^8$. In some embodiments, $R^2$ is substituted with at least one $R^7$ and substituted with 1 $R^8$. In some embodiments, $R^2$ is substituted with at least one $R^7$ and substituted with 2 $R^8$.

In some embodiments, $R^2$ is aryl, heteroaryl, cycloalkyl, or heterocycloalkyl; wherein $R^2$ is substituted with 1 $R^7$ and 0, 1, or 2 $R^8$. In some embodiments, $R^2$ is aryl, wherein $R^2$ is substituted with 1 $R^7$ and 0, 1, or 2 $R^8$. In some embodiments, $R^2$ is heteroaryl; wherein $R^2$ is substituted with 1 $R^7$ and 0, 1, or 2 $R^8$. In some embodiments, $R^2$ is cycloalkyl; wherein $R^2$ is substituted with 1 $R^7$ and 0, 1, or 2 $R^8$. In some embodiments, $R^2$ is heterocycloalkyl; wherein $R^2$ is substituted with 1 $R^7$ and 0, 1, or 2 $R^8$. In some embodiments, $R^2$ is monocyclic. In some embodiments, $R^2$ is phenyl, cyclopropyl, cyclobutyl, cyclopentyl, cyclohexyl, pyrrolyl, imidazolyl, pyrazolyl, triazolyl, tetrazolyl, thiazolyl, isothiazolyl, oxazolyl, isoxazolyl, pyridinyl, pyrimidinyl, pyridazinyl, pyrazinyl, or triazinyl; wherein $R^2$ is substituted with 1 $R^7$ and 0, 1, or 2 $R^8$. In some embodiments, $R^2$ is phenyl, cyclohexyl, or pyrrolyl; wherein $R^2$ is substituted with 1 $R^7$ and 0, 1, or 2 $R^8$. In some embodiments, $R^2$ is phenyl; wherein $R^2$ is substituted with 1 $R^7$ and 0, 1, or 2 $R^8$. In some embodiments, $R^2$ is cyclopropyl; wherein $R^2$ is substituted with 1 $R^7$ and 0, 1, or 2 $R^8$. In some embodiments, $R^2$ is cyclobutyl; wherein $R^2$ is substituted with 1 $R^7$ and 0, 1, or 2 $R^8$. In some embodiments, $R^2$ is cyclopentyl; wherein $R^2$ is substituted with 1 $R^7$ and 0, 1, or 2 $R^8$. In some embodiments, $R^2$ is cyclohexyl; wherein $R^2$ is substituted with 1 $R^7$ and 0, 1, or 2 $R^8$. In some embodiments, $R^2$ is pyrrolyl; wherein $R^2$ is substituted with 1 $R^7$ and 0, 1, or 2 $R^8$. In some embodiments, $R^2$ is imidazolyl; wherein $R^2$ is substituted with 1 $R^7$ and 0, 1, or 2 $R^8$. In some embodiments, $R^2$ is pyrazolyl; wherein $R^2$ is substituted with 1 $R^7$ and 0, 1, or 2 $R^8$. In some embodiments, $R^2$ is triazolyl; wherein $R^2$ is substituted with 1 $R^7$ and 0, 1, or 2 $R^8$. In some embodiments, $R^2$ is tetrazolyl; wherein $R^2$ is substituted with 1 $R^7$ and 0, 1, or 2 $R^8$. In some embodiments, $R^2$ is thiazolyl; wherein $R^2$ is substituted with 1 $R^7$ and 0, 1, or 2 $R^8$. In some embodiments, $R^2$ is isothiazolyl; wherein $R^2$ is substituted with 1 $R^7$ and 0, 1, or 2 $R^8$. In some embodiments, $R^2$ is oxazolyl; wherein $R^2$ is substituted with 1 $R^7$ and 0, 1, or 2 $R^8$. In some embodiments, $R^2$ is isoxazolyl; wherein $R^2$ is substituted with 1 $R^7$ and 0, 1, or 2 $R^8$. In some embodiments, $R^2$ is pyridinyl; wherein $R^2$ is substituted with 1 $R^7$ and 0, 1, or 2 $R^8$. In some embodiments, $R^2$ is pyrimidinyl; wherein $R^2$ is substituted with 1 $R^7$ and 0, 1, or 2 $R^8$. In some embodiments, $R^2$ is pyridazinyl; wherein $R^2$ is substituted with 1 $R^7$ and 0, 1, or 2 $R^8$. In some embodiments, $R^2$ is pyrazinyl; wherein $R^2$ is substituted with 1 $R^7$ and 0, 1, or 2 $R^8$. In some embodiments, $R^2$ is triazinyl; wherein $R^2$ is substituted with 1 $R^7$ and 0, 1, or 2 $R^8$. In some embodiments, $R^2$ is substituted with 1 $R^7$ and not substituted with $R^8$. In some embodiments, $R^2$ is substituted with 1 $R^7$ and substituted with 1 $R^8$. In some embodiments, $R^2$ is substituted with 1 $R^7$ and substituted with 2 $R^8$.

In some embodiments, $R^7$ is

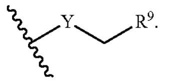

In some embodiments, $R^7$ is

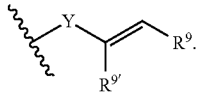

In some embodiments, $R^7$ is

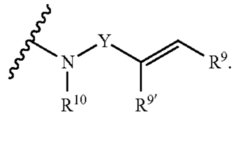

In some embodiments, $R^7$ is

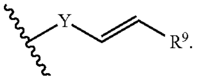

In some embodiments, $R^7$ is

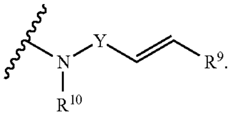

In some embodiments, Y is —C(═O)—. In some embodiments, Y is —S(═O)—. In some embodiments, Y is —$S(═O)_2$—.

In some embodiments, $R^7$ is

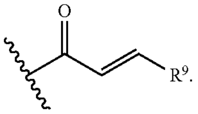

In some embodiments, $R^7$ is

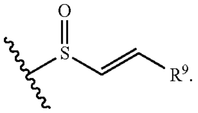

In some embodiments, $R^7$ is

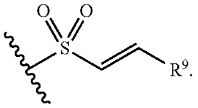

In some embodiments, $R^7$ is

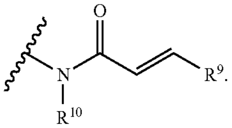

In some embodiments, $R^7$ is

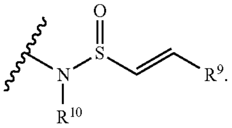

In some embodiments, $R^7$ is

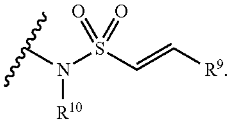

In some embodiments, $R^7$ is

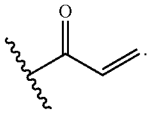 [SMILES: *C(=O)C=C]

In some embodiments, $R^7$ is

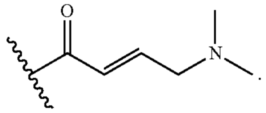 [SMILES: *C(=O)/C=C/CN(C)C]

In some embodiments, $R^7$ is

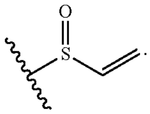 [SMILES: *S(=O)C=C]

In some embodiments, $R^7$ is

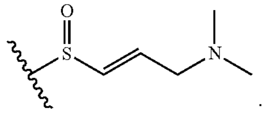 [SMILES: *S(=O)/C=C/CN(C)C]

In some embodiments, $R^7$ is

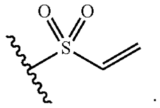 [SMILES: *S(=O)(=O)C=C]

In some embodiments, $R^7$ is

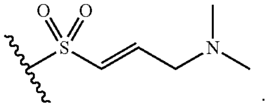 [SMILES: *S(=O)(=O)/C=C/CN(C)C]

In some embodiments, $R^7$ is

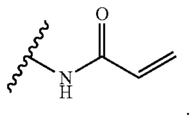 [SMILES: *NC(=O)C=C]

In some embodiments, $R^7$ is

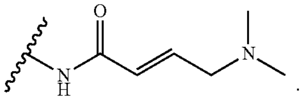 [SMILES: *NC(=O)/C=C/CN(C)C]

In some embodiments, $R^7$ is

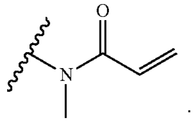 [SMILES: *N(C)C(=O)C=C]

In some embodiments, $R^7$ is

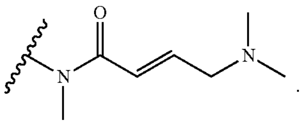 [SMILES: *N(C)C(=O)/C=C/CN(C)C]

In some embodiments, $R^7$ is

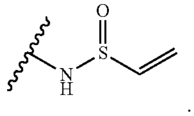 [SMILES: *NS(=O)C=C]

In some embodiments, $R^7$ is

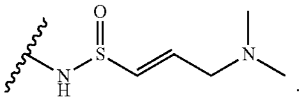 [SMILES: *NS(=O)/C=C/CN(C)C]

In some embodiments, $R^7$ is

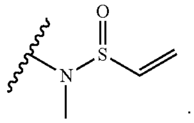 [SMILES: *N(C)S(=O)C=C]

In some embodiments, $R^7$ is

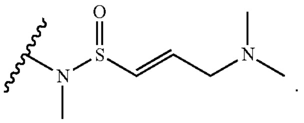 [SMILES: *N(C)S(=O)/C=C/CN(C)C]

In some embodiments, $R^7$ is

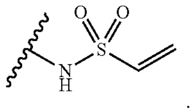 [SMILES: *NS(=O)(=O)C=C]

In some embodiments, $R^7$ is

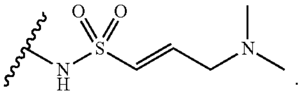 [SMILES: *NS(=O)(=O)/C=C/CN(C)C]

In some embodiments, $R^7$ is

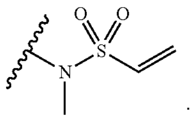 [SMILES: *N(C)S(=O)(=O)C=C]

In some embodiments, $R^7$ is

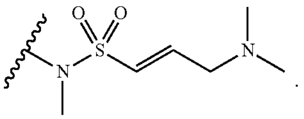 [SMILES: *N(C)S(=O)(=O)/C=C/CN(C)C]

In some embodiments, $R^9$ and $R^{9'}$ are independently hydrogen, halo, alkyl, heteroalkyl, haloalkyl, or (alkyl) heterocycloalkyl. In some embodiments, $R^9$ is hydrogen, halo, alkyl, cycloalkyl, or heteroalkyl. In some embodiments, $R^9$ is hydrogen, halo, or heteroalkyl. In some embodiments, $R^9$ and $R^{9'}$ are independently hydrogen, fluoro, chloro, methyl, hydroxyethyl, methoxyethyl, methoxymethyl, dimethylaminomethyl, 1-piperidinylmethyl, 1-morpholinylmethyl, or fluoromethyl. In some embodiments, $R^9$ is hydrogen, fluoro, chloro, hydroxyethyl, or methoxyethyl. In some embodiments, $R^9$ is hydrogen. In some embodiments, $R^9$ is fluoro. In some embodiments, $R^9$ is chloro. In some embodiments, $R^9$ is hydroxyethyl. In some embodiments, $R^9$ is methoxyethyl. In some embodiments, $R^9$ is methyl. In some embodiments, $R^9$ is methoxymethyl. In some embodiments, $R^9$ is dimethylaminomethyl. In some embodiments, $R^9$ is 1-piperidinylmethyl. In some embodiments, $R^9$ is 1-morpholinomethyl. In some embodiments, $R^9$ is fluoromethyl. In some embodiments, $R^{9'}$ is hydrogen. In some embodiments, $R^{9'}$ is fluoro. In some embodiments, $R^{9'}$ is chloro. In some embodiments, $R^{9'}$ is hydroxyethyl. In some embodiments, $R^{9'}$ is methoxyethyl. In some embodiments, $R^{9'}$ is methyl. In some embodiments, $R^{9'}$ is methoxymethyl. In some embodiments, $R^{9'}$ is dimethylaminomethyl. In some embodiments, $R^{9'}$ is 1-piperidinylmethyl.

In some embodiments, $R^{9'}$ is 1-morpholinomethyl. In some embodiments, $R^{9'}$ is fluoromethyl.

In some embodiments, $R^{10}$ is hydrogen or alkyl. In some embodiments, $R^{10}$ is hydrogen, methyl, ethyl, n-propyl, iso-propyl, n-butyl, iso-butyl, sec-butyl, or tert-butyl. In some embodiments, $R^{10}$ is hydrogen. In some embodiments, $R^{10}$ is methyl. In some embodiments, $R^{10}$ is ethyl. In some embodiments, $R^{10}$ is n-propyl. In some embodiments, $R^{10}$ is iso-propyl. In some embodiments, $R^{10}$ is n-butyl. In some embodiments, $R^{10}$ is iso-butyl. In some embodiments, $R^{10}$ is sec-butyl. In some embodiments, $R^{10}$ is tert-butyl.

In some embodiments, $R^2$ is not substituted with $R^8$. In some embodiments, $R^2$ is substituted with 1 or 2 $R^8$. In some embodiments, $R^2$ is substituted with 1 $R^8$. In some embodiments, $R^2$ is substituted with 2 $R^8$.

In some embodiments, each $R^8$ is independently methyl, ethyl, n-propyl, iso-propyl, n-butyl, iso-butyl, sec-butyl, tert-butyl, fluoro, chloro, heteroalkyl, cyano, hydroxy, amino, —$N(R^1)_2$, methoxy, ethoxy, or trifluoromethoxy. In some embodiments, each $R^8$ is independently methyl, ethyl, iso-propyl, tert-butyl, fluoro, chloro, —$N(R^1)_2$, hydroxyethyl, methoxyethyl, or cyano. In some embodiments, each $R^8$ is methyl. In some embodiments, each $R^8$ is ethyl. In some embodiments, each $R^8$ is n-propyl. In some embodiments, each $R^8$ is iso-propyl. In some embodiments, each $R^8$ is n-butyl. In some embodiments, each $R^8$ is iso-butyl. In some embodiments, each $R^8$ is sec-butyl. In some embodiments, each $R^8$ is tert-butyl. In some embodiments, each $R^8$ is fluoro. In some embodiments, each $R^8$ is chloro. In some embodiments, each $R^8$ is independently —$N(R^{11})_2$. In some embodiments, each $R^8$ is hydroxyethyl. In some embodiments, each $R^8$ is methoxyethyl. In some embodiments, each $R^8$ is cyano.

In some embodiments, each $R^{11}$ is independently alkyl, cycloalkyl, aryl, or heteroaryl. In some embodiments, each $R^{11}$ is independently alkyl or aryl. In some embodiments, each $R^{11}$ is independently alkyl. In some embodiments, each $R^{11}$ is independently cycloalkyl. In some embodiments, each $R^{11}$ is independently aryl. In some embodiments, each $R^{11}$ is independently heteroaryl. In some embodiments, each $R^{11}$ is independently methyl, ethyl, n-propyl, iso-propyl, n-butyl, iso-butyl, sec-butyl, tert-butyl, phenyl, naphthyl, anthracenyl, phenanthrenyl, chrysenyl, or pyrenyl. In some embodiments, each $R^{11}$ is independently methyl, ethyl, iso-propyl, tert-butyl, phenyl, or naphthyl. In some embodiments, each $R^{11}$ is independently methyl or phenyl. In some embodiments, each $R^{11}$ is methyl. In some embodiments, each $R^{11}$ is ethyl. In some embodiments, each $R^{11}$ is n-propyl. In some embodiments, each $R^{11}$ is iso-propyl. In some embodiments, each $R^{11}$ is n-butyl. In some embodiments, each $R^{11}$ is iso-butyl. In some embodiments, each $R^{11}$ is sec-butyl. In some embodiments, each $R^{11}$ is tert-butyl. In some embodiments, each $R^{11}$ is phenyl. In some embodiments, each $R^{11}$ is naphthyl. In some embodiments, each $R^{11}$ is anthracenyl. In some embodiments, each $R^{11}$ is phenanthrenyl. In some embodiments, each $R^{11}$ is chrysenyl. In some embodiments, each $R^{11}$ is pyrenyl.

In some embodiments, $R^3$ is pyrrolyl, imidazolyl, pyrazolyl, triazolyl, tetrazolyl, indolyl, indazolyl, benzimidazolyl, azaindolyl, thiazolyl, isothiazolyl, oxazolyl, isoxazolyl, pyridinyl, pyrimidinyl, pyridazinyl, pyrazinyl, triazinyl, quinolinyl, isoquinolinyl, quinoxalinyl, quinazolinyl, cinnolinyl, or naphthyridinyl; wherein $R^3$ is substituted with 0, 1, 2, or 3 $R^{12}$. In some embodiments, $R^3$ is imidazolyl, pyrazolyl, triazolyl, indolyl, indazolyl, thiazolyl, isothiazolyl, or pyridinyl; wherein $R^3$ is substituted with 0, 1, 2, or 3 $R^{12}$. In some embodiments, $R^3$ is pyrrolyl; wherein $R^3$ is substituted with 0, 1, 2, or 3 $R^{12}$. In some embodiments, $R^3$ is imidazolyl; wherein $R^3$ is substituted with 0, 1, 2, or 3 $R^{12}$. In some embodiments, $R^3$ is pyrazolyl; wherein $R^3$ is substituted with 0, 1, 2, or 3 $R^{12}$. In some embodiments, $R^3$ is triazolyl; wherein $R^3$ is substituted with 0, 1, 2, or 3 $R^{12}$. In some embodiments, $R^3$ is tetrazolyl; wherein $R^3$ is substituted with 0, 1, 2, or 3 $R^{12}$. In some embodiments, $R^3$ is indolyl; wherein $R^3$ is substituted with 0, 1, 2, or 3 $R^{12}$. In some embodiments, $R^3$ is indazolyl; wherein $R^3$ is substituted with 0, 1, 2, or 3 $R^{12}$. In some embodiments, $R^3$ is benzimidazolyl; wherein $R^3$ is substituted with 0, 1, 2, or 3 $R^{12}$. In some embodiments, $R^3$ is azaindolyl; wherein $R^3$ is substituted with 0, 1, 2, or 3 $R^{12}$. In some embodiments, $R^3$ is thiazolyl; wherein $R^3$ is substituted with 0, 1, 2, or 3 $R^{12}$. In some embodiments, $R^3$ is isothiazolyl; wherein $R^3$ is substituted with 0, 1, 2, or 3 $R^{12}$. In some embodiments, $R^3$ is oxazolyl; wherein $R^3$ is substituted with 0, 1, 2, or 3 $R^{12}$. In some embodiments, $R^3$ is isoxazolyl; wherein $R^3$ is substituted with 0, 1, 2, or 3 $R^{12}$. In some embodiments, $R^3$ is pyridinyl; wherein $R^3$ is substituted with 0, 1, 2, or 3 $R^{12}$. In some embodiments, $R^3$ is pyrimidinyl; wherein $R^3$ is substituted with 0, 1, 2, or 3 $R^{12}$. In some embodiments, $R^3$ is pyridazinyl; wherein $R^3$ is substituted with 0, 1, 2, or 3 $R^{12}$. In some embodiments, $R^3$ is pyrazinyl; wherein $R^3$ is substituted with 0, 1, 2, or 3 $R^{12}$. In some embodiments, $R^3$ is triazinyl; wherein $R^3$ is substituted with 0, 1, 2, or 3 $R^{12}$. In some embodiments, $R^3$ is quinolinyl; wherein $R^3$ is substituted with 0, 1, 2, or 3 $R^{12}$. In some embodiments, $R^3$ is isoquinolinyl; wherein $R^3$ is substituted with 0, 1, 2, or 3 $R^{12}$. In some embodiments, $R^3$ is quinoxalinyl; wherein $R^3$ is substituted with 0, 1, 2, or 3 $R^{12}$. In some embodiments, $R^3$ is quinazolinyl; wherein $R^3$ is substituted with 0, 1, 2, or 3 $R^{12}$. In some embodiments, $R^3$ is cinnolinyl; wherein $R^3$ is substituted with 0, 1, 2, or 3 $R^{12}$. In some embodiments, $R^3$ is naphthyridinyl; wherein $R^3$ is substituted with 0, 1, 2, or 3 $R^{12}$.

In some embodiments, $R^3$ is unsubstituted. In some embodiments, $R^3$ is substituted with at least 1 $R^{12}$. In some embodiments, $R^3$ is substituted with at least 2 $R^{12}$. In some embodiments, $R^3$ is substituted with 1 $R^{12}$. In some embodiments, $R^3$ is substituted with 2 $R^{12}$. In some embodiments, $R^3$ is substituted with 3 $R^{12}$.

In some embodiments, $R^3$ is

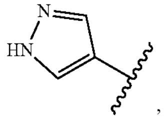
,
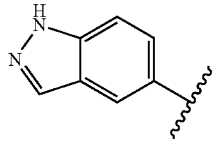
,
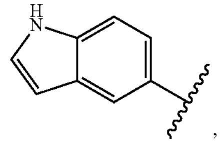
,
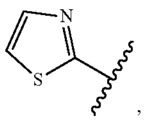
,
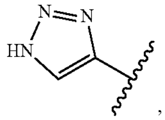
,
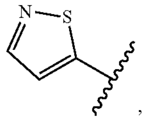
,
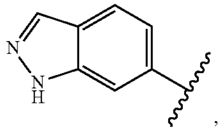
, or
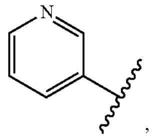
, wherein $R^3$ is substituted with 0 to 3 $R^{12}$.

In some embodiments, $R^3$ is
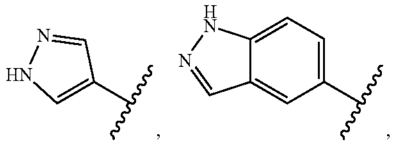
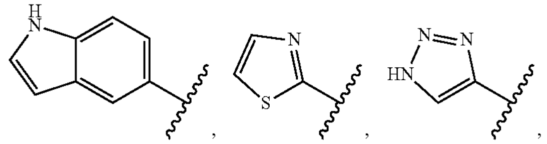
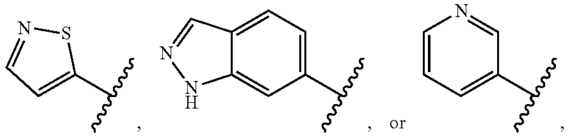
wherein $R^3$ is substituted with 1 or 2 $R^{12}$.
In some embodiments, $R^3$ is:
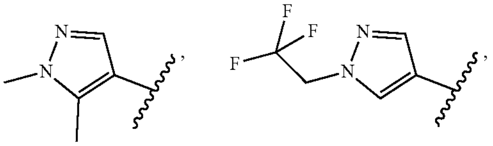
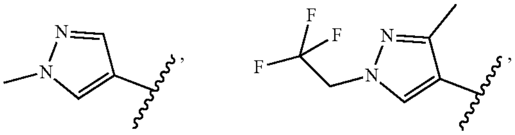
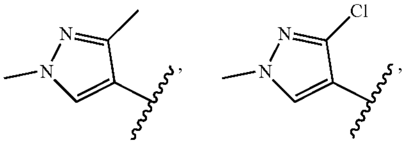
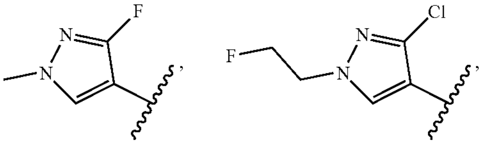
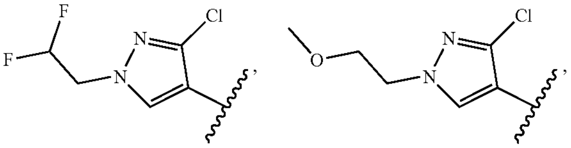
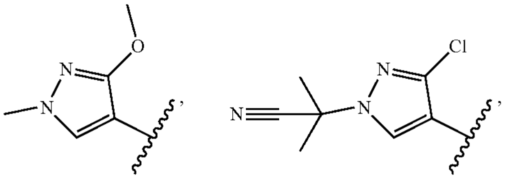
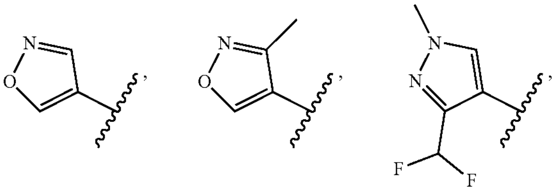
-continued
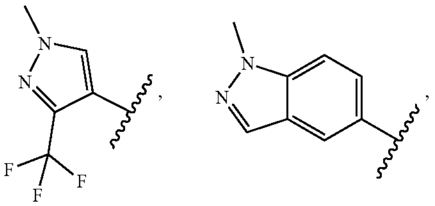
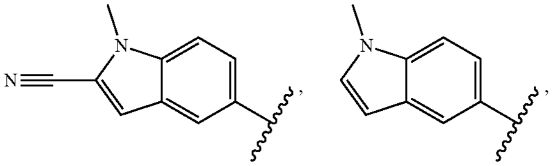
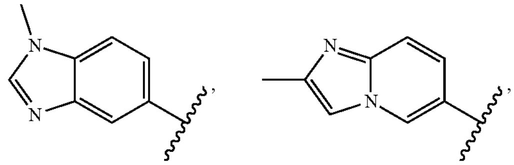
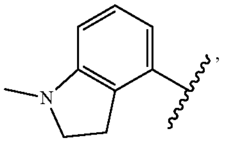
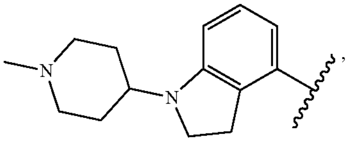
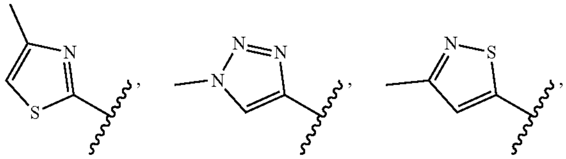
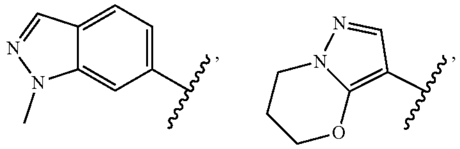
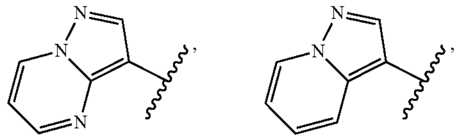
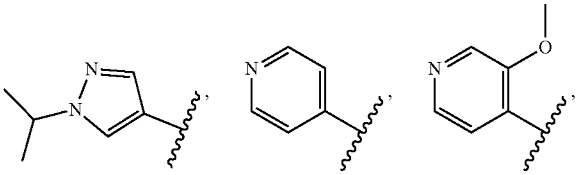
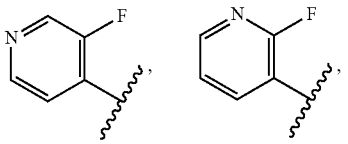

-continued
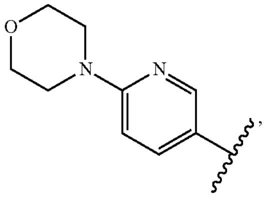,
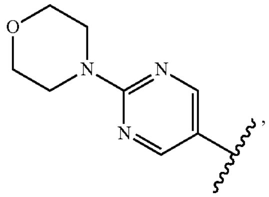,
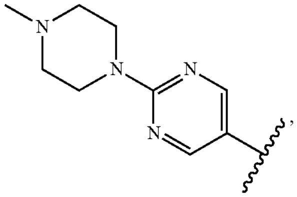,
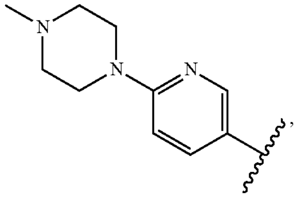,
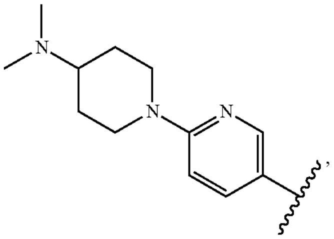,
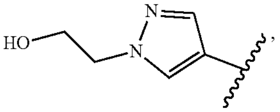,
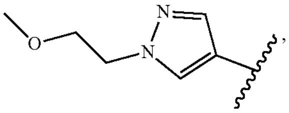,
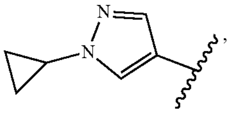,
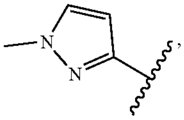,
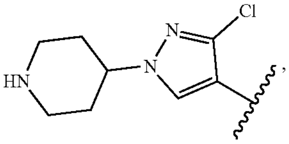,
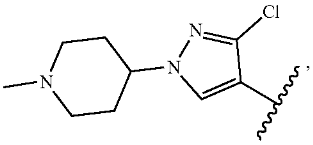,
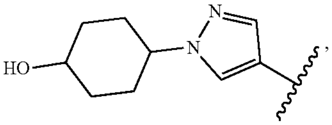,
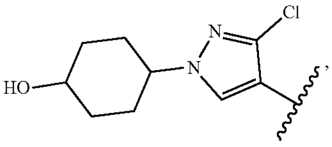,
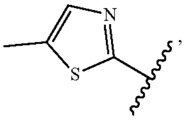,
-continued
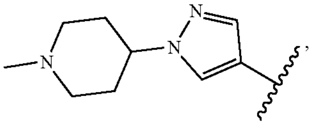,
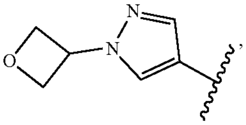,
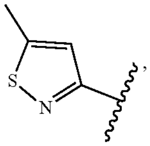,
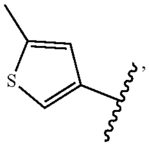,
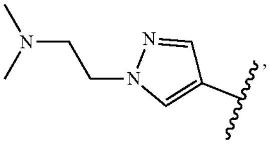,
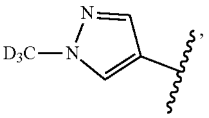, or 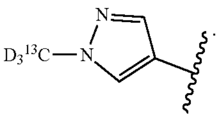.
In some embodiments, $R^3$ is:
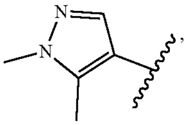,
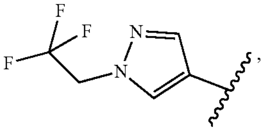,
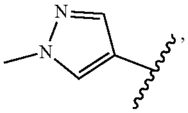,
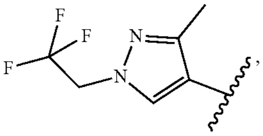,
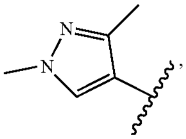,
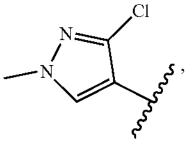,
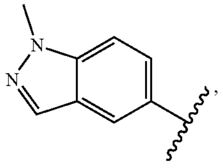,
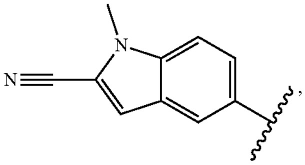,
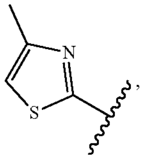,
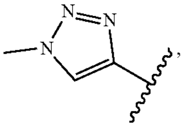,
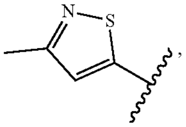,
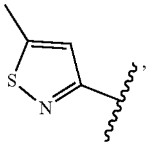,
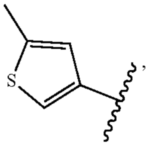,
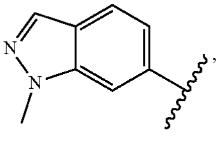,
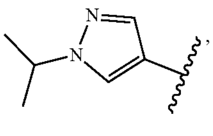, -continued
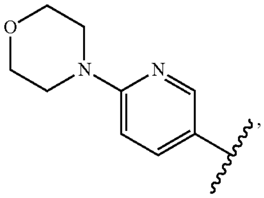,
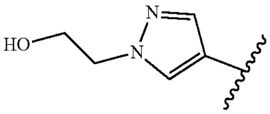,
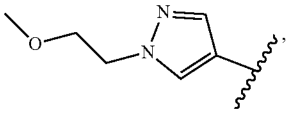,
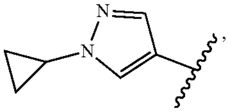,
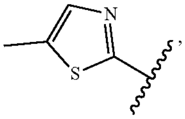,
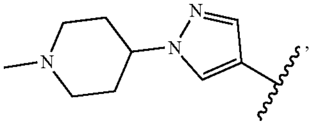,
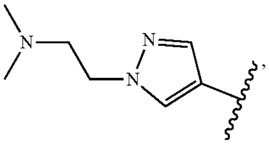,
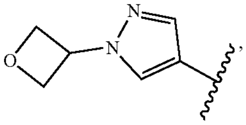,
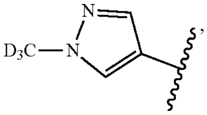,
or
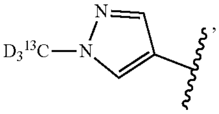.
In some embodiments, $R^3$ is:
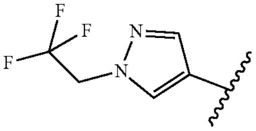,
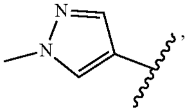,
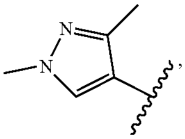,
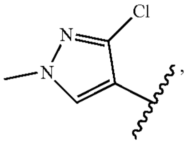,
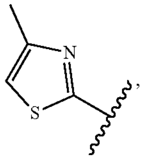,
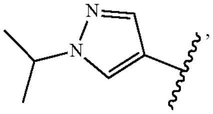,
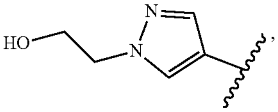,
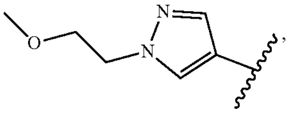,
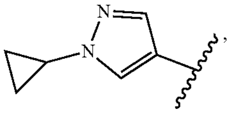,
or
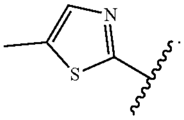.
In some embodiments, $R^3$ is
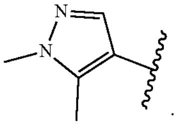 [SMILES: *c1cnn(C)c1C].
In some embodiments, $R^3$ is
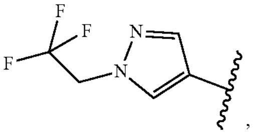 [SMILES: *c1cnn(CC(F)(F)F)c1],
In some embodiments, $R^3$ is
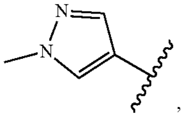 [SMILES: *c1cnn(C)c1],
In some embodiments, $R^3$ is
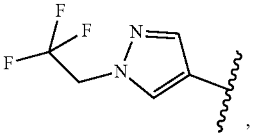 [SMILES: *c1cnn(CC(F)(F)F)c1],
In some embodiments, $R^3$ is
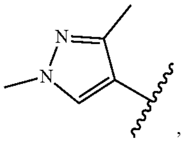 [SMILES: *c1cn(C)nc1C],
In some embodiments, $R^3$ is
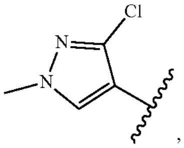 [SMILES: *c1cn(C)nc1Cl],
In some embodiments, $R^3$ is
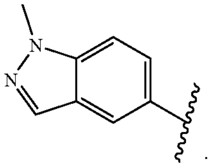 [SMILES: *c1ccc2c(cnn2C)c1].

In some embodiments, $R^3$ is
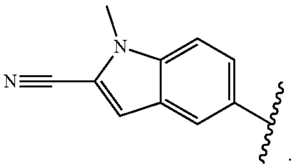 [SMILES: *c1ccc2c(c1)cc(C#N)n2C]
In some embodiments, $R^3$ is
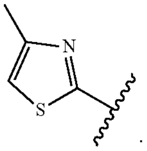 [SMILES: *c1nc(C)cs1]
In some embodiments, $R^3$ is
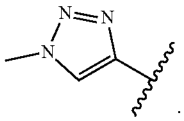 [SMILES: *c1cn(C)nn1]
In some embodiments, $R^3$ is
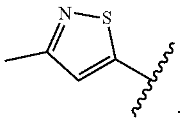 [SMILES: *c1cc(C)ns1]
In some embodiments, $R^3$ is
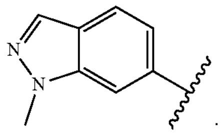 [SMILES: *c1ccc2cnn(C)c2c1]
In some embodiments, $R^3$ is
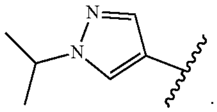 [SMILES: *c1cnn(C(C)C)c1]
In some embodiments, $R^3$ is
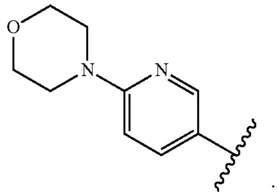 [SMILES: *c1ccc(N2CCOCC2)nc1]
In some embodiments, $R^3$ is
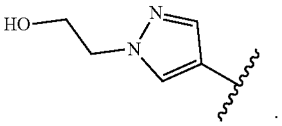 [SMILES: *c1cnn(CCO)c1]
In some embodiments, $R^3$ is
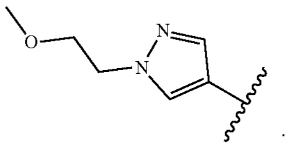 [SMILES: *c1cnn(CCOC)c1]
In some embodiments, $R^3$ is
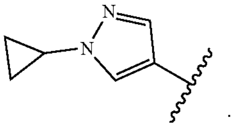 [SMILES: *c1cnn(C2CC2)c1]
In some embodiments, $R^3$ is
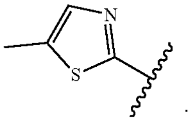 [SMILES: *c1ncc(C)s1]
In some embodiments, $R^3$ is
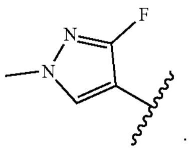 [SMILES: *c1cn(C)nc1F]
In some embodiments, $R^3$ is
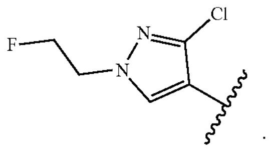 [SMILES: *c1cn(CCF)nc1Cl]

In some embodiments, $R^3$ is
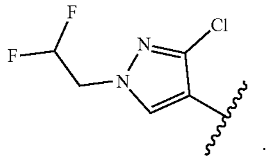 [SMILES: *c1cn(CC(F)F)nc1Cl]
In some embodiments, $R^3$ is
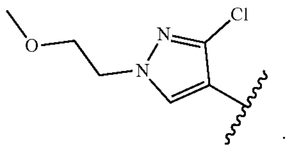 [SMILES: *c1cn(CCOC)nc1Cl]
In some embodiments, $R^3$ is
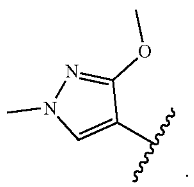 [SMILES: *c1cn(C)nc1OC]
In some embodiments, $R^3$ is
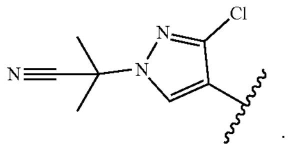 [SMILES: *c1cn(C(C)(C)C#N)nc1Cl]
In some embodiments, $R^3$ is
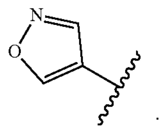 [SMILES: *c1cnoc1]
In some embodiments, $R^3$ is
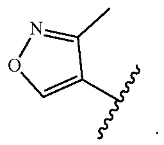 [SMILES: *c1conc1C]
In some embodiments, $R^3$ is
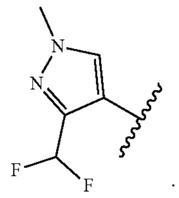
In some embodiments, $R^3$ is
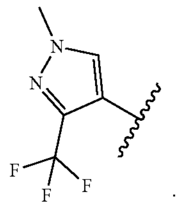 [SMILES: *c1cn(C)nc1C(F)(F)F]
In some embodiments, $R^3$ is
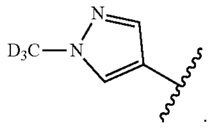 [SMILES: *c1cnn(C([2H])([2H])[2H])c1]
In some embodiments, $R^3$ is
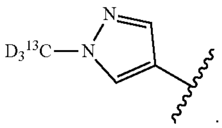
In some embodiments, $R^3$ is
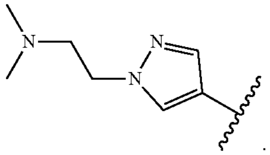 [SMILES: *c1cnn(CCN(C)C)c1]
In some embodiments, $R^3$ is
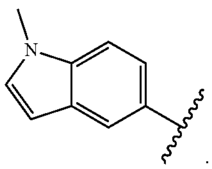 [SMILES: *c1ccc2c(ccn2C)c1]

In some embodiments, $R^3$ is
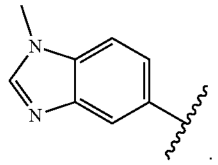 [SMILES: *c1ccc2c(c1)ncn2C]
In some embodiments, $R^3$ is
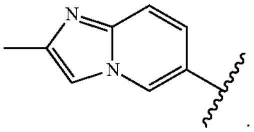 [SMILES: *c1ccc2nc(C)cn2c1]
In some embodiments $R^3$ is
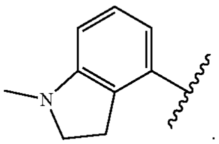 [SMILES: *c1cccc2c1CCN2C]
In some embodiments, $R^3$ is
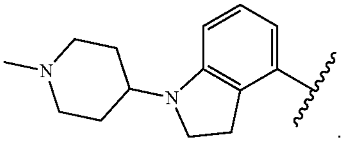 [SMILES: *c1cccc2c1CCN2C1CCN(C)CC1]
In some embodiments, $R^3$ is
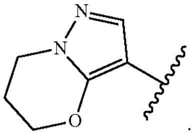 [SMILES: *c1cnn2c1OCCC2]
In some embodiments, $R^3$ is
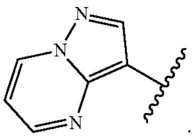 [SMILES: *c1cnn2cccnc12]
In some embodiments, $R^3$ is
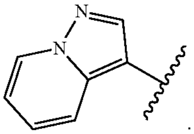 [SMILES: *c1cnn2ccccc12]
In some embodiments, $R^3$ is
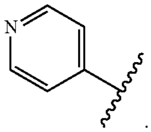 [SMILES: *c1ccncc1]
In some embodiments, $R^3$ is
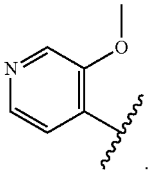 [SMILES: *c1ccncc1OC]
In some embodiments, $R^3$ is
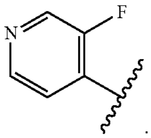 [SMILES: *c1ccncc1F]
In some embodiments, $R^3$ is
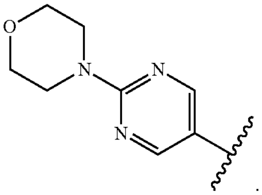 [SMILES: *c1cnc(N2CCOCC2)nc1]
In some embodiments, $R^3$ is
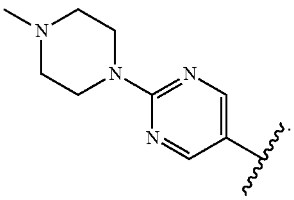 [SMILES: *c1cnc(N2CCN(C)CC2)nc1]

In some embodiments, $R^3$ is

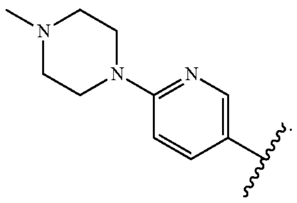 [SMILES: *c1ccc(N2CCN(C)CC2)nc1]

In some embodiments, $R^3$ is

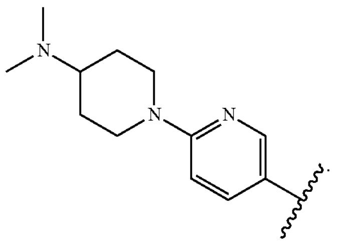 [SMILES: *c1ccc(N2CCC(N(C)C)CC2)nc1]

In some embodiments, $R^3$ is

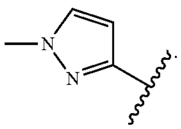 [SMILES: *c1ccn(C)n1]

In some embodiments, $R^3$ is

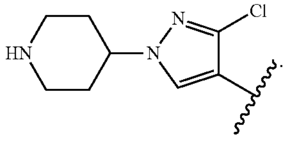

In some embodiments, $R^3$ is

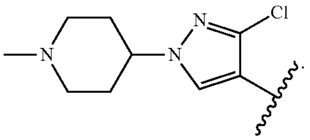 [SMILES: *c1cn(C2CCN(C)CC2)nc1Cl]

In some embodiments, $R^3$ is

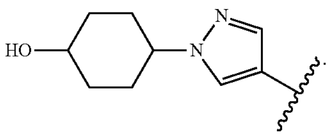 [SMILES: *c1cnn(C2CCC(O)CC2)c1]

In some embodiments, $R^3$ is

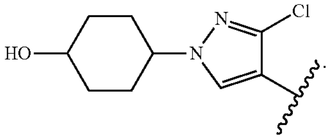 [SMILES: *c1cn(C2CCC(O)CC2)nc1Cl]

In some embodiments, $R^3$ is

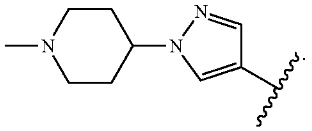 [SMILES: *c1cnn(C2CCN(C)CC2)c1]

In some embodiments, $R^3$ is

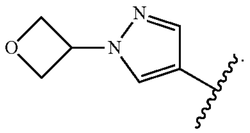 [SMILES: *c1cnn(C2COC2)c1]

In some embodiments, each $R^{12}$ is independently aryl, heteroaryl, alkyl, heteroalkyl, haloalkyl, halo, cyano, alkoxy, heterocycloalkyl, $—N(R^{13})_2$, $—S(=O)_2NH_2$, $—S(=O)_2$ alkyl, $—S(=O)_2$aryl, $—S(=O)_2$heteroaryl, or cycloalkyl. In some embodiments, each $R^{12}$ is independently alkyl, heteroalkyl, haloalkyl, halo, cyano, heterocycloalkyl, $—N(R^{13})_2$, or cycloalkyl. In some embodiments, each $R^{12}$ is independently aryl. In some embodiments, each $R^{12}$ is independently heteroaryl. In some embodiments, each $R^{12}$ is independently alkyl. In some embodiments, each $R^{12}$ is independently heteroalkyl. In some embodiments, each $R^{12}$ is independently haloalkyl. In some embodiments, each $R^{12}$ is independently halo. In some embodiments, each $R^{12}$ is cyano. In some embodiments, each $R^{12}$ is independently alkoxy. In some embodiments, each $R^{12}$ is independently heterocycloalkyl. In some embodiments, each $R^{12}$ is independently $—N(R^{13})_2$. In some embodiments, each $R^{12}$ is independently $—S(=O)_2NH_2$. In some embodiments, each $R^{12}$ is independently $—S(=O)_2$ alkyl. In some embodiments, each $R^{12}$ is independently $—S(=O)_2$aryl. In some embodiments, each $R^{12}$ is independently $—S(=O)_2$heteroaryl. In some embodiments, each $R^{12}$ is independently cycloalkyl. In some embodiments, each $R^{12}$ is independently methyl, ethyl, n-propyl, iso-propyl, n-butyl, iso-butyl, sec-butyl, tert-butyl, hydroxyethyl, methoxyethyl, trifluoromethyl, trifluoroethyl, pentafluoroethyl, fluoro, chloro, cyano, azetidinyl, oxetanyl, pyrrolidinyl, imidazolidinyl, tetrahydrofuranyl, piperidinyl, piperazinyl, tetrahydropyranyl, morpholinyl, $—N(R^{13})_2$, cyclopropyl, cyclobutyl, cyclopentyl, or cyclohexyl. In some embodiments, each $R^{12}$ is independently methyl, iso-propyl, tert-butyl, hydroxyethyl, methoxyethyl, trifluoromethyl, trifluoroethyl, chloro, cyano, morpholinyl, or cyclopropyl. In some embodiments, each $R^{12}$ is independently methyl, hydroxyethyl, methoxyethyl, trifluoroethyl, or chloro. In some embodiments, each $R^{12}$ is independently methyl or chloro. In some embodiments, each $R^{12}$ is methyl. In some embodiments, each $R^{12}$ is ethyl. In some embodiments, each $R^{12}$ is n-propyl. In some embodiments, each $R^{12}$ is iso-propyl. In some embodiments, each $R^{12}$ is n-butyl. In some embodiments, each $R^{12}$ is iso-butyl. In some embodiments, each $R^{12}$ is sec-butyl. In some embodiments, each $R^{12}$ is tert-butyl. In some embodiments, each $R^{12}$ is hydroxyethyl. In some embodiments, each $R^{12}$ is methoxyethyl. In some embodiments, each $R^{12}$ is trifluoromethyl. In some embodiments, each $R^{12}$ is trifluoroethyl. In some embodiments, each $R^{12}$ is pentafluoroethyl. In some embodiments, each $R^{12}$ is fluoro. In some embodiments, each $R^{12}$ is chloro. In some embodiments, each $R^{12}$ is azetidinyl. In some embodiments, each $R^{12}$ is oxetanyl. In some embodiments, each $R^{12}$ is pyrrolidinyl. In some embodiments, each $R^{12}$ is imidazolidinyl. In some embodiments, each $R^{12}$ is tetrahydrofuranyl. In some embodiments, each $R^{12}$ is piperidinyl. In some embodiments, each $R^{12}$ is piperazinyl. In some embodiments, each $R^{12}$ is tetrahydropyranyl. In some embodiments, each $R^{12}$ is morpholinyl. In some embodiments, each $R^{12}$ is cyclopropyl. In some embodiments, each $R^{12}$ is cyclobutyl. In some embodiments, each $R^{12}$ is cyclopentyl. In some embodiments, each $R^{12}$ is cyclohexyl.

In some embodiments, each $R^{13}$ is independently alkyl, cycloalkyl, aryl, or heteroaryl. In some embodiments, each $R^{13}$ is independently alkyl or cycloalkyl. In some embodiments, each $R^{13}$ is independently alkyl. In some embodiments, each $R^{13}$ is independently cycloalkyl. In some embodiments, each $R^{13}$ is independently aryl. In some embodiments, each $R^{13}$ is independently heteroaryl. In some embodiments, each $R^{13}$ is independently methyl, ethyl, n-propyl, iso-propyl, n-butyl, iso-butyl, sec-butyl, tert-butyl, cyclopropyl, cyclobutyl, cyclopentyl, or cyclohexyl. In some embodiments, each $R^{13}$ is independently methyl, ethyl, iso-propyl, tert-butyl, cyclopropyl, cyclopentyl, or cyclohexyl. In some embodiments, each $R^{13}$ is independently methyl, cyclopropyl, or cyclohexyl. In some embodiments, each $R^{13}$ is methyl. In some embodiments, each $R^{13}$ is ethyl. In some embodiments, each $R^{13}$ is n-propyl. In some embodiments, each $R^{13}$ is iso-propyl. In some embodiments, each $R^{13}$ is n-butyl. In some embodiments, each $R^{13}$ is iso-butyl. In some embodiments, each $R^{13}$ is sec-butyl. In some embodiments, each $R^{13}$ is tert-butyl. In some embodiments, each $R^{13}$ is cyclopropyl. In some embodiments, each $R^{13}$ is cyclobutyl. In some embodiments, each $R^{13}$ is cyclopentyl. In some embodiments, each $R^{13}$ is cyclohexyl.

In some embodiments, the aryl, heteroaryl, heterocycloalkyl, or cycloalkyl of $R^{12}$ is unsubstituted. In some embodiments, the aryl, heteroaryl, heterocycloalkyl, or cycloalkyl of $R^{12}$ is substituted with 1 or 2 $R^{14}$. In some embodiments, the aryl, heteroaryl, heterocycloalkyl, or cycloalkyl of $R^{12}$ is substituted with 1 $R^{14}$. In some embodiments, the aryl, heteroaryl, heterocycloalkyl, or cycloalkyl of $R^{12}$ is substituted with 2 $R^{14}$.

In some embodiments, each $R^{14}$ is independently aryl, heteroaryl, alkyl, cycloalkyl, heterocycloalkyl, halo, heteroalkyl, haloalkyl, cyano, hydroxy, amino, —$N(R^{15})_2$, —$S(=O)_2$ alkyl, —$S(=O)_2$aryl, —$S(=O)_2$heteroaryl, or alkoxy. In some embodiments, each $R^{14}$ is independently alkyl, cycloalkyl, heterocycloalkyl, halo, cyano, —$N(R^{15})_2$, or alkoxy. In some embodiments, each $R^{14}$ is independently aryl. In some embodiments, each $R^{14}$ is independently heteroaryl. In some embodiments, each $R^{14}$ is independently alkyl. In some embodiments, each $R^{14}$ is independently cycloalkyl. In some embodiments, each $R^{14}$ is independently heterocycloalkyl. In some embodiments, each $R^{14}$ is independently halo. In some embodiments, each $R^{14}$ is independently heteroalkyl. In some embodiments, each $R^{14}$ is independently haloalkyl. In some embodiments, each $R^{14}$ is cyano. In some embodiments, each $R^{14}$ is hydroxy. In some embodiments, each $R^{14}$ is amino. In some embodiments, each $R^{14}$ is independently —$N(R^{15})_2$. In some embodiments, each $R^{14}$ is independently —$S(=O)_2$ alkyl. In some embodiments, each $R^{14}$ is independently —$S(=O)_2$aryl. In some embodiments, each $R^{14}$ is independently —$S(=O)_2$heteroaryl. In some embodiments, each $R^{14}$ is independently alkoxy. In some embodiments, each $R^{14}$ is independently methyl, ethyl, n-propyl, iso-propyl, n-butyl, iso-butyl, sec-butyl, tert-butyl, cyclopropyl, cyclobutyl, cyclopentyl, cyclohexyl, azetidinyl, oxetanyl, pyrrolidinyl, imidazolidinyl, tetrahydrofuranyl, piperidinyl, piperazinyl, tetrahydropyranyl, morpholinyl, fluoro, chloro, cyano, —$N(R^{15})_2$, methoxy, ethoxy, or trifluoromethoxy. In some embodiments, each $R^{14}$ is independently methyl, ethyl, iso-propyl, tert-butyl, pyrrolidinyl, piperidinyl, morpholinyl, fluoro, chloro, —$N(R^{15})_2$, or methoxy. In some embodiments, each $R^{14}$ is methyl. In some embodiments, each $R^{14}$ is ethyl. In some embodiments, each $R^{14}$ is n-propyl. In some embodiments, each $R^{14}$ is iso-propyl. In some embodiments, each $R^{14}$ is n-butyl. In some embodiments, each $R^{14}$ is iso-butyl. In some embodiments, each $R^{14}$ is sec-butyl. In some embodiments, each $R^{14}$ is tert-butyl. In some embodiments, each $R^{14}$ is cyclopropyl. In some embodiments, each $R^{14}$ is cyclobutyl. In some embodiments, each $R^{14}$ is cyclopentyl. In some embodiments, each $R^{14}$ is cyclohexyl. In some embodiments, each $R^{14}$ is azetidinyl. In some embodiments, each $R^{14}$ is oxetanyl. In some embodiments, each $R^{14}$ is pyrrolidinyl. In some embodiments, each $R^{14}$ is imidazolidinyl. In some embodiments, each $R^{14}$ is tetrahydrofuranyl. In some embodiments, each $R^{14}$ is piperidinyl. In some embodiments, each $R^{14}$ is piperazinyl. In some embodiments, each $R^{14}$ is tetrahydropyranyl. In some embodiments, each $R^{14}$ is morpholinyl. In some embodiments, each $R^{14}$ is fluoro. In some embodiments, each $R^{14}$ is chloro. In some embodiments, each $R^{14}$ is methoxy. In some embodiments, each $R^{14}$ is ethoxy. In some embodiments, each $R^{14}$ is trifluoromethoxy.

In some embodiments, each $R^{15}$ is independently alkyl, cycloalkyl, aryl, or heteroaryl. In some embodiments, each $R^{15}$ is independently alkyl or cycloalkyl. In some embodiments, each $R^{15}$ is methyl, ethyl, n-propyl, iso-propyl, n-butyl, iso-butyl, sec-butyl, tert-butyl, cyclopropyl, cyclobutyl, cyclopentyl, or cyclohexyl. In some embodiments, each $R^{15}$ is methyl. In some embodiments, each $R^{15}$ is ethyl. In some embodiments, each $R^{15}$ is n-propyl. In some embodiments, each $R^{15}$ is iso-propyl. In some embodiments, each $R^{15}$ is n-butyl. In some embodiments, each $R^{15}$ is iso-butyl. In some embodiments, each $R^{15}$ is sec-butyl. In some embodiments, each $R^{15}$ is tert-butyl. In some embodiments, each $R^{15}$ is cyclopropyl. In some embodiments, each $R^{15}$ is cyclobutyl. In some embodiments, each $R^{15}$ is cyclopentyl. In some embodiments, each $R^{15}$ is cyclohexyl.

In some embodiments:

X is —NH— or —O—;

n is 0;

$R^5$ is phenyl substituted with 0 or 1 $R^{5'}$;

$R^2$ is phenyl substituted with at least one $R^7$ and 0, 1, or 2 $R^8$; and $R^3$ is pyrazolyl substituted with 0, 1, 2, or 3 $R^{12}$.

In some embodiments, $R^2$ is phenyl substituted with 1 $R^7$ and 0, 1, or 2 $R^8$.

In some embodiments, X is —NH—.

In some embodiments, $R^{5'}$ is fluoromethyl, difluoromethyl, or trifluoromethyl.

In some embodiments:

$R^7$ is

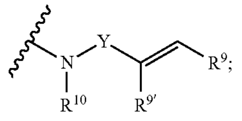

and $R^8$ is halo.

In some embodiments:

$R^8$ is fluoro;

Y is —C(═O)—;

$R^9$ and $R^{9'}$ are hydrogen; and $R^{10}$ is hydrogen.

In some embodiments, $R^{12}$ is alkyl.

In some embodiments, $R^{12}$ is methyl.

In some embodiments, the compound is of Formula I-A, Formula I-B, Formula I-C, Formula I-D, Formula I-E, Formula I-F, or Formula I-G:

Formula I-A

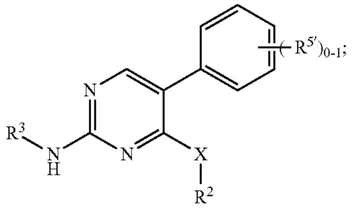

Formula I-B

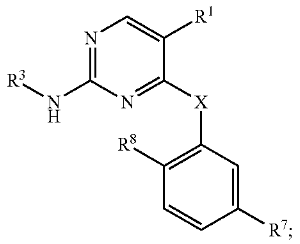

Formula I-C

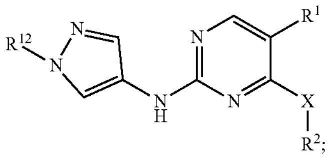

Formula I-D

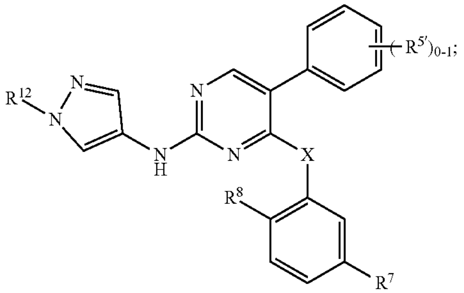

-continued

Formula I-E

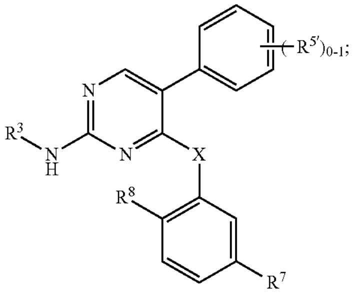

Formula I-F

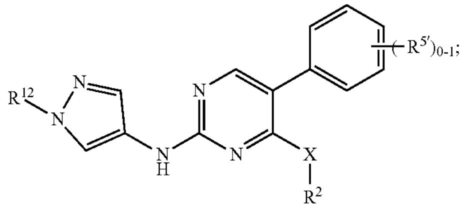

Formula I-G

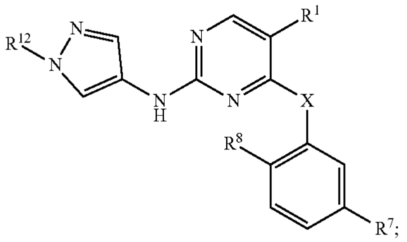

or a pharmaceutically acceptable salt or stereoisomer thereof.

In some embodiments, the compound is of Formula I-A:

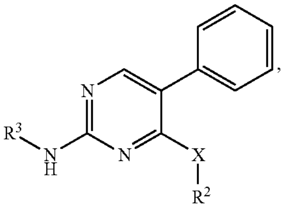

or a pharmaceutically acceptable salt or stereoisomer thereof. In some embodiments, the compound is of Formula I-A:

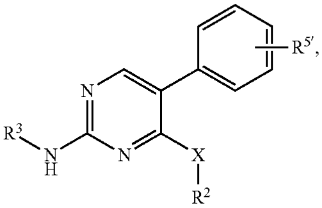

or a pharmaceutically acceptable salt or stereoisomer thereof.

In some embodiments, the compound is of Formula I-B:

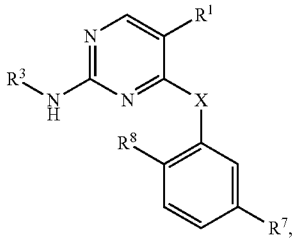

or a pharmaceutically acceptable salt or stereoisomer thereof. In some embodiments of the compound of Formula I-B, wherein $R^1$ is $R^5$. In some embodiments of the compound of Formula I-B, $R^5$ is substituted with 0 or 1 $R^{5'}$. In some embodiments of the compound of Formula I-B, $R^5$ is unsubstituted. In some embodiments of the compound of Formula I-B, $R^5$ is substituted with 1 $R^{5'}$.

In some embodiments, the compound is of Formula I-C:

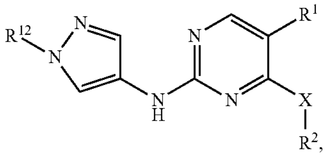

or a pharmaceutically acceptable salt or stereoisomer thereof. In some embodiments of the compound of Formula I-B, wherein $R^1$ is $R^5$. In some embodiments of the compound of Formula I-C, $R^5$ is substituted with 0 or 1 $R^{5'}$. In some embodiments of the compound of Formula I-C, $R^5$ is unsubstituted. In some embodiments of the compound of Formula I-C, $R^5$ is substituted with 1 $R^{5'}$.

In some embodiments, the compound is of Formula I-D:

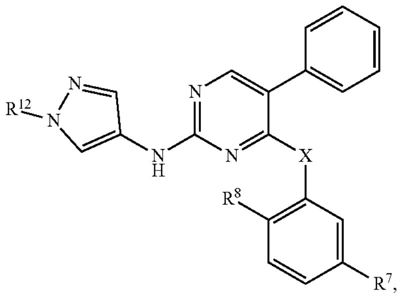

or a pharmaceutically acceptable salt or stereoisomer thereof. In some embodiments, the compound is of Formula I-D:

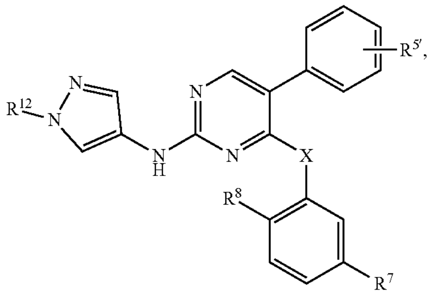

or a pharmaceutically acceptable salt or stereoisomer thereof.

In some embodiments, the compound is of Formula I-E:

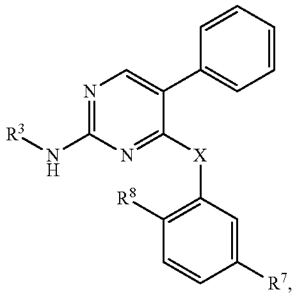

or a pharmaceutically acceptable salt or stereoisomer thereof. In some embodiments, the compound is of Formula I-E:

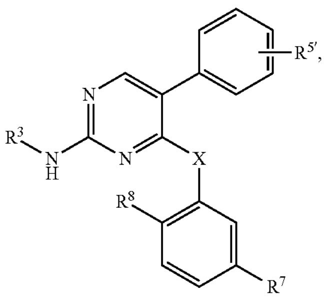

or a pharmaceutically acceptable salt or stereoisomer thereof.

In some embodiments, the compound is of Formula I-F:

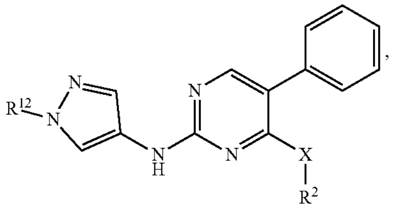

or a pharmaceutically acceptable salt or stereoisomer thereof. In some embodiments, the compound is of Formula I-F:

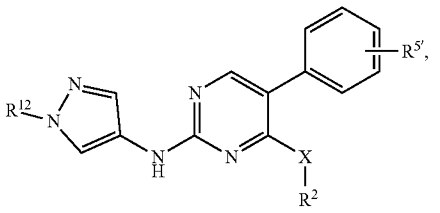

or a pharmaceutically acceptable salt or stereoisomer thereof.

In some embodiments, the compound is of Formula I-G:

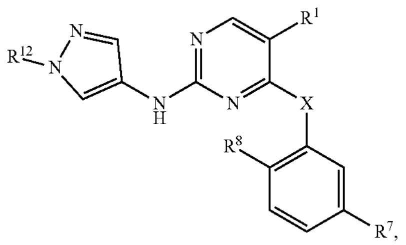

or a pharmaceutically acceptable salt or stereoisomer thereof. In some embodiments of the compound of Formula I-G, wherein $R^1$ is $R^5$. In some embodiments of the compound of Formula I-G, $R^5$ is substituted with 0 or 1 $R^{5'}$. In some embodiments of the compound of Formula I-G, $R^5$ is unsubstituted. In some embodiments of the compound of Formula I-G, $R^5$ is substituted with 1 $R^{5'}$.

In some embodiments, the compound of Formula I is:

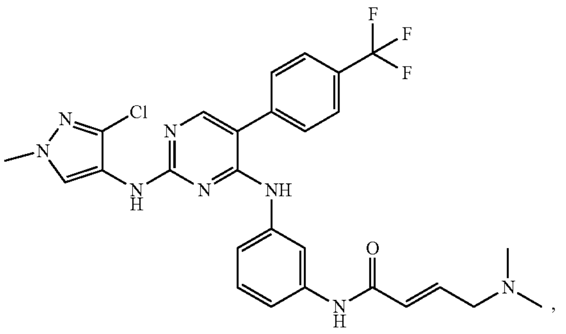

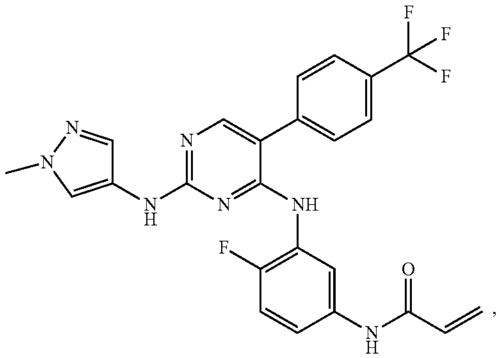

-continued

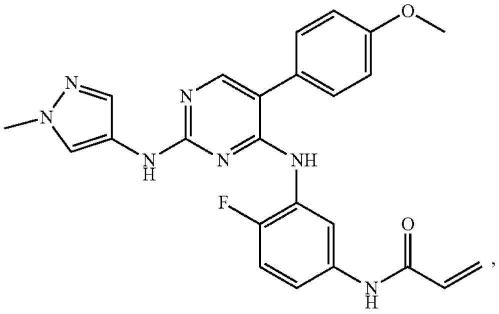

,

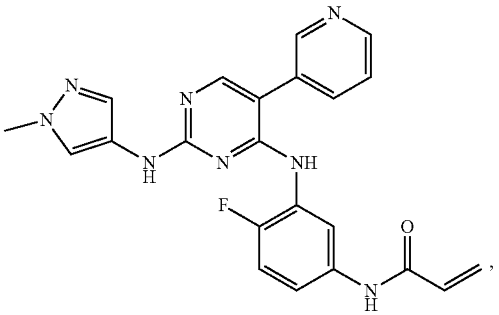

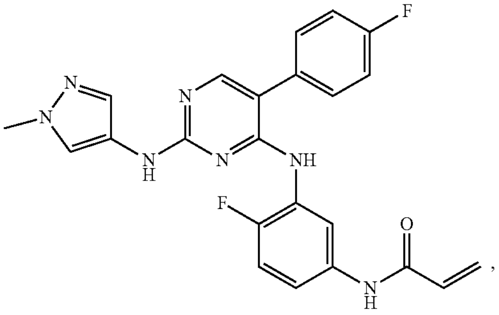

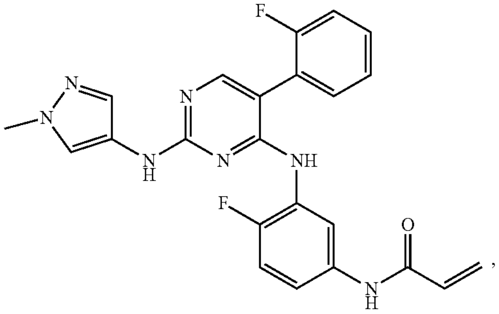

,

-continued
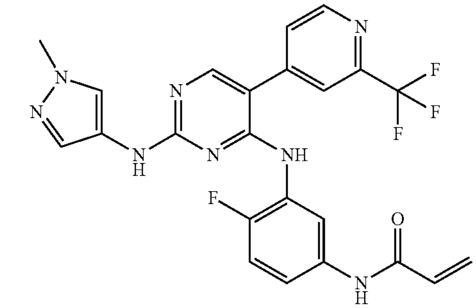
,
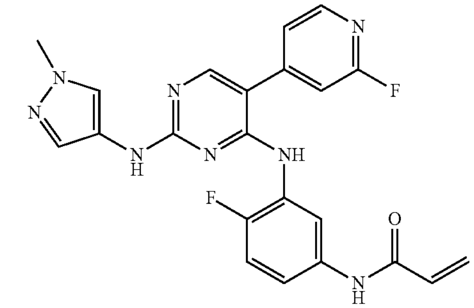
,
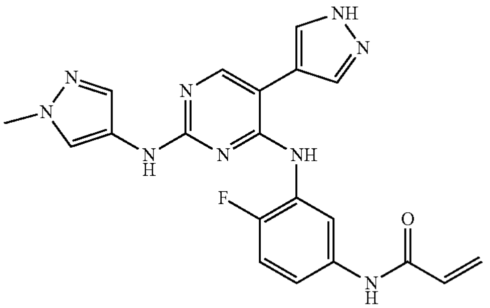
,
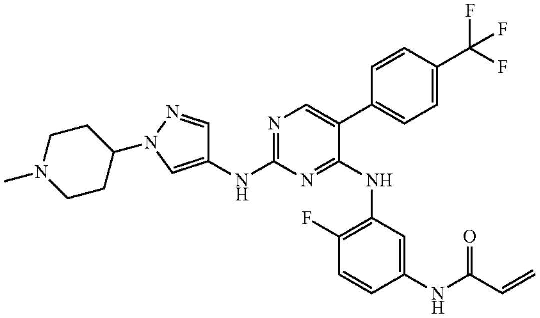
,
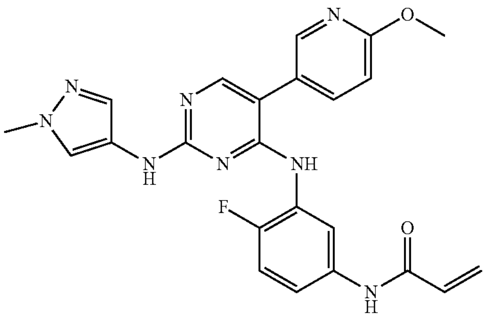
,
-continued
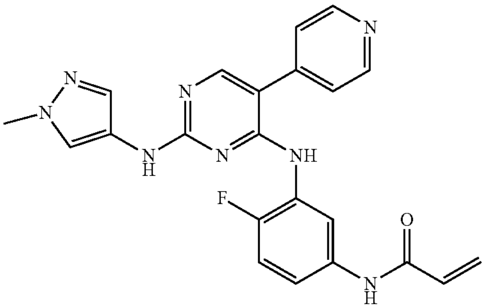
,
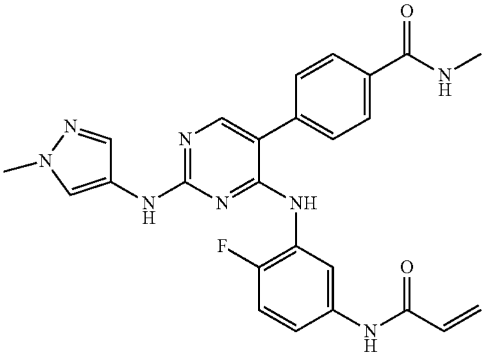
,
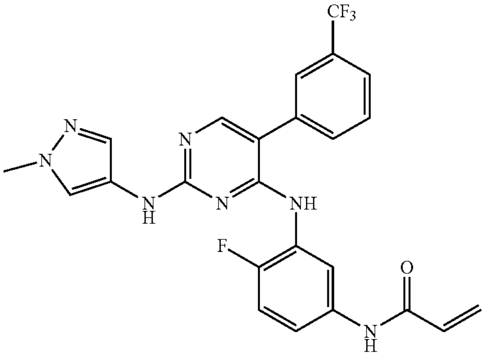
,
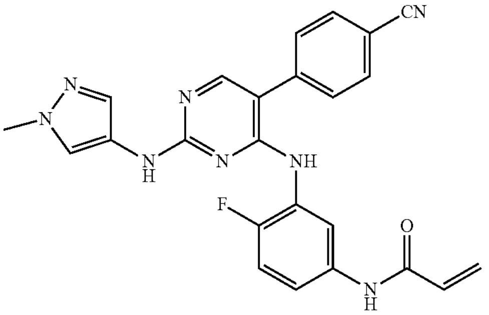
,
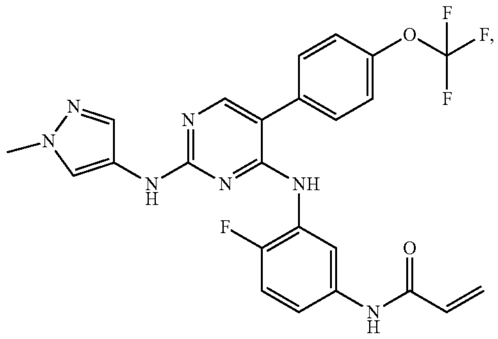

-continued
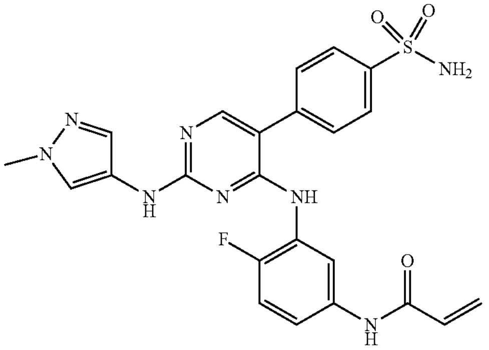
,
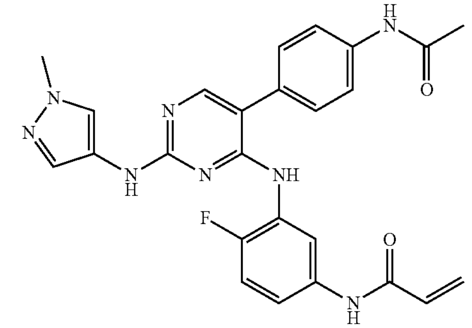
,
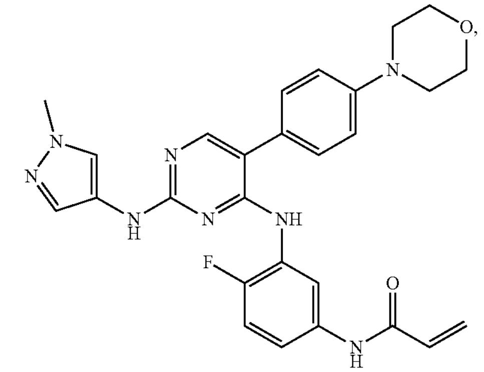
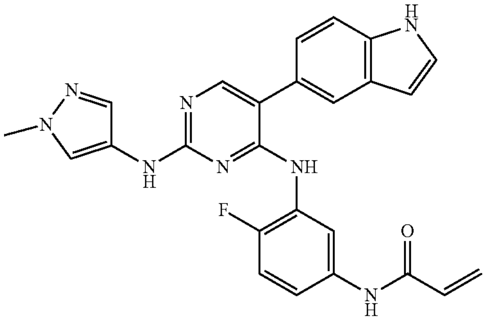
,
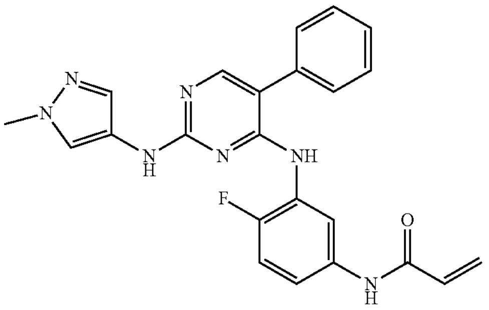
,
-continued
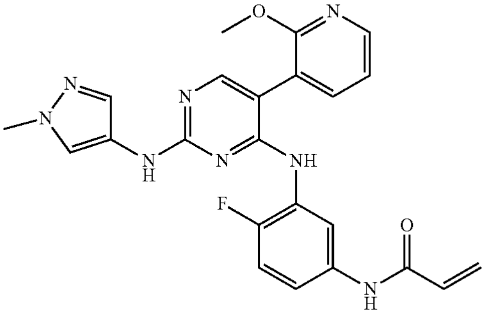
,
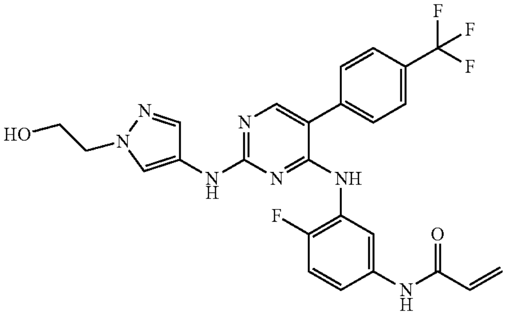
,
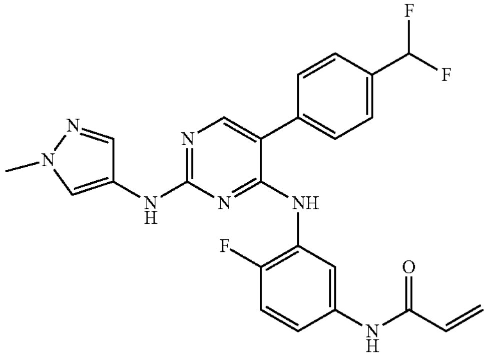
,
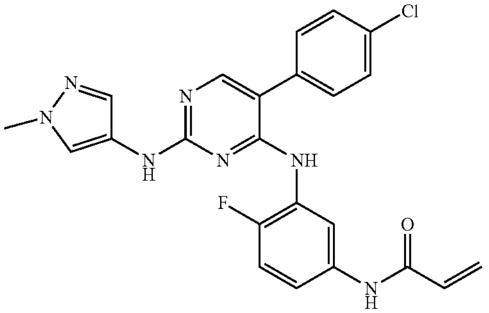
,
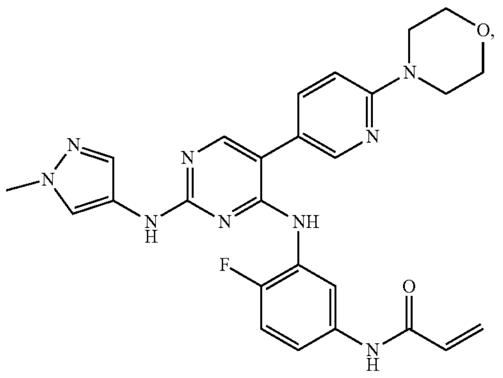

-continued
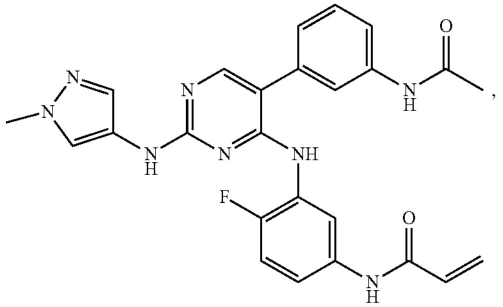
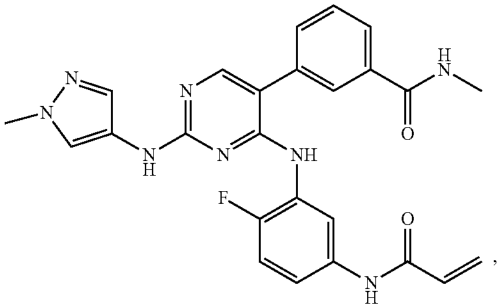
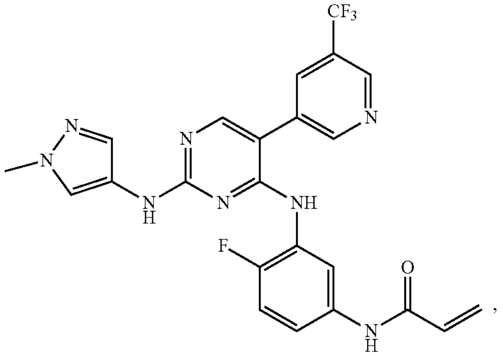
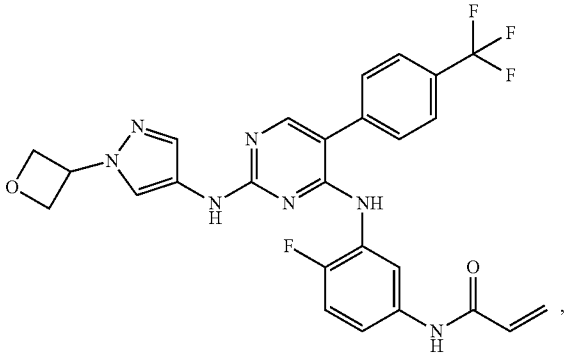
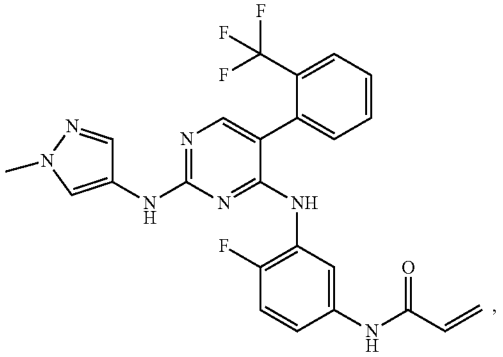
-continued
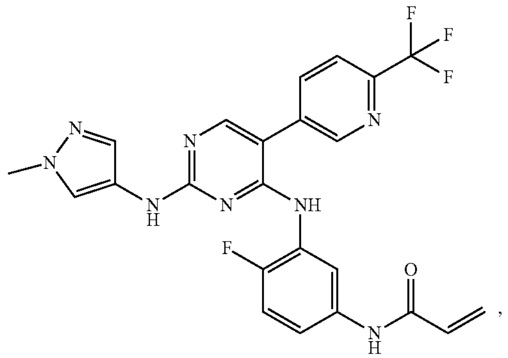
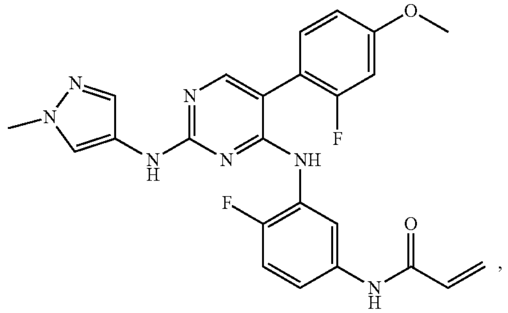
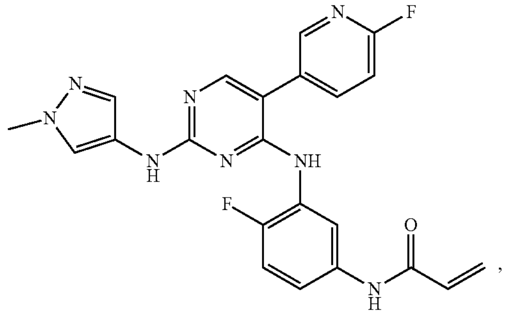
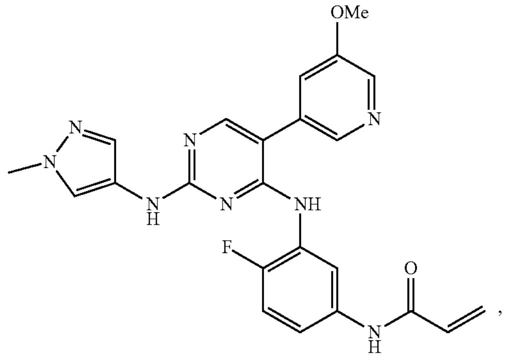
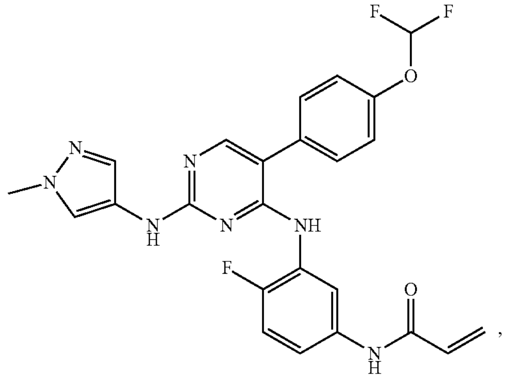

-continued
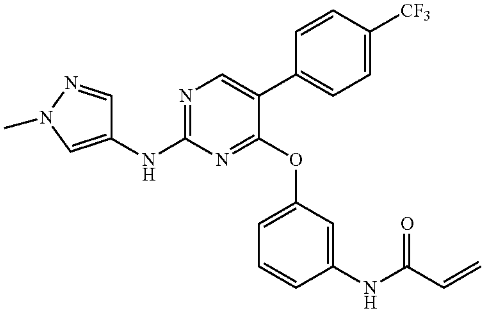
,
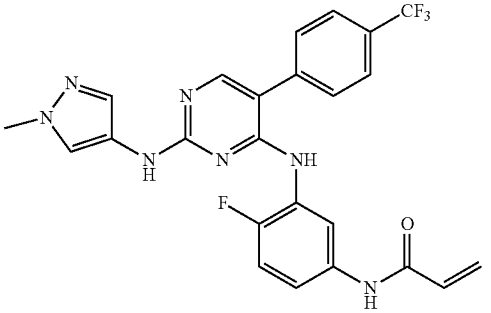
,
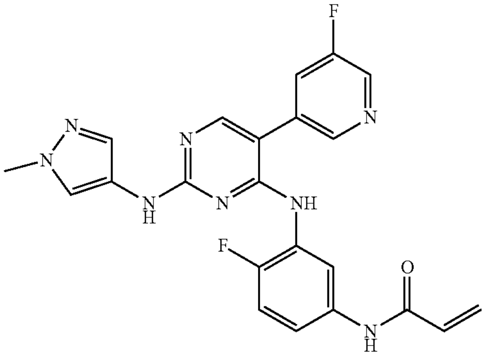
,
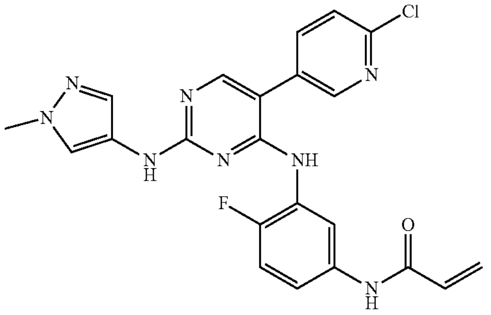
,
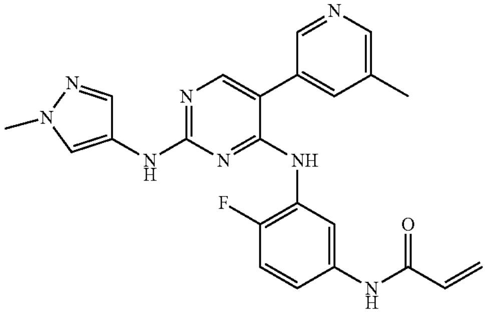
,
-continued
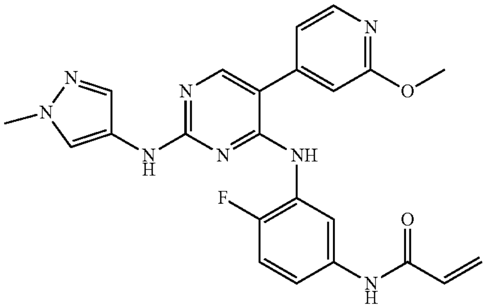
,
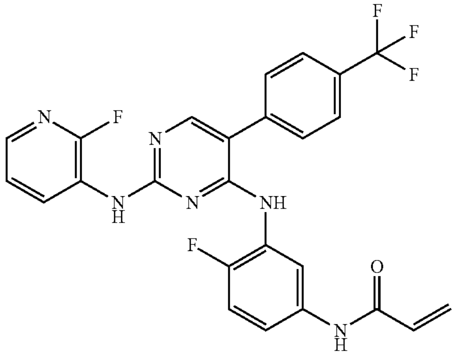
,
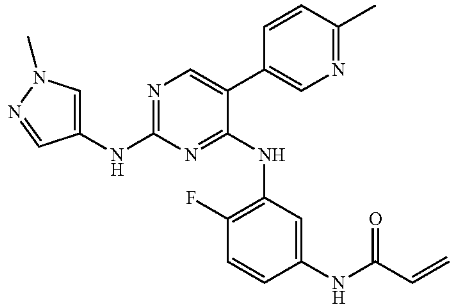
,
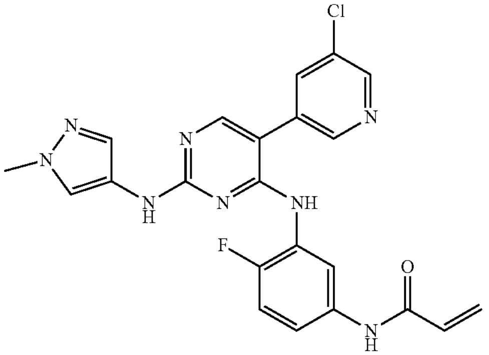
,
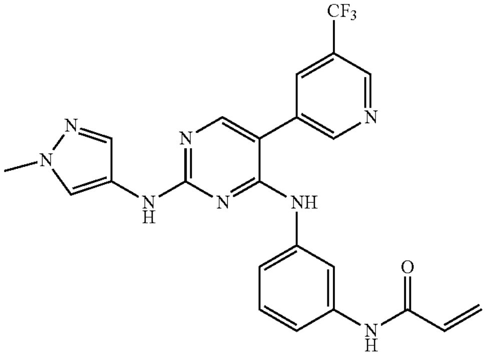
, -continued
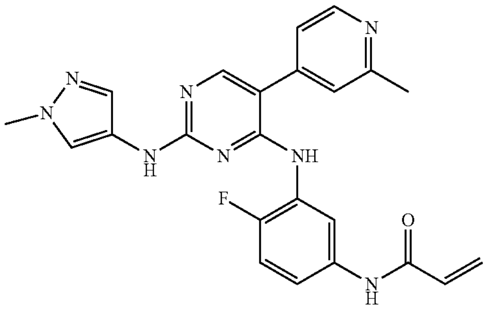
,
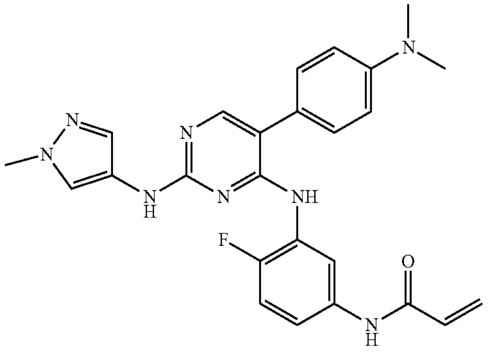
,
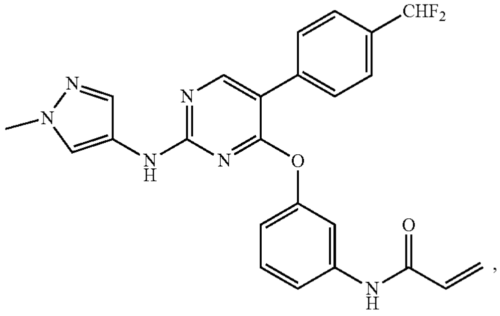
,
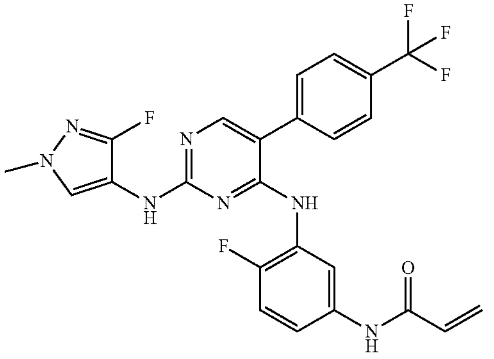
,
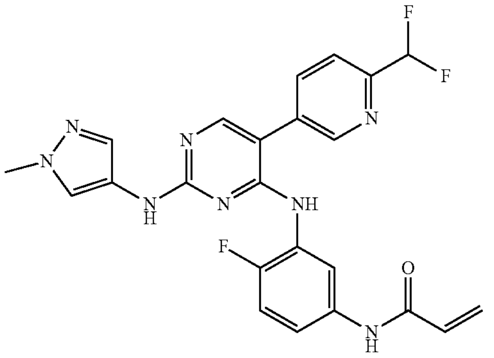
,
-continued
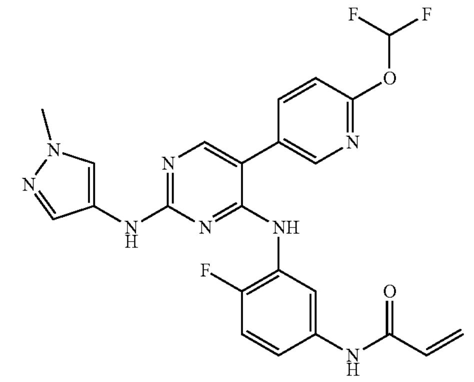
,
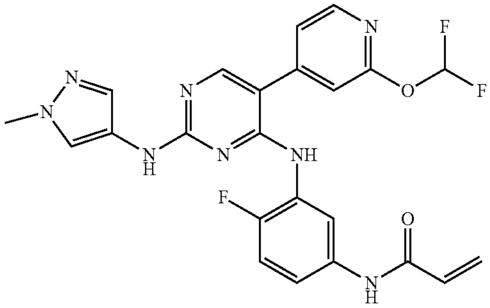
,
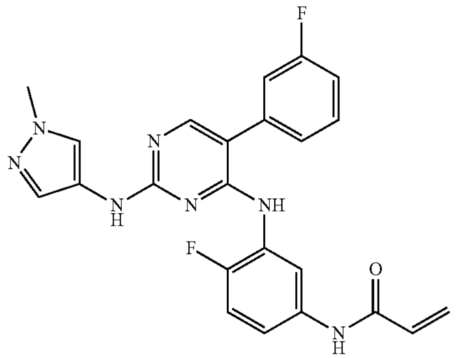
,
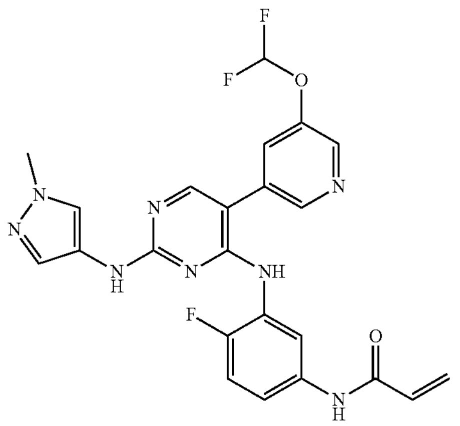
, -continued
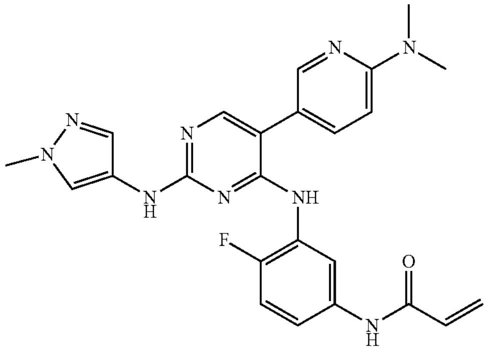
,
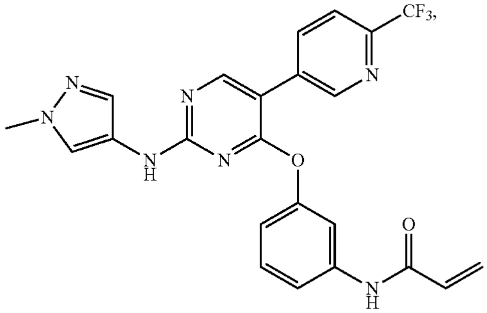
,
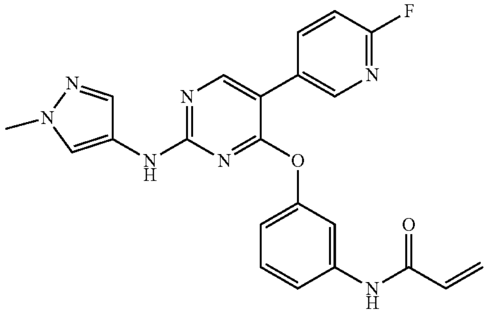
,
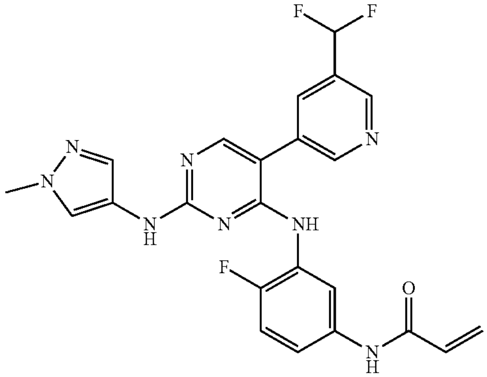
,
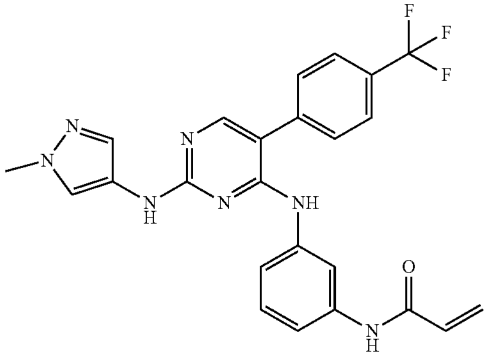
,
-continued
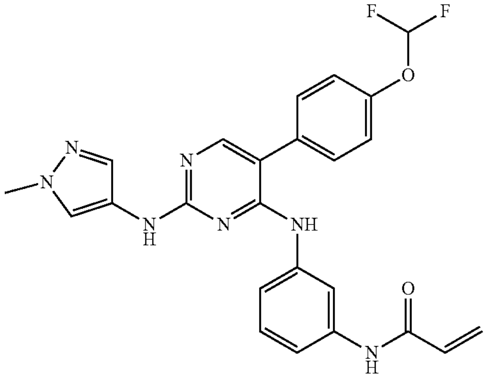
,
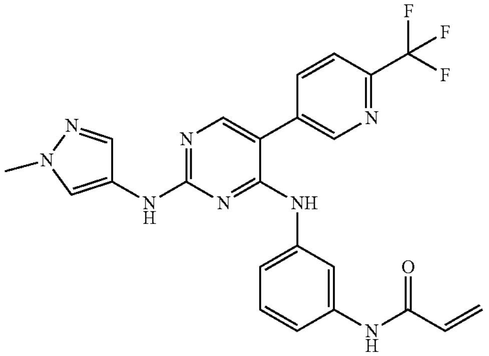
,
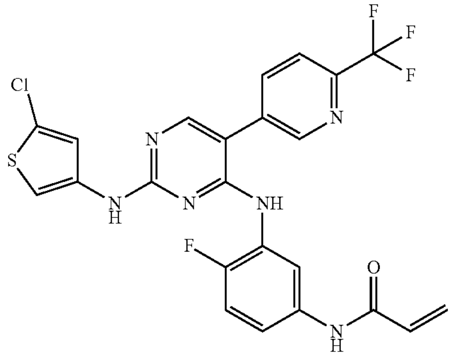
,
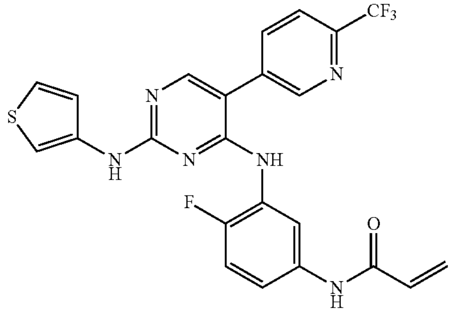
,
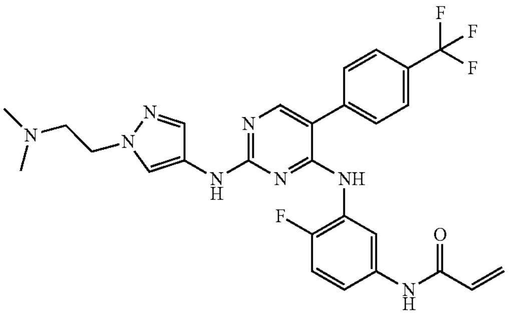
, -continued
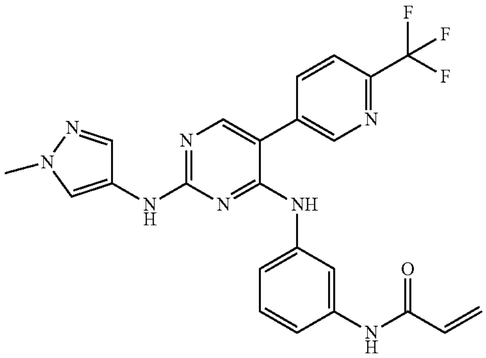
,
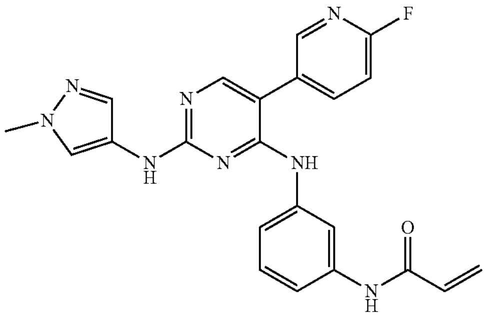
,
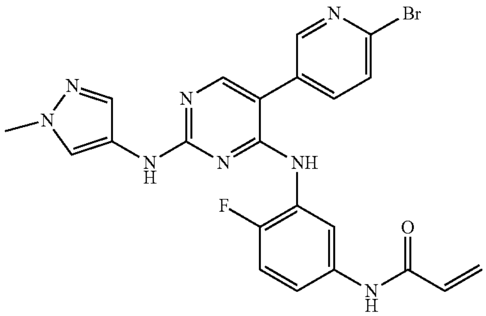
,
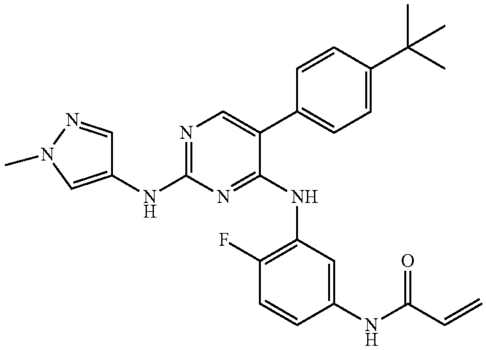
,
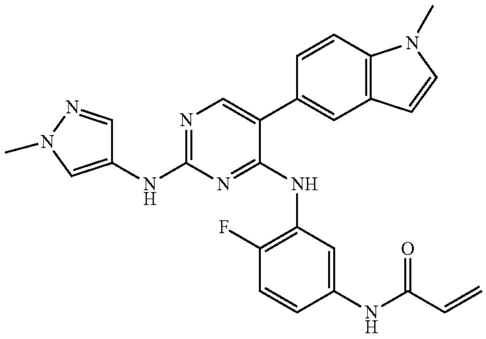
,
-continued
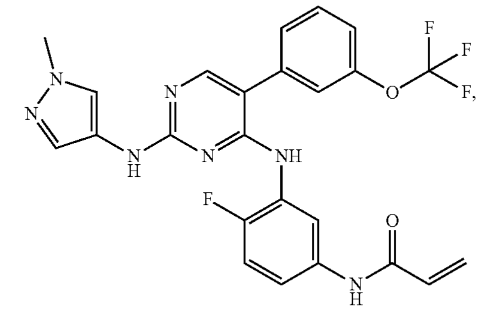
,
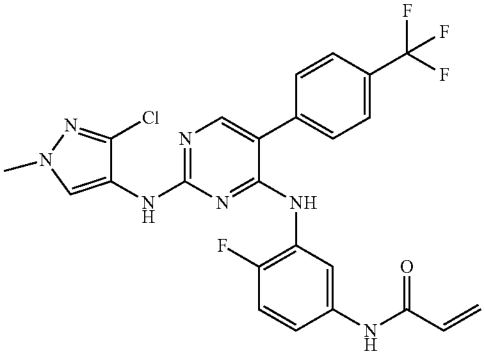
,
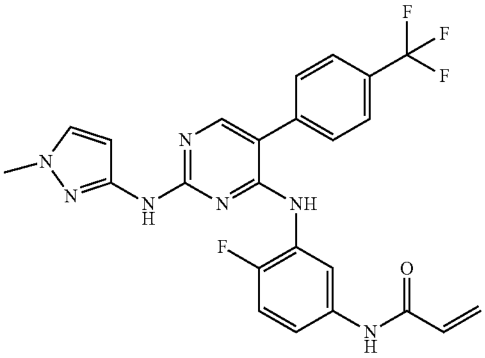
,
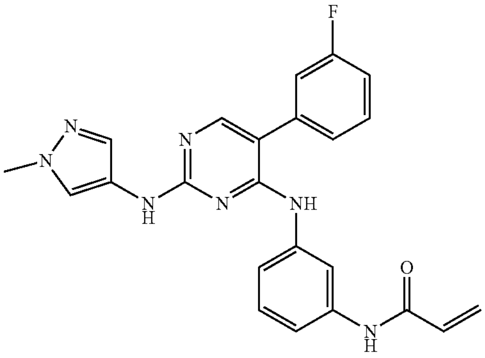
, -continued
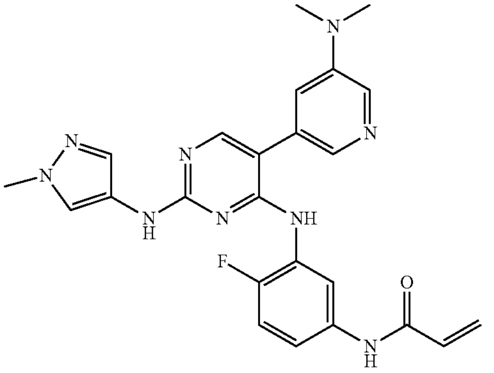
,
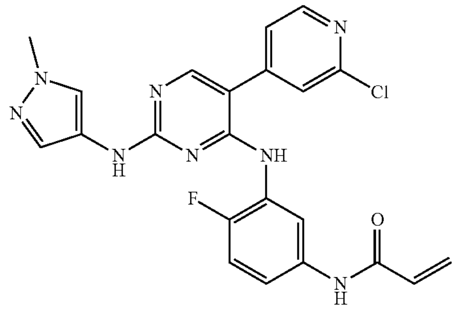
,
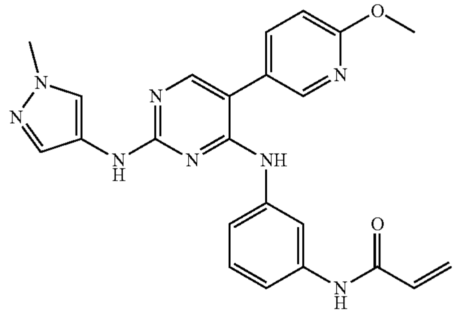
,
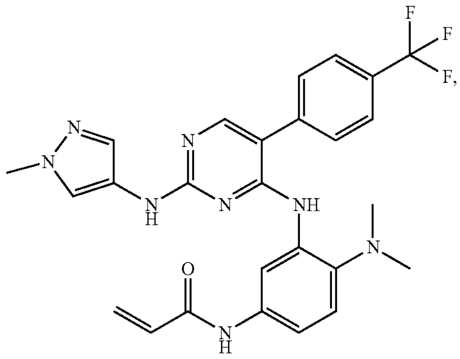
,
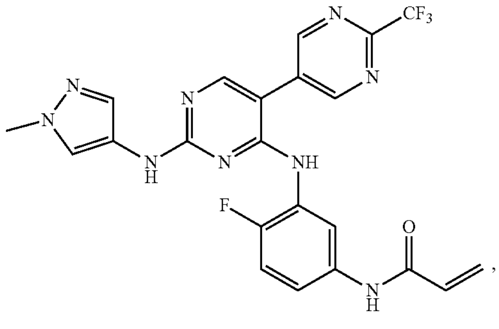
,
-continued
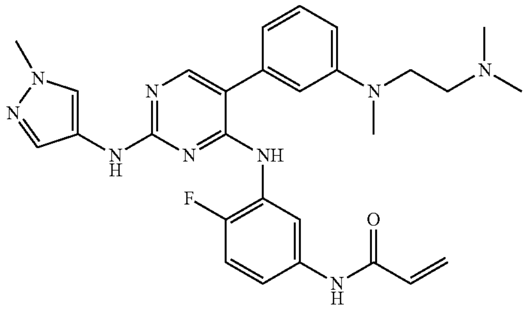
,
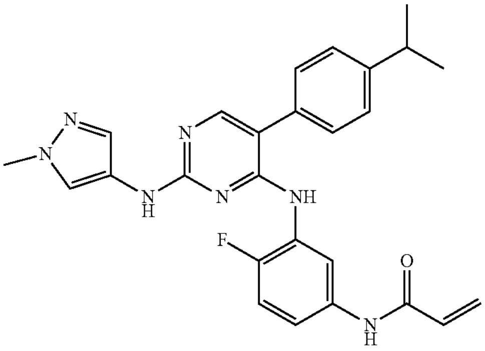
,
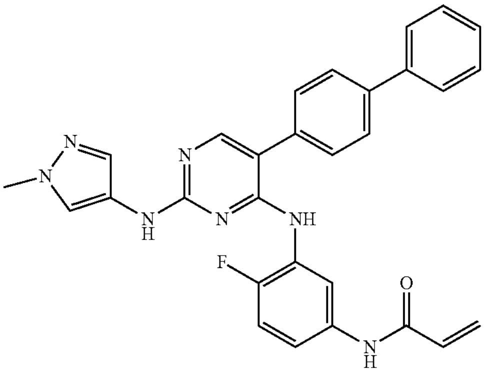
,
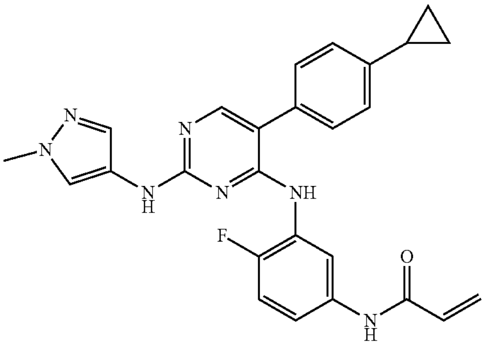
,
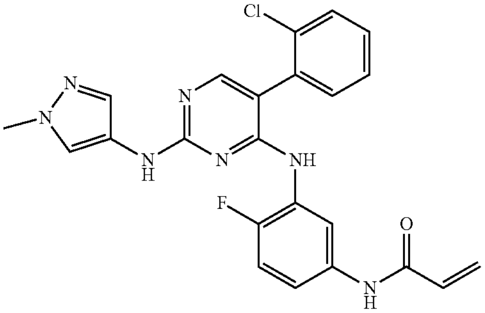
, -continued
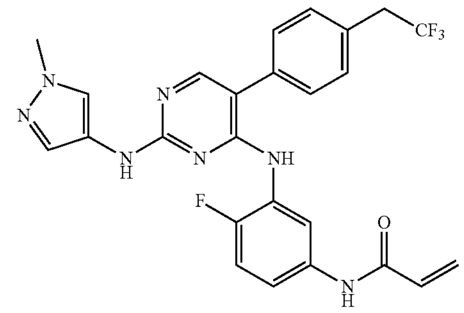
,
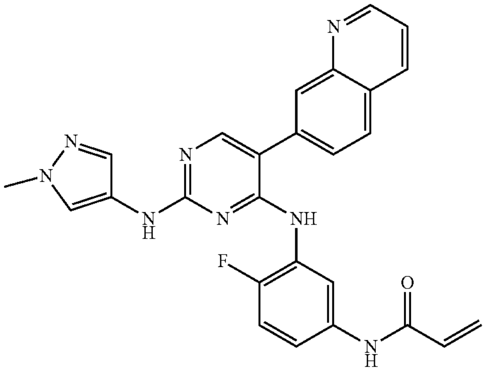
,
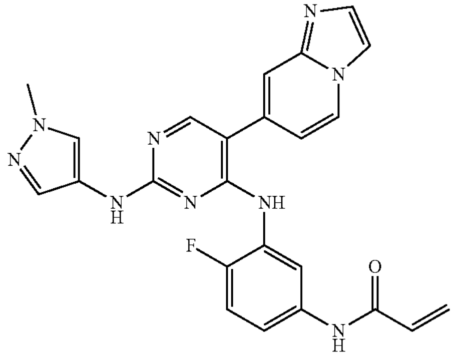
,
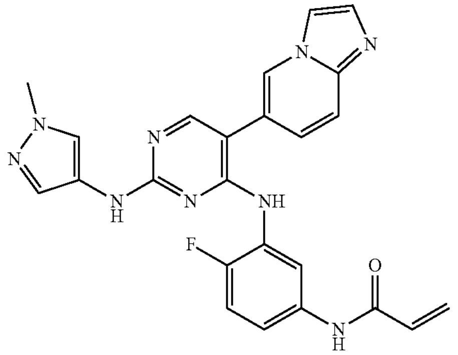
,
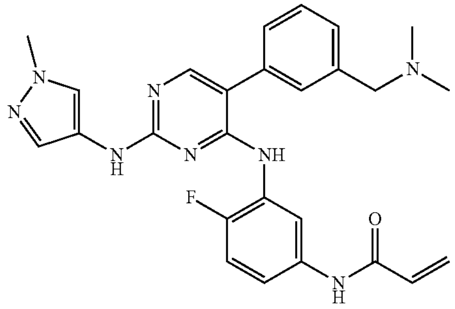
,
-continued
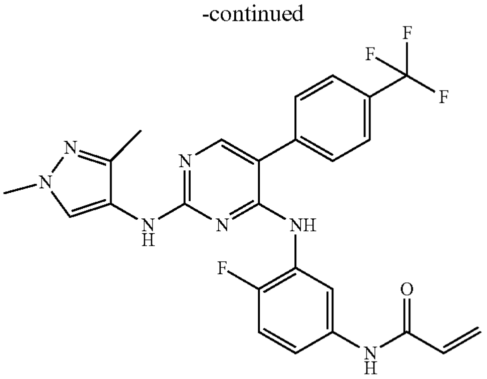
,
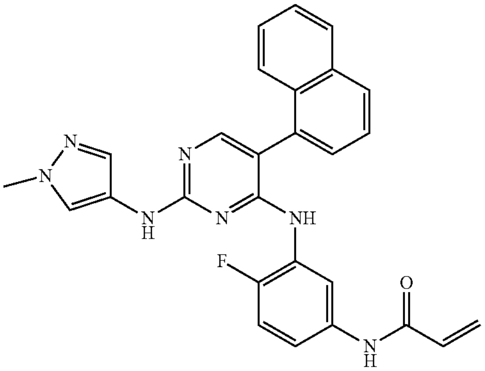
,
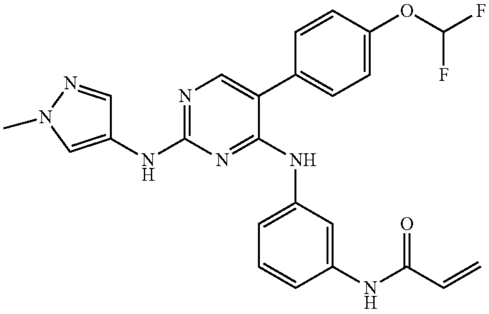
,
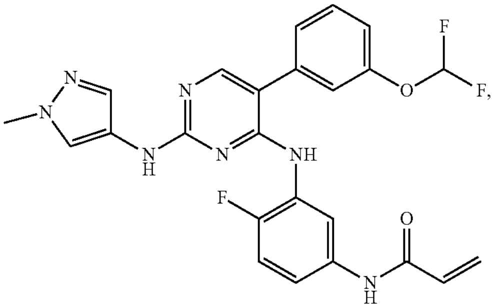
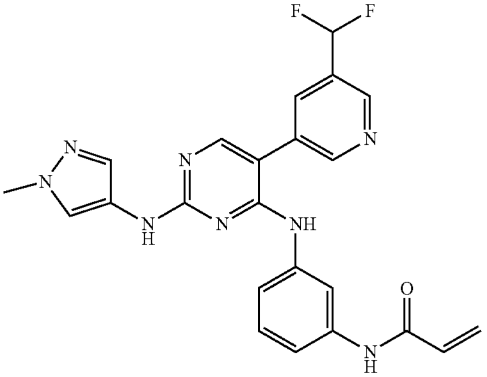
, -continued
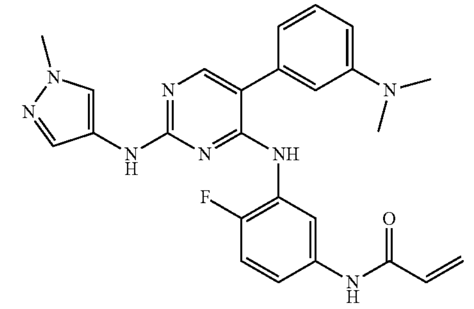
,
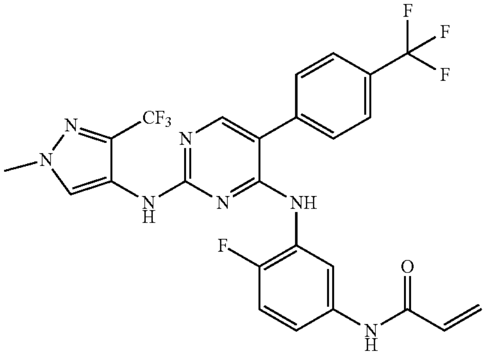
,
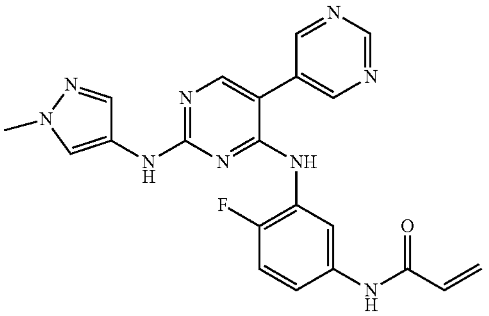
,
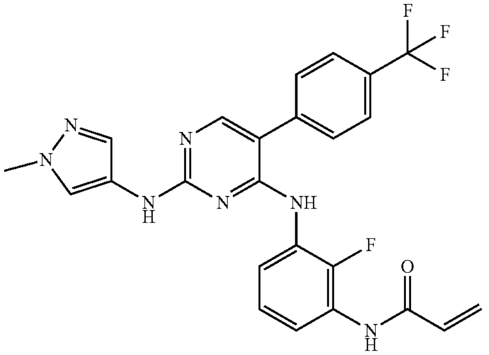
,
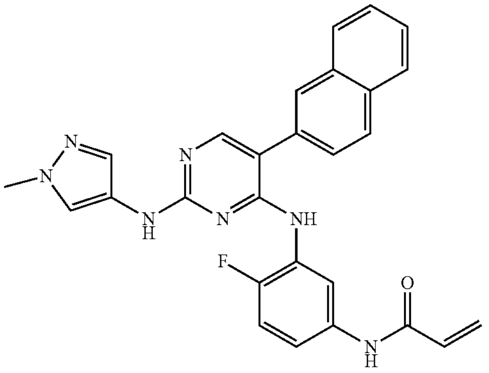
,
-continued
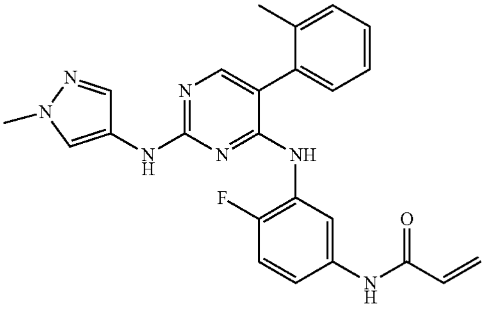
,
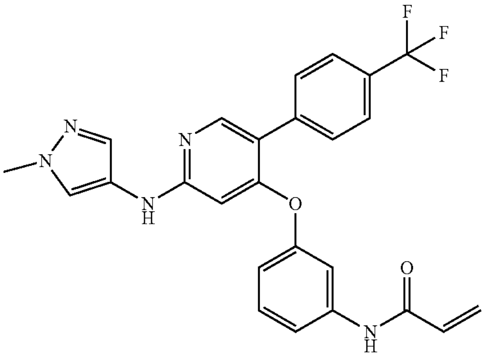
,
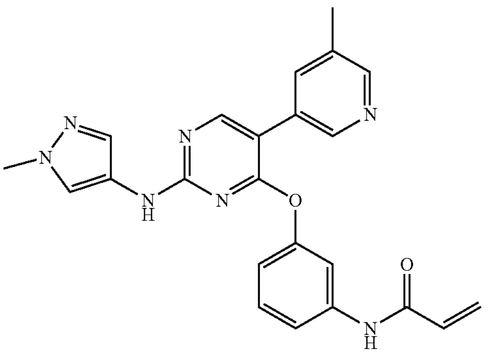
,
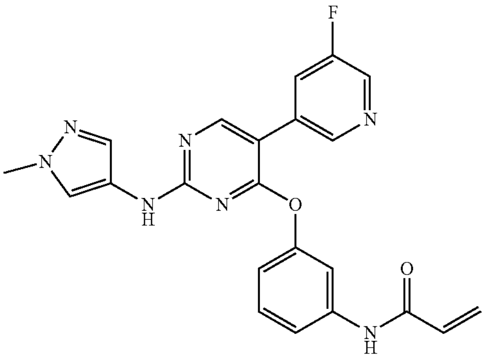
,
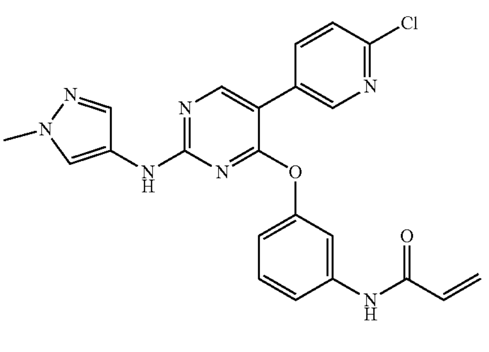
, -continued
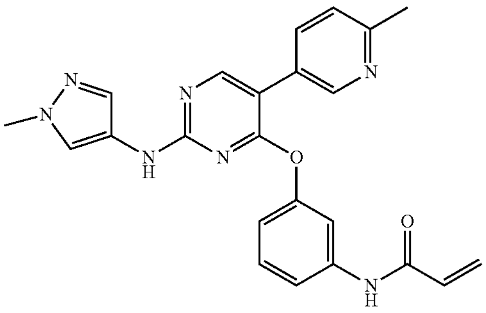
,
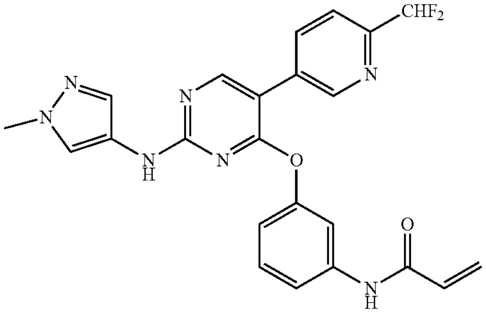
,
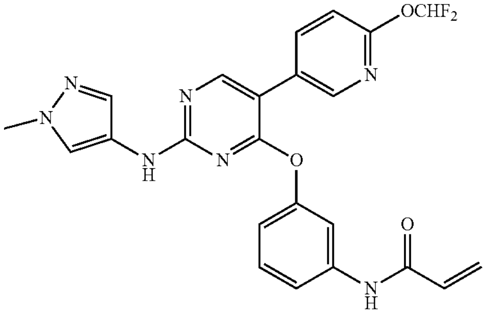
,
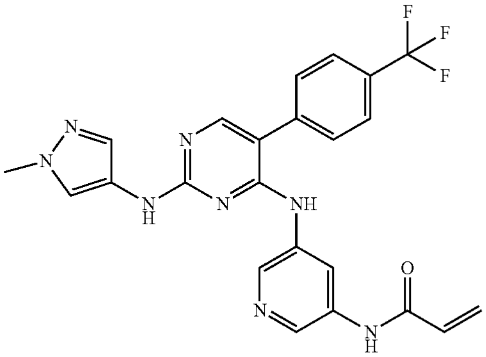
,
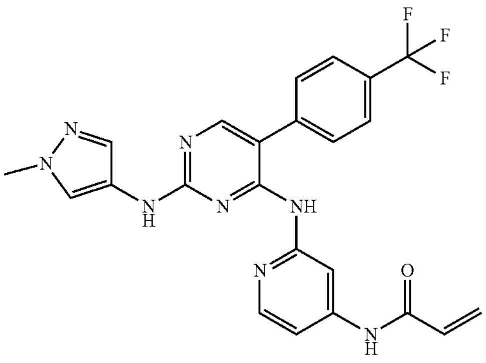
,
-continued
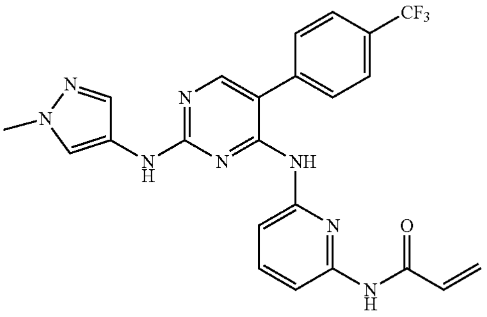
,
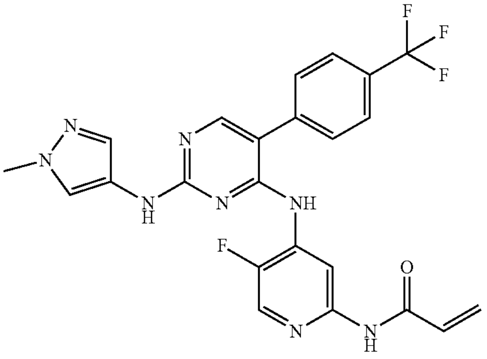
,
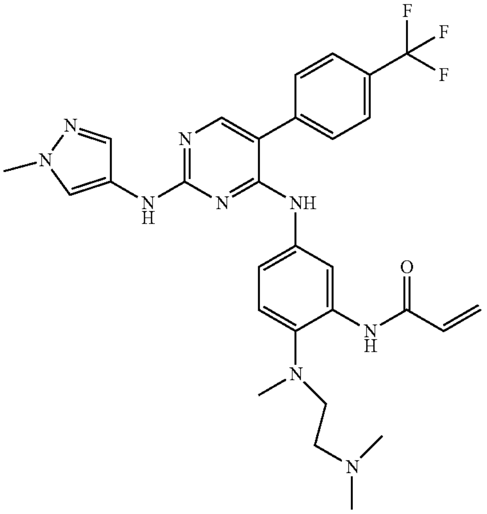
,
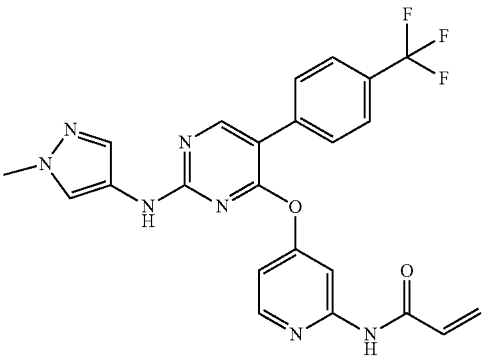
, -continued
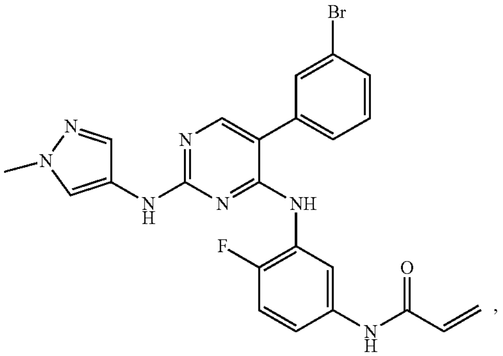
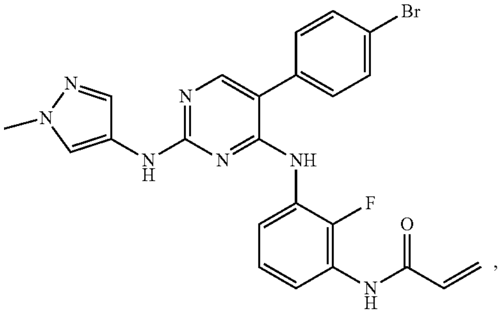
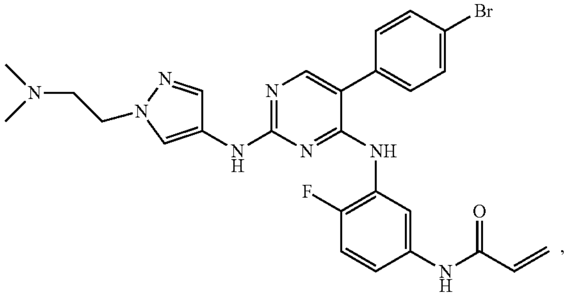
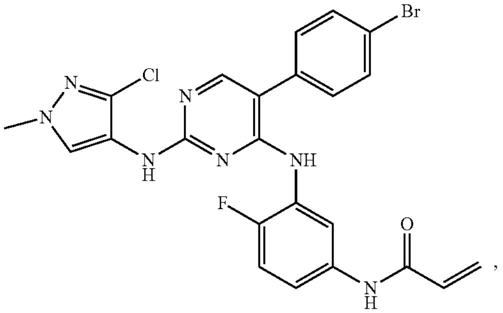
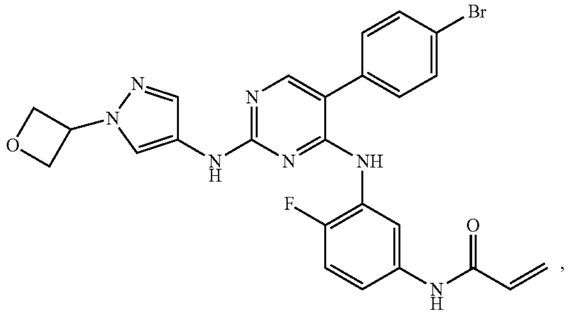
-continued
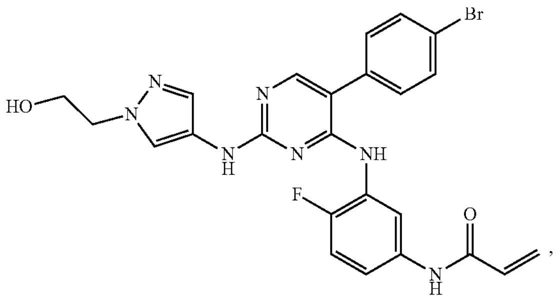
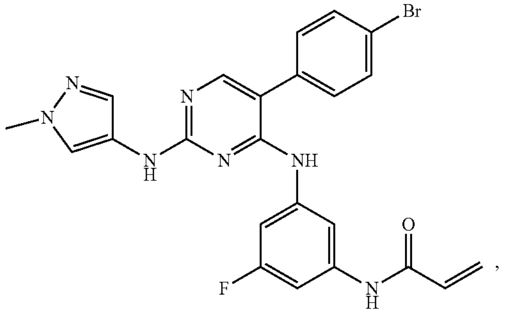
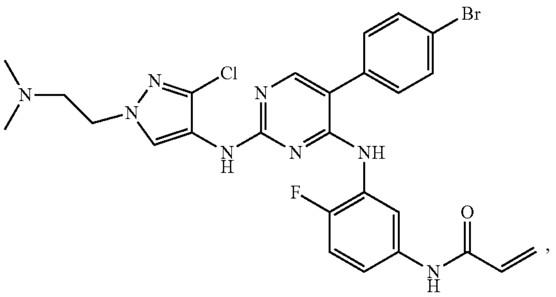
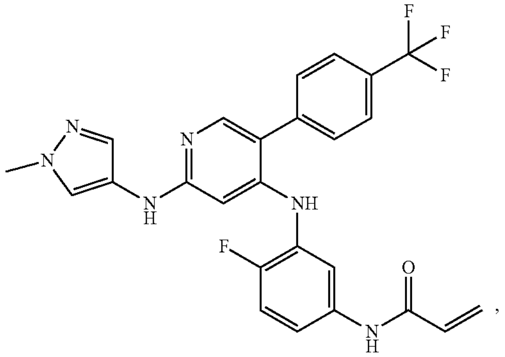
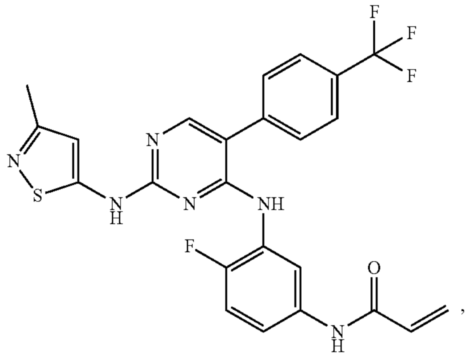

-continued
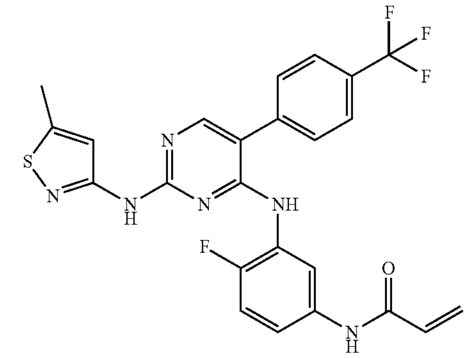
,
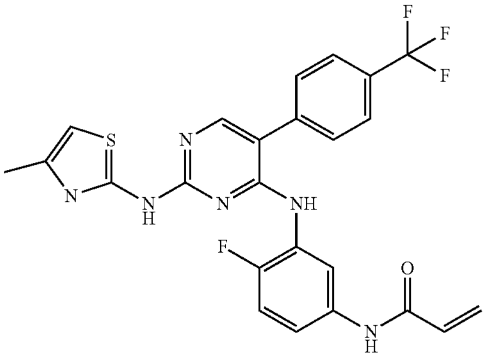
,
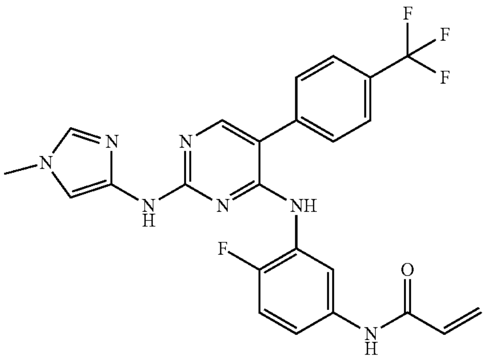
,
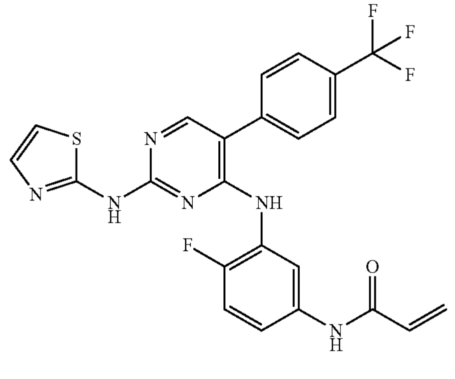
,
-continued
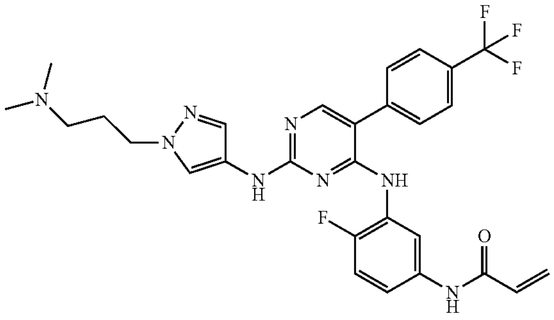
,
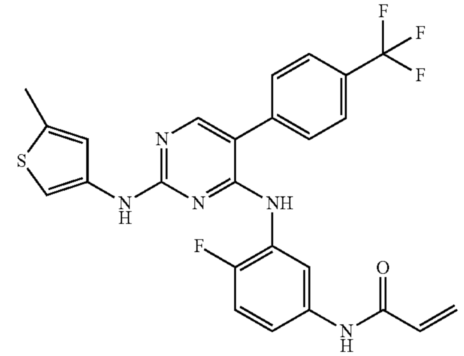
,
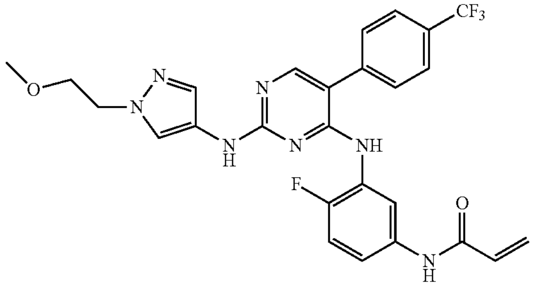
,
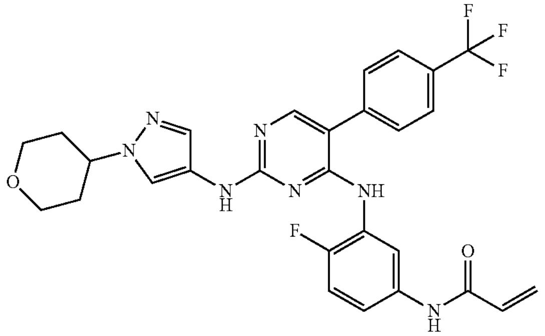
,
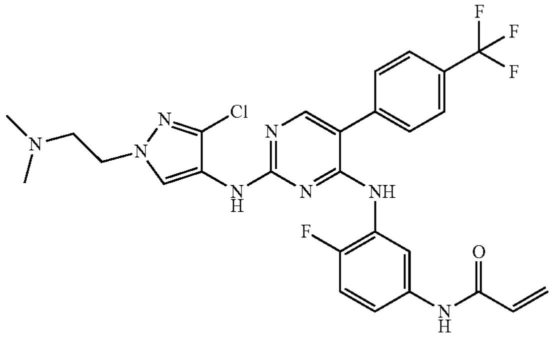
,, -continued
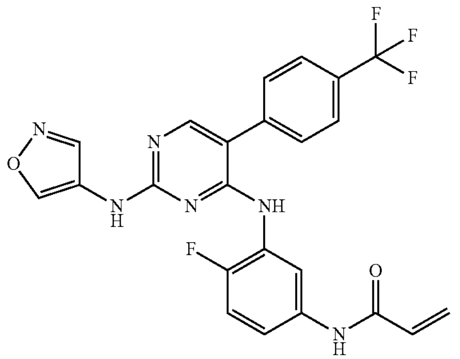
,
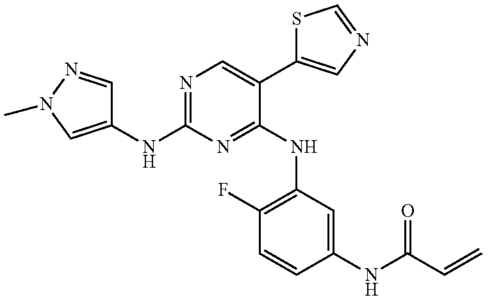
,
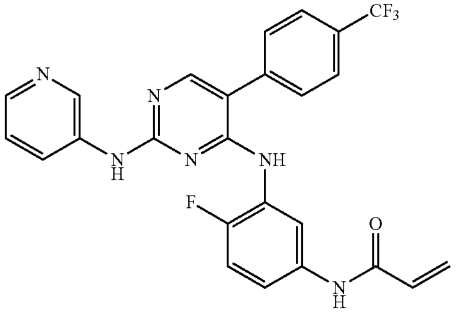
,
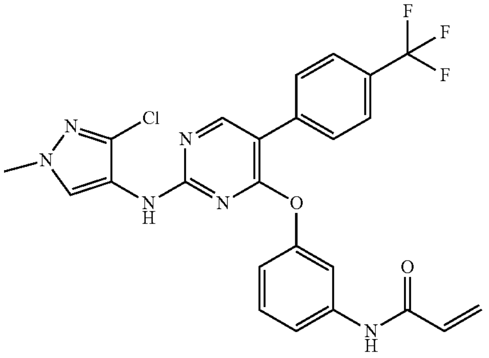
,
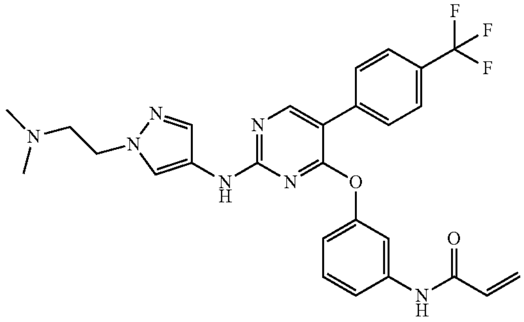
,
-continued
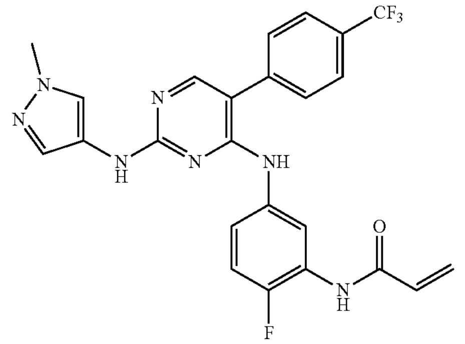
,
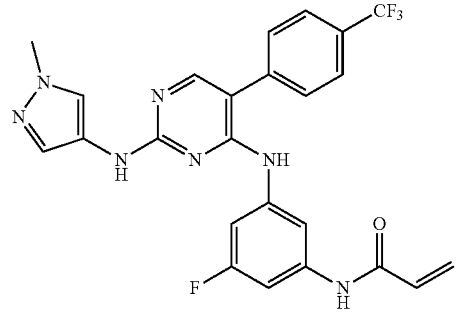
,
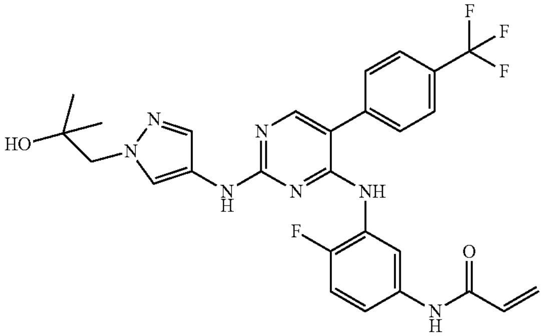
,
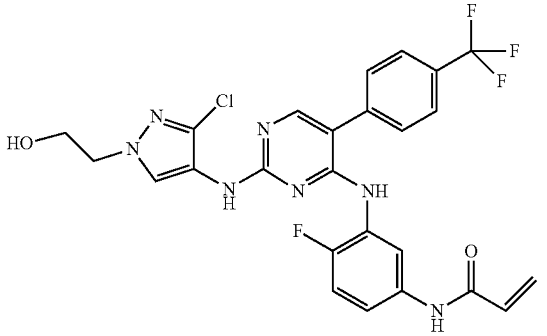
,
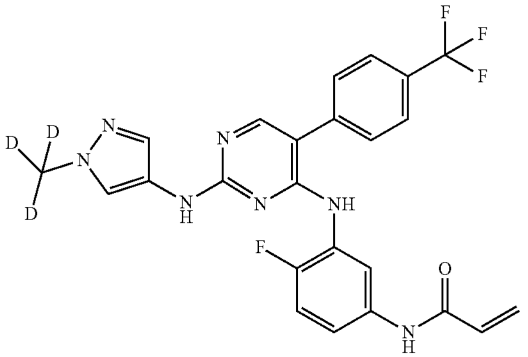
, -continued
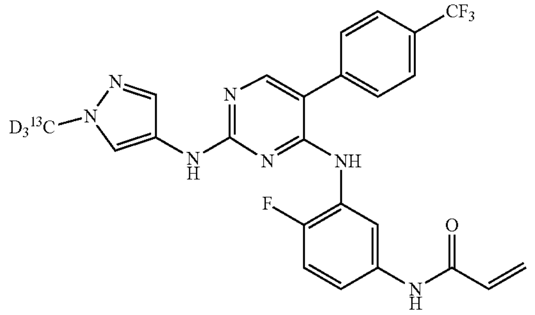
,
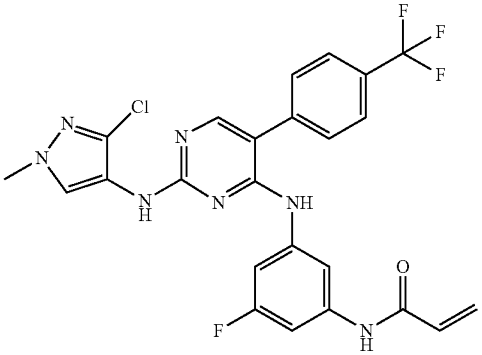
,
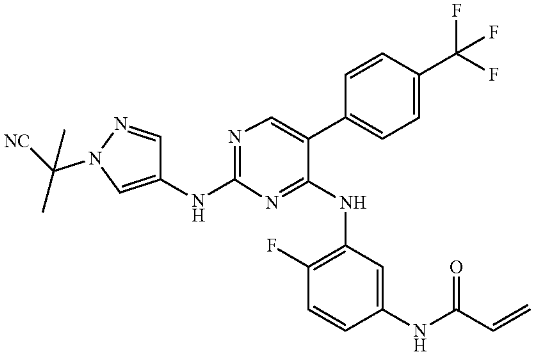
,
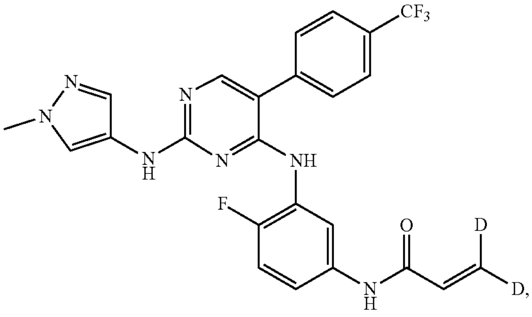
,
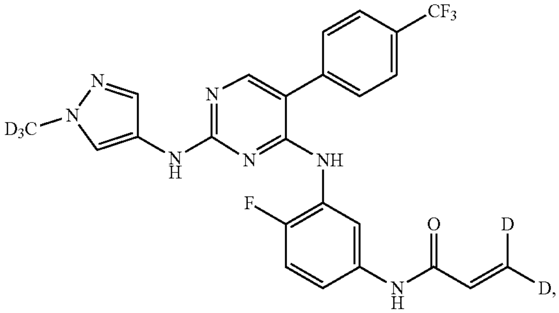
,
-continued
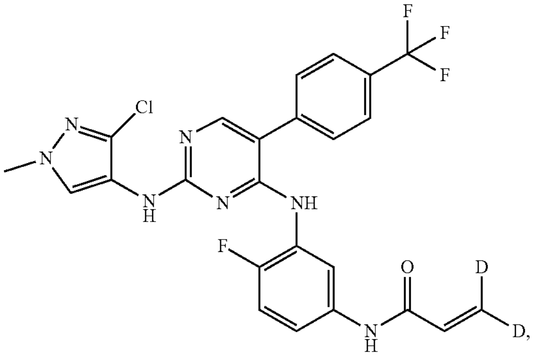
,
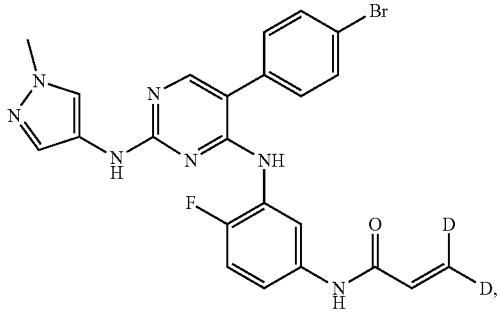
,
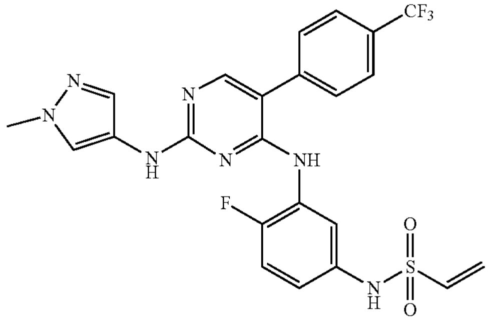
,
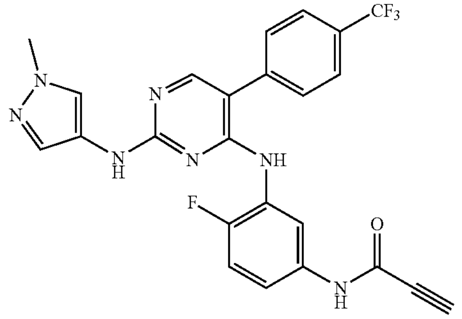
,
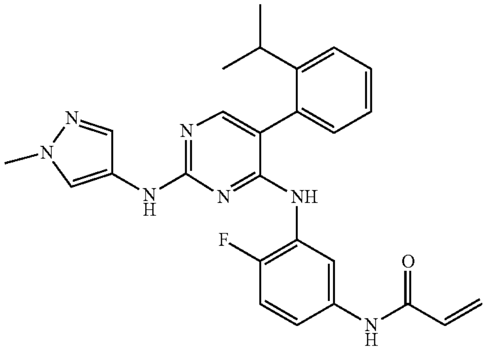
, -continued
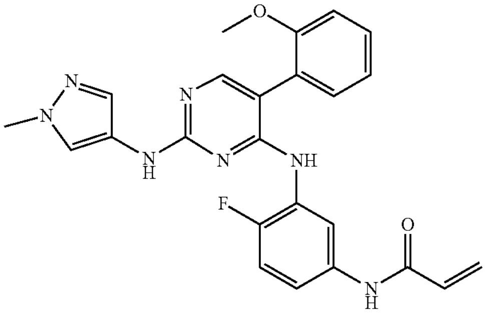
,
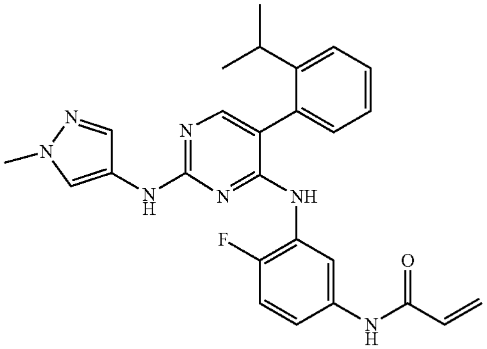
,
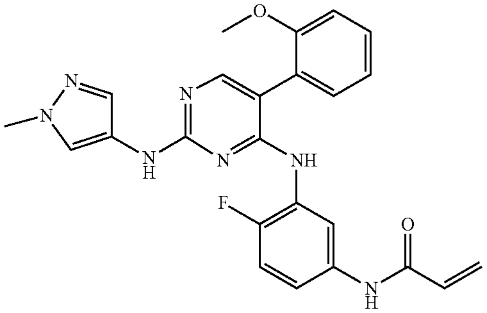
,
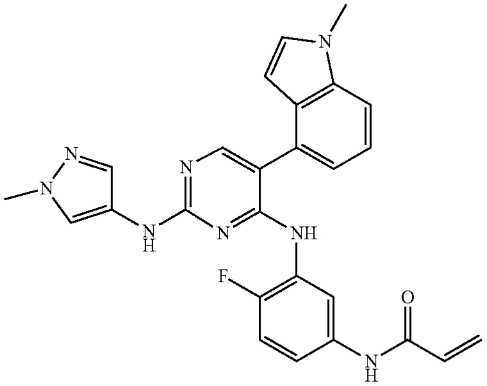
,
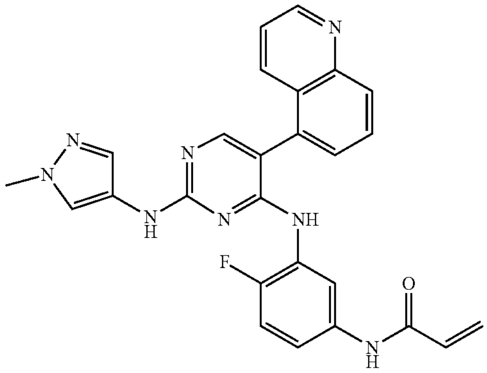
,
-continued
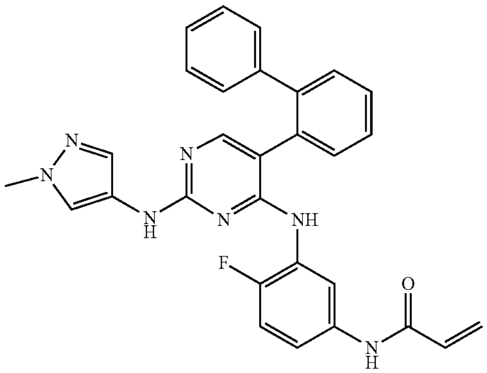
,
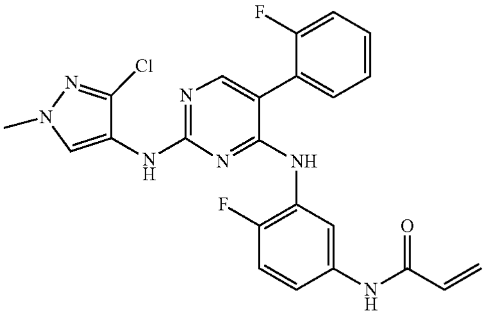
,
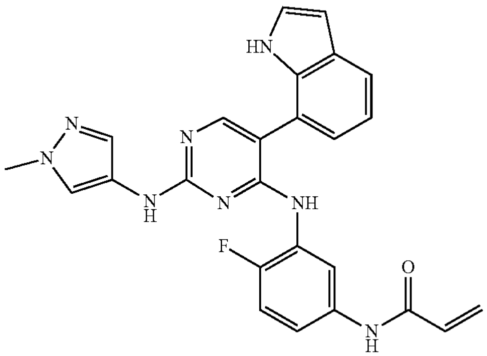
,
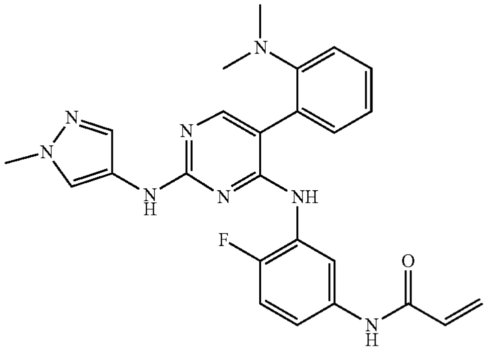
, -continued
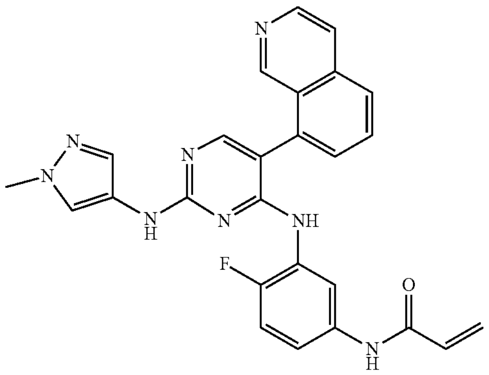
,
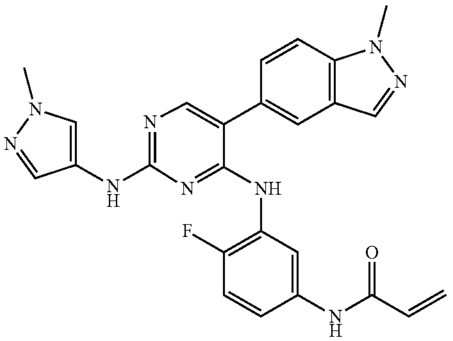
,
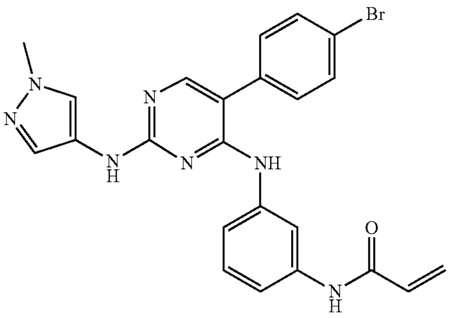
,
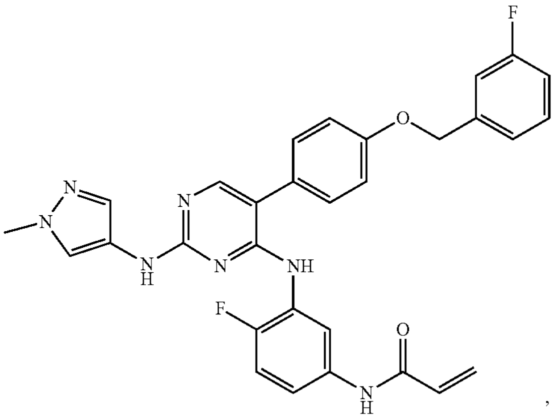
,
-continued
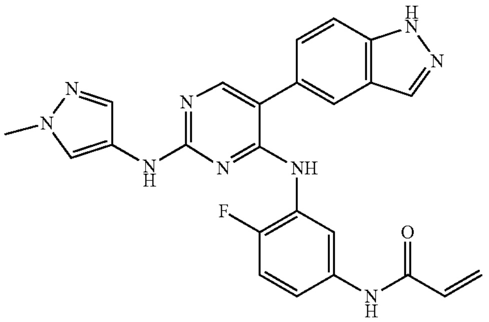
,
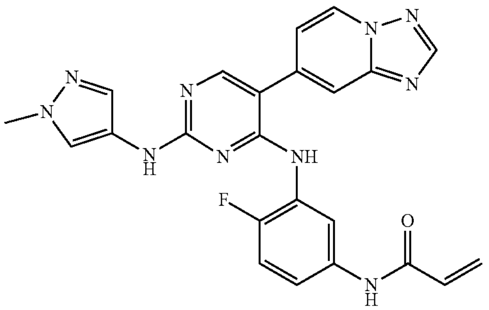
,
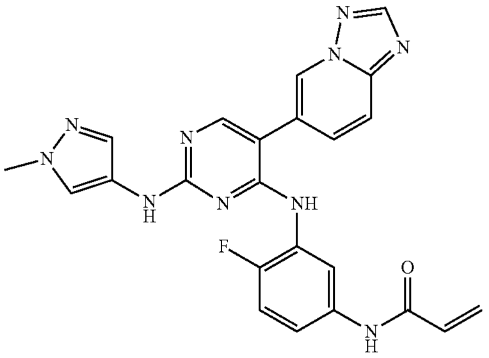
,
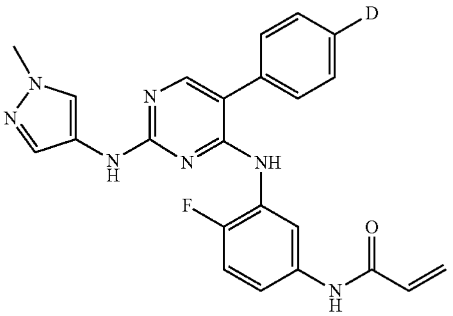
,
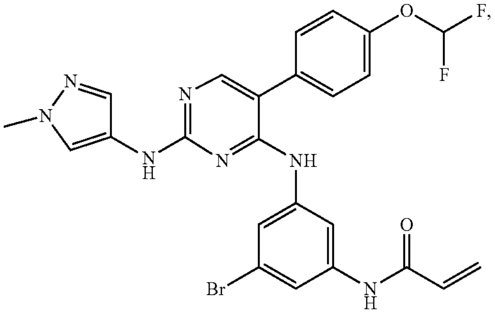

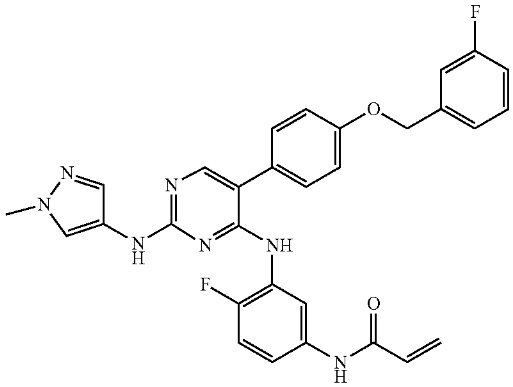
, ,
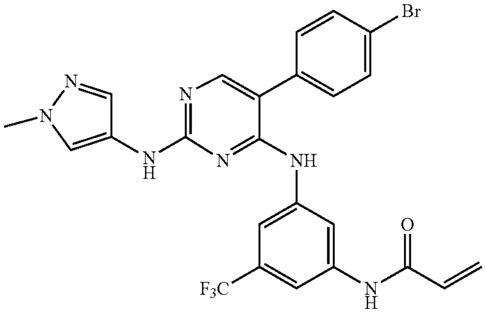
,
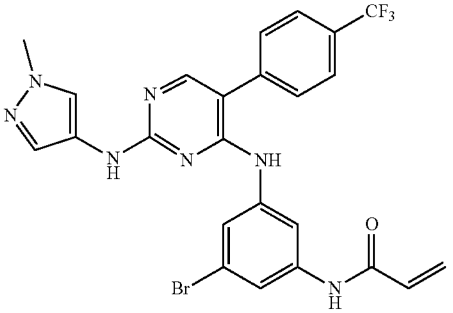
,
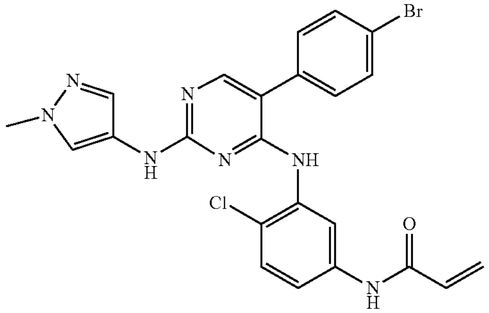
,
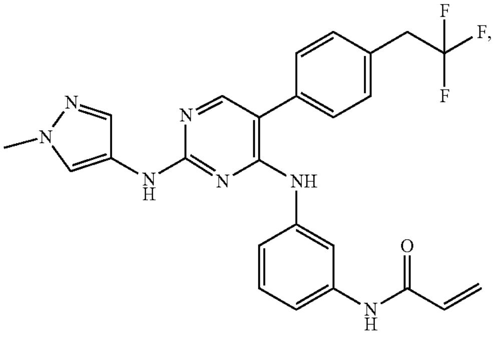
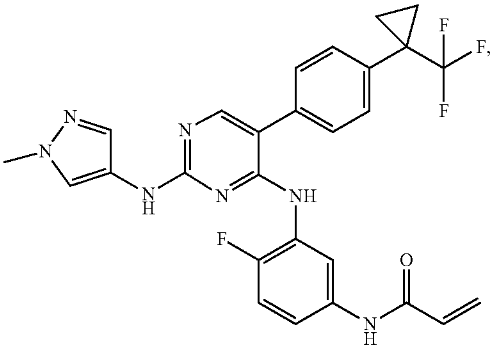
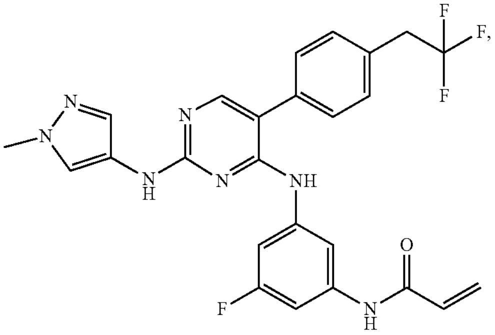
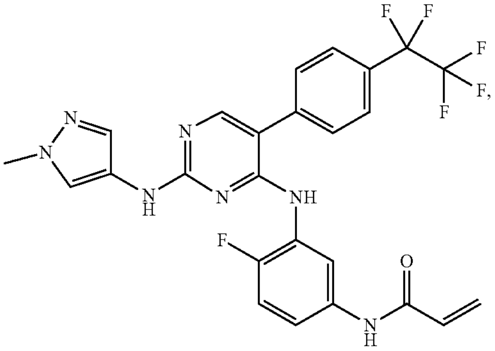
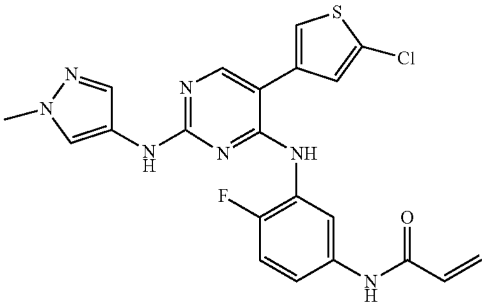
,
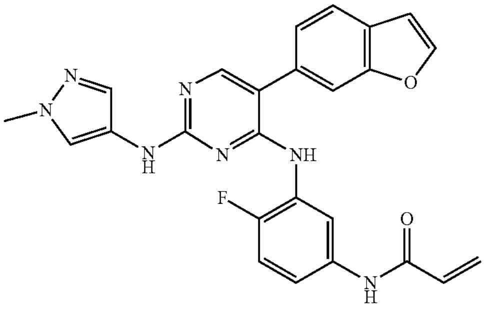
, -continued

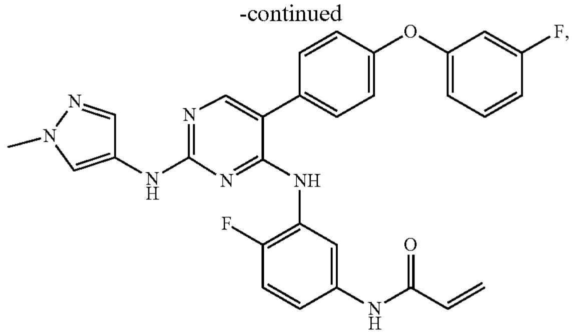

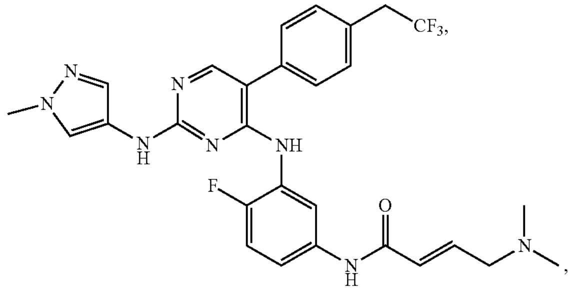

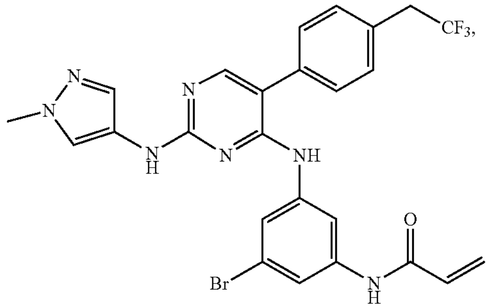

and

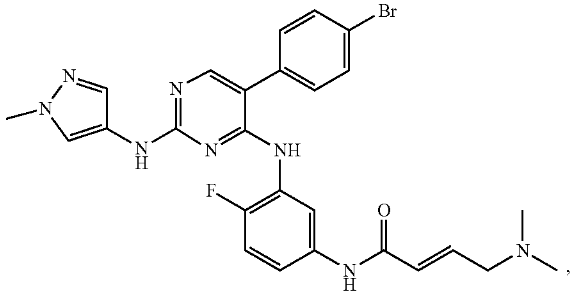

or a pharmaceutically acceptable salt thereof.

In another aspect, the present disclosure provides a pharmaceutical composition comprising a compound of Formula I, or a pharmaceutically acceptable salt or stereoisomer thereof, and a pharmaceutically acceptable carrier.

Particular embodiments of the present disclosure are compounds of Formula I or its stereoisomers, tautomers, pharmaceutically acceptable salts, stereoisomers, solvates, and hydrates thereof, selected from the group consisting of, N-(3-((5-chloro-2-((1-(4-hydroxycyclohexyl)-1H-pyrazol-4-yl)amino)pyrimidin-4-yl)amino)-4-fluorophenyl)acrylamide (Compound 1), N-(3-((5-chloro-2-((6-oxo-1,6-dihydropyridin-3-yl)amino)pyrimidin-4-yl)amino)-4-fluorophenyl)acrylamide (Compound 2), N-(3-((2-(4-amino-2-oxopyridin-1(2H)-yl)-5-chloropyrimidin-4-yl)amino)-4-fluorophenyl)acrylamide (Compound 3), (E)-N-(3-((5-chloro-2-((1-methyl-1H-pyrazol-4-yl)amino)pyrimidin-4-yl)amino)-4-fluorophenyl)-4-(dimethylamino)but-2-enamide (Compound 4), (E)-N-(3-((5-chloro-2-((1-(4-hydroxycyclohexyl)-1H-pyrazol-4-yl)amino)pyrimidin-4-yl)amino)-4-fluorophenyl)-4-(dimethylamino)but-2-enamide (Compound 5), (E)-N-(3-((5-chloro-2-((1-methyl-1H-pyrazol-4-yl)amino)pyrimidin-4-yl)amino)-4-fluorophenyl)-4-methoxybut-2-enamide (Compound 6), (E)-N-(3-((5-chloro-2-((1-methyl-1H-pyrazol-4-yl)amino)pyrimidin-4-yl)amino)-4-fluorophenyl)-4-fluorobut-2-enamide (Compound 7), N-(4-chloro-3-((5-chloro-2-((1-methyl-1H-pyrazol-4-yl)amino)pyrimidin-4-yl)amino)phenyl)acrylamide (Compound 8), (E)-N-(4-chloro-3-((5-chloro-2-((1-methyl-1H-pyrazol-4-yl)amino)pyrimidin-4-yl)amino)phenyl)-4-(dimethylamino)but-2-enamide (Compound 9), N-(4-((5-chloro-2-((1-methyl-1H-pyrazol-4-yl)amino)pyrimidin-4-yl)amino)-3-fluorophenyl)acrylamide (Compound 10), (E)-N-(3-((5-chloro-2-((1-methyl-1H-pyrazol-4-yl)amino)pyrimidin-4-yl)amino)-4-fluorophenyl)but-2-enamide (Compound 11), N-(3-((5-chloro-2-((1-methyl-1H-pyrazol-4-yl)amino)pyrimidin-4-yl)amino)-4-fluorophenyl)methacrylamide (Compound 12), N-(3-((5-chloro-2-((1-methyl-1H-pyrazol-4-yl)amino)pyrimidin-4-yl)amino)-4-methoxyphenyl)acrylamide (Compound 13), N-(3-((5-chloro-2-((1-(1-methylpiperidin-4-yl)-1H-pyrazol-4-yl)amino)pyrimidin-4-yl)amino)-4-fluorophenyl)acrylamide (Compound 14), N-(3-((5-chloro-2-((1-(2-hydroxyethyl)-1H-pyrazol-4-yl)amino)pyrimidin-4-yl)amino)-4-fluorophenyl)acrylamide (Compound 15), (E)-N-(3-((5-chloro-2-((1-(2-hydroxyethyl)-1H-pyrazol-4-yl)amino)pyrimidin-4-yl)amino)-4-fluorophenyl)-4-(dimethylamino)but-2-enamide (Compound 16), (E)-4-(dimethylamino)-N-(3-((2-((1-methyl-1H-pyrazol-4-yl)amino)-5-((phenylamino)methyl)pyrimidin-4-yl)amino)phenyl)but-2-enamide (Compound 17), N-(3-((2-((1-methyl-1H-pyrazol-4-yl)amino)-5-((N-phenylacetamido)methyl)pyrimidin-4-yl)amino)phenyl)acrylamide (Compound 18), N-(3-((2-((1-methyl-1H-pyrazol-4-yl)amino)-5-((N-(1-phenylethyl)acetamido)methyl)pyrimidin-4-yl)amino)phenyl)acrylamide (Compound 19), N-(3-((5-chloro-2-((1-methyl-1H-pyrazol-4-yl)amino)pyrimidin-4-yl)(phenyl)amino)-4-fluorophenyl)acrylamide (Compound 20), N-(3-((5-chloro-2-((5-(methoxymethyl)-1-methyl-1H-pyrazol-3-yl)amino)pyrimidin-4-yl)amino)-4-fluorophenyl)acrylamide (Compound 21), N-(3-((5-chloro-2-((6-methoxypyridin-3-yl)amino)pyrimidin-4-yl)amino)-4-fluorophenyl)acrylamide (Compound 22), N-(3-((5-chloro-2-((1-methyl-1H-pyrazol-4-yl)amino)pyrimidin-4-yl)amino)-4-fluorophenyl)-2-fluoroacrylamide (Compound 23), N-(3-((5-chloro-2-((1-methyl-1H-pyrazol-4-yl)amino)pyrimidin-4-yl)amino)cyclohexyl)-2-fluoroacrylamide (Compound 24), 1-(3-((5-chloro-2-((1-methyl-1H-pyrazol-4-yl)amino)pyrimidin-4-yl)amino)piperidin-1-yl)-2-fluoroprop-2-en-1-one (Compound 25), N-(3-((5-chloro-2-((1-(2-hydroxy-2-methylpropyl)-1H-pyrazol-4-yl)amino)pyrimidin-4-yl)amino)-4-fluorophenyl)acrylamide (Compound 26), (E)-N-(3-((5-chloro-2-((3-methylisothiazol-5-yl)amino)pyrimidin-4-yl)amino)-4-fluorophenyl)-4-(dimethylamino)but-2-enamide (Compound 27), N-(4-((3-acrylamidophenyl)amino)-2-((1-methyl-1H-pyrazol-4-yl)amino)pyrimidin-5-yl)benzamide (Compound 28), N-(3-((2-((1-methyl-1H-pyrazol-4-yl)amino)-5-(phenylsulfonamido)pyrimidin-4-yl)amino)phenyl)acrylamide (Compound 29), N-(3-((5-chloro-2-((1-methyl-1H-pyrazol-3-yl)amino)pyrimidin-4-yl)amino)-4-fluorophenyl)acrylamide (Compound 30), N-(3-((5-chloro-2-((1-methyl-1H-pyrazol-5-yl)amino)pyrimidin-4-yl)amino)-4-fluorophenyl)acrylamide (Compound 31), N-(3-((5-(benzylamino)-2-((1-methyl-1H-pyrazol-4-yl)amino)pyrimidin-4-yl)amino)phenyl)acrylamide (Compound 32), (E)-N-(3-((5-(benzylamino)-2-((1-methyl-1H-pyrazol-4-yl)amino)pyrimidin-4-yl)amino)phenyl)-4-(dimethylamino)but-2-enamide (Compound 33), 4-((3-acrylamidophenyl)amino)-2-((1-methyl-1H-pyrazol-4-yl)amino)-N-(1-phenylethyl)pyrimidine-5-carboxamide (Compound 34), (E)-4-((3-(4-(dimethylamino)but-2-enamido)phenyl)amino)-2-((1-methyl-1H-pyrazol-4-yl)amino)-N-(1-phenylethyl)pyrimidine-5-carboxamide (Compound 35), N-(4-fluoro-3-((2-((1-methyl-1H-pyrazol-4-yl)amino)-5-(trifluoromethyl)pyrimidin-4-yl)amino)phenyl)acrylamide (Compound 36), N-(4-fluoro-3-((2-((1-methyl-1H-pyrazol-4-yl)amino)-5-(4-(trifluoromethyl)phenyl)pyrimidin-4-yl)amino)phenyl)acrylamide (Compound 37), N-(4-fluoro-3-((2-((2-fluoropyridin-3-yl)amino)-5-(4-(trifluoromethyl)phenyl)pyrimidin-4-yl)amino)phenyl)acrylamide (Compound 38), N-(4-fluoro-3-((2-((2-methoxyphenyl)amino)-5-(4-(trifluoromethyl)phenyl)pyrimidin-4-yl)amino)phenyl)acrylamide trifluoroacetate (Compound 39),N-(3-((2-((2-chlorophenyl)amino)-5-(4-(trifluoromethyl)phenyl)pyrimidin-4-yl)amino)-4-fluorophenyl)acrylamide trifluoroacetate (Compound 40), N-(3-((2-((5-chlorothiophen-3-yl)amino)-5-(4-(trifluoromethyl)phenyl)pyrimidin-4-yl)amino)-4-fluorophenyl)acrylamide trifluoroacetate (Compound 41), N-(4-fluoro-3-((2-((1-methylpiperidin-4-yl)amino)-5-(4-(trifluoromethyl)phenyl)pyrimidin-4-yl)amino)phenyl)acrylamide trifluoroacetate (Compound 42), N-(3-((2-((2-(dimethylamino)ethyl)amino)-5-(4-(trifluoromethyl)phenyl)pyrimidin-4-yl)amino)-4-fluorophenyl)acrylamide trifluoroacetate (Compound 43), N-(3-((2-((4-(dimethylamino)phenyl)amino)-5-(4-(trifluoromethyl)phenyl)pyrimidin-4-yl)amino)-4-fluorophenyl)acrylamide trifluoroacetate (Compound 44), N-(3-((2-((4-((dimethylamino)methyl)phenyl)amino)-5-(4-(trifluoromethyl)phenyl)pyrimidin-4-yl)amino)-4-fluorophenyl)acrylamide trifluoroacetate (Compound 45), N-(4-fluoro-3-((2-(thiophen-3-ylamino)-5-(4-(trifluoromethyl)phenyl)pyrimidin-4-yl)amino)phenyl)acrylamide trifluoroacetate (Compound 46), N-(3-((5-(1-(N-benzylacetamido)ethyl)-2-((1-methyl-1H-pyrazol-4-yl)amino)pyrimidin-4-yl)amino)phenyl)acrylamide (Compound 47), N-(3-((5-((N-benzylacetamido)methyl)-2-((1-methyl-1H-pyrazol-4-yl)amino)pyrimidin-4-yl)amino)phenyl)acrylamide (Compound 48), 4-((5-acrylamido-2-fluorophenyl)amino)-N-methyl-2-((1-methyl-1H-pyrazol-4-yl)amino)-N-phenylpyrimidine-5-carboxamide (Compound 49), N-(4-((5-acrylamido-2-fluorophenyl)amino)-2-((1-methyl-1H-pyrazol-4-yl)amino)pyrimidin-5-yl)benzamide (Compound 50), N-(4-fluoro-3-((2-((1-methyl-1H-pyrazol-4-yl)amino)-5-(phenylsulfonamido)pyrimidin-4-yl)amino)phenyl)acrylamide (Compound 51), (E)-4-((3-(4-(dimethylamino)but-2-enamido)phenyl)amino)-2-((2-methoxy-4-(piperidin-1-yl)phenyl)amino)-N-methyl-N-phenylpyrimidine-5-carboxamide (Compound 52), (E)-N-(3-((2-((3-chloro-1-methyl-1H-pyrazol-4-yl)amino)-5-(4-(trifluoromethyl)phenyl)pyrimidin-4-yl)amino)phenyl)-4-(dimethylamino)but-2-enamide (Compound 53), (E)-N-(3-((2-((3-chloro-1-methyl-1H-pyrazol-4-yl)amino)-5-(trifluoromethyl)pyrimidin-4-yl)amino)phenyl)-4-(dimethylamino)but-2-enamide (Compound 54), N-(4-fluoro-3-((2-((1-methyl-1H-pyrazol-4-yl)amino)-5-(6-morpholinopyridin-3-yl)pyrimidin-4-yl)amino)phenyl)acrylamide (Compound 55), N-(4-fluoro-3-((2-((1-methyl-1H-pyrazol-4-yl)amino)-5-(5-(trifluoromethyl)pyridin-3-yl)pyrimidin-4-yl)amino)phenyl)acrylamide (Compound 56), N-(4-fluoro-3-((2-((1-methyl-1H-pyrazol-4-yl)amino)-5-(6-(trifluoromethyl)pyridin-3-yl)pyrimidin-4-yl)amino)phenyl)acrylamide (Compound 57), N-(3-((5-(4-acetamidophenyl)-2-((1-methyl-1H-pyrazol-4-yl)amino)pyrimidin-4-yl)amino)-4-fluorophenyl)acrylamide (Compound 58), N-(3-((5-(3-acetamidophenyl)-2-((1-methyl-1H-pyrazol-4-yl)amino)pyrimidin-4-yl)amino)-4-fluorophenyl)acrylamide (Compound 59), 3-(4-((5-acrylamido-2-fluorophenyl)amino)-2-((1-methyl-1H-pyrazol-4-yl)amino)pyrimidin-5-yl)-N-methylbenzamide (Compound 60), N-(3-((5-(4-chlorophenyl)-2-((1-methyl-1H-pyrazol-4-yl)amino)pyrimidin-4-yl)amino)-4-fluorophenyl)acrylamide (Compound 61), N-(3-((5-(4-cyanophenyl)-2-((1-methyl-1H-pyrazol-4-yl)amino)pyrimidin-4-yl)amino)-4-fluorophenyl)acrylamide (Compound 62), N-(4-fluoro-3-((5-(4-fluorophenyl)-2-((1-methyl-1H-pyrazol-4-yl)amino)pyrimidin-4-yl)amino)phenyl)acrylamide (Compound 63), 4-(4-((5-acrylamido-2-fluorophenyl)amino)-2-((1-methyl-1H-pyrazol-4-yl)amino)pyrimidin-5-yl)-N-methylbenzamide (Compound 64), N-(4-fluoro-3-((2-((1-methyl-1H-pyrazol-4-yl)amino)-5-(2-(trifluoromethyl)phenyl)pyrimidin-4-yl)amino)phenyl)acrylamide (Compound 65), N-(4-fluoro-3-((2-((1-methyl-1H-pyrazol-4-yl)amino)-5-(6-methylpyridin-3-yl)pyrimidin-4-yl)amino)phenyl)acrylamide (Compound 66), N-(4-fluoro-3-((2-((1-methyl-1H-pyrazol-4-yl)amino)-5-(5-methylpyridin-3-yl)pyrimidin-4-yl)amino)phenyl)acrylamide (Compound 67), N-(4-fluoro-3-((5-(2-methoxypyridin-4-yl)-2-((1-methyl-1H-pyrazol-4-yl)amino)pyrimidin-4-yl)amino)phenyl)acrylamide (Compound 68), N-(4-fluoro-3-((5-(5-fluoropyridin-3-yl)-2-((1-methyl-1H-pyrazol-4-yl)amino)pyrimidin-4-yl)amino)phenyl)acrylamide (Compound 69), N-(3-((5-(6-(difluoromethoxy)pyridin-3-yl)-2-((1-methyl-1H-pyrazol-4-yl)amino)pyrimidin-4-yl)amino)-4-fluorophenyl)acrylamide (Compound 70), N-(3-((5-(2-(difluoromethoxy)pyridin-4-yl)-2-((1-methyl-1H-pyrazol-4-yl)amino)pyrimidin-4-yl)amino)-4-fluorophenyl)acrylamide (Compound 71), N-(3-((2-((1-(2-(dimethylamino)ethyl)-1H-pyrazol-4-yl)amino)-5-(4-(trifluoromethyl)phenyl)pyrimidin-4-yl)amino)-4-fluorophenyl)acrylamide trifluoroacetate (Compound 72), N-(3-((2-((1-methyl-1H-pyrazol-4-yl)amino)-5-(6-(trifluoromethyl)pyridin-3-yl)pyrimidin-4-yl)amino)phenyl)acrylamide (Compound 73), N-(3-((5-(6-fluoropyridin-3-yl)-2-((1-methyl-1H-pyrazol-4-yl)amino)pyrimidin-4-yl)amino)phenyl)acrylamide (Compound 74), N-(3-((5-(4-bromophenyl)-2-((1-methyl-1H-pyrazol-4-yl)amino)pyrimidin-4-yl)amino)-4-fluorophenyl)acrylamide trifluoroacetate (Compound 75), N-(3-((5-(4-(tert-butyl)phenyl)-2-((1-methyl-1H-pyrazol-4-yl)amino)pyrimidin-4-yl)amino)-4-fluorophenyl)acrylamide trifluoroacetate (Compound 76), N-(4-fluoro-3-((5-(1-methyl-1H-indol-5-yl)-2-((1-methyl-1H-pyrazol-4-yl)amino)pyrimidin-4-yl)amino)phenyl)acrylamide trifluoroacetate (Compound 77), N-(4-fluoro-3-((2-((1-(2-hydroxyethyl)-1H-pyrazol-4-yl)amino)-5-(4-(trifluoromethyl)phenyl)pyrimidin-4-yl)amino)phenyl)acrylamide (Compound 78), N-(4-fluoro-3-((5-(2-methoxypyridin-3-yl)-2-((1-methyl-1H-pyrazol-4-yl)amino)pyrimidin-4-yl)amino)phenyl)acrylamide (Compound 79), N-(4-fluoro-3-((2-((1-methyl-1H-pyrazol-4-yl)amino)-5-(2-methylpyridin-4-yl)pyrimidin-4-yl)amino)phenyl)acrylamide (Compound 80), N-(1-(2-((1-methyl-1H-pyrazol-4-yl)amino)-5-(4-(trifluoromethyl)phenyl)pyrimidin-4-yl)-1H-indol-4-yl)acrylamide (Compound 81), N-(4-fluoro-3-((5-(2-fluoropyridin-4-yl)-2-((1-methyl-1H-pyrazol-4-yl)amino)pyrimidin-4-yl)amino)phenyl)acrylamide (Compound 82), N-(4-fluoro-3-((2-((1-methyl-1H-pyrazol-4-yl)amino)-5-(2-(trifluoromethyl)pyridin-4-yl)pyrimidin-4-yl)amino)phenyl)acrylamide (Compound 83), N-(4-fluoro-3-((2-((1-methyl-1H-pyrazol-4-yl)amino)-5-(pyridin-3-yl)pyrimidin-4-yl)amino)phenyl)acrylamide (Compound 84), N-(4-fluoro-3-((2-((1-(1-methylpiperidin-4-yl)-1H-pyrazol-4-yl)amino)-5-(4-(trifluoromethyl)phenyl)pyrimidin-4-yl)amino)phenyl)acrylamide (Compound 85), N-(4-fluoro-3-((5-(6-methoxypyridin-3-yl)-2-((1-methyl-1H-pyrazol-4-yl)amino)pyrimidin-4-yl)amino)phenyl)acrylamide (Compound 86), N-(4-fluoro-3-((2-((3-fluoro-1-methyl-1H-pyrazol-4-yl)amino)-5-(4-(trifluoromethyl)phenyl)pyrimidin-4-yl)amino)phenyl)acrylamide (Compound 87), N-(4-fluoro-3-((5-(3-fluorophenyl)-2-((1-methyl-1H-pyrazol-4-yl)amino)pyrimidin-4-yl)amino)phenyl)acrylamide (Compound 88), N-(4-fluoro-3-((2-((1-methyl-1H-pyrazol-4-yl)amino)-5-(3-(trifluoromethyl)phenyl)pyrimidin-4-yl)amino)phenyl)acrylamide (Compound 89), N-(4-fluoro-3-((5-(2-fluorophenyl)-2-((1-methyl-1H-pyrazol-4-yl)amino)pyrimidin-4-yl)amino)phenyl)acrylamide (Compound 90), N-(4-fluoro-3-((5-(4-methoxyphenyl)-2-((1-methyl-1H-pyrazol-4-yl)amino)pyrimidin-4-yl)amino)phenyl)acrylamide (Compound 91), N-(4-fluoro-3-((2-((1-methyl-1H-pyrazol-4-yl)amino)-5-(4-(trifluoromethoxy)phenyl)pyrimidin-4-yl)amino)phenyl)acrylamide (Compound 92), N-(4-fluoro-3-((2-((1-methyl-1H-pyrazol-4-yl)amino)-5-phenylpyrimidin-4-yl)amino)phenyl)acrylamide (Compound 93), N-(4-fluoro-3-((2-((1-methyl-1H-pyrazol-4-yl)amino)-5-(4-morpholinophenyl)pyrimidin-4-yl)amino)phenyl)acrylamide (Compound 94), N-(3-((5-(5-(difluoromethoxy)pyridin-3-yl)-2-((1-methyl-1H-pyrazol-4-yl)amino)pyrimidin-4-yl)amino)-4-fluorophenyl)acrylamide (Compound 95), N-(4-fluoro-3-((2-((1-methyl-1H-pyrazol-4-yl)amino)-5-(3-(trifluoromethoxy)phenyl)pyrimidin-4-yl)amino)phenyl)acrylamide trifluoroacetate (Compound 96), N-(3-((5-(1H-indol-5-yl)-2-((1-methyl-1H-pyrazol-4-yl)amino)pyrimidin-4-yl)amino)-4-fluorophenyl)acrylamide (Compound 97), N-(4-fluoro-3-((2-((1-methyl-1H-pyrazol-4-yl)amino)-5-(1H-pyrazol-4-yl)pyrimidin-4-yl)amino)phenyl)acrylamide (Compound 98), N-(3-((5-(4-(difluoromethyl)phenyl)-2-((1-methyl-1H-pyrazol-4-yl)amino)pyrimidin-4-yl)amino)-4-fluorophenyl)acrylamide (Compound 99), N-(4-fluoro-3-((5-(6-fluoropyridin-3-yl)-2-((1-methyl-1H-pyrazol-4-yl)amino)pyrimidin-4-yl)amino)phenyl)acrylamide (Compound 100), N-(3-((5-(6-chloropyridin-3-yl)-2-((1-methyl-1H-pyrazol-4-yl)amino)pyrimidin-4-yl)amino)-4-fluorophenyl)acrylamide (Compound 101), N-(3-((5-(5-chloropyridin-3-yl)-2-((1-methyl-1H-pyrazol-4-yl)amino)pyrimidin-4-yl)amino)-4-fluorophenyl)acrylamide (Compound 102), N-(3-((5-(4-(dimethylamino)phenyl)-2-((1-methyl-1H-pyrazol-4-yl)amino)pyrimidin-4-yl)amino)-4-fluorophenyl)acrylamide (Compound 103), N-(3-((2-((1-methyl-1H-pyrazol-4-yl)amino)-5-(5-(trifluoromethyl)pyridin-3-yl)pyrimidin-4-yl)oxy)phenyl)acrylamide (Compound 104), N-(3-((5-(4-(difluoromethyl)phenyl)-2-((1-methyl-1H-pyrazol-4-yl)amino)pyrimidin-4-yl)oxy)phenyl)acrylamide (Compound 105), N-(3-((5-(6-(difluoromethyl)pyridin-3-yl)-2-((1-methyl-1H-pyrazol-4-yl)amino)pyrimidin-4-yl)amino)-4-fluorophenyl)acrylamide (Compound 106), N-(3-((5-(6-(dimethylamino)pyridin-3-yl)-2-((1-methyl-1H-pyrazol-4-yl)amino)pyrimidin-4-yl)amino)-4-fluorophenyl)acrylamide (Compound 107), N-(3-((2-((1-methyl-1H-pyrazol-4-yl)amino)-5-(6-(trifluoromethyl)pyridin-3-yl)pyrimidin-4-yl)oxy)phenyl)acrylamide (Compound 108), N-(3-((5-(6-fluoropyridin-3-yl)-2-((1-methyl-1H-pyrazol-4-yl)amino)pyrimidin-4-yl)oxy)phenyl)acrylamide (Compound 109), N-(3-((5-(5-(difluoromethyl)pyridin-3-yl)-2-((1-methyl-1H-pyrazol-4-yl)amino)pyrimidin-4-yl)amino)-4-fluorophenyl)acrylamide (Compound 110), N-(3-((2-((1-methyl-1H-pyrazol-4-yl)amino)-5-(4-(trifluoromethyl)phenyl)pyrimidin-4-yl)amino)phenyl)acrylamide (Compound 111), N-(3-((2-((3-chloro-1-methyl-1H-pyrazol-4-yl)amino)-5-(4-(trifluoromethyl)phenyl)pyrimidin-4-yl)amino)-4-fluorophenyl)acrylamide trifluoroacetate (Compound 112), N-(4-fluoro-3-((2-((1-methyl-1H-pyrazol-3-yl)amino)-5-(4-(trifluoromethyl)phenyl)pyrimidin-4-yl)amino)phenyl)acrylamide trifluoroacetate (Compound 113), N-(4-fluoro-3-((5-(1-methyl-1,2,3,6-tetrahydropyridin-4-yl)-2-((1-methyl-1H-pyrazol-4-yl)amino)pyrimidin-4-yl)amino)phenyl)acrylamide (Compound 114),
N-(3-((5-(3-fluorophenyl)-2-((1-methyl-1H-pyrazol-4-yl)amino)pyrimidin-4-yl)amino)phenyl)acrylamide trifluoroacetate (Compound 115),
N-(3-((5-(5-(dimethylamino)pyridin-3-yl)-2-((1-methyl-1H-pyrazol-4-yl)amino)pyrimidin-4-yl)amino)-4-fluorophenyl)acrylamide trifluoroacetate (Compound 116),
N-(3-((5-(2-chloropyridin-4-yl)-2-((1-methyl-1H-pyrazol-4-yl)amino)pyrimidin-4-yl)amino)-4-fluorophenyl)acrylamide (Compound 117),
N-(3-((5-(6-methoxypyridin-3-yl)-2-((1-methyl-1H-pyrazol-4-yl)amino)pyrimidin-4-yl)amino)phenyl)acrylamide trifluoroacetate (Compound 118),
N-(4-(dimethylamino)-3-((2-((1-methyl-1H-pyrazol-4-yl)amino)-5-(4-(trifluoromethyl)phenyl)pyrimidin-4-yl)amino)phenyl)acrylamide trifluoroacetate (Compound 119),
N-(3-((5-cyclopropyl-2-((1-methyl-1H-pyrazol-4-yl)amino)pyrimidin-4-yl)amino)-4-fluorophenyl)acrylamide trifluoroacetate (Compound 120),
N-(4-fluoro-3-((2-(phenylamino)-5-(4-(trifluoromethyl)phenyl)pyrimidin-4-yl)amino)phenyl)acrylamide (Compound 121),
N-(4-fluoro-3-((2-((4-fluorophenyl)amino)-5-(4-(trifluoromethyl)phenyl)pyrimidin-4-yl)amino)phenyl)acrylamide trifluoroacetate (Compound 122),
N-(4-fluoro-3-((2-((1-methyl-1H-pyrazol-4-yl)amino)-2'-(trifluoromethyl)-[5,5'-bipyrimidin]-4-yl)amino)phenyl)acrylamide (Compound 123),
N-(3-((5-(3,6-dihydro-2H-pyran-4-yl)-2-((1-methyl-1H-pyrazol-4-yl)amino)pyrimidin-4-yl)amino)-4-fluorophenyl)acrylamide (Compound 124),
N-(3-((5-(3-((2-(dimethylamino)ethyl)(methyl)amino)phenyl)-2-((1-methyl-1H-pyrazol-4-yl)amino)pyrimidin-4-yl)amino)-4-fluorophenyl)acrylamide (Compound 125),
N-(4-fluoro-3-((5-(4-isopropylphenyl)-2-((1-methyl-1H-pyrazol-4-yl)amino)pyrimidin-4-yl)amino)phenyl)acrylamide trifluoroacetate (Compound 126),
N-(3-((5-([1,1'-biphenyl]-4-yl)-2-((1-methyl-1H-pyrazol-4-yl)amino)pyrimidin-4-yl)amino)-4-fluorophenyl)acrylamide (Compound 127),
N-(3-((5-(4-cyclopropylphenyl)-2-((1-methyl-1H-pyrazol-4-yl)amino)pyrimidin-4-yl)amino)-4-fluorophenyl)acrylamide trifluoroacetate (Compound 128),
N-(3-((5-(2-chlorophenyl)-2-((1-methyl-1H-pyrazol-4-yl)amino)pyrimidin-4-yl)amino)-4-fluorophenyl)acrylamide trifluoroacetate (Compound 129),
N-(4-fluoro-3-((2-((1-methyl-1H-pyrazol-4-yl)amino)-5-(4-(2,2,2-trifluoroethyl)phenyl)pyrimidin-4-yl)amino)phenyl)acrylamide trifluoroacetate (Compound 130),
N-(4-fluoro-3-((2-((1-methyl-1H-pyrazol-4-yl)amino)-5-(quinolin-7-yl)pyrimidin-4-yl)amino)phenyl)acrylamide (Compound 131),
N-(4-fluoro-3-((5-(imidazo[1,2-a]pyridin-7-yl)-2-((1-methyl-1H-pyrazol-4-yl)amino)pyrimidin-4-yl)amino)phenyl)acrylamide (Compound 132),
N-(4-fluoro-3-((5-(imidazo[1,2-a]pyridin-6-yl)-2-((1-methyl-1H-pyrazol-4-yl)amino)pyrimidin-4-yl)amino)phenyl)acrylamide trifluoroacetate (Compound 133),
N-(3-((5-(3-((dimethylamino)methyl)phenyl)-2-((1-methyl-1H-pyrazol-4-yl)amino)pyrimidin-4-yl)amino)-4-fluorophenyl)acrylamide (Compound 134),
N-(3-((2-((1,3-dimethyl-1H-pyrazol-4-yl)amino)-5-(4-(trifluoromethyl)phenyl)pyrimidin-4-yl)amino)-4-fluorophenyl)acrylamide trifluoroacetate (Compound 135),
N-(4-fluoro-3-((2-((1-methyl-1H-pyrazol-4-yl)amino)-5-(naphthalen-1-yl)pyrimidin-4-yl)amino)phenyl)acrylamide trifluoroacetate (Compound 136),
N-(4-fluoro-3-((2-((1-methyl-1H-pyrazol-4-yl)amino)-5-(pyridin-4-yl)pyrimidin-4-yl)amino)phenyl)acrylamide (Compound 137),
N-(4-fluoro-3-((2-((1-methyl-1H-pyrazol-4-yl)amino)-5-(4-sulfamoylphenyl)pyrimidin-4-yl)amino)phenyl)acrylamide (Compound 138),
N-(4-fluoro-3-((2-((1-(oxetan-3-yl)-1H-pyrazol-4-yl)amino)-5-(4-(trifluoromethyl)phenyl)pyrimidin-4-yl)amino)phenyl)acrylamide (Compound 139),
N-(3-((5-(4-(difluoromethoxy)phenyl)-2-((1-methyl-1H-pyrazol-4-yl)amino)pyrimidin-4-yl)amino)-4-fluorophenyl)acrylamide (Compound 140),
N-(4-fluoro-3-((5-(5-methoxypyridin-3-yl)-2-((1-methyl-1H-pyrazol-4-yl)amino)pyrimidin-4-yl)amino)phenyl)acrylamide (Compound 141),
N-(3-((5-(4-(difluoromethoxy)phenyl)-2-((1-methyl-1H-pyrazol-4-yl)amino)pyrimidin-4-yl)amino)phenyl)acrylamide trifluoroacetate (Compound 142),
N-(3-((5-(3-(difluoromethoxy)phenyl)-2-((1-methyl-1H-pyrazol-4-yl)amino)pyrimidin-4-yl)amino)-4-fluorophenyl)acrylamide trifluoroacetate (Compound 143),
N-(3-((5-(5-(difluoromethyl)pyridin-3-yl)-2-((1-methyl-1H-pyrazol-4-yl)amino)pyrimidin-4-yl)amino)phenyl)acrylamide trifluoroacetate (Compound 144),
N-(3-((5-(3-(dimethylamino)phenyl)-2-((1-methyl-1H-pyrazol-4-yl)amino)pyrimidin-4-yl)amino)-4-fluorophenyl)acrylamide (Compound 145),
N-(4-fluoro-3-((2-((1-methyl-3-(trifluoromethyl)-1H-pyrazol-4-yl)amino)-5-(4-(trifluoromethyl)phenyl)pyrimidin-4-yl)amino)phenyl)acrylamide trifluoroacetate (Compound 146),
N-(4-fluoro-3-((2-((1-methyl-1H-pyrazol-4-yl)amino)-[5,5'-bipyrimidin]-4-yl)amino)phenyl)acrylamide trifluoroacetate (Compound 147),
N-(2-fluoro-3-((2-((1-methyl-1H-pyrazol-4-yl)amino)-5-(4-(trifluoromethyl)phenyl)pyrimidin-4-yl)amino)phenyl)acrylamide trifluoroacetate (Compound 148),
N-(4-fluoro-3-((2-((1-methyl-1H-pyrazol-4-yl)amino)-5-(naphthalen-2-yl)pyrimidin-4-yl)amino)phenyl)acrylamide trifluoroacetate (Compound 149),
N-(3-((5-(2-chlorophenyl)-2-((1-methyl-1H-pyrazol-4-yl)amino)pyrimidin-4-yl)amino)-4-fluorophenyl)acrylamide 2,2,2-trifluoroacetate (Compound 150),
N-(3-((2-((1-methyl-1H-pyrazol-4-yl)amino)-5-(4-(trifluoromethyl)phenyl)pyrimidin-4-yl)oxy)phenyl)acrylamide (Compound 151),
N-(4-fluoro-3-((2-((1-methyl-1H-pyrazol-4-yl)amino)-5-(4-(trifluoromethyl)phenyl)pyrimidin-4-yl)oxy)phenyl)acrylamide (Compound 152),
N-(3-((3-chloro-6-((1-methyl-1H-pyrazol-4-yl)amino)pyrazin-2-yl)amino)-4-fluorophenyl)acrylamide (Compound 153),
N-(3-((3-chloro-6-((1-methyl-1H-pyrazol-4-yl)amino)pyrazin-2-yl)oxy)phenyl)acrylamide (Compound 154),
N-(3-((6-chloro-3-((1-methyl-1H-pyrazol-4-yl)amino)-1,2,4-triazin-5-yl)amino)-4-fluorophenyl)acrylamide (Compound 155),
N-(3-((6-chloro-3-((1-methyl-1H-pyrazol-4-yl)amino)-1,2,4-triazin-5-yl)amino)phenyl)acrylamide (Compound 156),
N-(3-((6-chloro-3-((1-methyl-1H-pyrazol-4-yl)amino)-1,2,4-triazin-5-yl)oxy)phenyl)acrylamide (Compound 157),
N-(3-((3-methyl-6-((1-methyl-1H-pyrazol-4-yl)amino)pyrazin-2-yl)oxy)phenyl)acrylamide (Compound 158), N-(3-(5-chloro-2-((1-methyl-1H-pyrazol-4-yl)amino)pyrimidin-4-yl)-4-fluorophenyl)acrylamide (Compound 159), (E)-N-(3-(5-chloro-2-((1-methyl-1H-pyrazol-4-yl)amino)pyrimidin-4-yl)-4-fluorophenyl)-4-(dimethylamino)but-2-enamide (Compound 160), N-(4-fluoro-3-((2-((1-methyl-1H-pyrazol-4-yl)amino)-5-(phenylethynyl)pyrimidin-4-yl)amino)phenyl)acrylamide (Compound 161), (E)-4-(dimethylamino)-N-(4-fluoro-3-((2-((1-methyl-1H-pyrazol-4-yl)amino)-5-(phenylethynyl)pyrimidin-4-yl)amino)phenyl)but-2-enamide (Compound 162), 4-acrylamido-2-((5-chloro-2-((1-methyl-1H-pyrazol-4-yl)amino)pyrimidin-4-yl)amino)-N-phenylbenzamide (Compound 163), 4-acrylamido-2-((2-((1-methyl-1H-pyrazol-4-yl)amino)pyrimidin-4-yl)amino)-N-phenylbenzamide (Compound 164), N-(4-chloro-3-((2-((1-methyl-1H-pyrazol-4-yl)amino)pyrimidin-4-yl)amino)phenyl)acrylamide (Compound 165), N-(3-((5-chloro-2-((1-methyl-1H-pyrazol-4-yl)amino)pyrimidin-4-yl)oxy)-4-fluorophenyl)acrylamide (Compound 166), N-(3-((5-chloro-2-((1-(2-hydroxyethyl)-1H-pyrazol-4-yl)amino)pyrimidin-4-yl)oxy)-4-fluorophenyl)acrylamide (Compound 167), N-(3-((5-chloro-2-((1-(1-methylpiperidin-4-yl)-1H-pyrazol-4-yl)amino)pyrimidin-4-yl)oxy)-4-fluorophenyl)acrylamide (Compound 168), N-(3-((5-chloro-2-((1-methyl-1H-pyrazol-4-yl)amino)pyrimidin-4-yl)oxy)-4-(trifluoromethyl)phenyl)acrylamide (Compound 169), N-(3-((5-chloro-2-((1-(1-methylpiperidin-4-yl)-1H-pyrazol-4-yl)amino)pyrimidin-4-yl)oxy)-4-methoxyphenyl)acrylamide (Compound 170), N-(3-((5-chloro-2-((1-(2-hydroxyethyl)-1H-pyrazol-4-yl)amino)pyrimidin-4-yl)oxy)-4-methoxyphenyl)acrylamide (Compound 171), N-(3-((5-chloro-2-((1-methyl-1H-pyrazol-4-yl)amino)pyrimidin-4-yl)oxy)-4-methoxyphenyl)acrylamide (Compound 172), N-(2-(((5-chloro-2-((1-methyl-1H-pyrazol-4-yl)amino)pyrimidin-4-yl)amino)methyl)-3-fluorophenyl)acrylamide (Compound 173), (E)-N-(2-(((5-chloro-2-((1-methyl-1H-pyrazol-4-yl)amino)pyrimidin-4-yl)amino)methyl)-3-fluorophenyl)-4-(dimethylamino)but-2-enamide (Compound 174), N-(2-((2-((1-methyl-1H-pyrazol-4-yl)amino)pyrimidin-4-yl)amino)-[1,1'-biphenyl]-4-yl)acrylamide (Compound 175), (E)-4-(dimethylamino)-N-(2-((2-((1-methyl-1H-pyrazol-4-yl)amino)pyrimidin-4-yl)amino)-[1,1'-biphenyl]-4-yl)but-2-enamide (Compound 176), N-(2-((5-chloro-2-((1-methyl-1H-pyrazol-4-yl)amino)pyrimidin-4-yl)amino)-[1,1'-biphenyl]-4-yl)acrylamide (Compound 177), N-(3-((5-chloro-2-((1-methyl-1H-pyrazol-4-yl)amino)pyrimidin-4-yl)amino)-4-(phenylethynyl)phenyl)acrylamide (Compound 178), (E)-N-(3-((5-chloro-2-((1-methyl-1H-pyrazol-4-yl)amino)pyrimidin-4-yl)amino)-4-(phenylethynyl)phenyl)-4-(dimethylamino)but-2-enamide (Compound 179), N-(3-((2-(cyclopropylamino)-5-(4-(trifluoromethyl)phenyl)pyrimidin-4-yl)amino)-4-fluorophenyl)acrylamide (Compound 180), N-(3-((2-(cyclobutylamino)-5-(4-(trifluoromethyl)phenyl)pyrimidin-4-yl)amino)-4-fluorophenyl)acrylamide (Compound 181), N-(3-((2-((1-methyl-1H-pyrazol-4-yl)amino)-5-(4-(trifluoromethyl)phenyl)pyridin-4-yl)oxy)phenyl)acrylamide (Compound 182), N-(3-((2-((1-methyl-1H-pyrazol-4-yl)amino)-5-(5-methylpyridin-3-yl)pyrimidin-4-yl)oxy)phenyl)acrylamide (Compound 183), N-(3-((5-(5-fluoropyridin-3-yl)-2-((1-methyl-1H-pyrazol-4-yl)amino)pyrimidin-4-yl)oxy)phenyl)acrylamide (Compound 184), N-(3-((5-(6-chloropyridin-3-yl)-2-((1-methyl-1H-pyrazol-4-yl)amino)pyrimidin-4-yl)oxy)phenyl)acrylamide (Compound 185), N-(3-((2-((1-methyl-1H-pyrazol-4-yl)amino)-5-(6-methylpyridin-3-yl)pyrimidin-4-yl)oxy)phenyl)acrylamide (Compound 186), N-(3-((5-(6-(difluoromethyl)pyridin-3-yl)-2-((1-methyl-1H-pyrazol-4-yl)amino)pyrimidin-4-yl)oxy)phenyl)acrylamide (Compound 187), N-(3-((5-(6-(difluoromethoxy)pyridin-3-yl)-2-((1-methyl-1H-pyrazol-4-yl)amino)pyrimidin-4-yl)oxy)phenyl)acrylamide (Compound 188), N-(3-((2-((2-chlorophenyl)amino)-5-(4-(trifluoromethyl)phenyl)pyrimidin-4-yl)oxy)phenyl)acrylamide (Compound 189), N-(3-((5-(1-methyl-1,2,3,6-tetrahydropyridin-4-yl)-2-((1-methyl-1H-pyrazol-4-yl)amino)pyrimidin-4-yl)oxy)phenyl)acrylamide (Compound 190), N-(3-((2-((2-methoxy-4-(4-methylpiperazin-1-yl)phenyl)amino)-5-(4-(trifluoromethyl)phenyl)pyrimidin-4-yl)oxy)phenyl)acrylamide (Compound 191), N-(3-((5-(3,6-dihydro-2H-pyran-4-yl)-2-((1-methyl-1H-pyrazol-4-yl)amino)pyrimidin-4-yl)oxy)phenyl)acrylamide (Compound 192), N-(3-((2-((2-methoxyphenyl)amino)-5-(4-(trifluoromethyl)phenyl)pyrimidin-4-yl)oxy)phenyl)acrylamide (Compound 193), N-(3-((2-(cyclopropylamino)-5-(4-(trifluoromethyl)phenyl)pyrimidin-4-yl)oxy)phenyl)acrylamide (Compound 194), N-(5-((2-((1-methyl-1H-pyrazol-4-yl)amino)-5-(4-(trifluoromethyl)phenyl)pyrimidin-4-yl)amino)pyridin-3-yl)acrylamide (Compound 195), N-(2-((2-((1-methyl-1H-pyrazol-4-yl)amino)-5-(4-(trifluoromethyl)phenyl)pyrimidin-4-yl)amino)pyridin-4-yl)acrylamide (Compound 196), N-(6-((2-((1-methyl-1H-pyrazol-4-yl)amino)-5-(4-(trifluoromethyl)phenyl)pyrimidin-4-yl)amino)pyridin-2-yl)acrylamide (Compound 197), N-(5-fluoro-4-((2-((1-methyl-1H-pyrazol-4-yl)amino)-5-(4-(trifluoromethyl)phenyl)pyrimidin-4-yl)amino)pyridin-2-yl)acrylamide (Compound 198), N-(2-((2-(dimethylamino)ethyl)(methyl)amino)-5-((2-((1-methyl-1H-pyrazol-4-yl)amino)-5-(4-(trifluoromethyl)phenyl)pyrimidin-4-yl)amino)phenyl)acrylamide (Compound 199), N-(4-((2-((1-methyl-1H-pyrazol-4-yl)amino)-5-(4-(trifluoromethyl)phenyl)pyrimidin-4-yl)amino)pyridin-2-yl)acrylamide (Compound 200), N-(3-((5-(3-bromophenyl)-2-((1-methyl-1H-pyrazol-4-yl)amino)pyrimidin-4-yl)amino)-4-fluorophenyl)acrylamide (Compound 201), N-(3-((5-(4-bromophenyl)-2-((1-methyl-1H-pyrazol-4-yl)amino)pyrimidin-4-yl)amino)-2-fluorophenyl)acrylamide (Compound 202), N-(3-((5-(4-bromophenyl)-2-((1-(2-(dimethylamino)ethyl)-1H-pyrazol-4-yl)amino)pyrimidin-4-yl)amino)-4-fluorophenyl)acrylamide (Compound 203),
N-(3-((5-(4-bromophenyl)-2-((3-chloro-1-methyl-1H-pyrazol-4-yl)amino)pyrimidin-4-yl)amino)-4-fluorophenyl)acrylamide (Compound 204),
N-(3-((5-(4-bromophenyl)-2-((1-(oxetan-3-yl)-1H-pyrazol-4-yl)amino)pyrimidin-4-yl)amino)-4-fluorophenyl)acrylamide (Compound 205),
N-(3-((5-(4-bromophenyl)-2-((1-(2-hydroxyethyl)-1H-pyrazol-4-yl)amino)pyrimidin-4-yl)amino)-4-fluorophenyl)acrylamide (Compound 206),
N-(3-((5-(4-bromophenyl)-2-((1-methyl-1H-pyrazol-4-yl)amino)pyrimidin-4-yl)amino)-5-fluorophenyl)acrylamide (Compound 207),
N-(3-((5-(4-bromophenyl)-2-((3-chloro-1-(2-(dimethylamino)ethyl)-1H-pyrazol-4-yl)amino)pyrimidin-4-yl)amino)-4-fluorophenyl)acrylamide (Compound 208),
N-(3-(2-((1-methyl-1H-pyrazol-4-yl)amino)-7-(trifluoromethyl)-9H-pyrimido[4,5-b]indol-9-yl)phenyl)acrylamide (Compound 209),
N-(4-fluoro-3-((2-((1-methyl-1H-pyrazol-4-yl)amino)-5-(4-(trifluoromethyl)phenyl)pyridin-4-yl)amino)phenyl)acrylamide (Compound 210),
N-(4-fluoro-3-((2-((3-methylisothiazol-5-yl)amino)-5-(4-(trifluoromethyl)phenyl)pyrimidin-4-yl)amino)phenyl)acrylamide (Compound 211),
N-(4-fluoro-3-((2-((5-methylisothiazol-3-yl)amino)-5-(4-(trifluoromethyl)phenyl)pyrimidin-4-yl)amino)phenyl)acrylamide (Compound 212),
N-(4-fluoro-3-((2-((4-methylthiazol-2-yl)amino)-5-(4-(trifluoromethyl)phenyl)pyrimidin-4-yl)amino)phenyl)acrylamide (Compound 213),
N-(4-fluoro-3-((2-((1-methyl-1H-imidazol-4-yl)amino)-5-(4-(trifluoromethyl)phenyl)pyrimidin-4-yl)amino)phenyl)acrylamide (Compound 214),
N-(4-fluoro-3-((2-(thiazol-2-ylamino)-5-(4-(trifluoromethyl)phenyl)pyrimidin-4-yl)amino)phenyl)acrylamide (Compound 215),
N-(3-((2-((1-(3-(dimethylamino)propyl)-1H-pyrazol-4-yl)amino)-5-(4-(trifluoromethyl)phenyl)pyrimidin-4-yl)amino)-4-fluorophenyl)acrylamide (Compound 216),
N-(4-fluoro-3-((2-((5-methylthiophen-3-yl)amino)-5-(4-(trifluoromethyl)phenyl)pyrimidin-4-yl)amino)phenyl)acrylamide (Compound 217),
N-(3-((2-((3-((dimethylamino)methyl)phenyl)amino)-5-(4-(trifluoromethyl)phenyl)pyrimidin-4-yl)amino)-4-fluorophenyl)acrylamide (Compound 218),
N-(4-fluoro-3-((2-((1-(2-methoxyethyl)-1H-pyrazol-4-yl)amino)-5-(4-(trifluoromethyl)phenyl)pyrimidin-4-yl)amino)phenyl)acrylamide (Compound 219),
N-(4-fluoro-3-((2-((1-(tetrahydro-2H-pyran-4-yl)-1H-pyrazol-4-yl)amino)-5-(4-(trifluoromethyl)phenyl)pyrimidin-4-yl)amino)phenyl)acrylamide (Compound 220),
N-(3-((2-((3-chloro-1-(2-(dimethylamino)ethyl)-1H-pyrazol-4-yl)amino)-5-(4-(trifluoromethyl)phenyl)pyrimidin-4-yl)amino)-4-fluorophenyl)acrylamide (Compound 221),
N-(4-fluoro-3-((2-((1-methyl-1H-pyrazol-4-yl)amino)-5-morpholinopyrimidin-4-yl)amino)phenyl)acrylamide (Compound 222),
N-(3-((2-((1-methyl-1H-pyrazol-4-yl)amino)-5-(4-methylpiperazin-1-yl)pyrimidin-4-yl)oxy)phenyl)acrylamide (Compound 223),
N-(3-((2-((1-methyl-1H-pyrazol-4-yl)amino)-6-(methylamino)-5-(4-(trifluoromethyl)phenyl)pyrimidin-4-yl)amino)phenyl)acrylamide (Compound 224),
N-(4-fluoro-3-((2-(isoxazol-4-ylamino)-5-(4-(trifluoromethyl)phenyl)pyrimidin-4-yl)amino)phenyl)acrylamide (Compound 225),
N-(4-fluoro-3-((2-((1-methyl-1H-pyrazol-4-yl)amino)-5-(1-methyl-2,5-dihydro-1H-pyrrol-3-yl)pyrimidin-4-yl)amino)phenyl)acrylamide (Compound 226),
N-(4-fluoro-3-((2-((1-methyl-1H-pyrazol-4-yl)amino)-5-(1-methylpyrrolidin-3-yl)pyrimidin-4-yl)amino)phenyl)acrylamide (Compound 227),
N-(4-fluoro-3-(methyl(2-((1-methyl-1H-pyrazol-4-yl)amino)-5-(4-(trifluoromethyl)phenyl)pyrimidin-4-yl)amino)phenyl)acrylamide (Compound 228),
N-(3-(methyl(2-((1-methyl-1H-pyrazol-4-yl)amino)-5-(4-(trifluoromethyl)phenyl)pyrimidin-4-yl)amino)phenyl)acrylamide (Compound 229),
N-(4-fluoro-3-((2-((1-methyl-1H-pyrazol-4-yl)amino)-5-(thiazol-5-yl)pyrimidin-4-yl)amino)phenyl)acrylamide (Compound 230),
N-(4-fluoro-3-((2-((1-methyl-1H-pyrazol-4-yl)amino)-6-(trifluoromethyl)quinazolin-4-yl)amino)phenyl)acrylamide (Compound 231),
N-(4-fluoro-3-((2-(pyridin-3-ylamino)-5-(4-(trifluoromethyl)phenyl)pyrimidin-4-yl)amino)phenyl)acrylamide (Compound 232),
N-(3-((2-((3-chloro-1-methyl-1H-pyrazol-4-yl)amino)-5-(4-(trifluoromethyl)phenyl)pyrimidin-4-yl)oxy)phenyl)acrylamide (Compound 233),
N-(3-((2-((4-((dimethylamino)methyl)phenyl)amino)-5-(4-(trifluoromethyl)phenyl)pyrimidin-4-yl)oxy)phenyl)acrylamide (Compound 234),
N-(3-((2-((1-(2-(dimethylamino)ethyl)-1H-pyrazol-4-yl)amino)-5-(4-(trifluoromethyl)phenyl)pyrimidin-4-yl)oxy)phenyl)acrylamide (Compound 235),
N-(3-((2-((2-(dimethylamino)ethyl)amino)-5-(4-(trifluoromethyl)phenyl)pyrimidin-4-yl)oxy)phenyl)acrylamide (Compound 236),
N-(3-((2-((3-chloro-1-methyl-1H-pyrazol-4-yl)amino)-5-(3,6-dihydro-2H-pyran-4-yl)pyrimidin-4-yl)amino)-4-fluorophenyl)acrylamide (Compound 237),
N-(2-fluoro-5-((2-((1-methyl-1H-pyrazol-4-yl)amino)-5-(4-(trifluoromethyl)phenyl)pyrimidin-4-yl)amino)phenyl)acrylamide (Compound 238),
N-(3-fluoro-5-((2-((1-methyl-1H-pyrazol-4-yl)amino)-5-(4-(trifluoromethyl)phenyl)pyrimidin-4-yl)amino)phenyl)acrylamide (Compound 239),
N-(4-fluoro-3-((2-((1-(2-hydroxy-2-methylpropyl)-1H-pyrazol-4-yl)amino)-5-(4-(trifluoromethyl)phenyl)pyrimidin-4-yl)amino)phenyl)acrylamide (Compound 240),
N-(3-((2-((3-chloro-1-(2-hydroxyethyl)-1H-pyrazol-4-yl)amino)-5-(4-(trifluoromethyl)phenyl)pyrimidin-4-yl)amino)-4-fluorophenyl)acrylamide (Compound 241),
N-(4-fluoro-3-((2-((1-(methyl-$d_3$)-1H-pyrazol-4-yl)amino)-5-(4-(trifluoromethyl)phenyl)pyrimidin-4-yl)amino)phenyl)acrylamide (Compound 242),
N-(4-fluoro-3-((2-((1-(methyl-$^{13}C$-$d_3$)-1H-pyrazol-4-yl)amino)-5-(4-(trifluoromethyl)phenyl)pyrimidin-4-yl)amino)phenyl)acrylamide (Compound 243),
N-(3-((5-(cyclopropylethynyl)-2-((1-methyl-1H-pyrazol-4-yl)amino)pyrimidin-4-yl)amino)-4-fluorophenyl)acrylamide (Compound 244),
N-(3-((2-((3-chloro-1-methyl-1H-pyrazol-4-yl)amino)-5-(4-(trifluoromethyl)phenyl)pyrimidin-4-yl)amino)-5-fluorophenyl)acrylamide (Compound 245),
N-(3-((2-((1-(2-cyanopropan-2-yl)-1H-pyrazol-4-yl)amino)-5-(4-(trifluoromethyl)phenyl)pyrimidin-4-yl)amino)-4-fluorophenyl)acrylamide (Compound 246), N-(4-fluoro-3-((2-((1-methyl-1H-pyrazol-4-yl)amino)-5-(4-(trifluoromethyl)phenyl)pyrimidin-4-yl)amino)phenyl) acrylamide-3,3-$d_2$ (Compound 247), N-(4-fluoro-3-((2-((1-(methyl-$d_3$)-1H-pyrazol-4-yl)amino)-5-(4-(trifluoromethyl)phenyl)pyrimidin-4-yl)amino)phenyl)acrylamide-3,3-$d_2$ (Compound 248), N-(3-((2-((3-chloro-1-methyl-1H-pyrazol-4-yl)amino)-5-(4-(trifluoromethyl)phenyl)pyrimidin-4-yl)amino)-4-fluorophenyl)acrylamide-3,3-$d_2$ (Compound 249), N-(3-((5-(4-bromophenyl)-2-((1-methyl-1H-pyrazol-4-yl) amino)pyrimidin-4-yl)amino)-4-fluorophenyl)acrylamide-3,3-$d_2$ (Compound 250), N-(4-fluoro-3-((2-((1-methyl-1H-pyrazol-4-yl)amino)-5-(4-(trifluoromethyl)phenyl)pyrimidin-4-yl)amino)phenyl) buta-2,3-dienamide (Compound 251), 2-chloro-N-(4-fluoro-3-((2-((1-methyl-1H-pyrazol-4-yl) amino)-5-(4-(trifluoromethyl)phenyl)pyrimidin-4-yl) amino)phenyl)acetamide (Compound 252), N-(4-fluoro-3-((2-((1-methyl-1H-pyrazol-4-yl)amino)-5-(4-(trifluoromethyl)phenyl)pyrimidin-4-yl)amino)phenyl) ethenesulfonamide (Compound 253), N-(4-fluoro-3-((2-((1-methyl-1H-pyrazol-4-yl)amino)-5-(4-(trifluoromethyl)phenyl)pyrimidin-4-yl)amino)phenyl) propiolamide (Compound 254), N-(4-fluoro-3-((2-((1-methyl-1H-pyrazol-4-yl)amino)-5-(tetrahydro-2H-pyran-4-yl)pyrimidin-4-yl)amino)phenyl) acrylamide (Compound 255), N-(3-((5-bromo-2-((1-methyl-1H-pyrazol-4-yl)amino)pyrimidin-4-yl)amino)-4-fluorophenyl)acrylamide (Compound 256), $N^4$-(5-amino-2-fluorophenyl)-$N^2$-(1-methyl-1H-pyrazol-4-yl)-5-(4-(trifluoromethyl)phenyl)pyrimidine-2,4-diamine (Compound 257), N-(4-fluoro-3-((5-(2-isopropylphenyl)-2-((1-methyl-1H-pyrazol-4-yl)amino)pyrimidin-4-yl)amino)phenyl)acrylamide (Compound 258), N-(4-fluoro-3-((5-(2-methoxyphenyl)-2-((1-methyl-1H-pyrazol-4-yl)amino)pyrimidin-4-yl)amino)phenyl)acrylamide (Compound 259), N-(4-fluoro-3-((5-(1-methyl-1H-indol-4-yl)-2-((1-methyl-1H-pyrazol-4-yl)amino)pyrimidin-4-yl)amino)phenyl) acrylamide (Compound 260), N-(3-((5-(2,5-dihydrofuran-3-yl)-2-((1-methyl-1H-pyrazol-4-yl)amino)pyrimidin-4-yl)amino)-4-fluorophenyl)acrylamide (Compound 261), N-(4-fluoro-3-((2-((1-methyl-1H-pyrazol-4-yl)amino)-5-(quinolin-5-yl)pyrimidin-4-yl)amino)phenyl)acrylamide (Compound 262), N-(3-((5-([1,1'-biphenyl]-2-yl)-2-((1-methyl-1H-pyrazol-4-yl)amino)pyrimidin-4-yl)amino)-4-fluorophenyl)acrylamide (Compound 263), N-(3-((2-((3-chloro-1-methyl-1H-pyrazol-4-yl)amino)-5-(2-fluorophenyl)pyrimidin-4-yl)amino)-4-fluorophenyl) acrylamide (Compound 264), N-(3-((5-(1H-indol-7-yl)-2-((1-methyl-1H-pyrazol-4-yl) amino)pyrimidin-4-yl)amino)-4-fluorophenyl)acrylamide (Compound 265), N-(4-fluoro-3-((2-((1-methyl-1H-pyrazol-4-yl)amino)-5-(tetrahydrofuran-3-yl)pyrimidin-4-yl)amino)phenyl)acrylamide (Compound 266), N-(3-((5-(2-(dimethylamino)phenyl)-2-((1-methyl-1H-pyrazol-4-yl)amino)pyrimidin-4-yl)amino)-4-fluorophenyl)acrylamide (Compound 267), N-(4-fluoro-3-((5-(isoquinolin-8-yl)-2-((1-methyl-1H-pyrazol-4-yl)amino)pyrimidin-4-yl)amino)phenyl)acrylamide (Compound 268), N-(4-fluoro-3-((2-((1-methyl-1H-pyrazol-4-yl)amino)-5-(piperidin-1-yl)pyrimidin-4-yl)amino)phenyl)acrylamide (Compound 269), N-(4-fluoro-3-((5-(1-methyl-1H-indazol-5-yl)-2-((1-methyl-1H-pyrazol-4-yl)amino)pyrimidin-4-yl)amino) phenyl)acrylamide (Compound 270), N-(3-((5-bromo-2-((1-(2-cyanopropan-2-yl)-1H-pyrazol-4-yl)amino)pyrimidin-4-yl)amino)-4-fluorophenyl)acrylamide (Compound 271), N-(3-((2-((1-(2-cyanopropan-2-yl)-1H-pyrazol-4-yl) amino)-5-(2,5-dihydrofuran-3-yl)pyrimidin-4-yl)amino)-4-fluorophenyl)acrylamide (Compound 272), N-(3-((5-bromo-2-((1-(2-hydroxy-2-methylpropyl)-1H-pyrazol-4-yl)amino)pyrimidin-4-yl)amino)-4-fluorophenyl)acrylamide (Compound 273), N-(3-((5-(4-bromophenyl)-2-((1-methyl-1H-pyrazol-4-yl) amino)pyrimidin-4-yl)amino)phenyl)acrylamide (Compound 274), N-(3-((5-chloro-4-((1-methyl-1H-pyrazol-4-yl)amino)pyrimidin-2-yl)amino)phenyl)acrylamide (Compound 275), N-(4-fluoro-3-((5-(4-((3-fluorobenzyl)oxy)phenyl)-2-((1-methyl-1H-pyrazol-4-yl)amino)pyrimidin-4-yl)amino) phenyl)acrylamide (Compound 276), N-(3-((5-(1H-indazol-5-yl)-2-((1-methyl-1H-pyrazol-4-yl) amino)pyrimidin-4-yl)amino)-4-fluorophenyl)acrylamide (Compound 277), N-(3-((5-([1,2,4]triazolo[1,5-a]pyridin-7-yl)-2-((1-methyl-1H-pyrazol-4-yl)amino)pyrimidin-4-yl)amino)-4-fluorophenyl)acrylamide (Compound 278), N-(3-((5-([1,2,4]triazolo[1,5-a]pyridin-6-yl)-2-((1-methyl-1H-pyrazol-4-yl)amino)pyrimidin-4-yl)amino)-4-fluorophenyl)acrylamide (Compound 279), N-(3-((5-fluoro-2-((1-methyl-1H-pyrazol-4-yl)amino)pyrimidin-4-yl)amino)phenyl)acrylamide (Compound 280), N-(4-fluoro-3-((2-((1-methyl-1H-pyrazol-4-yl)amino)-5-(phenyl-4-d)pyrimidin-4-yl)amino)phenyl)acrylamide (Compound 281), N-(3-bromo-5-((5-(4-(difluoromethoxy)phenyl)-2-((1-methyl-1H-pyrazol-4-yl)amino)pyrimidin-4-yl)amino) phenyl)acrylamide (Compound 282), N-(3-bromo-5-((5-chloro-2-((1-methyl-1H-pyrazol-4-yl) amino)pyrimidin-4-yl)amino)phenyl)acrylamide (Compound 283), N-(3-((5-chloro-2-((1-(2-(dimethylamino)ethyl)-1H-pyrazol-4-yl)amino)pyrimidin-4-yl)amino)-4-fluorophenyl) acrylamide (Compound 284), N-(4-fluoro-3-((5-fluoro-2-((1-methyl-1H-pyrazol-4-yl) amino)pyrimidin-4-yl)amino)phenyl)acrylamide (Compound 285), N-(3-((5-chloro-2-((3-chloro-1-methyl-1H-pyrazol-4-yl) amino)pyrimidin-4-yl)amino)-4-fluorophenyl)acrylamide (Compound 286), N-(3-((5-chloro-2-((4-((dimethylamino)methyl)phenyl) amino)pyrimidin-4-yl)amino)-4-fluorophenyl)acrylamide (Compound 287), N-(3-((5-chloro-2-((4-((2-(dimethylamino)ethyl)(methyl) amino)phenyl)amino)pyrimidin-4-yl)amino)-4-fluorophenyl)acrylamide (Compound 288), N-(3-((5-(4-bromophenyl)-2-((1-methyl-1H-pyrazol-4-yl) amino)pyrimidin-4-yl)amino)-5-(trifluoromethyl)phenyl) acrylamide (Compound 289), N-(3-bromo-5-((2-((1-methyl-1H-pyrazol-4-yl)amino)-5-(4-(trifluoromethyl)phenyl)pyrimidin-4-yl)amino)phenyl)acrylamide (Compound 290), N-(3-((5-chloro-2-((1-methyl-1H-pyrazol-4-yl)amino)pyrimidin-4-yl)amino)-5-(trifluoromethyl)phenyl)acrylamide (Compound 291), N-(3-((5-(4-bromophenyl)-2-((1-methyl-1H-pyrazol-4-yl)amino)pyrimidin-4-yl)amino)-4-chlorophenyl)acrylamide (Compound 292), N-(3-((2-((1-methyl-1H-pyrazol-4-yl)amino)-5-(4-(2,2,2-trifluoroethyl)phenyl)pyrimidin-4-yl)amino)phenyl)acrylamide (Compound 293), N-(4-fluoro-3-((2-((1-methyl-1H-pyrazol-4-yl)amino)-5-(4-(1-(trifluoromethyl)cyclopropyl)phenyl)pyrimidin-4-yl)amino)phenyl)acrylamide (Compound 294), N-(3-fluoro-5-((2-((1-methyl-1H-pyrazol-4-yl)amino)-5-(4-(2,2,2-trifluoroethyl)phenyl)pyrimidin-4-yl)amino)phenyl)acrylamide (Compound 295), N-(4-fluoro-3-((2-((1-methyl-1H-pyrazol-4-yl)amino)-5-(4-(perfluoroethyl)phenyl)pyrimidin-4-yl)amino)phenyl)acrylamide (Compound 296), N-(3-((5-chloro-2-((1-methyl-1H-pyrazol-4-yl)amino)pyrimidin-4-yl)amino)naphthalen-1-yl)acrylamide (Compound 297), N-(3-((5-(5-chlorothiophen-3-yl)-2-((1-methyl-1H-pyrazol-4-yl)amino)pyrimidin-4-yl)amino)-4-fluorophenyl)acrylamide (Compound 298), N-(3-((5-(benzofuran-6-yl)-2-((1-methyl-1H-pyrazol-4-yl)amino)pyrimidin-4-yl)amino)-4-fluorophenyl)acrylamide (Compound 299), N-(4-fluoro-3-((5-(4-(3-fluorophenoxy)phenyl)-2-((1-methyl-1H-pyrazol-4-yl)amino)pyrimidin-4-yl)amino)phenyl)acrylamide (Compound 300), (E)-4-(dimethylamino)-N-(4-fluoro-3-((2-((1-methyl-1H-pyrazol-4-yl)amino)-5-(4-(2,2,2-trifluoroethyl)phenyl)pyrimidin-4-yl)amino)phenyl)but-2-enamide (Compound 301), N-(3-bromo-5-((2-((1-methyl-1H-pyrazol-4-yl)amino)-5-(4-(2,2,2-trifluoroethyl)phenyl)pyrimidin-4-yl)amino)phenyl)acrylamide (Compound 302), (E)-4-fluoro-N-(4-fluoro-3-((2-((1-methyl-1H-pyrazol-4-yl)amino)-5-(4-(2,2,2-trifluoroethyl)phenyl)pyrimidin-4-yl)amino)phenyl)but-2-enamide (Compound 303), (E)-N-(3-((5-(4-bromophenyl)-2-((1-methyl-1H-pyrazol-4-yl)amino)pyrimidin-4-yl)amino)-4-fluorophenyl)-4-(dimethylamino)but-2-enamide (Compound 304), and N-(4-fluoro-3-((5-(3-fluoro-5-methoxyphenyl)-2-(methyl(1-methyl-1H-pyrazol-4-yl)amino)pyrimidin-4-yl)amino)phenyl)acrylamide (Compound 305).

An embodiment of the present disclosure relates to a compound of Formula I or its stereoisomers, tautomers, pharmaceutically acceptable salts, stereoisomers, solvates, and hydrates thereof, for treating disease associated with epidermal growth factor receptor (EGFR) family kinases.

Another embodiment of the present disclosure relates to a compound of Formula I or its stereoisomers, tautomers, pharmaceutically acceptable salts, stereoisomers, solvates, and hydrates thereof, for treating cancer.

Another embodiment of the present disclosure relates to a compound Formula I, or its stereoisomers, tautomers, pharmaceutically acceptable salts, stereoisomers, solvates, and hydrates thereof, for treating disease or condition associated with non-small cell or small cell lung cancer or prostate cancer or head and neck cancer or breast cancer or colorectal cancer.

The present disclosure relates to a pharmaceutical composition comprising a compound of Formula I or a pharmaceutically acceptable salt or stereoisomer thereof together with a pharmaceutically acceptable carrier, optionally in combination with one or more other pharmaceutical compositions.

The present disclosure further relates to the process of preparation of compounds of Formula I or its stereoisomers, tautomers, pharmaceutically acceptable salts, stereoisomers, solvates, and hydrates thereof.

In another aspect, the present disclosure provides a compound selected from:

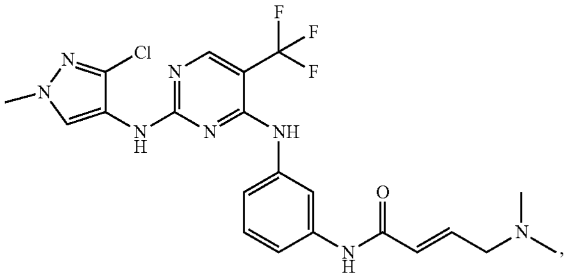

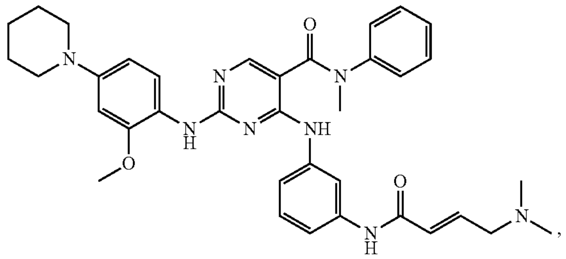

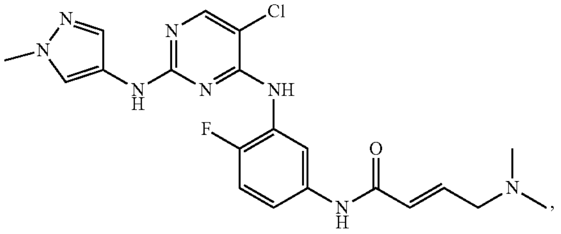

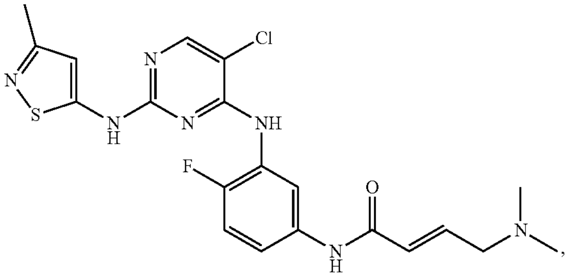

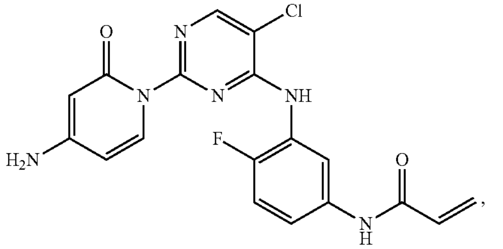

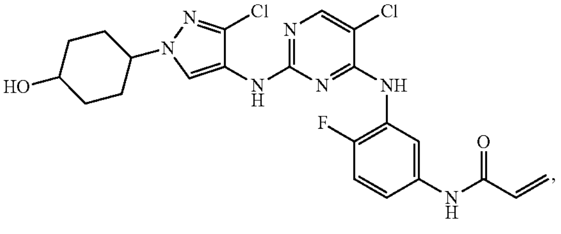

-continued
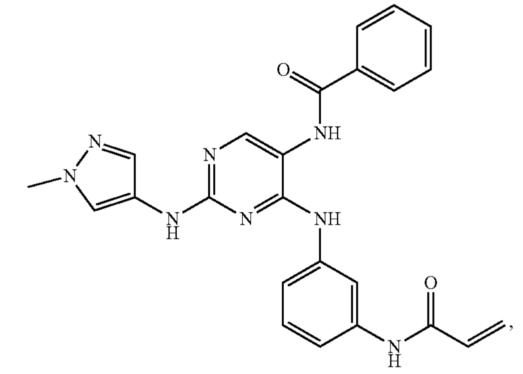
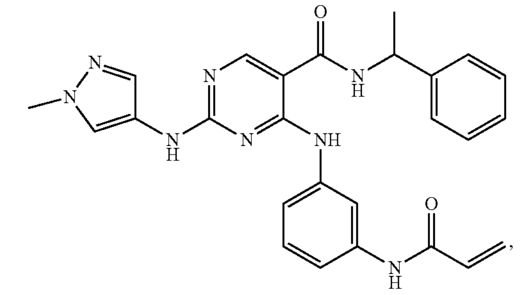
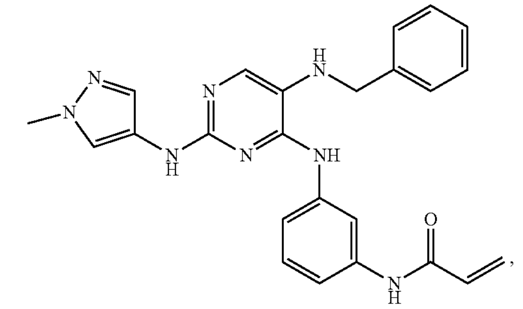
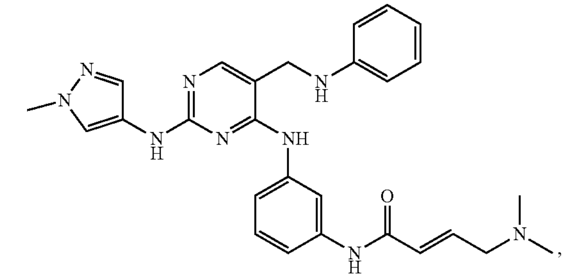
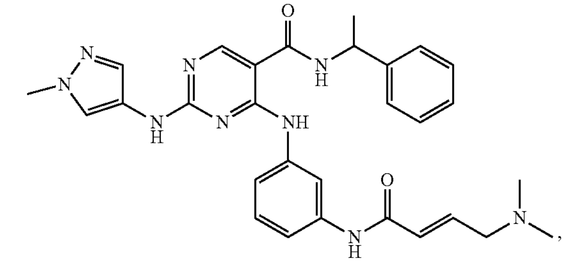
-continued
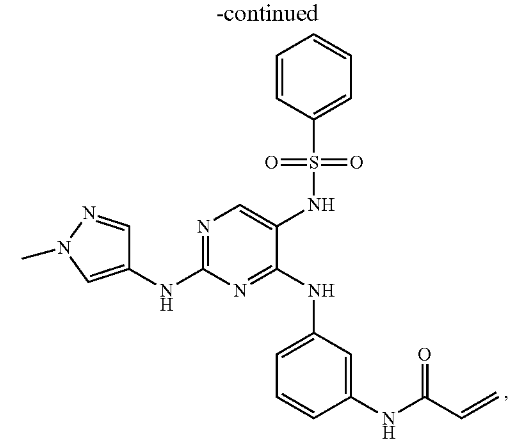
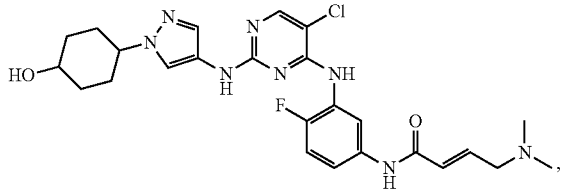
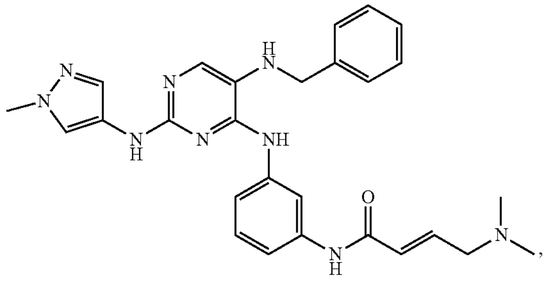
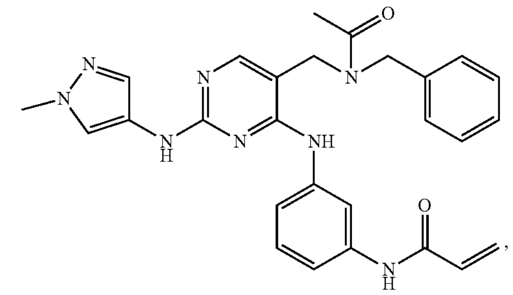
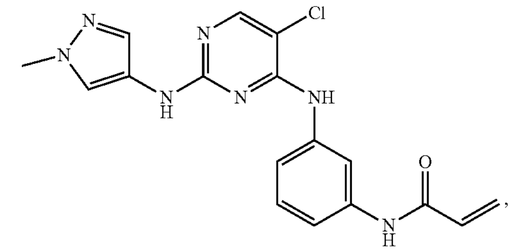

-continued
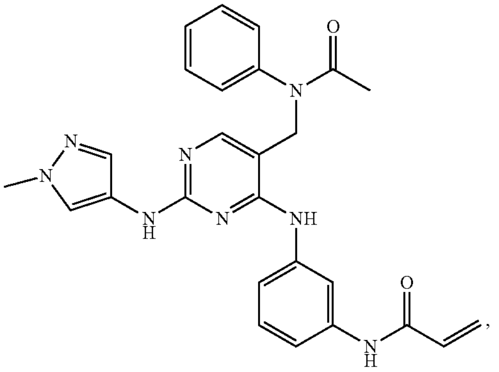
,
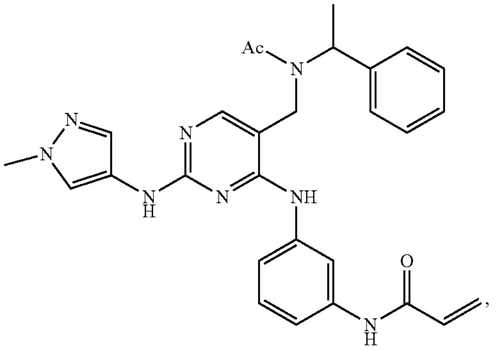
,
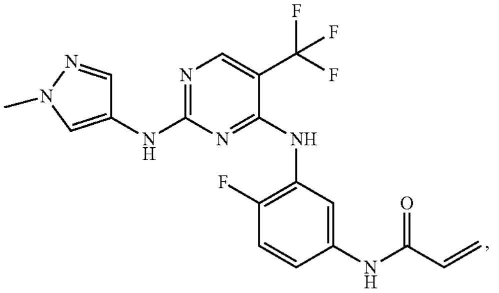
,
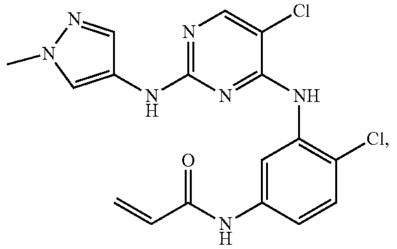
,
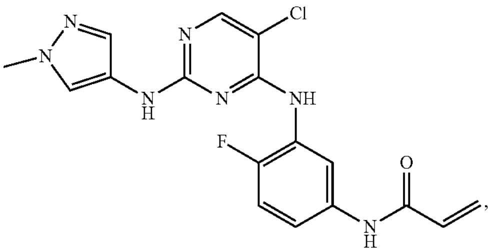
,
-continued
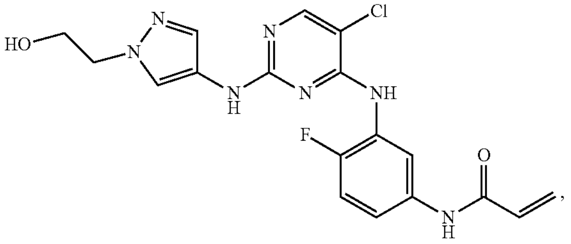
,
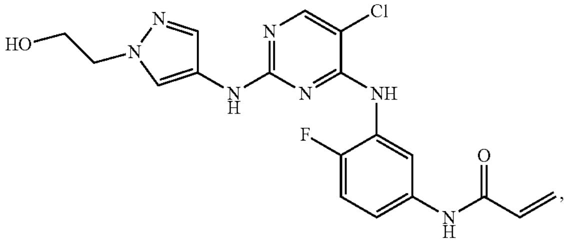
,
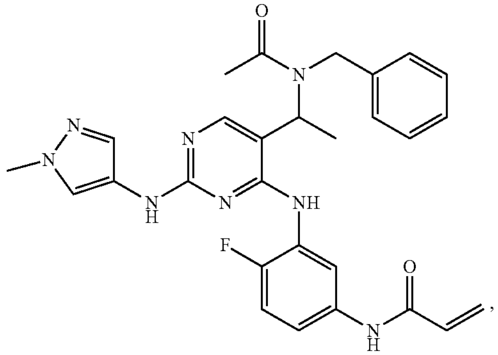
,
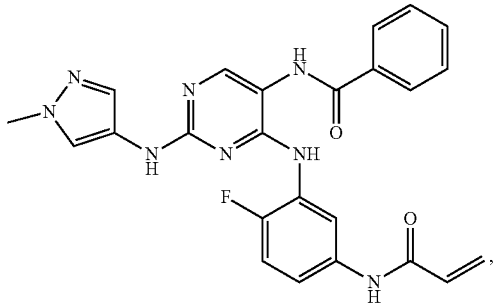
,
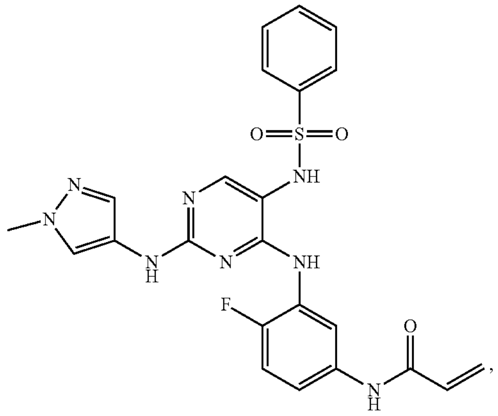
, -continued
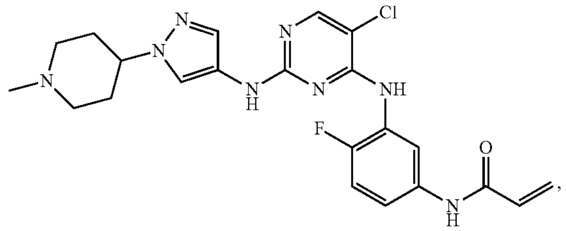
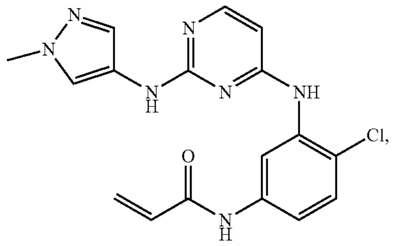
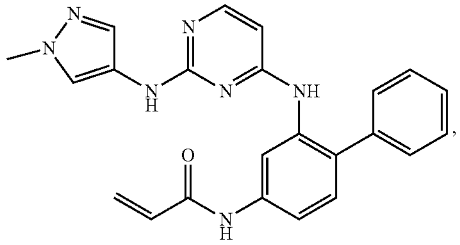
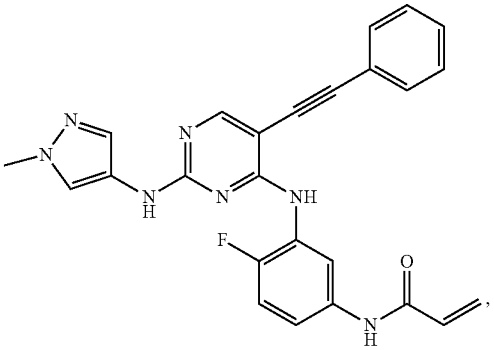
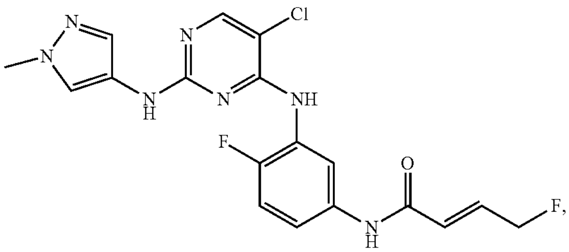
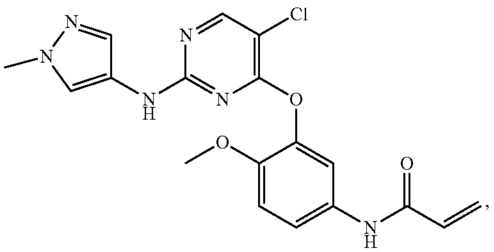
-continued
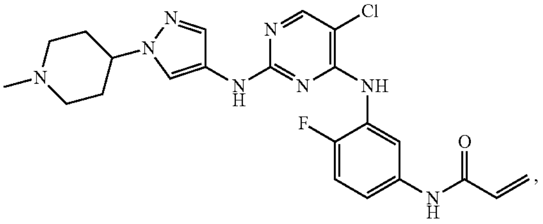
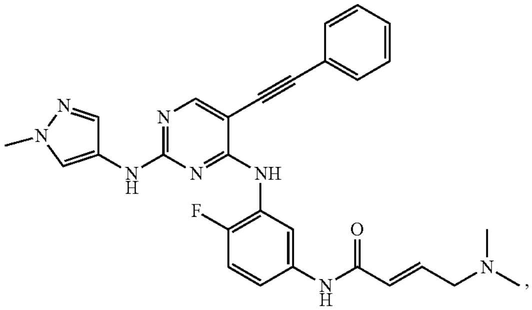
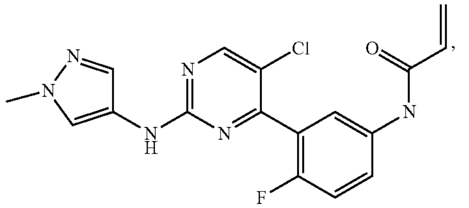
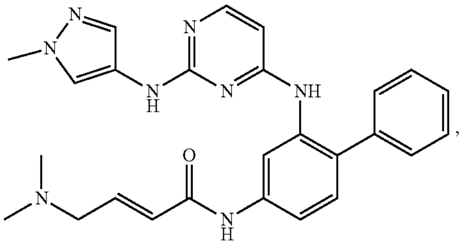
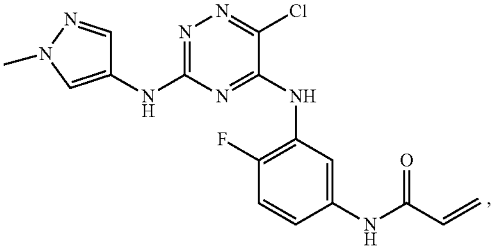
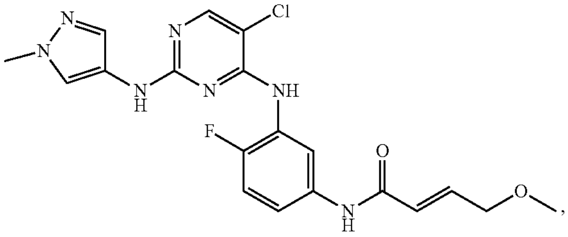
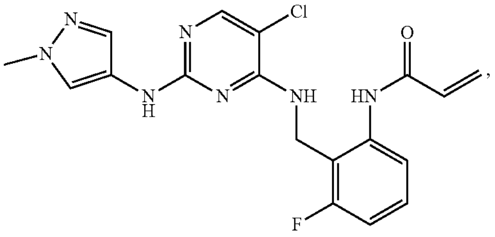

-continued
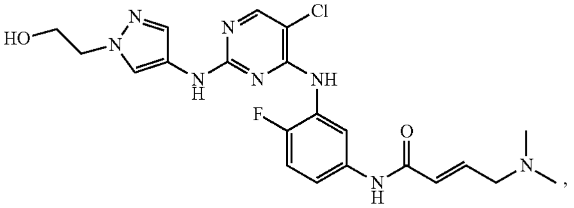
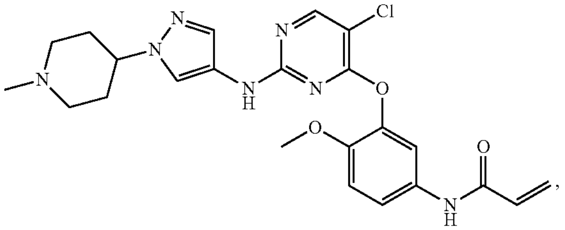
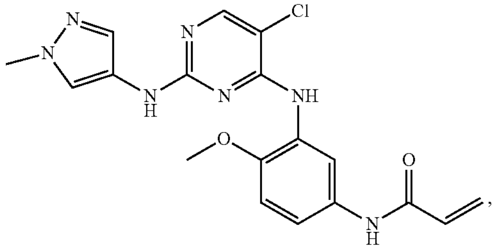
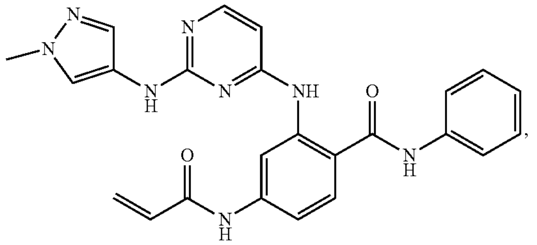
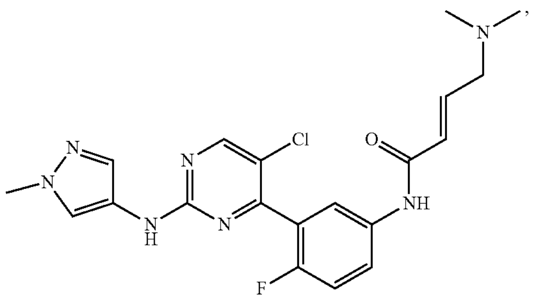
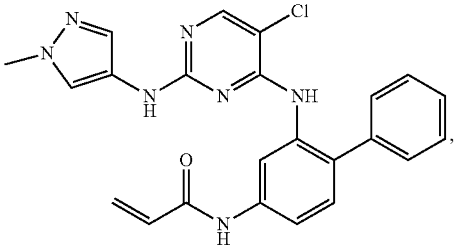
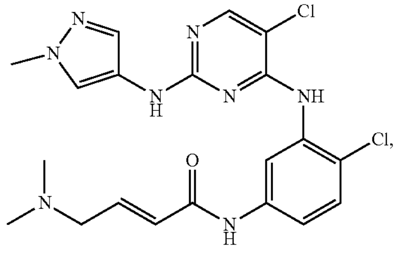
-continued
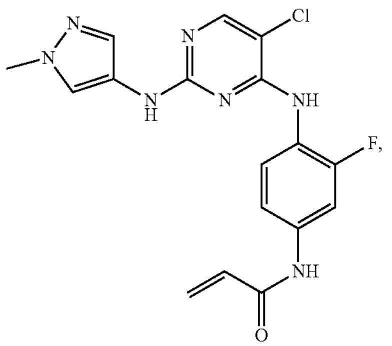
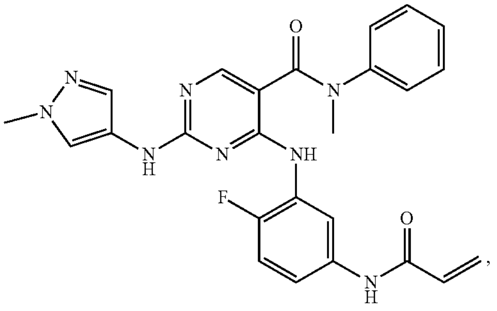
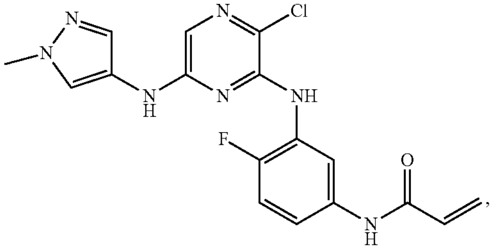
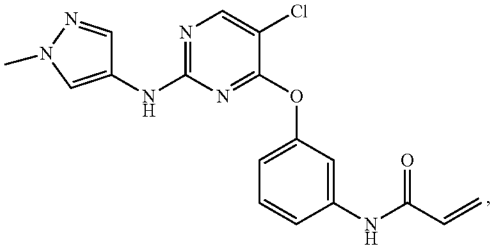
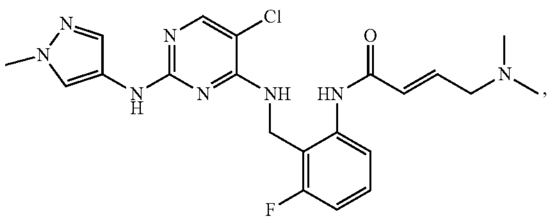
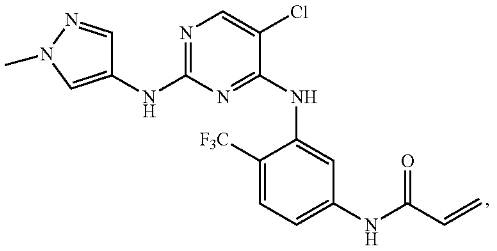

-continued
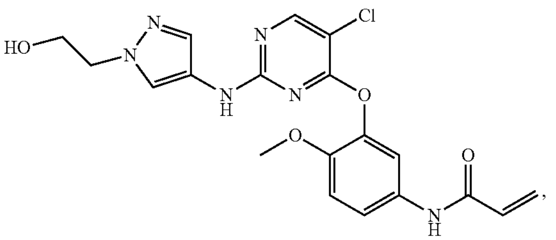
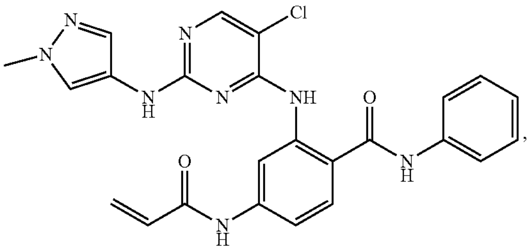
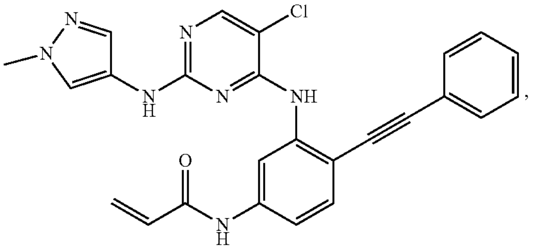
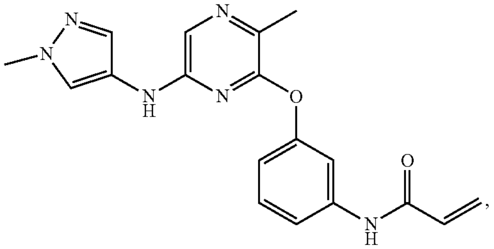
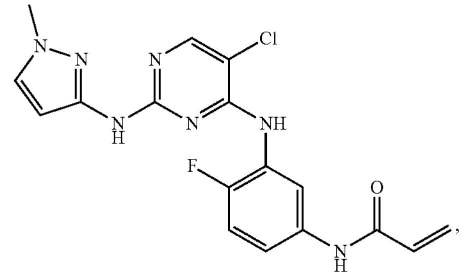
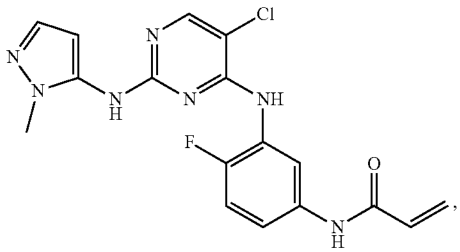
-continued
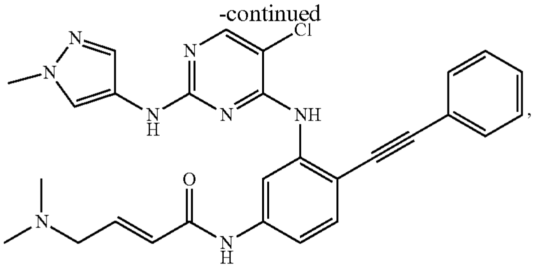
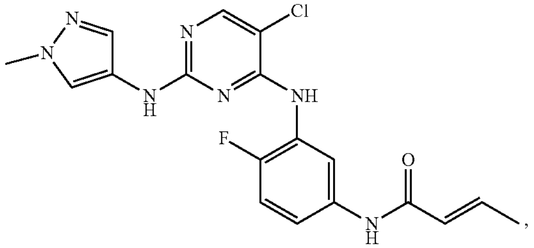
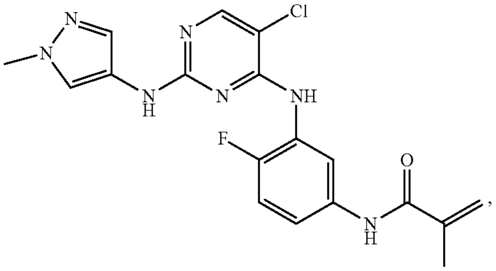
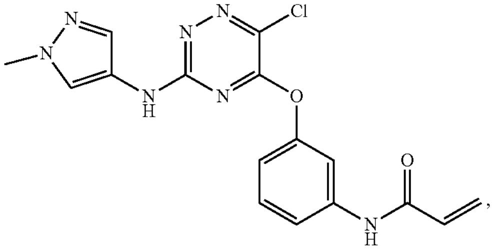
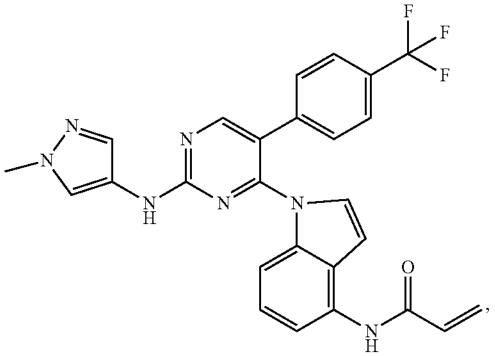
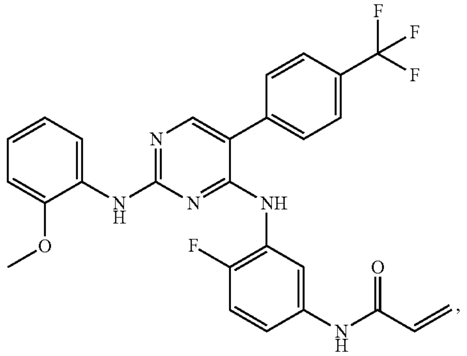

-continued
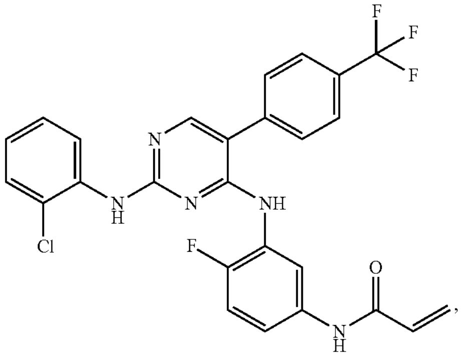
,
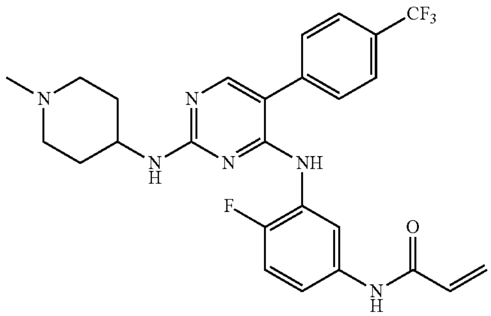
,
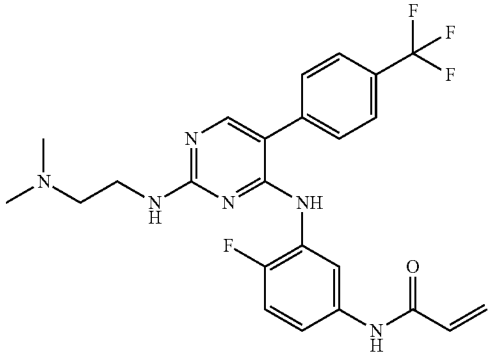
,
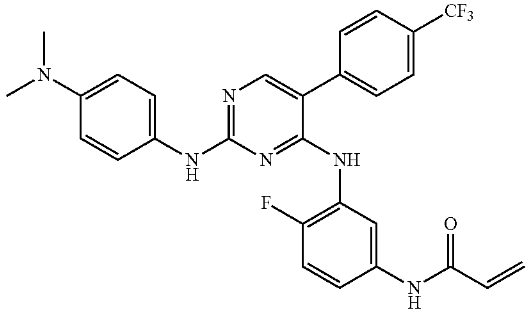
,
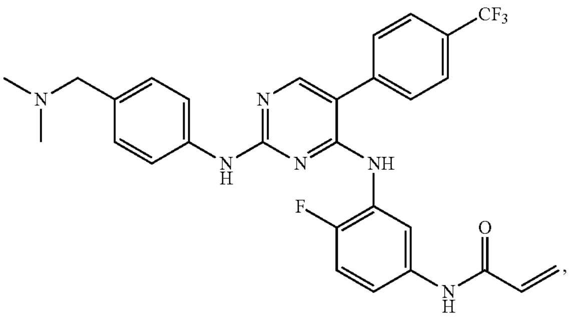
,
-continued
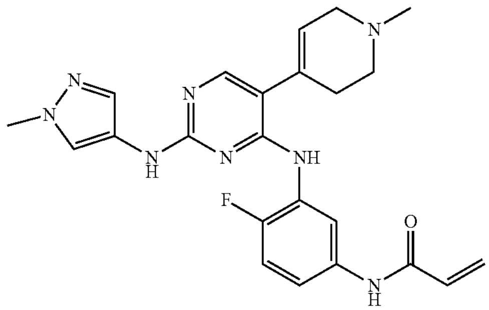
,
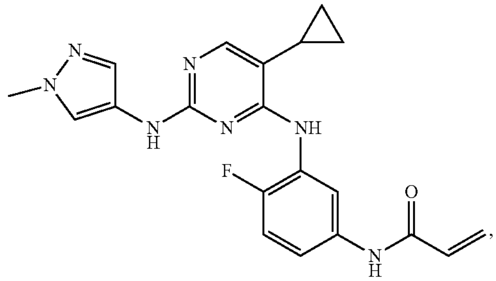
,
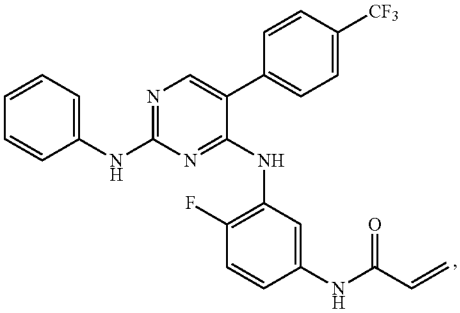
,
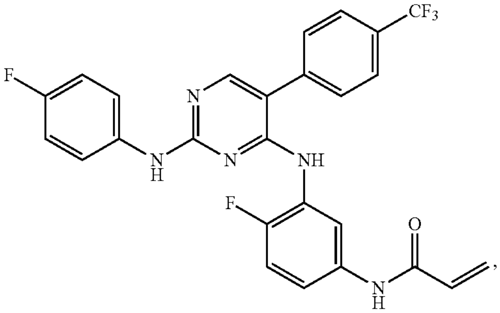
,
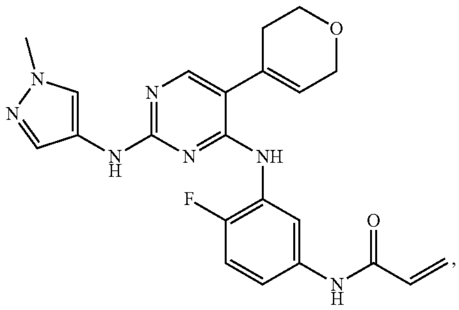
, -continued
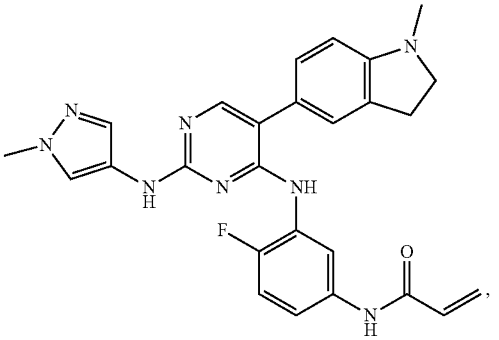
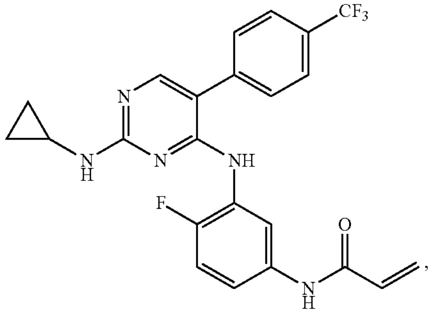
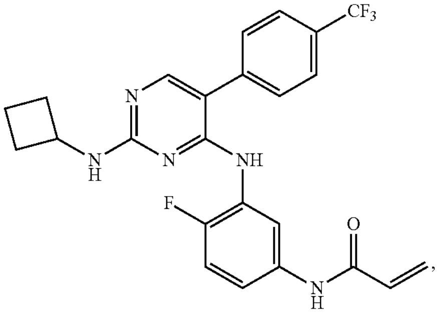
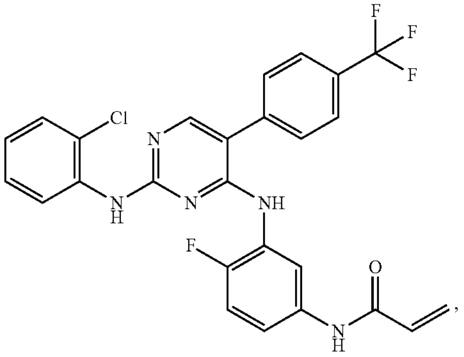
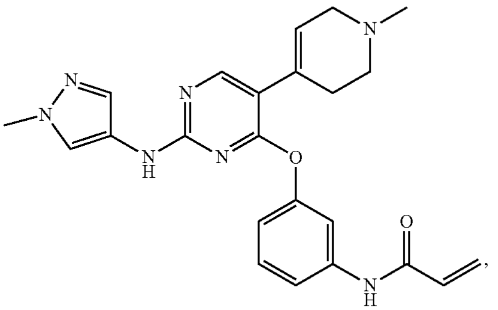
-continued
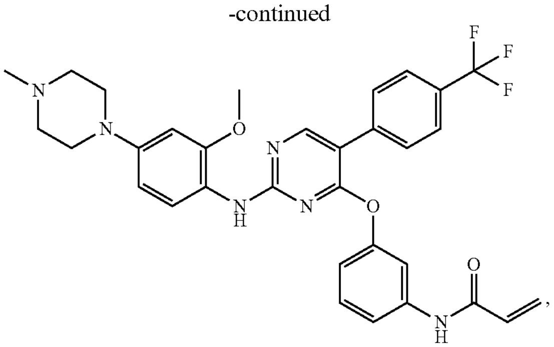
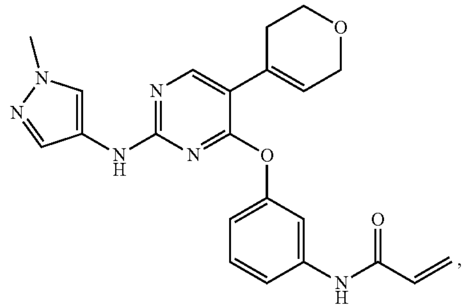
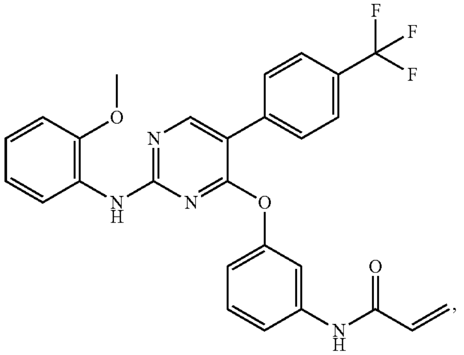
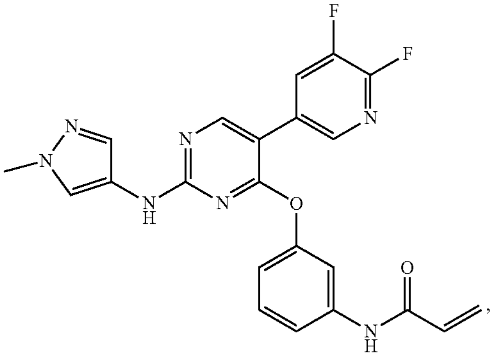
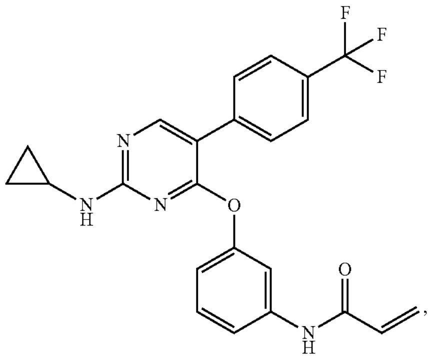

-continued
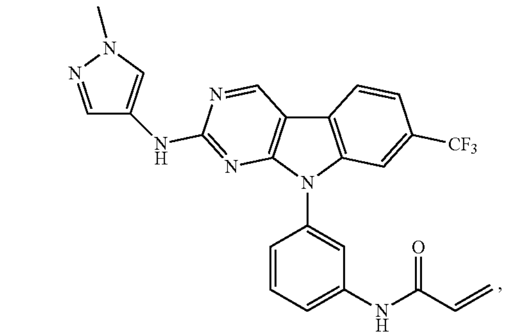,
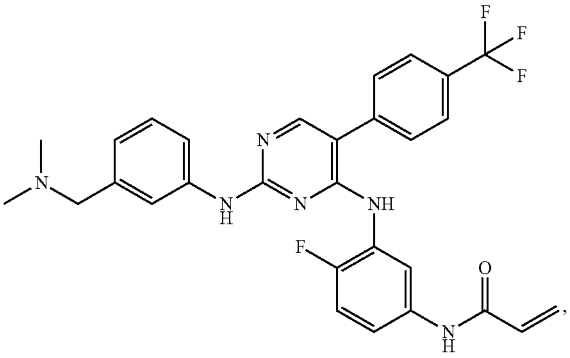,
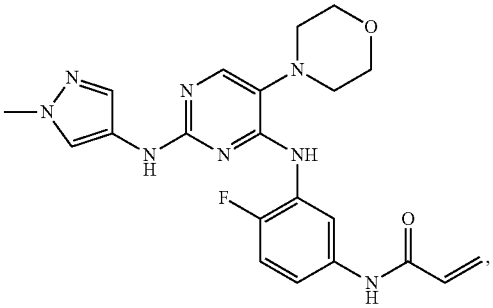,
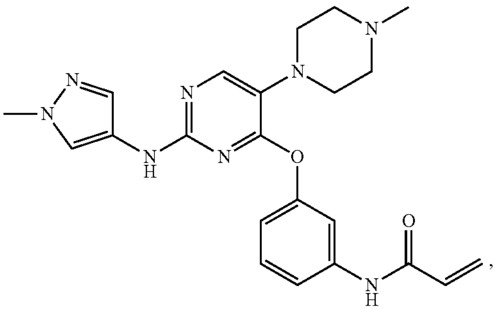,
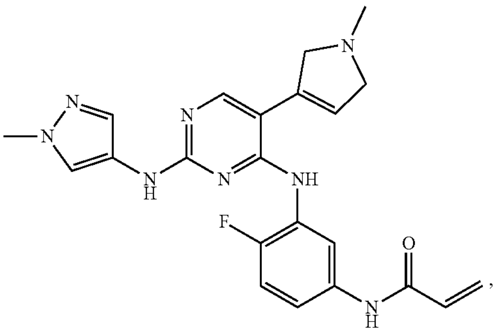,
-continued
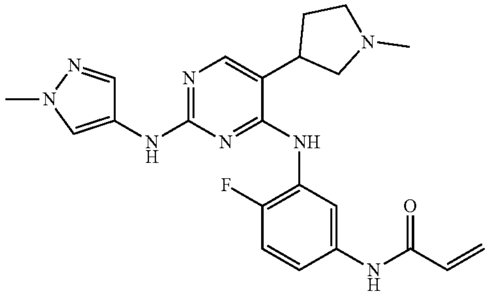,
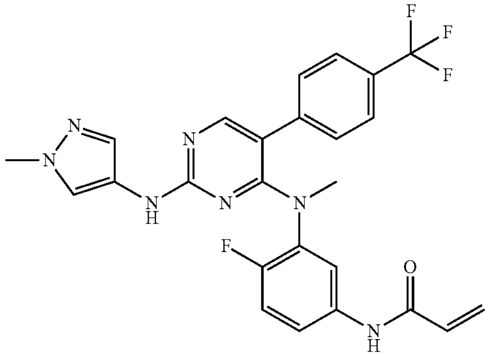,
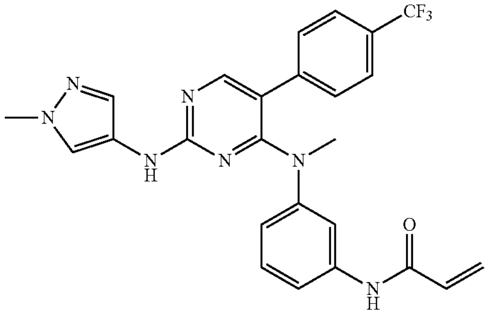,
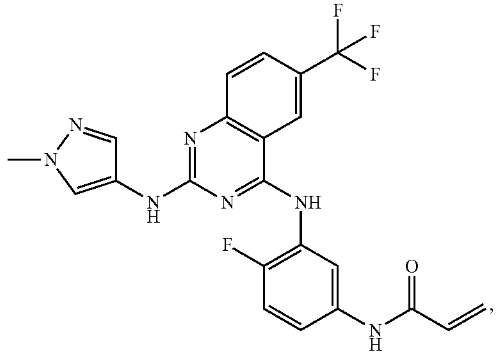,
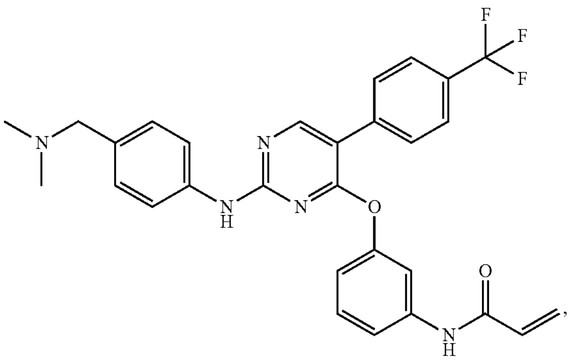, -continued
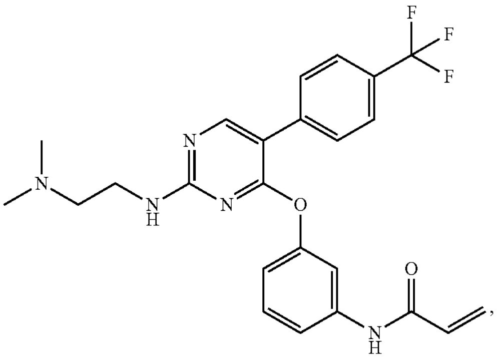
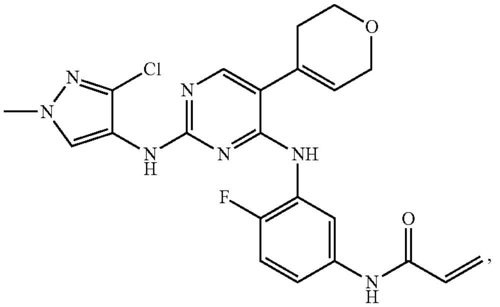
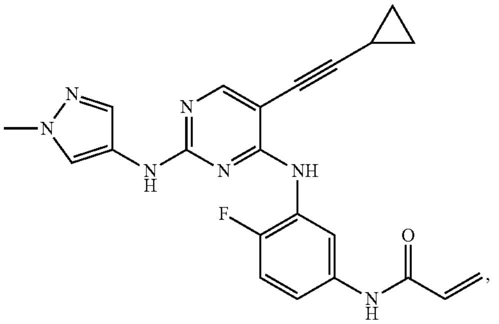
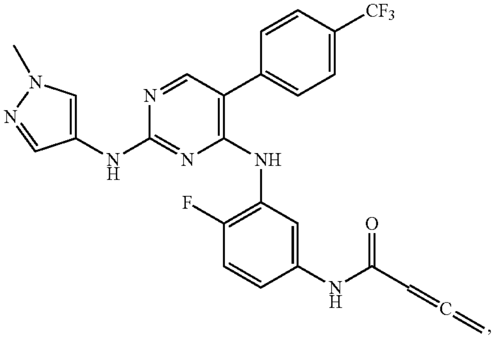
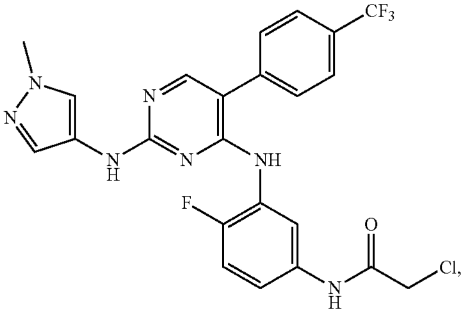
-continued
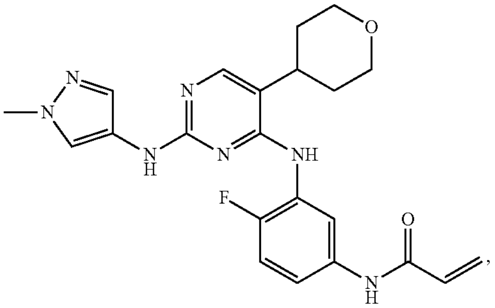
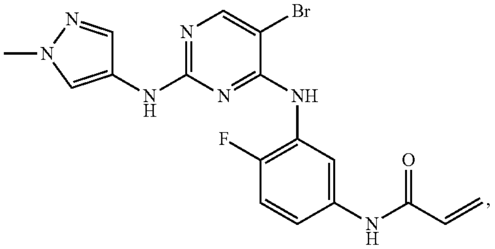
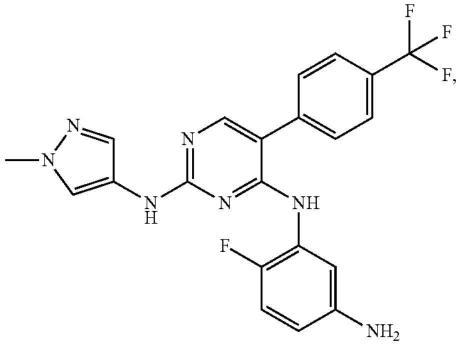
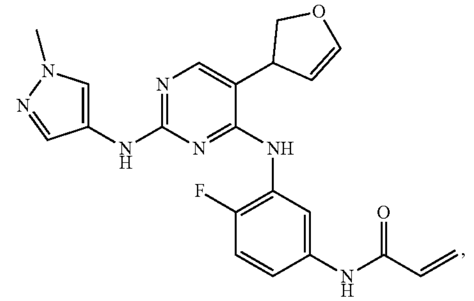
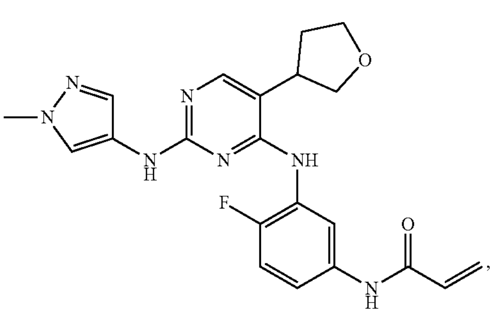

-continued
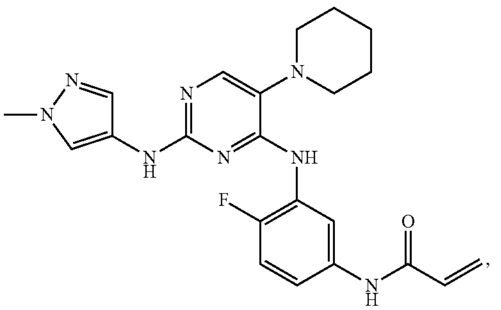
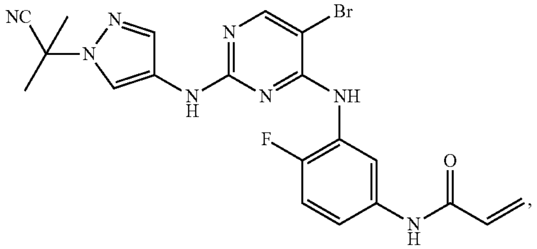
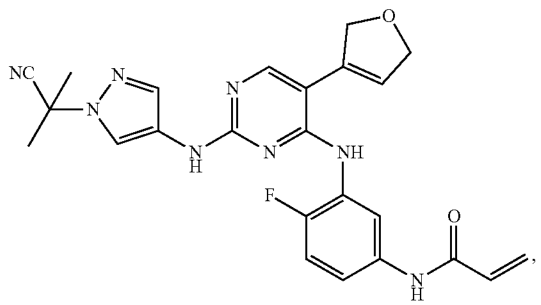
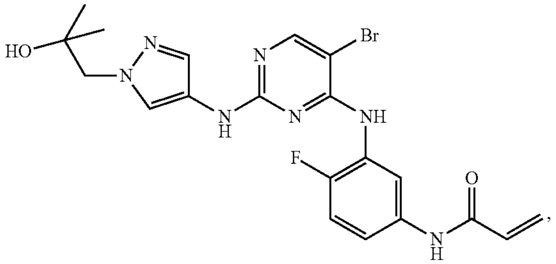
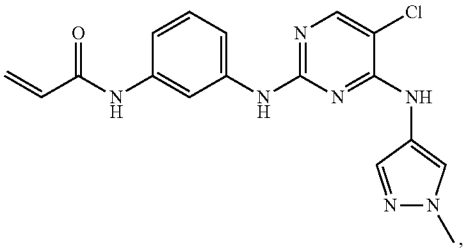
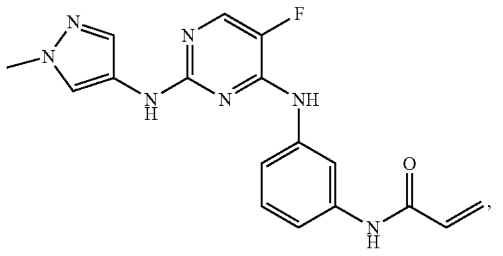
-continued
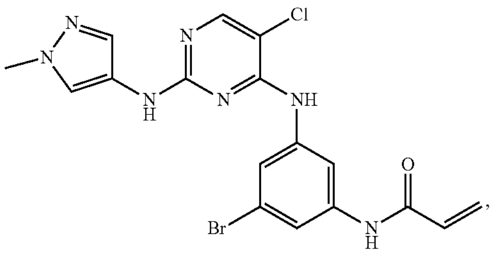
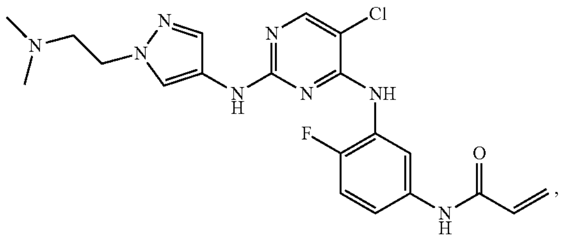
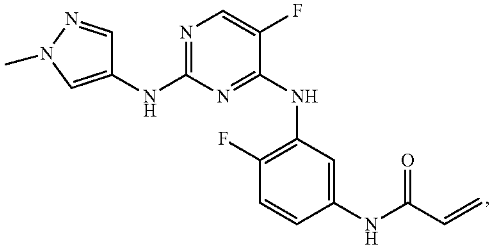
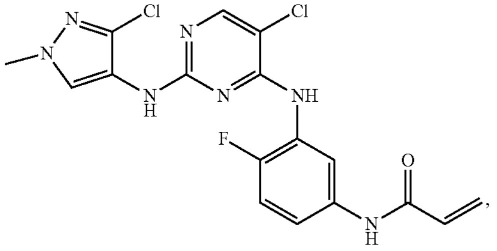
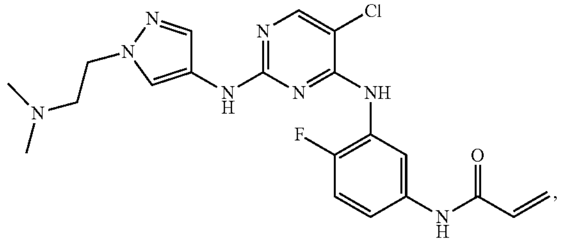
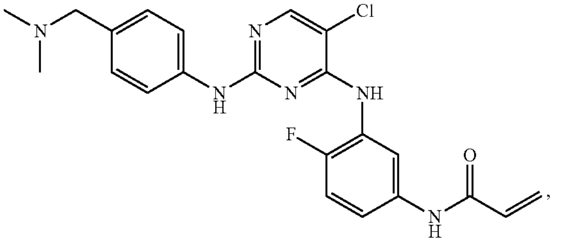
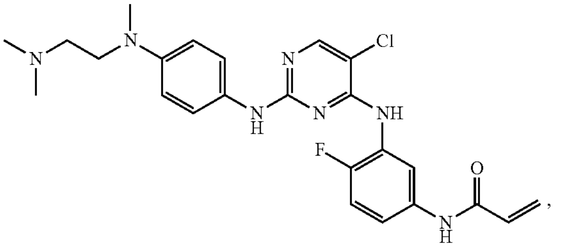

-continued

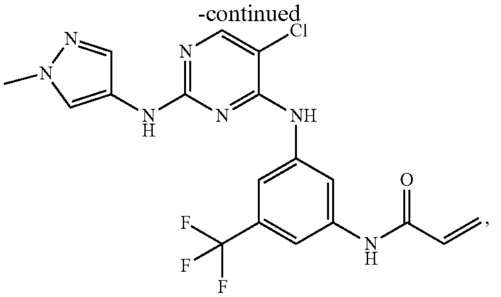

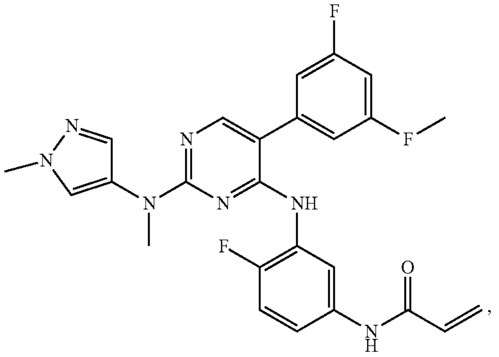

, and

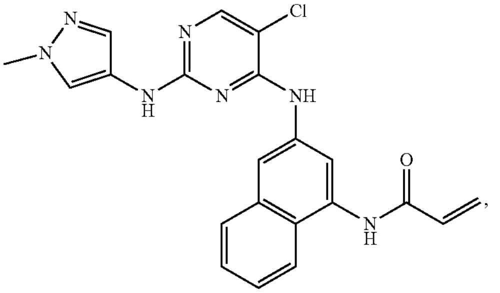

or a pharmaceutically acceptable salt or stereoisomer thereof.

Uses

Some embodiments provided herein describe a class of compounds that are useful as epidermal growth factor receptor (EGFR) family kinase inhibitors. Some embodiments provided herein describe a class of compounds that are useful as EGFR inhibitors. Some embodiments provided herein describe a class of compounds that are useful as EGFR del19/T790M inhibitors. Some embodiments provided herein describe a class of compounds that are useful as EGFR L858R/T790M inhibitors. In some embodiments, the compounds described herein have improved potency and/or beneficial activity profiles and/or beneficial selectivity profiles and/or increased efficacy and/or improved safety profiles (such as reduced side effects) and/or improved pharmacokinetic properties. In some embodiments, the compounds described herein are selective inhibitors of EGFR del19/T790M over WT EGFR. In some embodiments, the compounds described herein are selective inhibitors of EGFR L858R/T790M over WT EGFR.

In some embodiments, the compounds described herein are selective inhibitors of EGFR over HER2.

In some embodiments, the compounds described herein have improved safety profiles. In some embodiments, the compounds described herein have improved toxicity profile. In some embodiments, the compounds described herein have improved therapeutic index.

In some embodiments, the compounds described herein are useful to treat, prevent or ameliorate a disease or condition which displays drug resistance associated with EGFR del19/T790M activation. In some embodiments, the compounds described herein are useful to treat, prevent or ameliorate a disease or condition which displays drug resistance associated with EGFR L858R/T790M activation.

In some embodiments, EGFR family kinase mutants are detected with a commercially available test kit. In some embodiments, EGFR family kinase mutants are detected with a reverse transcription polymerase chain reaction (RT-PCR)-based method. In some embodiments, EGFR family kinase mutants are detected with a sequencing-based method. In some embodiments, EGFR family kinase mutants are detected with a mass spectrometry genotyping-based method. In some embodiments, EGFR family kinase mutants are detected with an immunohistochemistry-based method. In some embodiments, EGFR family kinase mutants are detected with a molecular diagnostics panel. In some embodiments, EGFR family kinase mutants are detected from a tumor sample. In some embodiments, EGFR family kinase mutants are detected from circulating DNA. In some embodiments, EGFR family kinase mutants are detected from tumor cells.

In one aspect, provided herein is a method of inhibiting an epidermal growth factor receptor (EGFR) family kinase mutant in a subject in need thereof, comprising administering to the subject a therapeutically effective amount of a compound of Formula I, or a pharmaceutically acceptable salt or stereoisomer thereof.

In another aspect, provided herein is a method of inhibiting a human epidermal growth factor receptor 2 (HER2) mutant in a subject in need thereof, comprising administering to the subject a therapeutically effective amount of a compound of Formula I, or a pharmaceutically acceptable salt or stereoisomer thereof. In some embodiments, the HER2 mutant comprises an insertion in exon 20, an in-frame deletion and insertion in exon 20, a substitution in the extracellular domain, an extracellular truncation, or a substitution in exon 30. In some embodiments, the HER2 mutant is selected from A775_G776insYVMA, A775_G776insSVMA, A775 G776insVVMA, G776del insVC, G776del insLC, G776del insAV, G776del insAVGC, S310F, S310Y, p95, V842I, P780_Y781insGSP, and any combination thereof. In some embodiments, the HER2 mutant is A775_G776insYVMA. In some embodiments, the HER2 mutant is A775_G776insSVMA. In some embodiments, the HER2 mutant is A775 G776insVVMA. In some embodiments, the HER2 mutant is G776del insVC. In some embodiments, the HER2 mutant is G776del insLC. In some embodiments, the HER2 mutant is G776del insAV. In some embodiments, the HER2 mutant is G776del insAVGC. In some embodiments, the HER2 mutant is S310F. In some embodiments, the HER2 mutant is S310Y. In some embodiments, the HER2 mutant is p95. In some embodiments, the HER2 mutant is V842I. In some embodiments, the HER2 mutant is P780_Y781insGSP.

In another aspect, provided herein is a method of inhibiting an epidermal growth factor receptor (EGFR) mutant in a subject in need thereof, comprising administering to the subject a therapeutically effective amount of a compound of Formula I, or a pharmaceutically acceptable salt or stereoisomer thereof.

In another aspect, provided herein is a method of inhibiting a drug-resistant epidermal growth factor receptor (EGFR) mutant in a subject in need thereof, comprising administering to the subject a therapeutically effective amount of a compound of Formula I, or a pharmaceutically acceptable salt or stereoisomer thereof. In some embodiments, the drug-resistant EGFR mutant is del19/T790M EGFR or L858R/T790M EGFR.

In another aspect, provided herein is a method of inhibiting human epidermal growth factor receptor 2 (HER2) in a subject in need thereof, comprising administering to the subject a therapeutically effective amount of a compound of Formula I, or a pharmaceutically acceptable salt or stereoisomer thereof, wherein the compound exhibits greater inhibition of a HER2 mutant relative to wild-type EGFR. In some embodiments, the HER2 mutant comprises an insertion in exon 20, an in-frame deletion and insertion in exon 20, a substitution in the extracellular domain, an extracellular truncation, or a substitution in exon 30. In some embodiments, the HER2 mutant is selected from A775_G776insYVMA, A775_G776insSVMA, A775 G776insVVMA, G776del insVC, G776del insLC, G776del insAV, G776del insAVGC, S310F, S310Y, p95, V842I, P780_Y781insGSP, and any combination thereof. In some embodiments, the HER2 mutant is A775_G776insYVMA. In some embodiments, the HER2 mutant is A775_G776insSVMA. In some embodiments, the HER2 mutant is A775 G776insVVMA. In some embodiments, the HER2 mutant is G776del insVC. In some embodiments, the HER2 mutant is G776del insLC. In some embodiments, the HER2 mutant is G776del insAV. In some embodiments, the HER2 mutant is G776del insAVGC. In some embodiments, the HER2 mutant is S310F. In some embodiments, the HER2 mutant is S310Y. In some embodiments, the HER2 mutant is p95. In some embodiments, the HER2 mutant is V842I. In some embodiments, the HER2 mutant is P780_Y781insGSP.

In another aspect, provided herein is a method of inhibiting epidermal growth factor receptor (EGFR) in a subject in need thereof, comprising administering to the subject a therapeutically effective amount of a compound of Formula I, or a pharmaceutically acceptable salt or stereoisomer thereof, wherein the compound exhibits greater inhibition of an EGFR mutant relative to wild-type EGFR.

In some embodiments, the EGFR mutant comprises a substitution in exon 18, a deletion in exon 19, a substitution in exon 20, an insertion in exon 20, a mutation in the extracellular domain, or a substitution in exon 21. In some embodiments, the EGFR mutant is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR (or D770 N771insSVD EGFR), 770insNPG EGFR (or D770_N771insNPG EGFR), 770insGT EGFR, 770insGF EGFR, 770insG EGFR, 771insH EGFR, 771insN EGFR, 772insNP EGFR, 773insNPH EGFR (or H773insNPH EGFR), 773insH EGFR, 773insPH EGFR, EGFRvii, EGFRviii, A767_dupASV EGFR, 773insAH EGFR, M766_A767insAI EGFR, and any combination thereof. In some embodiments, the EGFR mutant is del19/T790M EGFR or L858R/T790M EGFR. In some embodiments, the EGFR mutant is del19/T790M EGFR. In some embodiments, the EGFR mutant is L858R/T790M EGFR.

In another aspect, provided herein is a method of treating a disease or disorder associated with epidermal growth factor receptor (EGFR) in a subject in need thereof, comprising administering to the subject a therapeutically effective amount of a compound of Formula I, or a pharmaceutically acceptable salt or stereoisomer thereof.

In some embodiments, the disease or disorder in the subject comprises a HER2 mutation. In some embodiments, the HER2 mutation comprises an insertion in exon 20, an in-frame deletion and insertion in exon 20, a substitution in the extracellular domain, an extracellular truncation, or a substitution in exon 30. In some embodiments, the HER2 mutation is selected from A775_G776insYVMA, A775 G776insSVMA, A775_G776insVVMA, G776del insVC, G776del insLC, G776del insAV, G776del insAVGC, S310F, S310Y, p95, V842I, P780_Y781insGSP, and a combination thereof. In some embodiments, the HER2 mutation is A775_G776insYVMA. In some embodiments, the HER2 mutation is A775_G776insSVMA. In some embodiments, the HER2 mutation is A775_G776insVVMA. In some embodiments, the HER2 mutation is G776del insVC. In some embodiments, the HER2 mutation is G776del insLC. In some embodiments, the HER2 mutation is G776del insAV. In some embodiments, the HER2 mutation is G776del insAVGC. In some embodiments, the HER2 mutation is S310F. In some embodiments, the HER2 mutation is S310Y. In some embodiments, the HER2 mutation is p95. In some embodiments, the HER2 mutation is V842I. In some embodiments, the HER2 mutation is P780_Y781insGSP.

In some embodiments, the disease or disorder in the subject comprises an EGFR mutation. In some embodiments, the EGFR mutation comprises a substitution in exon 18, a deletion in exon 19, a substitution in exon 20, an insertion in exon 20, a mutation in the extracellular domain, or a substitution in exon 21. In some embodiments, the EGFR mutation is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR (or D770_N771insSVD EGFR), 770insNPG EGFR (or D770_N771insNPG EGFR), 770insGT EGFR, 770insGF EGFR, 770insG EGFR, 771insH EGFR, 771insN EGFR, 772insNP EGFR, 773insNPH EGFR (or H773insNPH EGFR), 773insH EGFR, 773insPH EGFR, EGFRvii, EGFRviii, A767_dupASV EGFR, 773insAH EGFR, M766_A767insAI EGFR, and any combination thereof. In some embodiments, the EGFR mutation is del19/T790M EGFR or L858R/T790M EGFR. In some embodiments, the EGFR mutation is del19/T790M EGFR. In some embodiments, the EGFR mutation is L858R/T790M EGFR.

In another aspect, provided herein is a method of treating cancer in a subject in need thereof, comprising administering to the subject a therapeutically effective amount of a compound of Formula I, or a pharmaceutically acceptable salt or stereoisomer thereof. In some embodiments, the cancer displays drug resistance associated with EGFR del19/T790M activation. In some embodiments, the cancer displays drug resistance associated with EGFR L858R/T790M activation. Other embodiments provided herein describe the use of the compounds described herein for treating cancer.

In some embodiments, the cancer is bladder cancer, prostate cancer, breast cancer, cervical cancer, colorectal cancer, endometrial cancer, gastric cancer, glioblastoma, head and neck cancer, lung cancer, or non-small cell lung cancer. In some embodiments, the cancer is non-small cell lung cancer, prostate cancer, head and neck cancer, breast cancer, colorectal cancer, or glioblastoma. In some embodiments, the cancer is non-small cell lung cancer. In some embodiments, the cancer is prostate cancer. In some embodiments, the cancer is head and neck cancer. In some embodiments, the cancer is breast cancer. In some embodiments, the cancer is colorectal cancer. In some embodiments, the cancer is glioblastoma.

In some embodiments, the cancer in the subject comprises a HER2 mutation. In some embodiments, the HER2 mutation comprises an insertion in exon 20, an in-frame deletion and insertion in exon 20, a substitution in the extracellular domain, an extracellular truncation, or a substitution in exon 30. In some embodiments, the HER2 mutation is selected from A775 G776insYVMA, A775_G776insSVMA, A775_G776insVVMA, G776del insVC, G776del insLC, G776del insAV, G776del insAVGC, S310F, S310Y, p95, V842I, P780_Y781insGSP, and a combination thereof. In some embodiments, the HER2 mutation is A775_G776insYVMA. In some embodiments, the HER2 mutation is A775_G776insSVMA. In some embodiments, the HER2 mutation is A775_G776insVVMA. In some embodiments, the HER2 mutation is G776del insVC. In some embodiments, the HER2 mutation is G776del insLC. In some embodiments, the HER2 mutation is G776del insAV. In some embodiments, the HER2 mutation is G776del insAVGC. In some embodiments, the HER2 mutation is S310F. In some embodiments, the HER2 mutation is S310Y. In some embodiments, the HER2 mutation is p95. In some embodiments, the HER2 mutation is V842I. In some embodiments, the HER2 mutation is P780_Y781insGSP.

In some embodiments, the cancer in the subject comprises an EGFR mutation. In some embodiments, the EGFR mutation comprises a substitution in exon 18, a deletion in exon 19, a substitution in exon 20, an insertion in exon 20, a mutation in the extracellular domain, or a substitution in exon 21. In some embodiments, the EGFR mutation is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR (or D770_N771insSVD EGFR), 770insNPG EGFR (or D770_N771insNPG EGFR), 770insGT EGFR, 770insGF EGFR, 770insG EGFR, 771insH EGFR, 771insN EGFR, 772insNP EGFR, 773insNPH EGFR (or H773insNPH EGFR), 773insH EGFR, 773insPH EGFR, EGFRvii, EGFRviii, A767_dupASV EGFR, 773insAH EGFR, M766_A767insAI EGFR, and any combination thereof. In some embodiments, the EGFR mutation is del19/T790M EGFR or L858R/T790M EGFR. In some embodiments, the EGFR mutation is del19/T790M EGFR. In some embodiments, the EGFR mutation is L858R/T790M EGFR.

In another aspect, provided herein is a method of treating inflammatory disease in a subject in need thereof, comprising administering to the subject a therapeutically effective amount of a compound of Formula I, or a pharmaceutically acceptable salt or stereoisomer thereof. Also described herein is the use of the compounds described herein for treating inflammatory diseases associated with EGFR del19/T790M activation. Also described herein is the use of the compounds described herein for treating inflammatory diseases associated with EGFR L858R/T790M activation.

In some embodiments, the inflammatory disease is psoriasis, eczema, or atherosclerosis. In some embodiments, the inflammatory disease is psoriasis. In some embodiments, the inflammatory disease is eczema. In some embodiments, the inflammatory disease is atherosclerosis.

In some embodiments, the inflammatory disease in the subject comprises a HER2 mutation. In some embodiments, the HER2 mutation comprises an insertion in exon 20, an in-frame deletion and insertion in exon 20, a substitution in the extracellular domain, an extracellular truncation, or a substitution in exon 30. In some embodiments, the HER2 mutation is selected from A775_G776insYVMA, A775 G776insSVMA, A775_G776insVVMA, G776del insVC, G776del insLC, G776del insAV, G776del insAVGC, S310F, S310Y, p95, V842I, P780_Y781insGSP, and any combination thereof. In some embodiments, the HER2 mutation is A775_G776insYVMA. In some embodiments, the HER2 mutation is A775 G776insSVMA. In some embodiments, the HER2 mutation is A775 G776insVVMA. In some embodiments, the HER2 mutation is G776del insVC. In some embodiments, the HER2 mutation is G776del insLC. In some embodiments, the HER2 mutation is G776del insAV. In some embodiments, the HER2 mutation is G776del insAVGC. In some embodiments, the HER2 mutation is S310F. In some embodiments, the HER2 mutation is S310Y. In some embodiments, the HER2 mutation is p95. In some embodiments, the HER2 mutation is V842I. In some embodiments, the HER2 mutation is P780_Y781insGSP.

In some embodiments, the inflammatory disease in the subject comprises an EGFR mutation. In some embodiments, the EGFR mutation comprises a substitution in exon 18, a deletion in exon 19, a substitution in exon 20, an insertion in exon 20, a mutation in the extracellular domain, or a substitution in exon 21. In some embodiments, the EGFR mutation is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR (or D770_N771insSVD EGFR), 770insNPG EGFR (or D770_N771insNPG EGFR), 770insGT EGFR, 770insGF EGFR, 770insG EGFR, 771insH EGFR, 771insN EGFR, 772insNP EGFR, 773insNPH EGFR (or H773insNPH EGFR), 773insH EGFR, 773insPH EGFR, EGFRvii, EGFRviii, A767_dupASV EGFR, 773insAH EGFR, M766_A767insAI EGFR, and any combination thereof. In some embodiments, the EGFR mutation is del19/T790M EGFR or L858R/T790M EGFR. In some embodiments, the EGFR mutation is del19/T790M EGFR. In some embodiments, the EGFR mutation is L858R/T790M EGFR.

Administration and Pharmaceutical Composition

In certain embodiments, the EGFR inhibitory compound as described herein is administered as a pure chemical. In other embodiments, the EGFR inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, PA (2005)).

Provided herein is a pharmaceutical composition comprising at least one EGFR inhibitory compound as described herein, or a stereoisomer, pharmaceutically acceptable salt, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition.

One embodiment provides a pharmaceutical composition comprising a compound disclosed herein, or a pharmaceutically acceptable salt, stereoisomer, solvate, or prodrug thereof, and a pharmaceutically acceptable excipient.

In certain embodiments, the EGFR inhibitory compound disclosed herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21st Ed. Mack Pub. Co., Easton, PA (2005)).

The dose of the composition comprising at least one EGFR inhibitory compound as described herein differ, depending upon the patient's condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

EXAMPLES

Example 1: Synthetic Procedures

Yields reported herein refer to purified products (unless specified) and are not optimised. Analytical TLC was performed on Merck silica gel 60 $F_{254}$ aluminum-backed plates. Compounds were visualised by UV light and/or stained either with iodine, potassium permanganate or ninhydrin solution. Flash column chromatography was performed on silica gel (100-200 M) or flash chromatography. $^1$H-NMR spectra were recorded on a Bruker Avance-400 MHz spectrometer with a BBO (Broad Band Observe) and BBFO (Broad Band Fluorine Observe) probe. Chemical shifts (δ) are expressed in parts per million (ppm) downfield by reference to tetramethylsilane (TMS) as the internal standard. Splitting patterns are designated as s (singlet), d (doublet), t (triplet), q (quartet), m (multiplet) and bs (broad singlet). Coupling constants (J) are given in hertz (Hz). LC-MS analyses were performed on either an Acquity BEH C-18 column (2.10×100 mm, 1.70 μm) or on a Acquity HSS-T3 column (2.10×100 mm, 1.80 μm) using the Electrospray Ionisation (ESI) technique.

The following solvents, reagents or scientific terminology may be referred to by their abbreviations:

TLC Thin Layer Chromatography
DCM Dichloromethane
THF Tetrahydrofuran
MeOH Methanol
EtOH Ethanol
IPA Isopropyl alcohol
EtOAc Ethyl acetate
$Et_2O$ Diethyl ether
DMA N,N-Dimethylacetamide
DMF N,N-Dimethylformamide
TEA/$Et_3N$ Triethylamine
DMSO Dimethylsulfoxide
DIPEA Diisopropylethylamine (Hunig's base)
Mel Methyliodide
NBS N-Bromosuccinimide
TBAB Tetrabutylammonium bromide
TBAI Tetrabutylammonium iodide
DIBAL-H Diisobutylaluminum hydride
TFA Trifluoroacetic acid
AcOH Acetic acid
Boc tert-butoxycarbonyl
Cat Catalytic
mL milliliters
mmol millimoles
h hour or hours
min minute or minutes
g grams
mg milligrams
μl Microlitres
eq Equivalents
rt or RT Room temperature, ambient, about 27° C.
MS Mass spectrometry
Boc tert-Butyloxycarbonyl
m-CPBA meta-Chloroperbenzoic acid
T3P Propane phosphonic acid anhydride
$BH_3$-DMS Borane dimethylsulfide complex
$LiBH_4$ Lithium aluminum hydride
$NaBH_4$ Sodium borohydride
$H_2$ Hydrogen
Pd/C Palladium on charcoal
1,2-DCE 1,2-Dichloroethane General Procedure A:

To an ice cold solution of aryl amines (1.0 eq) in tetrahydrofuran was added sodium hydride (60% dispersion in mineral oil, 3.0 eq) portion-wise. The resulting reaction mixture was stirred at room temperature for 30 minutes and followed by the addition of 2,4,5-trichloropyrimidine or 2,4-dichloro-5-bromopyrimidine (1.0 eq). The resulting reaction mixture was heated at 60° C. for 16 hours. After completion (TLC monitoring), quenched with ice, extracted with ethyl acetate (3 times). The combined organic layers were washed with water, brine, dried over anhydrous sodium sulfate, filtered and concentrated under reduced pressure. The crude was triturated with diethyl ether, filtered and dried under vacuum to get desired products.

General Procedure B:

To a solution of aryl halo (1.0 eq) in 1,4-dioxane or toluene were added cesium carbonate (3.0 eq) and aryl amines (1.2 eq). The resulting reaction mixture degassed under nitrogen for 15 minutes, followed by addition of 2-dicyclohexylphosphino-2',4',6'-triisopropylbiphenyl (XPhos, 0.1 eq) and tris(dibenzylideneacetone)dipalladium (0) (0.1 eq) under nitrogen atmosphere. The resulting reaction mixture was again degassed for 15 minutes and then heated at 100° C. for 16 hours. After completion of reaction (TLC monitoring), reaction mixture was cooled, diluted with water, extracted with dichloromethane (3 times). The combined organic layers were washed with brine dried over anhydrous sodium sulfate, filtered and concentrated under reduced pressure. The crude was purified by flash chromatography using 4-8% methanol in dichloromethane as eluent, desired fractions were concentrated under reduced pressure afforded the desired products.

General Procedure C:

To an ice-cold solution of primary or secondary aryl amines (1.0 eq)) in dichloromethane were added triethylamine (3.0 eq) and acetyl chloride (1.2 eq) drop wise. The resulting reaction mixture was stirred at room temperature for 1 hour. After completion of reaction (TLC monitoring), the reaction mixture was diluted with water and extracted with dichloromethane (3 times). The combined organic layers were washed with brine, dried over anhydrous sodium sulfate, filtered and concentrated under reduced pressure. The crude was purified by combiflash, eluted with 4-5% methanol in dichloromethane, desired fractions were concentrated under reduced pressure to afforded desired products.

General Procedure D:

To a solution of aldehydes (1.0 eq) in methanol were added respective amines (3.0 eq) and sodium acetate (5.0 eq). The resultant reaction mixture was stirred at room temperature for 16 hours. After completion of reaction (monitored by TLC), the reaction mixture was poured in ice-cold water and resulted solid was filtered. The solid was dried under vacuum to get the desired products.

General Procedure E:

To a solution of products (1.0 eq) obtained from General Procedure D in methanol (2.5 vol) was added acetic acid (1.0 vol) and followed by addition of sodium borohydride (1.0 eq). The resulting reaction mixture was stirred at room temperature for 16 hours. After completion of reaction (TLC monitoring), the reaction mixture was quenched with ice-cold water and resultant solid was filtered, washed with water. The solid was dried under vacuum to get the desired products.

General Procedure F:

To an ice-cold solution of products (1.0 eq) obtained from General Procedure E in tetrahydrofuran added di-isopropyl ethylamine (4.0 eq) followed by addition of triphosgene (0.4 eq). The resultant reaction mixture was stirred at room temperature for 16 hours. After completion of reaction (TLC monitoring) saturated sodium bicarbonate solution was added and extracted with dichloromethane (3 times). The organic layer was washed with brine dried over anhydrous sodium sulfate and evaporated under reduced pressure. The crude was triturated with diethyl ether to get the desired products.

General Procedure G:

To an ice-cold solution of products (1.0 eq) obtained from General Procedure F in dichloromethane was added m-chloroperbenzoic acid (2.0 eq). The resulting reaction mixture was stirred at room temperature for 4 hours. After completion of reaction (TLC monitoring) saturated solution of sodium bicarbonate was added to the reaction mixture and extracted with dichloromethane (3 times). The combined organic layers were washed with brine, dried over anhydrous sodium sulfate and evaporated under reduced pressure. The crude product was triturated with diethyl ether to get the desired products.

General Procedure H:

To an ice-cold solution of products (1.0 eq) obtained from General Procedure G in isopropanol was added respective amines (1.2 eq) and trifluoroacetic acid (2.0 eq). The reaction mixture was heated at 110° C. for 16 hours. After completion of the reaction (TLC monitoring), the reaction mixture was concentrated under reduced pressure, added saturated solution of sodium bicarbonate and extracted with dichloromethane (3 times). The combined organic layers were washed with brine solution, dried over anhydrous sodium sulfate and evaporated under reduced pressure. The crude residue was triturated with diethyl ether to get the desired products which was used directly for the next step.

General Procedure I:

An ice-cold solution of products (1.0 eq) obtained from General Procedure H in 20% trifluoroacetic acid in dichloromethane was stirred at room temperature for 3-16 hours. After completion of the reaction (TLC monitoring) the solvent was evaporated. The reaction mass diluted with saturated solution of sodium bicarbonate and extracted with 5% methanol in dichloromethane (3 times). The combined organic layers were washed with brine solution, dried over sodium sulfate and evaporated under reduced pressure. The crude was triturated with ether or purified over combiflash, elution with 5-10% methanol in dichloromethane to get the desired products.

General Procedure J:

To an ice-cold solution of products (1.0 eq) obtained from General Procedure I in dichloromethane was added triethylamine (3-5 eq) and respective acids (1.1 eq), followed by propylphosphonic anhydride ($T_3P$, 50% in ethyl acetate, 2.5 eq). The resulting reaction mixture was stirred at room temperature for 16 hours. After completion of reaction (TLC monitoring), reaction mass diluted with saturated solution of sodium bicarbonate and extracted with 5% methanol in dichloromethane. The combined organic layers were washed with brine, dried over anhydrous sodium sulfate, filtered and concentrated under reduced pressure. The crudes were purified over combiflash or Prep-TLC or Prep-HPLC purification to get the final compounds.

General Procedure K:

To a solution of products (1.0 eq) obtained from General Procedure I in dichloromethane:tetrahydrofuran (1:1) was cooled to −40° C. followed by triethylamine (3-5 eq) and acryloyl chloride (1.0 eq) were added. The mixture was stirred at the same temperature for 2 hours. After completion of reaction (monitored by TLC), added water and extracted with dichloromethane (3 times). The combined organic layers washed with brine, dried over anhydrous sodium sulfate, filtered and concentrated under reduced pressure. The crudes were purified by Prep-HPLC purification to get the final compounds.

General Procedure $K_1$:

To a solution of products (1.0 eq) obtained from General Procedure I in tetrahydrofuran and water (3:1) at −0° C. were added triethylamine (5 eq) and acryloyl chloride (1.0 eq). The reaction mixture was stirred at the same temperature for 2 hours. After completion of reaction (monitored by TLC), added water and extracted with ethyl acetate (3 times). The combined organic layers were washed with brine, dried over anhydrous sodium sulfate, filtered and concentrated under reduced pressure. The crude product was purified by Prep-HPLC purification to get the final compounds.

General Procedure $K_2$:

To a solution of products (1.0 eq) obtained from General Procedure I in tetrahydrofuran and water (3:1) at −0° C. were added triethylamine (5 eq) and 3-Chloropropionyl chloride (1.2 to 1.5 eq). The reaction mixture was stirred at the same temperature for 20 minutes to one hour. After completion of reaction (monitored by LCMS), added water and extracted with ethyl acetate (3 times). The combined organic layers were washed with brine, dried over anhydrous sodium sulfate, filtered and concentrated under reduced pressure. The crude product was purified by Prep-HPLC purification to get the final compounds.

General Procedure L:

To an ice cold solution of nitro derivatives (1.0 eq) in methanol:tetrahydrofuran:water (2:2:1) were added zinc-dust or iron powder (5 eq) and ammonium chloride (5 eq). The resultant reaction mixture was stirred at room temperature for 2 hours. After completion of reaction (TLC monitoring), reaction mixture passed through celite bed washed with 5% methanol in dichloromethane. The filtrate was washed with water, brine, dried over anhydrous sodium sulfate, filtered and concentrated to dryness to get the amino derivatives.

General Procedure $L_1$:

To a solution of nitro derivatives (1.0 eq) in methanol or ethanol (10 vol) was added 10% palladium on carbon (20% w/w). The reaction mixture was stirred under hydrogen atmosphere for 16 hours. After completion of reaction (TLC monitoring), reaction mixture was filtered through the celite bed and washed with methanol. The combined filtrate was concentrated under reduced pressure to get amino derivatives.

General Procedure $M_1$: (Suzuki Coupling)

To a solution of halo derivatives (1.0 eq) in acetonitrile was added respective boronate acid/ester derivatives (1.0 eq), followed by aqueous solution of potassium carbonate (2.0 eq) under argon purging. The resulting reaction mixture was degassed for 15 minutes, followed by [1,1'-Bis (diphenylphosphino)ferrocene]palladium (II) dichloride dichloromethane complex (0.1 eq) was added and the reaction mixture was heated at 80° C. for 16 hours. After completion of reaction (TLC monitoring), the reaction mixture was diluted with ice water and extracted with ethyl acetate (3 times). The combined organic layers were washed with brine, dried over anhydrous sodium sulfate, filtered and concentrated to dryness. The crude was purified over combiflash, eluted with 40-60% ethyl acetate in hexane, desired fractions were concentrated under reduced pressure to get the desired products.

General Procedure $M_2$:

To a solution of halo derivatives (1.0 eq) and respective boronic acids (1.1 eq) in toluene:ethanol (1:1) or dimethylformamide or dimethoxyethane and water (4:1) was added potassium carbonate (2.0 eq) or sodium bicarbonate (2.0 eq). The resulting reaction mixture was degassed with argon for 15 minutes, followed by addition of [1,1'-bis(diphenylphosphino)ferrocene]dichloropalladium(II) dichloromethane complex (0.05 eq). The resulting reaction mixture was heated at 90° C. for 5-16 hours. After completion of reaction (TLC monitoring), the reaction mixture was cooled to room temperature, water was added and extracted with ethyl acetate (3 times). The combined organic layers were washed with brine, dried over anhydrous sodium sulfate, filtered and concentrated under reduced pressure. The crude was purified over combiflash, elution with 30-50% ethyl acetate in hexane, desired fractions were concentrated under reduced pressure to the desired products.

General Procedure $M_3$:

To a solution of halo derivatives (1.0 eq) and respective boronate acid/ester derivatives (1.1 eq) in N,N-dimethylformamide:water (4:1) was added sodium carbonate or sodium bicarbonate (2.0 eq). The resulting reaction mixture was degassed under argon atmosphere for 15 minutes, followed by addition of tetrakis(triphenylphosphine)palladium(0) (0.1 eq). The resulting reaction mixture was heated at 90° C. for 16 hours. After completion of reaction (TLC monitoring), the reaction mixture was cooled to room temperature, water was added and extracted with ethyl acetate (3 times). The combined organic layers were washed with brine, dried over anhydrous sodium sulfate, filtered and concentrated under reduced pressure. The crude product was purified by using combiflash, desired fractions were concentrated under reduced pressure to afford the desired products.

General Procedure N:

To an ice-cold solution of N-(3-(2-chloro-6-fluoroquinazolin-8-yl)phenyl)acrylamide (1.0 eq) in dimethylformamide was added sodium hydride (60% dispersion in mineral oil, 10 eq) portion-wise and stirred at room temperature for 30 minutes, followed by addition of respective amines (1.2 eq). The resultant reaction mixture was stirred at room temperature for 16 hours. After completion of reaction (as per TLC monitoring), reaction mixture was diluted with ice-cold water and extracted with 5% methanol/dichloromethane (3 times). The combined organic layer dried over anhydrous sodium sulfate, filtered and concentrated under reduced pressure. The crude was purified over combiflash or Prep HPLC purification to get desired products.

General Procedure O:

To a solution of primary or secondary alcohols (1.0 eq) in dichloromethane was added activated manganese dioxide (10 eq) at room temperature under nitrogen atmosphere. The resultant reaction mixture was stirred at same temperature for 16 hours. After completion of reaction (TLC monitoring), the reaction mixture was filtered through celite bed and washed with dichloromethane (3 times). The combined filtrate was dried over anhydrous sodium sulfate and concentrated under reduced pressure to get desired products.

Scheme 1: Synthesis of tert-butyl (3-(7-chloro-2-oxo-3-phenyl-3,4-dihydropyrimido[4,5-d]pyrimidin-1(2H)-yl)phenyl)carbamate (8)

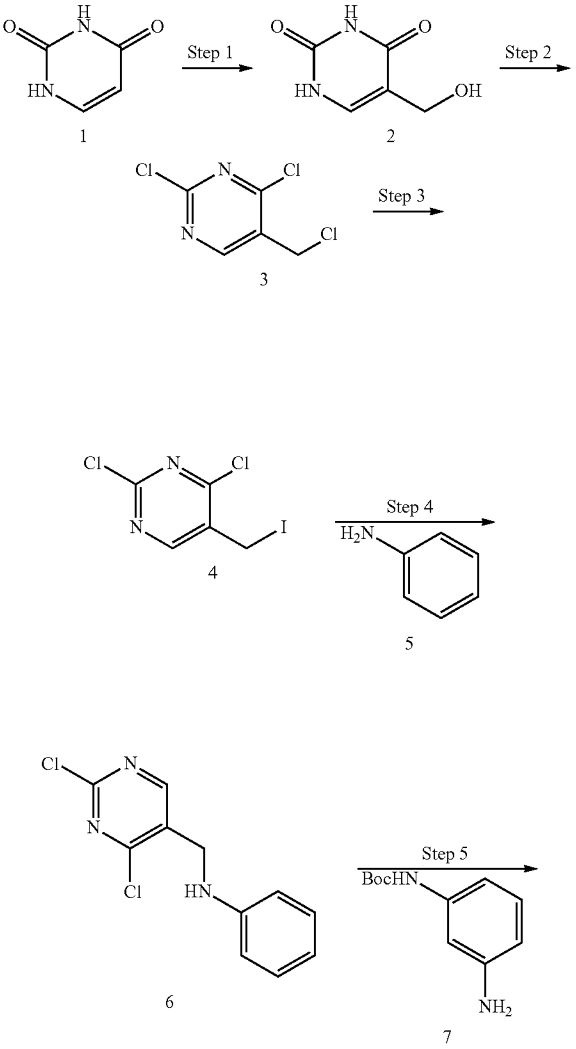

1 2 3 4 5 6 7

-continued

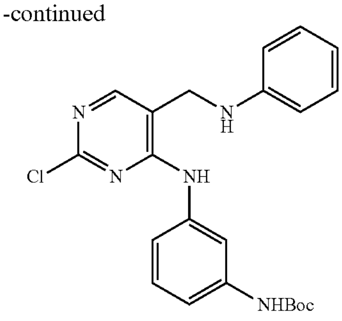

8

Step 1: Synthesis of 5-(hydroxymethyl)pyrimidine-2,4(1H,3H)-dione (2)

An ice-cold solution of pyrimidine-2,4(1H,3H)-dione (1) (10 g, 89.21 mmol) and paraformaldehyde (9.63 g, 107.05 mmol) in aqueous potassium hydroxide (132 mL, 0.5 M, 66.74 mmol) was heated at 55° C. for 14 hours. After completion of starting material (TLC), the reaction mixture was cooled to 0° C. and the pH was adjusted to 6 with 12N hydrochloric acid, the resulting white precipitate was filtered through sintered funnel and washed with diethyl ether afforded 2 as a white solid (6.3 g, Yield: 50%) which was used directly for the next step. $^1$H-NMR (400 MHz, DMSO-$d_6$): δ 10.98 (bs, 1H), 10.64 (bs, 1H), 7.24 (s, 1H), 4.78 (m, 1H), 4.12 (d, J=12.8 Hz, 2H). LCMS: $[M+H]^+$ 143.04.

Step 2: Synthesis of 2,4-dichloro-5-(chloromethyl)pyrimidine (3)

To an ice-cold solution of 5-(hydroxymethyl)pyrimidine-2,4(1H,3H)-dione (2) (10 g, 70.36 mmol) in toluene (25 mL) was added phosphoryl chloride (14 mL, 140.72 mmol) then N,N-diisopropylethylamine (37 mL, 211 mmol). The reaction mixture was heated at 120° C. for 16 hours. After the complete disappearance of starting material on TLC, the reaction mixture was quenched slowly with sodium bicarbonate solution and extracted with ethyl acetate (3×200 mL). The combined organic layer was washed with brine, dried over anhydrous sodium sulfate, filtered and evaporated under reduced pressure afforded 3 as a brown solid (12 g, Yield: 86%) which was used directly for the next step. $^1$H NMR (400 MHz, $CDCl_3$): δ 8.66 (s, 1H), 4.64 (s, 2H). MS: $[M+H]^+$ 197.0.

Step 3: Synthesis of 2,4-dichloro-5-(iodomethyl)pyrimidine (4)

To a solution of 2,4-dichloro-5-(chloromethyl)pyrimidine (3) (8.0 g, 40.51 mmol in acetone (40 mL) was added sodium iodide (9.71 g, 64.82 mmol). The reaction mixture was stirred at room temperature for 30 min and heated to reflux for 2 hours. After completion of reaction (TLC monitoring), the reaction mixture cooled to room temperature. The resulting white precipitate was filtered through sintered funnel and washed with acetone. The filtrate was concentrated under reduced pressure afforded 4 as a brown solid (10 g, Yield: 85%) which was used directly for the next step. $^1$H-NMR (400 MHz, $CDCl_3$): δ 8.60 (s, 1H), 4.39 (s, 2H).

Step 4: Synthesis of N-((2,4-dichloropyrimidin-5-yl)methyl)aniline (6)

To an ice-cold solution of 2, 4-dichloro-5-(iodomethyl) pyrimidine (4) (5.0 g, 17.30 mmol) in acetone (50 mL) was added potassium carbonate (5.26 g, 38.06 mmol) and aniline (5) (1.93 g, 20.76 mmol). The resulting reaction mixture was stirred at room temperature for 16 hours. After completion the reaction (as per TLC monitoring), the resulting white precipitate was filtered through sintered funnel and washed with acetone. The filtrate was concentrated under reduced pressure and crude was purified by column chromatography on silica gel (100-200 mesh) using 15% ethyl acetate-hexane as an eluent afforded 6 as a brown solid (2.5 g, Yield: 57%). $^1$H-NMR (400 MHz, $CDCl_3$): δ 8.61 (s, 1H), 7.07 (t, J=7.6 Hz, 2H), 6.58 (m, 3H), 6.30 (bs, 1H), 4.33 (m, 2H). LCMS: $[M+H]^+$ 254.03.

Step 5: Synthesis of tert-butyl (3-(7-chloro-2-oxo-3-phenyl-3,4-dihydropyrimido[4,5-d]pyrimidin-1(2H)-yl)phenyl)carbamate (8)

To an ice-cold solution of N-((2,4-dichloropyrimidin-5-yl)methyl)aniline (6) (500 mg, 1.96 mmol), in isopropanol (5 mL) was added N,N-diisopropylethylamine (1.47 mL, 8.42 mmol) and tert-butyl (3-aminophenyl)carbamate (7) (409 mg, 1.96 mmol). The resulting reaction mixture was heated at 100° C. for 16 hours in a sealed tube. After completion of reaction (TLC monitoring), the solvent was then evaporated under reduced pressure and resulting crude was purified by column chromatography on silica gel (100-200 mesh) using 30% ethyl acetate in hexane as an eluent afforded 8 as a brown solid (500 mg, Yield: 60%). $^1$H-NMR (400 MHz, DMSO-$d_6$): δ 9.41 (s, 1H), 8.96 (s, 1H), 8.10 (s, 1H), 7.73 (s, 1H), 7.25 (m, 2H), 7.12 (m, 3H), 6.61 (m, 3H), 6.14 (t, J=7.2 Hz, 1H), 4.26 (m, 2H), 1.53 (s, 9H). LCMS: $[M+H]^+$ 426.14.

Scheme 2: Synthesis of 2-(4-amino-1H-pyrazol-1-yl)ethan-1-ol (11)

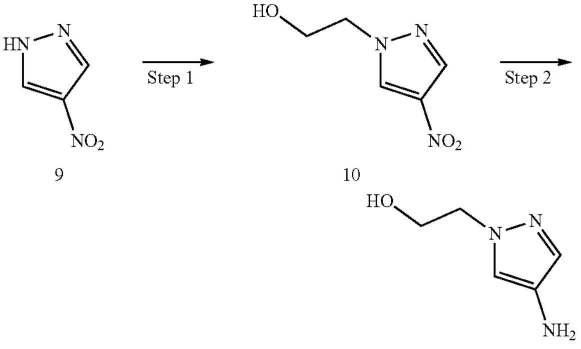

9 10 11

Step 1: Synthesis of 2-(4-nitro-1H-pyrazol-1-yl) ethan-1-ol (10)

To a stirred solution of 4-nitro-1H-pyrazole (9) (2.00 g, 17.7 mmol) in acetonitrile (20.0 mL) was added 2-bromoethan-1-ol (1.38 mL, 19.5 mmol), potassium carbonate (2.93 g, 21.2 mmol) and the reaction mixture was heated at 80° C. for 15 hours. The reaction mixture was cooled to room temperature, diluted with water (50 mL) and extracted with ethyl acetate (30 mL×4). The combined organic layer was washed with brine (30 mL), dried over anhydrous sodium sulfate and evaporated. The crude product was purified by column chromatography using combiflash purifier and was eluted with 45% ethyl acetate in hexane to get the title compound (10) as white solid (2.5 g, 90%). LCMS: $[M+H]^+$ 158.0.

Step 2: Synthesis of 2-(4-amino-1H-pyrazol-1-yl) ethan-1-ol (11)

To a stirred solution of 2-(4-nitro-1H-pyrazol-1-yl)ethan-1-ol (10) (2.50 g, 15.9 mmol) in ethanol (20 mL) nitrogen was purged for 5 min, added palladium on carbon (0.25 g, 10% w/w) and the reaction mixture was hydrogenated for 15 hours. The reaction mixture was filtered through celite and the filtrate was evaporated to get the title compound (11) as brown liquid (2.0 g, crude). $^1$H NMR (400 MHz, DMSO-$d_6$): δ 7.00 (s, 1H), 6.87 (s, 1H), 4.78 (t, J=4.8 Hz, 1H), 3.92 (t, J=6.0 Hz, 2H), 3.73 (bs, 2H), 3.63-3.59 (m, 2H).

Scheme 3: Synthesis of N-(3-((5-chloro-2-((1-(4-hydroxycyclohexyl)-1H-pyrazol-4-yl)amino)pyrimidin-4-yl)amino)-4-fluorophenyl)acrylamide (Compound 1)

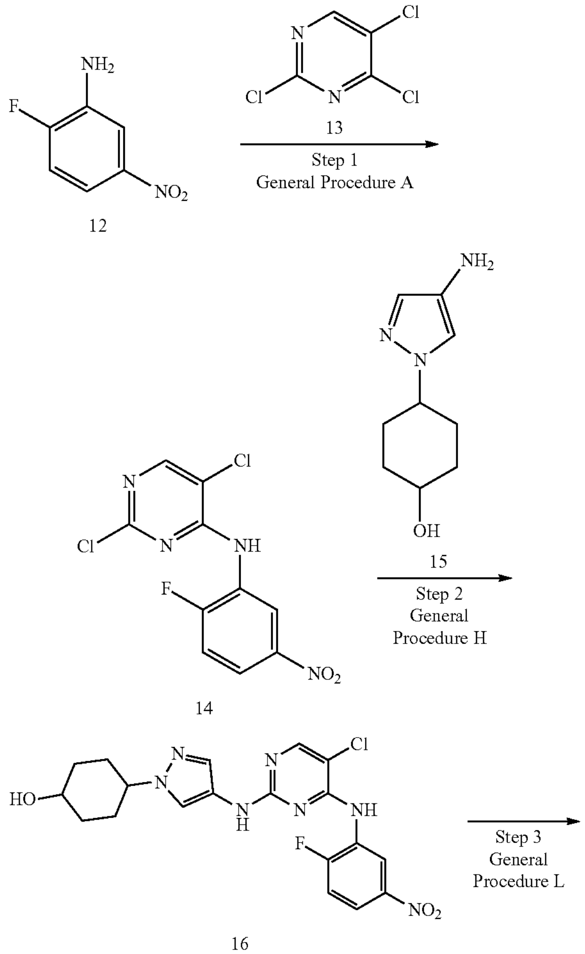

12, 13, 14, 15, 16

-continued

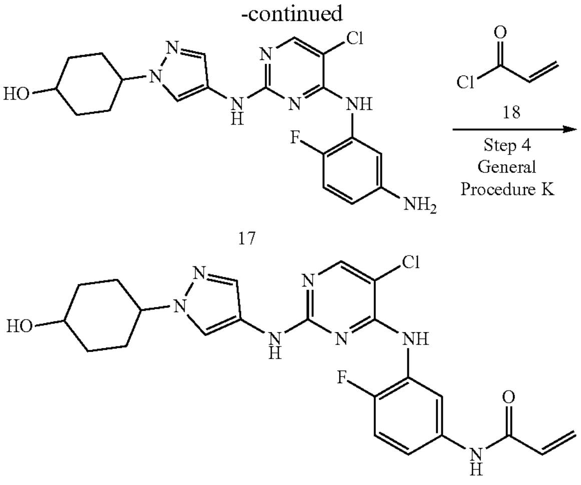

17, 18

Compound 1

Step 1: Synthesis of 2,5-dichloro-N-(2-fluoro-5-nitrophenyl) pyrimidin-4-amine (14)

Title compound was prepared in a manner substantially similar to procedure mentioned in General Procedure A. The crude was triturated with diethyl ether, filtered and dried under vacuum to get 2,5-dichloro-N-(2-fluoro-5-nitrophenyl)pyrimidin-4-amine (14) as pale yellow solid. (10.0 g, Yield: 34%). $^1$H-NMR (400 MHz, $CDCl_3$): δ 9.87 (s, 1H), 8.48 (s, 1H), 8.40-8.43 (m, 1H), 8.22-8.26 (m, 1H), 7.65 (t, J=9.2 Hz, 1H).

Step 2: Synthesis of 4-(4-((5-chloro-4-((2-fluoro-5-nitrophenyl)amino)pyrimidin-2-yl)amino)-1H-pyrazol-1-yl)cyclohexan-1-ol (16)

Title compound was prepared in a manner substantially similar to procedure mentioned in General Procedure H, to get desired product (16) as pale yellow solid (0.75 g, Yield: 84.7%), MS: $[M+H]^+$ 448.21.

Step 3: Synthesis of 4-(4-((4-((5-amino-2-fluorophenyl)amino)-5-chloropyrimidin-2-yl)amino)-1H-pyrazol-1-yl)cyclohexan-1-ol (17)

Title compound was prepared in a manner substantially similar to procedure mentioned in General Procedure L, to get desired product (17) as a brown solid. (0.55 g, Yield: 78.57%). MS: $[M+H]^+$ 418.18.

Step 4: Synthesis of N-(3-((5-chloro-2-((1-(4-hydroxycyclohexyl)-1H-pyrazol-4-yl)amino)pyrimidin-4-yl)amino)-4-fluorophenyl)acrylamide (Compound 1)

Title compound was prepared in a manner substantially similar to procedure mentioned in General Procedure K. The crude was purified by prep-HPLC purification to afforded Compound 1 (45 mg, Yield: 13.27%). $^1$H-NMR (400 MHz, DMSO-$d_6$): δ 10.32 (bs, 1H), 9.26 (bs, 1H), 8.86 (bs, 1H), 8.05 (s, 1H), 7.78-7.79 (m, 1H), 7.70 (s, 1H), 7.65 (bs, 1H), 7.31-7.34 (2, 1H), 7.08-7.13 (K, 2H), 6.38-6.45 (m, 1H), 6.24 (d, J=17.2 Hz, 1H), 5.75 (d, J=10.4 Hz, 1H), 4.62 (d, J=4.4 Hz, 1H), 3.60-3.62 (m, 1H), 1.83 (d, J=11.2 Hz, 2H), 1.23-1.63 (m, 6H). LCMS: $[M+H]^+$ 472.22.

TABLE 1

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 2 | 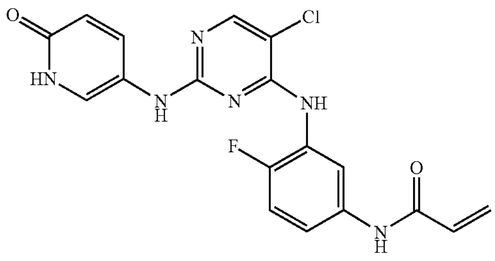 [SMILES: C=CC(=O)Nc1ccc(F)c(Nc2nc(Nc3ccc(=O)[nH]c3)ncc2Cl)c1] | K | 401.12 | δ 11.20 (s, 1H), 10.21 (s, 1H), 8.88-8.80 (m, 2H), 8.06 (s, 1H), 7.76-7.75 (m, 1H), 7.52-7.36 (m, 3H), 7.28 (t, J = 9.8 Hz, 1H), 6.45-6.38 (m, 1H), 6.27-6.13 (m, 2H), 5.75 (d, J = 10.1 Hz, 1H). |
| 3 | 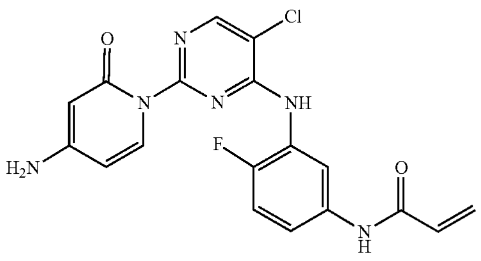 [SMILES: C=CC(=O)Nc1ccc(F)c(Nc2nc(-n3ccc(N)cc3=O)ncc2Cl)c1] | K | 401.28 | δ 10.24 (s, 1H), 9.27 (s, 1H), 8.22 (s, 1H), 8.06 (s, 1H), 7.79-7.75 (m, 1H), 7.64 (d, J = 5.6 Hz, 1H), 7.55-7.52 (m, 1H), 7.23 (t, J = 9.6 Hz, 1H), 6.46-6.39 (m, 1H), 6.32-6.24 (m, 2H), 6.17 (bs, 1H), 6.04 (m, 1H), 5.78-5.75 (m, 1H). |
| 4 | 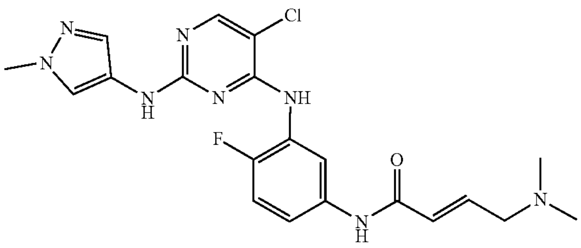 | J | 445.19 | δ 10.05 (bs, 1H), 10.13 (bs, 1H), 9.26 (bs, 1H), 8.93 (s, 1H), 8.05 (s, 1H), 7.68-8.80 (m, 2H), 7.35 (s, 1H), 6.72-7.11 (m, 2H), 6.40 (d, J = 15.4 Hz, 1H), 3.74 (s, 2H), 3.52 (s, 3H), 2.64 (s, 6H). |
| 5 | 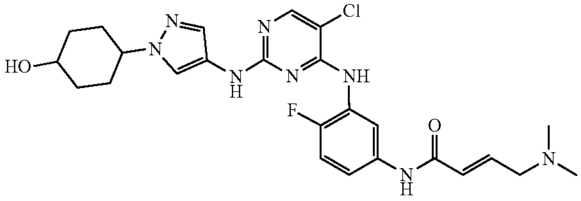 [SMILES: CN(C)C/C=C/C(=O)Nc1ccc(F)c(Nc2nc(Nc3cnn(C4CCC(O)CC4)c3)ncc2Cl)c1] | J | 529.35 | δ 10.23 (s, 1H), 9.26 (s, 1H), 8.85 (s, 1H), 8.04 (s, 1H), 7.78 (s, 1H), 7.68 (s, 1H), 7.33-7.31 (m, 1H), 7.13-7.08 (m, 1H), 6.76-6.70 (m, 1H), 6.25 (d, J = 11.6 Hz, 1H), 4.63 (d, J = 4.0 Hz, 1H), 3.61 (s, 1H), 3.43-3.39 (m, 2H), 3.05 (d, J = 4.0 Hz, 2H), 2.16 (s, 6H), 1.86-1.83 (m, 2H), 1.66 (s, H), 1.49-1.45 (m, 2H), 1.32-1.24 (m, 2H). |
| 6 | 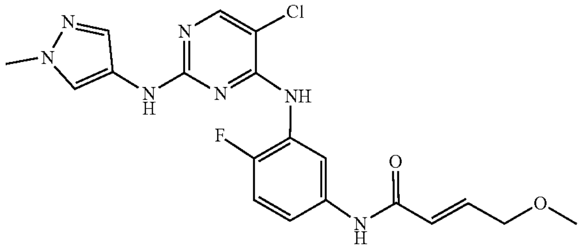 | J | 432.17 | δ 10.23 (bs, 1H), 9.24 (bs, 1H), 8.91 (bs, 1H), 8.05 (s, 1H), 7.75-7.76 (m, 1H), 7.65 (s, 1H), 7.33 (s, 1H), 7.01-7.11 (m, 2H), 6.71-6.82 (m, 1H), 6.28 (d, J = 15.6 Hz, 1H), 4.10 (s, 2H), 3.52 (s, 3H), 3.32 (s, 3H). |

TABLE 1-continued

The following compounds were prepared using the procedures described above:

| Cmpd. No. | Structure | General Procedure | LCMS [M + H] | $^1$H-NMR (400 MHz, DMSO-$d_6$) |
| --- | --- | --- | --- | --- |
| 7 | 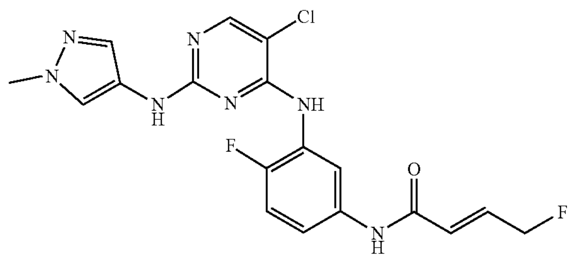 [SMILES: Cn1cc(Nc2ncc(Cl)c(Nc3cc(NC(=O)/C=C/CF)ccc3F)n2)cn1] | J | 420.28 | δ 10.32 (bs, 1H), 9.25 (bs, 1H), 8.92 (bs, 1H), 8.05 (s, 1H), 7.76-7.77 (m, 1H), 7.65 (s, 1H), 7.34 (s, 1H), 6.82-7.12 (m, 3H), 6.32 (d, J = 15.6 Hz, 1H), 5.18 (d, J = 48.0 Hz, 2H), 3.52 (s, 3H). |
| 8 | 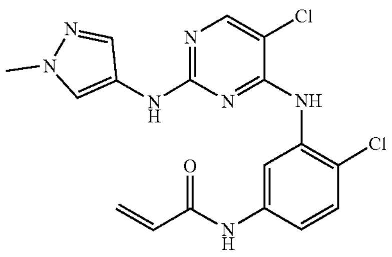 [SMILES: C=CC(=O)Nc1ccc(Cl)c(Nc2nc(Nc3cnn(C)c3)ncc2Cl)c1] | K | 404.0 | δ 10.34 (s, 1H), 9.20 (bs, 1H), 8.9 (bs, 1H), 8.04 (s, 1H), 7.83 (s, 1H), 7.72-7.70 (m, 1H), 7.58-7.57 (m, 1H), 7.20 (bs, 1H), 6.95 (bs, 1H), 6.41-6.37 (m, 1H), 6.27-6.23 (m, 1H), 5.77 (d, J = 10.4 Hz, 1H), 3.5 (s, 3H). |
| 9 | 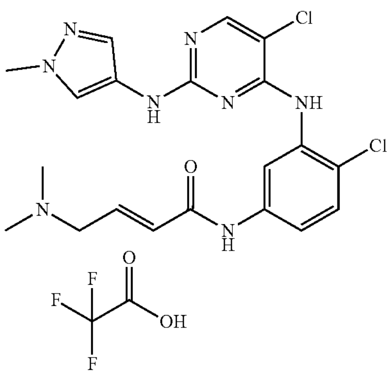 | J | 461.0 | δ 10.54 (s, 1H), 9.71 (s, 1H), 9.34 (s, 1H), 9.07 (s, 1H), 8.06 (s, 1H), 7.83 (s, 1H), 7.68 (bs, 1H), 7.60 (bs, 1H), 7.07 (bs, 1H), 6.90 (bs, 1H), 6.74-6.69 (m, 1H), 6.41 (d, J = 14.4 Hz, 1H), 3.92 (s, 2H), 3.57 (3H merged with DMSO water peak), 2.77 (s, 6H). |
| 10 | 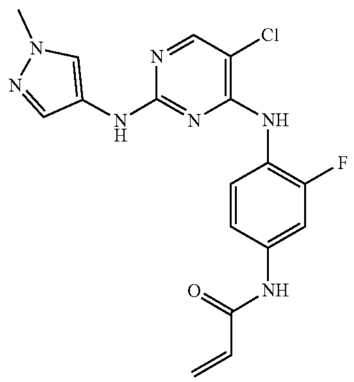 [SMILES: C=CC(=O)Nc1ccc(Nc2nc(Nc3cnn(C)c3)ncc2Cl)c(F)c1] | K | 387.9 | δ 10.43 (bs, 1H), 9.19 (bs, 1H), 8.78 (bs, 1H), 8.01 (s, 1H), 7.83 (d, J = 10.4 Hz, 1H), 7.42-7.38 (m, 2H), 7.11-6.96 (m, 2H), 6.46-6.39 (m, 1H), 6.31-6.26 (m, 1H), 5.80 (d, J = 10.4 Hz, 1H), 3.49 (s, 3H). |

TABLE 1-continued

The following compounds were prepared using the procedures described above:

| Cmpd. No. | Structure | General Procedure | LCMS [M + H] | $^1$H-NMR (400 MHz, DMSO-$d_6$) |
| --- | --- | --- | --- | --- |
| 11 | 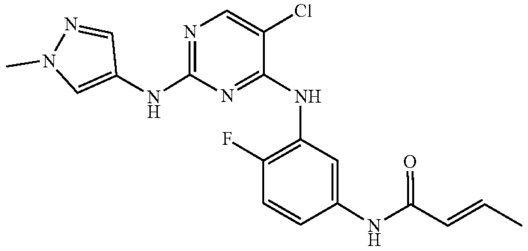 [SMILES: C/C=C/C(=O)Nc1ccc(F)c(Nc2nc(Nc3cnn(C)c3)ncc2Cl)c1] | J | 400 [M − H] | δ 10.10 (s, 1H), 9.21 (s, 1H), 8.87 (s, 1H), 8.02 (s, 1H), 7.74 (d, J = 5.6 Hz, 1H), 7.62 (s, 1H), 7.29 (s, 1H), 6.99-7.09 (m, 2H), 6.74-6.80 (m, 1H), 6.09 (d, J = 7.4 Hz, 1H), 3.49 (s, 3H), 1.84 (d, J = 6.8 Hz, 3H). |
| 12 | 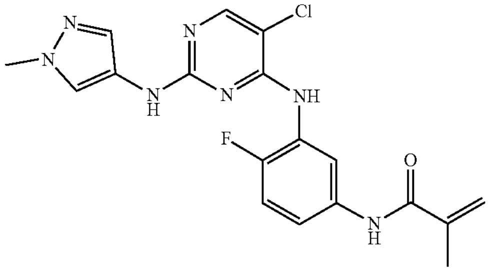 [SMILES: C=C(C)C(=O)Nc1ccc(F)c(Nc2nc(Nc3cnn(C)c3)ncc2Cl)c1] | J | 402.0 | δ 9.09 (s, 1H), 9.21 (s, 1H), 8.87 (s, 1H), 8.03 (s, 1H), 7.68-7.78 (m, 2H), 7.30 (s, 1H), 7.11 (s, 1H), 6.99 (m, 1H), 5.77 (s, 1H), 5.50 (s, 1H), 3.51 (s, 3H), 1.92 (s, 3H). |
| 13 | 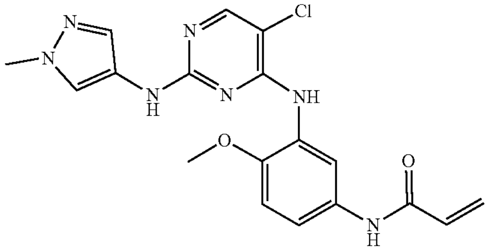 [SMILES: C=CC(=O)Nc1ccc(OC)c(Nc2nc(Nc3cnn(C)c3)ncc2Cl)c1] | K | 399.9 | δ 10.04 (s, 1H), 9.10 (s, 2H), 8.27 (bs, 1H), 8.01 (bs, 1H), 7.78 (bs, 1H), 7.64 (d, J = 7.6 Hz, 1H), 7.11 (d, J = 8.8 Hz, 2H), 6.43-6.36 (m, 1H), 6.21 (d, J = 17.2 Hz, 1H), 5.71 (d, J = 10.0 Hz, 1H), 3.73 (s, 3H), 3.53 (bs, 3H). |

Scheme 4: N-(3-((5-chloro-2-((1-(1-methylpiperidin-4-yl)-1H-pyrazol-4-yl)amino)pyrimidin-4-yl)amino)-4-fluorophenyl)acrylamide (Compound 14)

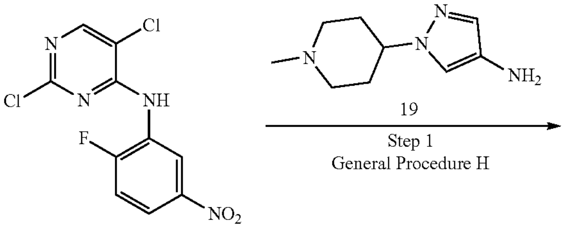

14

19

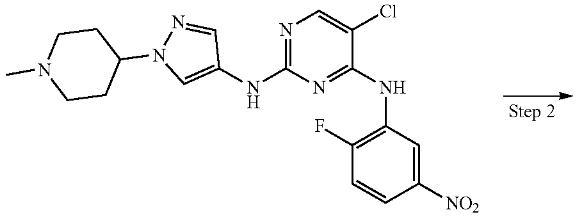

20

-continued

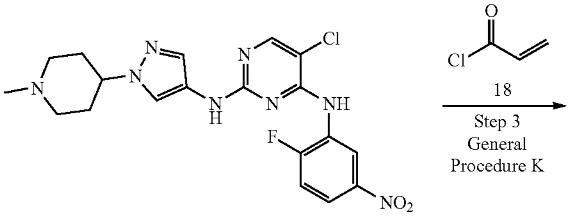

21

18

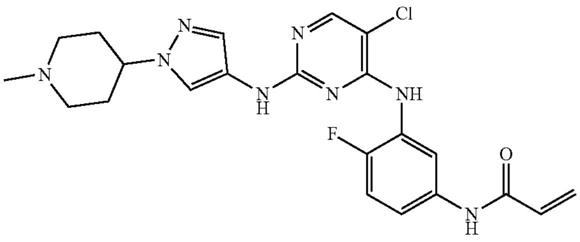

Compound 14

Step 1: 5-chloro-N4-(2-fluoro-5-nitrophenyl)-N2-(1-(1-methylpiperidin-4-yl)-1H-pyrazol-4-yl)pyrimidine-2,4-diamine (20)

Title compound was prepared in a manner substantially similar to procedure mentioned in General Procedure H, to get desired product (20) as pale yellow solid (0.2 g, Yield: 23%), LCMS: $[M+H]^+$ 447.2.

Step 2: N4-(5-amino-2-fluorophenyl)-5-chloro-N2-(1-(1-methylpiperidin-4-yl)-1H-pyrazol-4-yl)pyrimidine-2,4-diamine (21)

To a stirred solution of 5-chloro-N4-(2-fluoro-5-nitrophenyl)-N2-[1-(1-methylpiperidin-4-yl)-1H-pyrazol-4-yl]pyrimidine-2,4-diamine (20) (0.2 g, 0.44 mmol) in methanol (30 mL) was added Raney nickel (0.07 g, 1.34 mmol) and allowed to stir at room temperature under hydrogen atmosphere for 16 hours. The reaction mixture was filtered through celite bed and distilled to afford the title compound (21) as yellow solid (0.16 g, 85%). LCMS $[M+H]^+$ 417.1.

Step 3: N-(3-((5-chloro-2-((1-(1-methylpiperidin-4-yl)-1H-pyrazol-4-yl)amino)pyrimidin-4-yl)amino)-4-fluorophenyl)acrylamide (Compound 14)

Title compound was prepared in a manner substantially similar to procedure mentioned in General Procedure K. The crude was purified by prep-HPLC purification to afforded Compound 14 (17 mg, Yield: 14%). $^1$H-NMR (400 MHz, DMSO-$d_6$): δ 10.26 (s, 1H), 9.23 (s, 1H), 8.85 (s, 1H), 8.02 (s, 1H), 7.71 (d, J=6.4 Hz, 2H), 7.30 (s, 1H), 7.10 (t, J=15.2 Hz, 2H), 6.35-6.42 (m, 1H), 6.23 (d, J=17.2 Hz, 1H), 5.74 (d, J=10.0 Hz, 1H), 3.57 (s, 1H), 2.75 (d, J=10.0 Hz, 2H), 2.16 (s, 3H). 1.93 (s, 2H), 1.63 (s, 4H). LCMS: $[M+H]^+$ 471.0.

Scheme 5: Synthesis of (E)-4-(dimethylamino)-N-(3-((2-((1-methyl-1H-pyrazol-4-yl)amino)-5-((phenylamino)methyl)pyrimidin-4-yl)amino)phenyl)but-2-enamide (Compound 17)

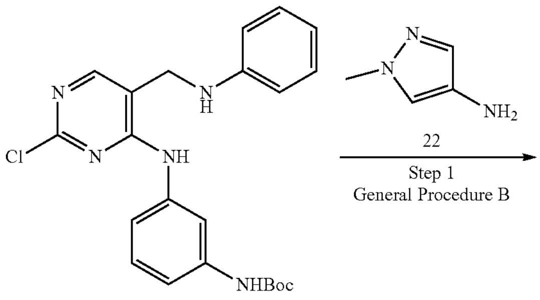

8

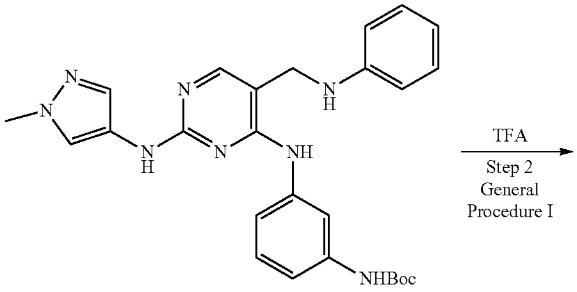

23

TABLE 2

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 15 | 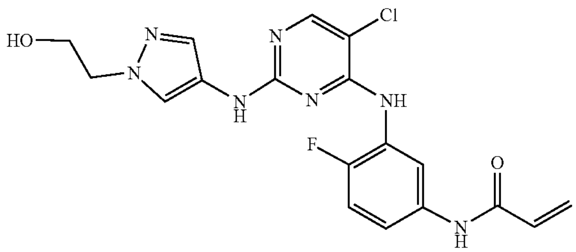 [SMILES: C=CC(=O)Nc1ccc(F)c(Nc2nc(Nc3cnn(CCO)c3)ncc2Cl)c1] | K | 418.1 | δ 10.22 (s, 1H), 9.18 (s, 1H), 8.84 (s, 1H), 8.04 (s, 1H), 7.77 (d, J = 5.2 Hz, 1H), 7.61 (s, 1H), 7.29 (t, J = 8.6 Hz, 1H), 7.15 (bs, 2H), 6.37-6.47 (m, 1H), 6.24 (d, J = 16.8 Hz, 1H), 5.75 (d, J = 10.0 Hz, 1H), 4.70 (s, 1H), 3.82 (s, 3H), 3.55 (s, 2H). |
| 16 | 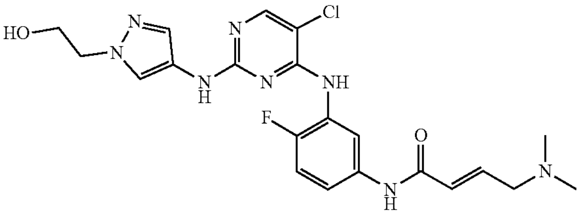 [SMILES: CN(C)C/C=C/C(=O)Nc1ccc(F)c(Nc2nc(Nc3cnn(CCO)c3)ncc2Cl)c1] | J | 475.1 | δ 10.23 (s, 1H), 9.21 (s, 1H), 8.72 (brs, 1H), 8.02 (s, 1H), 7.76 (d, J = 5.6 Hz, 1H), 7.59 (s, 1H), 7.28 (s, 1H), 7.11 (bs, 2H), 6.67-6.74 (m, 1H), 6.27 (d, J = 15.6 Hz, 1H), 4.71 (s, 1H), 3.78 (s, 2H), 3.22 (bs, 4H), 2.27 (s, 6H). |

-continued

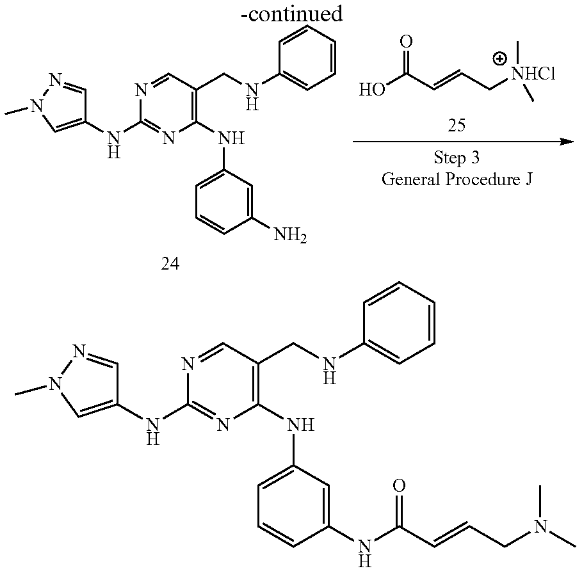

24

Compound 17

Step 1: Synthesis of tert-butyl (3-((2-((1-methyl-1H-pyrazol-4-yl)amino)-5-((phenylamino)methyl) pyrimidin-4-yl)amino)phenyl)carbamate (23)

Title compound was prepared in a manner substantially similar to procedure mentioned in General Procedure B. The crude was purified by combiflash chromatography using 5% methanol in dichloromethane as eluent, desired fractions were concentrated under reduced pressure to get tert-butyl (3-((2-((1-methyl-1H-pyrazol-4-yl)amino)-5-((phenylamino)methyl)pyrimidin-4-yl)amino)phenyl)carbamate (23) as light brown solid (500 mg; Yield: 87%). MS: $[M+H]^+$ 487.25.

Step 2: Synthesis of N4-(3-aminophenyl)-N2-(1-methyl-1H-pyrazol-4-yl)-5-((phenylamino)methyl) pyrimidine-2,4-diamine (24)

Title compound was prepared in a manner substantially similar to procedure mentioned in General Procedure I. The crude was triturated with diethyl ether afforded N4-(3-aminophenyl)-N2-(1-methyl-1H-pyrazol-4-yl)-5-((phenylamino)methyl)pyrimidine-2,4-diamine (24) as a brown solid. (0.50 g, Yield: 84%) as TFA salt, MS: $[M+H]^+$ 387.25.

Step 3: Synthesis of (E)-4-(dimethylamino)-N-(3-((2-((1-methyl-1H-pyrazol-4-yl)amino)-5-((phenylamino)methyl)pyrimidin-4-yl)amino)phenyl)but-2-enamide (Compound 17)

Title compound was prepared in a manner substantially similar to procedure mentioned in General Procedure J. The crude obtained was purified by combiflash elution with 8% methanol in dichloromethane. The title compound was further purified by prep-HPLC afforded the (E)-N-(3-((5-chloro-2-((1-(4-hydroxycyclohexyl)-1H-pyrazol-4-yl)amino)pyrimidin-4-yl)amino)-4-fluorophenyl)-4-(dimethylamino)but-2-enamide (Compound 17) as a white solid (66 mg; Yield: 20.52%). $^1$H-NMR (400 MHz, DMSO-$d_6$): δ 10.06 (bs, 1H), 8.91 (bs, 1H), 8.43 (s, 1H), 7.98 (s, 1H), 7.79 (s, 1H), 7.58-7.30 (m, 4H), 7.11-7.07 (m, 2H), 6.75-6.66 (m, 4H), 6.57 (t, J=7.2 Hz, 1H), 6.27 (d, J=15.2 Hz, 1H), 5.99-5.97 (m, 1H), 4.17 (d, J=4.0 Hz, 2H), 3.62 (s, 3H), 3.05 (d, J=5.2 Hz, 2H), 2.16 (s, 6H). LCMS: $[M+H]^+$ 498.38 (96.05%).

Scheme 6: Synthesis of (E)-4-(dimethylamino)-N-(3-((2-((1-methyl-1H-pyrazol-4-yl)amino)-5-((N-phenylacetamido)methyl)pyrimidin-4-yl)amino)phenyl)but-2-enamide (Compound 18)

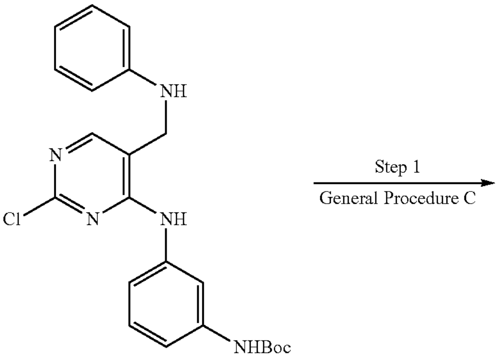

8

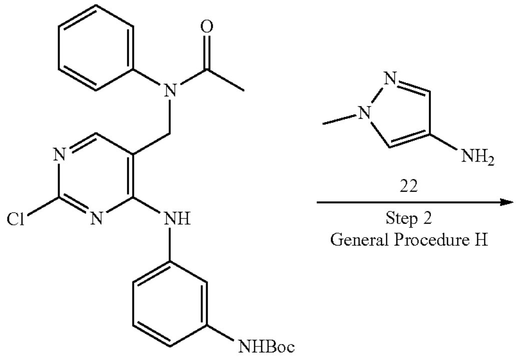

26

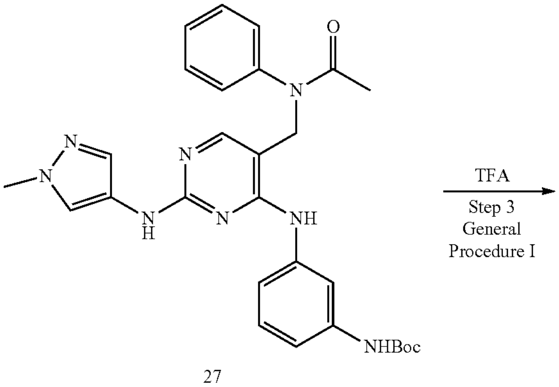

27

-continued

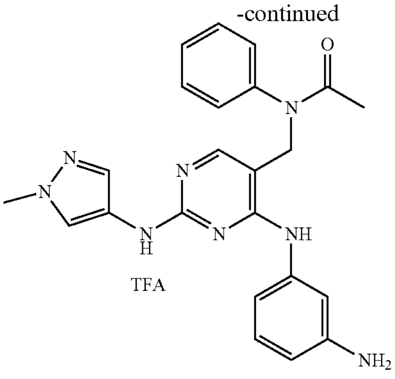

28

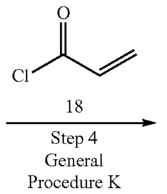

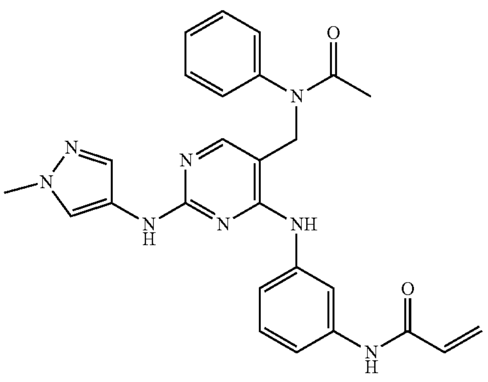

Compound 18

Step 1: Synthesis of tert-butyl (3-((2-chloro-5-((N-phenylacetamido)methyl)pyrimidin-4-yl)amino)phenyl)carbamate (26)

Title compound was prepared in a manner substantially similar to procedure mentioned in General Procedure C. The crude was purified over silica gel (100-200 mesh) eluted with 3-5% methanol in dichloromethane, desired fractions were concentrated to dryness, afforded tert-butyl (3-((2-chloro-5-((N-phenylacetamido)methyl)pyrimidin-4-yl)amino)phenyl)carbamate (26) as light brown solid. (300 mg, Yield: 54.84%). MS: $[M+H]^+$ 468.06.

Step 2: Synthesis of tert-butyl (3-((2-((1-methyl-1H-pyrazol-4-yl)amino)-5-((N-phenylacetamido)methyl)pyrimidin-4-yl)amino)phenyl)carbamate (27)

Title compound was prepared in a manner substantially similar to procedure mentioned in General Procedure H. The crude was purified over silica gel (100-200 mesh), eluted with 6-8% methanol in dichloromethane, desired fractions were concentrated under reduced pressure afforded tert-butyl (3-((2-((1-methyl-1H-pyrazol-4-yl)amino)-5-((N-phenylacetamido)methyl)pyrimidin-4-yl)amino)phenyl)carbamate (27) as light brown solid (290 mg, Yield: 85.5%), MS: $[M+H]^+$ 529.14.

Step 3: Synthesis of N-((4-((3-aminophenyl)amino)-2-((1-methyl-1H-pyrazol-4-yl)amino)pyrimidin-5-yl)methyl)-N-phenylacetamide (28)

Title compound was prepared in a manner substantially similar to procedure mentioned in General Procedure I. The crude was triturated with diethyl ether afforded N-((4-((3-aminophenyl)amino)-2-((1-methyl-1H-pyrazol-4-yl)amino)pyrimidin-5-yl)methyl)-N-phenylacetamide (28) as a brown solid. (130 mg, Yield: 55.3%) as TFA salt, MS: $[M+H]^+$ 429.25.

Step 4: Synthesis of N-(3-((5-chloro-2-((1-(4-hydroxycyclohexyl)-1H-pyrazol-4-yl)amino)pyrimidin-4-yl)amino)-4-fluorophenyl)acrylamide (Compound 18)

Title compound was prepared in a manner substantially similar to procedure mentioned in General Procedure K. The crude was purified by prep-HPLC purification afforded N-(3-((5-chloro-2-((1-(4-hydroxycyclohexyl)-1H-pyrazol-4-yl)amino)pyrimidin-4-yl)amino)-4-fluorophenyl)acrylamide (Compound 18) as a white solid (22 mg; Yield: 15.0%). $^1$H-NMR (400 MHz, DMSO-$d_6$): δ 10.27 (s, 1H), 9.30 (s, 1H), 8.98 (s, 1H), 8.00-7.60 (m, 3H), 7.54 (d, J=7.6 Hz, 1H), 7.47-7.32 (m, 6H), 7.20 (d, J=7.6 Hz, 2H), 6.51-6.44 (q, J=10.0 Hz, 1H), 6.28-6.23 (m, 1H), 5.77-5.74 (m, 1H), 4.74 (s, 2H), 3.66 (s, 3H), 1.84 (s, 3H). LCMS: $[M+H]^+$ 483.33

Scheme 7: Synthesis of N-(3-((2-((1-methyl-1H-pyrazol-4-yl)amino)-5-((N-(1-phenylethyl)acetamido)methyl)pyrimidin-4-yl)amino)phenyl)acrylamide (Compound 19)

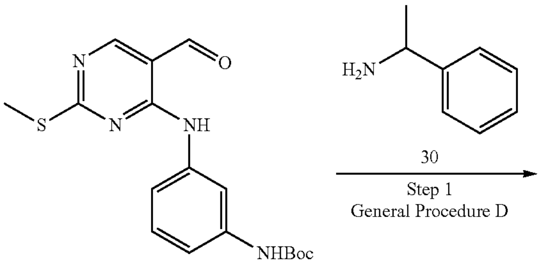

29

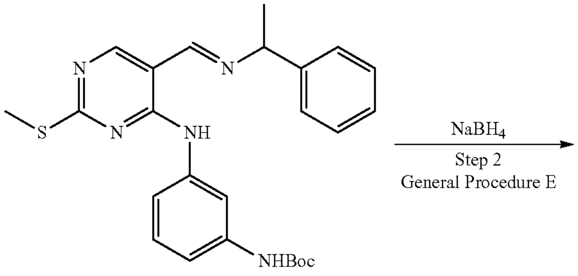

31

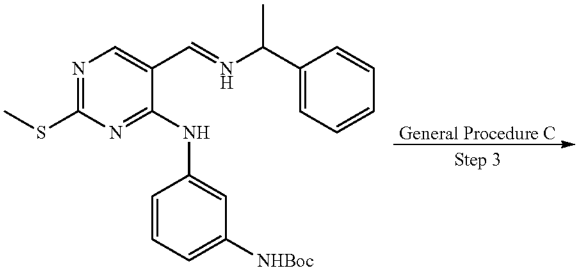

32

-continued

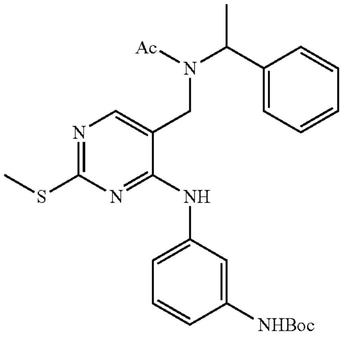

33

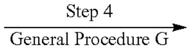

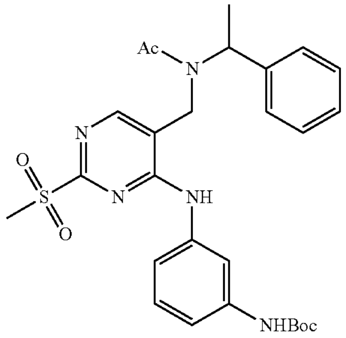

34

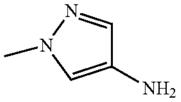

22

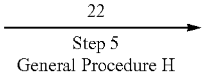

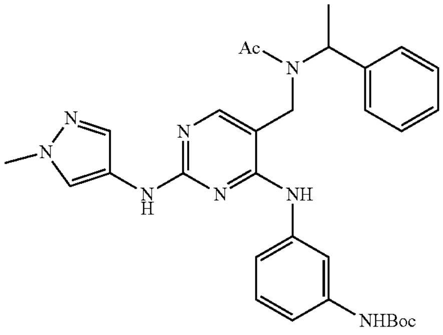

35

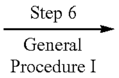

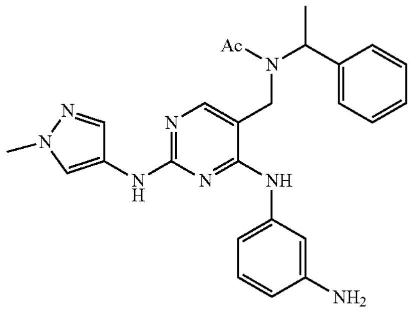

36

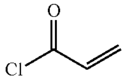

16

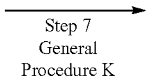

-continued

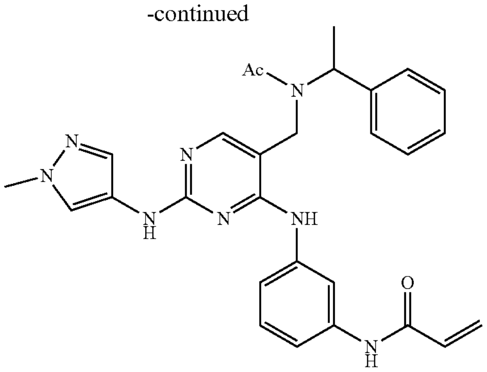

Compound 19

Step 1: Synthesis of tert-butyl (E)-(3-((2-(methylthio)-5-(((1-phenylethyl)imino)methyl)pyrimidin-4-yl)amino)phenyl)carbamate (31)

Title compound was prepared in a manner substantially similar to procedure mentioned in General Procedure D to get tert-butyl (E)-(3-((2-(methylthio)-5-(((1-phenylethyl)imino)methyl)pyrimidin-4-yl)amino)phenyl)carbamate (31) as light brown solid. (1.20 g, Yield: 93.70%). MS: $[M+H]^+$ 464.31.

Step 2: Synthesis of tert-butyl (3-((2-(methylthio)-5-(((1-phenylethyl)amino)methyl)pyrimidin-4-yl)amino)phenyl)carbamate (32)

Title compound was prepared in a manner substantially similar to procedure mentioned in General Procedure E to get tert-butyl (3-((2-(methylthio)-5-(((1-phenylethyl)amino)methyl)pyrimidin-4-yl)amino)phenyl)carbamate (32) as a pale yellow solid (1.0 g, Yield: 83%). MS: $[M+H]^+$ 466.25.

Step 3: Synthesis of tert-butyl (3-((2-(methylthio)-5-((N-(1-phenylethyl)acetamido)methyl)pyrimidin-4-yl)amino)phenyl)carbamate (33)

Title compound was prepared in a manner substantially similar to procedure mentioned in General Procedure C. The crude obtained was purified over silica gel (100-200 mesh), eluted with 4-5% methanol in dichloromethane, desired fractions were concentrated under reduced pressure afforded tert-butyl (3-((2-chloro-5-((N-phenylacetamido)methyl)pyrimidin-4-yl)amino)phenyl)carbamate (33) as light brown solid. (500 mg; Yield: 41.66%). MS: $[M+H]^+$ 508.25.

Step 4: Synthesis of tert-butyl (3-((2-(methylsulfonyl)-5-((N-(1-phenylethyl)acetamido)methyl)pyrimidin-4-yl)amino)phenyl)carbamate (34)

Title compound was prepared in a manner substantially similar to procedure mentioned in General Procedure G to get tert-butyl (3-((2-(methylsulfonyl)-5-((N-(1-phenylethyl)acetamido)methyl)pyrimidin-4-yl)amino)phenyl)carbamate (34) as off white solid (400 mg; Yield: 75%). MS: $[M+H]^+$ 540.15.

Step 5: Synthesis of tert-butyl (3-((2-((1-methyl-1H-pyrazol-4-yl)amino)-5-((N-(1-phenylethyl)acetamido)methyl)pyrimidin-4-yl)amino)phenyl)carbamate (35)

Title compound was prepared in a manner substantially similar to procedure mentioned in General Procedure H to get tert-butyl (3-((2-((1-methyl-1H-pyrazol-4-yl)amino)-5-((N-(1-phenylethyl)acetamido)methyl)pyrimidin-4-yl)amino)phenyl)carbamate (35) as light brown solid (200 mg; Yield: 48.54%), LCMS: $[M+H]^+$ 557.31.

Step 6: Synthesis of N-((4-((3-aminophenyl)amino)-2-((1-methyl-1H-pyrazol-4-yl)amino)pyrimidin-5-yl)methyl)-N-(1-phenylethyl)acetamide (36)

Title compound was prepared in a manner substantially similar to procedure mentioned in General Procedure I to get N-((4-((3-aminophenyl)amino)-2-((1-methyl-1H-pyrazol-4-yl)amino)pyrimidin-5-yl)methyl)-N-(1-phenylethyl)acetamide (36) as brown solid. (150 mg; Yield: 91.64%) as TFA salt, MS: $[M+H]^+$ 457.25.

Step 7: Synthesis of N-(3-((2-((1-methyl-1H-pyrazol-4-yl)amino)-5-((N-(1-phenylethyl)acetamido)methyl)pyrimidin-4-yl)amino)phenyl)acrylamide (Compound 19)

Title compound was prepared in a manner substantially similar to procedure mentioned in General Procedure K. The crude was purified by prep-HPLC to afford N-(3-((2-((1-methyl-1H-pyrazol-4-yl)amino)-5-((N-(1-phenylethyl)acetamido)methyl)pyrimidin-4-yl)amino)phenyl)acrylamide (Compound 19) as a white solid (30 mg; Yield: 15.0%). $^1$H NMR (400 MHz, DMSO $d_6$): δ 10.20 (s, 1H), 9.48 (s, 1H), 8.89 (s, 1H), 7.89 (s, 1H), 7.74-7.25 (m, 11H), 6.49-6.42 (m, 1H), 6.27-6.23 (m, 1H), 5-76-5.73 (m, 1H), 5.25-5.23 (m, 1H), 4.53-4.41 (m, 1H), 4.25-4.15 (m, 1H), 3.64 (bs, 3H), 2.15 (s, 3H), 1.61 (d, J=6.8 Hz, 3H). LCMS: $[M+H]^+$ 511.37.

Scheme 8: Synthesis of N-(3-((5-chloro-2-((1-methyl-1H-pyrazol-4-yl)amino)pyrimidin-4-yl)(phenyl)amino)-4-fluorophenyl)acrylamide (Compound 20)

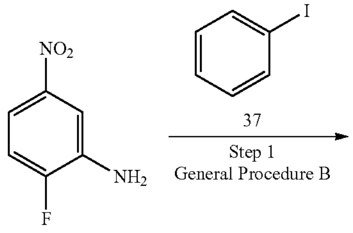

37

12

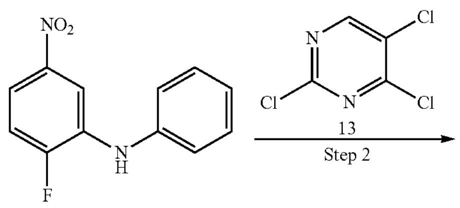

13

38

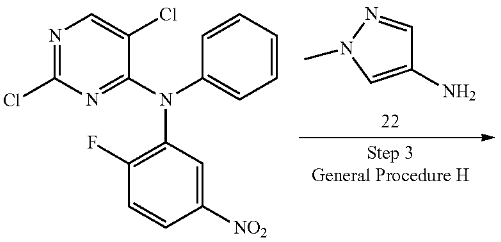

22

39

-continued

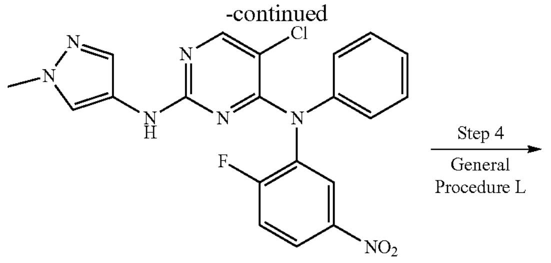

40

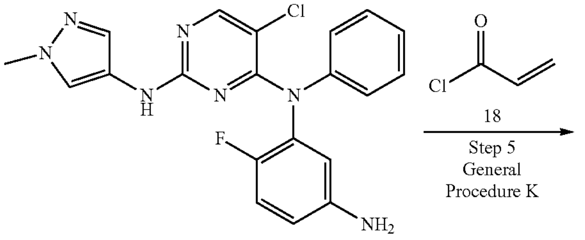

18

41

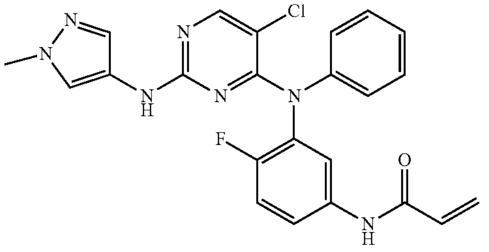

Compound 20

Step 1: Synthesis of 2-fluoro-5-nitro-N-phenylaniline (38)

Title compound was prepared in a manner substantially similar to procedure mentioned in General Procedure B. The crude was purified by combiflash chromatography using 10-20% ethyl acetate in hexane as eluent, desired fractions were concentrated under reduced pressure afforded 2-fluoro-5-nitro-N-phenylaniline (38) as light brown solid (4.0 g; Yield: 54.0%), MS: $[M-H]^-$ 230.96.

Step 2: Synthesis of 2,5-dichloro-N-(2-fluoro-5-nitrophenyl)-N-phenylpyrimidin-4-amine (39)

To a solution of 2,5-dichloro-N-(2-fluoro-5-nitrophenyl)pyrimidin-4-amine (38) (2.00 g, 8.61 mmol) in N,N-dimethylformamide (20 mL) were added potassium carbonate (2.40 g, 17.22 mmol) and 2,4,5-trichloropyrimidine (13) (1.60 g, 8.61 mmol). The resultant reaction mixture was heated at 100° C. for 16 hours. After completion of reaction (TLC monitoring), the reaction mixture was cooled, diluted with ice-cold water, extracted with ethyl acetate (3×100 mL). The combined organic layers were washed with brine, dried over anhydrous sodium sulfate, filtered and concentrated under reduced pressure. The crude was purified over flash chromatography using 5-10% ethyl acetate in hexane as eluent, desired fractions were concentrated under reduced pressure afforded 2,5-dichloro-N-(2-fluoro-5-nitrophenyl)-N-phenylpyrimidin-4-amine (39) as light brown solid (1.40 g; Yield: 42.9%). $^1$H-NMR (400 MHz, DMSO-$d_6$): δ 8.48 (s, 1H), 7.97-7.94 (m, 1H), 7.72-7.68 (m, 1H), 7.49-7.42 (m, 1H), 7.38-7.29 (m, 2H), 7.19-7.17 (m, 2H), 7.14-7.03 (m, 1H).

Step 3: Synthesis of 5-chloro-N4-(2-fluoro-5-nitrophenyl)-N2-(1-methyl-1H-pyrazol-4-yl)-N4-phenylpyrimidine-2,4-diamine (40)

Title compound was prepared in a manner substantially similar to procedure mentioned in General Procedure H, to get 5-chloro-N4-(2-fluoro-5-nitrophenyl)-N2-(1-methyl-1H-pyrazol-4-yl)-N4-phenylpyrimidine-2,4-diamine (40) as light brown solid (550 mg; Yield: 94.8%), MS: $[M+H]^+$ 440.17.

Step 4: Synthesis of N4-(5-amino-2-fluorophenyl)-5-chloro-N2-(1-methyl-1H-pyrazol-4-yl)-N4-phenylpyrimidine-2,4-diamine (41)

Title compound was prepared in a manner substantially similar to procedure mentioned in General Procedure L, to get N4-(5-amino-2-fluorophenyl)-5-chloro-N2-(1-methyl-1H-pyrazol-4-yl)-N4-phenylpyrimidine-2,4-diamine (41) as a brown solid. (450 mg; Yield: 88%). MS: $[M+H]^+$ 410.01.

Step 5: Synthesis of N-(3-((5-chloro-2-((1-methyl-1H-pyrazol-4-yl)amino)pyrimidin-4-yl)(phenyl)amino)-4-fluorophenyl)acrylamide (Compound 20)

Title compound was prepared in a manner substantially similar to procedure mentioned in General Procedure K. The crude was purified by prep-HPLC purification to afforded N-(3-((5-chloro-2-((1-methyl-1H-pyrazol-4-yl)amino)pyrimidin-4-yl)(phenyl)amino)-4-fluorophenyl)acrylamide (Compound 20) as a white solid (95 mg, Yield: 33.56%). $^1$H-NMR (400 MHz, DMSO-$d_6$): δ 10.25 (s, 1H), 9.58 (s, 1H), 8.19 (s, 1H), 7.69-7.05 (m, 9H), 6.62 (bs, 1H), 6.36-6.18 (m, 2H), 5.74-5.71 (m, 1H), 3.47 (s, 3H). LCMS: $[M+H]^+$ 464.18.

Scheme 9: Synthesis of N-(3-((5-chloro-2-((5-(methoxymethyl)-1-methyl-1H-pyrazol-3-yl)amino)pyrimidin-4-yl)amino)-4-fluorophenyl)acrylamide (Compound 21)

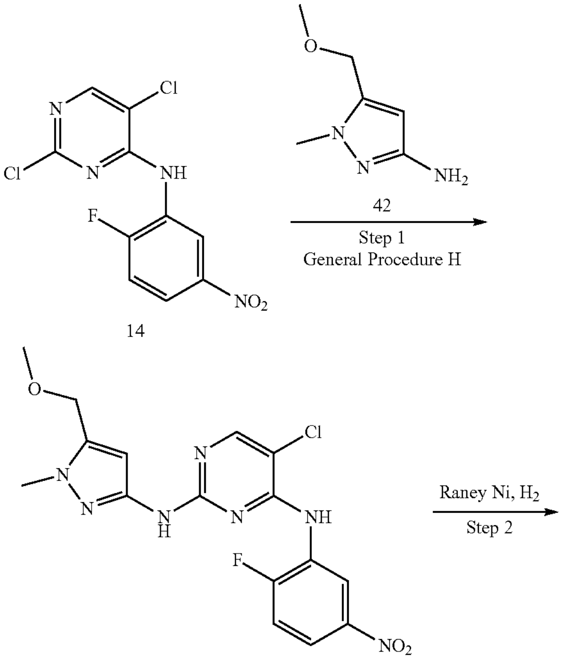

14

42

43

-continued

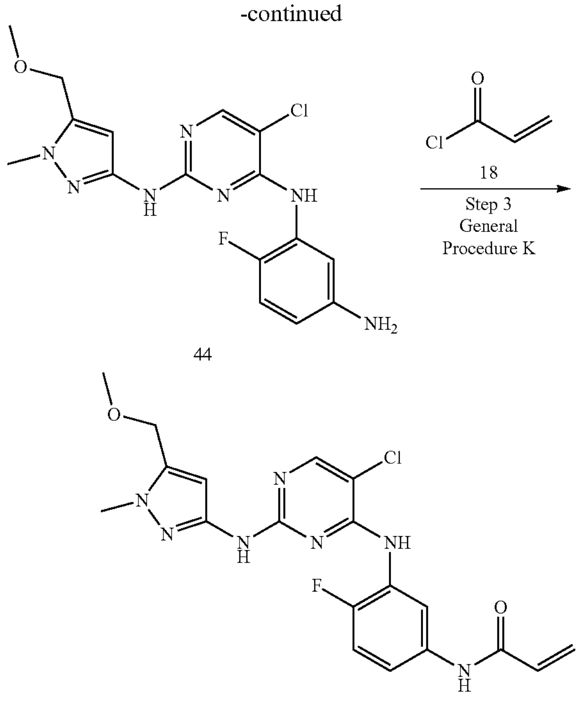

18

44

Compound 21

Step 1: Synthesis of 5-chloro-N4-(2-fluoro-5-nitrophenyl)-N2-(5-(methoxymethyl)-1-methyl-1H-pyrazol-3-yl)pyrimidine-2,4-diamine (43)

Title compound was prepared in a manner substantially similar to procedure mentioned in General Procedure H to get 5-chloro-N4-(2-fluoro-5-nitrophenyl)-N2-(5-(methoxymethyl)-1-methyl-1H-pyrazol-3-yl)pyrimidine-2,4-diamine (43) as light brown solid (500 mg; Yield: 62.11%). LCMS: $[M+H]^+$ 407.97.

Step 2: Synthesis of N4-(5-amino-2-fluorophenyl)-5-chloro-N2-(1-methyl-1H-pyrazol-4-yl)-N4-phenylpyrimidine-2,4-diamine (44)

To a solution of 5-chloro-N4-(2-fluoro-5-nitrophenyl)-N2-(5-(methoxymethyl)-1-methyl-1H-pyrazol-3-yl)pyrimidine-2,4-diamine (43) (250 mg, 0.61 mmol) in methanol (15 mL) was added Raney nickel (100 mg). The resulting reaction mixture was stirred at room temperature under hydrogen atmosphere for 16 hours. After completion of reaction (TLC monitoring), reaction mixture was filtered through celite bed, washed with 10% methanol in dichloromethane (3×5 mL). The combined organics was concentrated under reduced pressure to afforded N4-(5-amino-2-fluorophenyl)-5-chloro-N2-(5-(methoxymethyl)-1-methyl-1H-pyrazol-3-yl)pyrimidine-2,4-diamine (44) as a light brown solid. (200 mg, Yield: 86.58%). MS: $[M+H]^+$ 378.20.

Step 3: Synthesis of N-(3-((5-chloro-2-((5-(methoxymethyl)-1-methyl-1H-pyrazol-3-yl)amino)pyrimidin-4-yl)amino)-4-fluorophenyl)acrylamide (Compound 21)

Title compound was prepared in a manner substantially similar to procedure mentioned in General Procedure K, N4-(5-amino-2-fluorophenyl)-5-chloro-N2-(5-(methoxymethyl)-1-methyl-1H-pyrazol-3-yl)pyrimidine-2,4-diamine (44) and acryloyl chloride (18) gave N-(3-((5-chloro-2-((5-(methoxymethyl)-1-methyl-1H-pyrazol-3-yl)amino)pyrimidin-4-yl)amino)-4-fluorophenyl)acrylamide (Compound 21) as a white solid (45 mg, Yield: 19.77%). $^1$H NMR (400 MHz, DMSO-$d_6$): δ 10.26 (s, 1H), 9.46 (s, 1H), 8.89 (s, 1H), 8.06 (s, 1H), 7.76-7.68 (m, 2H), 7.28 (t, J=9.4 Hz, 1H), 6.45-6.23 (m, 2H), 5.86-5.75 (m, 2H), 4.14 (s, 2H), 3.57 (s, 3H), 3.12 (s, 3H). LCMS: $[M+H]^+$ 432.17.

Scheme 10: Synthesis of N-(3-((5-chloro-2-((6-methoxypyridin-3-yl)amino)pyrimidin-4-yl)amino)-4-fluorophenyl)acrylamide (Compound 22)

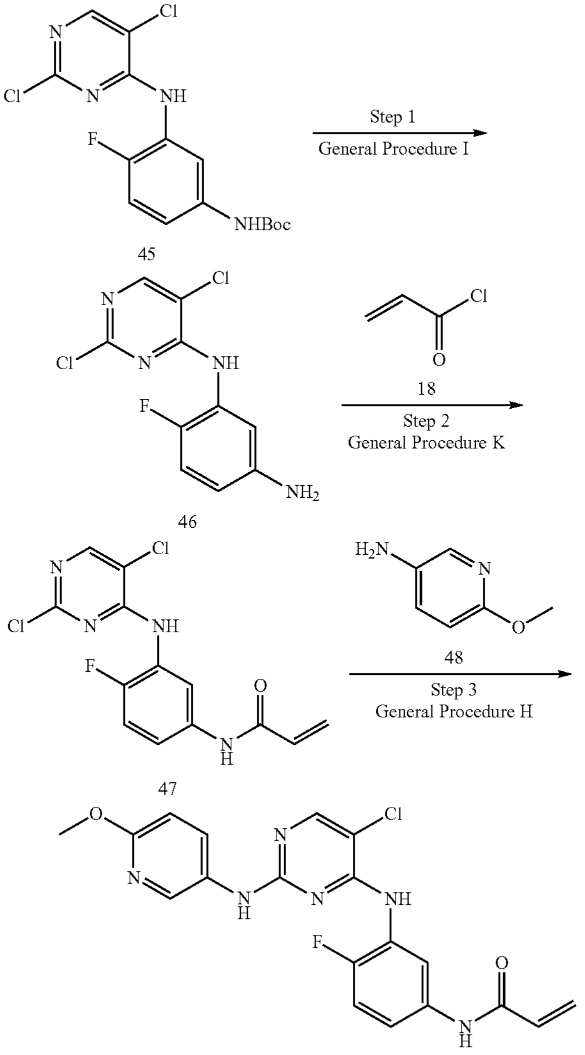

Compound 22

Step 1: Synthesis of N1-(2,5-dichloropyrimidin-4-yl)-6-fluorobenzene-1,3-diamine (46)

Title compound was prepared in a manner substantially similar to procedure mentioned in General Procedure I, to afforded N1-(2,5-dichloropyrimidin-4-yl)-6-fluorobenzene-1,3-diamine (46) as TFA salt as off white solid (2.0 g; Yield: 62.11%), LCMS: $[M+H]^+$ 272.88.

Step 2: Synthesis of N-(3-((2,5-dichloropyrimidin-4-yl)amino)-4-fluorophenyl)acrylamide (47)

Title compound was prepared in a manner substantially similar to procedure mentioned in General Procedure K. The crude obtained was purified by silica gel (100-200 mesh) elution with 3-5% methanol in dichloromethane, desired fractions were concentrated under reduced pressure to afforded N-(3-((2,5-dichloropyrimidin-4-yl)amino)-4-fluorophenyl)acrylamide (47) as off white solid (800 mg, Yield: 94.2%). $^1$H-NMR (400 MHz, DMSO-$d_6$): δ 10.39 (s, 1H), 8.40 (s, 1H), 7.80-7.83 (m, 1H), 7.53-7.57 (m, 2H), 7.27-7.32 (m, 1H), 6.39-6.46 (m, 1H), 6.22-6.29 (m, 2H).

Step 3: Synthesis of N-(3-((5-chloro-2-((6-methoxypyridin-3-yl)amino)pyrimidin-4-yl)amino)-4-fluorophenyl)acrylamide (Compound 22)

Title compound was prepared in a manner substantially similar to procedure mentioned in General Procedure H. The crude was purified over silica gel (100-200 mesh) elution with 4-6% methanol in dichloromethane, desired fractions were concentrated under reduced pressure. The resultant solid was again purified by prep-HPLC purification to afford N-(3-((5-chloro-2-((6-methoxypyridin-3-yl)amino)pyrimidin-4-yl)amino)-4-fluorophenyl)acrylamide (Compound 22) as off white solid (30 mg, Yield: 19.77%). $^1$H-NMR (400 MHz, DMSO-$d_6$): δ 10.22 (s, 1H), 9.21 (s, 1H), 8.94 (s, 1H), 8.12-8.09 (m, 2H), 7.81-7.77 (m, 2H), 7.58-7.54 (m, 1H), 7.28 (t, J=9.1 Hz, 1H), 6.50-6.37 (m, 2H), 6.27-6.22 (m, 1H), 5.77-5.54 (m, 1H), 3.73 (s, 3H). LCMS: $[M+H]^+$ 414.80.

Scheme 11: Synthesis of N-(3-((5-chloro-2-((1-methyl-1H-pyrazol-4-yl)amino)pyrimidin-4-yl)amino)-4-flourophenyl)-2-fluoroacrylamide (Compound 23)

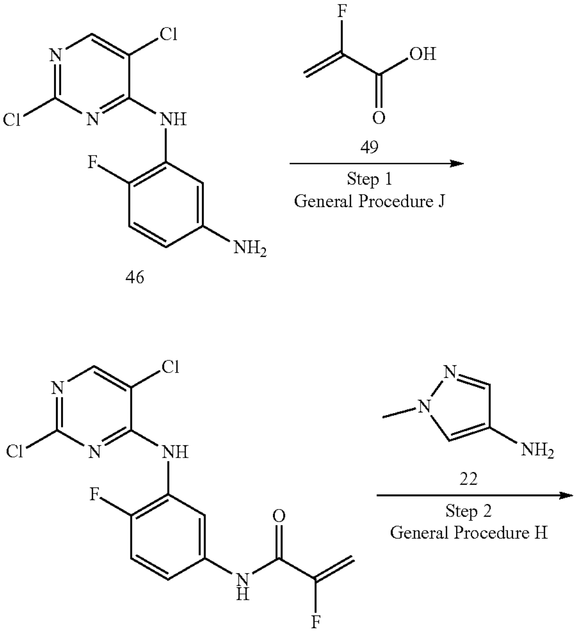

50

-continued

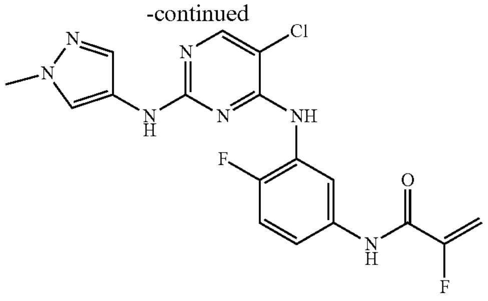

Compound 23

Step 1: Synthesis of N-(3-((2,5-dichloropyrimidin-4-yl)amino)-4-fluorophenyl)-2-fluoroacrylamide (50)

Title compound was prepared in a manner substantially similar to procedure mentioned in General Procedure J. The crude obtained was purified over combiflash, eluted with 10% methanol in dichloromethane, desired fractions were concentrated under reduced pressure to afford N-(3-((2,5-dichloropyrimidin-4-yl)amino)-4-fluorophenyl)-2-fluoroacrylamide (50) as an off white solid (350 mg; Yield: 34%). MS: $[M+H]^+$ 345.18

Step 2: Synthesis of N-(3-((5-chloro-2-((1-methyl-1H-pyrazol-4-yl)amino)pyrimidin-4-yl)amino)-4-fluorophenyl)-2-fluoroacrylamide (Compound 23)

Title compound was prepared in a manner substantially similar to procedure mentioned in General Procedure H. The crude was further purified by prep-HPLC purification afforded N-(3-((5-chloro-2-((1-methyl-1H-pyrazol-4-yl)amino)pyrimidin-4-yl)amino)-4-fluorophenyl)-2-fluoroacrylamide (Compound 23) as off white solid (55 mg, Yield: 31.42%). $^1H$ NMR (400 MHz, DMSO-$d_6$): δ 10.46 (s, 1H), 9.25 (s, 1H), 8.95 (s, 1H), 8.05 (s, 1H), 7.85-7.74 (m, 2H), 7.37 (s, 1H), 7.11 (m, 1H), 6.98 (m, 1H), 5.78-5.65 (m, 1H), 5.47-5.42 (m, 1H), 3.52 (s, 3H). LCMS: $[M+H]^+$ 405.82.

Scheme 12: Synthesis of N-(3-((5-chloro-2-((1-methyl-1H-pyrazol-4-yl)amino)pyrimidin-4-yl)amino)cyclohexyl)-2-flourophenyl)-2-fluoroacrylamide (Compound 24)

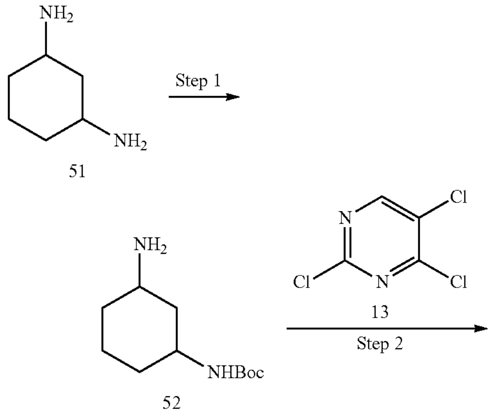

-continued

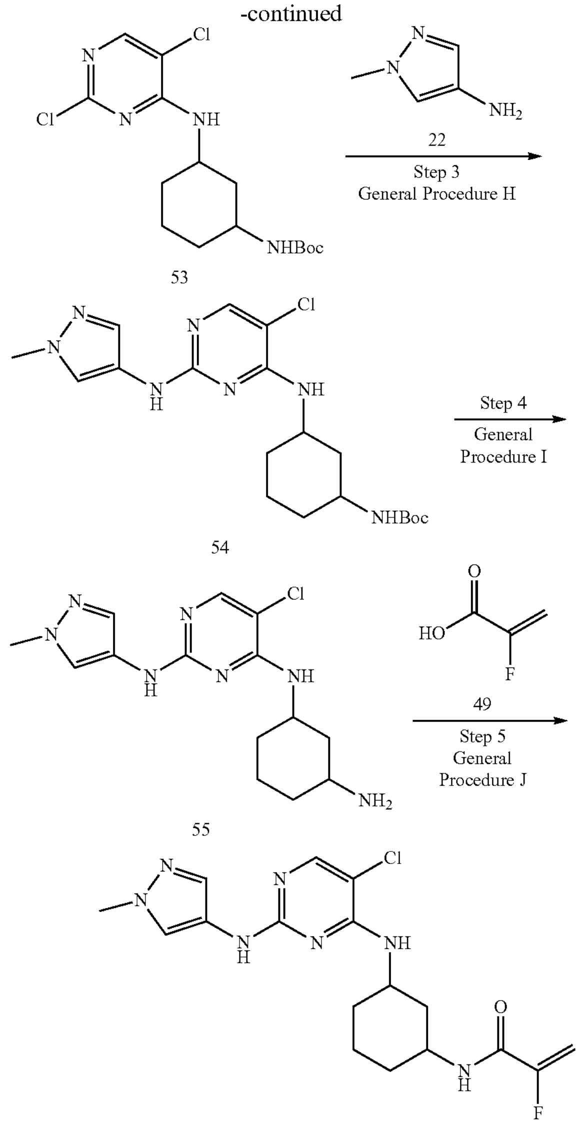

Compound 24

Step 1: Synthesis of tert-butyl (3-aminocyclohexyl)carbamate (52)

To an ice-cold solution of cyclohexane-1,3-diamine (51) (15.0 g, 131.57 mmol) in chloroform (300 mL) was added drop wise di-tert-butyl dicarbonate (14.93 mL, 65.78 mmol). The reaction mixture was stirred at room temperature for 16 hours. After completion of reaction (TLC monitoring), water was added and extracted with dichloromethane (3×200 mL). The combined organic layers were dried over anhydrous sodium sulfate, filtered and concentrated under reduced pressure. The crude obtained was purified over silica gel (100-200 mesh) eluted with 3-5% methanol in dichloromethane, desired fractions were concentrated under reduced pressure afforded tert-butyl (3-aminocyclohexyl) carbamate (52) as a white solid (21.0 g; Yield: 75%). $^1H$-NMR (400 MHz, DMSO-$d_6$): δ 8.29 (s, 2H), 5.74 (s, 1H), 3.72-3.76 (m, 2H), 3.01-3.20 (m, 4H), 1.40-1.84 (m, 4H), 1.36 (s, 9H).

Step 2: Synthesis of tert-butyl (3-((2,5-dichloropyrimidin-4-yl)amino)cyclohexyl)carbamate (53)

To an ice-cold solution of tert-butyl (3-aminocyclohexyl) carbamate (52) (2.33 g, 10.9 mmol) in ethanol (20 mL), was added N,N-diisopropylethylamine (9.5 mL, 54.51 mmol) and 2,4,5-trichloropyrimidine (13) (2.0 g, 10.9 mmol). The resultant reaction mixture was heated at 90° C. for 16 hours. After completion of reaction (TLC monitoring), reaction mixture was diluted water, extracted with ethyl acetate (3×100 mL). The combined organics washed with water, brine, dried over anhydrous sodium sulfate, filtered and concentrated under vacuum. The crude was purified using flash chromatography using 30-50% ethyl acetate in hexane as eluent, desired fractions were concentrated under reduced pressure afforded tert-butyl (3-((2,5-dichloropyrimidin-4-yl) amino)cyclohexyl)carbamate (53) as light brown solid (1.20 g; Yield: 30.4%), MS: $[M+H]^+$ 360.97.

Step 3: Synthesis of tert-butyl (3-((5-chloro-2-((1-methyl-1H-pyrazol-4-yl)amino)pyrimidin-4-yl) amino)cyclohexyl)carbamate (54)

Title compound was prepared in a manner substantially similar to procedure mentioned in General Procedure H. The crude was purified by silica gel (100-200 mesh) elution with 2-4% methanol in dichloromethane, desired fractions were concentrated under reduced pressure to get the tert-butyl (3-((5-chloro-2-((1-methyl-1H-pyrazol-4-yl)amino)pyrimidin-4-yl)amino)cyclohexyl)carbamate (54) as light brown solid (600 mg, Yield: 85.83%), MS: $[M+H]^+$ 422.38.

Step 4: Synthesis of N4-(3-aminocyclohexyl)-5-chloro-N2-(1-methyl-1H-pyrazol-4-yl)pyrimidine-2,4-diamine (55)

Title compound was prepared in a manner substantially similar to procedure mentioned in General Procedure I afforded N4-(3-aminocyclohexyl)-5-chloro-N2-(1-methyl-1H-pyrazol-4-yl)pyrimidine-2,4-diamine (55) as TFA salt as light brown solid (400 mg; Yield: 88%). MS: $[M+H]^+$ 322.25.

Step 5: Synthesis of N-(3-((5-chloro-2-((1-methyl-1H-pyrazol-4-yl)amino)pyrimidin-4-yl)(phenyl) amino)-4-fluorophenyl)acrylamide (Compound 24)

Title compound was prepared in a manner substantially similar to procedure mentioned in General Procedure J. The crude was purified by prep-HPLC purification afforded N-(3-((5-chloro-2-((1-methyl-1H-pyrazol-4-yl)amino)pyrimidin-4-yl)(phenyl)amino)-4-fluorophenyl)acrylamide (Compound 24) as white solid (35 mg; Yield: 10%). $^1$H-NMR (400 MHz, DMSO-$d_6$): δ 9.05 (s, 1H), 8.47 (d, J=8.0 Hz, 1H), 7.90-7.75 (m, 2H), 7.36 (s, 1H), 6.78-6.76 (m, 1H), 5.57-5.73 (m, 1H), 5.25-5.20 (m, 1H), 4.03 (s, 1H), 3.83-3.76 (m, 4H), 2.01-1.23 (in 8H). LCMS: $[M+H]^+$ 394.14.

TABLE 3

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 25 | 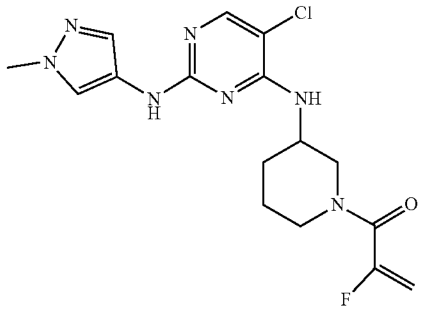 [SMILES: C=C(F)C(=O)N1CCCC(Nc2nc(Nc3cnn(C)c3)ncc2Cl)C1] | J | 380.08 | δ 8.73 (s, 1H), 7.89 (s, 1H), 7.71 (s, 1H), 7.40 (s, 1H), 6.43-6.45 (m, 1H), 5.04-5.20 (m, 2H), 4.10-4.12 (m, 2H), 3.75-3.80 (m, 4H), 3.10-3.16 (m, 1H), 2.00-2.02 (m, 1H), 1.52-1.83 (m, 4H). |
| 26 | 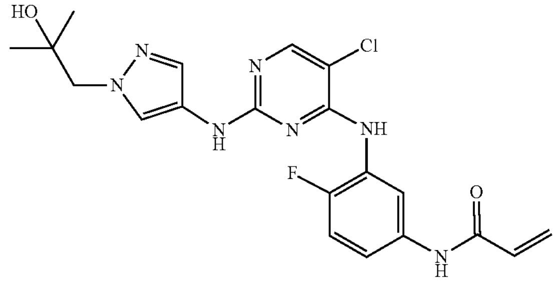 [SMILES: C=CC(=O)Nc1ccc(F)c(Nc2nc(Nc3cnn(CC(C)(C)O)c3)ncc2Cl)c1] | K | 445.82 | δ 10.27 (bs, 1H), 9.25 (bs, 1H), 8.89 (bs, 1H), 8.05 (s, 1H), 7.76-7.77 (m, 1H), 7.65 (s, 1H), 7.16-7.31 (m, 3H), 6.38-6.44 (m, 1H), 6.23-6.27 (m, 1H), 5.75 (d, J = 10.4 Hz, 1H), 4.49 (bs, 1H), 3.66-3.83 (m, 2H), 0.93 (s, 6H) |

Scheme 13: Synthesis of (E)-N-(3-((5-chloro-2-((3-methylisothiazol-5-yl)amino)pyrimidin-4-yl)amino)-4-flourophenyl)-4-(dimethylamino)but-2-enamide (Compound 27)

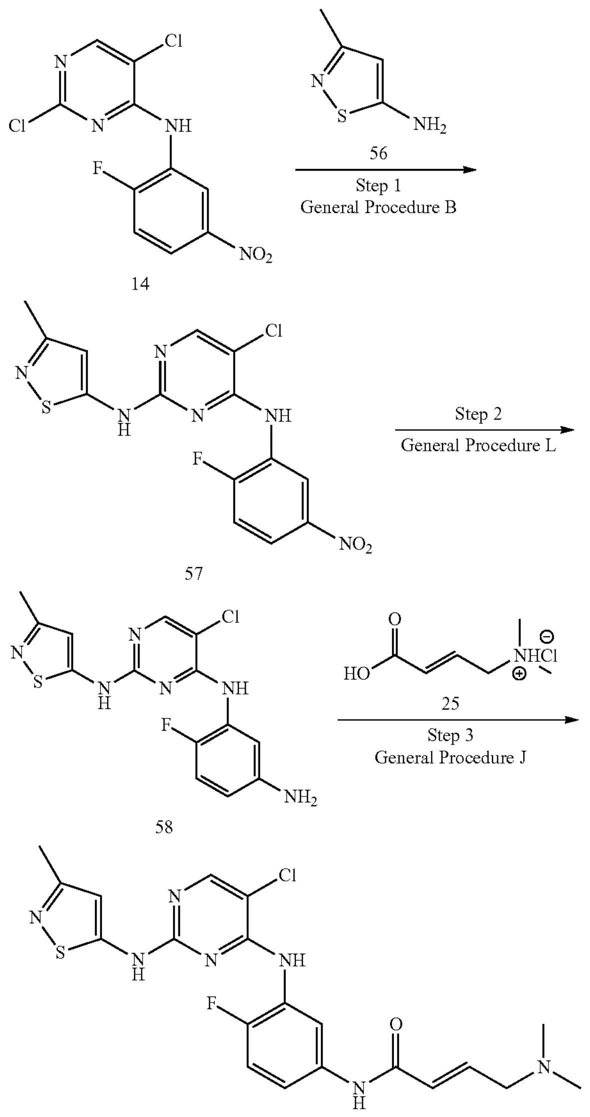

56, 14, 57, 25, 58

Compound 27

Step 1: Synthesis of 5-chloro-N4-(2-fluoro-5-nitrophenyl)-N2-(3-methylisothiazol-5-yl)pyrimidine-2,4-diamine (57)

Title compound was prepared in a manner substantially similar to procedure mentioned in General Procedure B. The crude was purified by silica gel (100-200 mesh) elution with 3-500 methanol in dichloromethane, desired fractions were concentrated to dryness to get the 5-chloro-N4-(2-fluoro-5-nitrophenyl)-N2-(3-methylisothiazol-5-yl)pyrimidine-2,4-diamine (57) as light brown solid (500 mg; Yield: 79.740%), MS: $[M+H]^+$ 381.13.

Step 2: Synthesis of N4-(5-amino-2-fluorophenyl)-5-chloro-N2-(1-methyl-1H-pyrazol-4-yl)pyrimidine-2,4-diamine (58)

Title compound was prepared in a manner substantially similar to procedure mentioned in General Procedure L to get N4-(5-amino-2-fluorophenyl)-5-chloro-N2-(1-methyl-1H-pyrazol-4-yl)pyrimidine-2,4-diamine (58) as a brown solid. (300 mg; Yield: 65%), MS: $[M+H]^+$ 350.94.

Step 3: Synthesis of (E)-N-(3-((5-chloro-2-((3-methylisothiazol-5-yl)amino)pyrimidin-4-yl)amino)-4-fluorophenyl)-4-(dimethylamino)but-2-enamide (Compound 27)

Title compound was prepared in a manner substantially similar to procedure mentioned in General Procedure J. The crude was purified over combiflash, eluted with 8% methanol in dichloromethane, desired fractions were concentrated under reduced pressure and again purified using prep-HPLC afforded (E)-N-(3-((5-chloro-2-((3-methylisothiazol-5-yl)amino)pyrimidin-4-yl)amino)-4-fluorophenyl)-4-(dimethylamino)but-2-enamide (Compound 27) as white solid (20 mg, Yield: 5.06%). $^1$H-NMR (400 MHz, DMSO-$d_6$): δ 11.05 (bs, 1H), 10.19 (bs 1H), 9.22 (bs, 1H), 8.24 (s, 1H), 7.79 (s, 1H), 7.59 (s, 1H), 7.27 (t, J=9.4 Hz, 1H), 6.69-6.76 (m, 1H), 6.49 (s, 1H), 6.25 (d, J=15.4 Hz, 1H), 3.04-3.05 (m, 2H), 2.17 (m, 9H). LCMS: $[M+H]^+$ 462.13.

Scheme 14: Synthesis of N-(4-((3-acrylamidophenyl)amino)-2-((1-methyl-1H-pyrazol-4-yl)amino)pyrimidin-5-yl)benzamide (Compound 28)

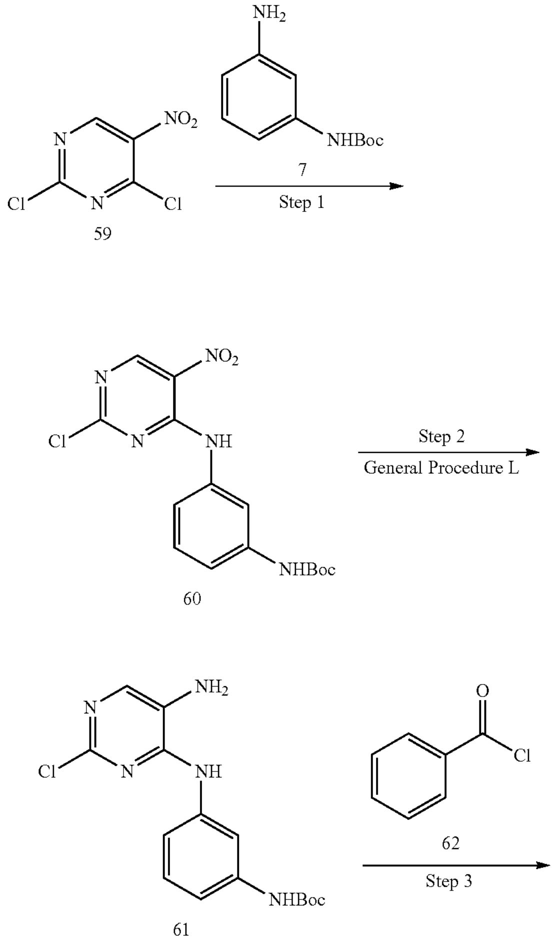

7, 59, 60, 62, 61

-continued

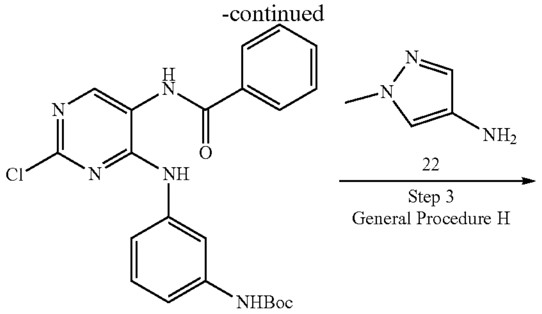

63

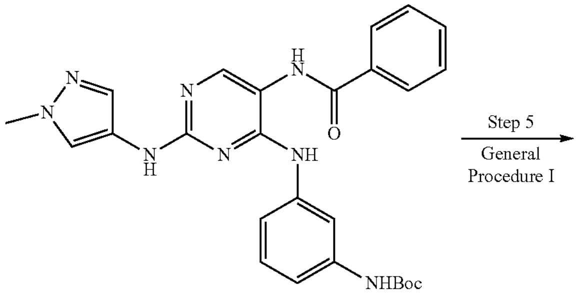

64

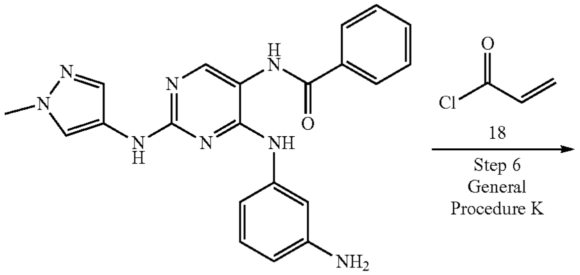

65

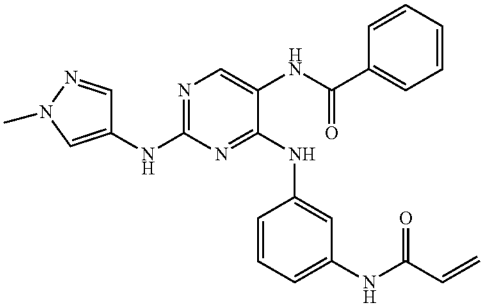

Compound 28

Step 1: Synthesis of tert-butyl (3-((2-chloro-5-nitro-pyrimidin-4-yl)amino)phenyl)carbamate (60)

To an ice-cold solution of tert-butyl (3-aminophenyl) carbamate (7) (5.0 g, 26.04 mmol) in tetrahydrofuran (45 mL) was added N,N-diisopropylethylamine (9.3 mL, 52.082 mmol) and 2,4-dichloro-5-nitropyrimidine (59) (5.0 g, 26.04 mmol). The resultant reaction mixture was stirred at room temperature for 1 hour. After completion of reaction (TLC monitoring), ice-cold water was added, the resulted solid precipitate was filtered and dried under vacuum to get desired product (60) as pale yellow solid (8.1 g, Yield: 85.23%). $^1$H-NMR (400 MHz, DMSO-$d_6$): δ 10.25 (s, 1H), 9.16 (s, 1H), 9.03 (s, 1H), 7.95 (s, 1H), 7.23 (d, J=15.2 Hz, 2H), 7.13 (s, 1H), 1.47 (s, 9H). LCMS: $[M+H]^+$ 366.09.

Step 2: Synthesis of tert-butyl (3-((5-amino-2-chloropyrimidin-4-yl)amino)phenyl)carbamate (61)

Title compound was prepared in a manner substantially similar to procedure mentioned in General Procedure L to get desired product (61) as brown solid (6.4 g, Yield: 85%). LCMS: $[M+H]^+$ 336.11.

Step 3: Synthesis of tert-butyl (3-((5-benzamido-2-chloropyrimidin-4-yl)amino)phenyl)carbamate (63)

To an ice-cold solution of tert-butyl (3-((5-amino-2-chloropyrimidin-4-yl)amino)phenyl)carbamate (61) (1.0 g, 2.9 mmol) in tetrahydrofuran (20 mL) was added pyridine (0.9 mL, 11.9 mmol) and benzoyl chloride (62) (417.12 mg, 2.9 mmol) under nitrogen atmosphere. The resultant reaction mixture was stirred at room temperature for 30 minutes. After completion of reaction mixture (TLC monitoring), reaction mixture was quenched with water (100 mL) and extracted with dichloromethane (3×100 mL). The combined organic layer was washed with brine, dried over anhydrous sodium sulfate, filtered and concentrated under reduced pressure. The crude was purified over combiflash, eluted with 20% ethyl acetate in hexane to get desired product (63) as brown solid (1.1 g, Yield: 84%). LCMS: $[M+H]^+$ 440.14.

Step 4: Synthesis of tert-butyl (3-((5-benzamido-2-((1-methyl-1H-pyrazol-4-yl)amino)pyrimidin-4-yl) amino)phenyl)carbamate (64)

Title compound was prepared in a manner substantially similar to procedure mentioned in General Procedure H. The crude was purified over combiflash chromatography, eluted with 4% methanol in dichloromethane to get desired product (64) as brown solid (720 mg; Yield: 57%). LCMS: $[M+H]^+$ 501.23.

Step 5: Synthesis of N-(4-((3-aminophenyl)amino)-2-((1-methyl-1H-pyrazol-4-yl)amino)pyrimidin-5-yl) benzamide (65)

Title compound was prepared in a manner substantially similar to procedure mentioned in General Procedure I to get desired product (65) as brown solid (510 mg, Yield: 91.01%). MS: $[M+H]^+$ 401.21.

Step 6: Synthesis of N-(4-((3-acrylamidophenyl) amino)-2-((1-methyl-1H-pyrazol-4-yl)amino)pyrimidin-5-yl)benzamide (Compound 28)

Title compound was prepared in a manner substantially similar to procedure mentioned in General Procedure K. The crude was purified by prep HPLC to get desired product Compound 28 as off white (65 mg, Yield: 19.12%). $^1$H-NMR (400 MHz, DMSO-$d_6$): δ 10.15 (bs, 1H), 9.59 (bs, 1H), 7.07 (bs, 1H), 8.72 (bs, 1H), 8.03-8.06 (m, 2H), 7.94 (s, 1H), 7.83 (s, 1H), 7.51-7.59 (m, 4H), 7.31-7.43 (m, 4H), 6.40-6.47 (m, 1H), 6.21-6.26 (m, 1H), 5.73 (dd, J=2.0 & 10.4 Hz, 1H), 3.64 (s, 3H). LCMS: $[M+H]^+$ 455.28.

Scheme 15: Synthesis of N-(3-((2-(1-methyl-1H-pyrazol-4-yl)amino)-5-(phenylsulfonamido)pyrimidin-4-yl)amino)phenyl)acrylamide (Compound 29)

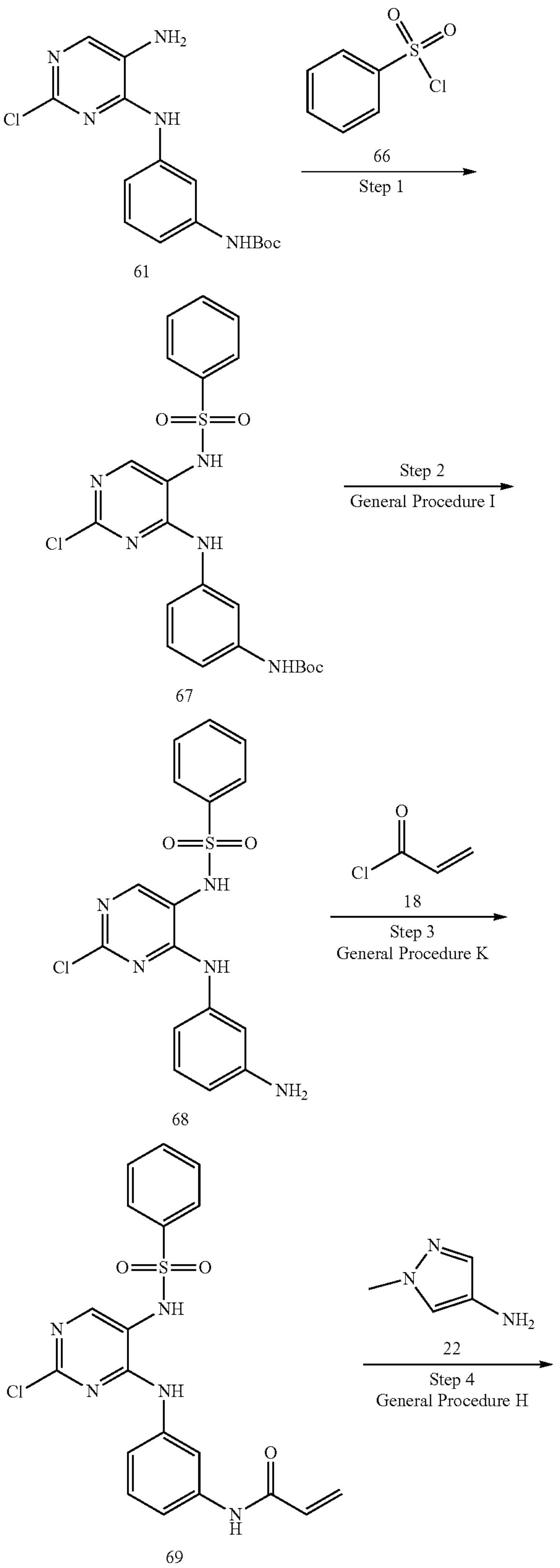

-continued

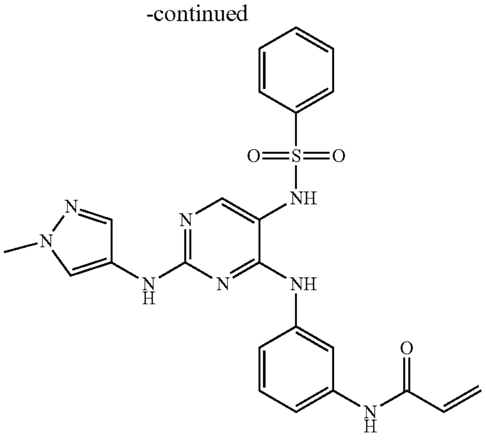

Compound 29

Step 1: Synthesis of tert-butyl (3-((2-chloro-5-(phenylsulfonamido)pyrimidin-4-yl)amino)phenyl)carbamate (67)

To an ice-cold solution of tert-butyl (3-((5-amino-2-chloropyrimidin-4-yl)amino)phenyl)carbamate (61) (1.0 g, 2.98 mmol) in dichloromethane (15 mL) was added pyridine (0.69 mL, 11.98 mmol) and benzene sulfonyl chloride (66) (525 mg, 2.98 mmol) at same temperature under nitrogen atmosphere. The reaction mixture was stirred at room temperature for 1 hour. After completion of reaction mixture (TLC monitoring), the reaction was diluted with water and extracted with dichloromethane (3 times). The combined organic layer was washed with brine, dried anhydrous sodium sulfate, concentrated under reduced pressure to get desired product (67) as semi solid (700 mg, Yield: 50%). LCMS: $[M+H]^+$ 476.11.

Step 2: Synthesis of N-(4-((3-aminophenyl)amino)-2-chloropyrimidin-5-yl)benzenesulfonamide (68)

Title compound was prepared in a manner substantially similar to procedure mentioned in General Procedure I to get desired product (68) as brown solid (480 mg, Yield: 96%). LCMS: $[M+H]^+$ 376.11.

Step 3: Synthesis of N-(3-((2-chloro-5-(phenylsulfonamido)pyrimidin-4-yl)amino)phenyl)acrylamide (69)

Title compound was prepared in a manner substantially similar to procedure mentioned in General Procedure K. The crude was purified by combiflash eluted with 4% methanol in dichloromethane to get desired product (69) as brown solid (340 mg, Yield: 67%). MS: $[M+H]^+$ 430.07.

Step 4: Synthesis of N-(3-((2-((1-methyl-1H-pyrazol-4-yl)amino)-5-(phenylsulfonamido)pyrimidin-4-yl)amino)phenyl)acrylamide (Compound 29)

Title compound was prepared in a manner substantially similar to procedure mentioned in General Procedure H. The crude was purified by prep HPLC purification to get desired product Compound 29 as off white solid (10 mg, Yield: 9%). $^1$H-NMR (400 MHz, DMSO-$d_6$): δ 10.13 (bs, 1H), 9.25 (bs, 1H), 8.23 (bs, 1H), 7.73-7.75 (m, 2H), 7.65 (s, 1H), 7.53-7.57 (m, 4H), 7.44-7.51 (m, 3H), 7.25 (s, 2H), 7.00-7.02 (m, 1H), 6.41-6.48 (m, 1H), 6.24 (d, J=15.2 Hz, 1H), 5.74 (dd, J=10.4 & 2.0 Hz, 1H), 3.59 (s, 3H). LCMS: $[M+H]^+$ 491.26.

TABLE 4
The following compounds were prepared using the procedures described above:
| Cmpd. No. | Structure | General Procedure | LCMS [M + H] | $^1$H-NMR (400 MHz, DMSO-$d_6$) |
|---|---|---|---|---|
| 30 | 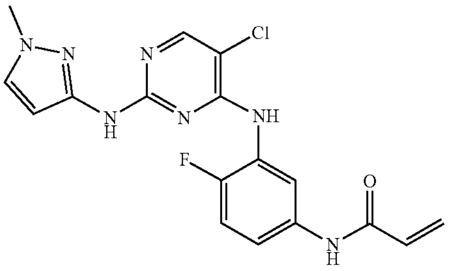 [SMILES: C=CC(=O)Nc1ccc(F)c(Nc2nc(Nc3ccn(C)n3)ncc2Cl)c1] | H | 388.0 | δ 10.18 (s, 1H), 9.34 (s, 1H), 8.80 (s, 1H), 8.04 (s, 1H), 7.76-7.75 (m, 1H), 7.57 (bs, 1H), 7.24-7.21 (m, 2H), 6.43-6.36 (m, 1H), 6.26-6.22 (m, 1H), 5.91 (s, 1H), 5.75 (d, J = 9.6 Hz, 1H), 3.61 (s, 3H). |
| 31 | 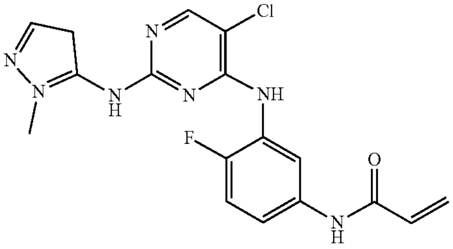 | H | 388.0 | δ 10.13 (s, 1H), 9.04 (s, 1H), 78.86 (s, 1H), 8.08 (s, 1H), 7.73 (s, 1H), 7.51 (s, 1H), 7.19 (s, 1H), 7.08 (s, 1H), 6.43-6.36 (m, 1H), 6.26-6.22 (m, 1H), 5.88 (s, 1H), 5.75 (s, 1H), 3.53 (s, 3 H). |
Scheme 16: Synthesis of N-(3-((5-(benzylamino)-2-((1-methyl-1H-pyrazol-4-yl)amino)pyrimidin-4-yl)amino)phenyl)acrylamide (Compound 32)
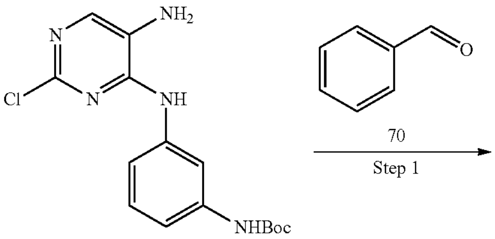
61
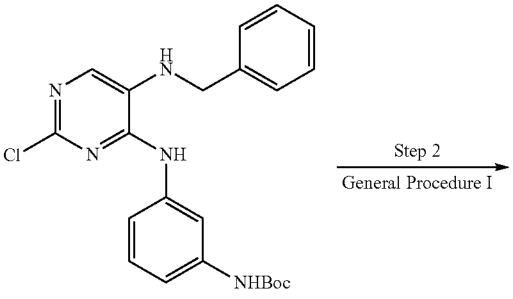
71
-continued
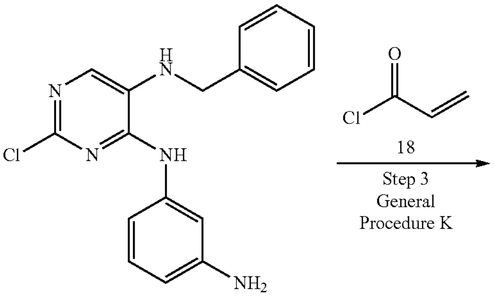
72
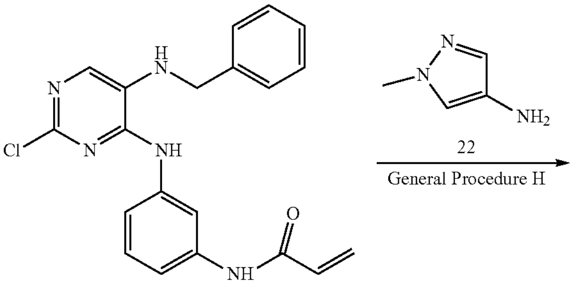
73

-continued

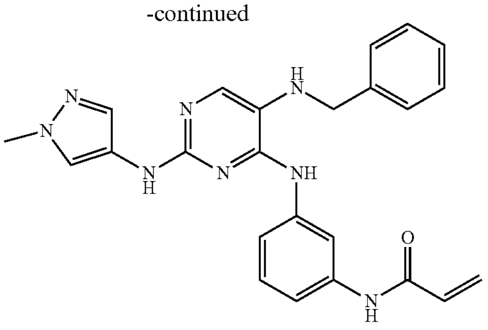

Compound 32

Step 1: Synthesis of tert-butyl (3-((5-(benzylamino)-2-chloropyrimidin-4-yl)amino)phenyl)carbamate (71)

To an ice-cold solution of tert-butyl (3-((5-amino-2-chloropyrimidin-4-yl)amino)phenyl)carbamate (61) (1.5 g, 4.477 mmol) in dichloroethane (15 mL) were added benzaldehyde (70) (570 mg, 5.37 mmol) and sodium tri-acetoxyborohydride (2.8 g, 13.431 mmol) at same temperature under nitrogen atmosphere. The resultant reaction mixture was stirred at room temperature for 16 hours. After completion of reaction, the reaction mixture was diluted with water (100 mL) and extracted with ethyl acetate (3×100 mL). The combined organic layers were washed with brine, dried anhydrous sodium sulfate and concentrated under reduced pressure. The crude was purified over combiflash purifier eluted with 40% ethyl acetate in hexane to get desired product (71) as brown solid (1.1 g, Yield: 57%). MS: $[M+H]^+$ 426.17.

Step 2: Synthesis of N-(3-aminophenyl)-N5-benzyl-2-chloropyrimidine-4,5-diamine (72)

Title compound was prepared in a manner substantially similar to procedure mentioned in General Procedure I to get desired product (72) as off white solid (820 mg, Yield: 97%). MS: $[M+H]^+$ 326.17.

Step 3: Synthesis of N-(3-((5-(benzylamino)-2-chloropyrimidin-4-yl)amino)phenyl)acrylamide (73)

Title compound was prepared in a manner substantially similar to procedure mentioned in General Procedure K. The crude was purified over combiflash elution with 2% methanol in dichloromethane to get desired product (73) as off white solid (260 mg; Yield: 55.7%). MS: $[M+H]^+$ 380.13

Step 4: Synthesis of N-(3-((5-(benzylamino)-2-((1-methyl-1H-pyrazol-4-yl)amino)pyrimidin-4-yl)amino)phenyl)acrylamide (Compound 32)

Title compound was prepared in a manner substantially similar to procedure mentioned in General Procedure H. The crude was purified by prep HPLC purification to get desired product Compound 32 as white solid (40 mg; Yield: 14%). $^1$H-NMR (400 MHz, DMSO-$d_6$): δ 10.12 (bs, 1H), 8.39 (bs, 2H), 7.91 (s, 1H), 7.67 (s, 1H), 7.53-7.54 (m, 1H), 7.43-7.44 (m, 3H), 7.34-7.37 (m, 3H), 7.24-7.27 (m, 3H), 6.42-6.49 (m, 1H), 6.23-6.27 (m, 1H), 5.74 (dd, J=10.0 Hz & 1.6 Hz, 1H), 5.05-5.07 (m, 1H), 4.25 (d, J=6.0 Hz, 2H), 3.65 (s, 3H). LCMS: $[M+H]^+$ 441.28.

Scheme 17: Synthesis of (E)-N-(3-((5-(benzylamino)-2-((1-methyl-1H-pyrazol-4-yl)amino)pyrimidin-4-yl)amino)phenyl)-4-(dimethylamino)but-2-enamide (Compound 33)

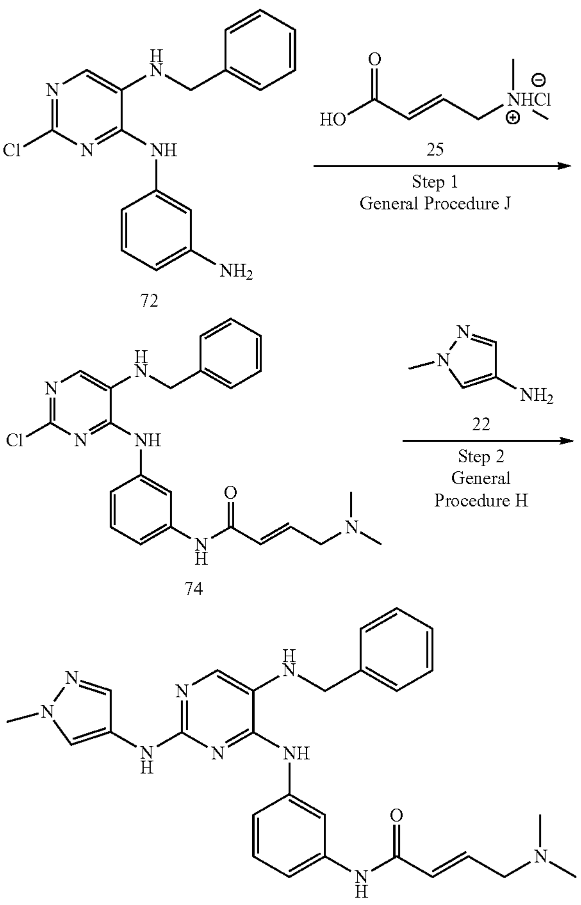

72

74

Compound 33

Step 1: Synthesis of (E)-N-(3-((5-(benzylamino)-2-chloropyrimidin-4-yl)amino)phenyl)-4-(dimethylamino)but-2-enamide (74)

Title compound was prepared in a manner substantially similar to procedure mentioned in General Procedure J to get desired product (74) as off white solid (210 mg; Yield: 40%). MS: $[M+H]^+$ 437.17.

Step 2: (E)-N-(3-((5-(benzylamino)-2-((1-methyl-1H-pyrazol-4-yl)amino)pyrimidin-4-yl)amino)phenyl)-4-(dimethylamino)but-2-enamide (Compound 33)

Title compound was prepared in a manner substantially similar to procedure mentioned in General Procedure H. The crude was purified by prep HPLC purification to get desired product Compound 33 as off white solid (35 mg; Yield: 16%). $^1$H-NMR (400 MHz, DMSO-$d_6$): δ 10.02 (bs, 1H), 8.40 (bs, 2H), 7.90 (s, 1H), 7.67 (s, 1H), 7.51-7.52 (m, 1H), 7.43-7.44 (m, 3H), 7.33-7.37 (m, 3H), 7.24-7.27 (m, 3H), 6.69-6.76 (m, 1H), 6.26 (d, J=15.4 Hz, 1H), 5.04-5.06 (m, 1H), 4.25 (d, J=5.6 Hz, 2H), 3.65 (s, 3H), 3.04 (d, J=5.2 Hz, 2H), 2.17 (s, 6H). LCMS: $[M+H]^+$ 498.30.

Scheme 18: Synthesis of 4-((3-acrylamidophenyl)amino)-2-((1-methyl-1H-pyrazol-4-yl)amino)-N-(1-phenylethyl)pyrimidine-5-carboxamide (Compound 34)

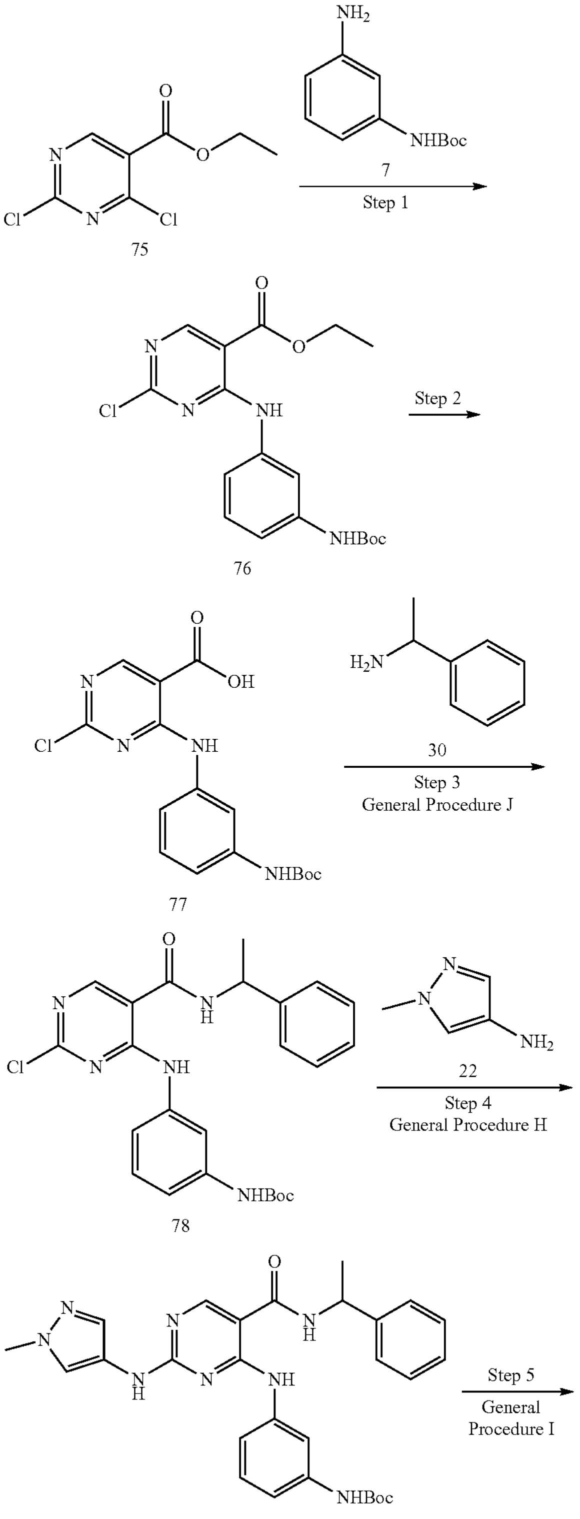

79

-continued

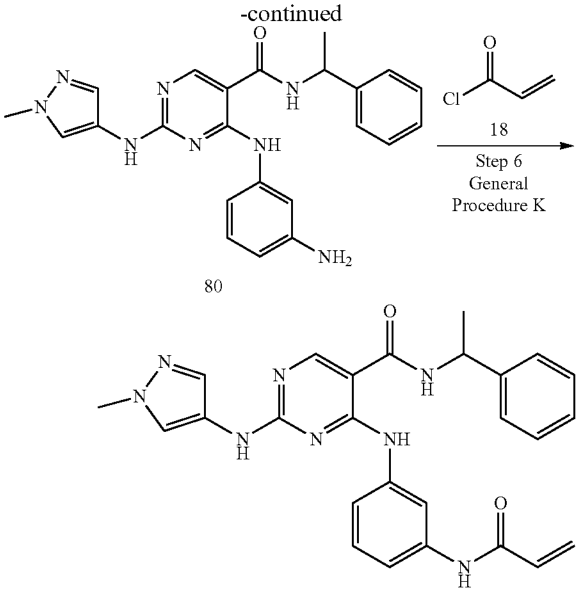

Compound 34

Step 1: Synthesis of ethyl 4-((3-((tert-butoxycarbonyl)amino)phenyl)amino)-2-chloropyrimidine-5-carboxylate (76)

To a solution of ethyl 2,4-dichloropyrimidine-5-carboxylate (75) (3.0 g, 13.56 mmol) in tetrahydrofuran (30 mL) were added N,N-diisopropylethylamine (4.82 mL, 27.02 mmol) and tert-butyl (3-aminophenyl)carbamate (7) (2.82 g, 13.56 mmol) at room temperature. The resultant reaction mixture was heated at 100° C. for 4 hours. After completion of reaction (TLC monitoring), the reaction mixture was diluted with water (100 mL) and extracted with ethyl acetate (3×100 mL). The combined organic layers were washed with brine, dried anhydrous sodium sulfate, filtered and concentrated under reduced pressure to get desired product (76) (4.5 g, Yield: 84.42%). LCMS: $[M+H]^+$ 392.98.

Step 2: Synthesis of 4-((3-((tert-butoxycarbonyl)amino)phenyl)amino)-2-chloropyrimidine-5-carboxylic acid (77)

To an ice-cold solution of ethyl 4-((3-((tert-butoxycarbonyl)amino)phenyl)amino)-2-chloropyrimidine-5-carboxylate (76) (4.5 g, 4.82 mmol) in tetrahydrofuran (50 mL) was added sodium hydroxide (386 mg, 9.65 mmol) in water (10 mL). The resulting reaction mixture was heated at 50° C. for 8 hours. After completion of reaction (TLC monitoring), the mixture was concentrated under reduced pressure. The crude was diluted with ice-cold water (25 mL) and acidified with 1N hydrochloric acid (adjusted the pH~5). The obtained precipitate was filtered and dried under vacuum to get desired product (77) as off white sold (2.6 g; Yield: 63.14%). LCMS: $[M+H]^+$ 364.94.

Step 3: Synthesis of tert-butyl (3-((2-chloro-5-((1-phenylethyl)carbamoyl)pyrimidin-4-yl)amino)phenyl)carbamate (78)

Title compound was prepared in a manner substantially similar to procedure mentioned in General Procedure J to get desired product (78) as off white solid (800 mg; Yield: 66.62%). MS: $[M+H]^+$ 468.17.

Step 4: Synthesis of tert-butyl (3-((2-((1-methyl-1H-pyrazol-4-yl)amino)-5-((1-phenylethyl)carbamoyl)pyrimidin-4-yl)amino)phenyl)carbamate (79)

Title compound was prepared in a manner substantially similar to procedure mentioned in General Procedure H. The crude was purified over combiflash elution with 2% methanol in dichloromethane to get desired product (79) as semi-solid (600 mg; Yield: 61.32%). LCMS: $[M+H]^+$ 529.16.

Step 5: Synthesis of 4-((3-aminophenyl)amino)-2-((1-methyl-1H-pyrazol-4-yl)amino)-N-(1-phenylethyl)pyrimidine-5-carboxamide (80)

Title compound was prepared in a manner substantially similar to procedure mentioned in General Procedure I to get desired product (80) as off white solid (430 mg, Yield: 88.21%). LCMS: $[M+H]^+$ 429.21.

Step 6: Synthesis of 4-((3-acrylamidophenyl)amino)-2-((1-methyl-1H-pyrazol-4-yl)amino)-N-(1-phenylethyl)pyrimidine-5-carboxamide (Compound 34)

Title compound was prepared in a manner substantially similar to procedure mentioned in General Procedure K. The crude was purified by prep HPLC purification to get desired product Compound 34 as off white solid (40 mg; Yield: 14.21%). $^1$H NMR (400 MHz, DMSO-$d_6$): δ 11.15 (bs, 1H), 10.19 (bs, 1H), 9.68 (bs, 1H), 8.73-8.84 (m, 2H), 7.47-7.93 (m, 4H), 7.39-7.41 (m, 2H), 7.29-7.35 (m, 3H), 7.21-7.24 (m, 2H), 6.39-6.46 (m, 1H), 6.22-6.26 (m, 1H), 5.74 (dd, J=10.4 & 2.0 Hz, 1H), 5.12-5.19 (m, 1H) 3.61 (s, 3H), 1.47 (d, J=2.2 Hz, 3H). LCMS: $[M+H]^+$ 483.28.

Scheme 19: Synthesis of (E)-4-((3-(4-dimethylamino)but-2-enamido)phenyl)amino)-2-((1-methyl-1H-pyrazol-4-yl)amino)-N-(1-phenylethyl)pyrimidine-5-carboxamide (Compound 35)

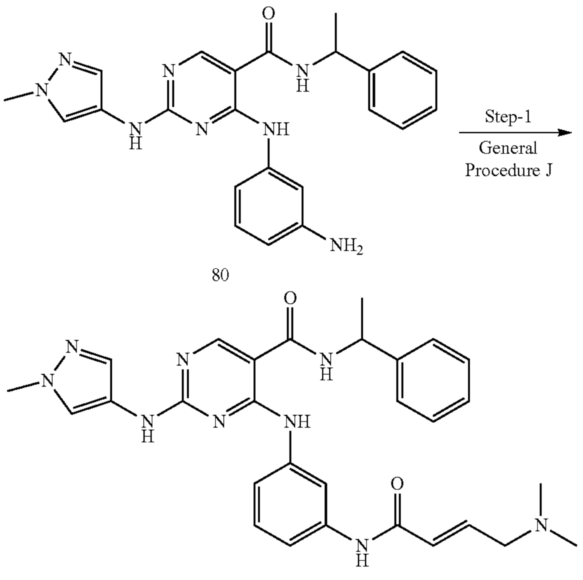

Title compound was prepared in a manner substantially similar to procedure mentioned in General Procedure J. The crude was purified by prep HPLC purification to get desired product Compound 35 as off white solid (48 mg; Yield: 15.23%). $^1$H-NMR (400 MHz, DMSO-$d_6$): δ 11.14 (bs, 1H), 10.13 (bs, 1H), 9.67 (bs, 1H), 8.77-8.79 (m, 2H), 7.86-7.92 (m, 1H), 7.58-7.79 (m, 2H), 7.21-7.41 (m, 8H), 6.72 (s, 1H), 6.26 (s, 1H), 5.14-5.19 (m, 1H) 3.62 (s, 3H), 3.11-3.13 (m, 2H), 2.02 (s, 6H), 1.47 (d, J=2.2 Hz, 3H). LCMS: $[M+H]^+$ 540.40.

Scheme 20: Synthesis of N-(4-fluoro-3-((2-((1-methyl-1H-pyrazol-4-yl)amino)-5-(trifluoromethyl)pyrimidin-4-yl)amino)phenyl)acrylamide (Compound 36)

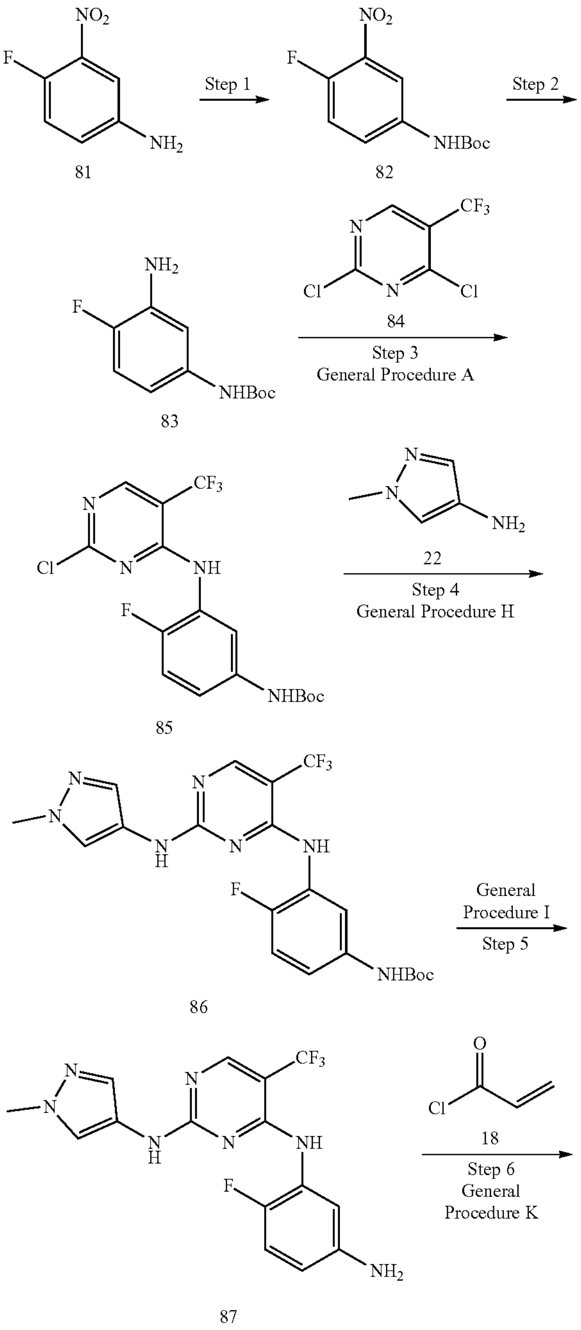

-continued

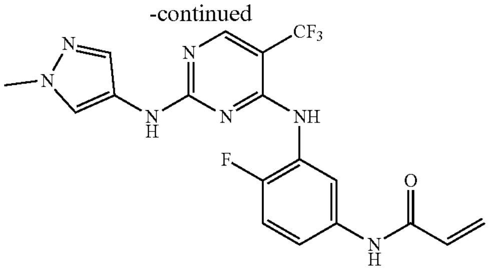

Compound 36

Step 1: Synthesis of tert-butyl (4-fluoro-3-nitrophenyl)carbamate (82)

To a solution of 4-fluoro-3-nitroaniline (81) (10 g, 64.102 mmol) in tert-butanol (50 mL) was added boc-anhydride (13.99 g, 64.102 mmol) at room temperature. The resultant reaction was heated at 80° C. for 16 hours. After completion of reaction (as per TLC monitoring), the mixture was concentrated under reduced pressure. The residue was washed with hexane and dried under vacuum to get desired product (82) as pale yellow solid (14 g; Yield: 85.32%). $^1$H NMR (400 MHz, DMSO-$d_6$): δ 9.9 (s, 1H), 8.36 (s, 1H), 7.76 (d, J=8.0 Hz, 1H), 7.49-7.54 (m, 1H), 1.49 (s, 9H).

Step 2: Synthesis of tert-butyl (3-amino-4-fluorophenyl)carbamate (83)

To a solution of tert-butyl (4-fluoro-3-nitrophenyl)carbamate (82) (14 g, 54.68 mmol) in ethanol (50 mL) was added 10% palladium on carbon (1.4 g, 10% w/w). The resultant reaction was stirred at room temperature for 16 hours under hydrogen atmosphere. After completion of reaction (TLC monitoring), the reaction mixture was filtered and washed with ethyl acetate (200 mL). The combined filtrated was concentrated under reduced pressure to get desired product (83) as off white solid (11 g; Yield: 89.21%). $^1$H NMR (400 MHz, DMSO-$d_6$): δ 9.01 (bs, 1H), 6.60-7.20 (m, 3H), 5.21 (s, 2H), 1.49 (s, 9H). LCMS: $[M+1H]^+$ 227.24.

Step 3: Synthesis of tert-butyl (3-((2-chloro-5-(trifluoromethyl)pyrimidin-4-yl)amino)-4-fluorophenyl) carbamate (85)

Title compound was prepared in a manner substantially similar to procedure mentioned in General Procedure A. The crude was purified over combiflash eluted with 70% ethyl acetate in hexane to get desired product (85) (600 mg; Yield: 21.42%). MS: $[M+H]^+$ 407.08.

Step 4: Synthesis of tert-butyl (4-fluoro-3-((2-((1-methyl-1H-pyrazol-4-yl)amino)-5-(trifluoromethyl) pyrimidin-4-yl)amino)phenyl)carbamate (86)

Title compound was prepared in a manner substantially similar to procedure mentioned in General Procedure H. The crude was purified by combiflash eluted with 1% methanol in dichloromethane to get (86) (300 mg; Yield: 43.47%). MS: $[M+H]^+$ 468.17

Step 5: Synthesis of N4-(5-amino-2-fluorophenyl)-N2-(1-methyl-1H-pyrazol-4-yl)-5-(trifluoromethyl) pyrimidine-2,4-diamine (87)

Title compound was prepared in a manner substantially similar to procedure mentioned in General Procedure I to get desired product (87) (150 mg; Yield: 63.24%). MS: $[M+H]^+$ 368.15

Step 6: N-(4-fluoro-3-((2-((1-methyl-1H-pyrazol-4-yl)amino)-5-(trifluoromethyl)pyrimidin-4-yl)amino) phenyl)acrylamide (Compound 36)

Title compound was prepared in a manner substantially similar to procedure mentioned in General Procedure K. The crude was purified by prep HPLC purification to get Compound 36 as off white solid (20 mg; Yield: 12.62%). $^1$H NMR (400 MHz, DMSO-$d_6$): δ 10.30 (bs, 1H), 9.71 (bs, 1H), 8.82 (bs, 1H), 8.35 (s, 1H), 7.70-7.77 (m, 2H), 7.28-7.42 (m, 1H), 7.10 (s, 1H), 6.89 (s, 1H), 6.37-6.44 (m, 1H), 6.23-6.28 (m, 1H), 5.76 (d, J=8.0 Hz, 1H), 3.50 (s, 3H). LCMS: $[M+H]^+$ 422.23.

Scheme 21: Synthesis of N-(4-fluoro-3-((2-((1-methyl-1H-pyrazol-4-yl)amino)-5-(4-(trifluoromethyl)phenyl)pyrimidin-4-yl)amino)phenyl)acrylamide (Compound 37)

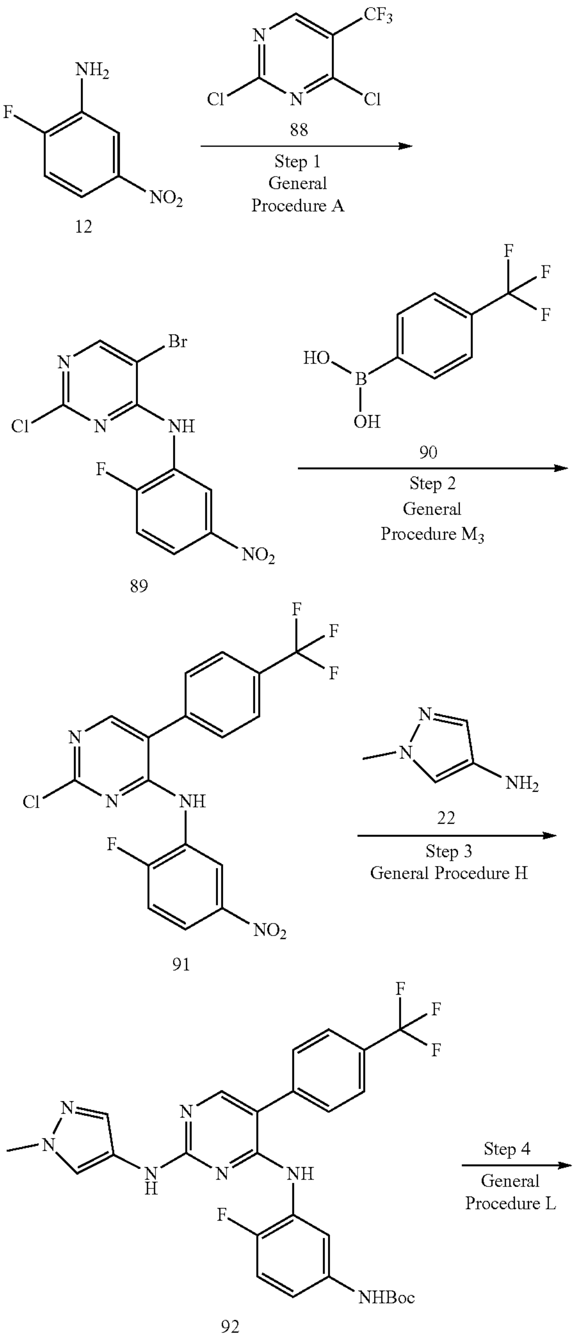

-continued

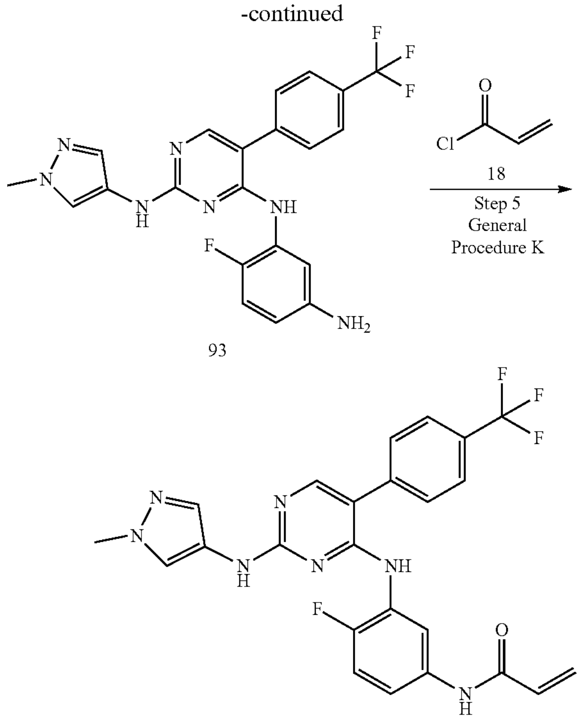

93

18

Compound 37

Step 1: Synthesis of 5-bromo-2-chloro-N-(2-fluoro-5-nitrophenyl)pyrimidin-4-amine (89)

Title compound was prepared in a manner substantially similar to procedure mentioned in General Procedure A. The crude was purified by combiflash eluted with 40% ethyl acetate in hexane to get (89) as pale yellow solid (1.3 g, Yield: 44.24%). MS: $[M+H]^+$ 346.97.

Step 2: Synthesis of 2-chloro-N-(2-fluoro-5-nitrophenyl)-5-(4-(trifluoromethyl)phenyl)pyrimidin-4-amine (91)

Title compound was prepared in a manner substantially similar to procedure mentioned in General Procedure $M_3$. The crude was purified by combiflash eluted with 35% ethyl acetate in hexane to get desired product (91) as light yellow solid (700 mg; Yield: 50.12%). MS: $[M+H]^+$ 413.10

Step 3: Synthesis of N4-(2-fluoro-5-nitrophenyl)-N2-(1-methyl-1H-pyrazol-4-yl)-5-(4-(trifluoromethyl)phenyl)pyrimidine-2,4-diamine (92)

Title compound was prepared in a manner substantially similar to procedure mentioned in General Procedure H. The crude was purified by combiflash eluted with 1% methanol in dichloromethane to get desired product (92) as pale yellow solid (500 mg; Yield: 70.24%). MS: $[M+H]^+$ 474.09

Step 4: Synthesis of N4-(5-amino-2-fluorophenyl)-N2-(1-methyl-1H-pyrazol-4-yl)-5-(4-(trifluoromethyl)phenyl)pyrimidine-2,4-diamine (93)

Title compound was prepared in a manner substantially similar to procedure mentioned in General Procedure L to get (93) as semi solid (350 mg; Yield: 74.78%). MS: $[M+H]^+$ 444.11

Step 5: Synthesis of N-(4-fluoro-3-((2-((1-methyl-1H-pyrazol-4-yl)amino)-5-(4-(trifluoromethyl)phenyl)pyrimidin-4-yl)amino)phenyl)acrylamide (Compound 37)

Title compound was prepared in a manner substantially similar to procedure mentioned in General Procedure K. The crude was purified by Prep HPLC to get Compound 37 as off white solid (30 mg, Yield: 13.33%). $^1$H NMR (400 MHz, DMSO-$d_6$): δ 10.21 (bs, 1H), 9.24 (bs, 1H), 8.53 (bs, 1H), 7.99 (s, 1H), 7.71-7.81 (m, 5H), 7.57 (s, 1H), 7.08-7.16 (m, 3H), 6.37-6.44 (m, 1H), 6.21-6.26 (m, 1H), 5.74 (d, J=8.4 Hz, 1H), 3.54 (s, 3H). LCMS: $[M+H]^+$498.35.

TABLE 5

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 38 | 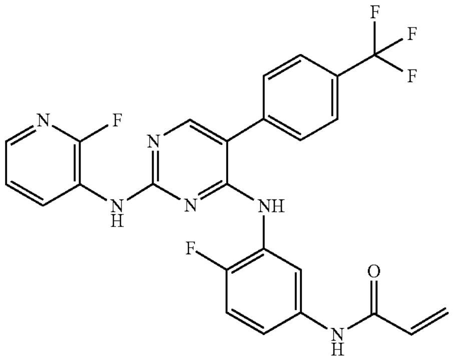 [SMILES: C=CC(=O)Nc1ccc(F)c(Nc2nc(Nc3cccnc3F)ncc2-c2ccc(C(F)(F)F)cc2)c1] | K | 513.3 | δ 10.11 (s, 1H), 8.85 (s, 1H), 8.58 (s, 1H), 8.17 (t, J = 18.0 Hz, 1H), 8.05 (s, 1H), 7.82-7.72 (m, 6H), 7.44 (bs, 1H), 7.22 (t, J = 10.0 Hz, 1H), 6.98 (bs, 1H), 6.41-6.35 (m, 1H), 6.22 (d, J = 16.8 Hz, 1H), 5.73 (d, J = 10.0 Hz, 1H). |

TABLE 5-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 39 | 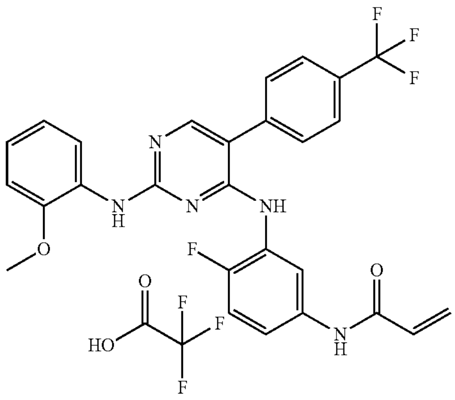 | $K_1$ | 524.1 | δ 10.25 (s, 1H), 9.37 (s, 1H), 8.79 (s, 1H), 8.11 (s, 1H), 7.89 (d, J = 8.4 Hz, 3H), 7.78-7.71 (m, 3H), 7.54-7.50 (m, 1H), 7.33-7.28 (m, 1H), 7.03-6.98 (m, 3H), 6.68-6.65 (m, 1H), 6.45-6.38 (m, 1H), 6.27-6.22 (m, 1H), 5.76 (dd, J = 8.0 Hz, 1H), 3.84 (s, 3H). |
| 40 | 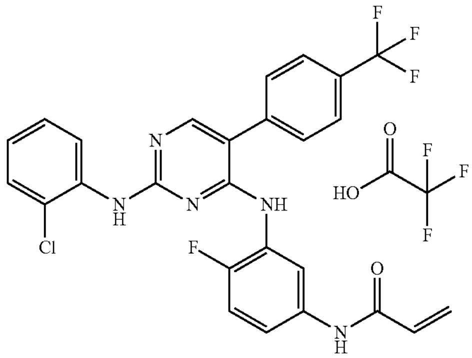 | $K_1$ | 528.1 | δ 10.15 (s, 1H), 8.88 (s, 1H), 8.50 (s, 1H), 8.07 (s, 1H), 7.87-7.82 (m, 4H), 7.75 (d, J = 8.0 Hz, 2H), 7.47-7.41 (m, 3H), 7.24 (t, J = 12.0 Hz, 1H), 7.10-7.01 (m, 2H), 6.40 (q, J = 6.8 Hz, 1H), 6.24 (dd, J = 16.8, 1.6 Hz, 1H), 5.76 (dd, J = 10.0 Hz, 1.6 Hz, 1H) |
| 41 | 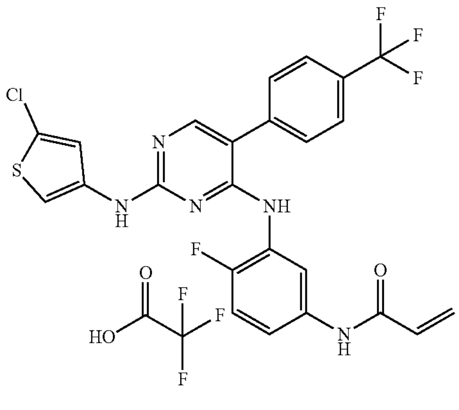 | $K_1$ | 534.1 | δ 10.18 (s, 1H), 9.70 (s, 1H), 8.62 (s, 1H), 8.05 (s, 1H), 7.83-7.73 (m, 5H), 7.52-7.48 (m, 1H), 7.24 (d, J = 9.6 Hz, 1H), 7.06 (s, 1H), 6.85 (bs, 2H), 6.38-6.45 (m, 1H), 6.24 (dd, J = 16.0 Hz, 2.0 Hz, 1H), 5.75 (dd, J = 8.4 Hz, 1.6 Hz, 1H) |
| 42 | 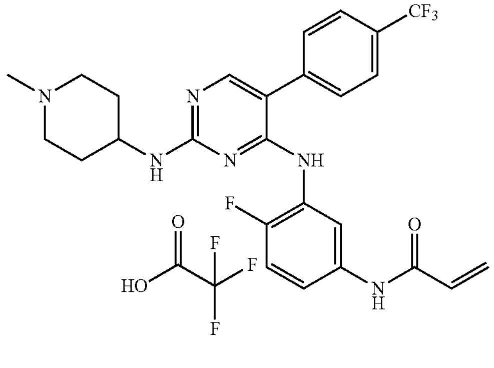 | K | 515.2 | 10.2 (s, 1H), 9.2 (s, 2H), 7.96 (s, 1H), 7.84 (s, 2H), 7.69 (d, J = 7.2 Hz, 2H), 6.95-7.37 (m, 4H), 6.38 (q, J = 10.4 Hz, 1H), 6.23 (d, J = 16.4 Hz, 1H), 5.76 (d, J = 9.2 Hz, 1H), 3.6 (s, 1H), 3.40 (bs, 1H), 3.20 (s, 2H), 2.90-2.65 (m, 4H), 2.03 (d, J = 13.6 Hz, 1H), 2.89 (s, 1H), 1.62 (bs, 2H). |

TABLE 5-continued
The following compounds were prepared using the procedures described above:
| Cmpd. No. | Structure | General Procedure | LCMS [M + H] | $^1$H-NMR (400 MHz, DMSO-$d_6$) |
|---|---|---|---|---|
| 43 | 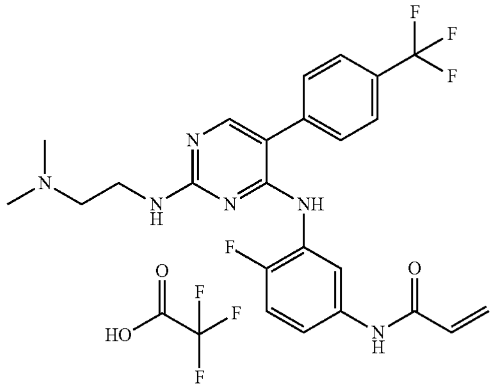 | K | 488.97 | δ 10.10 (s, 1H), 8.14 (s, 1H), 8.14-7.97 (m, 1H), 7.88-7.97 (m, 2H), 7.77-7.79 (m, 2H), 7.66-7.68 (m, 2H), 7.37 (bs, 1H), 7.12-7.17 (m, 1H), 6.77 (m, 1H), 6.36-6.43 (m, 1H), 6.21-6.25 (m, 1H), 5.75 (d, J = 10.0 Hz, 1H), 3.29-3.22 (m, 2H), 2.30-2.26 (m, 2H), 2.05 (bs, 6H). |
| 44 | 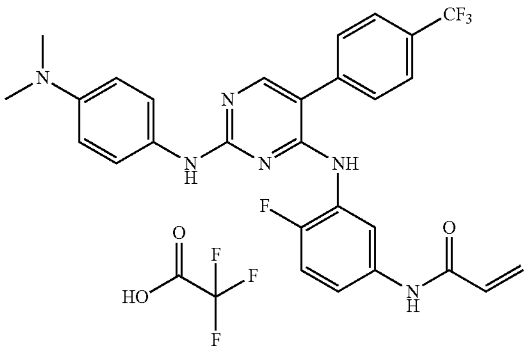 | K | 536.94 | δ 10.25 (s, 1H), 9.80 (s, 1H), 9.24 (s, 1H), 7.98 (bs, 1H), 7.86-7.88 (m, 2H), 7.74-7.80 (m, 3H), 7.53-7.55 (m, 1H), 7.29-7.33 (m, 3H), 7.00-7.20 (m, 1H), 6.77 (bs, 2H), 6.37-6.44 (m, 1H), 6.22-6.26 (m, 1H), 5.77 (d, J = 10.0 Hz, 1H), 2.91 (s, 6H) |
| 45 | 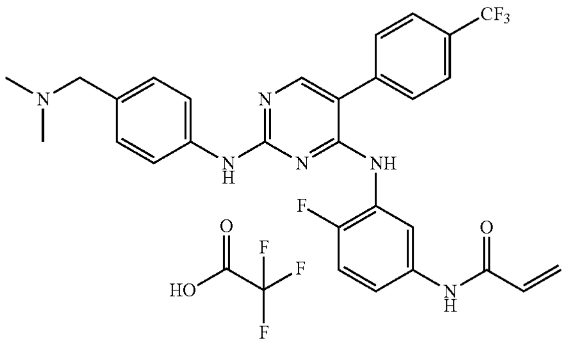 | K | 551.3 | δ 10.21 (s, 1H), 9.64 (s, 1H), 8.77 (s, 1H), 8.09 (bs, 1H), 7.83-7.85 (m, 2H), 7.74-7.76 (m, 2H), 7.68-7.70 (m, 1H), 7.58-7.60 (m, 3H), 7.17-7.29 (m, 4H), 6.36-6.43 (m, 1H), 6.21-6.26 (m, 1H), 5.77 (d, J = 10.0 Hz, 1H), 4.11-4.13 (m, 2H), 2.67 (m, 6H) |
| 46 | 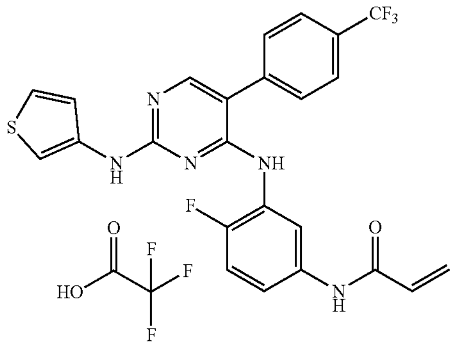 | K | 499.91 | δ 10.23 (s, 1H), 10.04 (bs, 1H), 8.91-8.99 (m, 1H), 8.05 (s, 1H), 7.84-7.86 (m, 3H), 7.74-7.76 (m, 2H), 7.49-7.52 (m, 1H), 7.24-7.32 (m, 2H), 7.04-7.24 (m, 3H), 6.37-6.43 (m, 1H), 6.21-6.26 (m, 1H), 5.77 (d, J = 10.0 Hz, 1H) |

Scheme 22: Synthesis of N-(3-((5-(1-(N-benzylacetamido)ethyl)-2-((1-methyl-1H-pyrazol-4-yl)amino)pyrimidin-4-yl)amino)phenyl)acrylamide (Compound 47)

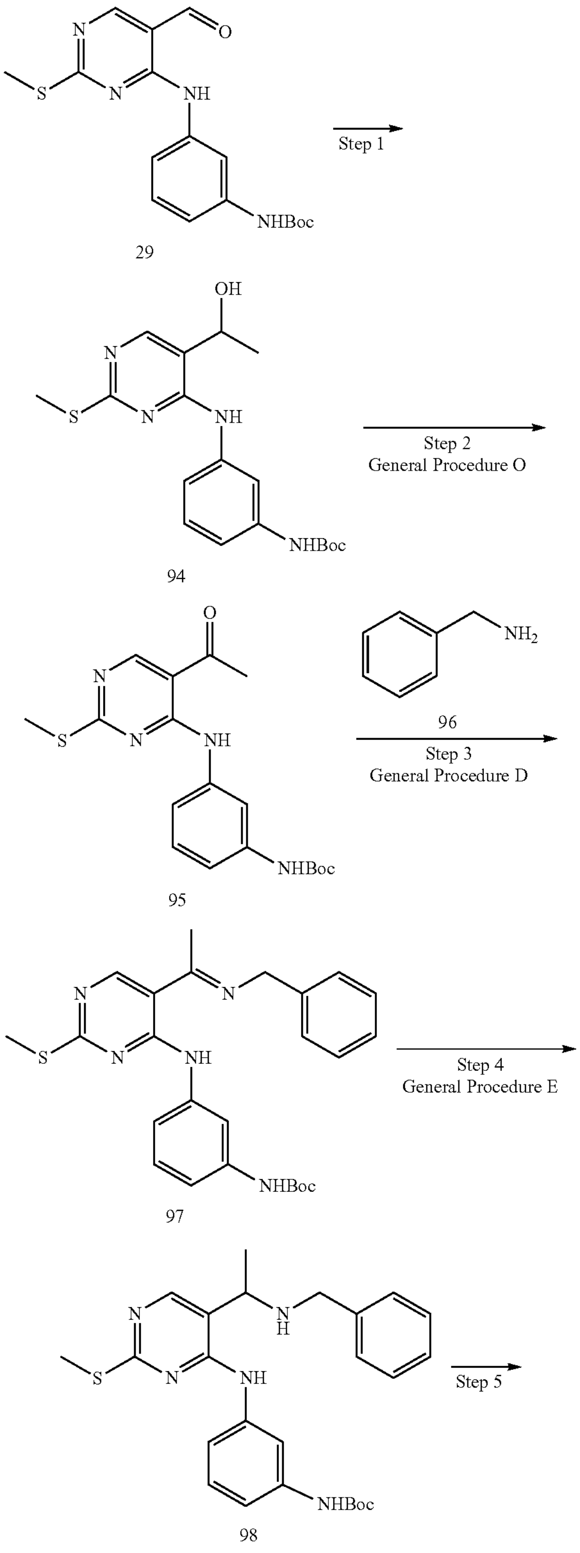

-continued

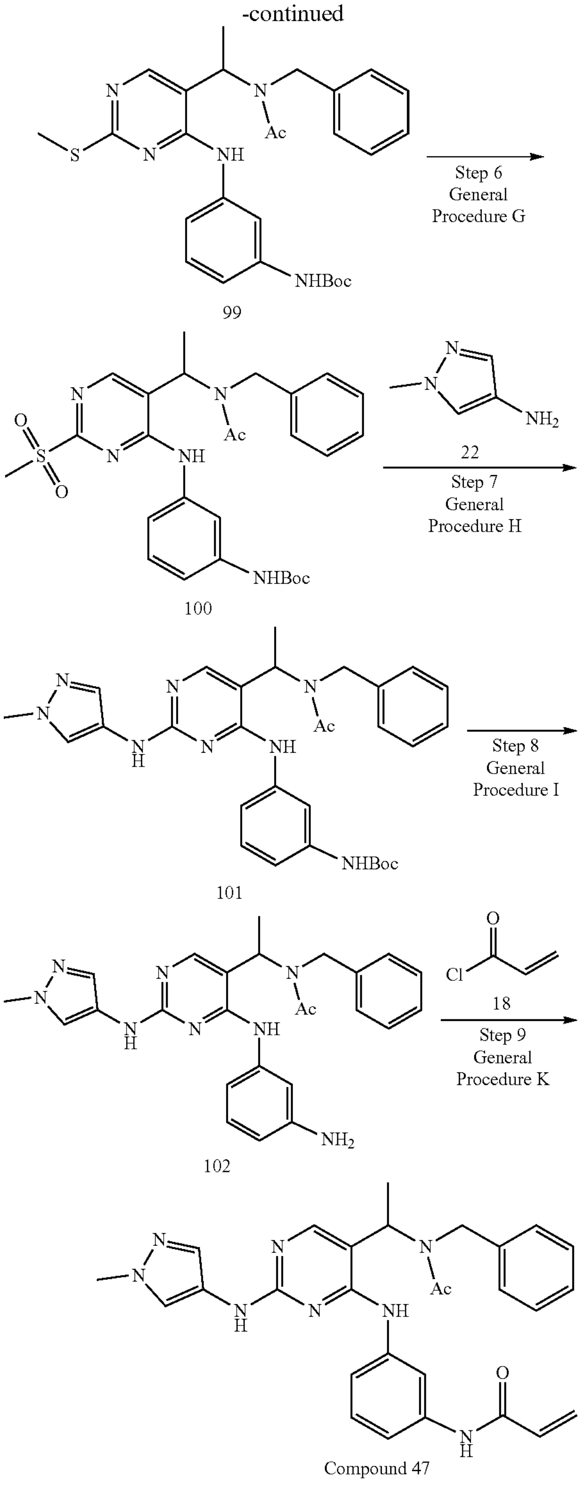

Step 1: Preparation tert-butyl (3-((5-(1-hydroxyethyl)-2-(methylthio)pyrimidin-4-yl)amino)phenyl) carbamate (94)

To a solution of tert-butyl (3-((5-formyl-2-(methylthio) pyrimidin-4-yl)amino)phenyl)carbamate (29) (8.0 g, 22.22 mmol) in tetrahydrofuran (150 mL) was cooled at −78° C., followed by addition of methyl magnesium bromide (3.0 M in diethyl ether, 22.22 mL, 66.66 mmol). The resultant reaction mixture was stirred at room temperature for 16 hours. After completion of reaction (monitored by TLC), the reaction mixture was quenched with saturated solution of ammonium chloride (100 mL) and extracted with dichloromethane (3×100 mL). The combined organic layers were washed with brine, dried over anhydrous sodium sulfate, filtered and concentrated under reduced pressure. The crude was purified over silica gel (100-200 mesh) elution with 40-50% ethyl acetate in hexane, desired fractions were concentrated to dryness to get tert-butyl (3-((5-(1-hydroxyethyl)-2-(methylthio)pyrimidin-4-yl)amino)phenyl)carbamate (94) as an off white solid (4.0 g; Yield: 48%). MS: $[M+H]^+$ 377.43.

Step 2: Synthesis of tert-butyl (3-((5-acetyl-2-(methylthio)pyrimidin-4-yl)amino)phenyl)carbamate (95)

Title compound was prepared in a manner substantially similar to procedure mentioned in General Procedure O to get the tert-butyl (3-((5-acetyl-2-(methylthio)pyrimidin-4-yl)amino)phenyl)carbamate (95) as a light brown solid (1.5 g; Yield: 60%). MS: $[M+H]^+$ 375.42.

Step 3: Preparation tert-butyl (E)-(3-((5-(1-(benzylimino)ethyl)-2-(methylthio)pyrimidin-4-yl)amino)phenyl)carbamate (97)

Title compound was prepared in a manner substantially similar to procedure mentioned in General Procedure D to get desired product (97) as off white solid (1.0 g; Yield: 58%). MS: $[M+H]^+$ 464.25.

Step 4: Synthesis of tert-butyl (3-((5-(1-(benzylamino)ethyl)-2-(methylthio)pyrimidin-4-yl)amino)phenyl)carbamate (98)

Title compound was prepared in a manner substantially similar to procedure mentioned in General Procedure E. The crude obtained was purified over silica gel (100-200 mesh), eluted with 4-5% methanol in dichloromethane, desired fractions were concentrated under reduced pressure to afforded tert-butyl (3-((5-(1-(benzylamino)ethyl)-2-(methylthio)pyrimidin-4-yl)amino)phenyl)carbamate (98) as a pale yellow solid (400 mg; Yield: 40%). MS: $[M+H]^+$ 466.30.

Step 5: Synthesis of tert-butyl (3-((5-(1-(N-benzylacetamido)ethyl)-2-(methylthio)pyrimidin-4-yl)amino)phenyl)carbamate (99)

Title compound was prepared in a manner substantially similar to procedure mentioned in General Procedure C. The crude was purified over silica gel (100-200 mesh) eluted with 3% methanol in dichloromethane, desired fractions were concentrated under reduced pressure to get tert-butyl (3-((5-(1-(N-benzylacetamido)ethyl)-2-(methylthio)pyrimidin-4-yl)amino)phenyl)carbamate (99) as light brown solid. (220 mg; Yield: 50.45%). MS: $[M+H]^+$ 508.27.

Step 6: Synthesis of tert-butyl (3-((5-(1-(N-benzylacetamido)ethyl)-2-(methylsulfonyl)pyrimidin-4-yl)amino)phenyl)carbamate (100)

Title compound was prepared in a manner substantially similar to procedure mentioned in General Procedure G to get desired product (100) as off white solid (130 mg; Yield: 61%). MS: $[M+H]^+$ 540.06.

Step 7: Synthesis of tert-butyl (3-((5-(1-(N-benzylacetamido)ethyl)-2-((1-methyl-11H-pyrazol-4-yl)amino)pyrimidin-4-yl)amino)phenyl)carbamate (101)

Title compound was prepared in a manner substantially similar to procedure mentioned in General Procedure H to get tert-butyl (3-((5-(1-(N-benzylacetamido)ethyl)-2-((1-methyl-1H-pyrazol-4-yl)amino)pyrimidin-4-yl)amino)phenyl)carbamate (101) as light brown solid (100 mg; 74.6%). MS: $[M+H]^+$ 557.41.

Step 8: Synthesis of N-(1-(4-((3-aminophenyl)amino)-2-((1-methyl-1H-pyrazol-4-yl)amino)pyrimidin-5-yl)ethyl)-N-benzylacetamide (102)

Title compound was prepared in a manner substantially similar to procedure mentioned in General Procedure I to get N-(1-(4-((3-aminophenyl)amino)-2-((1-methyl-1H-pyrazol-4-yl)amino)pyrimidin-5-yl)ethyl)-N-benzylacetamide (102) as TFA salt as light brown solid. (100 mg; Yield: 98%). MS: $[M-H]^-$ 455.33.

Step 9: Synthesis of N-(3-((5-(1-(N-benzylacetamido)ethyl)-2-((1-methyl-1H-pyrazol-4-yl)amino)pyrimidin-4-yl)amino)phenyl)acrylamide (Compound 47)

Title compound was prepared in a manner substantially similar to procedure mentioned in General Procedure K. The crude was purified by prep-HPLC purification to get Compound 47 as off white solid (6.0 mg, 6.7%). $^1$H NMR (400 MHz, DMSO-$d_6$): δ 10.27 (s, 1H), 9.61 (bs, 1H), 7.87-7.94 (m, 2H), 7.55-7.57 (m, 2H), 7.10-7.37 (m, 8H), 6.45-6.51 (m, 1H), 6.24 (d, J=16.8 Hz, 1H), 5.96-6.01 (m, 1H), 5.76 (d, J=10.4 Hz, 1H), 4.60 (s, 2H), 3.66 (s 3H), 2.53 (s, 1H), 2.02 (s, 3H), 1.50 (d, J=6.8 Hz, 3H). LCMS: $[M+H]^+$ 511.37.

Scheme 23: Synthesis of N-(3-((5-((N-benzylacetamido)methyl)-2-((1-methyl-1H-pyrazol-4-yl)amino)pyrimidin-4-yl)amino)phenyl)acrylamide (Compound 48)

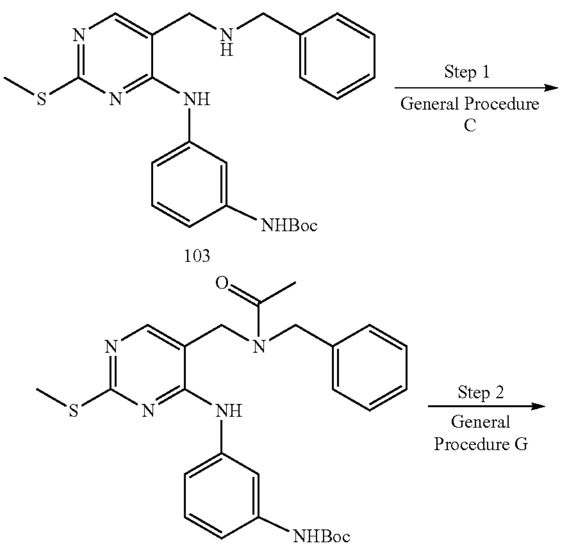

104

-continued

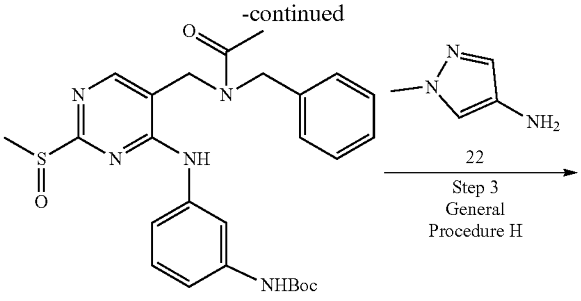

105

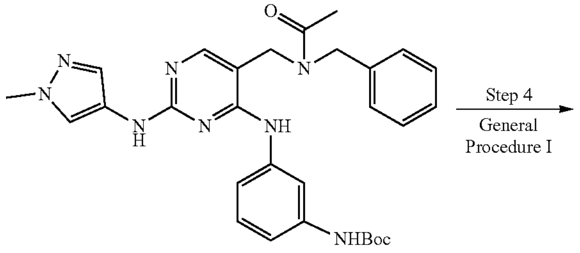

106

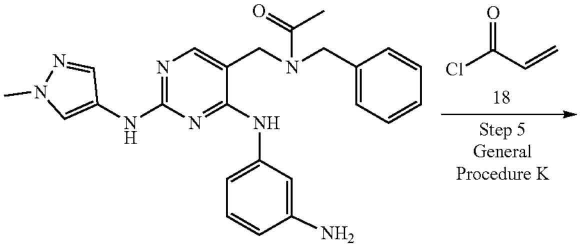

107

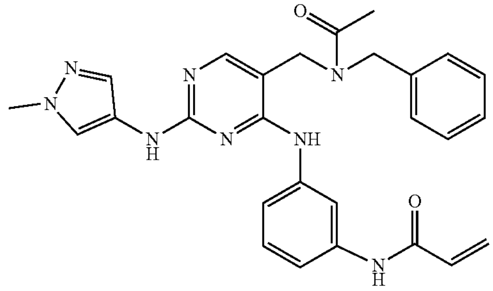

Compound 48

Step 1: Synthesis of tert-butyl (3-((5-((N-benzylacetamido)methyl)-2-(methylthio)pyrimidin-4-yl) amino)phenyl)carbamate (104)

Title compound was prepared in a manner substantially similar to procedure mentioned in General Procedure C to afforded tert-butyl (3-((5-((N-benzylacetamido)methyl)-2-(methylthio)pyrimidin-4-yl)amino)phenyl)carbamate (104) as a brown solid (700 mg, quantitative yield). MS: $[M+H]^+$ 494.37.

Step 2: Synthesis of tert-butyl (3-((5-((N-benzylacetamido)methyl)-2-(methylsulfinyl)pyrimidin-4-yl) amino)phenyl)carbamate (105)

Title compound was prepared in a manner substantially similar to procedure mentioned in General Procedure G afforded desired product (105) as an off white solid (650 mg; Yield: 90%). MS: $[M+H]^+$ 510.34.

Step 3: Synthesis of tert-butyl (3-((5-((N-benzylacetamido)methyl)-2-((1-methyl-1H-pyrazol-4-yl) amino)pyrimidin-4-yl)amino)phenyl)carbamate (106)

Title compound was prepared in a manner substantially similar to procedure mentioned in General Procedure H afforded desired product (106) as off white solid (650 mg, Yield: 92%). MS: $[M+H]^+$ 543.18.

Step 4: Synthesis of N-((4-((3-aminophenyl)amino)-2-((1-methyl-1H-pyrazol-4-yl)amino)pyrimidin-5-yl) methyl)-N-benzylacetamide (107)

Title compound was prepared in a manner substantially similar to procedure mentioned in General Procedure I afforded desired product (107) as off white solid (450 mg; Yield: 94.9%). MS: $[M+H]^+$ 443.19

Step 5: Preparation of N-(3-((5-((N-benzylacetamido)methyl)-2-((1-methyl-1H-pyrazol-4-yl) amino)pyrimidin-4-yl)amino)phenyl)acrylamide (Compound 48)

Title compound was prepared in a manner substantially similar to procedure mentioned in General Procedure K. The final compound was purified by prep HPLC purification to get the N-(3-((5-((N-benzylacetamido)methyl)-2-((1-methyl-1H-pyrazol-4-yl)amino)pyrimidin-4-yl)amino)phenyl)acrylamide (Compound 48) as off white solid (30 mg; Yield: 15%). $^1$H-NMR (400 MHz, DMSO $d_6$): δ 10.15 (bs, 1H), 9.50 (bs, 1H), 9.01 (bs, 1H), 7.87 (s, 1H), 7.65 (s, 1H), 7.62 (s, 1H), 7.53 (d, J=7.2 Hz, 1H), 7.40-7.36 (m, 4H), 7.31-7.27 (m, 3H), 7.24 (d, J=7.6 Hz, 1H), 6.47 (d, J=16.8 Hz, 1H), 6.23 (d, J=1.6 Hz, 1H), 5.74 (d, J=1.6 Hz, 1H), 4.62 (s, 2H), 4.37 (s, 2H), 3.68 (s, 3H), 2.12 (s, 3H). LCMS: $[M+H]^+$ 497.31.

Scheme 24: Synthesis of 4-((5-acrylamido-2-fluorophenyl)amino)-N-methy-2-((1-methyl-1H-pyrazol-4-yl)amino)-N-phenylpyrimidine-5-carboxamide (Compound 49)

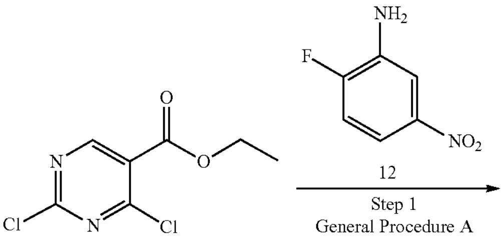

75

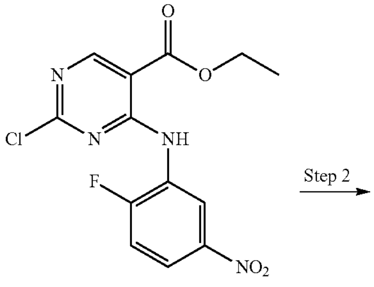

108

-continued

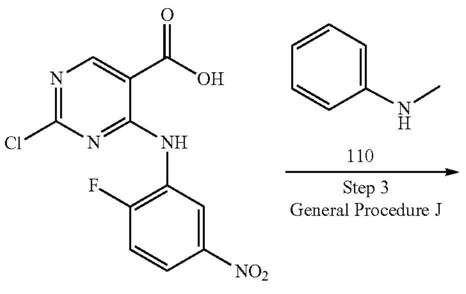

109

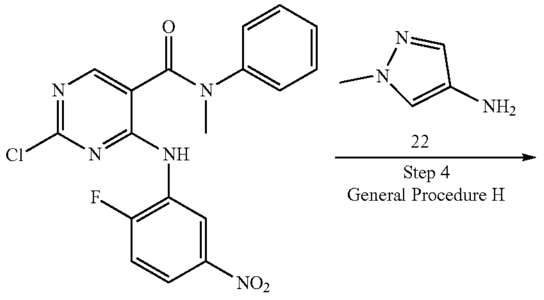

111

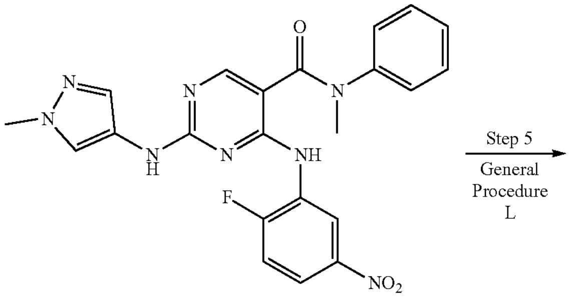

112

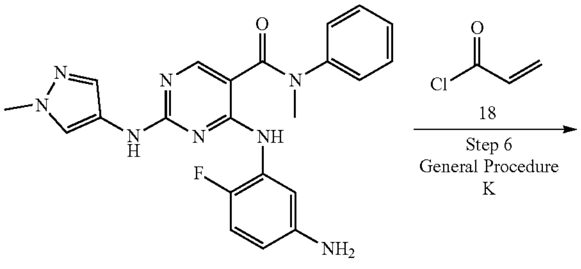

113

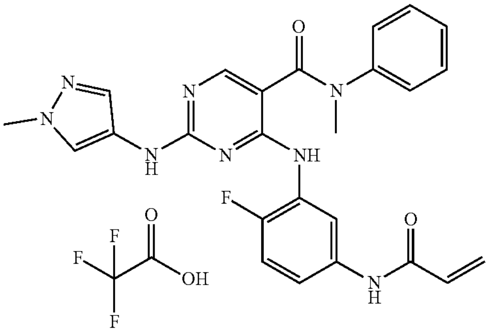

Compound 49

Step 1: Synthesis of ethyl 2-chloro-4-((2-fluoro-5-nitrophenyl)amino)pyrimidine-5-carboxylate (108)

Title compound was prepared in a manner substantially similar to procedure mentioned in General Procedure A. The crude was purified by column chromatography on silica gel (100-200 mesh) using 20-25% ethyl acetate in hexane as eluent to afford ethyl 2-chloro-4-((2-fluoro-5-nitrophenyl)amino)pyrimidine-5-carboxylate (108) as a brown solid (1.6 g, Yield: 15.78%). MS: $[M+H]^+$ 341.04.

Step 2: Synthesis of 2-chloro-4-((2-fluoro-5-nitrophenyl)amino)pyrimidine-5-carboxylic acid (109)

To an ice-cold solution of ethyl 2-chloro-4-[(2-fluoro-5-nitrophenyl)amino]pyrimidine-5-carboxylate (108) (800 mg, 2.35 mmol) in tetrahydrofuran (10 mL) and water (2.00 mL) was added lithium hydroxide mono hydrate (246 mg, 5.87 mmol). The resulting reaction mixture was stirred at room temperature for 2 hours. After completion of reaction (TLC monitoring), the reaction mass was concentrated under reduced pressure. The crude was diluted with ice-cold water and adjust pH~4 using 1N-hydrochloric acid. The resulting precipitates was filtered and dried under vacuum to get the 2-chloro-4-((2-fluoro-5-nitrophenyl)amino)pyrimidine-5-carboxylic acid (109) as off white solid (720 mg; Yield: 98%). LCMS: $[M-H]^-$ 311.26.

Step 3: Synthesis of 2-chloro-4-((2-fluoro-5-nitrophenyl)amino)-N-methyl-N-phenylpyrimidine-5-carboxamide (111)

Title compound was prepared in a manner substantially similar to procedure mentioned in General Procedure J to afford 2-chloro-4-((2-fluoro-5-nitrophenyl)amino)-N-methyl-N-phenylpyrimidine-5-carboxamide (111) as off white solid (150 mg; Yield: 20%). LCMS: $[M+H]^+$ 401.98.

Step 4: Synthesis of 4-((2-fluoro-5-nitrophenyl)amino)-N-methyl-2-((1-methyl-1H-pyrazol-4-yl)amino)-N-phenylpyrimidine-5-carboxamide (112)

Title compound was prepared in a manner substantially similar to procedure mentioned in General Procedure H. The residue was purified by combiflash, elution with 60% ethyl acetate in hexane to get desired product (112) as off white solid. (300 mg, Yield: 52.13%). LCMS: $[M+H]^+$ 463.27.

Step 5: Synthesis of 4-((5-amino-2-fluorophenyl)amino)-N-methyl-2-((1-methyl-1H-pyrazol-4-yl)amino)-N-phenylpyrimidine-5-carboxamide (113)

Title compound was prepared in a manner substantially similar to procedure mentioned in General Procedure L to get 4-((5-amino-2-fluorophenyl)amino)-N-methyl-2-((1-methyl-1H-pyrazol-4-yl)amino)-N-phenylpyrimidine-5-carboxamide (113) as light green solid (220 mg; Yield: 48.62%). MS: $[M+H]^+$ 433.20.

Step 6: Synthesis of 4-((5-acrylamido-2-fluorophenyl)amino)-N-methyl-2-((1-methyl-1H-pyrazol-4-yl)amino)-N-phenylpyrimidine-5-carboxamide (Compound 49)

Title compound was prepared in a manner substantially similar to procedure mentioned in General Procedure K. The residue was purified by prep HPLC purification to get 4-((5-acrylamido-2-fluorophenyl)amino)-N-methyl-2-((1-methyl-1H-pyrazol-4-yl)amino)-N-phenylpyrimidine-5-carboxamide as off white solid (Compound 49) as off white solid (10 mg, Yield: 8%). $^1$H-NMR (400 MHz, DMSO-$d_6$): δ 10.25 (bs, 1H), 9.61 (bs, 1H), 9.48 (s, 1H), 7.94 (bs, 1H), 7.68 (s, 1H), 7.58 (s, 1H), 7.35-7.39 (m, 2H), 7.31 (d, J=6.8 Hz, 3H), 7.23 (d, J=7.2 Hz, 2H), 7.15 (s, 1H), 6.43 (d, J=16.4 Hz, 1H), 6.25 (d, J=17.6 Hz, 1H), 5.77 (d, J=11.6 Hz, 1H), 3.56 (s, 3H), 3.37 (s, 3H). LCMS: $[M+H]^+$ 487.35.

Scheme 25: Synthesis of N-(4-((5-acrylamido-2-fluorophenyl)amino)-2-((1-methyl-1H-pyrazol-4-yl)amino)pyrimidin-5-yl)benzamide (Compound 50)

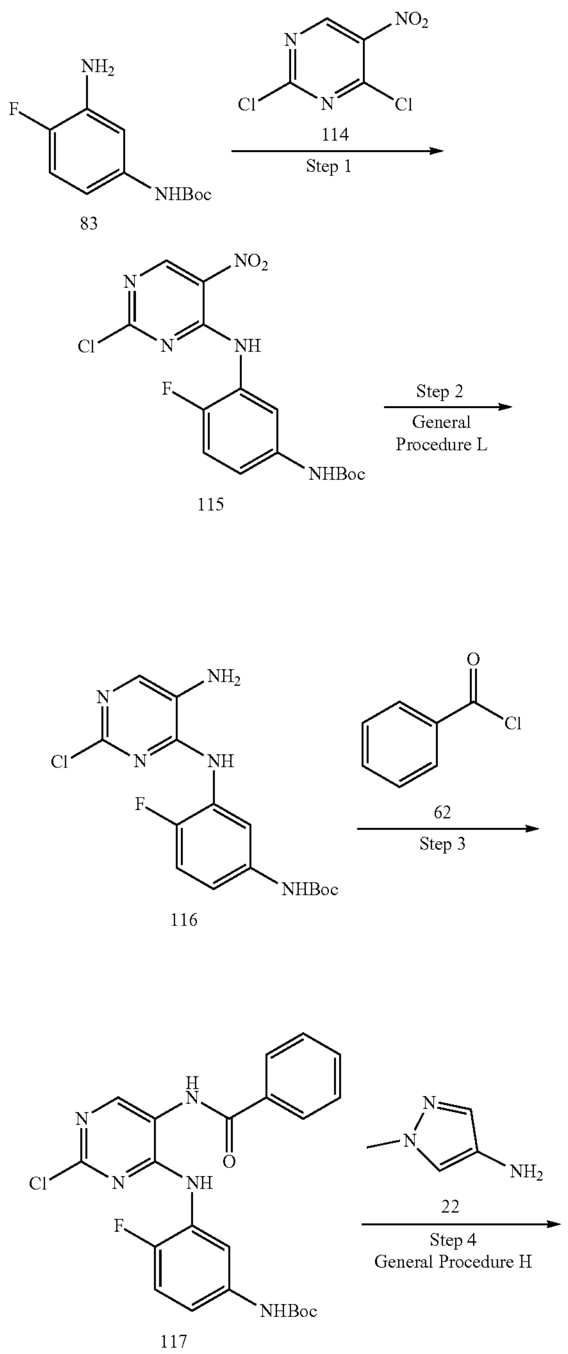

-continued

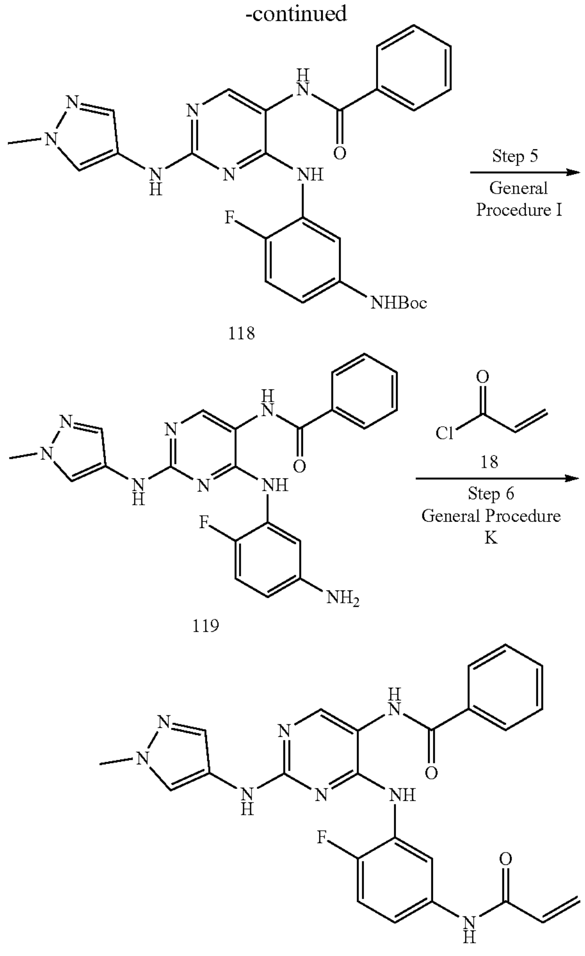

Compound 50

Step 1: Synthesis of tert-butyl (3-((2-chloro-5-nitropyrimidin-4-yl)amino)-4-fluorophenyl)carbamate (115)

To an ice-cold solution of tert-butyl (3-amino-4-fluorophenyl)carbamate (83) (5.0 g, 22.12 mmol) in tetrahydrofuran (50 mL) was added N,N-diisopropylethylamine (7.82 mL, 44.24 mmol) then 2,4-dichloro-5-nitropyrimidine (114) (4.24 g, 22.12 mmol). The resultant reaction mixture was stirred at room temperature for 1 hour. The progress of reaction was monitored by TLC, after completion of reaction mixture diluted with water (100 mL) and extracted with ethyl acetate (3×100 mL). The combined organics washed with brine, dried anhydrous sodium sulfate, filtered and concentrated under reduced pressure to get tert-butyl (3-((2-chloro-5-nitropyrimidin-4-yl)amino)-4-fluorophenyl)carbamate (115) (6.1 g, Yield: 60.24%), MS: $[M+H]^+$ 384.12.

Step 2: Synthesis of tert-butyl (3-((5-amino-2-chloropyrimidin-4-yl)amino)-4-fluorophenyl)carbamate (116)

Title compound was prepared in a manner substantially similar to procedure mentioned in General Procedure L to get tert-butyl (3-((5-amino-2-chloropyrimidin-4-yl)amino)-4-fluorophenyl)carbamate (116) (4.8 g, Yield: 85.40%), LCMS: $[M+H]^+$ 353.81.

Step 3: Synthesis of tert-butyl (3-((5-benzamido-2-chloropyrimidin-4-yl)amino)-4-fluorophenyl)carbamate (117)

To an ice-cold solution of tert-butyl (3-((5-amino-2-chloropyrimidin-4-yl)amino)-4-fluorophenyl)carbamate (116) (1.0 g, 2.831 mmol) in tetrahydrofuran (10 mL) was added pyridine (810 mg, 11.32 mmol) then benzoyl chloride (62) (400 mg, 2.831 mmol) under nitrogen atmosphere. The resultant reaction mixture was stirred at room temperature for 1 hour. After completion of reaction (TLC monitoring), the reaction mixture was diluted with water (100 mL) and extracted with dichloromethane (3×100 mL). The combined organic layers were washed with brine, dried over anhydrous sodium sulfate, filtered and concentrated under reduced pressure. The crude was purified by combiflash eluted with 8% ethyl acetate in hexane to get tert-butyl (3-((5-benzamido-2-chloropyrimidin-4-yl)amino)-4-fluorophenyl)carbamate (117) (800 mg, Yield: 61.53%), MS: $[M+H]^+$ 458.23.

Step 4: Synthesis of tert-butyl (3-((5-benzamido-2-((1-methyl-1H-pyrazol-4-yl)amino)pyrimidin-4-yl)amino)-4-fluorophenyl)carbamate (118)

Title compound was prepared in a manner substantially similar to procedure mentioned in General Procedure H. The residue was purified by combiflash elution with 2% methanol in dichloromethane to get tert-butyl (3-((5-benzamido-2-((1-methyl-1H-pyrazol-4-yl)amino)pyrimidin-4-yl)amino)-4-fluorophenyl)carbamate (118) (450 mg, Yield: 49.61%), MS: $[M+H]^+$ 519.13

Step 5: Synthesis of N-(4-((5-Amino-2-fluorophenyl)amino)-2-((1-methyl-1H-pyrazol-4-yl)amino)pyrimidin-5-yl)benzamide (119)

Title compound was prepared in a manner substantially similar to procedure mentioned in General Procedure I to get N-(4-((5-amino-2-fluorophenyl)amino)-2-((1-methyl-1H-pyrazol-4-yl)amino)pyrimidin-5-yl)benzamide (119) (280 mg, Yield: 77.10%), MS: $[M+H]^+$ 419.24

Step 6: Synthesis of N-(4-((5-acrylamido-2-fluorophenyl)amino)-2-((1-methyl-1H-pyrazol-4-yl)amino)pyrimidin-5-yl)benzamide (Compound 50)

Title compound was prepared in a manner substantially similar to procedure mentioned in General Procedure K. The crude was purified by prep HPLC purification to get N-(4-((5-acrylamido-2-fluorophenyl)amino)-2-((1-methyl-1H-pyrazol-4-yl)amino)pyrimidin-5-yl)benzamide Compound 50 (17 mg, Yield: 10.03%). $^1$H-NMR (400 MHz, DMSO-$d_6$): δ 10.22 (bs, 1H), 9.68 (bs, 1H), 9.04 (bs, 1H), 8.63 (bs, 1H), 8.06-8.08 (m, 2H), 7.95 (s, 1H), 7.84-7.85 (m, 1H), 7.50-7.59 (m, 4H) 7.21-7.31 (m, 3H), 6.37-6.44 (m, 1H), 6.22 (d, J=16.8 Hz, 1H), 5.74 (d, J=11.2 Hz, 1H), 3.57 (s, 3H), LCMS: $[M+H]^+$ 473.35.

Scheme 26: Synthesis of N-(4-fluoro-3-((2-((1-methyl-1H-pyrazol-4-yl)amino)-5-(phenylsulfonamido)pyrimidin-4-yl)amino)phenyl)acrylamide (Compound 51)

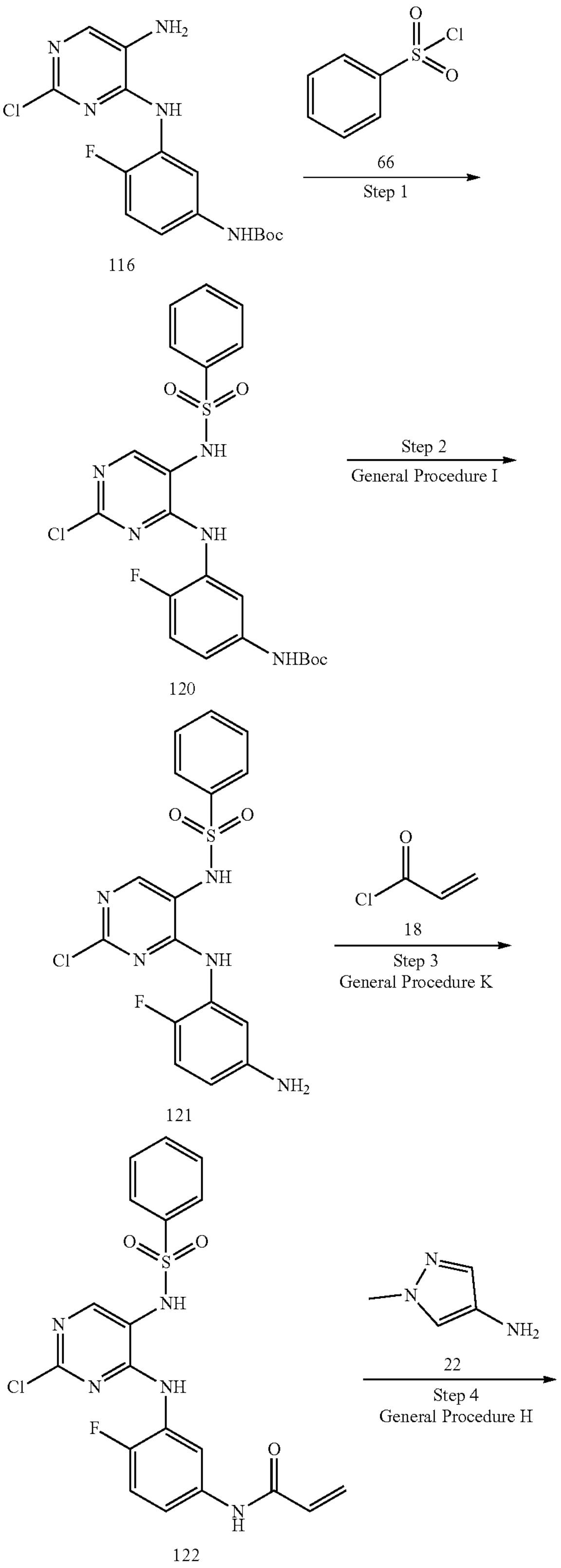

-continued

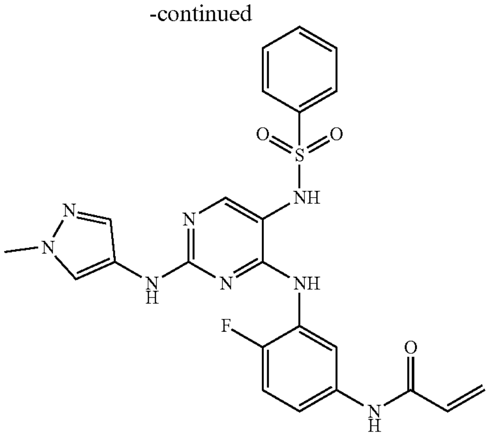

Compound 51

Step 1: Synthesis of tert-butyl (3-((2-chloro-5-(phenylsulfonamido)pyrimidin-4-yl)amino)-4-fluorophenyl)carbamate (120)

To an ice-cold of solution of tert-butyl (3-((5-amino-2-chloropyrimidin-4-yl)amino)-4-fluorophenyl)carbamate (116) (1.0 g, 2.83 mmol) in tetrahydrofuran (10 mL) were added pyridine (0.95 mL, 11.32 mmol), benzenesulfonyl chloride (66) (0.36 ml, 2.83 mmol) and catalytic amount of N,N-dimethyl amino pyridine under nitrogen atmosphere. The resultant reaction mixture was stirred at room temperature for 16 hours. The progress of reaction was monitored by TLC, after completion of reaction, the reaction mixture was dilute with water (100 mL) and extracted with ethyl acetate (3×100 mL). The combined organic layers were washed with brine, dried anhydrous sodium sulfate, filtered and concentrated under reduced pressure. The crude was purified by combiflash eluted with 40% ethyl acetate in hexane to get tert-butyl (3-((2-chloro-5-(phenylsulfonamido)pyrimidin-4-yl)amino)-4-fluorophenyl)carbamate (120) (600 mg, Yield 42.85%). MS: $[M+H]^+$ 494.10.

Step 2: Synthesis of N-(4-((5-amino-2-fluorophenyl)amino)-2-chloropyrimidin-5-yl)benzenesulfonamide (121)

Title compound was prepared in a manner substantially similar to procedure mentioned in General Procedure I to get the desired product (121) (410 mg; Yield: 54.14%). MS: $[M+H]^+$ 394.21

Step 3: Synthesis of N-(3-((2-chloro-5-(phenylsulfonamido)pyrimidin-4-yl)amino)-4-fluorophenyl)acrylamide (122)

Title compound was prepared in a manner substantially similar to procedure mentioned in General Procedure K to get the desired product (122) (330 mg; Yield: 29.48%). MS: $[M+H]^+$ 448.11

Step 4: Synthesis of N-(4-fluoro-3-((2-((1-methyl-1H-pyrazol-4-yl)amino)-5-(phenylsulfonamido)pyrimidin-4-yl)amino)phenyl)acrylamide (Compound 51)

Title compound was prepared in a manner substantially similar to procedure mentioned in General Procedure H. The final compound was purified by prep-HPLC to get the desired product N-(4-fluoro-3-((2-((1-methyl-1H-pyrazol-4-yl)amino)-5-(phenylsulfonamido)pyrimidin-4-yl)amino)phenyl)acrylamide Compound 51 (43 mg; Yield: 19.14%). $^1H$-NMR (400 MHz, DMSO-$d_6$): δ 10.17 (bs, 1H), 9.02 (bs, 1H), 8.24 (bs, 1H), 7.74-7.79 (m, 3H), 7.53-7.60 (m, 5H), 7.38 (s, 1H), 7.19-7.24 (m, 3H), 6.38-6.45 (m, 1H) 6.23-6.27 (m, 1H), 5.77 (d, J=10.0 Hz, 1H), 3.56 (s, 3H), LCMS: $[M+H]^+$ 509.35.

Scheme 27: Synthesis of (E)-4-((3-(4-(dimethylamino)but-2-enamido)phenyl)amino)-2-((2-methoxy-4-(piperidin-1-yl)phenyl)amino)-N-methyl-N-phenylpyrimidine-5-carboxamide (Compound 52)

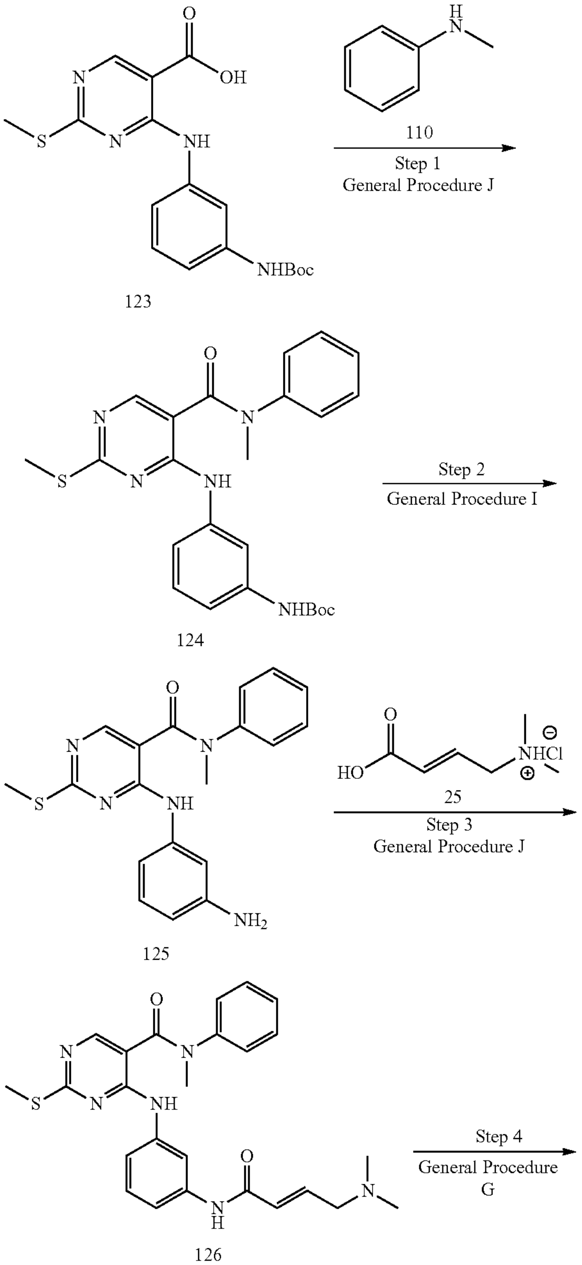

-continued

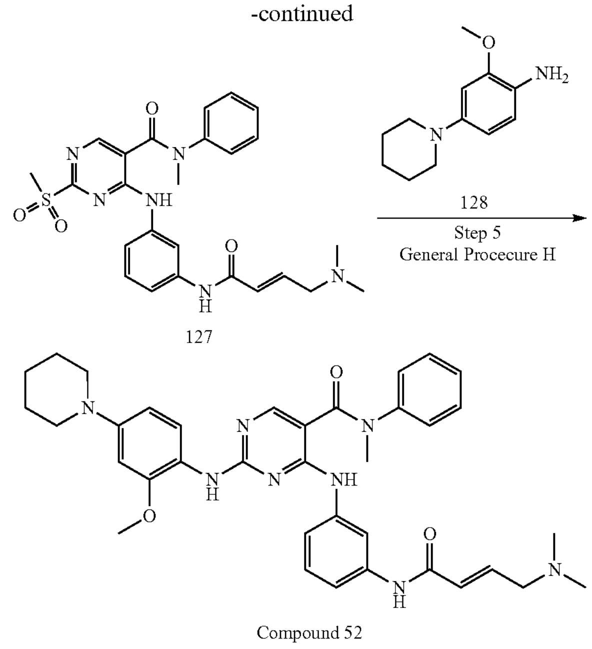

127

Compound 52

Step 1: Synthesis of tert-butyl (3-((2-chloro-5-(methyl(phenyl)carbamoyl)pyrimidin-4-yl)amino)phenyl)carbamate (124)

Title compound was prepared in a manner substantially similar to procedure mentioned in General Procedure J to get tert-butyl (3-((5-(methyl(phenyl)carbamoyl)-2-(methylthio)pyrimidin-4-yl)amino)phenyl)carbamate (124) (1.8 g, Yield: 75.21%), MS: $[M+H]^+$ 466.21.

Step 2: Synthesis of 4-((3-Aminophenyl)amino)-N-methyl-2-(methylthio)-N-phenylpyrimidine-5-carboxamide (125)

Title compound was prepared in a manner substantially similar to procedure mentioned in General Procedure I to get 4-((3-aminophenyl)amino)-N-methyl-2-(methylthio)-N-phenylpyrimidine-5-carboxamide (125) (1.1 g, Yield: 78.15%), MS: $[M+H]^+$ 366.18

Step 3: Synthesis of (E)-4-((3-(4-(dimethylamino)but-2-enamido)phenyl)amino)-N-methyl-2-(methylthio)-N-phenylpyrimidine-5-carboxamide (126)

Title compound was prepared in a manner substantially similar to procedure mentioned in General Procedure J. The crude was purified by combiflash eluted with 2.5% methanol in dichloromethane to get (E)-4-((3-(4-(dimethylamino)but-2-enamido)phenyl)amino)-N-methyl-2-(methylthio)-N-phenylpyrimidine-5-carboxamide (126) (600 mg; Yield: 46.15%), MS: $[M+H]^+$ 477.23

Step 4: Synthesis of (E)-4-((3-(4-(dimethylamino)but-2-enamido)phenyl)amino)-N-methyl-2-(methylsulfonyl)-N-phenylpyrimidine-5-carboxamide (127)

Title compound was prepared in a manner substantially similar to procedure mentioned in General Procedure G get (E)-4-((3-(4-(dimethylamino)but-2-enamido)phenyl)amino)-N-methyl-2-(methylsulfonyl)-N-phenylpyrimidine-5-carboxamide (127) (510 mg, Yield: 79.68%), MS: $[M+H]^+$ 509.19.

Step 5: Synthesis of (E)-4-((3-(4-(dimethylamino)but-2-enamido)phenyl)amino)-2-((2-methoxy-4-(piperidin-1-yl)phenyl)amino)-N-methyl-N-phenylpyrimidine-5-carboxamide (Compound 52)

Title compound was prepared in a manner substantially similar to procedure mentioned in General Procedure H. The final compound was purified by prep-HPLC to get the Compound 52 (44 mg, Yield: 7.06%) as off white solid. $^1$H-NMR (400 MHz, DMSO-$d_6$): δ 10.01 (bs, 1H), 9.59 (bs, 1H), 7.84-7.86 (m, 2H), 7.62 (s, 1H), 7.47 (d, J=6.4 Hz, 1H), 7.28-7.37 (m, 6H), 7.14-7.23 (m, 2H), 6.70-6.77 (m, 1H), 6.54 (s, 1H), 6.25-6.32 (m, 2H), 3.72 (s, 3H), 3.37 (s, 3H), 3.03-3.06 (m, 6H), 2.17 (s, 6H), 1.61 (s, 4H), 1.51-1.52 (m, 2H). LCMS: $[M+H]^+$ 635.18.

Scheme 28: Synthesis of (E)-N-(3-((2-((3-chloro-1-methyl-1H-pyrazol-4-yl)amino)-5-(4-(trifluoromethyl)phenyl)pyrimidin-4-yl)amino)phenyl)-4-(dimethylamino)but-2-enamide (Compound 53)

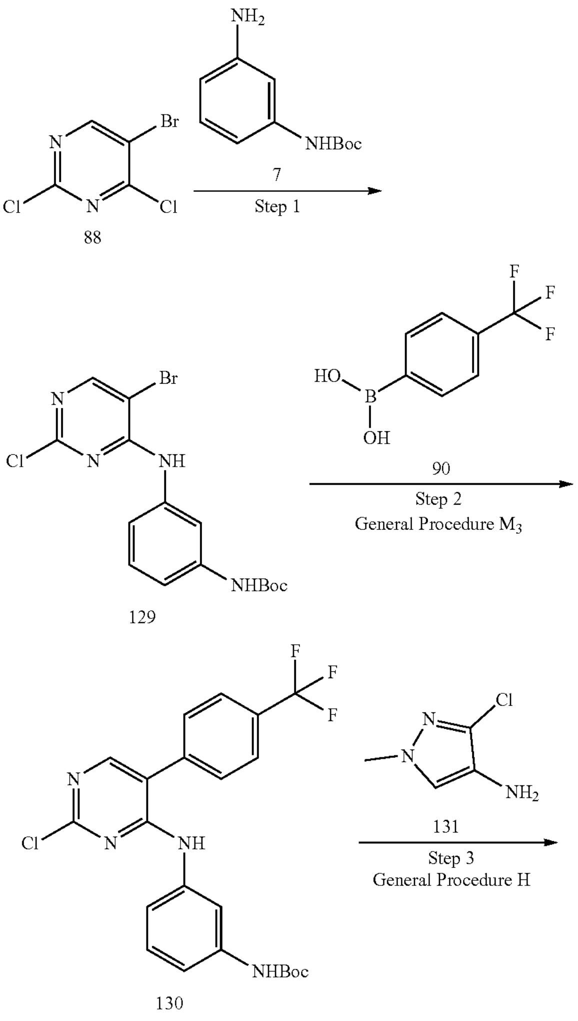

88

129

130

-continued

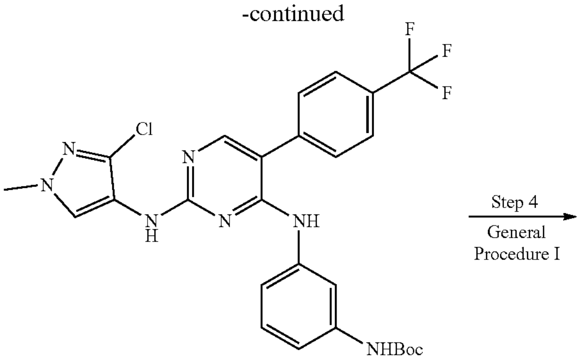

132

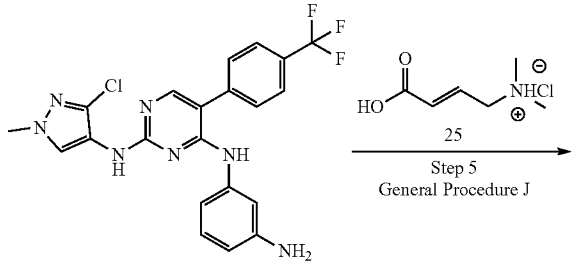

133

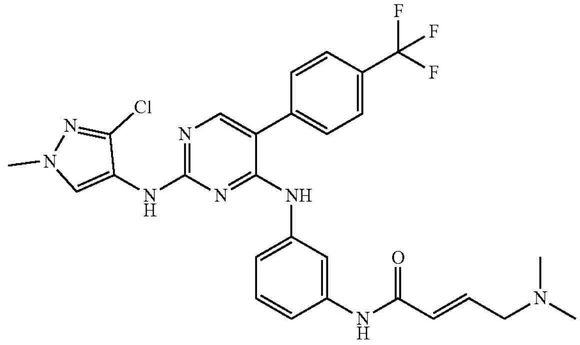

Compound 53

Step 1: Synthesis of tert-butyl (3-((5-bromo-2-chloropyrimidin-4-yl)amino)phenyl)carbamate (129)

To a solution of tert-butyl (3-aminophenyl)carbamate (7) (5 g, 22.13 mmol) in N,N-dimethylformamide (50 mL) were added potassium carbonate (6.10 g, 44.26 mmol) and 5-bromo-2,4-dichloropyrimidine (88) (4.97 g, 22.13 mmol) at room temperature. The resultant reaction mixture was heated at 110° C. for 16 hours. After completion of reaction (TLC monitoring), reaction mixture was cooled to room temperature and ice-cold water (100 mL) was added. The resulting solid precipitate was filtered and dried under vacuum to get tert-butyl (3-((5-bromo-2-chloropyrimidin-4-yl)amino)phenyl)carbamate (129) (3.5 g; Yield: 39.98%), LCMS: $[M+H]^+$ 399.48.

Step 2: Synthesis of tert-butyl (3-((2-chloro-5-(4-(trifluoromethyl)phenyl)pyrimidin-4-yl)amino)phenyl)carbamate (130)

Title compound was prepared in a manner substantially similar to procedure mentioned in General Procedure H to get desired product (130) (1.4 g; Yield: 35.12%). LCMS: $[M+H]^+$ 465.38.

Step 3: Synthesis of tert-butyl (3-((2-((3-chloro-1-methyl-1H-pyrazol-4-yl)amino)-5-(4-(trifluoromethyl)phenyl)pyrimidin-4-yl)amino)phenyl)carbamate (132)

Title compound was prepared in a manner substantially similar to procedure mentioned in General Procedure H to get the desired product (132) (600 mg; Yield: 37.54%). LCMS: $[M+H]^+$ 559.17.

Step 4: Synthesis of N4-(3-aminophenyl)-N2-(3-chloro-1-methyl-1H-pyrazol-4-yl)-5-(4-(trifluoromethyl)phenyl)pyrimidine-2,4-diamine (133)

Title compound was prepared in a manner substantially similar to procedure mentioned in General Procedure I to get the desired product (133) (320 mg, Yield: 65.04%). MS: $[M+H]^+$ 460.48.

Step 5: Synthesis of (E)-N-(3-((2-((3-chloro-1-methyl-1H-pyrazol-4-yl)amino)-5-(4-(trifluoromethyl)phenyl)pyrimidin-4-yl)amino)phenyl)-4-(dimethylamino)but-2-enamide (Compound 53)

Title compound was prepared in a manner substantially similar to procedure mentioned in General Procedure J. The final compound was purified by prep-HPLC purification to get the desired product Compound 53 (35 mg, Yield: 18.86%) as white solid. $^1$H-NMR (400 MHz, DMSO-$d_6$): δ 10.25 (bs, 1H), 10.13 (bs, 1H), 8.46-8.50 (m, 2H), 7.98 (s, 1H), 7.78-7.80 (m, 3H), 7.68-7.70 (m, 2H), 7.39-7.41 (m, 1H), 7.22-7.32 (m, 2H) 6.70-6.77 (m, 1H), 6.42 (d, J=15.2 Hz, 1H), 3.79 (s, 2H), 3.65 (s, 3H), 2.67 (s, 6H). LCMS: $[M+H]^+$ 571.12.

Scheme 29: Synthesis of (E)-N-(3-((2-((3-chloro-1-methyl-1H-pyrazol-4-yl)amino)-5-(trifluoromethyl)pyrimidin-4-yl)amino)phenyl)-4-(dimethylamino)but-2-enamide (Compound 54)

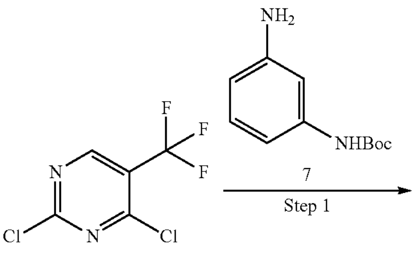

84

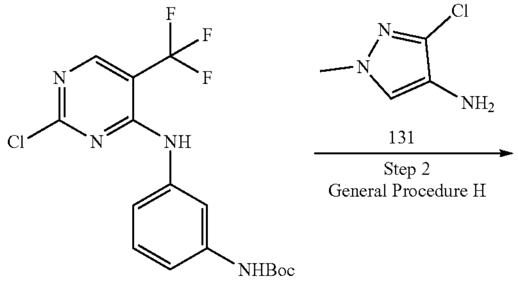

134

-continued

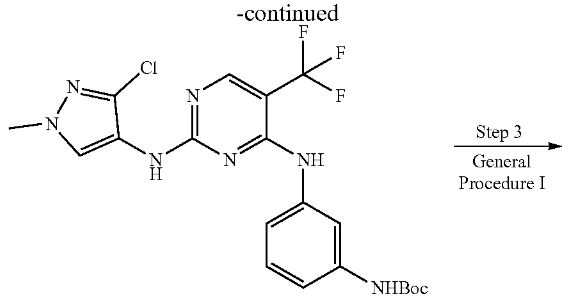

135

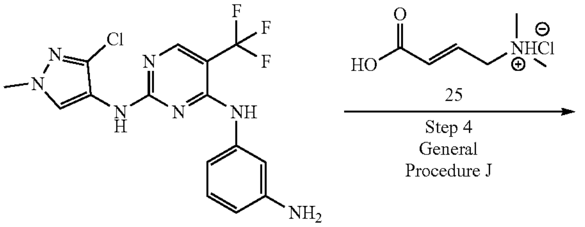

136

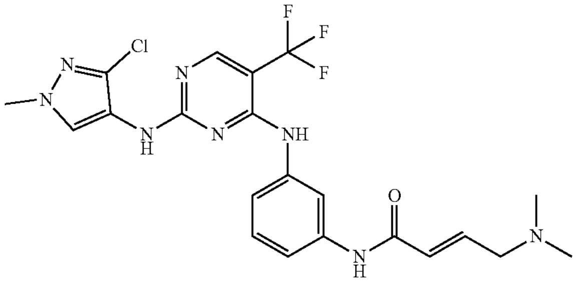

Compound 54

Step 1: Synthesis of tert-butyl (3-((2-chloro-5-(trifluoromethyl)pyrimidin-4-yl)amino)phenyl)carbamate (134)

To a solution of tert-butyl (3-aminophenyl)carbamate (84) (5.0 g, 24.038 mmol) in N,N-dimethylformamide (50 mL) was added potassium carbonate (6.63 g, 48.16 mmol) and 2,4-dichloro-5-(trifluoromethyl)pyrimidine (7) (5.16 g, 24.038 mmol) at room temperature. The resultant reaction mixture was heated at 100° C. for 16 hours. After completion of reaction (TLC monitoring), reaction mixture was diluted with ice-cold water (200 mL). The resulting solid precipitate was filtered and dried under vacuum to get the tert-butyl (3-((2-chloro-5-(trifluoromethyl)pyrimidin-4-yl)amino)phenyl)carbamate (134) (4.4 g; Yield: 48.88%), LCMS: $[M+H]^+$ 389.48.

Step 2: Synthesis of tert-butyl (3-((2-((3-chloro-1-methyl-1H-pyrazol-4-yl)amino)-5-(trifluoromethyl) pyrimidin-4-yl)amino)phenyl)carbamate (135)

Title compound was prepared in a manner substantially similar to procedure mentioned in General Procedure H to get the desired product (135) (400 mg; Yield: 32.25%), MS: $[M+H]^+$ 484.24.

Step 3: Synthesis of N4-(3-aminophenyl)-N2-(3-chloro-1-methyl-1H-pyrazol-4-yl)-5-(trifluoromethyl)pyrimidine-2,4-diamine (136)

Title compound was prepared in a manner substantially similar to procedure mentioned in General Procedure H to get the desired product (136) (310 mg; Yield: 97.12%), LCMS: $[M+H]^+$ 384.11.

Step 4: Synthesis of (E)-N-(3-((2-((3-chloro-1-methyl-1H-pyrazol-4-yl)amino)-5-(trifluoromethyl) pyrimidin-4-yl)amino)phenyl)-4-(dimethylamino) but-2-enamide (Compound 54)

Title compound was prepared in a manner substantially similar to procedure mentioned in General Procedure J to get the desired product Compound 54 (40 mg, Yield: 15.56%) as off white solid, after prep-HPLC purification. $^1$H-NMR (400 MHz, DMSO-$d_6$): δ 10.22 (bs, 1H), 9.09 (bs, 1H), 8.84 (bs, 1H), 8.31 (s, 1H), 7.70 (s, 1H), 7.55-7.57 (m, 1H), 7.32-7.34 (m, 1H), 7.09 (s, 1H) 6.70-6.77 (m, 1H), 6.32 (d, J=14.8 Hz, 1H), 3.86-3.65 (m, 1H), 3.52 (s, 3H), 3.32-3.39 (m, 2H), 2.40 (s, 6H), LCMS: $[M+H]^+$ 495.16.

Scheme 30: Synthesis of N-[4-fluoro-3-({2-[(1-methyl-1H-pyrazol-4-yl) amino]-5-[6-(morpholin-4-yl) pyridin-3-yl] pyrimidin-4-yl} amino) phenyl] prop-2-enamide (Compound 55)

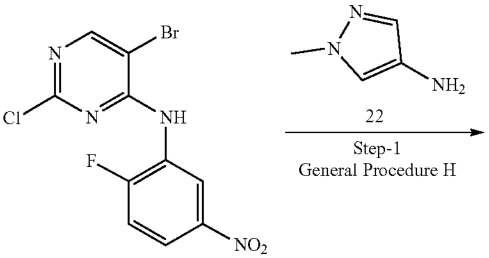

89

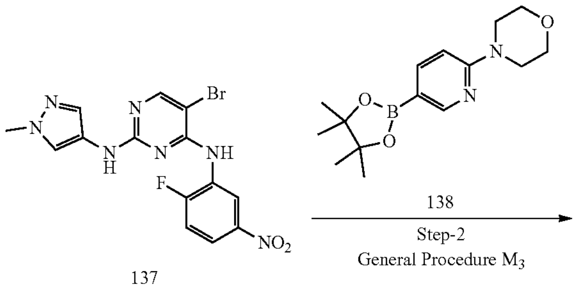

137

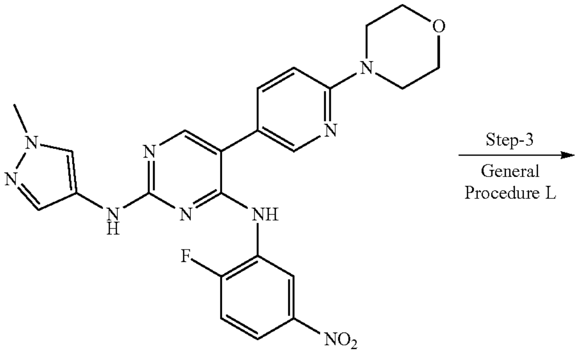

139

-continued

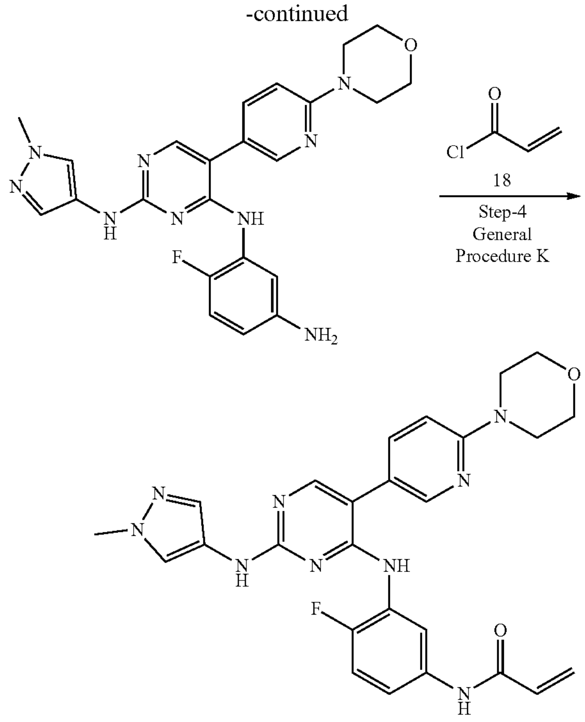

Compound 55

Step 1: Synthesis of 5-bromo-N4-(2-fluoro-5-nitrophenyl)-N2-(1-methyl-1H-pyrazol-4-yl)pyrimidine-2,4-diamine (137)

Title compound was prepared in a manner substantially similar to procedure mentioned in General Procedure H, to get desired product (137) as light yellow solid (Yield: 70%), LCMS: [M+H]$^+$ 407.90.

Step 2: Synthesis of N4-(2-fluoro-5-nitrophenyl)-N2-(1-methyl-1H-pyrazol-4-yl)-5-[6-(morpholin-4-yl) pyridin-3-yl] pyrimidine-2,4-diamine (139)

The title compound was prepared in a manner substantially similar to procedure mentioned in General Procedure M3, to get desired product (139) as a reddish solid. LCMS: [M+H]$^+$ 492.50

Step 3: Synthesis of N4-(5-amino-2-fluorophenyl)-N2-(1-methyl-1H-pyrazol-4-yl)-5-[6-(morpholin-4-yl) pyridin-3-yl] pyrimidine-2,4-diamine (140)

The title compound was prepared in a manner substantially similar to procedure mentioned in General Procedure L to get desired product (140) as pale yellow solid. LCMS: [M+H]$^+$ 462.0

Step 4: Synthesis of N-[4-fluoro-3-({2-[(1-methyl-1H-pyrazol-4-yl) amino]-5-[6-(morpholin-4-yl) pyridin-3-yl] pyrimidin-4-yl} amino) phenyl] prop-2-enamide (Compound 55)

The title compound was prepared in a manner substantially similar to procedure mentioned in General Procedure K to get desired product as off white solid. $^1$H NMR (400 MHz, DMSO-d6): δ 10.19 (s, 1H), 9.08 (bs, 1H), 8.19 (s, 1H), 7.84 (s, 1H), 7.74 (d, J=5.6 Hz, H), 7.63 (d, J=6.8 Hz, 1H), 7.55 (b s, H), 7.25 (bs, 2H), 7.13-7.11 (m, 2H), 6.92 (d, J=8.8 Hz, 1H), 6.42-6.36 (K, 1H), 6.24-6.20 (m, 1H), 5.74 (d, J=11.6 Hz, 1H), 3.70 (s, 3H), 3.53-3.48 (m, 4H), 3.30 (4H, merged with DMSO water peak). LCMS: [M+H]$^+$ 516.0.

TABLE 6

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 56 | 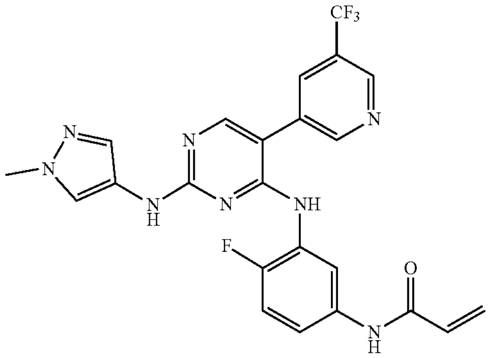 [SMILES: C=CC(=O)Nc1ccc(F)c(Nc2nc(Nc3cnn(C)c3)ncc2-c2cncc(C(F)(F)F)c2)c1] | K | 499.13 | δ 10.25 (s, 1H), 9.50 (bs, 1H), 8.94-8.95 (m, 3H), 8.24 (s, 1H), 8.04 (s, 1H), 7.78-7.79 (m, 1H), 7.56 (s, 1H), 7.15-7.31 (m, 3H), 6.37-6.44 (m, 1H), 6.22 (dd, J = 17.2 Hz, & 2.0 Hz, 1H), 5.74 (dd, J = 10.0 Hz, & 2.0 Hz, 1H), 3.56 (s, 3H). |

TABLE 6-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 57 | 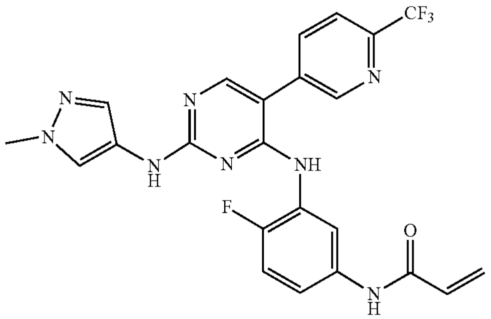 [SMILES: C=CC(=O)Nc1ccc(F)c(Nc2nc(Nc3cnn(C)c3)ncc2-c2ccc(C(F)(F)F)nc2)c1] | K | 499.11 | δ 10.26 (s, 1H), 9.36 (bs, 1H), 8.86 (s, 1H), 8.75 (s, 1H), 8.16 (d, J = 8.0 Hz, 1H), 8.04 (s, 1H) 7.94 (d, J = 8.0 Hz, 1H), 7.76-7.77 (m, 1H), 7.57 (s, 1H), 7.31 (s, 1H), 7.10-7.16 (m, 2H), 6.38-6.44 (m, 1H), 6.22 (dd, J = 17.2 & 1.6 Hz, 1H), 5.74 (dd, J = 11.6 & 1.6 Hz, 1H), 3.54 (s, 3H). |
| 58 | 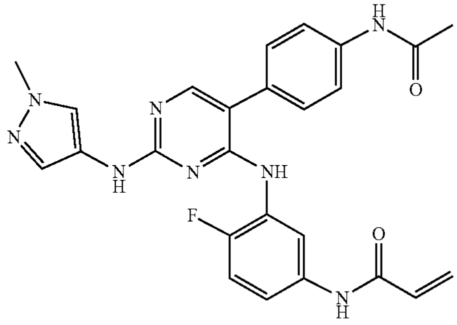 [SMILES: C=CC(=O)Nc1ccc(F)c(Nc2nc(Nc3cnn(C)c3)ncc2-c2ccc(NC(C)=O)cc2)c1] | K | 487.3 | δ 10.35 (s, 1H), 10.07 (s, 1H), 9.12 (s, 1H), 8.18 (s, 1H), 7.87 (s, 1H), 7.67-7.60 (m, 4H), 7.39 (d, J = 8.4 Hz, 2H), 7.24-7.17 (m, 3H), 6.44 (s, 1H), 6.22 (d, J = 16.8 Hz, 1H), 5.72 (d, J = 10 Hz, 1H), 3.52 (s, 3H), 2.04 (s, 3H). |
| 59 | 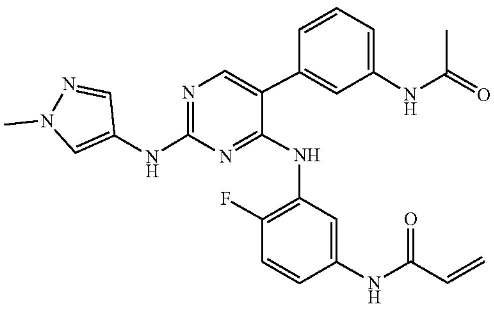 [SMILES: C=CC(=O)Nc1ccc(F)c(Nc2nc(Nc3cnn(C)c3)ncc2-c2cccc(NC(C)=O)c2)c1] | $K_1$ | 487.3 | δ 10.20 (s, 1H), 10.0 (s, 1H), 9.11 (s, 1H), 8.22 (s, 1H), 7.87 (s, 1H), 7.77 (s, 1H), 7.65-7.56 (m, 3H), 7.36 (t, J = 7.2 Hz, 1H), 7.26 (s, 1H), 7.12 (d, J = 8.0 Hz, 3H), 6.42-6.35 (m, 1H), 6.22 (d, J = 15.2 Hz, 1H), 5.73 (d, J = 11.2 Hz, 1H), 3.55 (s, 3H), 2.03 (s, 3H). |
| 60 | 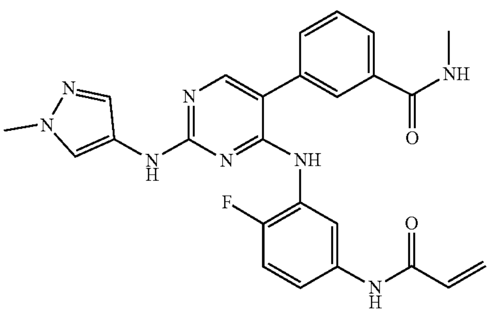 [SMILES: C=CC(=O)Nc1ccc(F)c(Nc2nc(Nc3cnn(C)c3)ncc2-c2cccc(C(=O)NC)c2)c1] | $K_1$ | 487.0 | δ 10.21 (s, 1H), 9.17 (s, 1H), 8.47 (bs, 1H), 8.45 (bs, 1H), 7.95-7.90 (m, 2H), 7.78-7.76 (m, 2H), 7.62-7.46 (m, 3H), 7.27-7.08 (m, 3H), 6.47-6.36 (m, 1H), 6.24-6.20 (m, 1H), 5.72 (d, J = 1.6 Hz, 1H), 3.53 (s, 3H), 2.79 (s, 3H) |

TABLE 6-continued
The following compounds were prepared using the procedures described above:
| Cmpd. No. | Structure | General Procedure | LCMS [M + H] | $^1$H-NMR (400 MHz, DMSO-$d_6$) |
|---|---|---|---|---|
| 61 | 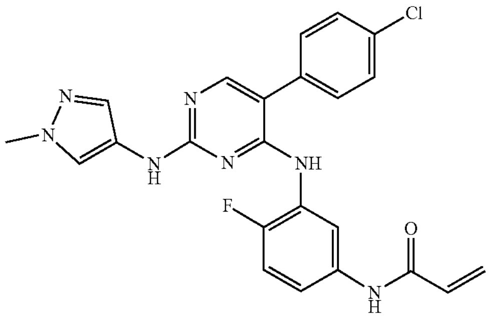 [SMILES: C=CC(=O)Nc1ccc(F)c(Nc2nc(Nc3cnn(C)c3)ncc2-c2ccc(Cl)cc2)c1] | K | 464.2 | δ 10.2 (s, 1H), 9.16 (s, 1H), 8.36 (s, 1H), 7.90 (s, 1H), 7.74 (dd, J = 6.8 Hz & 2.4 Hz, 1H), 7.49-7.56 (m, 4H), 7.07-7.27 (m, 4H), 6.39 (dd, J = 17.0 Hz, & 10.4 Hz, 1H), 6.23 (dd, J = 17.0 Hz & 2.2 Hz, 1H), 5.74 (dd, J = 10.0 Hz, & 1.6 Hz, 1H), 3.53 (s, 3H). |
| 62 | 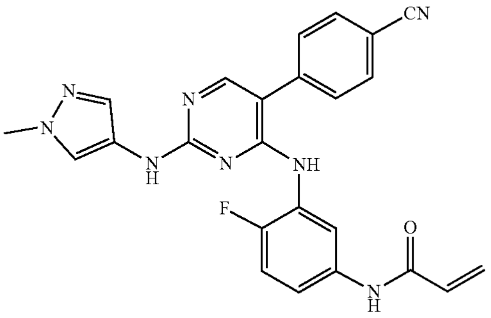 [SMILES: C=CC(=O)Nc1ccc(F)c(Nc2nc(Nc3cnn(C)c3)ncc2-c2ccc(C#N)cc2)c1] | K | 455.3 | δ 10.21 (s, 1H), 9.25 (s, 1H), 8.52 (bs, 1H), 7.98 (s, 1H), 7.88 (d, J = 8.4 Hz, 2H), 7.75 (d, J = 5.2 Hz, 1H), 7.69 (d, J = 8.0 Hz, 2H), 7.55 (bs, 1H), 7.08-7.21 (m, 3H), 6.32-6.43 (m, 1H), 6.20-6.24 (m, 1H), 5.72 (t, J = 10.0 Hz, 1H), 3.53 (s, 3H). |
| 63 | 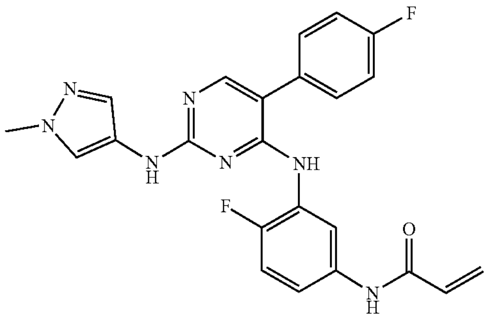 [SMILES: C=CC(=O)Nc1ccc(F)c(Nc2nc(Nc3cnn(C)c3)ncc2-c2ccc(F)cc2)c1] | K | 448.1 | δ 10.17 (s, 1H), 9.06 (bs, 1H), 8.20 (s, 1H), 7.87 (s, 1H), 7.75-7.74 (m, 1H), 7.54-7.47 (m, 3H) 7.29-7.24 (m, 3H), 7.16 (bs, 2H,), 6.42-6.35 (m, 1H), 6.24-6.20 (m, 1H), 5.73 (d, J = 10.4 Hz, 1H), 3.54 (s, 3H). |
| 64 | 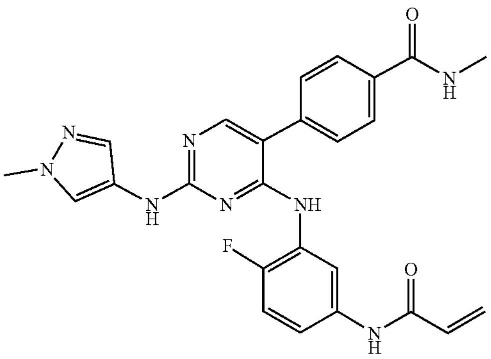 | K | 487.2 | δ 10.38 (s, 1H), 9.20 (s, 1H), 8.47 (s, 2H), 7.94-7.90 (m, 3H) 7.72-7.76 (m, 2H), 7.72-7.70 (m, 3H) 7.24-7.14 (m, 3H), 6.4 (s, 1H), 6.23-6.19 (m, 1H), 3.57 (s, 3H), 2.72 (s, 3H). |

TABLE 6-continued
| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 65 | 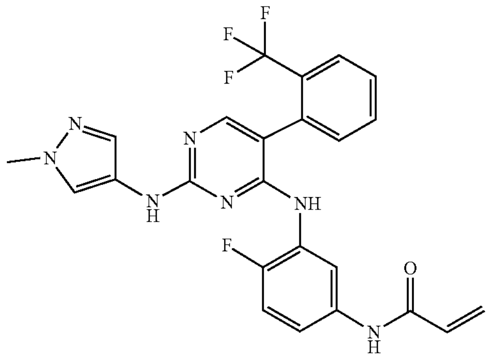 [SMILES: C=CC(=O)Nc1ccc(F)c(Nc2nc(Nc3cnn(C)c3)ncc2-c2ccccc2C(F)(F)F)c1] | $K_1$ | 498.5 | δ 10.23 (s, 1H), 9.75 (s, 1H), 8.85 (s, 1H), 7.88 (d, J = 7.2 Hz, 2H), 7.78 (t, J = 7.6 Hz, 2H), 7.68 (t, J = 7.6 Hz, 1H), 7.58-7.54 (m, 2H), 7.30-7.12 (m, 3H), 6.41-6.34 (m, 1H), 6.25-6.20 (m, 1H), 5.75-5.72 (m, 1H), 3.55 (s, 3 H). |
| 66 | 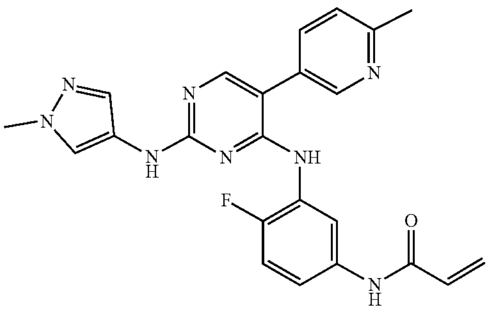 [SMILES: C=CC(=O)Nc1ccc(F)c(Nc2nc(Nc3cnn(C)c3)ncc2-c2ccc(C)nc2)c1] | $K_1$ | 445.0 | δ 10.27 (s, 1H), 9.18 (s, 1H), 8.54 (s, 1H), 8.46 (s, 1H), 7.92 (s, 1H), 7.77 (d, J = 7.2 Hz, 2H), 7.59 (s, 1H), 7.35-7.11 (m, 4H), 6.47-6.22 (m, 2H), 5.75 (d, J = 10.0 Hz, 1H), 3.55 (s, 3H), 2.67 (s, 3H) |
| 67 | 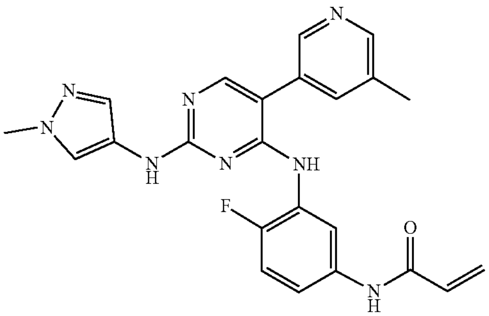 [SMILES: C=CC(=O)Nc1ccc(F)c(Nc2nc(Nc3cnn(C)c3)ncc2-c2cncc(C)c2)c1] | K | 445.13 | δ 10.22 (bs, 1H), 9.21 (bs, 1H), 8.46 (s, 2H), 8.38 (s, 1H), 7.93 (s, 1H), 7.70-7.76 (m, 2H), 7.58 (s, 1H), 7.11-7.29 (m, 3H), 6.37-6.44 (m, 1H), 6.22-6.26 (m, 1H), 5.74 (d, J = 10.0 Hz, 1H), 3.54 (s, 3H), 2.35 (s, 3H). |
| 68 | 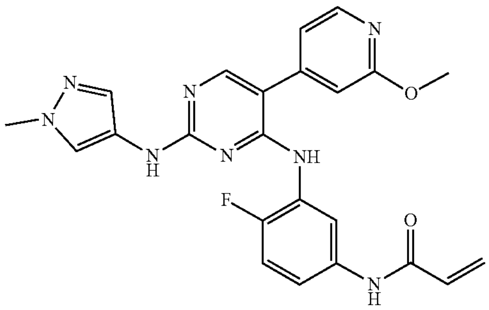 [SMILES: C=CC(=O)Nc1ccc(F)c(Nc2nc(Nc3cnn(C)c3)ncc2-c2ccnc(OC)c2)c1] | K | 461.18 | δ 10.23 (bs, 1H), 9.31 (bs, 1H), 8.58 (bs, 1H), 8.19 (d, J = 5.2 Hz, 1H), 8.02 (s, 1H), 7.73-7.76 (m, 1H), 7.60 (s, 1H), 7.31 (s, 1H), 7.06-7.13 (m, 3H), 6.93 (s, 1H), 6.37-6.44 (m, 1H), 6.22-6.26 (m, 1H), 5.74 (d, J = 10.0 Hz, 1H), 3.88 (s, 3H), 3.53 (s, 3H). |

TABLE 6-continued
| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 69 | 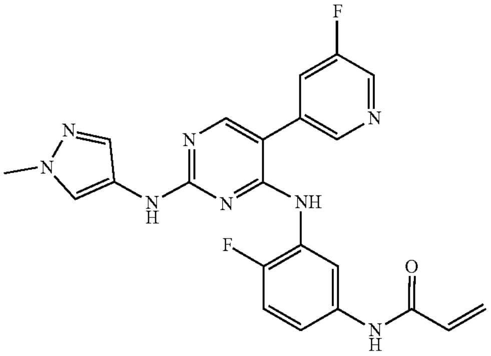 [SMILES: C=CC(=O)Nc1ccc(F)c(Nc2nc(Nc3cnn(C)c3)ncc2-c2cncc(F)c2)c1] | K | 449.3 | δ 10.23 (s, 1H), 9.29 (bs, 1H), 8.63 (s, 1H), 8.53 (s, 2H), 7.99 (s, 1H), 7.75-7.83 (m, 2H), 7.57 (s, 1H), 7.09-7.14 (m, 3H), 6.36-6.43 (m, 1H), 6.23 (d, J = 8.6 Hz, 1H), 5.74 (d, J = 10.0 Hz, 1H), 3.53 (s, 3H). |
| 70 | 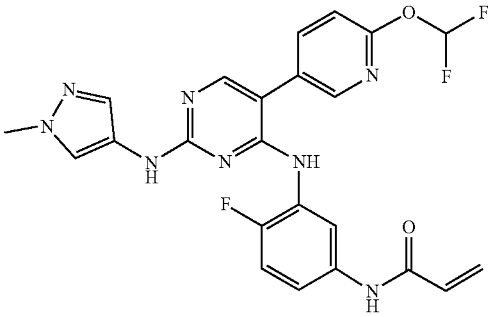 [SMILES: C=CC(=O)Nc1ccc(F)c(Nc2nc(Nc3cnn(C)c3)ncc2-c2ccc(OC(F)F)nc2)c1] | $K_1$ | 497.2 | δ 10.28 (s, 1H), 9.90 (s, 1H), 9.28 (s, 1H), 8.37 (s, 1H), 8.05-7.79 (m, 4H), 7.59 (d, J = 17.6 Hz, 1H), 7.35-7.16 (m, 4H), 6.45-6.38 (m, 1H), 6.25 (d, J = 16.8 Hz, 1H), 5.77 (d, J = 10.0 Hz, 1H), 3.57 (s, 3H) |
| 71 | 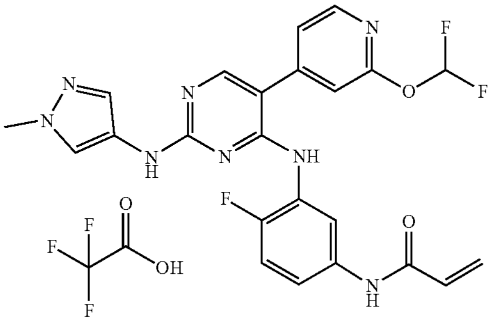 | $K_1$ | 497.3 | δ 10.28 (s, 1H), 9.81 (s, 1H), 9.17 (s, 1H), 8.32-8.30 (d, J = 5.2 Hz 1H), 8.08 (s, 1H), 7.95-7.59 (m, 4H), 7.41-7.35 (m, 2H), 7.22-7.07 (m, 3H), 6.43-6.36 (m, 1H), 6.25-6.21 (m, 1H), 5.75 (d, J = 11.6 Hz, 1H), 3.61 (s, 3H) |
| 72 | 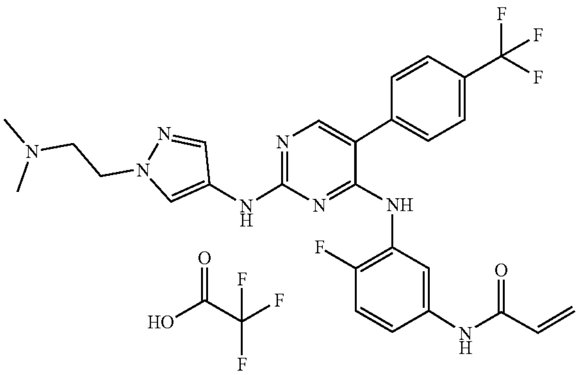 [SMILES: C=CC(=O)Nc1ccc(F)c(Nc2nc(Nc3cnn(CCN(C)C)c3)ncc2-c2ccc(C(F)(F)F)cc2)c1 ; O=C(O)C(F)(F)F] | $K_1$ | 555.2 | δ 10.30-10.20 (m, 2H), 9.48-9.21 (m, 2H), 8.04 (s, 1H), 7.93-7.32 (m, 8H), 7.23-6.98 (m, 1H), 6.43-6.36 (m, 1H), 6.25-6.21 (m, 1H), 5.75 (dd, J = 10.0 Hz, 1.6 Hz, 1H), 4.23 (bs, 2H), 3.42 (s, 2H), 2.75 (s, 6H). |

TABLE 6-continued
| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 73 | 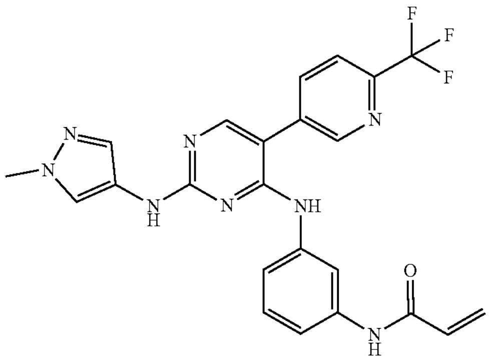 [SMILES: C=CC(=O)Nc1cccc(Nc2nc(Nc3cnn(C)c3)ncc2-c2ccc(C(F)(F)F)nc2)c1] | K | 481.0 | δ 10.22 (s, 1H), 9.80 (s, 1H), 8.67 (s, 1H), 8.19-8.20 (m, 1H), 7.97-8.03 (m, 2H), 7.83 (s, 1H), 7.44-7.35 (m, 5H), 7.12 (s, 1H), 6.45-6.39 (m, 1H), 6.20 (d, J = 2.0 Hz, 1H), 5.74 (d, J = 8.0 Hz, 1H), 3.44 (s, 3H). |
| 74 | 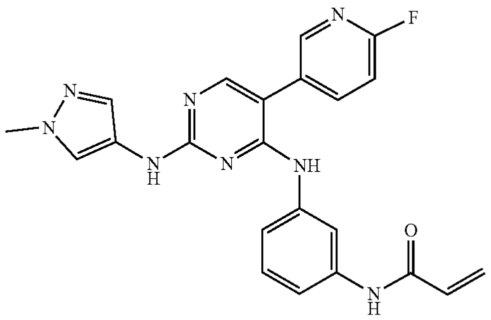 [SMILES: C=CC(=O)Nc1cccc(Nc2nc(Nc3cnn(C)c3)ncc2-c2ccc(F)nc2)c1] | K | 431.0 | δ 10.13 (s, 1H), 9.21 (s, 1H), 8.54 (s, 1H), 8.22 (s, 1H), 8.04 (t, J = 8.0 Hz, 1H), 7.92 (s, 1H), 7.76 (s, 1H), 7.42-7.11 (m, 6H), 6.46-6.39 (m, 1H), 6.21 (d, J = 16.0 Hz, 1H), 5.72 (d, J = 12.0 Hz, 1H), 3.58 (s, 3 H). |
| 75 | 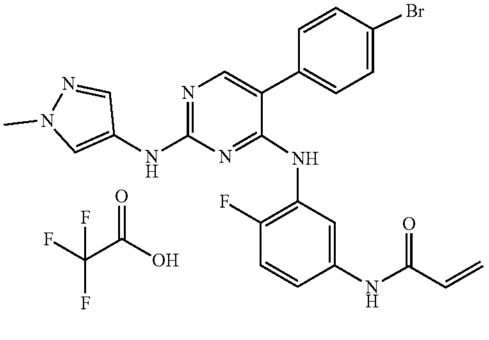 | $K_1$ | 508.1 | δ 10.28 (s, 1H), 9.87 (bs, 1H), 9.21 (bs, 1H), 7.91-7.81 (m, 2H), 7.54-(d, J = 8.4 Hz, 2H), 7.55 (bs, 2H), 7.46 (d, J = 8.0 Hz, 2H), 7.33 (bs, 1H), 7.20-7.09 (m, 2H), 6.42-6.36 (m, 1H), 6.23 (dd, J = 16.8 Hz, 2.0 Hz, 1H), 5.75 (dd, J = 10.0 Hz, 1.6 Hz, 1H), 3.43 (s, 3H) |
| 76 | 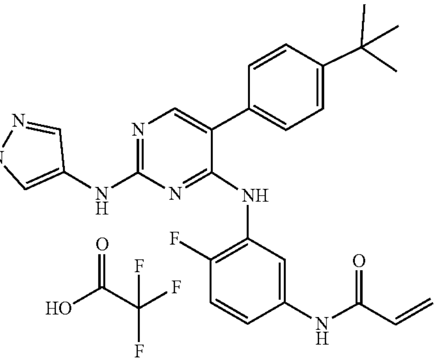 | $K_1$ | 464.2 | δ 10.29 (s, 1H), 9.99 (bs, 1H), 9.33 (bs, 1H), 7.90-7.83 (m, 2H), 7.54-7.09 (m, 8H), 6.43-6.21 (m, 3H), 5.76-5.74 (m, 1H), 3.55 (s, 3H), 1.32 (s, 9 H) |

TABLE 6-continued

| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 77 | 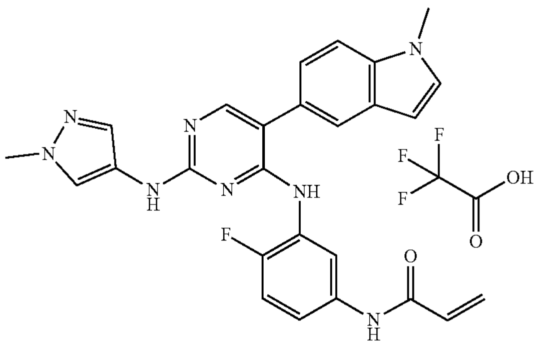 | $K_2$ | 483.2 | δ 10.28 (s, 1H), 10.0 (bs, 1H), 9.4 (bs, 1H), 7.85 (d, J = 4.4 Hz, 2H), 7.67 (s, 1H), 7.58 (d, J = 8.4 Hz, 2H), 7.42-7.14 (m, 6H), 6.50 (d, J = 2.8 Hz, 1H, 6.42-6.25 (m, 1H), 6.23 (d, J = 15.2 Hz, 1H), 5.75-5.73 (m, 1H), 3.56 (s, 3H), 3.15 (s, 3H, merged in the DMSO peak). |
| 78 | 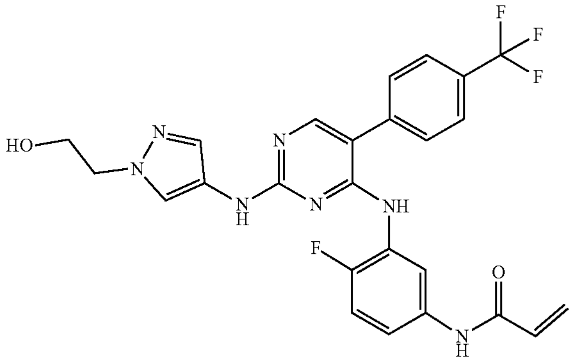 [SMILES: C=CC(=O)Nc1ccc(F)c(Nc2nc(Nc3cnn(CCO)c3)ncc2-c2ccc(C(F)(F)F)cc2)c1] | $K_1$ | 528.5 | δ10.19 (s, 1H), 9.22 (s, 1H), 8.52 (s, 1H), 7.97 (s, 1H), 7.79-7.69 (m, 5H), 7.51 (s, 1H), 7.24-7.16 (m, 3H), 6.42-6.35 (m, 1H), 6.24-6.19 (m, 1H), 5.74-5.71 (m, 1H), 4.74 (s, 1H), 3.81 (s, 2H), 3.54 (s, 2H). |
| 79 | 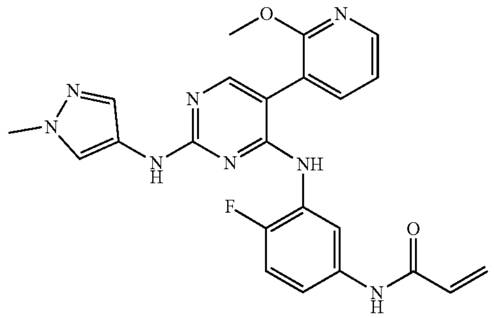 [SMILES: C=CC(=O)Nc1ccc(F)c(Nc2nc(Nc3cnn(C)c3)ncc2-c2cccnc2OC)c1] | $K_1$ | 461.3 | δ 10.17 (s, 1H), 9.05 (bs, 2H), 8.18-8.17 (m, 2H), 7.81-7.55 (m, 4H), 7.23-7.04 (m, 3H), 6.42-6.35 (m, 1H), 6.24-6.20 (m, 1H), 5.74-5.72 (d, J = 8.0 Hz, 1H), 3.89 (s, 3H), 3.55 (bs, 3H). |
| 80 | 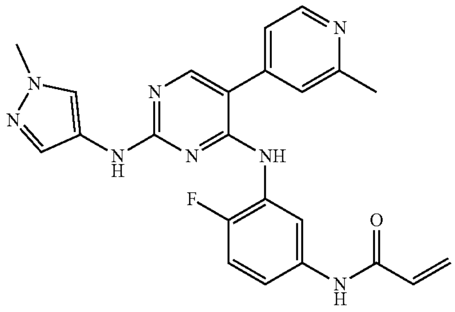 [SMILES: C=CC(=O)Nc1ccc(F)c(Nc2nc(Nc3cnn(C)c3)ncc2-c2ccnc(C)c2)c1] | $K_1$ | 445.3 | δ 10.30 (s, 1H), 9.78 (s, 1H), 9.11 (s, 1H), 8.69 (d, J = 4.8 Hz, 1H), 8.28 (s, 1H), 7.98-7.86 (m, 3H), 7.54 (s, 1H), 7.36 (s, 1H), 7.18-7.10 (m, 2H), 6.44-6.37 (m, 1H), 6.23 (d, J = 17.2 Hz, 1H), 5.75 (d, J = 10.0 Hz, 1H), 3.55 (s, 3H), 2.68 (s, 3H) |

TABLE 6-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 81 | 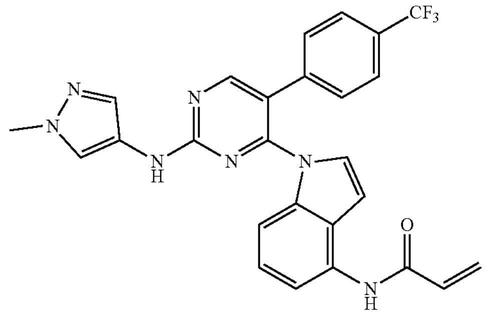 [SMILES: C=CC(=O)Nc1cccc2c1ccn2-c1nc(Nc2cnn(C)c2)ncc1-c1ccc(C(F)(F)F)cc1] | $K_1$ | 504.0 | δ 9.98 (s, 1H), 9.87 (s, 1H), 8.69 (s, 1H), 7.88 (m, 2H), 7.81 (d, J = 6.8 Hz, 2H), 7.67-7.53 (m, 2H), 7.35 (d, J = 7.6 Hz, 2H), 7.15 (t, J = 7.6 Hz, 1H), 7.02 (s, 1H), 6.85 (s, 1H), 6.71-6.64 (m, 1H), 6.29 (d, J = 16.8 Hz, 1H), 5.77 (d, J = 10.0 Hz, 1H), 3.79 (s, 3H). |
| 82 | 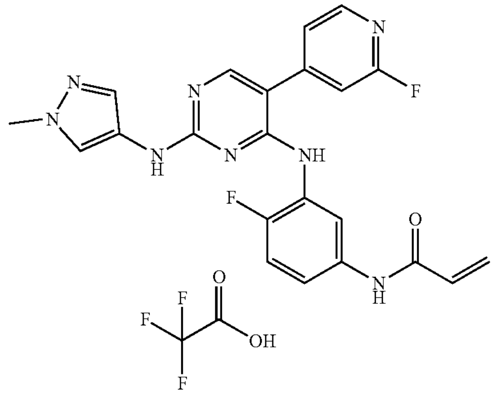 | K | 449.2 | δ 10.26 (bs, 1H), 9.91 (bs, 1H), 9.22 (bs, 1H), 8.29 (s, 1H), 8.09 (s, 1H), 7.82 (s, 2H), 7.56 (bs, 1H), 7.49 (s, 1H), 7.32 (bs, 2H), 7.20-7.07 (m, 2H), 6.42-6.36 (m, 1H), 6.25-6.20 (m, 1H), 5.74 (d, J = 10.4 Hz, 1H), 3.54 (s, 3H). |
| 83 | 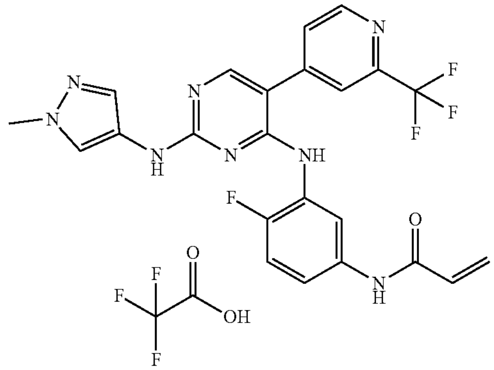 [SMILES: C=CC(=O)Nc1ccc(F)c(Nc2nc(Nc3cnn(C)c3)ncc2-c2ccnc(C(F)(F)F)c2)c1 ; O=C(O)C(F)(F)F] | K | 499.1 | δ 10.26 (bs, 1H), 9.88 (bs, 1H), 9.27 (bs, 2H), 8.79 (bs, 1H), 8.12 (s, 1H), 7.98 (s, 1H), 7.82 (bs, 2H), 7.55 (s, 1H), 7.32 (bs, 1H), 7.19-7.06 (m, 2H), 6.42-6.35 (m, 1H), 6.24-6.20 (m, 1H), 5.74 (d, J = 9.6 Hz, 1H), 3.55 (s, 3H). |
| 84 | 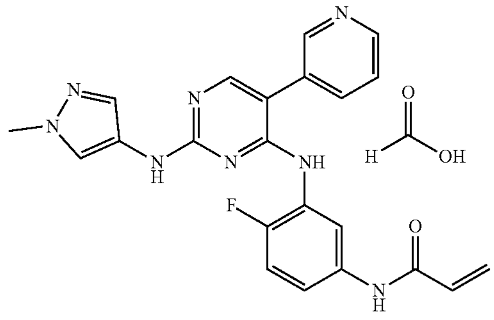 | K | 431.5 | δ 10.18 (bs, 1H), 9.16-8.99 (m, 2H), 8.65 (s, 1H), 8.53-8.49 (m, 2H), 8.16 (s, 1H), 7.92 (s, 1H), 7.87 (d, J = 7.6 Hz, 1H), 7.74 (d, J = 5.6 Hz, 1H), 7.55 (bs, 1H), 7.46-7.43 (m, 1H), 7.26-7.16 (m, 3H), 6.42-6.35 (m, 1H), 6.24-6.20 (m, 1H), 5.73 (d, J = 10.80 Hz, 1H), 3.53 (s, 3H). |

TABLE 6-continued
| Cmpd. No. | Structure | General Procedure | LCMS [M + H] | $^1$H-NMR (400 MHz, DMSO-$d_6$) |
|---|---|---|---|---|
| The following compounds were prepared using the procedures described above: | | | | |
| 85 | 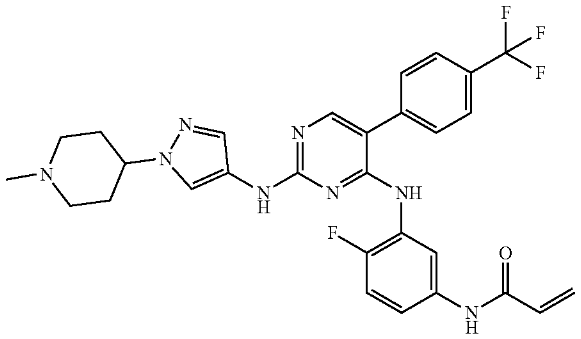 [SMILES: C=CC(=O)Nc1ccc(F)c(Nc2nc(Nc3cnn(C4CCN(C)CC4)c3)ncc2-c2ccc(C(F)(F)F)cc2)c1] | K | 581.2 | δ 10.20 (s, 1H), 9.24 (s, 1H), 8.47 (s, 1H), 7.96 (s, 1H), 7.77 (m, 2H), 7.71 (m, 2H), 7.62 (m, 2H), 7.25 (s, 1H), 7.16 (s, 2H), 6.42-6.35 (m, 1H), 6.22 (d, J = 17.2 Hz, 1H), 5.73 (d, J = 10.0 Hz, 1H), 3.60 (s, 1H), 2.75 (d, J = 8.8 Hz, 2H), 2.16 (s, 3H), 1.94 (s, 2H), 1.64 (s, 4H). |
| 86 | 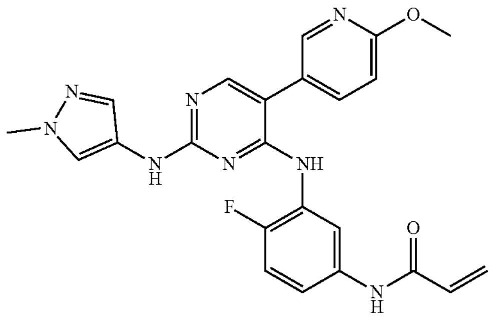 [SMILES: C=CC(=O)Nc1ccc(F)c(Nc2nc(Nc3cnn(C)c3)ncc2-c2ccc(OC)nc2)c1] | K | 461.2 | δ 10.17 (s, 1H), 9.07 (s, 1H), 8.30 (s, 1H), 8.21 (s, 1H), 7.86 (s, 1H), 7.76-7.26 (m, 2H), 7.54 (s, 1H), 7.25-7.16 (m, 3H), 6.88 (d, J = 8.4 Hz, 1H), 6.42-6.35 (m, 1H), 6.22 (d, J = 16.0 Hz, 1H), 5.72 (d, J = 10.4 Hz, 1H), 3.87 (s, 3H), 3.54 (s, 3H). |
| 87 | 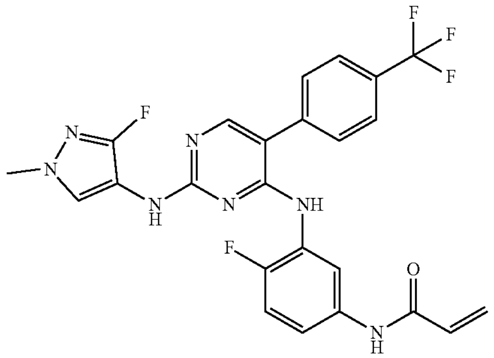 [SMILES: C=CC(=O)Nc1ccc(F)c(Nc2nc(Nc3cn(C)nc3F)ncc2-c2ccc(C(F)(F)F)cc2)c1] | K | 516.3 | δ 10.14 (s, 1H), 8.95 (bs, 1H), 8.49 (bs, 2H), 7.96 (s, 1H), 7.80-7.69 (m, 4H), 7.51 (bs, 1H), 7.27-7.13 (m, 2H), 6.43-6.36 (m, 1H), 6.25-6.21 (m, 1H), 5.74 (d, J = 10.0 Hz, 1H), 3.48 (s, 3H). |

TABLE 6-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 88 | 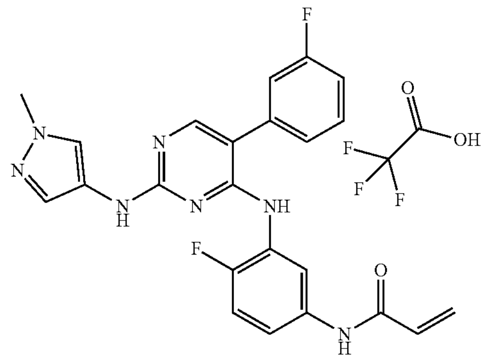 | K | 448.3 | δ 10.28 (s, 1H), 9.95 (s, 1H), 9.25 (s, 1H), 7.97 (s, 1H), 7.85 (s, 1H), 7.57 (t, J = 6.8 Hz, 2H), 7.37-7.25 (m, 7H), 6.39-6.23 (m, 2H), 5.77 (d, J = 8.0 Hz, 1H), 3.59 (s, 3H) |

Scheme 31: Synthesis of N-[4-fluoro-3-({2-[(1-methyl-1H-pyrazol-4-yl)amino]-5-[3-(trifluoromethyl)phenyl]pyrimidin-4-yl}amino)phenyl]prop-2-enamide (Compound 89)

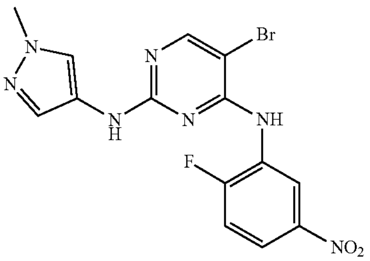

137

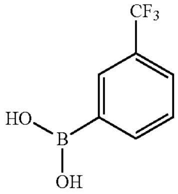

147

Step 1
General Procedure
$M_3$

-continued

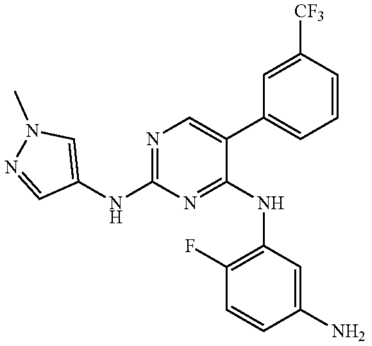

142

Step 3
General Procedure
K

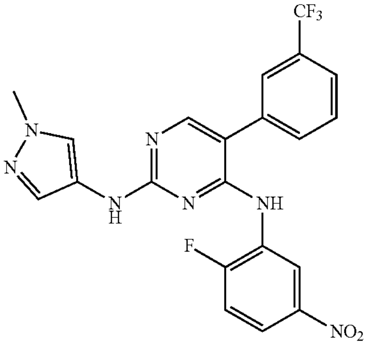

141

Step 2
General Procedure
$L_1$

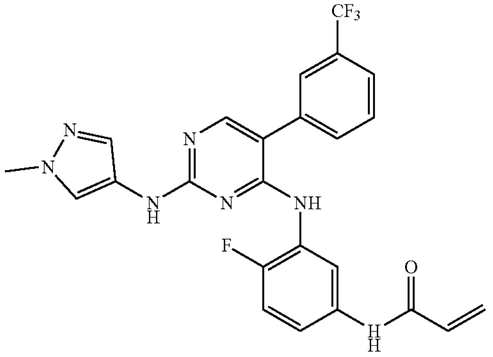

Compound 89

Step 1: Synthesis of N4-(2-fluoro-5-nitrophenyl)-N2-(1-methyl-1H-pyrazol-4-yl)-5-[3-(trifluoromethyl)phenyl]pyrimidine-2,4-diamine (141)

The title compound was prepared in a manner substantially similar to procedure mentioned in General Procedure $M_3$ to afford the desired product (141) off white solid (0.4 g, 97% yield). LCMS: $[M+H]^+$ 474.1.

Step 2: Synthesis of N4-(5-amino-2-fluorophenyl)-N2-(1-methyl-1H-pyrazol-4-yl)-5-[3-(trifluoromethyl)phenyl]pyrimidine-2,4-diamine (142)

The title compound was prepared in a manner substantially similar to procedure mentioned in General Procedure L1 to afford the desired product (142) brown liquid (0.2 g, crude). LCMS: $[M+H]^+$ 444.2.

Step 3: Synthesis of N-[4-fluoro-3-({2-[(1-methyl-1H-pyrazol-4-yl)amino]-5-[3-(trifluoromethyl)phenyl]pyrimidin-4-yl}amino)phenyl]prop-2-enamide (Compound 89)

The title compound was prepared in a manner substantially similar to procedure mentioned in General Procedure K to afford off white solid (0.13 g, crude). MH NMR (400 MHz, DMSO-d6): δ 10.22 (s, 1H), 9.40 (bs, 1H), 8.65 (bs, 1H), 7.96 (s, 1H), 7.77 (s, 2H), 7.68 (s, 2H), 7.55 (s, 2H), 7.28-7.10 (m, 3H), 6.40-6.35 (m, 1H), 6.24-6.20 (s, 1H), 5.74 (d, J=10.0 Hz, 1H), 3.53 (s, 3H). LCMS: $[M+H]^+$ 498.3.

TABLE 7

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 90 | 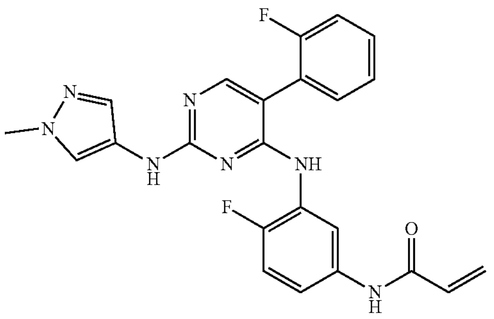 [SMILES: C=CC(=O)Nc1ccc(F)c(Nc2nc(Nc3cnn(C)c3)ncc2-c2ccccc2F)c1] | K | 448.0 | δ 10.16 (s, 1H), 9.11 (s, 1H), 8.18 (s, 1H), 7.85 (s, 1H), 7.71 (d, J = 5.2 Hz, 1H), 7.57 (bs, 1H), 7.45-7.42 (m, 2H), 7.29-7.18 (m, 5H), 6.42-6.37 (m, 1H), 6.22 (d, J = 16.4 Hz, 1H), 5.73 (d, J = 9.6 Hz, 1H), 3.54 (s, 3H). |
| 91 | 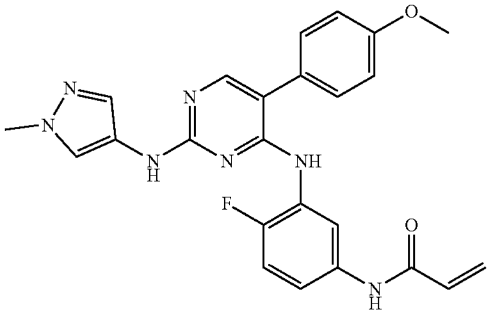 [SMILES: C=CC(=O)Nc1ccc(F)c(Nc2nc(Nc3cnn(C)c3)ncc2-c2ccc(OC)cc2)c1] | K | 460.0 | δ 10.28 (s, 1H), 9.82 (s, 1H), 9.01 (s, 1H), 7.84 (s, 2H), 7.56 (bs, 2H), 7.41 (d, J = 8.4 Hz, 2H), 7.21-7.31 (m, 2H), 7.06 (d, J = 8.4 Hz, 2H), 6.36-6.42 (m, 1H), 6.20-6.24 (m, 1H), 5.74 (d, J = 5.4 Hz, 1H), 3.79 (s, 3H), 3.36 (s, 3H). |
| 92 | 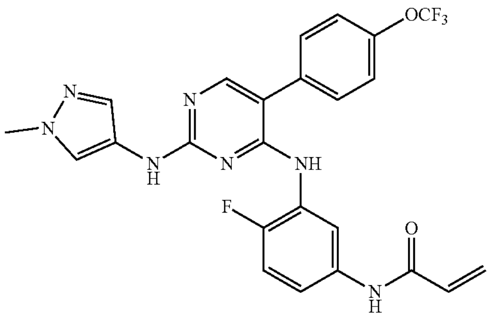 [SMILES: C=CC(=O)Nc1ccc(F)c(Nc2nc(Nc3cnn(C)c3)ncc2-c2ccc(OC(F)(F)F)cc2)c1] | K | 514.3 | δ: 10.20 (s, 1H), 9.12 (s, 1H), 8.36 (s, 1H), 7.92 (s, 1H), 7.74 (d, J = 5.2 Hz, 1H), 7.59 (d, J = 8.4 Hz, 3H), 7.42 (d, J = 8.4 Hz, 2H), 7.15-7.26 (m, 3H), 6.39 (dd, J = 11.4 Hz, J = 10.0 Hz, 1H), 6.21-6.25 (m, 1H), 5.72-5.75 (m, 1H), 3.54 (s, 3H). |

TABLE 7-continued

The following compounds were prepared using the procedures described above:

| Cmpd. No. | Structure | General Procedure | LCMS [M + H] | $^1$H-NMR (400 MHz, DMSO-d$_6$) |
|---|---|---|---|---|
| 93 | 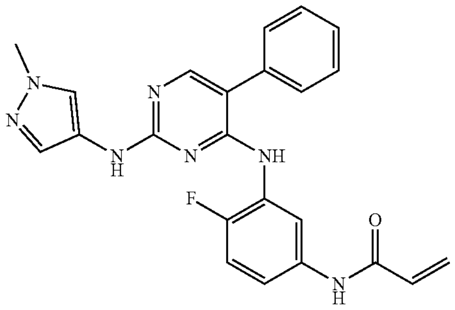 [SMILES: C=CC(=O)Nc1ccc(F)c(Nc2nc(Nc3cnn(C)c3)ncc2-c2ccccc2)c1] | K$_1$ | 430.0 | δ 10.19 (s, 1H), 9.1 (bs, 1H), 8.24 (bs, 1H), 7.9 (s, 1H), 7.6-7.53 (m, 3H), 7.49-7.43 (m, 4H), 7.36-7.33 (m, 1H), 7.26 (bs, 1H), 7.26-7.15 (m, 1H), 6.25-6.20 (m, 2H), 5.72 (d, J = 1.6 Hz, 1H), 3.53 (s, 3H). |
| 94 | 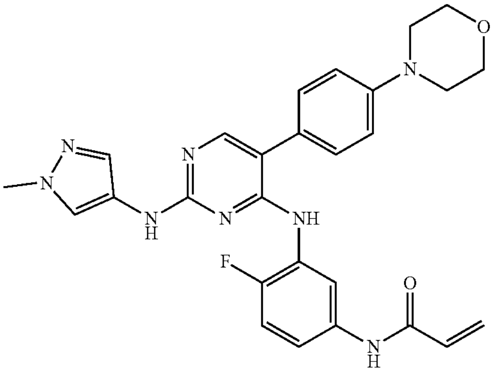 | K$_1$ | 515.6 | δ 10.15 (s, 1H), 8.97 (s, 1H), 8.01 (s, 1H), 7.83 (d, J = 18.0 Hz, 2H), 7.55 (s, 1H), 7.34-7.22 (m, 5H), 7.03 (d, J = 8.4 Hz, 2H), 6.43-6.36 (m, 1H), 6.22 (d, J = 16.4 Hz, 1H), 5.73 (d, J = 11.6 Hz, 1H), 3.74 (t, J = 3.6 Hz, 3H), 3.55 (s, 4H), 3.14 (d, J = 4.4 Hz, 4H). |
| 95 | 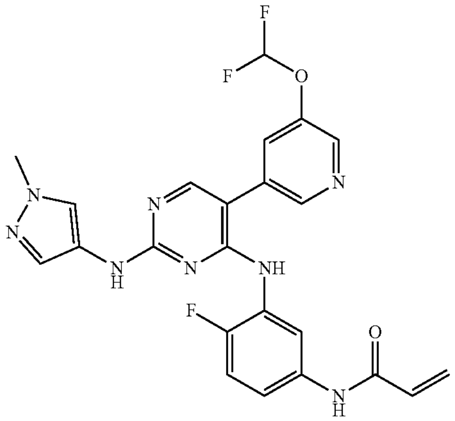 [SMILES: C=CC(=O)Nc1ccc(F)c(Nc2nc(Nc3cnn(C)c3)ncc2-c2cncc(OC(F)F)c2)c1] | K$_1$ | 497.3 | δ 10.20 (s, 1H), 9.27 (s, 1H), 8.60-8.56 (m, 2H), 8.44 (s, 1H), 7.99 (s, 1H), 7.74 (s, 2H), 7.57-7.54 (m, 1H), 7.36-7.17 (m, 4H), 6.43-6.37 (m, 1H), 6.23 (d, J = 16.8 Hz, 1H), 5.74 (d, J = 10.4 Hz, 1H), 3.54 (s, 3H). |
| 96 | 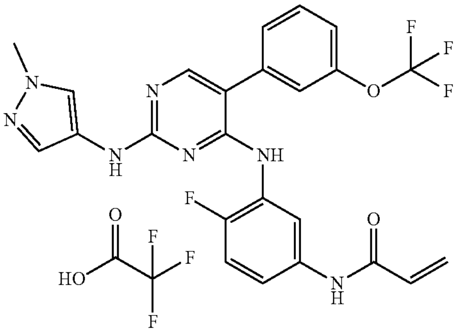 | K$_1$ | 514.4 | δ 10.27 (s, 1H), 9.84 (bs, 1H), 9.23 (bs, 1H), 7.98 (s, 1H), 7.84 (d, J = 4.0 Hz, 1H), 7.58 (m, 4H), 7.42 (d, J = 4.0 Hz, 1H), 7.25-7.35 (m, 3H), 7.16 (s, 1H), 6.45-6.38 (m, 1H), 6.25 (d, J = 20.0 Hz, 1H), 5.75-5.73 (d, J = 2.0 Hz, 1H, 3.59 (bs, 3H). |

Scheme 32: Synthesis of N-(4-fluoro-3-{[5-(1H-indol-5-yl)-2-[(1-methyl-1H-pyrazol-4-yl)amino]pyrimidin-4-yl)]amino}phenyl)prop-2-enamide (Compound 97)

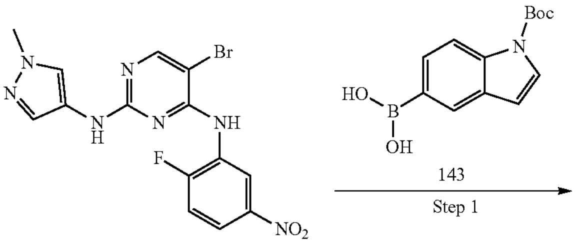

137

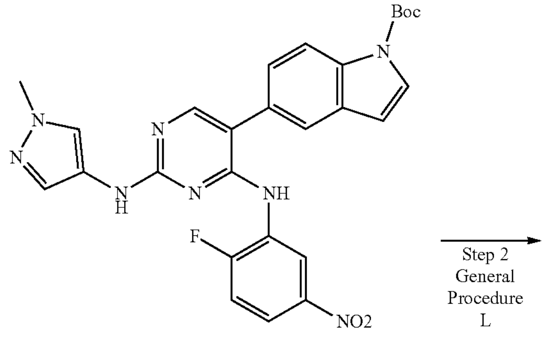

144

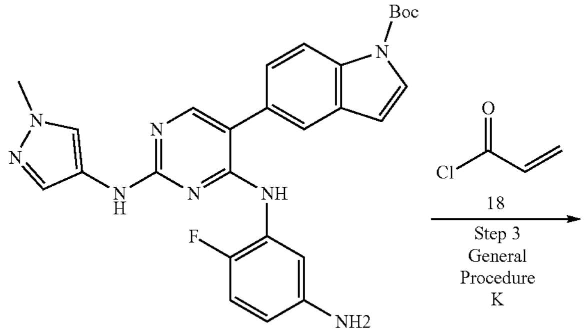

145

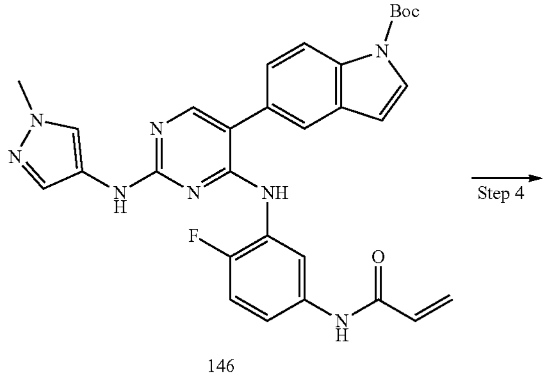

146

-continued

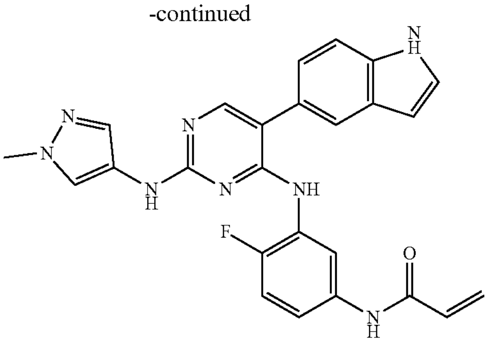

Compound 97

Step 1: Synthesis of tert-butyl 5-{4-[(2-fluoro-5-nitrophenyl)amino]-2-[(1-methyl-1H-pyrazol-4-yl)amino]pyrimidin-5-yl}-1H-indole-1-carboxylate (144)

To a stirred solution of 5-bromo-N4-(2-fluoro-5-nitrophenyl)-N2-(1-methyl-1H-pyrazol-4-yl)pyrimidine-2,4-diamine (137) (0.35 g, 0.85 mmol) in 1,4-dioxane (4.50 mL), water (0.5 mL) were added cesium carbonate (0.83 g, 2.57 mmol) and {1-[(tert-butoxy)carbonyl]-1H-indol-5-yl}boronic acid (143) (0.269 g, 1.2 eq., 1.03 mmol). Then the reaction mixture was purged with nitrogen for 5 minutes, added [1,1'-Bis(diphenylphosphino)ferrocene]dichloropalladium(II) (0.7 g, 0.085 mmol) and the reaction mixture was heated at 100° C. for 16 hours. The progress of the reaction was monitored by TLC/LCMS. The reaction mixture was diluted with water (20 mL) and extracted with ethyl acetate (20 mL×3). The combined organic layer was washed with water (25 mL×2), brine (25 mL), dried over anhydrous sodium sulfate and evaporated. The crude product was purified by column chromatography using combiflash purifier and was eluted with 40-60% ethyl acetate in hexane to afford the title compound (144) as pale yellow solid. LCMS: $[M+H]^+$ 545.2.

Step 2: Synthesis of tert-butyl 5-{4-[(5-amino-2-fluorophenyl)amino]-2-[(1-methyl-1H-pyrazol-4-yl)amino]pyrimidin-5-yl}-1H-indole-1-carboxylate (145)

The title compound was prepared in a manner substantially similar to procedure mentioned in General Procedure L to afford the desired product (145) brown solid (0.2 g, crude). LCMS: $[M+H]^+$ 515.2.

Step 3: Synthesis of tert-butyl 5-(4-{[2-fluoro-5-(prop-2-enamido)phenyl]amino}-2-[(1-methyl-1H-pyrazol-4-yl)amino]pyrimidin-5-yl)-1H-indole-1-carboxylate (146)

The title compound was prepared in a manner substantially similar to procedure mentioned in General Procedure K to afford the desired product (146) white solid (0.19 g). LCMS: $[M+H]^+$ 569.3.

Step 4: Synthesis of N-(4-fluoro-3-{[5-(1H-indol-5-yl)-2-[(1-methyl-1H-pyrazol-4-yl)amino]pyrimidin-4-yl]amino}phenyl)prop-2-enamide (Compound 97)

To a stirred solution of tert-butyl 5-(4-{[2-fluoro-5-(prop-2-enamido)phenyl]amino}1-2-[(1-methyl-1H-pyrazol-4-yl)

amino]pyrimidin-5-yl)-1H-indole-1-carboxylate (0.15 g, 0.264 mmol) in dichloromethane (10.0 mL) was added trifluoroacetic acid (1.00 mL) and stirred for 2 hours at room temperature. Progress of the reaction was monitored by LCMS/TLC. Then the reaction mixture was concentrated under reduced pressure. The crude compound was purified by Prep HPLC to afford the title compound (0.05 g, 0.107 mmol) as pale brown solid. $^1$H NMR (400 MHz, DMSO-d6): δ11.24 (s, 1H), 10.6 (s, 1H), 9.99 (s, 1H), 9.38 (s, 1H), 7.88 (s, 2H), 7.77 (s, 1H), 7.67-7.43 (m, 2H), 7.33 (s, 1H), 7.27 (s, 2H), 7.18 (d, J=8.0 Hz, 2H), 6.51 (s, 1H), 6.42-6.24 (m, 1H), 6.21 (s, 1H), 5.76-5.73 (m, 1H), 3.53 (s, 3H). LCMS: $[M+H]^+$ 469.3.

TABLE 8

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 98 | 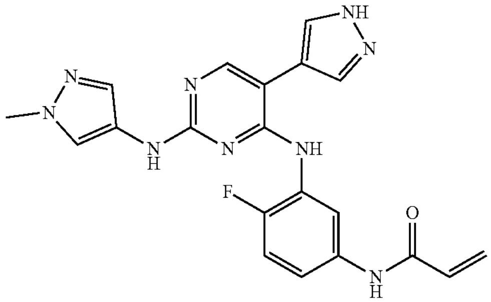 [SMILES: C=CC(=O)Nc1ccc(F)c(Nc2nc(Nc3cnn(C)c3)ncc2-c2cn[nH]c2)c1] | K | 420.2 | δ 13.00 (s, 1H), 10.20 (s, 1H), 8.91 (s, 1H), 7.99 (s, 2H), 7.82 (s, 1H), 7.71 (s, 1H), 7.58 (s, 1H), 7.15-7.25 (m, 3H), 6.36-6.43 (m, 2H), 6.22 (d, J = 8.4 Hz, 1H), 5.73 (d, J = 10.0 Hz, 1H), 3.53 (s, 3H). |
| 99 | 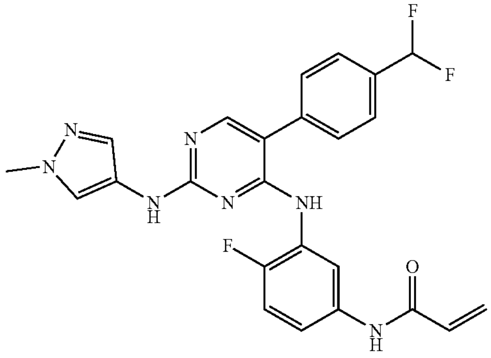 | K | 480.3 | δ 10.22 (s, 1H), 9.19 (bs, 1H), 8.43 (bs, 1H), 7.94 (s, 1H), 7.75 (d, J = 5.2 Hz, 1H), 7.63 (t, J = 8.8 Hz, 4H), 7.57 (s, 1H), 7.27 (s, 1H), 7.21-6.93 (m, 3H), 6.24-6.43 (m, 1H), 6.20 (d, J = 4.8 Hz, 1H), 5.72-5.74 (m, 1H), 3.52 (s, 3H). |
| 100 | 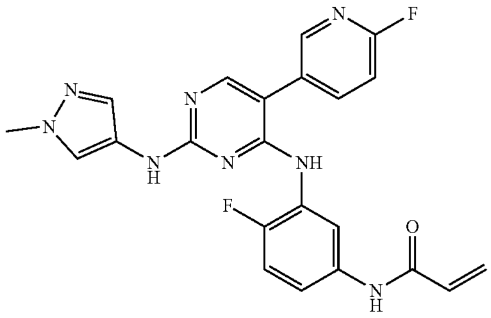 [SMILES: C=CC(=O)Nc1ccc(F)c(Nc2nc(Nc3cnn(C)c3)ncc2-c2ccc(F)nc2)c1] | $K_1$ | 449.2 | δ 10.23 (s, 1H), 9.61 (s, 1H), 8.94 (s, 1H), 8.31 (s, 1H), 8.06 (s, 1H), 7.94 (s, 1H), 7.79 (s, 1H), 7.54 (s, 1H), 7.29-7.27 (m, 4H), 6.43-6.36 (m, 1H), 6.23 (d, J = 17.2 Hz, 1H), 5.74 (d, J = 10.0 Hz, 1H), 3.56 (s, 3H). |
| 101 | 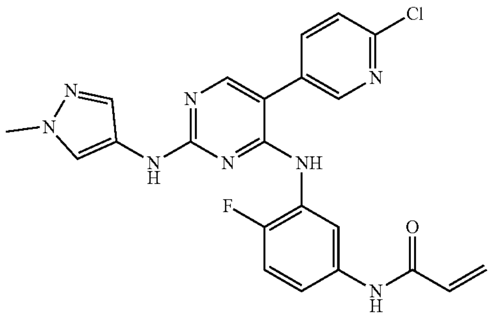 | $K_1$ | 465.3 | δ 10.19 (s, 1H), 9.21 (s, 1H), 8.49 (s, 1H), 7.94 (s, 2H), 7.72 (s, 1H), 7.56 (d, J = 8.4 Hz, 2H), 7.27-7.15 (m, 4H), 6.41-6.36 (m, 1H), 6.23 (d, J = 17.2 Hz, 1H), 5.73 (d, J = 10.0 Hz, 1H), 3.54 (s, 3 H). |

TABLE 8-continued
| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 102 | 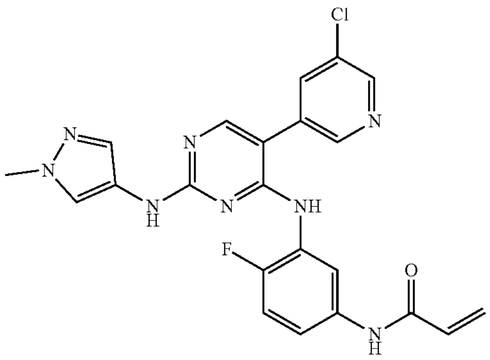 [SMILES: C=CC(=O)Nc1ccc(F)c(Nc2nc(Nc3cnn(C)c3)ncc2-c2cncc(Cl)c2)c1] | K | 465.09 | δ 10.25 (bs, 1H), 9.31 (bs, 1H), 8.69 (s, 1H), 8.58-8.61 (m, 2H), 7.99-8.00 (m, 2H), 7.75-7.76 (m, 1H), 7.57 (s, 1H), 7.31 (s, 1H), 7.01-7.16 (m, 2H), 6.37-6.44 (m, 1H), 6.21-6.26 (m, 1H), 5.74 (d, J = 10.0 Hz, 1H), 3.54 (s, 3H). |
| 103 | 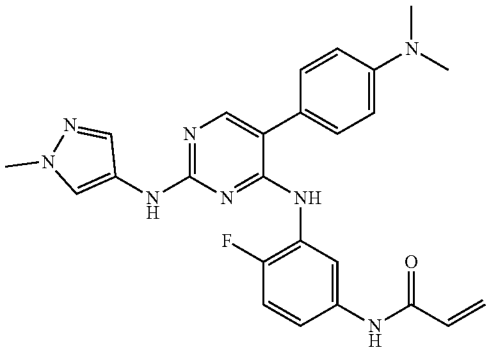 | K | 473.00 | δ 10.19 (bs, 1H), 8.99 (bs, 1H), 7.97 (s, 1H), 7.85 (s, 2H), 7.58 (s, 1H), 7.09-7.31 (m, 5H), 6.83 (d, J = 8.8 Hz, 2H), 6.38-6.45 (m, 1H), 6.22-6.26 (m, 1H), 5.74 (d, J = 10.0 Hz, 1H), 3.56 (s, 3H), 2.94 (s, 6H). |
| 104 | 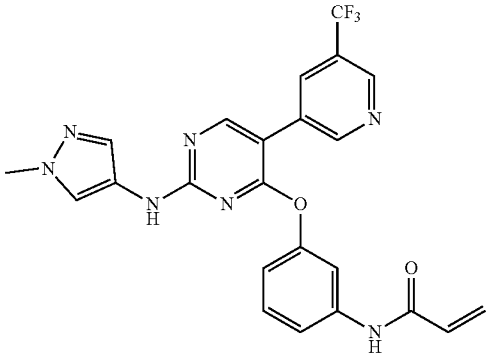 | K | 482.16 | δ 10.38 (bs, 1H), 9.92 (bs, 1H), 9.23 (s, 1H), 8.93 (s, 1H), 8.62 (s, 1H), 8.51 (s, 1H), 7.73 (s, 1H), 7.63-7.65 (m, 1H), 7.50-7.53 (m, 1H), 7.07-7.12 (m, 2H), 6.88 (s, 1H), 6.39-6.44 (m, 1H), 6.23-6.27 (m, 1H), 5.75 (d, J = 10.0 Hz, 1H), 3.51 (s, 3H) |
| 105 | 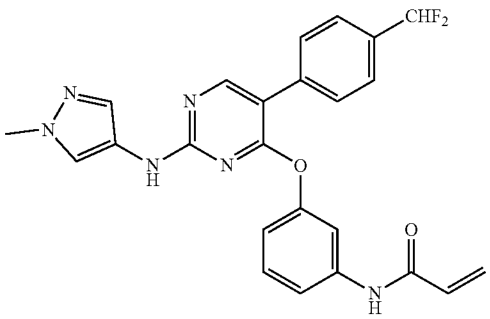 [SMILES: C=CC(=O)Nc1cccc(Oc2nc(Nc3cnn(C)c3)ncc2-c2ccc(C(F)F)cc2)c1] | K | 463.02 | δ 10.37 (bs, 1H), 9.77 (bs, 1H), 8.48 (s, 1H), 7.83-7.85 (m, 2H), 7.62-7.70 (m, 4H), 7.50 (s, 1H), 6.93-7.21 (m, 3H), 6.86 (s, 1H), 6.39-6.45 (m, 1H), 6.22-6.27 (m, 1H), 5.75 (d, J = 10.0 Hz, 1H), 3.50 (s, 3H) |

TABLE 8-continued
The following compounds were prepared using the procedures described above:
| Cmpd. No. | Structure | General Procedure | LCMS [M + H] | $^1$H-NMR (400 MHz, DMSO-$d_6$) |
|---|---|---|---|---|
| 106 | 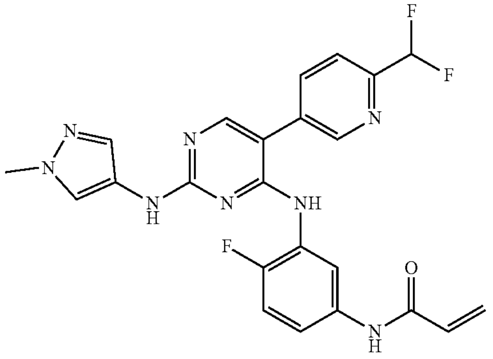 [SMILES: C=CC(=O)Nc1ccc(F)c(Nc2nc(Nc3cnn(C)c3)ncc2-c2ccc(C(F)F)nc2)c1] | K | 481.3 | δ 10.20 (s, 1H), 9.26 (bs, 1H), 8.76 (s, 1H), 8.64 (bs, 1H), 8.08 (d, J = 8.0 Hz, 1H), 7.99 (s, 1H), 7.75 (d, J = 16.8 Hz, 2H), 7.55 (bs, 1H), 6.85-7.28 (m, 4H), 6.36-6.43 (m, 1H), 6.23 (d, J = 16.8 Hz, 1H), 5.73 (d, J = 10.0 Hz, 1H), 3.54 (s, 3H) |
| 107 | 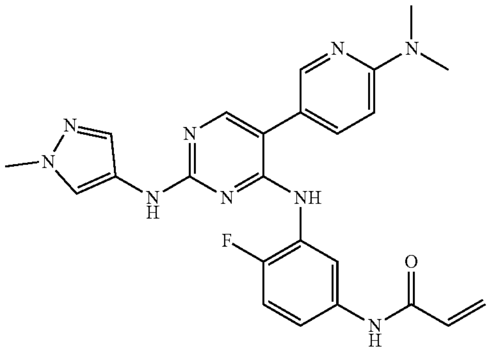 | K | 474.06 | δ 9.99 (bs, 1H), 9.17 (bs, 1H), 8.33 (d, J = 4.0 Hz, 1H), 7.98-8.14 (m, 4H), 7.53 (d, J = 8.8 Hz, 2H), 7.34 (d, J = 6.8 Hz, 2H), 7.13 (d, J = 8.40 Hz, 1H), 6.42-6.48 (m, 1H), 6.20-6.25 (m, 1H), 5.73 (d, J = 10 Hz, 1H), 3.62 (s, 3H), 2.48 (s, 6H). |
| 108 | 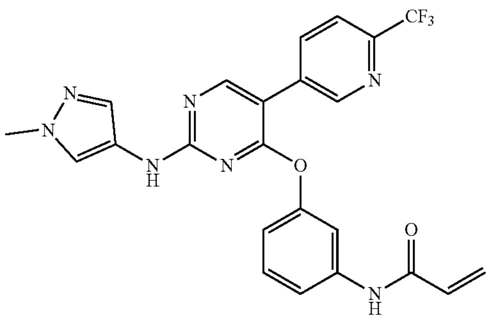 [SMILES: C=CC(=O)Nc1cccc(Oc2nc(Nc3cnn(C)c3)ncc2-c2ccc(C(F)(F)F)nc2)c1] | K | 481.99 | δ 10.39 (bs, 1H), 9.94 (bs, 1H), 9.11 (s, 1H), 8.62 (s, 1H), 8.42 (d, J = 8.0 Hz, 1H), 7.43-8.01 (m, 4H), 7.06-7.12 (m, 2H), 6.88 (s, 1H), 6.39-6.46 (m, 1H), 6.23-6.27 (m, 1H), 5.75 (d, J = 10.4 Hz, 1H), 3.51 (s, 3H) |
| 109 | 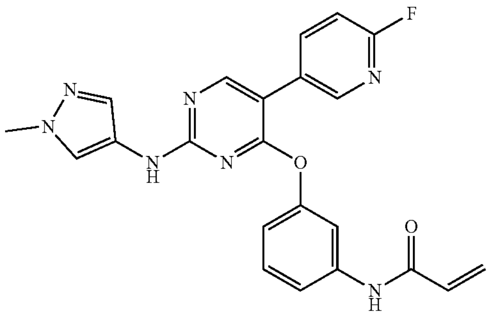 [SMILES: C=CC(=O)Nc1cccc(Oc2nc(Nc3cnn(C)c3)ncc2-c2ccc(F)nc2)c1] | K | 432.03 | δ 10.38 (bs, 1H), 9.81 (bs, 1H), 8.32-8.54 (m, 3H), 6.87-7.61 (m, 7H), 6.39-6.46 (m, 1H), 6.23-6.27 (m, 1H), 5.75 (d, J = 10.4 Hz, 1H), 3.50 (s, 3H) |

TABLE 8-continued
The following compounds were prepared using the procedures described above:
| Cmpd. No. | Structure | General Procedure | LCMS [M + H] | $^1$H-NMR (400 MHz, DMSO-$d_6$) |
| --- | --- | --- | --- | --- |
| 110 | 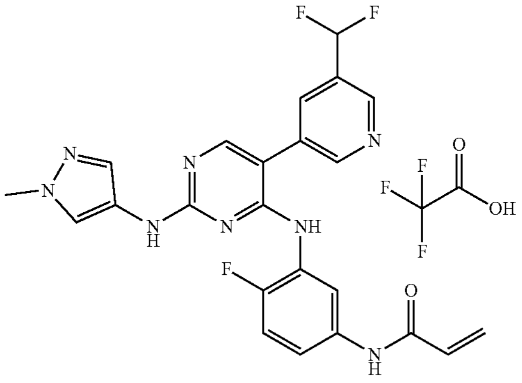 | $K_1$ | 481.3 | δ 10.29 (s, 1H), 9.91 (bs, 2H), 9.37 (bs, 1H), 8.83 (d, J = 10.4 Hz, 2H), 8.10 (s, 1H), 8.03 (s, 1H), 7.83 (s, 1H), 7.56 (s, 1H), 7.34-6.94 (m, 4H), 6.43-6.36 (m, 1H), 6.23 (d, J = 16.0 Hz, 1H), 5.75 (d, J = 11.6 Hz, 1H), 3.56 (s, 3H) |
| 111 | 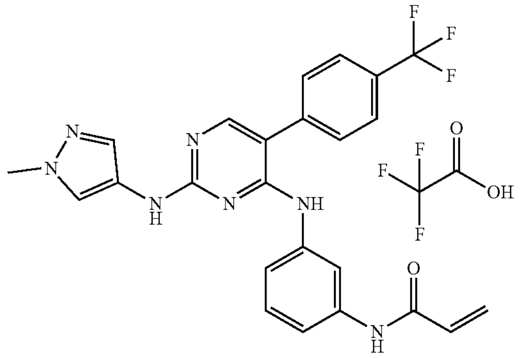 | $K_1$ | 480.3 | δ 10.2 (s, 1H), 9.81 (bs, 1H), 9.32 (bs, 1H), 7.96-7.74 (m, 6H), 7.47-7.37 (m, 4H), 7.21-6.95 (m, 2H), 6.48-6.41 (m, 1H), 6.25 (d, J = 16.8 Hz, 1H), 5.76 (d, J = 9.6 Hz, 1H), 3.26 (s, 3H) |
| 112 | 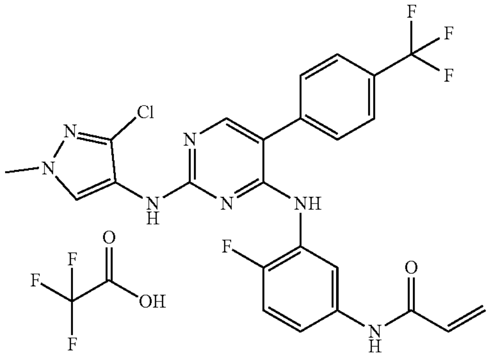 | K | 532.2 | δ 10.20 (s, 1H), 8.70 (bs, 2H), 8.00 (s, 1H), 7.84-7.72 (m, 6H), 7.55-7.53 (m, 1H), 7.31-7.26 (m, 2H), 6.45-6.38 (m, 1H), 6.28-6.23 (m, 1H), 5.78-5.75 (m, 1H), 3.60 (s, 3H) |
| 113 | 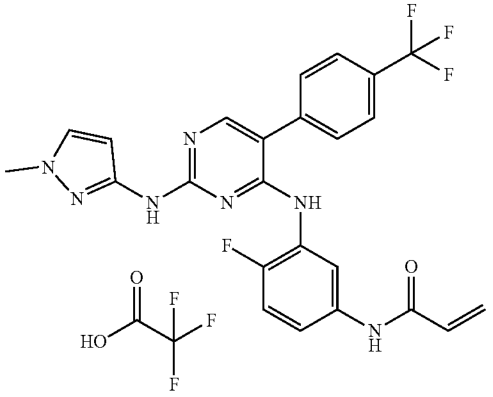 | K | 498.2 | δ 10.23 (s, 1H), 9.38 (bs, 1H), 8.32 (bs, 1H), 8.02 (s, 1H), 7.96 (d, J = 7.6 Hz, 1H), 7.68-7.89 (m, 4H), 7.49-7.66 (m, 2H), 7.06-7.25 (m, 1H), 7.20-6.94 (m, 1H), 6.35-6.42 (m, 1H), 6.23 (dd, J = 17.2 Hz, 2.0 Hz, 1H), 5.93 (s, 1H), 5.75 (dd, J = 10.0 Hz, 2.0 Hz, 1H), 3.70 (s, 3H). |

TABLE 8-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 114 | 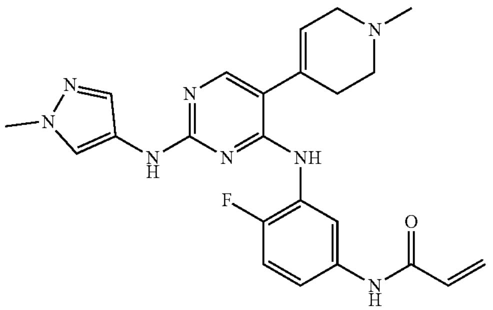 [SMILES: C=CC(=O)Nc1ccc(F)c(Nc2nc(Nc3cnn(C)c3)ncc2C2=CCN(C)CC2)c1] | K | 449.2 | δ 10.20 (s, 1H), 8.93 (s, 1H), 8.08 (s, 1H), 7.83-7.80 (m, 2H), 7.60-7.58 (m, 1H), 7.28 (t, J = 9.2 Hz, 1H), 7.18 (bs, 2H), 6.46-6.39 (m, 1H), 6.28-6.23 (m, 1H), 5.80-5.75 (m, 2H), 3.56 (s, 3H), 3.00 (s, 2H), 2.58-2.55 (m, 2H), 2.38 (s, 2H), 2.23 (s, 3H) |
| 115 | 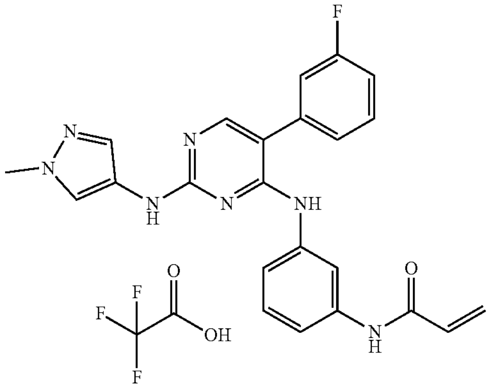 | K | 430.5 | 10.16 (bs, 1H), 9.17 (bs, 1H), 8.14 (bs, 1H) 7.93 (s, 1H), 7.77 (s, 1H), 7.48-7.74 (m, 3H), 7.29-7.18 (m, 7H), 6.39-6.45 (m, 1H), 6.22 (d, J = 16.6 Hz, 1H), 5.73 (d, J = 11.2 Hz, 1H), 3.56 (s, 3H). |
| 116 | 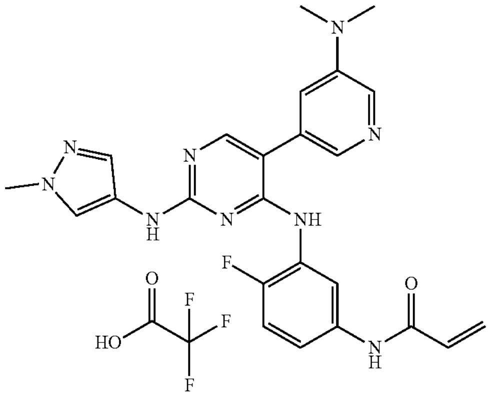 | $K_1$ | 474.3 | 10.30 (bs, 1H), 9.74 (bs, 1H), 9.04 (bs, 1H), 8.17 (d, J = 10.8 Hz, 2H), 8.08 (bs, 1H), 7.87 (s, 1H), 7.73 (bs, 1H), 7.53 (bs, 1H), 7.34 (bs, 1H), 7.18-7.14 (m, 2H), 7.08-6.95 (m, 1H), 6.43-6.37 (m, 1H), 6.23 (d, J = 16.0 Hz, 1H), 5.75 (d, J = 11.2 Hz, 1H), 3.54 (s, 3H), 3.09 (s, 6H). |
| 117 | 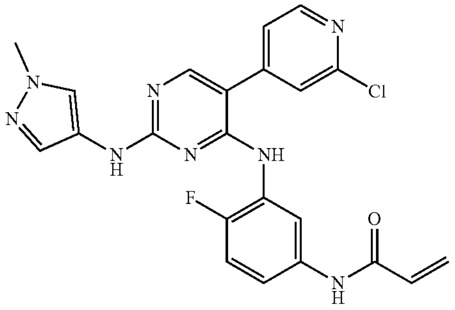 [SMILES: C=CC(=O)Nc1ccc(F)c(Nc2nc(Nc3cnn(C)c3)ncc2-c2ccnc(Cl)c2)c1] | $K_1$ | 465.0 | δ 10.31 (s, 1H), 9.91 (s, 1H), 9.31 (s, 1H), 8.76 (d, J = 5.2 Hz, 1H), 8.09 (s, 1H), 7.61 (d, J = 34.8 Hz, 3H), 7.27-7.15 (m, 4H), 6.41-6.36 (m, 1H), 6.23 (d, J = 17.2 Hz, 1H), 5.73 (d, J = 10.0 Hz, 1H), 3.67 (s, 3H) |

TABLE 8-continued
The following compounds were prepared using the procedures described above:
| Cmpd. No. | Structure | General Procedure | LCMS [M + H] | $^1$H-NMR (400 MHz, DMSO-$d_6$) |
|---|---|---|---|---|
| 118 | 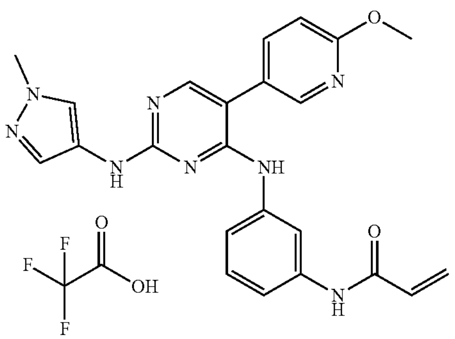 | $K_1$ | 443.3 | δ 10.24 (s, 2H), 9.57 (bs, 1H), 8.28 (s, 1H), 7.90-7.81 (m, 3H), 7.51-6.95 (m, 7H), 6.48-6.41 (m, 1H), 6.27-6.23 (m, 1H), 5.78-5.75 (m, 1H), 3.97 (s, 6H). |
| 119 | 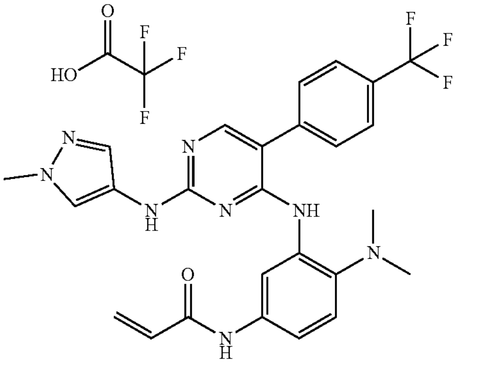 | $K_1$ | 523.2 | δ 10.14 (bs, 2H), 9.10 (bs, 1H), 7.99-7.26 (m, 11H), 6.44-6.37 (m, 1H), 6.21 (d, J = 16.0 Hz, 1H), 5.74 (d, J = 11.2 Hz, 1H), 3.57 (s, 3H), 2.48 (s, 6H, merged with DMSO). |
| 120 | 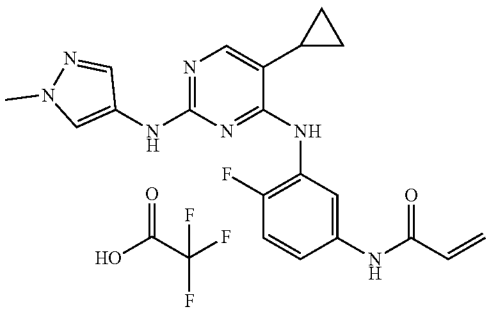 | $K_1$ | 394.2 | δ 10.23 (s, 1H), 8.90 (s, 1H), 8.35 (s, 1H), 7.86-7.84 (m, 1H), 7.83 (s, 1H), 7.60 (s, 1H), 7.32-7.27 (m, 4H), 6.43-6.37 (m, 1H), 6.26-6.21 (m, 1H), 5.76-5.73 (m, 1H), 3.53 (s, 3H), 1.69-1.62 (m, 1H), 0.88-0.84 (m, 2H), 0.56-0.52 (m, 2H). |
| 121 | 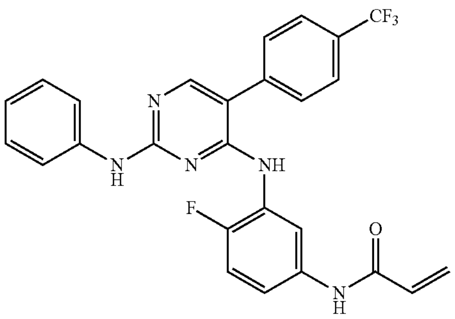 [SMILES: C=CC(=O)Nc1ccc(F)c(Nc2nc(Nc3ccccc3)ncc2-c2ccc(C(F)(F)F)cc2)c1] | K | 493.93 | δ 10.22 (s, 1H), 9.67 (s, 1H), 9.02 (bs, 1H), 8.06 (s, 1H), 7.87-7.77 (m, 5H), 7.53-7.52 (m, 1H), 7.46 (d, J = 8.0 Hz, 2H), 7.29 (t, J = 8.0 Hz, 2H), 7.08 (t, J = 8.0 Hz, 2H), 6.90-6.87 (m, 1H), 6.43-6.36 (m, 1H), 6.25-6.21 (m, 1H), 5.73 (d, J = 10.0 Hz, 1H) |

TABLE 8-continued
| Cmpd. No. | Structure | General Procedure | LCMS [M + H] | $^1$H-NMR (400 MHz, DMSO-$d_6$) |
|---|---|---|---|---|
| | The following compounds were prepared using the procedures described above: | | | |
| 122 | 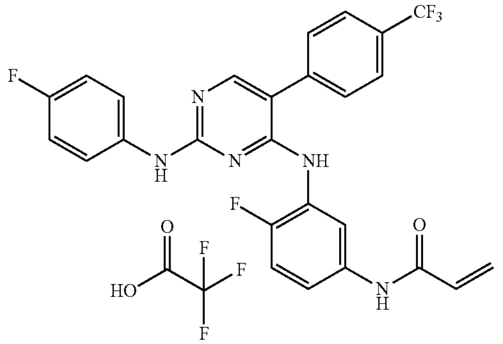 | K | 512.24 | δ 10.22 (s, 1H), 9.70 (s, 1H), 9.02 (bs, 1H), 8.05 (s, 1H), 7.86-7.74 (m, 5H), 7.47-7.29 (m, 5H), 6.89 (t, J = 8.4 Hz, 2H), 6.43-6.36 (m, 1H), 6.25-6.21 (m, 1H), 5.73 (d, J = 10.0 Hz, 1H) |
| 123 | 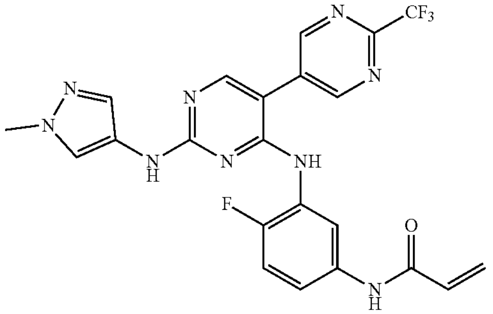 | K | 500.23 | δ 10.29 (s, 1H), 9.78 (s, 1H), 9.17-9.23 (m, 3H), 8.12 (s, 1H), 7.79-7.85 (m, 1H), 7.56 (bs, 1H), 7.35-7.38 (m, 1H), 7.16-7.23 (m, 2H), 6.38-6.44 (m, 1H), 6.22-6.27 (m, 1H), 5.77 (d, J = 10.0 Hz, 1H), 3.56 (s, 3H) |
| 124 | 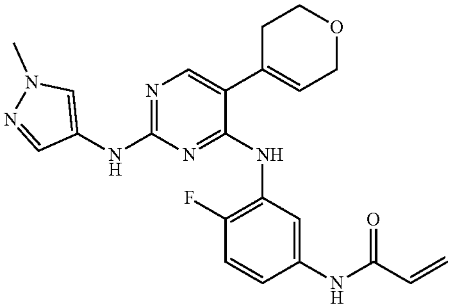 [SMILES: C=CC(=O)Nc1ccc(F)c(Nc2nc(Nc3cnn(C)c3)ncc2C2=CCOCC2)c1] | K | 436.18 | δ 10.23 (bs, 1H), 9.01 (bs, 1H), 8.24 (s, 1H), 7.82-7.79 (m, 2H), 7.58 (s, 1H), 7.32-7.04 (m, 3H), 6.45-6.38 (m, 1H), 6.27-6.23 (m, 1H), 5.88 (s, 1H), 5.74 (d, J = 11.2 Hz, 1H), 4.19 (s, 2H), 3.84-3.81 (m, 2H), 3.54 (s, 3H), 2.34 (s, 2H) |
| 125 | 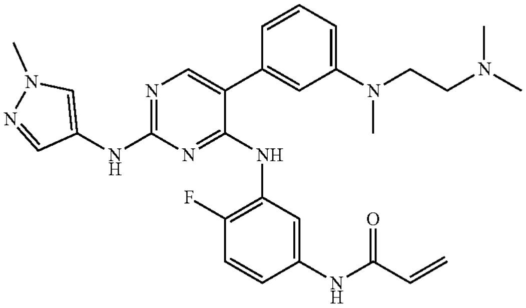 [SMILES: C=CC(=O)Nc1ccc(F)c(Nc2nc(Nc3cnn(C)c3)ncc2-c2cccc(N(C)CCN(C)C)c2)c1] | K | 530.2 | δ 10.31 (bs, 1H), 10.10 (bs, 1H), 9.59 (bs, 1H), 9.11 (s, 1H), 8.03 (s, 2H), 7.89 (s, 1H), 7.34-7.48 (m, 2H), 7.20 (s, 1H), 6.84-6.88 (m, 3H), 6.40-6.46 (m, 1H), 6.23-6.28 (dd, J = 18.8 Hz, 1.6 Hz, 1H), 5.76-5.79 (dd, J = 12.0 Hz, 1.6 Hz, 1H), 3.79 (t, J = 6.8 Hz, 2H), 3.60 (s, 3H), 3.28 (bs, 2H), 3.03 (s, 3H), 2.81 (s, 6H). |

TABLE 8-continued
The following compounds were prepared using the procedures described above:
| Cmpd. No. | Structure | General Procedure | LCMS [M + H] | $^1$H-NMR (400 MHz, DMSO-$d_6$) |
|---|---|---|---|---|
| 126 | 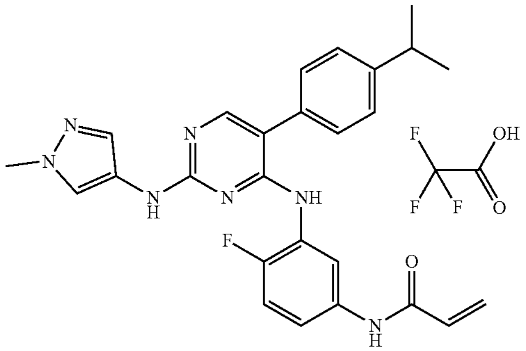 | $K_2$ | 472.2 | δ 10.29 (s, 1H), 10.00 (bs, 1H), 9.35 (bs, 1H), 7.89 (bs, 1H), 7.89-7.83 (m, 2H), 7.57 (s, 1H), 7.44-7.34 (m, 4H), 7.22 (s, 1H), 7.09 (m, 2H), 6.36-6.26 (m, 1H), 6.25-6.21 (m, 1H), 5.77-5.74 (m, 1H), 3.56 (s, 3H), 3.15-2.90 (m, 1H), 2.25 (s, 3H), 1.23 (s, 3H) |
| 127 | 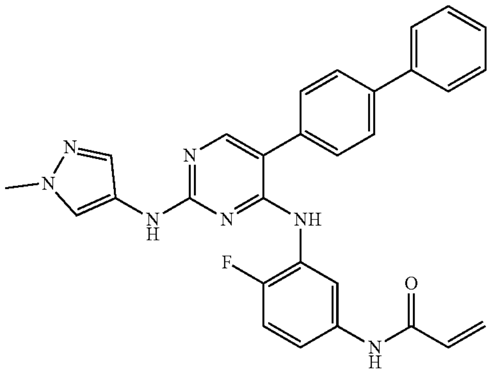 [SMILES: C=CC(=O)Nc1ccc(F)c(Nc2nc(Nc3cnn(C)c3)ncc2-c2ccc(-c3ccccc3)cc2)c1] | $K_2$ | 506.2 | δ 10.19 (s, 1H), 9.14 (bs, 1H), 8.37 (bs, 1H), 7.96 (s, 1H), 7.77-7.69 (m, 4H), 7.60-7.58 (m, 3H), 7.49-7.46 (m, 2H), 7.38-7.34 (m, 1H), 7.27 (s, 2H), 7.15 (bs, 2H), 6.43-6.36 (m, 1H), 6.25-6.20 (m, 1H), 5.75-5.73 (m, 1H), 3.54 (s, 3H). |
| 128 | 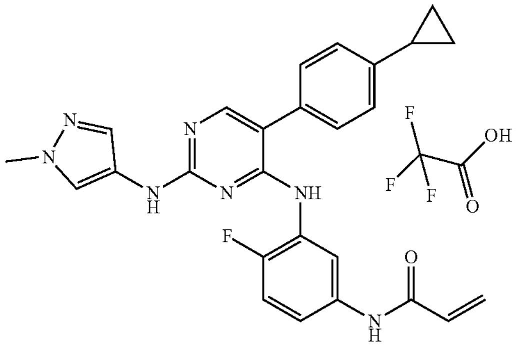 | $K_2$ | 470.2 | δ 10.20 (s, 1H), 9.09 (bs, 1H), 9.16 (bs, 1H), 7.78-7.76 (m, 2H), 7.51 (m, 1H), 7.27 (s, 1H), 7.33-7.25 (m, 3H), 7.16-7.07 (m, 4H), 6.37-6.31 (m, 1H), 6.20-6.17 (m, 1H), 5.71-5.68 (m, 1H), 3.52 (s, 3H), 1.95-1.82 (m, 1H), 0.95-0.91 (m, 2H), 0.69-0.63 (m, 2H). |
| 129 | 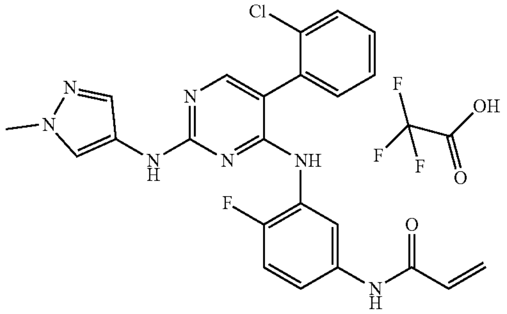 | $K_2$ | 464.1 | δ 10.26 (s, 1H), 9.81 (bs, 1H), 9.02 (bs, 1H), 7.89 (s, 1H), 7.81 (dd, J = 4.8 Hz, 1H), 7.63-7.61 (m, 2H), 7.52-7.47 (m, 4H), 7.33-7.08 (m, 3H), 6.44-6.37 (m, 1H), 6.27-6.23 (m, 1H), 5.78-5.75 (m, 1H), 3.58 (s, 3H). |

TABLE 8-continued
The following compounds were prepared using the procedures described above:
| Cmpd. No. | Structure | General Procedure | LCMS [M + H] | $^1$H-NMR (400 MHz, DMSO-$d_6$) |
| --- | --- | --- | --- | --- |
| 130 | 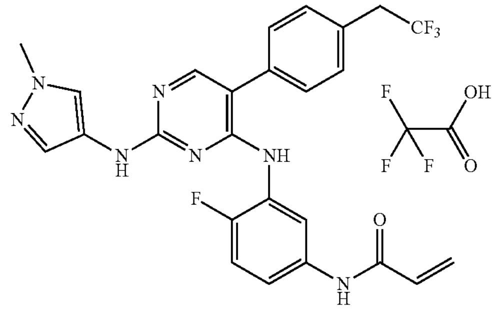 | $K_2$ | 512.2 | δ 10.26 (s, 1H), 9.8-6.69 (m, 1H), 9.29-9.06 (m, 1H), 7.9-7.8 (m, 2H), 7.58-7.49 (m, 5H), 7.34-7.12 (m, 4H), 6.45-6.23 (m, 2H), 5.77 (dd, J = 16.5 Hz, 1.6 Hz, 1H), 3.73 (q, J = 11.6 Hz, 2H), 3.59 (s, 3H). |
| 131 | 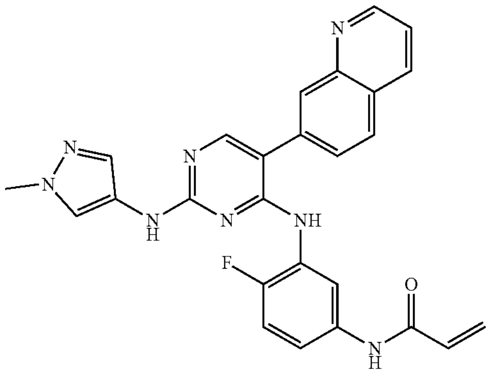 [SMILES: C=CC(=O)Nc1ccc(F)c(Nc2nc(Nc3cnn(C)c3)ncc2-c2ccc3cccnc3c2)c1] | $K_2$ | 481.2 | δ 10.20 (s, 1H), 9.20 (bs, 1H), 8.93 (m, 1H), 8.52 (s, 1H), 8.40 (d, J = 7.6 Hz, 1H), 8.12-8.06 (m, 3H), 7.79-7.73 (m, 2H), 7.59-7.53 (m, 2H), 7.30 (bs, 2H), 7.21 (bs, 1H), 6.45-6.38 (m, 1H), 6.27-6.22 (m, 1H), 5.76-5.73 (m, 1H), 3.58 (s, 3H). |
| 132 | 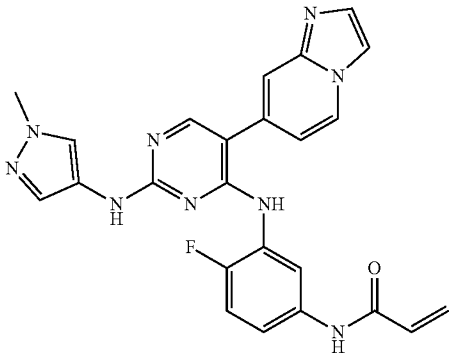 [SMILES: C=CC(=O)Nc1ccc(F)c(Nc2nc(Nc3cnn(C)c3)ncc2-c2ccn3ccnc3c2)c1] | $K_2$ | 470.15 | δ 10.21 (bs, 1H), 9.21 (bs, 1H), 8.60 (d, J = 4.4 Hz, 1H), 8.52 (bs, 1H), 8.05 (s, 1H), 7.97 (s, 1H), 7.78-7.75 (m, 1H), 7.63-7.48 (m, 4H), 7.30-7.02 (m, 2H), 7.02-7.00 (m, 1H), 6.45-6.38 (m, 1H), 6.27-6.22 (m, 1H), 5.77-5.74 (m, 1H), 3.57 (s, 3H). |
| 133 | 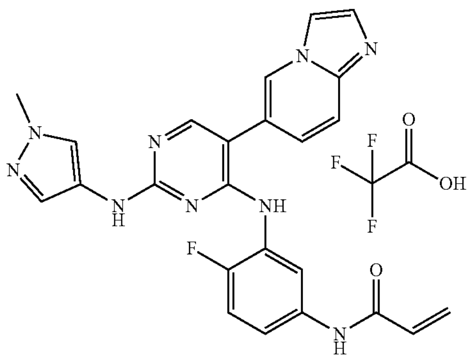 | $K_2$ | 470.2 | δ 10.23 (s, 1H), 9.21 (bs, 1H), 8.64 (bs, 1H), 8.54 (s, 1H), 7.98 (d, J = 4.8 Hz, 2H), 7.44 (t, J = 6.8 Hz, 1H), 7.65-7.56 (m, 3H), 7.29-7.18 (m, 5H), 6.45-6.38 (m, 1H), 6.27-6.22 (m, 1H), 5.77-5.74 (m, 1H), 3.56 (bs, 3H). |

TABLE 8-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 134 | 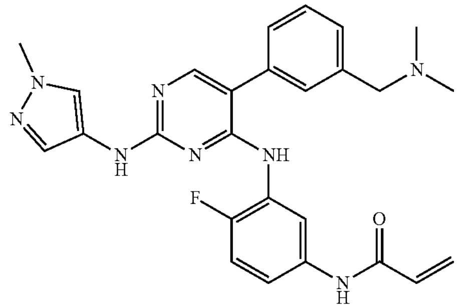 [SMILES: C=CC(=O)Nc1ccc(F)c(Nc2nc(Nc3cnn(C)c3)ncc2-c2cccc(CN(C)C)c2)c1] | $K_1$ | 487.2 | δ 10.19 (s, 1H), 9.12 (bs, 1H), 8.21 (bs, 1H), 7.90 (bs, 1H), 7.79 (bs, 1H), 7.56 (bs, 1H), 7.43 (bs, 1H), 7.41-7.16 (m, 6H), 6.43-6.36 (m, 1H), 6.39 (dd, J = 18.8 Hz, 1.6 Hz, 1H), 5.74 (dd, J = 11.6 Hz, 1.6 Hz, 1H), 3.53-3.30 (m, 5H), 2.17 (s, 6H). |
| 135 | 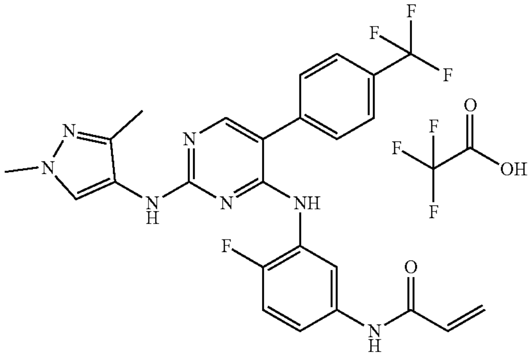 | K | 512.2 | δ 10.32 (s, 1H), 9.87-9.58 (m, 2H), 8.08 (bs, 1H), 7.93-7.73 (m, 5H), 7.54 (bs, 2H), 7.35 (bs, 1H), 7.00 (bs, 1H), 6.43-6.36 (m, 1H), 6.23 (dd, J = 16.8 Hz, 1.6 Hz, 1H), 5.75 (dd, J = 10.0 Hz, 4.0 Hz, 1H), 3.47 (s, 3H), 2.05 (s, 3H). |
| 136 | 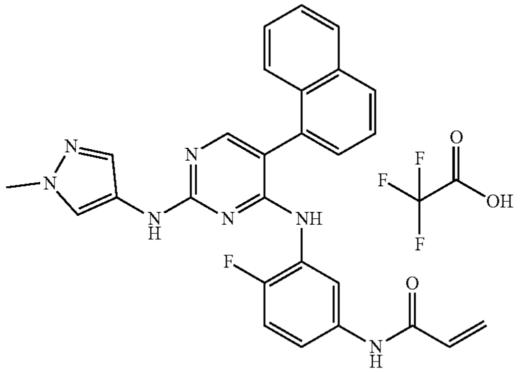 | $K_2$ | 480.2 | δ 10.36-10.28 (m, 2H), 9.20 (bs, 1H), 8.10-8.01 (m, 3H), 7.83-7.81 (m, 1H), 7.75-7.73 (m, 1H), 7.68-7.56 (m, 6H), 7.33-7.23 (m, 3H), 6.43-6.36 (m, 1H), 6.26-6.21 (m, 1H), 5.77-5.74 (m, 1H), 3.62 (s, 3H). |

Scheme 33: Synthesis of N-(4-fluoro-3-((2-((1-methyl-1H-pyrazol-4-yl)amino)-5-(pyridin-4-yl)pyrimidin-4-yl)amino)phenyl)acrylamide (Compound 137)

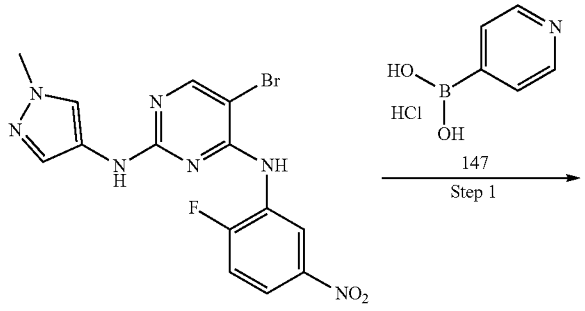

137

-continued

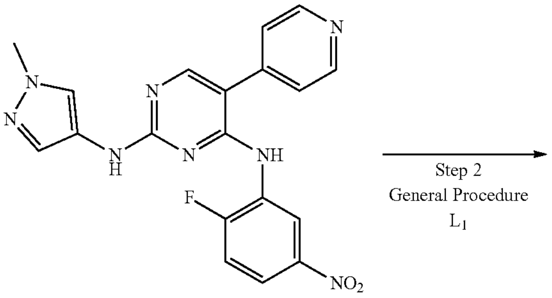

148

-continued

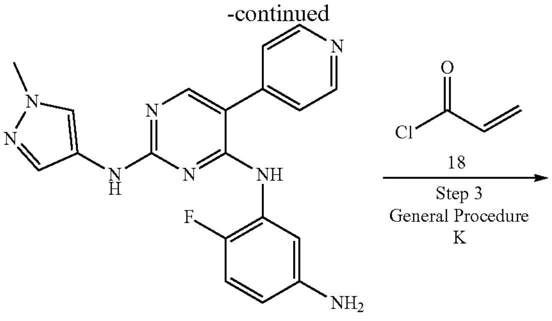

149

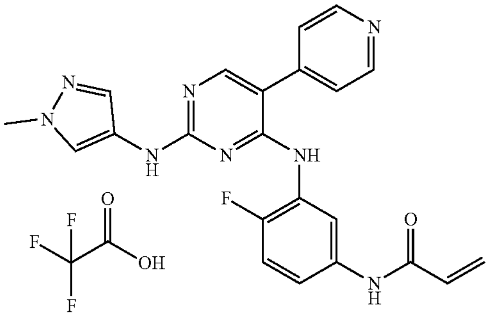

Compound 137

Step 1: Synthesis of N4-(2-fluoro-5-nitrophenyl)-N2-(1-methyl-1H-pyrazol-4-yl)-5-(pyridin-4-yl)pyrimidine-2,4-diamine (148)

To a stirred solution of 5-bromo-N4-(2-fluoro-5-nitrophenyl)-N2-(1-methyl-1H-pyrazol-4-yl)pyrimidine-2,4-diamine (137) (300 mg, 0.73 mmol) in 1,4-dioxane (4.00 mL), water (1.0 mL) was added cesium carbonate (599 mg, 1.84 mmol) and (pyridin-4-yl)boronic acid (147) (111 mg, 0.904 mmol). Then the reaction mixture was purged with nitrogen for 5 minutes, added [1,1'-bis(diphenylphosphino)ferrocene] palladium(II) chloride (60.0 mg, 0.073 mmol) and the reaction mixture was heated at 100° C. for 16 hours. The progress of the reaction was monitored by TLC. The reaction water was diluted with water (20 mL) and extracted with ethyl acetate (3x50 mL). The combined organic layer was washed with water (20 mL), brine (20 mL), dried over anhydrous sodium sulfate and evaporated. The crude compound was purified by combiflash column chromatography using 20% ethyl acetate in hexane as eluent to afford the title compound (155) (300 mg, 100%). LCMS: $[M+H]^+$ 407.0

Step 2: Synthesis of N4-(5-amino-2-fluorophenyl)-N2-(1-methyl-1H-pyrazol-4-yl)-5-(pyridin-4-yl)pyrimidine-2,4-diamine (149)

The title compound was prepared in a manner substantially similar to procedure mentioned in General Procedure $L_1$ to afford the desired product (149) brown solid (0.22 g, crude). LCMS: $[M+H]^+$ 377.

Step 3: Synthesis of N-(4-fluoro-3-((2-((1-methyl-1H-pyrazol-4-yl) amino)-5-(pyridin-4-yl)pyrimidin-4-yl)amino)phenyl)acrylamide (Compound 137)

The title compound was prepared in a manner substantially similar to procedure mentioned in General Procedure K to afford off white solid (0.028 g, 12.24%). $^1$H NMR (400 MHz, DMSO-d6): δ 10.21 (s, 1H), 9.30 (bs, 1H), 8.58-8.577 (m, 3H), 8.02 (s, 1H), 7.27 (s, 1H), 7.56-7.50 (m, 3H), 7.28 (bs, 2H), 7.13-7.05 (m, 2H), 6.42-6.35 (m, 1H), 6.23 (d, J=16.8 Hz, 1H), 5.73 (d, J=10.0 Hz, 1H), 3.51 (s, 3H). LCMS: $[M+H]^+$ 431.2

TABLE 9

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 138 | 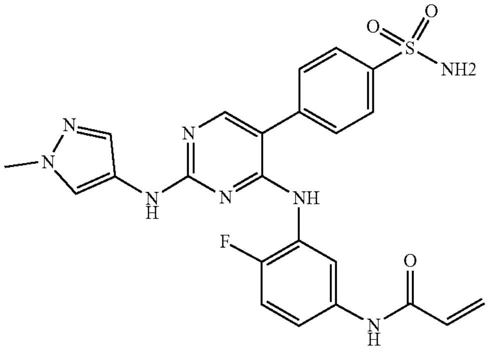 [SMILES: C=CC(=O)Nc1ccc(F)c(Nc2nc(Nc3cnn(C)c3)ncc2-c2ccc(S(N)(=O)=O)cc2)c1] | K | 509.0 | δ 10.18 (s, 1H), 9.19 (s, 1H), 8.49 (s, 1H), 7.96 (s, 1H), 7.87 (d, J = 8.4 Hz, 2H), 7.75 (d, J = 4.8 Hz, 1H), 7.67 (d, J = 8.0 Hz, 2H), 7.56 (bs, 1H), 7.36 (s, 2H), 7.26 (s, 1H), 7.15-7.07 (m, 2H), 6.43-6.36 (m, 1H), 6.25-6.20 (m, 1H), 5.74-5.72 (m, 1H), 3.53 (s, 3H). |

TABLE 9-continued
| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 139 | 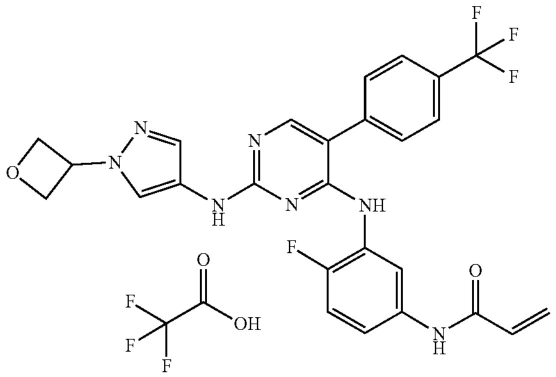 | $K_1$ | 540.3 | δ 10.28 (s, 1H), 9.87 (bs, 1H), 9.17 (bs, 1H), 7.99 (s, 1H), 7.84-7.83 (m, 3H), 7.73-7.32 (m, 2H), 7.55 (bs, 1H), 7.39-7.33 (m, 2H), 7.21 (bs, 1H), 7.06-6.93 (m, 1H), 6.43-6.36 (m, 1H), 6.25-6.21 (m, 1H), 5.75 (d, J = 10.0 Hz, 1H), 5.12 (bs, 1H), 4.80-4.69 (m, 4H). |
| 140 | 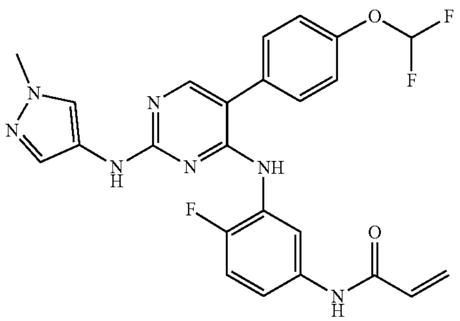 [SMILES: C=CC(=O)Nc1ccc(F)c(Nc2nc(Nc3cnn(C)c3)ncc2-c2ccc(OC(F)F)cc2)c1] | $K_1$ | 496.3 | δ 10.1 (s, 1H), 9.1 (bs, 1H), 8.3 (bs, 1H), 7.9 (s, 1H), 7.7 (s, 1H), 7.54-7.45 (m, 4H), 7.27-7.08 (m, 4H), 6.39-6.37 (m, 1H), 6.39-6.37 (m, 1H), 6.23 (d, J = 13.2 Hz, 1H), 5.74 (d, J = 8.0 Hz, 1H), 3.56 (bs, 3H). |
| 141 | 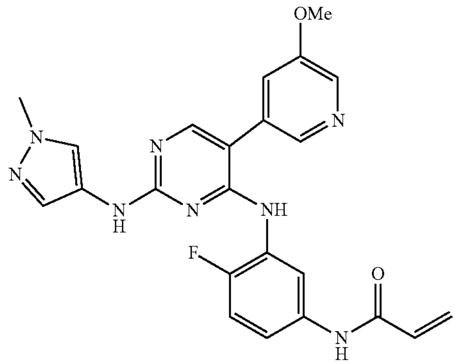 [SMILES: C=CC(=O)Nc1ccc(F)c(Nc2nc(Nc3cnn(C)c3)ncc2-c2cncc(OC)c2)c1] | $K_1$ | 461.1 | δ 10.2 (s, 1H), 9.20 (bs, 1H), 8.5 (bs, 1H), 8.25 (s, 2H), 7.90 (s, 1H), 7.75 (d, J = 8.0 Hz, 1H), 7.57 (bs, 1H), 7.45 (s, 1H), 7.82 (s, 1H), 7.16 (s, 1H), 6.43-6.36 (m, 1H), 6.23 (d, J = 16.0 Hz, 2H), 5.74 (d, J = 8.0 Hz, 1H), 3.87 (bs, 3H), 3.53 (bs, 3H). |
| 142 | 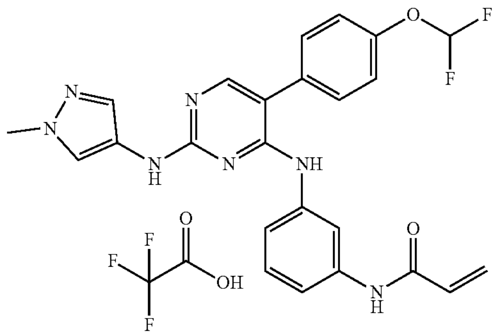 | $K_1$ | 478.2 | δ 7.95 (s, 1H), 7.72 (bs, 1H), 7.59-7.17 (m, 10H), 7.10 (s, 1H), 6.92 (s, 1H), 6.74 (s, 1H), 6.46-6.33 (m, 3H), 5.80-5.77 (m, 1H), 3.66 (bs, 3H) |

TABLE 9-continued

| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 143 | 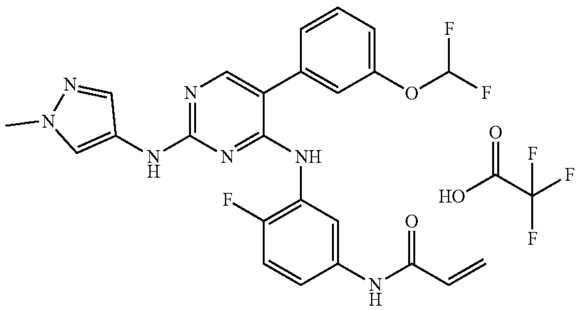 | $K_1$ | 496.3 | δ 10.29 (s, 1H), 9.88 (bs, 1H), 9.21 (bs, 1H) 7.96 (bs, 1H), 7.86-7.85 (m, 2H), 7.59-7.56 (m, 2H), 7.49-7.12 (m, 7H), 6.46-6.38 (m, 1H), 6.26 (dd, J = 16.0 Hz, 2.0 Hz, 1H), 5.78 (d, J = 1.6 Hz, 1H), 3.53 (bs, 3H, merged with DMSO-$H_2O$ peak). |
| 144 | 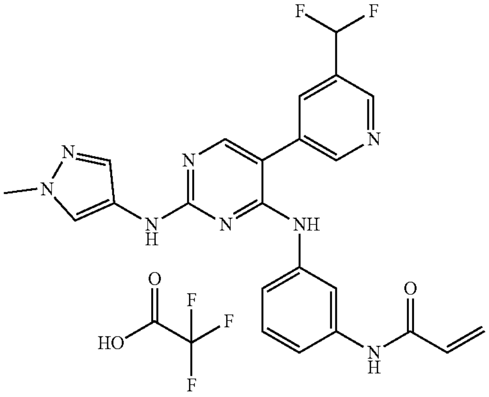 | $K_1$ | 463.2 | δ 10.25 (s, 1H), 10.07 (s, 1H), 9.63 (bs, 1H), 8.83 (s, 2H), 8.12 (s, 1H), 8.0 (s, 1H), 7.85 (s, 1H), 7.47-7.34 (m, 4H), 7.21-7.07 (m, 2H), 7.06-6.94 (m, 1H), 6.45-6.39 (m, 1H), 6.24-6.08 (m, 1H), 5.74 (d, J = 11.2 Hz, 1H), 3.67 (bs, 3H). |
| 145 | 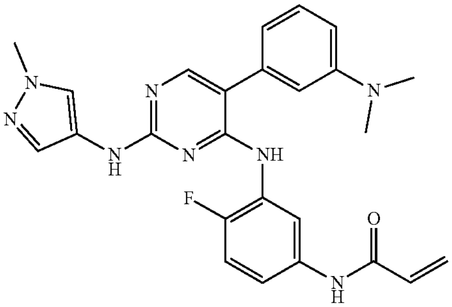 [SMILES: C=CC(=O)Nc1ccc(F)c(Nc2nc(Nc3cnn(C)c3)ncc2-c2cccc(N(C)C)c2)c1] | $K_1$ | 473.2 | δ 10.19 (bs, 1H), 9.09 (bs, 1H), 8.10 (bs, 1H), 7.92 (s, 1H), 7.80-7.81 (m, 1H), 7.58-7.59 (m, 1H), 7.16-7.28 (m, 4H), 6.71-6.78 (m, 3H), 6.36-6.43 (m, 1H), 6.23 (dd, J = 17.6, 2.2 Hz, 1H), 5.76 (dd, J = 10.4, 2.2 Hz, 1H), 3.54 (s, 3H), 2.93 (s, 6H). |
| 146 | 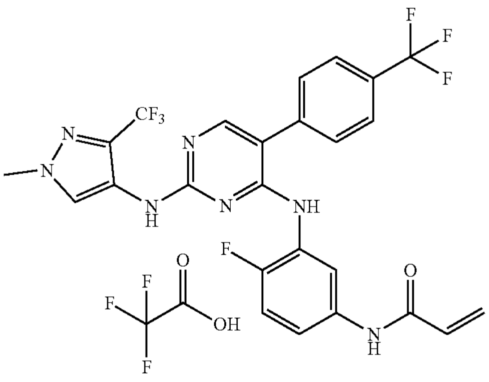 | $K_1$ | 566.2 | δ 10.28 (s, 1H), 9.39 (bs, 2H), 8.03 (s, 1H), 7.87-7.73 (m, 6H), 7.52-7.50 (m, 1H), 7.38-7.31 (m, 1H), 7.21-7.09 (bs, 1H), 6.43-6.36 (m, 1H), 6.26-6.22 (d, J = 15.2 Hz, 1H), 5.77-5.74 (m, 1H), 3.74 (s, 3H). |

TABLE 9-continued
The following compounds were prepared using the procedures described above:
| Cmpd. No. | Structure | General Procedure | LCMS [M + H] | $^1$H-NMR (400 MHz, DMSO-$d_6$) |
|---|---|---|---|---|
| 147 | 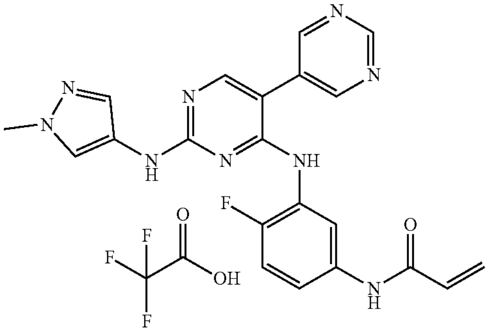 | $K_1$ | 432.2 | δ 10.15 (bs, 1H), 9.23 (bs, 1H), 9.08 (s, 1H), 8.82-8.67 (m, 3H), 7.93 (s, 1H), 7.69-7.11 (m, 6H), 6.37-6.30 (m, 1H), 6.20-6.15 (m, 1H), 5.70-5.67 (m, 1H), 3.59 (s, 3H). |
| 148 | 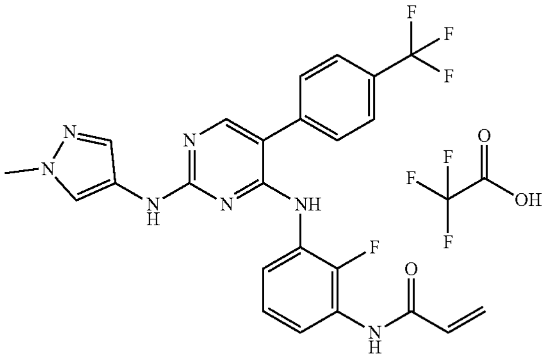 | $K_2$ | 498.1 | δ 10.03 (s, 1H), 9.86 (bs, 1H), 9.20 (s, 1H), 8.08-8.02 (m, 2H), 7.88-7.86 (m, 2H), 7.78-7.74 (m, 2H), 7.27-7.21 (m, 3H), 7.08-6.96 (m, 2H), 6.68-6.61 (m, 1H), 6.31-6.27 (m, 1H), 5.80-5.77 (m, 1H), 3.57 (s, 3H). |
| 149 | 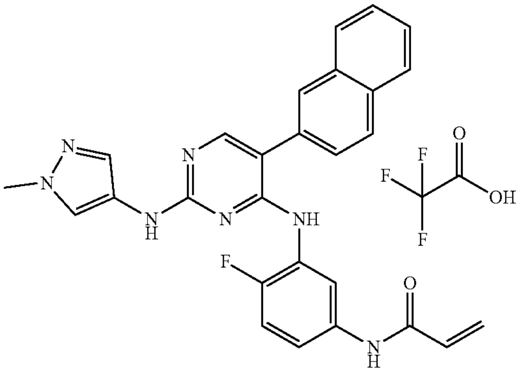 | $K_2$ | 480.2 | δ 10.34 (s, 1H), 10.07 (bs, 1H), 9.87 (bs, 1H), 8.13-8.04 (m, 5H), 7.92 (d, J = 4.8 Hz, 1H), 7.78-7.75 (m, 5H), 7.68-7.71 (m, 3H), 6.50-6.64 (m, 1H), 6.30 (d, J = 16.8 Hz, 1H), 5.82 (d, J = 11.6 Hz, 1H), 3.65 (s, 3H). |
| 150 | 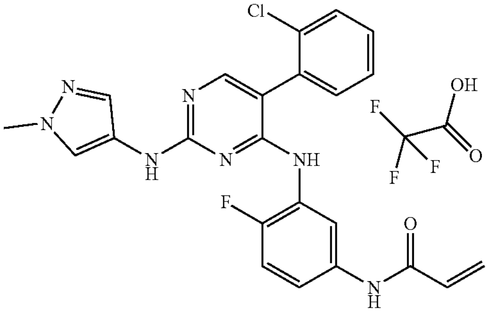 | $K_2$ | 442.2 | δ 10.27 (s, 1H), 9.88 (bs, 1H), 8.99 (bs, 1H), 7.81-7.80 (m, 2H), 7.58 (s, 1H), 7.42-7.21 (m, 8H), 6.44-6.37 (m, 1H), 6.27-6.23 (m, 1H), 5.78-5.75 (m, 1H), 3.60 (s, 3H), 2.27 (s, 3H). |

TABLE 9-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 152 | 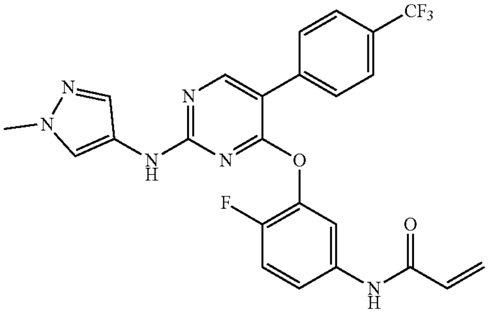 [SMILES: C=CC(=O)Nc1ccc(F)c(Oc2nc(Nc3cnn(C)c3)ncc2-c2ccc(C(F)(F)F)cc2)c1] | K | 499.14 | δ 10.41 (bs, 1H), 9.93 (bs, 1H), 8.56 (s, 1H), 7.82-7.93 (m, 5H), 7.46-7.62 (m, 2H), 7.11 (s, 1H), 6.83 (s, 1H), 6.38-6.44 (m, 1H), 6.24-6.29 (m, 1H), 5.77 (d, J = 10.0 Hz, 1H), 3.53 (s, 3H) |

Scheme 34: 4 Synthesis of N-(3-((2-((1-methyl-1H-pyrazol-4-yl)amino)-5-(4-(trifluoromethyl)phenyl)pyrimidin-4-yl)oxy)phenyl)acrylamide (Compound 151)

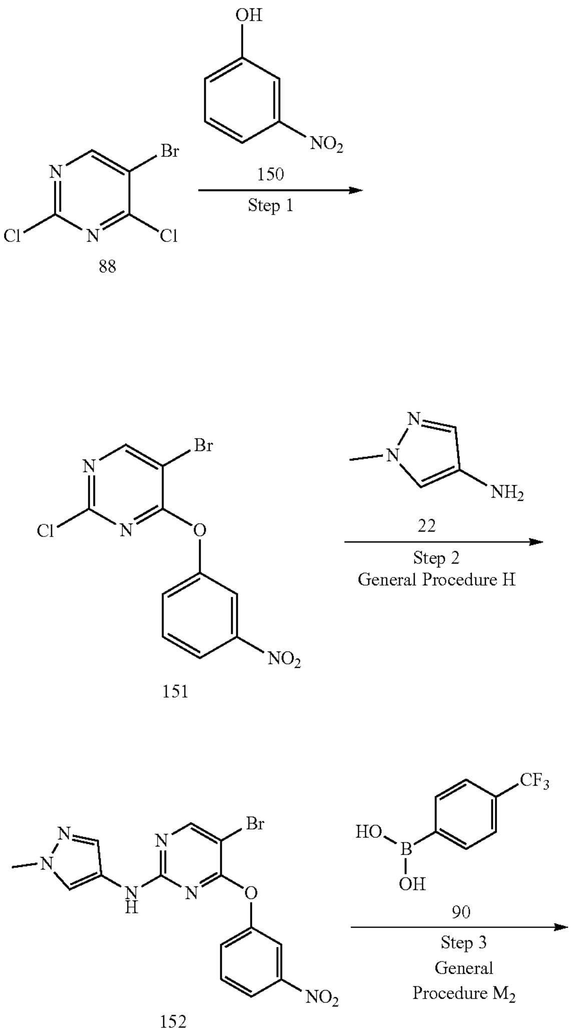

-continued

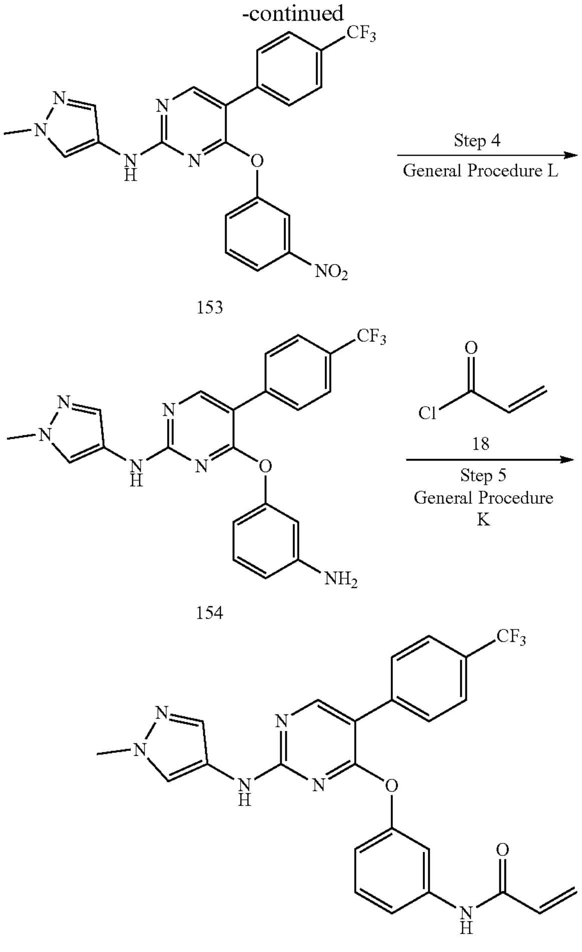

Compound 151

Step 1: Synthesis of 5-bromo-2-chloro-4-(3-nitrophenoxy)pyrimidine (151)

To a stirred solution of 5-bromo-2,4-dichloropyrimidine (88) (20.0 g, 87.76 mmol) and 3-nitrophenol (150) (12.20 g, 87.76 mmol) in N,N-dimethylformamide (100.0 mL) was added potassium carbonate (14.53 g, 105.31 mmol) and the reaction mixture was stirred at room temperature for 16 hours. After completion of reaction (TLC monitoring), the reaction mixture was cooled down to room temperature, diluted with ice-cold water (250 mL). The solid precipitated out was filtered and washed with ice-cold water (2×100 mL). The solid was dried under vacuum to get the desired product (151) as off white solid (25 g, Yield: 86%). $^1$H NMR (400 MHz, DMSO-$d_6$): δ 8.94 (s, 1H), 8.28 (s, 1H), 8.21-8.23 (m, 1H), 7.78-7.830 (m, 2H). LCMS: $[M+H]^+$ 330.22.

Step 2: Synthesis of 5-bromo-N-(1-methyl-1H-pyrazol-4-yl)-4-(3-nitrophenoxy)pyrimidin-2-amine (152)

The title compound was prepared in a manner substantially similar to procedure mentioned in General Procedure H, to afford the desired compound as yellow solid (5.0 g, Yield: 30%). LCMS: $[M+H]^+$ 391.27.

Step 3: Synthesis of N-(1-methyl-1H-pyrazol-4-yl)-4-(3-nitrophenoxy)-5-(4-(trifluoromethyl)phenyl) pyrimidin-2-amine (153)

The title compound was prepared in a manner substantially similar to procedure mentioned in General Procedure M3, to afford the desired compound as off white solid (0.2 g, Yield: 38%). LCMS: $[M+H]^+$ 457.13

Step 4: Synthesis of 4-(3-aminophenoxy)-N-(1-methyl-1H-pyrazol-4-yl)-5-(4-(trifluoromethyl)phenyl)pyrimidin-2-amine (154)

The title compound was prepared in a manner substantially similar to procedure mentioned in General Procedure L, to afford the desired compound as off white solid (0.12 g, Yield: 65%). LCMS: $[M+H]^+$ 427.07

Step 5: Synthesis of N-(3-((2-((1-methyl-1H-pyrazol-4-yl)amino)-5-(4-(trifluoromethyl)phenyl)pyrimidin-4-yl)oxy)phenyl)acrylamide (Compound 151)

The title compound was prepared in a manner substantially similar to procedure mentioned in General Procedure K, to afford the desired compound, after prep-HPLC purification as an off white solid (0.010 g, Yield: 15%). $^1$H-NMR (400 MHz, DMSO-$d_6$): δ 10.37 (bs, 1H), 9.78 (bs, 1H), 8.52 (s, 1H), 7.93-7.95 (m, 2H), 7.80-7.82 (m, 2H), 7.72 (s, 1H), 7.61 (s, 1H), 7.51 (s, 1H), 7.11 (s, 1H), 7.03 (d, J=6.4 Hz, 1H), 6.86 (s, 1H), 6.39-6.46 (m, 1H), 6.23-6.27 (m, 1H), 5.75 (d, J=10.0 Hz, 1H), 3.51 (s, 3H). LCMS: $[M+H]^+$ 481.17

Scheme 35: Synthesis of N-(3-((3-chloro-6-((1-methyl-1H-pyrazol-4-yl)amino)pyrazin-2-yl)amino)-4-fluorophenyl)acrylamide (Compound 153)

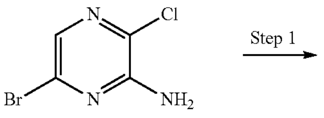

155

-continued

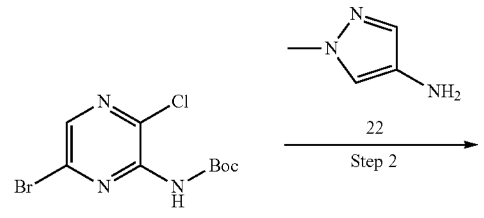

156

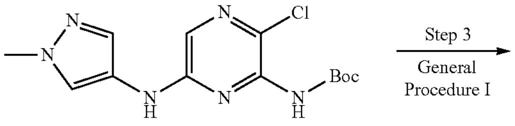

157

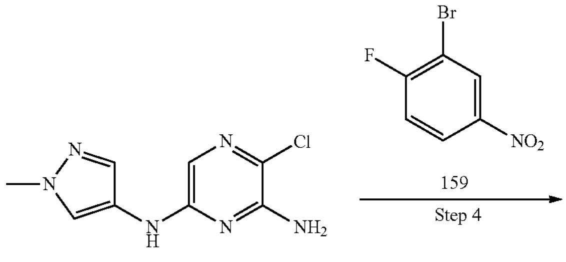

158

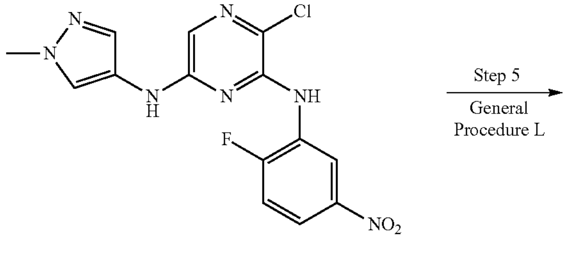

160

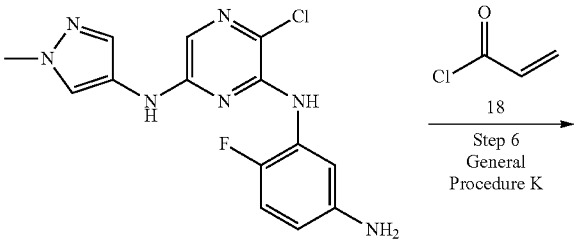

161

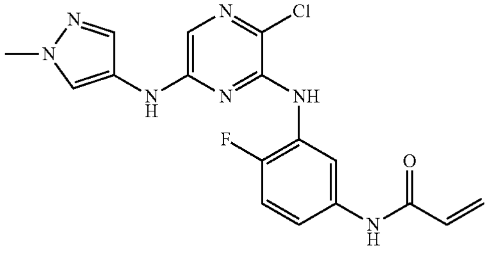

Compound 153

Step 1: Synthesis of tert-butyl (6-bromo-3-chloropyrazin-2-yl)carbamate (156)

To a solution of 6-bromo-3-chloropyrazin-2-amine (155) (500 mg, 2.40 mmol) in dichloromethane (10.0 mL) were added triethylamine (170 mg, 1.68 mmol), N,N-dimethylpyridin-4-amine (29.3 mg, 0.240 mmol) and di-tert-butyl dicarbonate (1.05 g, 4.80 mmol) at room temperature. The resultant reaction mixture was stirred at same temperature for 16 hours. After completion of reaction (as per TLC monitoring), reaction mixture was concentrated under reduced pressure and the residue was taken in water (30 mL) and extracted with dichloromethane (3×50 mL). The combined organic layers were dried over anhydrous sodium sulfate, filtered and concentrated under reduced pressure. The crude residue was purified by combiflash column chromatography, eluted with 10-40% ethyl acetate in heptane to get tert-butyl (6-bromo-3-chloropyrazin-2-yl)carbamate (156) (600 mg, Yield: 81%) as a white solid. LCMS: $[M-tBu+H]^+$ 251.97.

Step 2: Synthesis of tert-butyl (3-chloro-6-((1-methyl-1H-pyrazol-4-yl)amino)pyrazin-2-yl)carbamate (157)

To a solution of tert-butyl (6-bromo-3-chloropyrazin-2-yl)carbamate (156) (400 mg, 1.30 mmol) in 1,4-dioxane (10.0 mL) was added cesium carbonate (845 mg, 2.59 mmol), then reaction mixture was purged with nitrogen for 15 minutes, 1-methyl-1H-pyrazol-4-amine (22) (126 mg, 1.30 mmol), tris(dibenzylideneacetone) dipalladium(0) (119 mg, 0.130 mmol) and xanthphos (150 mg, 0.26 mmol) were added at room temperature. The resultant reaction mixture was heated at 120° C. for 16 hours. After completion of reaction (as per TLC monitoring), reaction solution was cooled to room temperature, filtered through celite pad and washed with ethyl acetate (3×30 mL). The combined filtrate was concentrated under reduced pressure to get tert-butyl (3-chloro-6-((1-methyl-1H-pyrazol-4-yl)amino)pyrazin-2-yl)carbamate (157) (800 mg, Yield: 68.41%), which was used for the next step without further purification. MS: $[M+H]^+$ 325.16.

Step 3: Synthesis of 5-chloro-N2-(1-methyl-1H-pyrazol-4-yl)pyrazine-2,6-diamine (158)

Title compound was prepared in a manner substantially similar to procedure mentioned in General Procedure H, to get 5-chloro-N2-(1-methyl-1H-pyrazol-4-yl)pyrazine-2,6-diamine (158) (150 mg, Yield: 27.1%) as a green solid. LC-MS: $[M+H]^+$ 225.12.

Step 4: Synthesis of 3-chloro-N2-(2-fluoro-5-nitrophenyl)-N6-(1-methyl-1H-pyrazol-4-yl)pyrazine-2,6-diamine (160)

To a stirred solution of 5-chloro-N2-(1-methyl-1H-pyrazol-4-yl)pyrazine-2,6-diamine (158) (50.0 mg, 0.223 mmol) and 2-bromo-1-fluoro-4-nitrobenzene (159) (49.0 mg, 0.223 mmol) in 1,4-dioxane (2.0 mL) was added cesium carbonate (145 mg, 0.45 mmol) at room temperature. The reaction mass was purged with nitrogen for 15 minutes, then tris(dibenzylideneacetone)dipalladium(0) (20.4 mg, 0.022 mmol) and [5-(diphenylphosphanyl)-9,9-dimethyl-9H-xanthen-4-yl]diphenylphosphane (25.8 mg, 0.044 mmol) were added to the reaction mixture. The resultant reaction mixture was heated at 120° C. for 16 hours. After completion of reaction (as per TLC monitoring) reaction solution was cooled to room temperature, poured into ice-cold water (50 mL) and extracted with ethyl acetate (2×50 mL). The combined organic layers were dried over anhydrous sodium sulfate, filtered and concentrated under reduced pressure to get 3-chloro-N2-(2-fluoro-5-nitrophenyl)-N6-(1-methyl-1H-pyrazol-4-yl)pyrazine-2,6-diamine (160) (30.0 mg, Yield: 13%) as semi-solid. MS: $[M+H]^+$ 364.23.

Step 5: Synthesis of N2-(5-amino-2-fluorophenyl)-3-chloro-N6-(1-methyl-1H-pyrazol-4-yl)pyrazine-2,6-diamine (161)

Title compound was prepared in a manner substantially similar to procedure mentioned in General Procedure L, to get N2-(5-amino-2-fluorophenyl)-3-chloro-N6-(1-methyl-1H-pyrazol-4-yl)pyrazine-2,6-diamine (161) (60.0 mg, Yield: 63%). MS: $[M+H]^+$ 334.09.

Step 6: Synthesis of N-(3-((3-chloro-6-((1-methyl-1H-pyrazol-4-yl)amino)pyrazin-2-yl)amino)-4-fluorophenyl)acrylamide (Compound 153)

Title compound was prepared in a manner substantially similar to procedure mentioned in in General Procedure J, N2-(5-amino-2-fluorophenyl)-3-chloro-N6-(1-methyl-1H-pyrazol-4-yl)pyrazine-2,6-diamine (161) and acryloyl chloride (18) gave N-(3-((3-chloro-6-((1-methyl-1H-pyrazol-4-yl)amino)pyrazin-2-yl)amino)-4-fluorophenyl)acrylamide Compound 153 as a white solid after prep-HPLC purification (8.0 mg, Yield: 4.92%). $^1$H-NMR (400 MHz, DMSO-$d_6$): δ 10.27 (s, 1H), 9.27 (s, 1H), 8.48 (s, 1H), 7.80-7.78 (m, 1H), 7.64-7.62 (m, 1H), 7.33 (t, J=9.6 Hz, 1H), 7.25 (s, 1H), 7.15-7.14 (m, 2H), 6.38-6.45 (m, 1H), 6.23 (d, J=15.6 Hz, 1H), 5.74 (d, J=11.2 Hz, 1H), 3.54 (s, 3H). LCMS: $[M+H]^+$ 388.21.

Scheme 36: Synthesis of N-(3-((3-chloro-6-((1-methyl-1H-pyrazol-4-yl)amino)pyrazin-2-yl)oxy)phenyl)acrylamide (Compound 218)

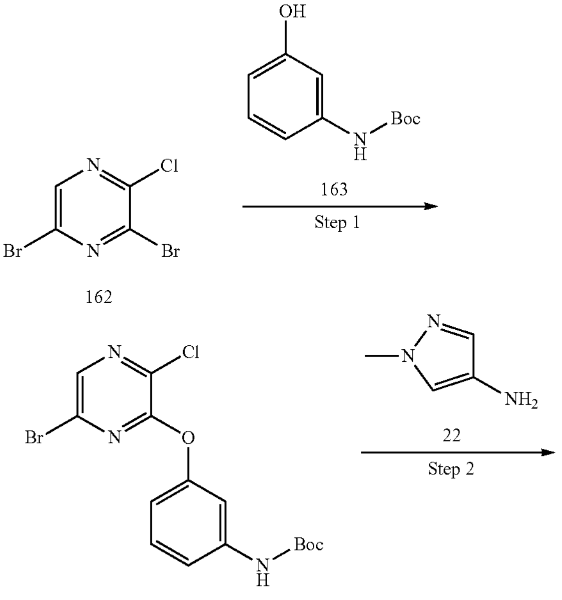

162

164

-continued

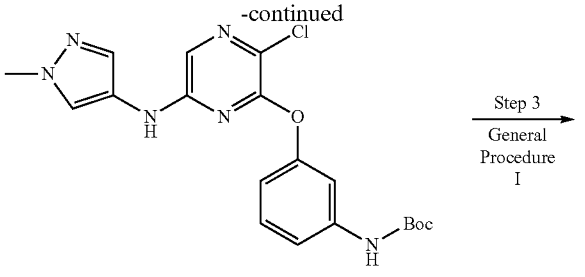

165

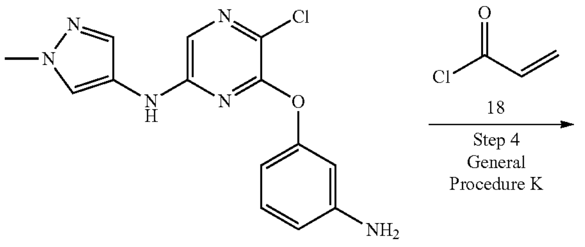

166

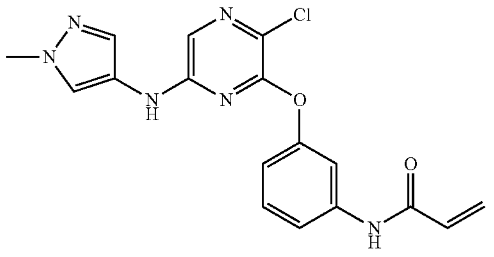

Compound 154

Step 1: Synthesis of tert-butyl (3-((6-bromo-3-chloropyrazin-2-yl)oxy)phenyl)carbamate (164)

To a stirred solution of tert-butyl (3-hydroxyphenyl)carbamate (163) (1.84 g, 8.81 mmol) in acetonitrile (10.0 mL) were added triethylamine (3.01 mL, 22.0 mmol) and 3,5-dibromo-2-chloropyrazine (162) (2.0 g, 7.34 mmol) at room temperature. The reaction mixture was stirred at 85° C. for 16 hours. After consumption of starting material (as per TLC monitoring), reaction mixture was diluted with water (100 mL) and then extracted with ethyl acetate (3×100 mL). The combined organic layers were washed with brine (100 mL), dried over anhydrous sodium sulfate, filtered and concentrated under reduced pressure. The crude residue was purified by silica-gel flash column chromatography (5-25% ethyl acetate in heptane) to get tert-butyl (3-((6-bromo-3-chloropyrazin-2-yl)oxy)phenyl)carbamate (164) (1.90 g, Yield: 64.57%) as a yellow solid. LCMS: $[M-H]^-$ 397.97.

Step 2: Synthesis of tert-butyl (3-((3-chloro-6-((1-methyl-1H-pyrazol-4-yl)amino)pyrazin-2-yl)oxy)phenyl)carbamate (165)

To a stirred solution of 1-methyl-1H-pyrazol-4-amine (22) (654 mg, 6.74 mmol) in toluene (10.0 mL) were added cesium carbonate (2.20 g, 6.74 mmol) and tert-butyl (3-((6-bromo-3-chloropyrazin-2-yl)oxy)phenyl)carbamate (164) (900 mg, 2.25 mmol). The resulting reaction mixture was purged with nitrogen for 20 minutes, then 1,1'-bis(diphenylphosphino)ferrocene-palladium(II)dichloride dichloromethane complex (367 mg, 0.449 mmol) was added and resultant reaction mixture was stirred at 110° C. for 20 hours. After completion of reaction (as per TLC monitoring), reaction mixture was filtered through celite pad and concentrated under reduced pressure. The crude residue was taken in water (20 mL) and extracted with ethyl acetate (3×50 mL) The organic layer was washed with brine (50 mL), dried over anhydrous sodium sulfate, filtered and concentrated under reduced pressure to get tert-butyl (3-((3-chloro-6-((1-methyl-1H-pyrazol-4-yl)amino)pyrazin-2-yl)oxy)phenyl)carbamate (165) (1.30 g, Yield: 28.75%) as a brown solid, which was used as such for the next step. MS: $[M+H]^+$ 417.28.

Step 3: Preparation 6-(3-aminophenoxy)-5-chloro-N-(1-methyl-1H-pyrazol-4-yl)pyrazin-2-amine (166)

Title compound was prepared in a manner substantially similar to procedure mentioned in General Procedure I, tert-butyl (3-((3-chloro-6-((1-methyl-1H-pyrazol-4-yl)amino)pyrazin-2-yl)oxy)phenyl)carbamate (165) gave 6-(3-aminophenoxy)-5-chloro-N-(1-methyl-1H-pyrazol-4-yl)pyrazin-2-amine (166) as a green solid (720 mg; Yield: 72.89%). MS: $[M+H]^+$ 317.15.

Step 4: Synthesis of N-(3-((3-chloro-6-((1-methyl-1H-pyrazol-4-yl)amino)pyrazin-2-yl)oxy)phenyl)acrylamide (Compound 154)

Title compound was prepared in a manner substantially similar to procedure mentioned in in General Procedure J, 6-(3-aminophenoxy)-5-chloro-N-(1-methyl-1H-pyrazol-4-yl)pyrazin-2-amine (166) and acryloyl chloride (18) gave N-(3-((3-chloro-6-((1-methyl-1H-pyrazol-4-yl)amino)pyrazin-2-yl)oxy)phenyl)acrylamide Compound 154 as a brown solid after prep-HPLC purification (64.0 mg, Yield: 7.81%). $^1$H-NMR (400 MHz, DMSO-$d_6$): δ 10.38 (s, 1H), 9.71 (s, 1H), 7.67-7.61 (m, 3H), 7.50 (t, J=8.0 Hz, 1H), 7.14 (s, 1H), 7.09-6.98 (m, 2H), 6.39-6.45 (m, 1H), 6.23 (d, J=16.0 Hz, 1H), 5.76 (d, J=10.0 Hz, 1H), 3.53 (s, 3H). LCMS: $[M+H]^+$ 371.18.

Scheme 37: Synthesis of N-(3-((6-chloro-3-((1-methyl-1H-pyrazol-4-yl)amino)-1,2,4-triazin-5-yl)amino)-4-fluorophenyl)acrylamid (Compound 155)

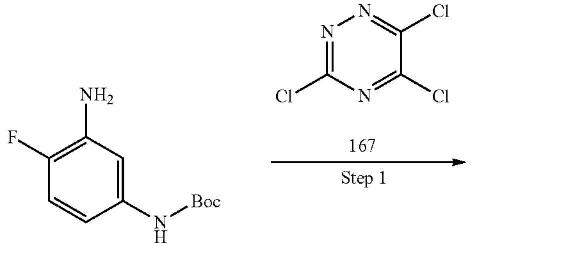

83

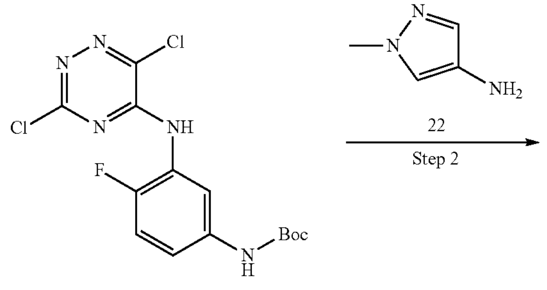

168

-continued

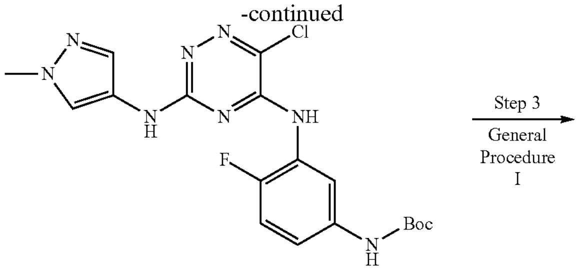

169

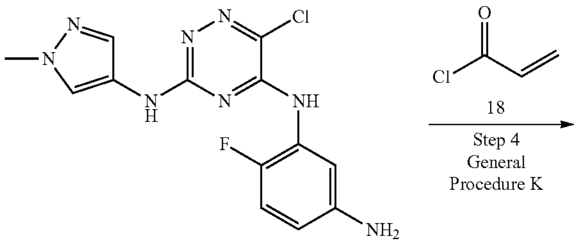

170

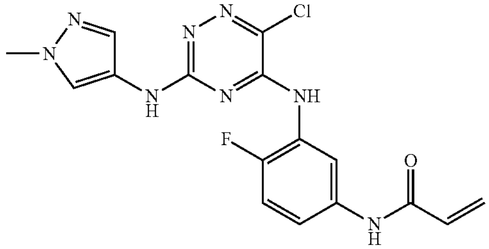

Compound 155

Step 1: Synthesis of tert-butyl (3-((3,6-dichloro-1,2,4-triazin-5-yl)amino)-4-fluorophenyl)carbamate (168)

To stirred a solution of 3,5,6-trichloro-1,2,4-triazine (167) (1.40 g, 7.59 mmol) in dichloromethane (10 mL) were added triethylamine (1.54 g, 15.2 mmol) and tert-butyl (3-amino-4-fluorophenyl)carbamate (83) (2.06 g, 9.11 mmol) at 0° C. The reaction mixture was stirred at room temperature for 16 hours. After completion of reaction (as per TLC monitoring), reaction mixture was diluted with water (20 mL) and extracted with dichloromethane (3×100 mL). The combined organic layers were washed with brine, dried over anhydrous sodium sulfate, filtered and concentrated under reduced pressure to get tert-butyl (3-((3,6-dichloro-1,2,4-triazin-5-yl)amino)-4-fluorophenyl)carbamate (168) (1.70 g, Yield: 13.2%) as a yellow solid, which was used as it is for the next step. MS: $[M+H]^+$ 374.04.

Step 2: Synthesis of tert-butyl (3-((6-chloro-3-((1-methyl-1H-pyrazol-4-yl)amino)-1,2,4-triazin-5-yl)amino)-4-fluorophenyl)carbamate (169)

To a stirred solution tert-butyl (3-((3,6-dichloro-1,2,4-triazin-5-yl)amino)-4-fluorophenyl)carbamate (168) (1.10 g, 2.94 mmol) in isopropanol (3.0 mL) were added 1-methyl-1H-pyrazol-4-amine (22) (714 mg, 7.35 mmol) and camphor sulfonic acid (478 mg, 2.06 mmol). The reaction mixture was heated at 100° C. for 16 hours. After completion of reaction (as per TLC monitoring), the reaction mixture was diluted with water (50 mL) and extracted with ethyl acetate (3×50 mL). The combined organic layers were washed with brine, dried over anhydrous sodium sulfate, filtered and concentrated under reduced pressure to get tert-butyl (3-((6-chloro-3-((1-methyl-1H-pyrazol-4-yl)amino)-1,2,4-triazin-5-yl)amino)-4-fluorophenyl)carbamate (169) (2.20 g, Yield: 44.13%) as viscous liquid. MS: $[M+H]^+$ 435.53.

Step 3: Preparation N5-(5-amino-2-fluorophenyl)-6-chloro-N3-(1-methyl-1H-pyrazol-4-yl)-1,2,4-triazine-3,5-diamin (170)

Title compound was prepared in a manner substantially similar to procedure mentioned in General Procedure I, tert-butyl (3-((6-chloro-3-((1-methyl-1H-pyrazol-4-yl)amino)-1,2,4-triazin-5-yl)amino)-4-fluorophenyl)carbamat (169) gave N5-(5-amino-2-fluorophenyl)-6-chloro-N3-(1-methyl-1H-pyrazol-4-yl)-1,2,4-triazine-3,5-diamin (170) as viscous liquid (700 mg; Yield: 20.58%). MS: $[M+H]^+$ 335.12.

Step 4: Synthesis of N-(3-((6-chloro-3-((1-methyl-1H-pyrazol-4-yl)amino)-1,2,4-triazin-5-yl)amino)-4-fluorophenyl)acrylamid (Compound 155)

Title compound was prepared in a manner substantially similar to procedure mentioned in in General Procedure K, N5-(5-amino-2-fluorophenyl)-6-chloro-N3-(1-methyl-1H-pyrazol-4-yl)-1,2,4-triazine-3,5-diamine (170) and acryloyl chloride (18) gave N-(3-((6-chloro-3-((1-methyl-1H-pyrazol-4-yl)amino)-1,2,4-triazin-5-yl)amino)-4-fluorophenyl) acrylamide Compound 155 as a white solid after prep-HPLC purification (3.5 mg, Yield: 5.29%). $^1$H-NMR (400 MHz, DMSO-$d_6$): δ 10.34 (s, 1H), 9.81-9.58 (bs, 2H), 7.83 (s, 1H), 7.66 (s, 1H), 7.38 (s, 1H), 7.20 (bs, 2H), 6.38-6.45 (m, 1H), 6.25 (d, J=16.8 Hz, 1H), 5.77 (d, J=11.6 Hz, 1H), 3.60 (s, 3H). LCMS: $[M+H]^+$ 389.21.

Scheme 38: Synthesis of N-(3-((6-chloro-3-((1-methyl-1H-pyrazol-4-yl)amino)-1,2,4-triazin-5-yl)amino)phenyl)acrylamide (Compound 156)

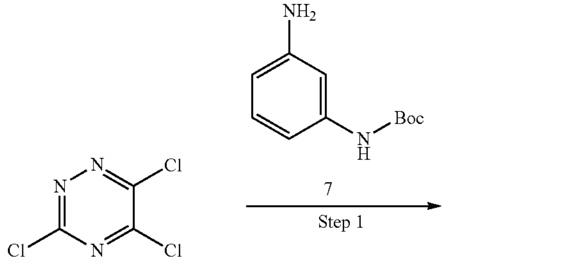

167

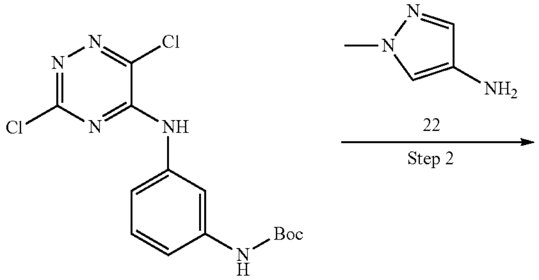

171

-continued

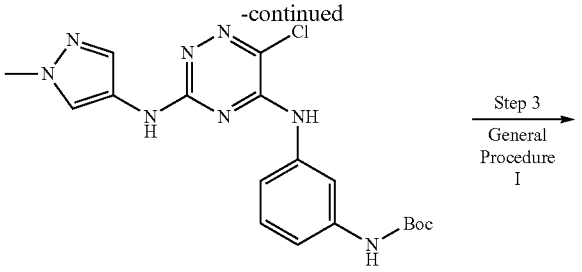

172

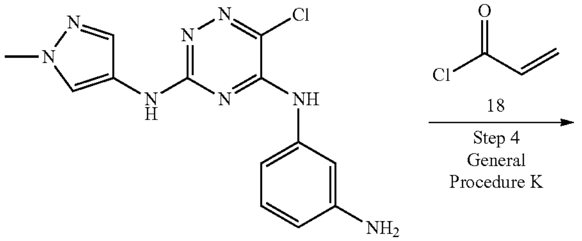

173

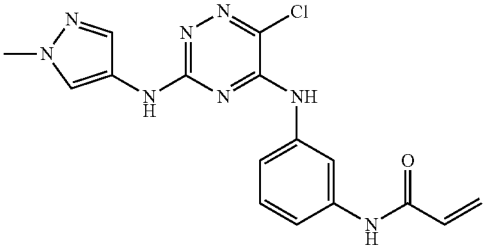

Compound 156

Step 1: Synthesis of tert-butyl (3-((3,6-dichloro-1,2,4-triazin-5-yl)amino)phenyl)carbamate (171)

To stirred a solution of 3,5,6-trichloro-1,2,4-triazine (167) (3.0 g, 16.3 mmol) in dichloromethane (30.0 mL) were added triethylamine (3.29 g, 32.5 mmol) and tert-butyl (3-aminophenyl)carbamate (7) (2.37 g, 11.4 mmol) at room temperature. The reaction mixture was stirred at same temperature for 3 hours. After completion of reaction (as per TLC monitoring), reaction mixture was diluted with water (20 mL) and extracted with dichloromethane (3×100 mL). The combined organic layer was washed with brine (50 mL), dried over anhydrous sodium sulfate, filtered and concentrated under reduced pressure. The crude product was purified by combiflash column chromatography (10-20% ethyl acetate in heptane) to get tert-butyl (3-((3,6-dichloro-1,2,4-triazin-5-yl)amino)phenyl)carbamate (171) as a yellow solid (2.0 g, Yield: 34.51%). LCMS: $[M+H]^+$ 356.09.

Step 2: Synthesis of tert-butyl (3-((6-chloro-3-((1-methyl-1H-pyrazol-4-yl)amino)-1,2,4-triazin-5-yl)amino)phenyl)carbamate (172)

To a stirred solution of tert-butyl (3-((3,6-dichloro-1,2,4-triazin-5-yl)amino)phenyl)carbamate (171) (1.50 g, 4.21 mmol) in propan-2-ol (5.0 mL) were added 1-methyl-1H-pyrazol-4-amine (22) (1.02 g, 10.5 mmol) and camphor sulfonic acid (685 mg, 2.95 mmol). The reaction mixture was stirred at 80° C. for 16 hours. After completion of reaction (as per TLC monitoring), the reaction mixture was diluted with water (20 mL) and extracted with ethyl acetate (3×100 mL). The combined organic layers were washed with brine, dried over anhydrous sodium sulfate, filtered and concentrated under reduced pressure. The crude residue was purified by combiflash column chromatography, eluted with 10-20% ethyl acetate in heptane) to get tert-butyl (3-((6-chloro-3-((1-methyl-1H-pyrazol-4-yl)amino)-1,2,4-triazin-5-yl)amino)phenyl)carbamate (172) (700 mg, 1.68 mmol) as a yellow solid. $[M+H]^+$ 417.49.

Step 3: Synthesis of N5-(3-aminophenyl)-6-chloro-N3-(1-methyl-1H-pyrazol-4-yl)-1,2,4-triazine-3,5-diamine (173)

Title compound was prepared in a manner substantially similar to procedure mentioned in General Procedure I, tert-butyl (3-((6-chloro-3-((1-methyl-1H-pyrazol-4-yl)amino)-1,2,4-triazin-5-yl)amino)phenyl)carbamate (172) gave N5-(3-aminophenyl)-6-chloro-N3-(1-methyl-1H-pyrazol-4-yl)-1,2,4-triazine-3,5-diamine (173) as a reddish solid (350 mg; Yield: 76%). MS: $[M+H]^+$ 317.17.

Step 4: Synthesis of N-(3-((6-chloro-3-((1-methyl-1H-pyrazol-4-yl)amino)-1,2,4-triazin-5-yl)amino)phenyl)acrylamide (Compound 156)

Title compound was prepared in a manner substantially similar to procedure mentioned in in General Procedure K, N5-(3-aminophenyl)-6-chloro-N3-(1-methyl-1H-pyrazol-4-yl)-1,2,4-triazine-3,5-diamine (173) and acryloyl chloride (18) gave N-(3-((6-chloro-3-((1-methyl-1H-pyrazol-4-yl)amino)-1,2,4-triazin-5-yl)amino)phenyl)acrylamide Compound 156 as a white solid after prep-HPLC purification (15.0 mg, Yield: 4.21%). $^1$H-NMR (400 MHz, DMSO-$d_6$): δ 10.26 (s, 1H), 9.52 (bs, 2H), 7.88 (s, 1H), 7.59-7.57 (m, 1H), 7.42-7.30 (m, 4H), 6.42-6.48 (m, 1H), 6.23 (dd, J=16.8 Hz, 2.0 Hz 1H), 5.75 (d, J=10.4 Hz, 1H), 3.63 (bs, 3H). LCMS: $[M+H]^+$ 371.15

Scheme 39: Synthesis of N-(3-((6-chloro-3-((1-methyl-1H-pyrazol-4-yl)amino)-1,2,4-triazin-5-yl)oxy)phenyl)acrylamide (Compound 157)

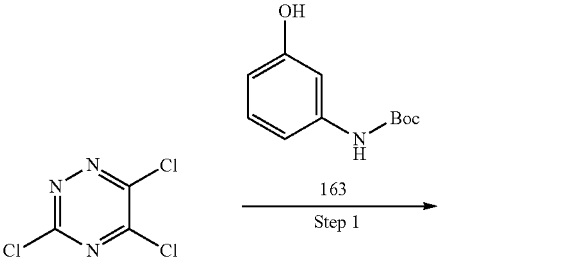

167

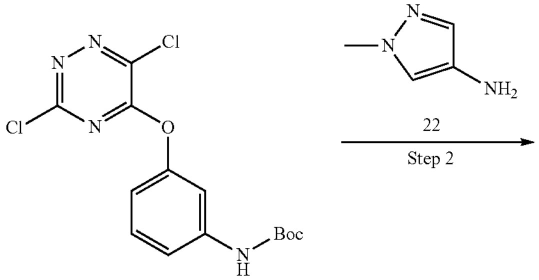

174

-continued

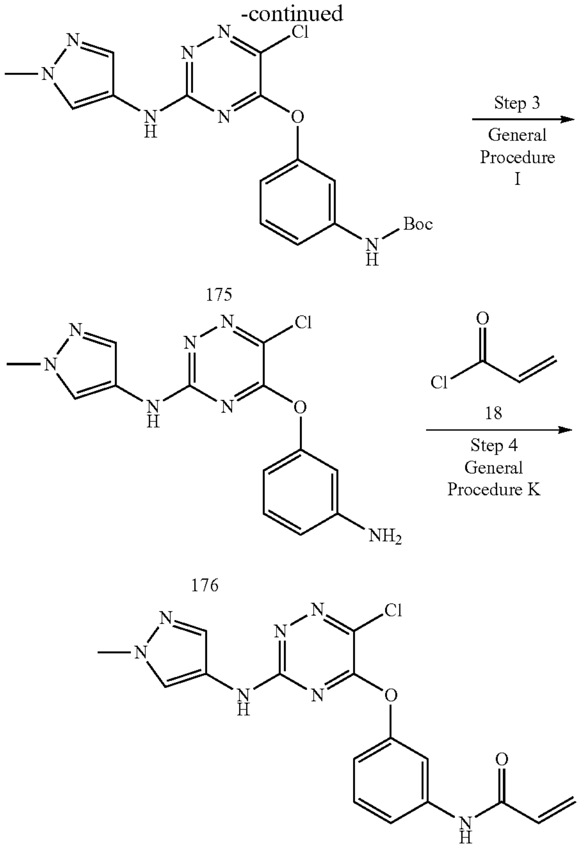

175

176

Compound 157

Step 1: Synthesis of tert-butyl (3-((3,6-dichloro-1,2,4-triazin-5-yl)oxy)phenyl)carbamate (174)

To a stirred solution of 3,5,6-trichloro-1,2,4-triazine (177) (2.0 g, 10.8 mmol) in dichloromethane (30 mL) were added triethylamine (1.44 g, 14.2 mmol) and tert-butyl (3-hydroxyphenyl)carbamate (163) (1.75 g, 8.34 mmol) at 0° C., then allowed to room temperature and stirred at same temperature for 16 hours. After completion of reaction (as per TLC monitoring), water (50 mL) was added and extracted with dichloromethane (5×50 mL). The combined organic layers were washed with brine, dried over anhydrous sodium sulfate, filtered and concentrated under reduced pressure. The crude residue was purified by combiflash column chromatography, eluted with 5-10% in ethyl acetate in heptane) to get tert-butyl (3-((3,6-dichloro-1,2,4-triazin-5-yl)oxy)phenyl)carbamate (174) as a white solid (1.90 g; Yield: 63.76%). LCMS: $[M-H]^-$ 355.11.

Step 2: Synthesis of tert-butyl (3-((6-chloro-3-((1-methyl-1H-pyrazol-4-yl)amino)-1,2,4-triazin-5-yl)oxy)phenyl)carbamate (175)

To a stirred solution of tert-butyl (3-((3,6-dichloro-1,2,4-triazin-5-yl)oxy)phenyl)carbamate (174) (500 mg, 1.40 mmol) and 1-methyl-1H-pyrazol-4-amine (22) (136 mg, 1.40 mmol) in toluene (3.0 mL) was added cesium carbonate (1.37 g, 4.20 mmol) at room temperature. The resulting reaction mixture was purged with nitrogen for 15 minutes, then [1,1'-bis(diphenylphosphino)ferrocene]dichloropalladium(II), complex with dichloromethane (229 mg, 0.28 mmol) was added. The resultant reaction mixture was heated at 110° C. for 16 hours. After completion of reaction (as per TLC monitoring), reaction mixture was concentrated under reduced pressure. The crude was taken in water (50 mL) and extracted with ethyl acetate (3×50 mL). The combined organic layers were washed with brine, dried over anhydrous sodium sulfate, filtered and concentrated under reduced pressure to get tert-butyl (3-((6-chloro-3-((1-methyl-1H-pyrazol-4-yl)amino)-1,2,4-triazin-5-yl)oxy)phenyl)carbamate (175) as a yellow gel (200 mg; Yield: 34.19%). MS: $[M+H]^+$ 418.32.

Step 3: Synthesis of 5-(3-aminophenoxy)-6-chloro-N-(1-methyl-1H-pyrazol-4-yl)-1,2,4-triazin-3-amine (176)

Title compound was prepared in a manner substantially similar to procedure mentioned in General Procedure I, tert-butyl (3-((6-chloro-3-((1-methyl-1H-pyrazol-4-yl)amino)-1,2,4-triazin-5-yl)oxy)phenyl)carbamate (175) gave 5-(3-aminophenoxy)-6-chloro-N-(1-methyl-1H-pyrazol-4-yl)-1,2,4-triazin-3-amine (176) as a brown solid (280 mg; Yield: 28%). MS: $[M+H]^+$ 318.08.

Step 4: Synthesis of N-(3-((6-chloro-3-((1-methyl-1H-pyrazol-4-yl)amino)-1,2,4-triazin-5-yl)oxy)phenyl)acrylamide (Compound 157)

Title compound was prepared in a manner substantially similar to procedure mentioned in in General Procedure K, 5-(3-aminophenoxy)-6-chloro-N-(1-methyl-1H-pyrazol-4-yl)-1,2,4-triazin-3-amine (176) and acryloyl chloride (18) gave N-(3-((6-chloro-3-((1-methyl-1H-pyrazol-4-yl)amino)-1,2,4-triazin-5-yl)oxy)phenyl)acrylamide Compound 157 as a white solid after prep-HPLC purification (20 mg, Yield: 6.1%). $^1$H-NMR (400 MHz, DMSO-$d_6$): δ 10.37-10.35 (m, 2H), 7.70 (s, 1H), 7.57 (d, J=8.4 Hz, 1H), 7.49-7.45 (m, 2H), 7.41 (s, 1H), 7.00 (d, J=8.0 Hz, 1H), 6.39-6.46 (m, 1H), 6.24 (d, J=16.8 Hz, 1H), 5.77 (d, J=10.0 Hz, 1H), 3.64 (s, 3H). LCMS: $[M+H]^+$ 372.15

Scheme 40: Synthesis of N-(3-((3-methyl-6-((1-methyl-1H-pyrazol-4-yl)amino)pyrazin-2-yl)oxy)phenyl)acrylamide (Compound 158)

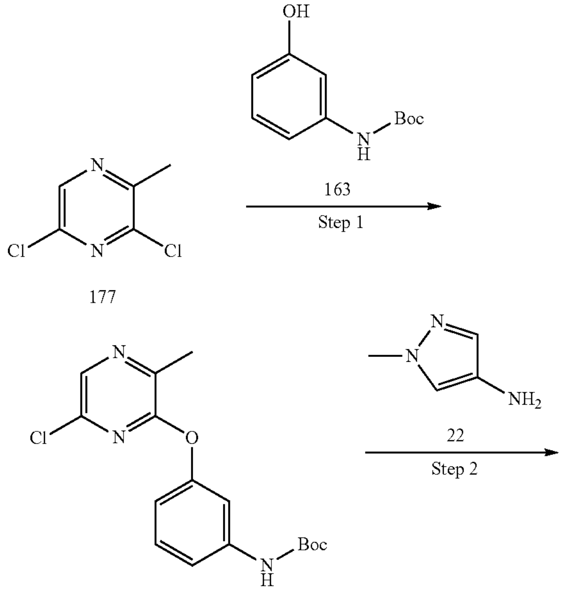

177

178

-continued

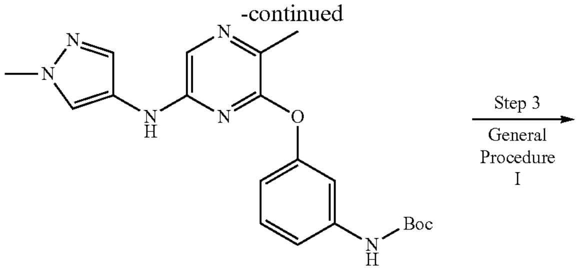

179

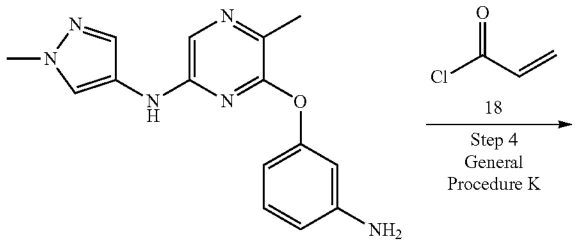

180

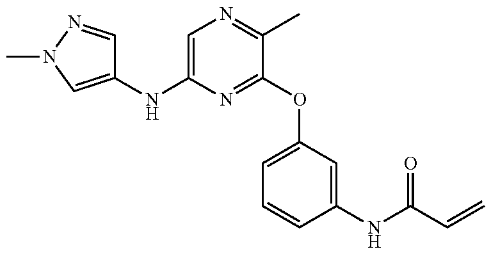

Compound 158

Step 1: Synthesis of tert-butyl (3-((6-chloro-3-methylpyrazin-2-yl)oxy)phenyl)carbamate (178)

To a solution of 3,5-dichloro-2-methylpyrazine (177) (1.00 g, 6.13 mmol) in dimethyl sulfoxide (10.0 mL) were added cesium fluoride (2.80 g, 18.4 mmol) and tert-butyl (3-hydroxyphenyl)carbamate (163) (1.28 g, 6.13 mmol) at room temperature. The reaction mixture was stirred at room temperature for 5 hours. After completion of reaction (as per TLC monitoring), reaction mixture was diluted with water (100 mL) and extracted with ethyl acetate (3×100 mL). The combined organic layers were washed with brine (50 mL), dried over anhydrous sodium sulfate, filtered and concentrated under reduced pressure. The crude residue was purified by silica-gel flash column chromatography, elution with 15-25% ethyl acetate in heptane to get tert-butyl (3-((6-chloro-3-methylpyrazin-2-yl)oxy)phenyl)carbamate (178) as a white solid (1.90 g; Yield: 82.08%). LCMS: $[M+H]^+$ 336.25

Step 2: Synthesis of tert-butyl (3-((3-methyl-6-((1-methyl-1H-pyrazol-4-yl)amino)pyrazin-2-yl)oxy)phenyl)carbamate (179)

To a stirred solution of 1-methyl-1H-pyrazol-4-amine (22) (1.30 g, 3 eq., 13.4 mmol) in toluene (15.0 mL) were added cesium carbonate (4.37 g, 13.4 mmol) and tert-butyl (3-((6-chloro-3-methylpyrazin-2-yl)oxy)phenyl)carbamate (178) (1.50 g, 4.47 mmol) at room temperature. The reaction mixture was degassed with nitrogen for 15 minutes then [1,1'-bis(diphenylphosphino)ferrocene]dichloropalladium (II), complex with dichloromethane (1.09 g, 1.34 mmol) was added at room temperature. Resultant reaction mixture was stirred at 110° C. for 16 hours. After completion of reaction (as per TLC monitoring), reaction mixture was cooled at room temperature, ice cold water (100 mL) was added and extracted with ethyl acetate (3×100 mL). The combined organic layers were washed with brine (100 mL), dried over anhydrous sodium sulfate, filtered and concentrated under reduced pressure to get tert-butyl (3-((3-methyl-6-((1-methyl-1H-pyrazol-4-yl)amino)pyrazin-2-yl)oxy)phenyl)carbamate (179) as viscous liquid (1.00 g). MS: $[M+H]^+$ 397.32.

Step 3: Synthesis of 6-(3-aminophenoxy)-5-methyl-N-(1-methyl-1H-pyrazol-4-yl)pyrazin-2-amine (180)

Title compound was prepared in a manner substantially similar to procedure mentioned in General Procedure I, tert-butyl (3-((3-methyl-6-((1-methyl-1H-pyrazol-4-yl)amino)pyrazin-2-yl)oxy)phenyl)carbamate (179) gave 6-(3-aminophenoxy)-5-methyl-N-(1-methyl-1H-pyrazol-4-yl)pyrazin-2-amine (180) as a brown liquid (1.40 g; Yield: 28.95%). MS: $[M+H]^+$297.36.

Step 4: Synthesis of N-(3-((3-methyl-6-((1-methyl-1H-pyrazol-4-yl)amino)pyrazin-2-yl)oxy)phenyl)acrylamide (Compound 158)

Title compound was prepared in a manner substantially similar to procedure mentioned in in General Procedure K, 6-(3-aminophenoxy)-5-methyl-N-(1-methyl-1H-pyrazol-4-yl)pyrazin-2-amine (180) and acryloyl chloride (18) gave N-(3-((3-methyl-6-((1-methyl-1H-pyrazol-4-yl)amino)pyrazin-2-yl)oxy)phenyl)acrylamide Compound 158 as a light brown solid after prep-HPLC purification (76.0 mg, Yield: 5.09%). $^1$H-NMR (400 MHz, DMSO-$d_6$): δ 10.33 (s, 1H), 9.25 (s, 1H), 7.70 (s, 1H), 7.62 (s, 1H), 7.58 (d, J=8.0 Hz, 1H), 7.46 (t, J=8.0 Hz, 1H), 7.12 (s, 1H), 7.02 (s, 1H), 6.92 (d, J=6.4 Hz, 1H), 6.38-6.45 (m, 1H), 6.23 (d, J=16.8 Hz, 1H), 5.76 (d, J=11.6, 1H), 3.52 (s, 3H), 2.40 (s, 3H). LCMS: $[M+H]^+$ 351.18.

Scheme 41: Synthesis of N-(3-{5-chloro-2-[(1-methyl-1H-pyrazol-4-yl)amino]pyrimidin-4-yl}-4-fluorophenyl)prop-2-enamide (Compound 159)

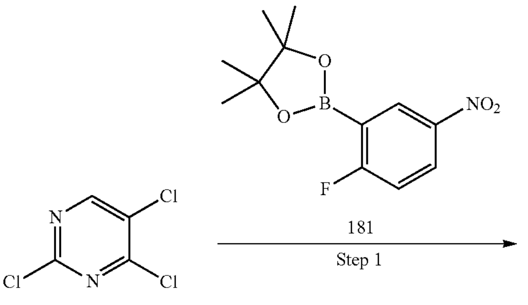

13

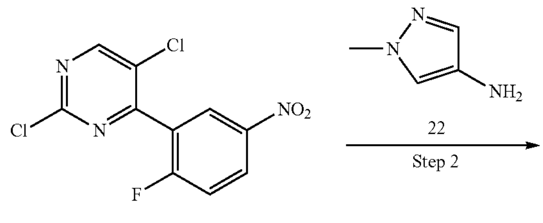

182

-continued

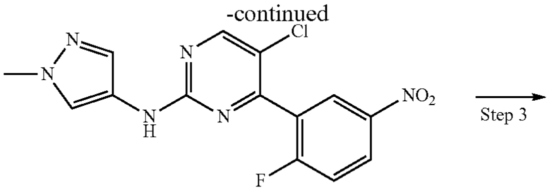

183

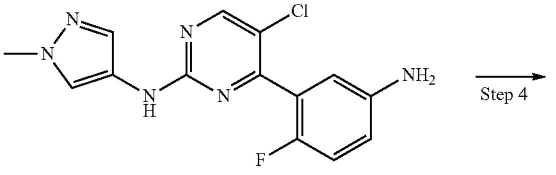

184

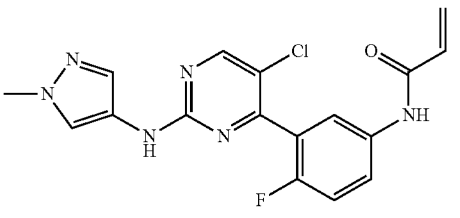

Compound 159

Step 1: Synthesis of 2,5-dichloro-4-(2-fluoro-5-nitrophenyl)pyrimidine (182)

To a stirred solution of 2,4,5-trichloropyrimidine (13) (0.3 g, 1.64 mmol) in 1,4-dioxane (5.00 mL), water (0.5 mL) were added 2-(2-fluoro-5-nitrophenyl)-4,4,5,5-tetramethyl-1,3,2-dioxaborolane (181) (0.52 g, 1.96 mmol), sodium carbonate (0.34 g, 3.27 mmol) and purged with nitrogen for 5 minutes. Then added [1,1'-bis(diphenylphosphino)ferrocene]dichloropalladium(II), complex with dichloromethane (0.067 g, 0.081 mmol) and stirred at 90° C. for 2 hours. The progress of the reaction was monitored by LCMS. After completion of the reaction, reaction mixture was diluted with water and extracted with ethyl acetate (50 mL×2). The combined organic layers were concentrated under reduced pressure. The crude product was purified by using combiflash purifier and was eluted with 1-5% ethyl acetate in hexane to afford the title compound (182) as off white solid (0.5 g, 90%). LCMS: $[M+H]^+$ 288.0

Step 2: Synthesis of 5-chloro-4-(2-fluoro-5-nitrophenyl)-N-(1-methyl-1H-pyrazol-4-yl)pyrimidin-2-amine (183)

To a stirred solution of 2,5-dichloro-4-(2-fluoro-5-nitrophenyl)pyrimidine (182) (0.35 g, 1.22 mmol) in propan-2-ol (10.0 mL), were added 1-methyl-1H-pyrazol-4-amine (22) (0.118 g, 1.22 mmol), N,N-diisopropylethylamine (0.43 mL, 2.43 mmol) and stirred at 100° C. in sealed tube for 16 hours. The progress of the reaction was monitored by LCMS. After completion of the reaction, reaction mixture was diluted with water (10 mL) and extracted with ethyl acetate (50 mL×2). The combined organic layers were concentrated under reduced pressure. The crude product was purified by combiflash column chromatography eluted with 5-7% methanol in dichloromethane to afford title compound (183) (0.36 g, 84%). LCMS: $[M+H]^+$ 349.1

Step 3: Synthesis of 4-(5-amino-2-fluorophenyl)-5-chloro-N-(1-methyl-1H-pyrazol-4-yl)pyrimidin-2-amine (184)

To a stirred solution of 5-chloro-4-(2-fluoro-5-nitrophenyl)-N-(1-methyl-1H-pyrazol-4-yl)pyrimidin-2-amine (183) (0.36 g, 1.03 mmol) in tetrahydrofuran (10.0 mL), methanol (10.0 mL), water (10.0 mL) were added zinc (0.34 g, 5.16 mmol) and ammonium chloride (0.27 g, 5.16 mmol) at 0° C. The reaction mixture was stirred at room temperature for 16 hours. The progress of the reaction was monitored by LCMS. After completion of the reaction, reaction mixture was filtered through celite bed and washed with ethyl acetate. The filtrate was diluted with water (20 mL) and extracted with ethyl acetate (100 mL×2). The combined organic layers were concentrated under reduced pressure. The crude product was purified by combiflash purifier and product was eluted with 4-6% methanol in dichloromethane to afford title compound as off reddish brown gummy solid (184) (0.2 g, 60.7%). $^1$H NMR (400 MHz, DMSO-d6) δ 9.66 (s, 1H), 8.48 (s, 1H), 7.75 (s, 1H), 7.45 (s, 1H), 6.97-6.93 (m, 1H), 6.67-6.62 (m, 2H), 5.07 (s, 2H), 3.75 (s, 3H). LCMS $[M+H]^+$ 319.0.

Step 4: Synthesis of N-(3-{5-chloro-2-[(1-methyl-1H-pyrazol-4-yl)amino]pyrimidin-4-yl}-4-fluorophenyl)prop-2-enamide (Compound 159)

To a stirred solution of 4-(5-amino-2-fluorophenyl)-5-chloro-N-(1-methyl-1H-pyrazol-4-yl)pyrimidin-2-amine (184) (0.1 g, 0.314 mmol) in dichloromethane (10.0 mL) were added triethylamine (0.088 mL, 0.63 mmol) and prop-2-enoyl chloride (0.031 g, 0.35 mmol) in dichloromethane (2 mL) at −30° C. The progress of the reaction was immediately monitored by TLC. After completion of the reaction, reaction mixture was quenched with saturated sodium bicarbonate solution (5 mL) at −30° C. and extracted with ethyl acetate (50 mL×2). The combined organic layers were concentrated under reduced pressure. The crude product was purified by combiflash chromatography eluted with 24% methanol in dichloromethane to obtain crude product. The crude was purified by Prep-HPLC to get the title compound as off yellow solid (0.038 g, 33.1%). $^1$H NMR (400 MHz, DMSO-d6) δ 10.35 (s, 1H), 8.55 (s, 1H), 7.94 (s, 2H), 7.82 (s, 1H), 7.73 (s, 1H), 7.45 (s, 1H), 7.35-7.31 (m, 1H), 6.43-6.36 (m, 1H), 6.27-6.23 (d, J=16.0 Hz, 1H), 5.77-5.75 (d, J=11.6 Hz, 1H), 3.76 (s, 3H). LCMS: $[M+H]^+$ 372.9.

Scheme 42: Synthesis of (E)-N-(3-(5-chloro-2-((1-methyl-1H-pyrazol-4-yl)amino)pyrimidin-4-yl)-4-fluorophenyl)-4-(dimethylamino)but-2-enamide (Compound 160)

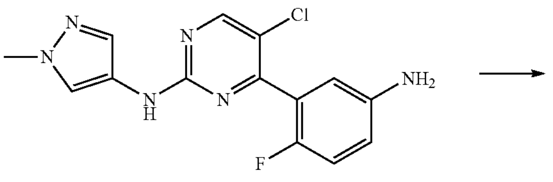

184

-continued

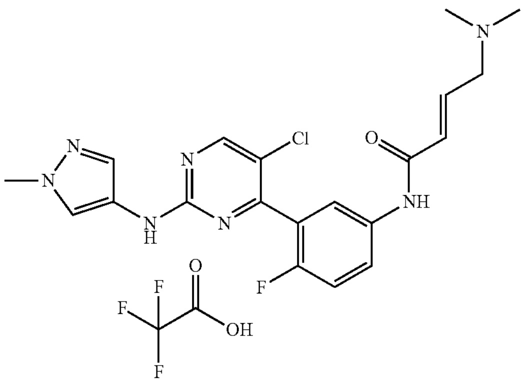

Compound 160

Title compound was prepared in a manner substantially similar to procedure mentioned in General Procedure J as a yellow solid (0.016 g; Yield: 12%). $^1$H NMR (400 MHz, DMSO-d6) δ 10.57 (s, 1H), 9.85 (s, 1H), 9.65 (s, 1H), 8.56 (s, 1H), 7.94-7.75 (m, 3H), 7.46 (s, 1H), 7.35 (s, 1H), 6.71 (s, 1H), 6.43-6.39 (d, J=15.2 Hz, 1H), 3.93 (s, 2H), 3.76 (s, 3H), 2.78 (s, 6H). LCMS: $[M+H]^+$ 430.2.

Scheme 46: N-[4-fluoro-3-({2-[(1-methyl-1H-pyrazol-4-yl)amino]-5-(2-phenylethynyl)pyrimidin-4-yl}amino)phenyl]prop-2-enamide. TFA Salt (Compound 161)

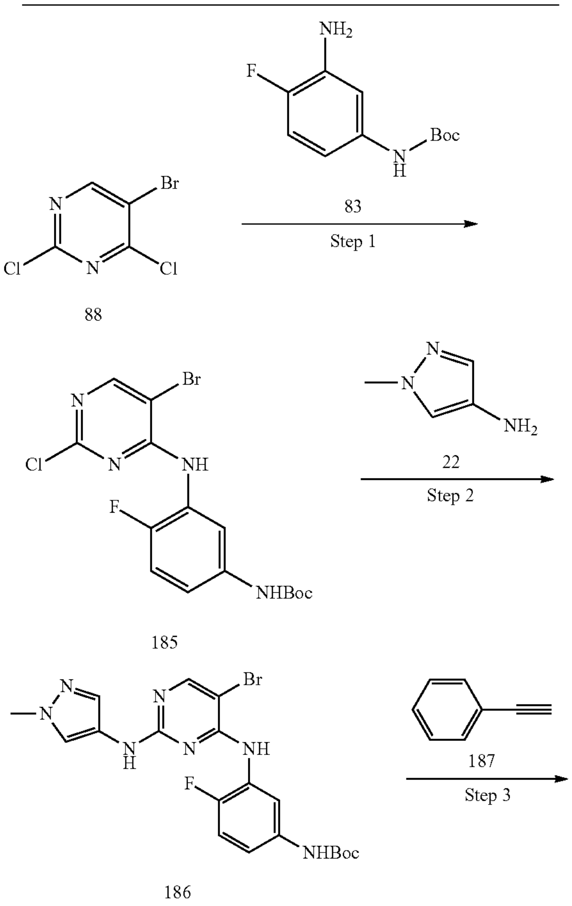

-continued

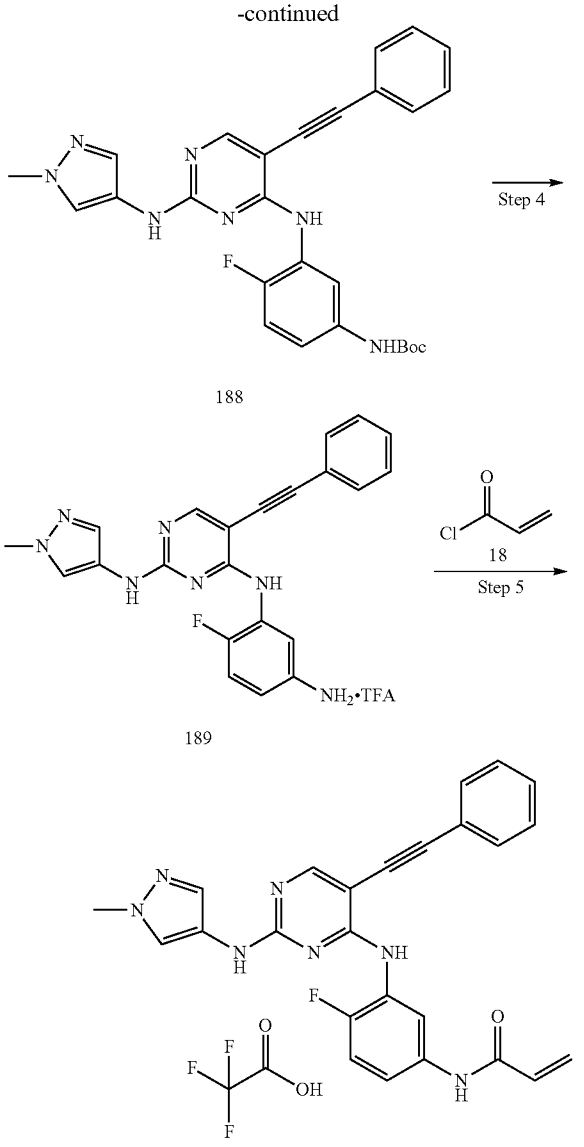

Compound 161

Step 1: Synthesis of tert-butyl (3-((5-bromo-2-chloropyrimidin-4-yl)amino)-4-fluorophenyl)carbamate (185)

To a microwave vial were added, 5-bromo-2,4-dichloropyrimidine (88) (1.00 g, 4.39 mmol), tert-butyl N-(3-amino-4-fluorophenyl)carbamate (83) (0.993 g, 4.39 mmol), N,N-dimethylformamide (10.0 mL) and dipotassium carbonate (1.21 g, 8.78 mmol). The reaction mixture was heated at 100° C. for 1 hour in microwave. The reaction was monitored by TLC and LCMS. After completion of the reaction, reaction mixture was diluted with cold water (25 mL) and extracted with ethyl acetate (3×20 mL). The combined organic layers were washed with brine (20 mL), water (20 mL), dried over anhydrous sodium sulfate and evaporated under reduced pressure to give crude compound. The crude residue was purified by combiflash purifier using 50% ethyl acetate in hexane to afford title compound (185) as light yellow solid (1.1 g, crude). LCMS: $[M+H]^+$ 417.0

Step 2: Synthesis of tert-butyl N-[3-({5-bromo-2-[(1-methyl-1H-pyrazol-4-yl)amino]pyrimidin-4-yl}amino)-4-fluorophenyl]carbamate (186)

To a stirred solution of tert-butyl N-{3-[(5-bromo-2-chloropyrimidin-4-yl)amino]-4-fluorophenyl}carbamate (185) (1.00 g, 2.39 mmol), 1-methyl-1H-pyrazol-4-amine (22) (0.233 g, 2.39 mmol) in propan-2-ol (10.0 mL) was added trifluoroacetic acid (0.1 mL). The reaction mixture was heated at 90° C. for 30 minutes in microwave. The reaction mixture was evaporated under reduced pressure. The crude product was purified by combiflash purifier with 50% ethyl acetate in hexane as an eluent give the title compound (186) as brown solid (0.75 g, 65%). LCMS: $[M+H]^+$ 478.1

Step 3: Synthesis of tert-butyl N-[4-fluoro-3-({2-[(1-methyl-1H-pyrazol-4-yl)amino]-5-(2-phenylethynyl)pyrimidin-4-yl}amino)phenyl]carbamate (188)

To a sealed tube, were added tert-butyl N-[3-({5-bromo-2-[(1-methyl-1H-pyrazol-4-yl)amino]pyrimidin-4-yl}amino)-4-fluorophenyl]carbamate (186) (0.6 g, 1.25 mmol), N,N-dimethylformamide (10.0 mL) and triethylamine (0.35 mL, 2.51 mmol). The reaction mixture was degassed with nitrogen for 10 minutes and added copper iodide (0.048 g, 0.25 mmol), bis(triphenylphosphine)palladium(II) dichloride (0.088 g, 0.125 mmol) and ethynylbenzene (197) (0.19 g, 1.88 mmol). The reaction mixture was heated at 85° C. for 9 hours. The reaction was monitored by LCMS and TLC. The reaction mixture was diluted with water (20 mL) and extracted with ethyl acetate (2×20 mL). The combined organic layer was washed with brine (20 mL), dried over anhydrous sodium sulfate, filtered and evaporated under reduced pressure to give crude product. The crude product was purified by column chromatography by using silica column with 60% ethyl acetate in hexane as eluent to give the title compound (188) as yellow solid (0.4 g, crude). LCMS: $[M+H]^+$ 500.3

Step 4: Synthesis of 2,2,2-trifluoro-N-[4-fluoro-3-({2-[(1-methyl-1H-pyrazol-4-yl)amino]-5-(2-phenylethynyl)pyrimidin-4-yl}amino)phenyl]acetamide (189)

To a stirred solution of tert-butyl N-[4-fluoro-3-({2-[(1-methyl-1H-pyrazol-4-yl)amino]-5-(2-phenylethynyl)pyrimidin-4-yl}amino)phenyl]carbamate (188) (0.375 g, 0.75 mmol) in dichloromethane (5 mL) at 0° C. was added trifluoroacetic acid (0.4 mL) drop wise and the reaction mixture was stirred at room temperature for 2 hours. The reaction mixture was evaporated under reduced pressure to give crude product. The crude product was triturated with diethyl ether (20 mL) and dried to give 2,2,2-trifluoro-N-[4-fluoro-3-({2-[(1-methyl-1H-pyrazol-4-yl)amino]-5-(2-phenylethynyl)pyrimidin-4-yl}amino)phenyl]acetamide (189) as brown solid (0.1 g, crude). LCMS: $[M+H]^+$ 400.2

Step 5: Synthesis of N-[4-fluoro-3-({2-[(1-methyl-1H-pyrazol-4-yl)amino]-5-(2-phenylethynyl)pyrimidin-4-yl}amino)phenyl]prop-2-enamide·TFA Salt (Compound 161)

To a stirred solution of 2,2,2-trifluoro-N-[4-fluoro-3-({2-[(1-methyl-1H-pyrazol-4-yl)amino]-5-(2-phenylethynyl)pyrimidin-4-yl}amino)phenyl]acetamide (189) (0.1 g, 0.2 mmol) in dichloromethane (5 mL) was added triethylamine (0.08 mL, 0.60 mmol) and cooled to −40° C., stirred for 10 minutes. After 10 minutes, prop-2-enoyl chloride (18) (0.02 g, 0.2 mmol) was added and stirred for 20 minutes at −40° C. The reaction mixture was quenched with water (5 mL) and extracted in to dichloromethane (2×5 mL). The combined organic layer was washed with water (5 mL), brine (5 mL), dried over anhydrous sodium sulfate and evaporated under reduced pressure. The crude product was purified by combiflash purifier with 5% methanol in dichloromethane as an eluent. It was further purified by preparative HPLC to give the title compound (Compound 161) as white solid (0.02 g, 22%). $^1$H NMR (400 MHz, DMSO d6) δ 10.3 (s, 1H), 9.72 (s, 1H), 9.15 (s, 1H), 8.24 (s, 1H), 7.87 (bs, 2H), 7.63-7.62 (m, 3H), 7.41-7.39 (m, 4H), 7.17-7.11 (m, 2H), 6.44-6.38 (m, 1H), 6.27-6.23 (m, 1H), 5.76 (d, J=10.0 Hz, 1H), 3.56 (s, 3H). LCMS: $[M+H]^+$ 454.5

Scheme 43: Synthesis of (2E)-4-(dimethylamino)-N-[4-fluoro-3-({2-[(1-methyl-1H-pyrazol-4-yl)amino]-5-(2-phenylethynyl)pyrimidin-4-yl}amino)phenyl]but-2-enamide (Compound 162)

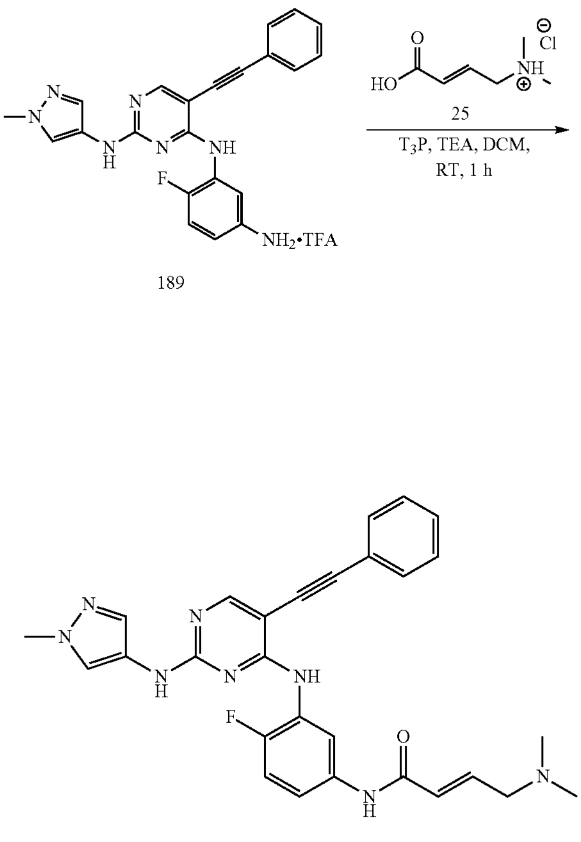

Compound 162

Title compound (Compound 162) was prepared in a manner substantially similar to procedure mentioned in General Procedure J as white solid (0.035 g, 28%). $^1$H NMR (400 MHz, DMSO d6) δ 10.20 (s, 1H), 9.47 (s, 1H), 8.83 (s, 1H), 8.20 (s, 1H), 7.82 (d, J=5.6 Hz, 1H), 7.65-7.60 (m, 3H), 7.40-7.35 (m, 4H), 7.14-7.10 (m, 2H), 6.76-6.69 (m, 1H), 6.26-6.22 (m, 1H), 3.52 (s, 3H), 3.04 (d, J=5.2 Hz, 2H), 2.15 (s, 6H). LCMS: $[M+H]^+$ 511.5.

Scheme 48: Synthesis of 2-({5-chloro-2-[(1-methyl-1H-pyrazol-4-yl) amino] pyrimidin-4-yl}amino)-N-phenyl-4-(prop-2-enamido) benzamide (Compound 163)

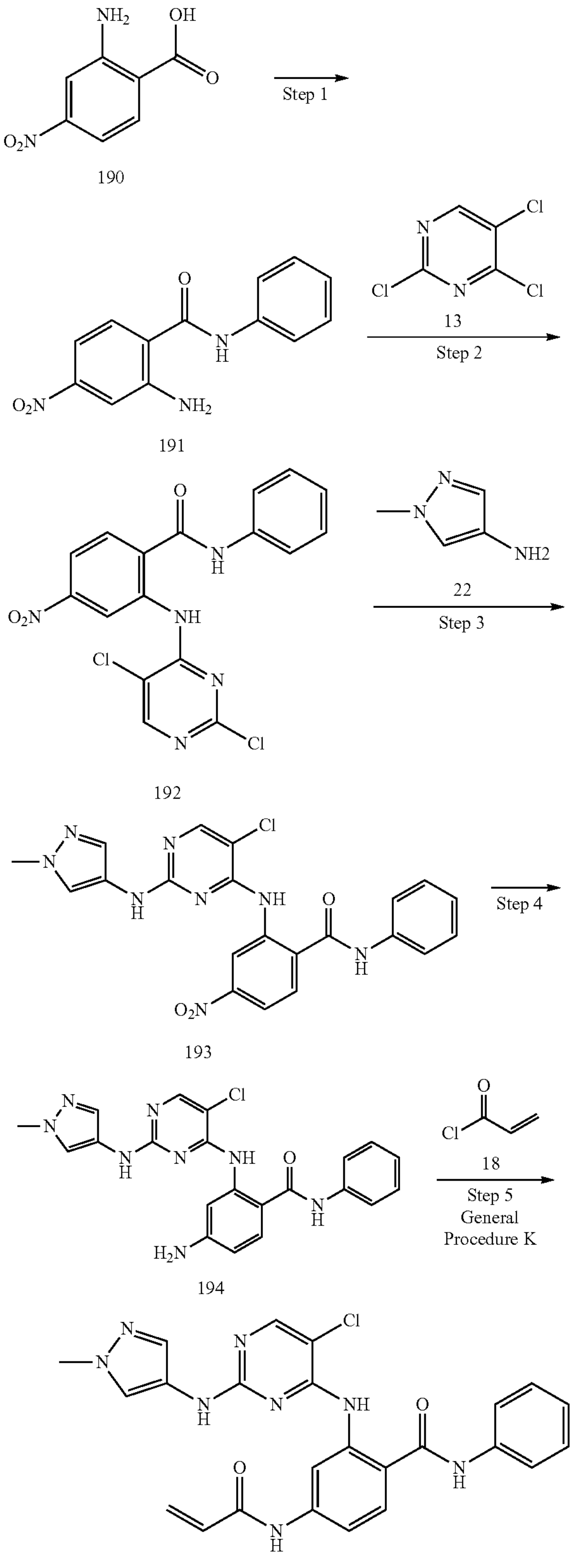

190

191

192

193

194

Compound 163

Step 1: Synthesis of 2-amino-4-nitro-N-phenylbenzamide (191)

To a stirred solution of 2-amino-4-nitrobenzoic acid (190) (2.00 g, 11.0 mmol) in dichloromethane (30.0 mL) were added 1H-1,2,3-benzotriazol-1-ol hydrate (1.68 g, 11.0 mmol), (3-{[(ethylimino)methylidene] amino} propyl) dimethylamine (1.70 g, 11.0 mmol) followed by N,N-diisopropylethylamine (2.13 g, 16.5 mmol) and aniline (1.12 g, 12.1 mmol) at 25° C. and stirred at 25° C. for 6 hours. The reaction mixture was diluted with water (30 mL) and extracted with dichloromethane (3x25 mL). The combined organic layer was washed with water (25 mL), brine (25 mL), dried over anhydrous sodium sulfate and evaporated under reduced pressure. The crude product was purified by column chromatography and was eluted with 12-20% ethyl acetate in hexane to afford (191) (1.70 g, 60%). LCMS: $[M+H]^+$ 258.1.

Step 2: Synthesis of 2-[(2,5-dichloropyrimidin-4-yl) amino]-4-nitro-N-phenylbenzamide (192)

To a stirred solution of 2-amino-4-nitro-N-phenylbenzamide (191) (1.00 g, 3.89 mmol) in N, N-dimethylformamide (10.0 mL) were added sodium hydride (0.187 g, 7.77 mmol) followed by 2,4,5-trichloropyrimidine (1.07 g, 5.83 mmol) at 25° C. and stirred at 25° C. for 3 hours. Then the reaction mixture was quenched with water (25 mL) and extracted with ethyl acetate (3x30 mL). The combined organic layers were washed with brine (25 mL), dried over anhydrous sulfate and evaporated under reduced pressure to get (192) (0.55 g, 35%). LCMS: $[M+H]^+$ 404.0.

Step 3: Synthesis of 2-({5-chloro-2-[(1-methyl-1H-pyrazol-4-yl) amino] pyrimidin-4-yl}amino)-4-nitro-N-phenylbenzamide (193)

To a stirred solution of 2-[(2,5-dichloropyrimidin-4-yl) amino]-4-nitro-N-phenylbenzamide (194) (0.5 g, 1.24 mmol) in propan-2-ol (7.00 mL) were added 1-methyl-1H-pyrazol-4-amine (22) (0.12 g, 1.24 mmol), trifluoroacetic acid (0.141 g, 1.24 mmol) and the reaction mixture was heated at 100° C. for 12 hours. The reaction mixture was diluted with isopropanol (4 mL) and filtered. The solid obtained was dried to afford (193) (0.550 g, 95%). LCMS: $[M+H]^+$ 464.1

Step 4: Synthesis of 4-amino-2-({5-chloro-2-[(1-methyl-1H-pyrazol-4-yl) amino] pyrimidin-4-yl} amino)-N-phenylbenzamide (194)

Title compound was prepared in a manner substantially similar to procedure mentioned in in General Procedure L, to get the desired compound 194 as brown solid (0.15 g, Yield: 53%). LCMS: $[M+H]^+$ 435.1.

Step 5: Synthesis of 2-({5-chloro-2-[(1-methyl-1H-pyrazol-4-yl) amino] pyrimidin-4-yl}amino)-N-phenyl-4-(prop-2-enamido) benzamide (Compound 163)

The title compound was prepared in a manner substantially similar to procedure mentioned in General Procedure K, to afford the desired compound as white solid. $^1H$ NMR (400 MHz, DMSO-$d_6$): δ 10.95 (bs, 1H), 10.43 (s, 1H), 9.19 (s, 1H), 8.78 (s, 1H), 8.01 (s, 1H), 7.84-7.81 (m, 2H), 7.42-7.38 (m, 3H), 7.11-6.96 (m, 3H), 6.42 (m, 2H), 6.31-6.26 (m, 1H), 5.81-5.78 (m, 1H), 5.73 (s, 1H), 3.49 (s, 3H). LCMS: $[M+H]^+$ 489.1.

Scheme 44: Synthesis of N4-(5-amino-2-chlorophenyl)-N2-(1-methyl-1H-pyrazol-4-yl)pyrimidine-2,4-diamineprop-2-enoyl chloride (Compound 165)

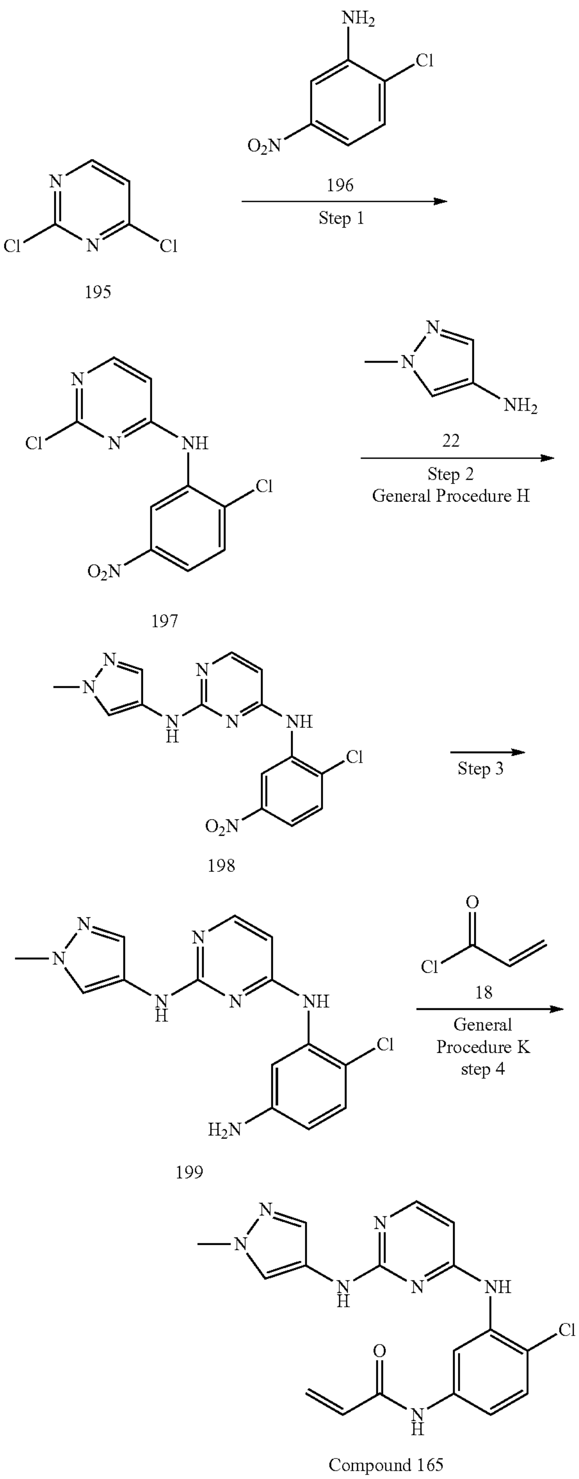

Compound 165

Step 1: Synthesis of 2-chloro-N-(2-chloro-5-nitrophenyl) pyrimidin-4-amine (197)

To a stirred solution of 2-chloro-5-nitroaniline (196) (1.16 g, 1 eq., 6.71 mmol) in N,N-dimethylformamide (10.0 mL) was added sodium hydride (805 mg, 3 eq., 20.1 mmol) and stirred for 10 minutes then 2,4-dichloropyrimidine (195) (1.00 g, 6.71 mmol) was added and the reaction mixture was stirred for 1 hour. After completion of reaction (TLC monitoring), The crude was diluted with ice water (200 mL) and extracted with ethyl acetate (3×200 mL). The combined organic layer was dried over anhydrous sodium sulfate, filtered and concentrated under reduced pressure to get the crude compound which was purified by combiflash column chromatography and the compound was eluted at 20% ethyl acetate in hexane to afford the title compound (197) (0.50 g, 26%). LCMS: $[M+H]^+$ 285.0.

Step 2: Synthesis of N4-(2-chloro-5-nitrophenyl)-N2-(1-methyl-1H-pyrazol-4-yl) pyrimidine-2,4-di amine (198)

The title compound was prepared in a manner substantially similar to procedure mentioned in General Procedure H, to afford the desired compound as white solid (198) (300 mg, 49%). LCMS: $[M+H]^+$ 346.0.

Step 3: Synthesis of N4-(5-amino-2-chlorophenyl)-N2-(1-methyl-1H-pyrazol-4-yl) pyrimidine-2,4-diamine (199)

To a stirred suspension of N4-(2-chloro-5-nitrophenyl)-N2-(1-methyl-1H-pyrazol-4-yl)pyrimidine-2,4-diamine (198) (0.50 g, 1.45 mmol) in anhydrous methanol (20.0 mL) at room temperature was added Raney® nickel (0.255 g, 4.34 mmol) and the reaction mixture was stirred in a hydrogen atmosphere for 2 hours. After completion (TLC monitoring), the reaction mixture was filtered through celite, washed with methanol, the filtrate was concentrated under reduced pressure to afford the title compound as a colorless gummy solid (199). LCMS $[M+H]^+$ 316.1.

Step 4: Synthesis of N4-(5-amino-2-chlorophenyl)-N2-(1-methyl-1H-pyrazol-4-yl)pyrimidine-2,4-diamineprop-2-enoyl chloride (Compound 165)

The title compound was prepared in a manner substantially similar to procedure mentioned in General Procedure K, to afford the desired compound as white solid (25 mg, 21%). $^1$H NMR (400 MHz, DMSO-d6): δ10.35 (s, 1H), 9.18 (bs, 2H), 7.95 (d, J=5.6 Hz, 2H), 7.63 (d, J=8.4 Hz, 1H), 7.50 (d, J=8.4 Hz, 2H), 7.27 (bs, 1H), 6.44-6.37 (m, 1H), 6.24 (d, J=16.8 Hz, 1H), 6.15 (d, J=6.0 Hz, 1H), 5.76 (d, J=10.0 Hz, 1H), 3.58 (s, 3H). LCMS: $[M+H]^+$ 370.0.

Scheme 45: Synthesis of N-(3-((5-chloro-2-((1-methyl-1H-pyrazol-4-yl)amino)pyrimidin-4-yl)oxy)-4-fluorophenyl)acrylamide (Compound 166)

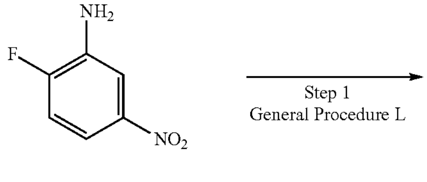

200

-continued

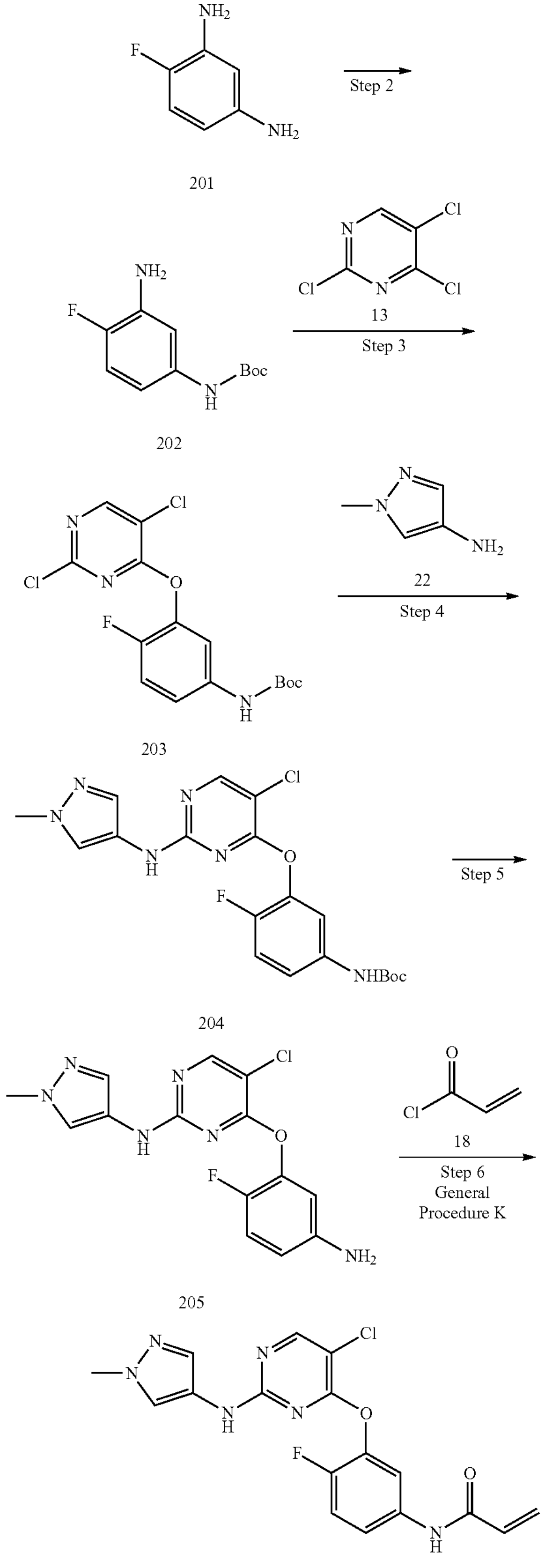

Compound 166

Step 1: Synthesis of 5-amino-2-fluorophenol (201)

The title compound was prepared in a manner substantially similar to procedure mentioned in General Procedure L1, to afford the desired compound as off white solid (201) (0.4 g, 49%). $^1$H NMR (400 MHz, DMSO-$d_6$): δ 9.20 (s, 1H), 6.72-6.67 (m, 1H), 6.14 (dd, J=8.0 Hz & 2.0 Hz, 1H), 5.91-5.89 (m, 1H), 4.72 (s, 2H).

Step 2: Synthesis of tert-butyl (4-fluoro-3-hydroxyphenyl)carbamate (202)

To a stirred solution of 5-amino-2-fluorophenol (201) (0.2 g, 1.57 mmol) in tetrahydrofuran (5.00 mL) at 0° C. was added di-tert-butyl dicarbonate (0.542 mL, 2.36 mmol) and the reaction mixture was heated at 70° C. for 15 hours. The reaction mixture was cooled to room temperature, diluted with water (20 mL) and extracted with ethyl acetate (20 mL×3). The combined organic layer was washed with brine (20 mL), dried over anhydrous sodium sulfate and evaporated. The crude product was purified by column chromatography using combiflash purifier and was eluted with 25% ethyl acetate in hexane to afford the title compound (202) as brown liquid (0.28 g, 78%). $^1$H NMR (400 MHz, DMSO-$d_6$): δ 9.67 (s, 1H), 9.18 (s, 1H), 7.19 (d, J=6.8 Hz, 1H), 6.97-6.92 (m, 1H), 6.77-6.75 (m, 1H), 1.44 (s, 9H).

Step 3: Synthesis of tert-butyl (3-((2,5-dichloropyrimidin-4-yl)oxy)-4-fluorophenyl)carbamate (203)

To a stirred solution of 2,4,5-trichloropyrimidine (13) (0.10 g, 0.545 mmol) and tert-butyl N-(4-fluoro-3-hydroxyphenyl)carbamate (202) (0.124 g, 0.545 mmol) in N,N-dimethylformamide (3.00 mL) was added potassium carbonate (0.124 g, 0.54 mmol) and the reaction mixture was heated at 60° C. for 2 hours. Then the reaction mixture was cooled to room temperature, diluted with water (25 mL) and extracted with ethyl acetate (20 mL×3). The combined organic layers were washed with water (25 mL×2), brine (25 mL), dried over anhydrous sodium sulfate and concentrated under reduced pressure. The crude product was purified by column chromatography using combiflash purifier and was eluted with 25% ethyl acetate in hexane to afford the title compound (203) as white solid (0.15 g, 73%). LCMS: $[M+H]^+$ 374.0

Step 4: Synthesis of tert-butyl (3-((5-chloro-2-((1-methyl-1H-pyrazol-4-yl)amino)pyrimidin-4-yl)oxy)-4-fluorophenyl)carbamate (204)

To a stirred solution of tert-butyl N-{3-[(2,5-dichloropyrimidin-4-yl)oxy]-4-fluorophenyl}carbamate (203) (0.140 g, 0.374 mmol) in propan-2-ol (3.00 mL) was added 1-methyl-1H-pyrazol-4-amine (22) (0.043 g, 0.449 mmol) and N,N-diisopropylethylamine (0.14 mL, 0.748 mmol) and the reaction mixture was heated at 100° C. for 5 hours. The reaction mixture was cooled to room temperature and evaporated. The residue was diluted with water and extracted with ethyl acetate (10 mL×3). The combined organic layer was washed with brine (10 mL), dried over anhydrous sodium sulfate and evaporated. The crude compound was purified by column chromatography using combiflash purifier and was eluted with 40% ethyl acetate in hexane to afford the title compound (204) as off white solid (0.15 g, 92%). LCMS: $[M+H]^+$ 435.2.

Step 5: Synthesis of 4-(5-amino-2-fluorophenoxy)-5-chloro-N-(1-methyl-1H-pyrazol-4-yl)pyrimidin-2-amine (205)

To a stirred solution of tert-butyl N-[3-({5-chloro-2-[(1-methyl-1H-pyrazol-4-yl)amino]pyrimidin-4-yl}oxy)-4-fluorophenyl]carbamate (204) (0.1 g, 0.230 mmol) in dichloromethane (3.00 mL) at 0° C. was added trifluoroacetic acid (0.5 mL) and the reaction mixture was stirred at room temperature for 2 hours. The reaction mixture was evaporated to dryness. The residue was washed with ether (20 mL), pentane (20 mL) and dried to afford the title compound (205) as off white solid (0.1 g, crude). LCMS: $[M+H]^+$ 335.1.

Step 6: Synthesis of N-(3-((5-chloro-2-((1-methyl-1H-pyrazol-4-yl)amino)pyrimidin-4-yl)oxy)-4-fluorophenyl)acrylamide, (Compound 166)

The title compound was prepared in a manner substantially similar to procedure mentioned in General Procedure K, to afford the desired compound as white solid (0.045 g, 51%). $^1H$ NMR (400 MHz, $CD_3OD$): δ 8.28 (s, 1H), 7.47-7.65 (m, 2H), 7.33-7.20 (m, 2H), 6.93 (bs, 1H), 6.45-6.34 (m, 2H), 5.79 (d, J=8.8 Hz, 1H), 3.62 (s, 3H). LCMS: $[M+H]^+$ 389.0

Scheme 46: Synthesis of N-(3-((5-chloro-2-((1-(2-hydroxyethyl)-1H-pyrazol-4-yl)amino)pyrimidin-4-yl)oxy)-4-fluorophenyl)acrylamide (Compound 167)

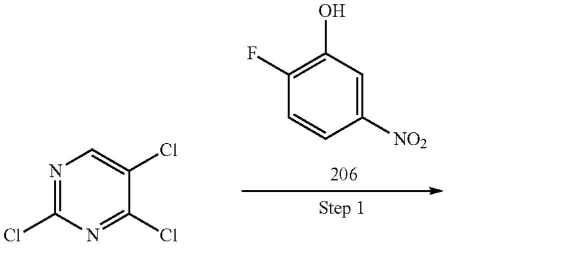

13

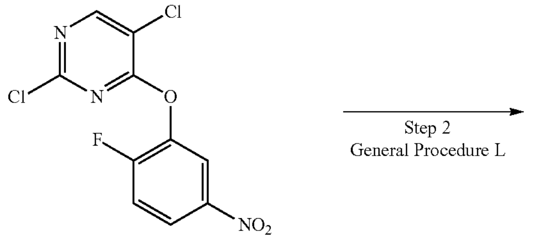

207

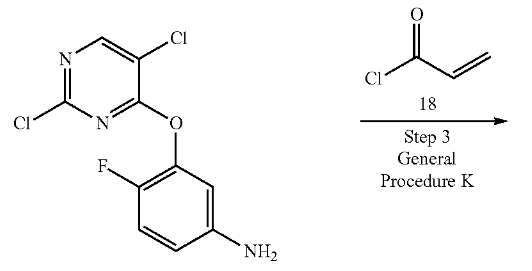

208

-continued

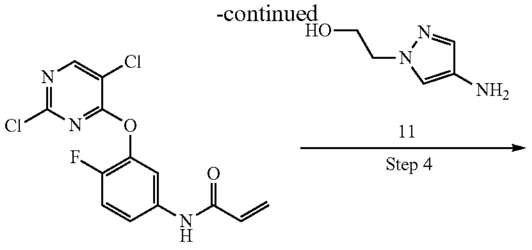

209

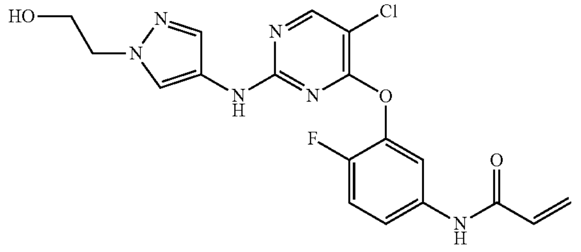

Compound 167

Step 1: Synthesis of 2,5-dichloro-4-(2-fluoro-5-nitrophenoxy)pyrimidine (207)

To a stirred solution of 2,4,5-trichloropyrimidine (13) (1.10 g, 6.00 mmol) and 2-fluoro-5-nitrophenol (206) (0.942 g, 6.00 mmol) in N,N-dimethylformamide (10.0 mL) was added potassium carbonate (1.24 g, 9.0 mmol) and the reaction mixture was heated at 60° C. for 3 hours. Then the reaction mixture was cooled to room temperature, diluted with water (25 mL) and extracted with ethyl acetate (20 mL×3). The combined organic layer was washed with water (25 mL×2), brine (25 mL), dried over anhydrous sodium sulfate and evaporated. The crude product was purified by column chromatography using combiflash purifier and was eluted with 6% ethyl acetate in hexane to get the title compound (207) as white solid (1.4 g, 76.78%). $^1H$ NMR (400 MHz, DMSO-$d_6$): δ 8.94 (s, 1H), 8.55-8.53 (m, 1H), 8.34-8.31 (m, 1H), 7.80 (t, J=9.2 Hz, 1H).

Step 2: Synthesis of 3-((2,5-dichloropyrimidin-4-yl)oxy)-4-fluoroaniline (208)

The title compound was prepared in a manner substantially similar to procedure mentioned in General Procedure L, to afford the desired compound as yellow solid (208) (0.64 g, 78%). LCMS: $[M+H]^+$ 274.

Step 3: Synthesis of N-(3-((2,5-dichloropyrimidin-4-yl)oxy)-4-fluorophenyl)acrylamide (209)

The title compound was prepared in a manner substantially similar to procedure mentioned in General Procedure K, to afford the desired compound as off white solid (209) (0.6 g, 77%). LCMS: $[M+H]^+$ 328.0

Step 4: Synthesis of N-(3-((5-chloro-2-((1-(2-hydroxyethyl)-1H-pyrazol-4-yl)amino)pyrimidin-4-yl)oxy)-4-fluorophenyl)acrylamide (Compound 167)

To a stirred solution of N-{3-[(2,5-dichloropyrimidin-4-yl)oxy]-4-fluorophenyl}prop-2-enamide (209) (0.15 g, 0.457 mmol) and 2-(4-amino-MH-pyrazol-1-yl)ethan-1H-ol

(11) (0.087 g, 0.686 mmol) in propan-2-ol (3.00 mL) was added N,N-diisopropyl ethylamine (0.169 mL, 0.914 mmol) and the reaction mixture was heated in a sealed tube at 100° C. for 15 hours. The reaction mixture was cooled and evaporated. The residue was diluted with water (25 mL) and extracted with ethyl acetate (25 mL×3). The combined organic layers were washed with brine (25 mL), dried over anhydrous sodium sulfate and evaporated. The crude product was purified by column chromatography using combi-flash purifier and was eluted with 4.500 methanol in dichloromethane to get the title compound (Compound 167) as off white solid (0.1 g, 52%). $^1H$ NMR (400 MHz, DMSO-$d_6$): δ 10.36 (bs, 1H), 9.84 (bs, 1H), 8.42 (s, 1H), 7.85 (bs, 1H), 7.57 (bs, 1H), 7.44 (bs, 1H), 7.06 (s, 1H), 6.90 (bs, 1H), 6.42-6.36 (m, 1H), 6.27-6.23 (m, 1H), 5.77 (d, JP 10.0 Hz, 1H), 4.70 (bs, 1H), 3.80 (bs, 2H), 3.53 (bs, 2H). LCMS: $[M+H]^+$ 419.0

TABLE 10

The following compounds were prepared using the procedures described above:

| Cmpd. No. | Structure | General Procedure | LCMS [M + H] | $^1H$-NMR (400 MHz, DMSO-$d_6$) |
|---|---|---|---|---|
| 164 | 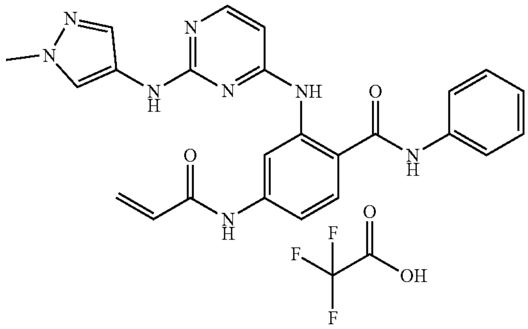 | K | 455.0 | δ 10.54-10.49 (m, 2H), 10.24 (s, 1H), 8.13 (s, 1H),7.88 (s, 1H), 7.79-7.63 (m, 6H), 7.36-7.28 (m, 4H), 7.07-7.02 (m, 1H), 6.51-6.44 (m, 1H), 6.37-6.26 (m, 2H), 5.81 (d, J = 10.4 Hz, 1H), 3.64 (s, 3H). |
| 168 | 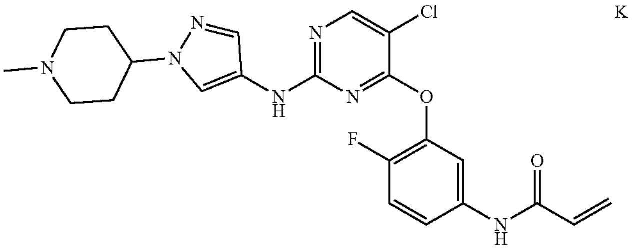 | K | 472.0 | δ 10.41 (bs, 1H), 9.90 (bs, 1H), 8.43 (s, 1H), 7.81 (bs, 1H), 7.66 (bs, 1H), 7.50 (bs, 1H), 7.13 (s, 1H), 6.89 (bs, 1H), 6.43-6.36 (m, 1H), 6.28-6.24 (m, 1H), 5.78 (d, J = 10.4 Hz, 1H), 3.59 (bs, 1H), 2.78-2.75 (m, 2H), 2.18 (s, 3H), 1.95 (bs, 2H), 1.63 (bs, 4H) |
| 169 | 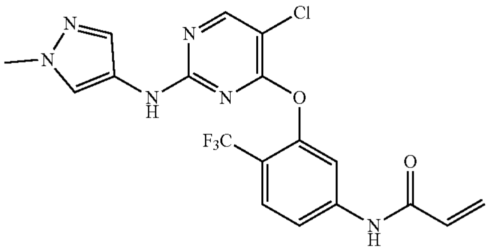 [SMILES: C=CC(=O)Nc1ccc(C(F)(F)F)c(Oc2nc(Nc3cnn(C)c3)ncc2Cl)c1] | H | 439.1 | δ 10.73 (s, 1H), 9.85 (s, 1H), 8.43 (s, 1H), 7.84 (d, J = 17.2 Hz, 3H), 7.04 (s, 1H), 6.81 (s, 1H), 6.40-6.46 (m, 1H), 6.29 (d, J = 16.8 Hz, 1H), 5.82 (d, J = 10.0 Hz, 1H), 3.49 (s, 3H). |
| 170 | 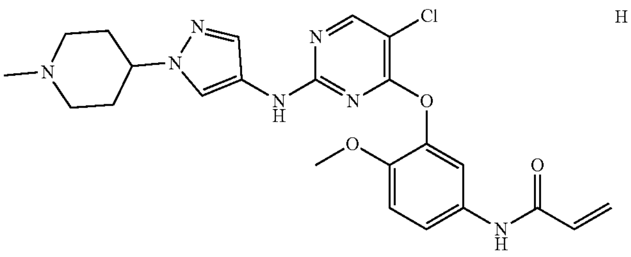 | H | 484.0 | δ 10.19 (s, 1H), 9.74 (s, 1H), 8.35 (s, 1H), 7.63 (s, 2H), 7.22-7.12 (s, 2H), 6.86 (s, 1H), 6.42-6.37 (m, 1H), 6.23 (d, J = 8.6 Hz, 1H), 5.73 (d, J = 10.4 Hz, 1H), 3.66-3.58 (m, 4H), 2.77 (d, J = 9.6 Hz, 2H), 2.18 (s, 3H), 1.96-1.94 (m, 2H), 1.63 (bs, 4H). |

TABLE 10-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 171 | 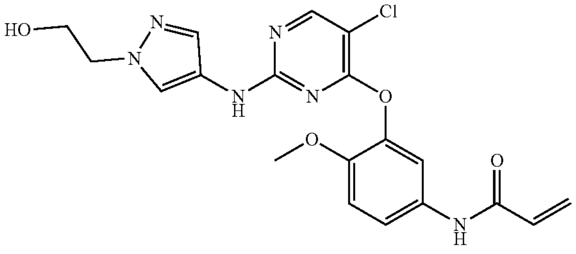 [SMILES: C=CC(=O)Nc1ccc(OC)c(Oc2nc(Nc3cnn(CCO)c3)ncc2Cl)c1] | H | 431.0 | δ 10.18 (s, 1H), 9.73 (s, 1H), 8.34 (s, 1H), 7.55-7.65 (m, 2H), 7.22 (s, 1H), 7.04 (s, 1H), 6.82 (s, 1H), 6.33-6.40 (m, 1H), 6.20 (d, J = 8.4 Hz, 1H), 5.71 (d, J = 8.0 Hz, 1H), 4.72 (s, 1H), 3.77 (s, 2H), 3.66 (s, 3H), 3.51 (s, 2H). |

Scheme 47: Synthesis of N-[3-({5-chloro-2-[(1-methyl-1H-pyrazol-4-yl) amino] pyrimidin-4-yl} oxy)-4-methoxyphenyl] prop-2-enamide (Compound 172)

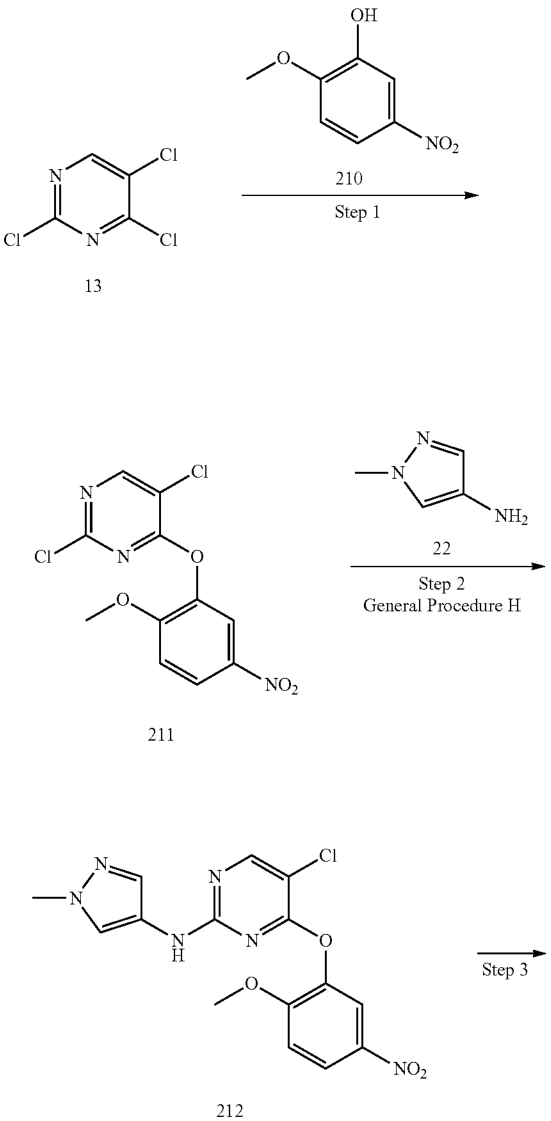

-continued

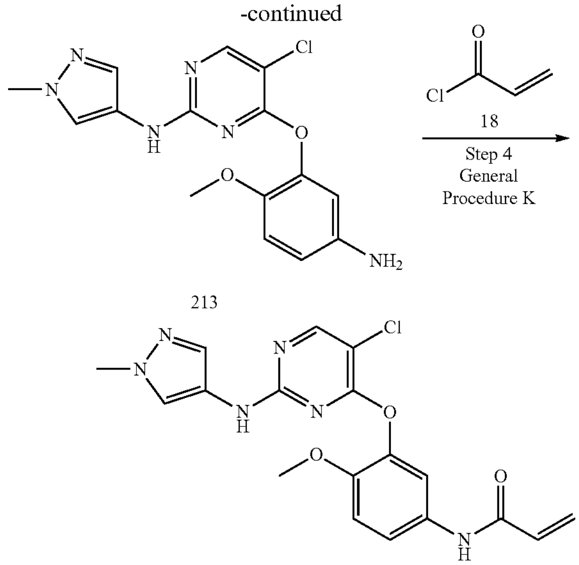

Compound 172

Step 1: Synthesis of 2,5-dichloro-4-(2-methoxy-5-nitrophenoxy) pyrimidine (211)

To a stirred solution of 2,4,5-trichloropyrimidine (13) (3.0 g, 16.4 mmol) in N, N-dimethylformamide (20 mL) were added potassium carbonate (6.78 g, 49.1 mmol), 2-methoxy-5-nitrophenol (210) (2.77 g, 16.4 mmol) and allowed to stir at 60° C. for 3 hours. The reaction mixture was poured into ice water (100 mL) and extracted with 5% methanol in dichloromethane (50 mL×3). The combined organic layers were washed with water (50 mL), brine (50 mL), dried over anhydrous sodium sulfate, filtered and concentrated. The crude material was purified by flash column chromatography using 25% ethyl acetate in hexane as an eluent to afford the title compound (211) as off white solid. (4.8 g, Yield: 92.84%); LCMS: $[M+H]^+$ 316.0

Step 2: Synthesis of 5-Chloro-4-(2-methoxy-5-nitrophenoxy)-N-(1-methyl-1H-pyrazol-4-yl) pyrimidin-2-amine (212)

The title compound was prepared in a manner substantially similar to procedure mentioned in General Procedure H, to afford the desired compound as off white solid (212) (0.15 g, crude). LCMS: $[M+H]^+$ 377.1

Step 3: Synthesis of 4-(5-amino-2-methoxyphenoxy)-5-chloro-N-(1-methyl-1H-pyrazol-4-yl) pyrimidin-2-amine (213)

To a stirred solution of 5-chloro-4-(2-methoxy-5-nitrophenoxy)-N-(1-methyl-1H-pyrazol-4-yl)pyrimidin-2-amine (212) (0.30 g, 0.796 mmol) in methanol (30 mL) was added Raney nickel (0.140 g) and allowed to stir at room temperature under hydrogen atmosphere for 16 hours. The reaction mixture was filtered through celite bed and evaporated to afford the title compound (213) as brown solid (0.167 g, Yield: 60%). LCMS: $[M+H]^+$ 347.0

Step 4: Synthesis of N-[3-({5-chloro-2-[(1-methyl-1H-pyrazol-4-yl) amino] pyrimidin-4-yl}oxy)-4-methoxyphenyl] prop-2-enamide (Compound 172)

The title compound was prepared in a manner substantially similar to procedure mentioned in General Procedure K, to afford the desired compound (Compound 172) as white solid (0.03 g, 23%). $^1$H NMR (400 MHz, DMSO-d6): δ10.21 (s, 1H), 9.74 (s, 1H), 8.35 (s, 1H), 7.63 (s, 2H), 7.23 (s, 1H), 7.03 (s, 1H), 6.72 (s, 1H), 6.33-6.40 (m, 1H), 6.19-6.23 (m, 1H), 5.72 (d, J=10.0 Hz, 1H), 3.66 (s, 3H), 3.49 (s, 3H). LCMS: $[M+H]^+$ 401.1.

Scheme 48: Synthesis of N-(2-(((5-chloro-2-((1-methyl-1H-pyrazol-4-yl) amino)pytimidin-4-yl)amino)methyl)-3-fluorophenyl)acrylamide (Compound 173)

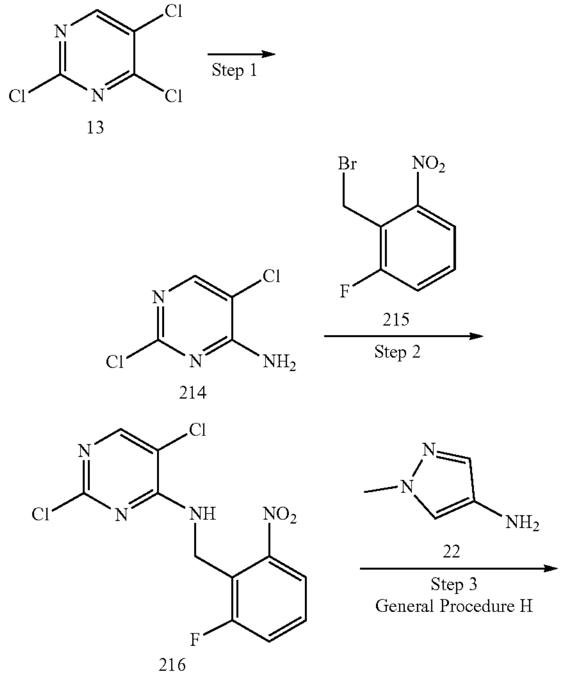

-continued

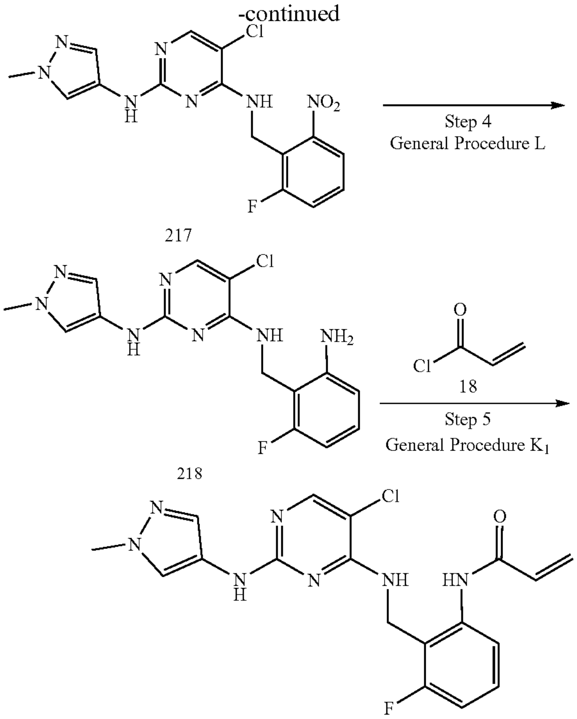

Compound 173

Step 1: Synthesis of 2,5-dichloropyrimidin-4-amine (214)

To a stirred solution of 2,4,5-trichloropyrimidine (13) (2.00 g, 10.9 mmol) in methanol (2 mL) was added ammonia in methanol (20 mL) and the reaction mixture was stirred room temperature for 15 hours. The reaction mixture was evaporated to dryness. The residue was taken in water, the precipitated solid was filtered, washed with water and dried to afford the title compound (214) as white solid (1.6 g, 89%). $^1$H-NMR (400 MHz, DMSO-$d_6$): δ 8.16 (s, 2H), 7.52 (bs, 1H).

Step 2: Synthesis of 2,5-dichloro-N-(2-fluoro-6-nitrobenzyl)pyrimidin-4-amine (216)

To a stirred solution of 2,5-dichloropyrimidin-4-amine (214) (0.50 g, 3.05 mmol) in N,N-dimethylformamide (10.0 mL) at 0° C. was added sodium hydride (0.18 g, 4.57 mmol) and the reaction mixture was stirred at room temperature for 20 minutes. Then the reaction mixture was cooled to 0° C. and added a solution of 2-(bromomethyl)-1-fluoro-3-nitrobenzene (215) (0.71 g, 3.05 mmol) in N,N-dimethylformamide (10 mL) and the reaction mixture was stirred at room temperature for 1 hour. The reaction was monitored by TLC. The reaction mixture was quenched with water (50 mL) and extracted with ethyl acetate (3×50 mL). The combined organic extract was washed with water (2×50 mL), brine (25 mL), dried over anhydrous sulfate and evaporated. The crude product was purified by column chromatography using combiflash purifier and was eluted with 25% ethyl acetate in hexane to afford the title compound (216) as off white solid (0.8 g, 82%). LCMS: $[M+H]^+$ 317.0

Step 3: Synthesis of 5-chloro-N4-(2-fluoro-6-nitrobenzyl)-N2-(1-methyl-1H-pyrazol-4-yl)pyrimidine-2,4-diamine (217)

Title compound was prepared in a manner substantially similar General Procedure H to afford the title compound as reddish brown solid (217) (0.85 g; Yield: 89%). LCMS: $[M+H]^+$ 378.1

Step 4: Synthesis of N4-(2-amino-6-fluorobenzyl)-5-chloro-N2-(1-methyl-1H-pyrazol-4-yl)pyrimidine-2,4-diamine (218)

Title compound was prepared in a manner substantially similar General Procedure L to afford the title compound as off white solid (218) (0.55 g; Yield: 80%). LCMS: $[M+H]^+$ 348.1.

Step 5: Synthesis of N-(2-(((5-chloro-2-((1-methyl-1H-pyrazol-4-yl)amino)pyrimidin-4-yl)amino)methyl)-3-fluorophenyl)acrylamide (Compound 173)

Title compound was prepared in a manner substantially similar General Procedure K1 to afford the title compound (Compound 173), as a white solid (80 mg; Yield: 46%). $^1$H-NMR (400 MHz, DMSO-$d_6$): δ 9.84 (bs, 1H), 8.94 (bs, 1H), 7.87 (s, 1H), 7.76 (s, 1H), 7.42 (s, 1H), 7.34 (bs, 2H), 7.07-7.01 (m, 2H), 6.47-6.41 (m, 1H), 6.25-6.21 (m, 1H), 5.74 (bs, 1H), 4.64 (s, 2H), 3.75 (s, 3H). LCMS: $[M+H]^+$ 402.0

Scheme 49: Synthesis of N-[2-({2-[(1-methyl-1H-pyrazol-4-yl)amino]pyrimidin-4-yl}amino)-[1,1′-biphenyl]-4-yl]prop-2-enamide (Compound 175)

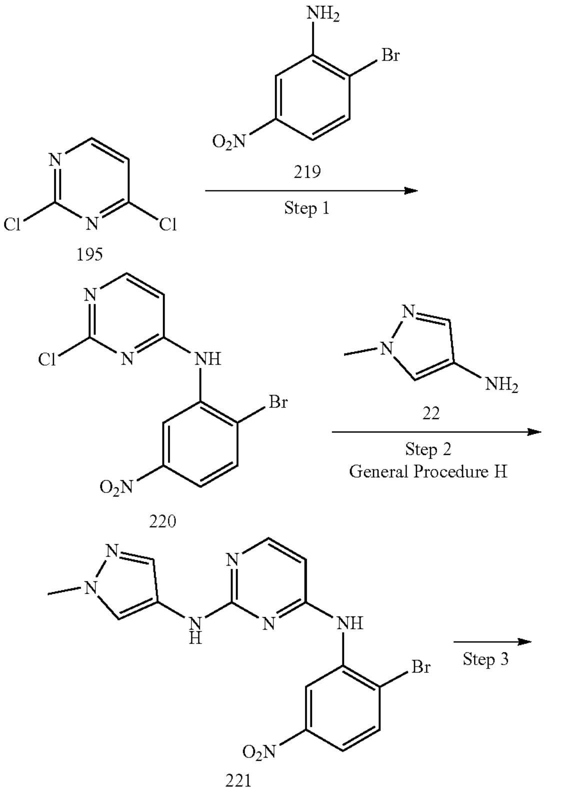

219
195
22
220
221

-continued

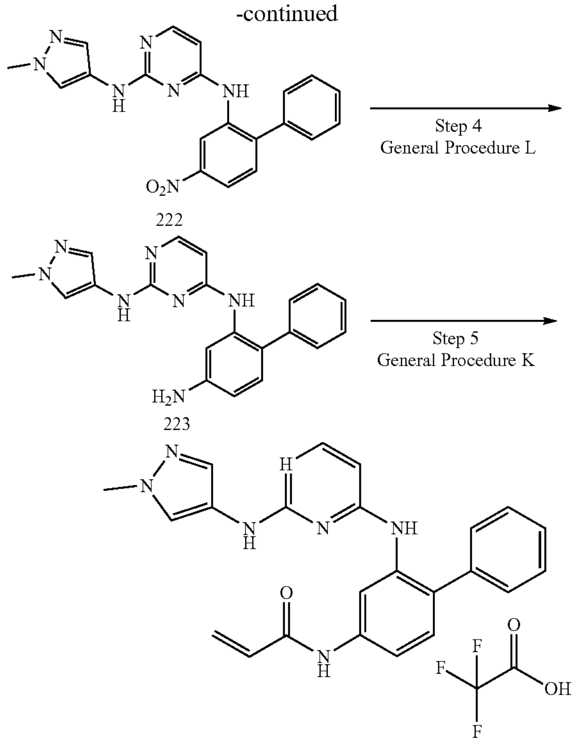

222
223

Compound 175

Step 1: Synthesis of N-(2-bromo-5-nitrophenyl)-2 chloropyrimidin-4-amine (220)

To a stirred solution of 2-bromo-5-nitroaniline (219) (1.00 g, 4.61 mmol) in N,N-dimethylformamide (3 mL) was added sodium hydride (0.83 g, 20.7 mmol, 60%) at 0° C. and the reaction mixture was stirred at room temperature for 1 hour. Then 2,4-dichloropyrimidine (195) (0.82 g, 5.53 mmol) was added and the reaction mixture was stirred room temperature for 1 hour. The reaction mixture was diluted with water (250 mL) and extracted with ethyl acetate (200 mL×3). The combined organic layer was washed with water (250 mL×2), brine (50 mL), dried over anhydrous sodium sulfate and evaporated. The crude product was purified by column chromatography using combiflash purifier and was eluted with 60% ethyl acetate in hexane to get the title compound (220) as brown solid (450 mg, 30%). $^1$H NMR (400 MHz, DMSO-$d_6$): δ 9.09 (s, 1H), 8.53 (s, 1H), 8.24 (d, J=8.0 Hz, 1H), 8.02-7.91 (m, 2H), 6.87 (d, J=8.0 Hz, 1H).

Step 2: Synthesis of N4-(2-bromo-5-nitrophenyl)-N2-(1-methyl-1H-pyrazol-4-yl) pyrimidine-2,4-diamine (221)

Title compound was prepared in a manner substantially similar General Procedure H to afford the title compound (221) as yellow solid (0.25 g; Yield: 70%). LCMS: $[M+H]^+$ 390.1

Step 3: Synthesis of N2-(1-methyl-1H-pyrazol-4-yl)-N4-{4-nitro-[1,1'-biphenyl]-2-yl}pyrimidine-2,4-diamine (222)

To a stirred solution of N4-(2-bromo-5-nitrophenyl)-N2-(1-methyl-1H-pyrazol-4-yl)pyrimidine-2,4-diamine (221)

(400 mg, 1.03 mmol) in 1,4-dioxane (4.00 mL), water (1.00 mL) was added phenylboronic acid (137 mg, 1.13 mmol), potassium carbonate (283 mg, 2.05 mmol). Then the reaction mixture was purged with nitrogen for 10 minutes, added bis(triphenylphosphine)palladium(II) dichloride (72.0 mg, 0.103 mmol) and the reaction mixture was heated at 100° C. for 12 hours. The reaction mixture was cooled, diluted with water (25 mL) and extracted with ethyl acetate (50 mL×3). The combined organic layer was washed with water (25 mL×2), brine (25 mL), dried over anhydrous sodium sulfate and evaporated. The crude product was purified by column chromatography using combiflash purifier and was eluted with 70% ethyl acetate in hexane to get white solid (222) (350 mg, 88%). LCMS: $[M+H]^+$ 388.0

Step 4: Synthesis of Synthesis of N4-{4-amino-[1,1'-biphenyl]-2-yl}-N2-(1-methyl-11H-pyrazol-4-yl)pyrimidine-2,4-diamine (223)

Title compound was prepared in a manner substantially similar General Procedure L to afford the title compound (223) as white solid (0.32 g; Yield: 99%). LCMS: $[M+H]^+$ 358.38

Step 5: Synthesis of N-[2-({2-[(1-methyl-1H-pyrazol-4-yl)amino]pyrimidin-4-yl}amino)-[1,1'-biphenyl]-4-yl]prop-2-enamide (Compound 175)

Title compound was prepared in a manner substantially similar General Procedure K to afford the title compound (Compound 175) as yellow solid (0.07 g; Yield: 40%). $^1H$ NMR (400 MHz, DMSO-d6): δ 10.51 (bs, 1H), 10.45 (s, 2H), 7.93 (s, 2H), 7.81 (bs, 1H), 7.71 (d, J=8.5 Hz, 2H), 7.36-7.29 (m, 6H), 7.18-6.96 (m, 1H), 6.48-6.41 (m, 1H), 6.29-6.19 (m, 2H), 5.79 (d, J=10.0 Hz, 1H), 3.53 (s, 3H, merged with DMSO water peak). LCMS: $[M+H]^+$ 412.5

TABLE 11

The following compounds were prepared using the procedures described above:

| Cmpd. No. | Structure | General Procedure | LCMS [M + H] | $^1H$-NMR (400 MHz, DMSO-$d_6$) |
|---|---|---|---|---|
| 174 | 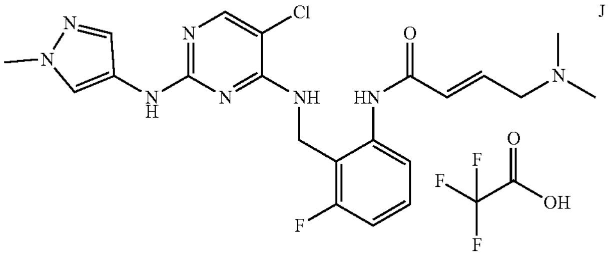 | J | 459.1 | δ 10.05 (s, 1H), 9.87 (bs, 1H), 9.47 (bs, 1H), 7.96 (s, 1H), 7.80 (s, 1H), 7.58 (bs, 1H), 7.47 (s, 1H), 7.40-7.30 (m, 2H), 7.13-7.08 (m, 1H), 6.74-6.66 (m, 1H), 6.48-6.44 (m, 1H), 4.67 (bs, 2H), 3.87 (d, J = 6.4 Hz, 2H), 3.77 (s, 3H), 2.74 (s, 6H). |
| 176 | 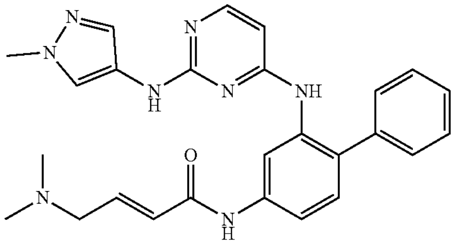 [SMILES: CN(C)C/C=C/C(=O)Nc1ccc(-c2ccccc2)c(Nc2ccnc(Nc3cnn(C)c3)n2)c1] | J | 469.1 | δ 10.2 (s, 1H), 8.84 (s, 1H), 8.63 (s, 1H), 7.80-7.69 (m, 3H), 7.51 (bs, 2H), 7.36-7.32 (m, 4H), 7.25-7.24 (m, 2H), 6.74-6.68 (m, 1H), 6.27-6.23 (m, 1H), 5.85 (d, J = 5.2 Hz, 1H), 3.57 (s, 3H), 3.04 (d, J = 5.2 Hz, 2H), 2.15 (s, 6H). |
| 177 | 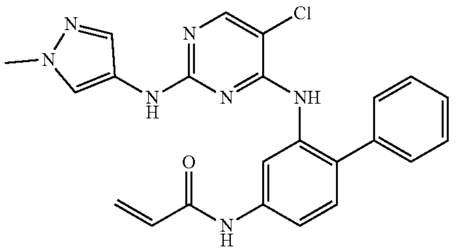 [SMILES: C=CC(=O)Nc1ccc(-c2ccccc2)c(Nc2nc(Nc3cnn(C)c3)ncc2Cl)c1] | K | 446.0 | δ 10.43 (s, 1H), 9.06 (s, 1H), 8.78 (bs, 1H), 7.86-7.69 (m, 3H), 7.44-7.21 (m, 6H), 7.07-6.95 (m, 1H), 6.50-6.43 (m, 1H), 6.4 (m, 1H), 6.27-6.23 (m, 1H), 5.76 (d, J = 10.4 Hz, 1H), 3.52 (s, 3H). |

Scheme 55: Synthesis of N-[3-({5-chloro-2-[(1-methyl-1H-pyrazol-4-yl) amino] pyrimidin-4-yl} amino)-4-(2-phenylethynyl) phenyl] prop-2-enamide (Compound 178)

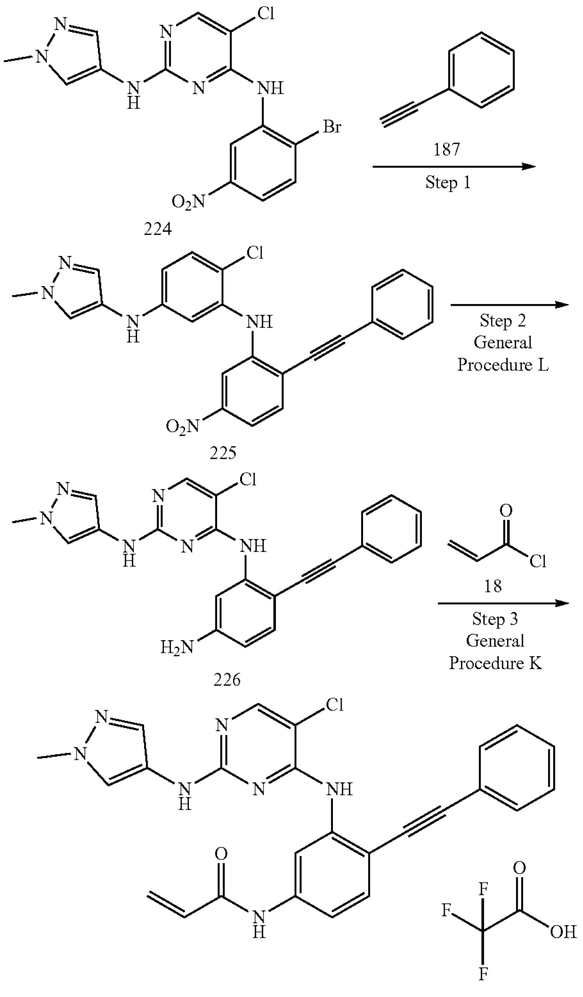

Compound 178

Step 1: Synthesis of 5-chloro-N2-(1-methyl-1H-pyrazol-4-yl)-N4-[5-nitro-2-(2-phenylethynyl)phenyl]pyrimidine-2,4-diamine (225)

To stirred solution of N4-(2-bromo-5-nitrophenyl)-5-chloro-N2-(1-methyl-1H-pyrazol-4-yl)pyrimidine-2,4-diamine (224) (600 mg, 1.41 mmol), triethylamine (394 μL, 2 eq., 2.83 mmol) in N,N-dimethylformamide (3.0 mL) was added copper iodide (53.8 mg, 0.283 mmol) and the reaction mixture was purged with nitrogen for 10 minutes. Then added bis(triphenylphosphine)palladium(II) dichloride (99.2 mg, 0.141 mmol), ethynylbenzene (187) (0.233 mL, 2.12 mmol) and the reaction mixture was heated in a sealed tube at 85° C. for 9 hours. The reaction was monitored by LCMS and TLC. The reaction mixture was diluted with water (20 mL) and extracted with ethyl acetate (2×20 mL). The combined organic layer was washed with brine (20 mL), dried over anhydrous sodium sulfate, filtered and evaporated under reduced pressure to give crude product. The crude product was purified by column chromatography using combiflash purifier and was eluted with 10% methanol in dichloromethane to get the title compound (225) as white solid (0.330 g, 53%). LCMS: $[M+H]^+$ 444.1

Step 2: N4-[5-amino-2-(2-phenylethynyl) phenyl]-5-chloro-N2-(1-methyl-1H-pyrazol-4-yl) pyrimidine-2,4-diamine (226)

Title compound was prepared in a manner substantially similar General Procedure L to afford the title compound (226) as white solid (0.25 g; Yield: 68%). LCMS: $[M+H]^+$ 416.9

Step 3: Synthesis of N-[3-({5-chloro-2-[(1-methyl-1H-pyrazol-4-yl) amino] pyrimidin-4-yl}amino)-4-(2-phenylethynyl) phenyl] prop-2-enamide (Compound 178)

Title compound was prepared in a manner substantially similar General Procedure K to afford the title compound (Compound 178) as white solid (0.045 g; Yield: 33%). δ 10.45 (s, 1H), 9.30 (s, 1H) 9.01 (bs, 2H), 8.12 (s, 1H) 7.97 (s, 1H), 7.76-7.74 (d, J=8.0 Hz, 1H), 7.62 (s, 1H), 7.36-7.18 (m, 7H), 6.50-6.44 (m, 1H), 6.29-6.25 (m, 1H), 5.79 (d, J=10.0 Hz, 1H), 3.54 (s, 3H merged with DMSO water peak). LCMS: $[M+H]^+$ 470.0.

Scheme 50: Synthesis of N-(3-((2-(cyclopropylamino)-5-(4-(trifluoromethyl)phenyl)pyrimidin-4-yl)amino)-4-fluorophenyl)acrylamide (Compound 249)

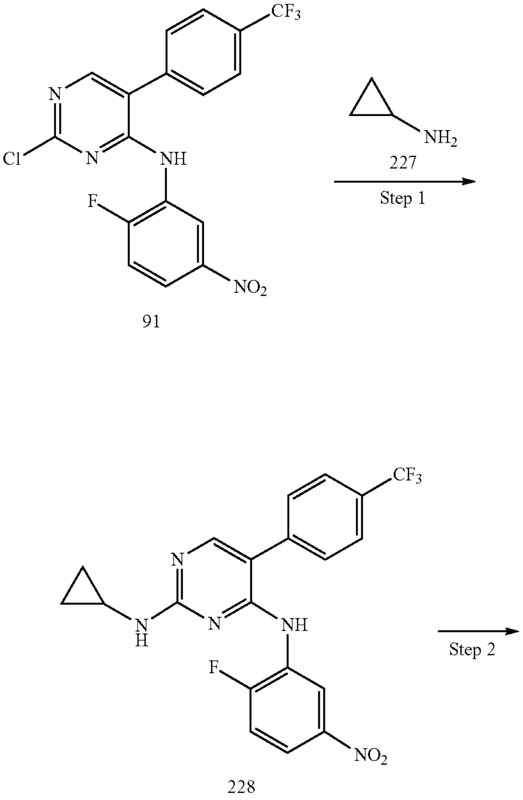

-continued

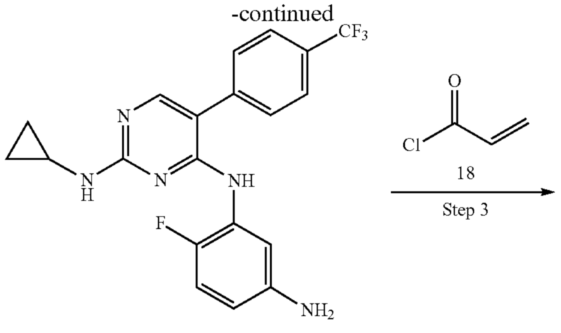

229

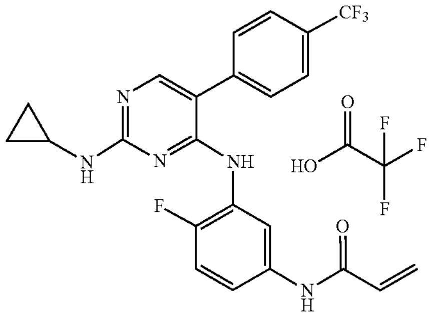

Compound 180

Step 1: Synthesis of N2-cyclopropyl-N4-(2-fluoro-5-nitrophenyl)-5-[4-(trifluoromethyl)phenyl]pyrimidine-2,4-diamine (228)

To a solution of 2-chloro-N-(2-fluoro-5-nitrophenyl)-5-[4-(trifluoromethyl)phenyl]pyrimidin-4-amine (91) (0.6 g, 1.45 mmol) and cyclopropanamine (227) (0.125 g, 2.18 mmol) in propan-2-ol (7.00 mL) was added N,N-diisopropylethylamine (0.76 mL, 4.36 mmol). The reaction mixture was heated at 100° C. for 36 hours. The progress reaction mixture was monitored by TLC & LCMS. After completion of reaction, the reaction mixture was diluted with water (50 mL) and extracted with ethyl acetate (3×50 mL). The combined organic layer was washed with brine (20 mL), dried over anhydrous sodium sulphate, filtered and concentrated under reduced pressure. The crude product was purified by flash chromatography using combiflash purifier and was eluted with 40% ethyl acetate in hexane to get the N2-cyclopropyl-N4-(2-fluoro-5-nitrophenyl)-5-[4-(trifluoromethyl)phenyl]pyrimidine-2,4-diamine (228) (0.5 g). LCMS $[M+H]^+$ 434.03

Step 2: Synthesis of N4-(5-amino-2-fluorophenyl)-N2-cyclopropyl-5-[4-(trifluoromethyl)phenyl]pyrimidine-2,4-diamine (229)

The title compound was prepared in a manner substantially similar to procedure mentioned in General Procedure L to get desired product (229) as brown solid. LCMS $[M+H]^+$ 404.04

Step 3: Synthesis of N-(3-{[2-(cyclopropylamino)-5-[4-(trifluoromethyl)phenyl]pyrimidin-4-yl]amino}-4-fluorophenyl)prop-2-enamide (Compound 180)

The title compound was prepared in a manner substantially similar to procedure mentioned in General Procedure K to get desired product (Compound 180) as off white solid. 1H NMR (400 MHz, DMSO-d6): δ 10.23 (s, 1H), 9.37 (bs, 1H), 7.98 (s, 1H), 7.88-7.93 (m, 2H), 7.69-7.80 (m, 3H), 7.43-7.28 (m, 3H), 6.36-6.43 (m, 1H), 6.21-6.26 (m, 1H), 5.78 (d, J=10.0 Hz, 1H), 2.53 (m, 1H), 1.22 (m, 1H), 0.58-0.85 (m, 4H). LCMS $[M+H]^+$ 458.15

Scheme 51: Synthesis of N-(3-((2-((1-methyl-1H-pyrazol-4-yl)amino)-5-(4-(trifluoromethyl)phenyl)pyridin-4-yl)oxy)phenyl)acrylamide (Compound 182)

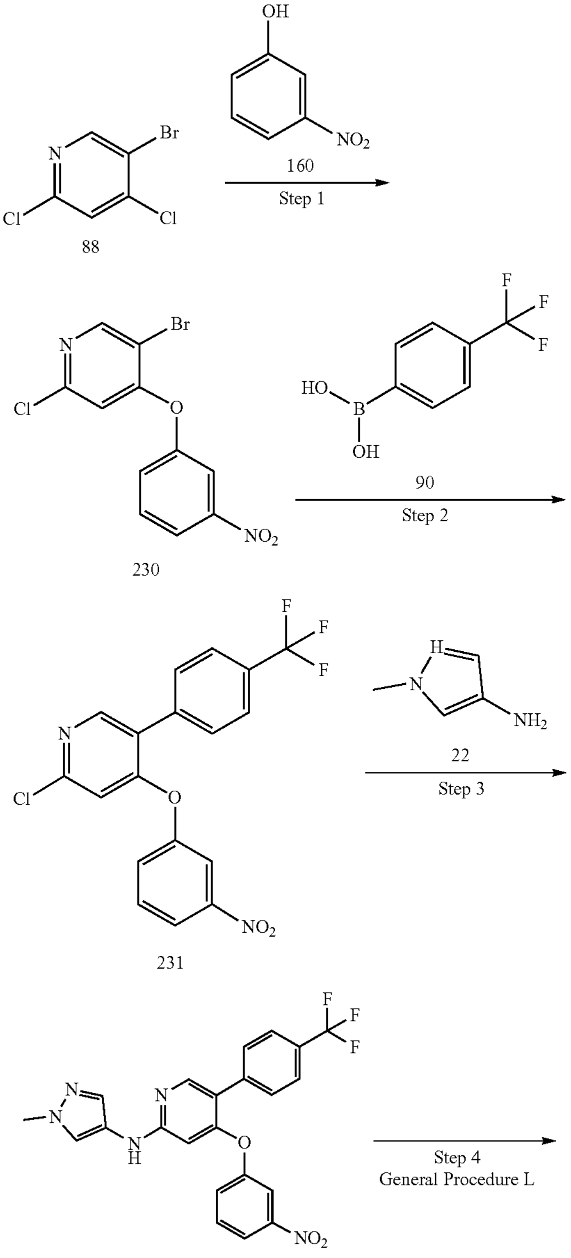

232

-continued

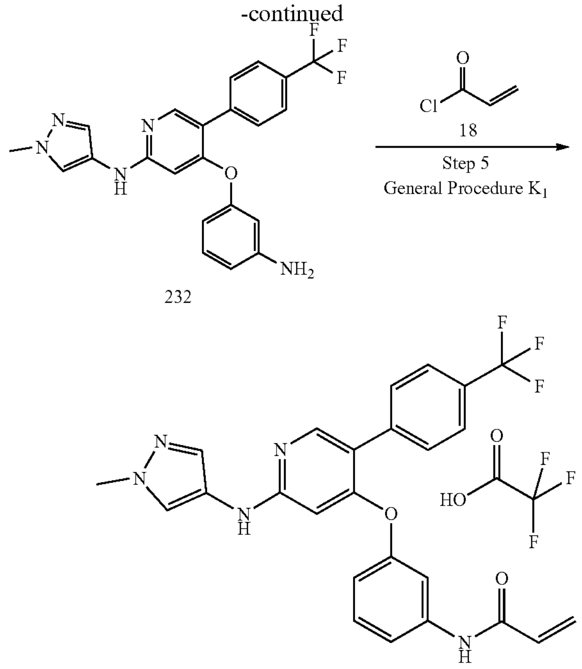

Compound 162

Step 1: Synthesis of 5-bromo-2-chloro-4-(3-nitrophenoxy)pyridine (230)

To a stirred solution of 3-nitrophenol (160) (1.53 g, 11 mmol) in dimethyl sulfoxide (15 mL) was added potassium tert-butoxide (16.5 mL, 16.5 mmol) and stirred for 20 minutes at room temperature. 5-bromo-2,4-dichloropyridine (88) (2.5 g, 11 mmol) in dimethyl sulfoxide (5 mL) was added to the above reaction mixture and the reaction mixture was heated at 60° C. for 1 hour. Progress of the reaction monitored by TLC and LCMS. After completion of starting materials, the reaction mixture was diluted with cold water (25 mL), the precipitated solid was filtered, washed with cold water (150 mL) and dried to get desired product (230) as yellow solid. (2.5 g, 68.85%). LCMS $[M+H]^+$ 328.0.

Step 2: Synthesis of 5-bromo-2-chloro-4-(3-nitrophenoxy)pyridine (231)

To a stirred solution of 5-bromo-2-chloro-4-(3-nitrophenoxy)pyridine (230) (2.00 g, 6.07 mmol) in 1,4 dioxane (50 mL) and water (10 mL) were added [4-(trifluoromethyl) phenyl]boronic acid (90) (1.38 g, 7.28 mmol), sodium hydrogen carbonate (1.02 g, 12.1 mmol) and the reaction mixture was purged with nitrogen for 10 minutes. [1,1'-bis (diphenylphosphino)ferrocene]dichloropalladium(II), complex with dichloromethane (496 mg, 0.607 mmol) was added and the reaction mixture was heated in a seal tube at 90° C. for 1.5 hours. Progress of the reaction monitored by TLC & LCMS. The reaction mixture was cooled, diluted with water (50 mL) and extracted with the ethyl acetate (150 mL×2). The combined organic layer was washed with brine (25 mL), dried over anhydrous sodium sulphate and evaporated under reduced pressure. The crude product was purified using combiflash purifier to get the desired product (231) as white solid (1.3 g, 58.4%). LCMS $[M+H]^+$ 395.1

Step 3: N-(1-methyl-1H-pyrazol-4-yl)-4-(3-nitrophenoxy)-5-(4-(trifluoromethyl)phenyl)pyridin-2-amine (232)

To a stirred solution of 2-chloro-4-(3-nitrophenoxy)-5-[4-(trifluoromethyl)phenyl]pyridine (251) (1.3 g, 3.29 mmol) in 1,4-dioxane (30 mL) were added 1-methyl-1H-pyrazol-4-amine (22) (0.48 g, 4.94 mmol), cesium carbonate (2.15 g, 6.59 mmol) and the reaction mixture was purged with nitrogen for 15 minutes. Then xantphos (0.19 g, 0.032 mmol) and tris(dibenzylideneacetone)dipalladium(0) (0.30 g, 0.032 mmol) were added then the reaction mixture was heated at 100° C. for 16 hours in a seal tube. Reaction was monitored by TLC and LCMS. The reaction mixture was cooled, filtered through celite and the filtrate was concentrated. The crude product was purified by using combiflash purifier with 0 to 60% ethyl acetate in heptane as eluent to get desired product (232) as yellow solid (0.7 g, 41.54%). LCMS $[M+H]^+$ 456.1

Step 4: 4-(3-aminophenoxy)-N-(1-methyl-1H-pyrazol-4-yl)-5-[4-(trifluoromethyl)phenyl]pyridin-2-amine (233)

The title compound was prepared in a manner substantially similar to procedure mentioned in General Procedure L to get desired product (233) as brown solid. LCMS $[M+H]^+$ 426.4

Step 5: N-[3-({2-[(1-methyl-1H-pyrazol-4-yl)amino]-5-[4-(trifluoromethyl)phenyl]pyridin-4-yl}oxy)phenyl]prop-2-enamide; trifluoroacetic acid (Compound 182)

The title compound was prepared in a manner substantially similar to procedure mentioned in General Procedure K1 to get desired product (Compound 182) as white solid (0.07 g, 13.56%). $^1$H NMR @ 90° C. (400 MHz, DMSO-d6) δ 10.35 (s, 1H), 9.15 (bs, 1H), 8.11 (s, 1H), 7.88-7.60 (m, 7H), 7.48-7.38 (m, 3H), 6.97-6.95 (m, 1H), 6.44-6.37 (m, 1H), 6.27-6.22 (m, 1H), 6.11 (s, 1H), 5.77 (dd, J=8.0 Hz, 1.6 Hz, 1H), 3.78 (s, 3H). LCMS $[M+H]^+$ 480.3

Scheme 52: Synthesis of N-(3-((2-((1-methyl-1H-pyrazol-4-yl)amino)-5-(5-methylpyridin-3-yl)pyrimidin-4-yl)oxy)phenyl)acrylamide (Compound 183)

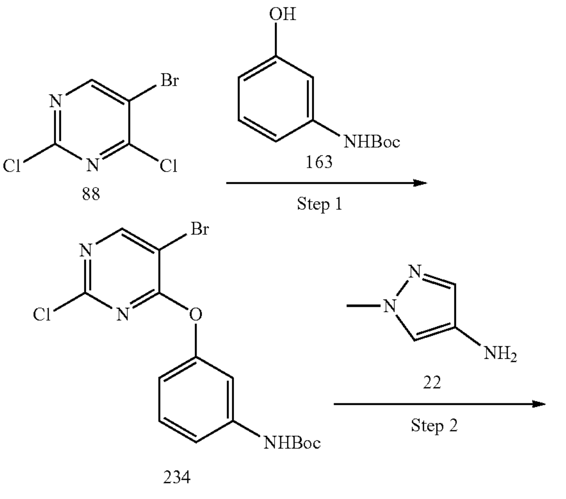

-continued

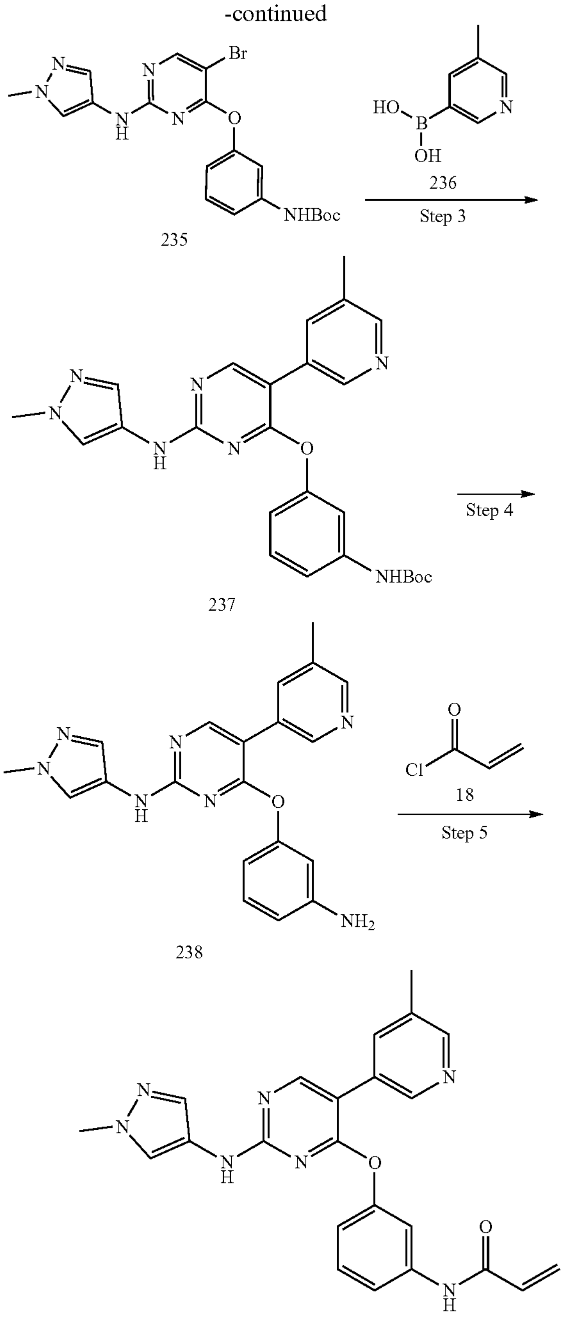

235

237

238

Compound 183

Step 1: Synthesis of tert-butyl N-{3-[(5-bromo-2-chloropyrimidin-4-yl)oxy]phenyl}carbamate (234)

To a stirred solution of 5-bromo-2,4-dichloropyrimidine (88) (10.0 g, 43.9 mmol) and tert-butyl N-(3-hydroxyphenyl)carbamate (163) (9.18 g, 43.9 mmol) in N,N-dimethylformamide (100.0 mL) was added potassium carbonate (12.1 g, 87.8 mmol) and the reaction mixture was stirred at room temperature for 16 hours. After completion of reaction (TLC monitoring), the reaction mixture was cooled down to room temperature, diluted with ice-cold water (250 mL). The solid precipitated out was filtered and washed with ice-cold water (2×100 mL). The solid was dried under vacuum to get the desired product (234) as off white solid (55 g, Yield: 80%). LCMS $[M+H]^+$ 399.9

Step 2: Synthesis of tert-butyl N-[3-({5-bromo-2-[(1-methyl-1H-pyrazol-4-yl)amino]pyrimidin-4-yl}oxy)phenyl]carbamate (235)

The title compound was prepared in a manner substantially similar to procedure mentioned in General Procedure H, to afford the desired compound as yellow solid (3.5 g, Yield: 57%). LCMS $[M+H]^+$ 461.07.

Step 3: Synthesis of tert-butyl (3-((2-((1-methyl-1H-pyrazol-4-yl)amino)-5-(5-methylpyridin-3-yl)pyrimidin-4-yl)oxy)phenyl)carbamate (237)

To a solution of tert-butyl (3-((5-bromo-2-((1-methyl-1H-pyrazol-4-yl)amino)pyrimidin-4-yl)oxy)phenyl)carbamate (235) (1.00 g, 2.17 mmol) in N,N-dimethylformamide (10.0 mL) was added (5-methylpyridin-3-yl)boronic acid (236) (0.356 g, 2.60 mmol) and cesium carbonate (2.12 g, 6.50 mmol) in water (2.00 mL). The reaction mass was degassed under nitrogen for 10 minutes then [1,1'bis(diphenylphosphino)ferrocene]dichloropalladium (II), complex with dichloromethane (0.177 g, 0.217 mmol) was added and the reaction mixture was heated at 100° C. for 16 hours. After completion of reaction (monitored by TLC), the reaction mixture was diluted with cold water (100 mL) and extracted with ethyl acetate (100 mL×2). The combined organic layer was washed with brine (200 mL), dried over anhydrous sodium sulphate, filtered and concentrated under reduced pressure. The crude product was purified by combiflash purifier and was eluted with 65% ethyl acetate in hexane to get tert-butyl (3-((5-bromo-2-((1-methyl-1H-pyrazol-4-yl)amino)pyrimidin-4-yl)oxy)phenyl)carbamate (237) (0.480 g, Yield: 48%), LCMS $[M+H]^+$ 474.44.

Step 4: 4-(3-aminophenoxy)-N-(1-methyl-1H-pyrazol-4-yl)-5-(5-methylpyridin-3-yl)pyrimidin-2-amine (238)

To an ice-cold solution of tert-butyl N-[3-({2-[(1-methyl-1H-pyrazol-4-yl)amino]-5-(5-methylpyridin-3-yl)pyrimidin-4-yl}oxy)phenyl]carbamate (237) (0.480 g, 1.01 mmol) in dichloromethane (10.0 mL) was added trifluoroacetic acid (5.0 mL) and the reaction mixture was stirred at room temperature for 3 hours. The reaction was monitored by TLC, After completion of the starting material, the reaction mixture was concentrated under reduced pressure to get 4-(3-aminophenoxy)-N-(1-methyl-1H-pyrazol-4-yl)-5-(5-methylpyridin-3-yl)pyrimidin-2-amine (238) (0.350 g, Yield: 92.51%), LCMS $[M+H]^+$ 374.08

Step 5: Synthesis of N-[3-({2-[(1-methyl-1H-pyrazol-4-yl)amino]-5-(5-methylpyridin-3-yl)pyrimidin-4-yl}oxy)phenyl]prop-2-enamide (Compound 183)

The title compound was prepared in a manner substantially similar to procedure mentioned in General Procedure K, to afford the desired compound (Compound 183), after prep-HPLC purification as off white solid. $^1H$ NMR (400 MHz, DMSO-d6): δ 10.37 (bs, 1H), 9.78 (bs, 1H), 8.69 (bs, 1H), 8.48 (s, 1H), 8.38 (s, 1H), 7.91 (s, 1H), 7.70 (bs, 1H), 7.62 (bs, 1H), 7.51 (bs, 1H), 7.11 (bs, 1H), 7.05-7.03 (m, 1H), 6.86 (bs, 1H), 6.46-6.39 (m, 1H), 6.27-6.23 (m, 1H), 5.75 (d, J=10.0 Hz, 1H), 3.50 (s, 3H), 2.36 (s, 3H). LCMS $[M+H]^+$ 428.02

TABLE 12
The following compounds were prepared using the procedures described above:
| Cmpd. No. | Structure | General Procedure | LCMS [M + H] | $^1$H-NMR (400 MHz, DMSO-$d_6$) |
|---|---|---|---|---|
| 179 | 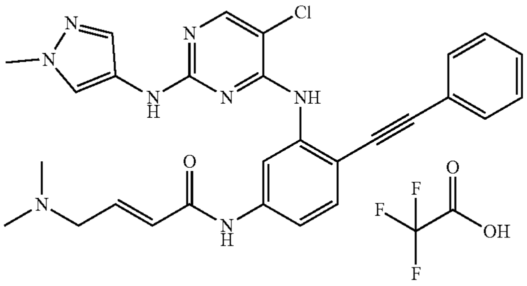 | J | 525.0 | δ 8.36 (s, 2H), 8.09 (bs, 1H) 7.61 (bs, 3H), 7.44-7.36 (m, 5H), 6.89-6.85 (m, 1H), 6.95-6.55 (m, 1H), 4.01 (d, J = 6.4 Hz, 2H), 3.71 (s, 3H), 2.93 (s, 6H). |
| 181 | 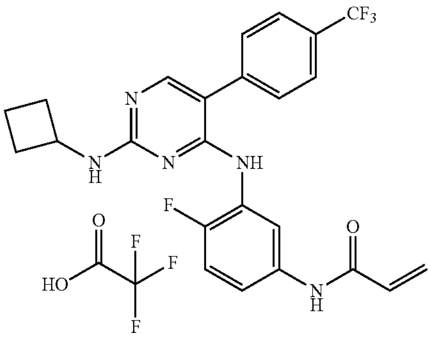 | K | 472.18 | δ 10.24 (s, 1H), 9.12-9.45 (m, 1H), 8.33-8.37 (m, 1H), 8.05 (bs, 1H), 7.86-7.92 (m, 3H), 7.71-7.73 (m, 2H), 7.38-7.24 (m, 3H), 6.37-6.44 (m, 1H), 6.22-6.27 (m, 1H), 5.78 (d, J = 10.0 Hz, 1H), 4.06 (bs, 1H), 1.96-2.24 (m, 4H), 1.51-1.59 (m, 2H). |
| 184 | 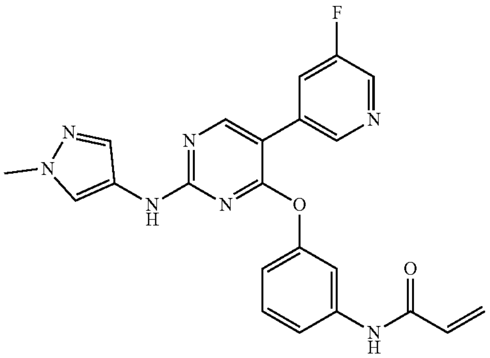 [SMILES: C=CC(=O)Nc1cccc(Oc2nc(Nc3cnn(C)c3)ncc2-c2cncc(F)c2)c1] | K | 431.98 | δ 10.37 (bs, 1H), 9.87 (s, 1H), 8.81 (s, 1H), 8.54-8.57 (m, 2H), 8.09 (d, J = 9.6 Hz, 1H), 7.06-7.88 (m, 5H), 7.87 (s, 1H), 6.39-6.46 (m, 1H), 6.23-6.27 (m, 1H), 5.78 (d, J = 10.0 Hz, 1H), 3.51 (bs, 3H). |
| 185 | 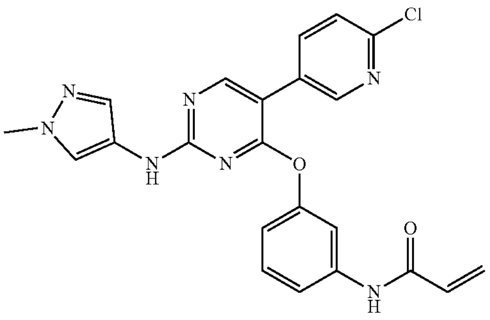 | K | 447.9 | δ 10.37 (s, 1H), 9.85 (bs, 1H), 8.73 (s, 1H), 8.53 (s, 1H), 8.21 (d, J = 6.8 Hz, 1H), 7.72 (s, 1H), 7.61 (d, J = 8.4 Hz, 2H), 7.51-7.53 (m, 1H), 7.11 (s, 1H), 7.05 (d, J = 7.6 Hz, 1H), 6.87 (s, 1H), 6.39-6.46 (m, 1H), 6.22-6.27 (m, 1H), 5.78 (d, J = 10.0 Hz, 1H), 3.50 (s, 3H) |

TABLE 12-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 186 | 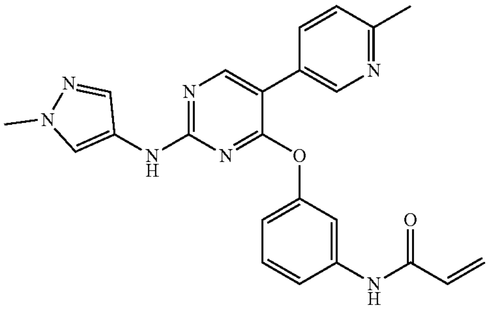 [SMILES: C=CC(=O)Nc1cccc(Oc2nc(Nc3cnn(C)c3)ncc2-c2ccc(C)nc2)c1] | K | 427.98 | δ 10.37 (s, 1H), 9.75 (bs, 1H), 8.74 (s, 1H), 8.47 (s, 1H), 7.93-7.99 (m, 1H), 7.69 (s, 1H), 7.62 (s, 1H), 7.50 (s, 1H), 7.35 (d, J = 8.0 Hz, 1H), 7.11 (s, 1H), 7.02-7.04 (m, 1H), 6.87 (s, 1H), 6.39-6.46 (m, 1H), 6.22-6.27 (m, 1H), 5.78 (d, J = 10.0 Hz, 1H), 3.50 (s, 3H), 2.50 (s, 3H) |
| 187 | 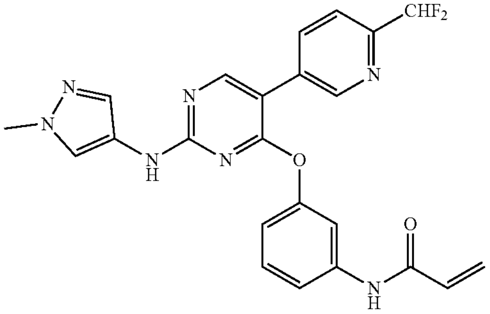 | K | 463.94 | δ 10.37 (bs, 1H), 9.87 (s, 1H), 9.01 (s, 1H), 8.58 (s, 1H), 8.33 (d, J = 6.8 Hz, 1H), 7.79 (d, J = 8.4 Hz, 1H), 7.73 (s, 1H), 7.61 (d, J = 8.4 Hz, 1H), 7.46 (t, J = 8.0 Hz, 1H), 7.24 (bs, 2H), 6.80-7.07 (m, 2H), 6.39-6.46 (m, 1H), 6.23-6.28 (m, 1H), 5.76 (d, J = 10.0 Hz, 1H), 3.60 (s, 3H) |
| 188 | 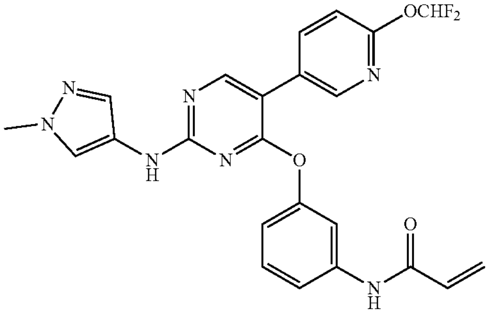 [SMILES: C=CC(=O)Nc1cccc(Oc2nc(Nc3cnn(C)c3)ncc2-c2ccc(OC(F)F)nc2)c1] | K | 479.97 | δ 10.37 (bs, 1H), 9.79 (s, 1H), 8.57 (s, 1H), 8.49 (s, 1H), 8.25 (d, J = 8.4 Hz, 1H), 7.61-7.95 (m, 3H), 7.51-7.56 (m, 1H), 7.11-7.21 (m, 2H), 7.05 (d, J = 7.6 Hz, 1H), 6.87 (bs, 1H), 6.39-6.46 (m, 1H), 6.23-6.27 (m, 1H), 5.78 (d, J = 10.0 Hz, 1H), 3.50 (s, 3H). |
| 189 | 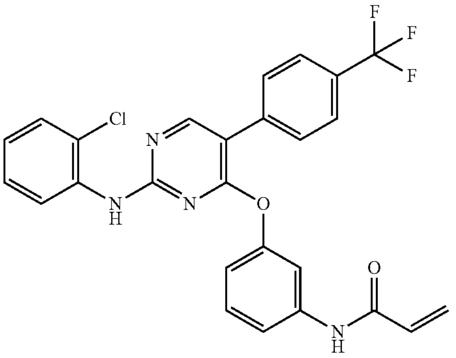 [SMILES: C=CC(=O)Nc1cccc(Oc2nc(Nc3ccccc3Cl)ncc2-c2ccc(C(F)(F)F)cc2)c1] | $K_1$ | 511.1 | δ 10.27 (s, 1H), 8.93 (s, 1H), 8.52 (s, 1H), 7.90 (d, J = 8.4 Hz, 2H), 7.81 (d, J = 8.4 Hz, 2H), 7.65 (s, 1H), 7.55-7.58 (m, 1H), 7.46-7.54 (m, 1H), 7.34-7.44 (m, 2H), 6.97-7.05 (m, 3H), 6.37-6.44 (m, 1H), 6.24 (dd, J = 16.8 Hz, 1.2 Hz, 1H), 5.75 (d, J = 10.0 Hz, 1H). |

TABLE 12-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 190 | 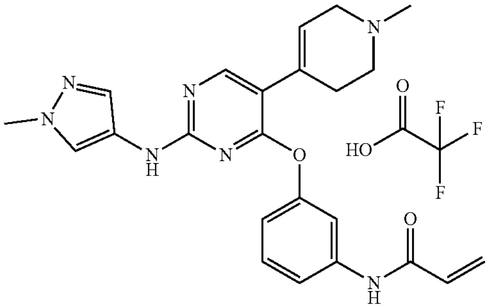 | K | 432.3 | At 90° C., δ 10.39 (s, 1H), 9.76-9.70-9.76 (m, 2H), 8.29 (s, 1H), 7.73 (bs, 1H), 7.51-7.48 (m, 2H), 7.06 (s, 1H), 6.96-6.94 (m, 1H), 6.79 (s, 1H), 6.44-6.37 (m, 1H), 6.25-6.14 (m, 2H), 5.77-5.74 (m, 1H), 4.00-3.83 (m, 2H), 3.60-3.57 (m, 2H), 3.48 (s, 3H), 3.27-3.14 (m, 1H), 2.88-2.86 (m, 3H), 2.86-2.76 (s, 1H) |
| 191 | 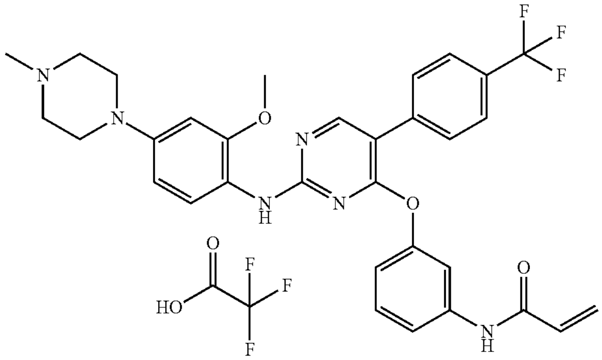 | $K_1$ | 605.0 | δ 10.29 (s, 1H), 9.56 (s, 1H), 8.47 (s, 1H), 8.15 (s, 1H), 7.79-7.90 (m, 3H), 7.56 (s, 2H) 7.31-7.41 (m, 3H), 6.97-6.99 (m, 1H), 6.61 (s, 1H), 6.38-6.44 (m, 1H), 6.24 (d, J = 16.0 Hz, 2H), 5.74-5.77 (d, J = 12.0 Hz, 1H), 3.71 (s, 4H), 3.48 (s, 4H), 3.09-3.14 (m, 2H), 2.84-2.88 (m, 4H). |
| 192 | 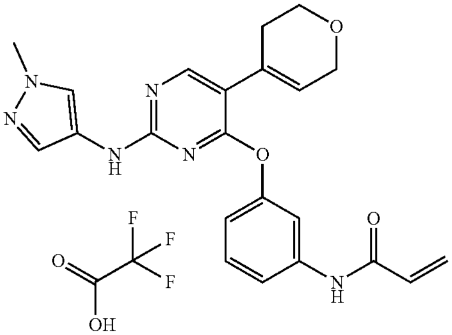 | $K_1$ | 419.0 | δ 10.35 (s, 1H), 9.57 (s, 1H), 8.25 (s, 1H), 7.05-7.63 (m, 4H), 6.79-7.05 (m, 3H), 6.37-6.44 (m, 1H), 6.17-6.25 (m, 2H), 5.74-5.75 (d, J = 5.2 Hz, 1H), 4.21 (s, 2H), 3.79 (t, J = 8.0 Hz, 2H), 3.47 (s, 3H), 3.31 (2H merged with DMSO-$H_2O$ peak). |

Scheme 53: Synthesis of N-(3-((2-((2-methoxyphenyl)amino)-5-(4-(trifluoromethyl)phenyl)pyrimidin-4-yl)oxy)phenyl)acrylamide (Compound 193)

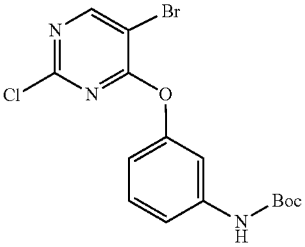

234

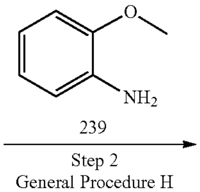

239

Step 2

General Procedure H

-continued

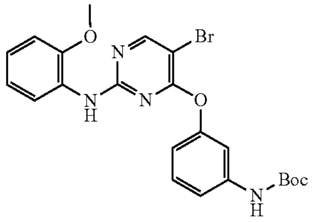

240

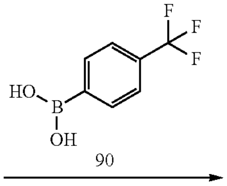

90

Step 3

-continued

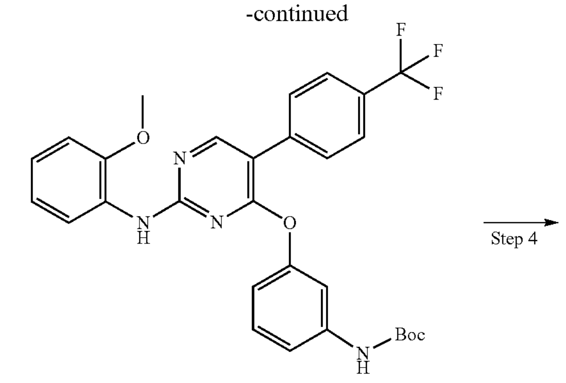

241

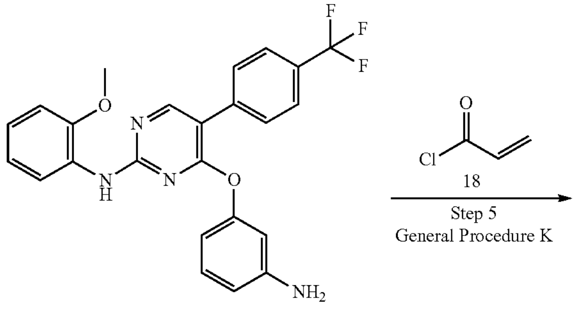

242

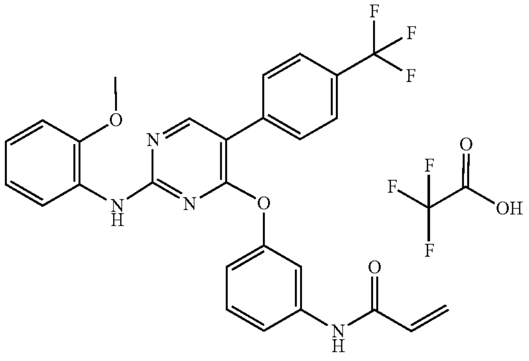

Compound 193

Step 1: Synthesis of tert-butyl N-[3-({5-bromo-2-[(2-methoxyphenyl)amino]pyrimidin-4-yl}oxy)phenyl]carbamate (240)

The title compound was prepared in a manner substantially similar to procedure mentioned in General Procedure H, to afford the desired compound (260) as off white solid. LCMS $[M+H]^+$ 487.1

Step 2: Synthesis of tert-butyl N-[3-({2-[(2-methoxyphenyl)amino]-5-[4-(trifluoromethyl)phenyl]pyrimidin-4-yl}oxy)phenyl]carbamate (241)

The title compound was prepared in a manner substantially similar to procedure mentioned in General Procedure $M_2$, to afford the desired compound (241) as off white solid. LCMS $[M+H]^+$ 553.2

Step 3: Synthesis of 4-(3-aminophenoxy)-N-(2-methoxyphenyl)-5-[4-(trifluoromethyl)phenyl]pyrimidin-2-amine (242)

The title compound was prepared in a manner substantially similar to procedure mentioned in General Procedure I, to afford the desired compound (242) as off white solid. LCMS $[M+H]^+$ 452.4

Step 4: Synthesis of N-[3-({2-[(2-methoxyphenyl)amino]-5-[4-(trifluoromethyl) phenyl]pyrimidin-4-yl} oxy)phenyl]prop-2-enamide (Compound 193)

The title compound was prepared in a manner substantially similar to procedure mentioned in General Procedure K, to afford the desired compound (Compound 193) as off white solid. $^1H$ NMR (400 MHz, DMSO-d6): δ 10.30 (s, 1H), 8.55 (s, 1H), 8.18 (s, 1H), 7.72-7.79 (m, 4H), 7.01-7.69 (m, 4H), 6.89-7.01 (m, 3H), 6.56-6.59 (m, 2H), 6.37-6.44 (m, 1H), 6.22-6.37 (m, 1H), 5.73-5.76 (m, 1H), 3.78 (s, 3H). LCMS $[M+H]^+$ 507.2

Scheme 54: Synthesis of N-(5-((2-((1-methyl-1H-pyrazol-4-yl)amino)-5-(4-(trifluoromethyl)phenyl)pyrimidin-4-yl)amino)pyridin-3-yl)acrylamide (Compound 195)

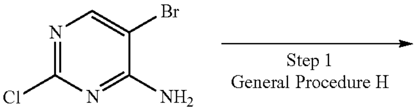

243

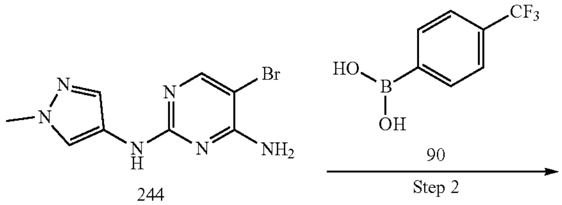

244

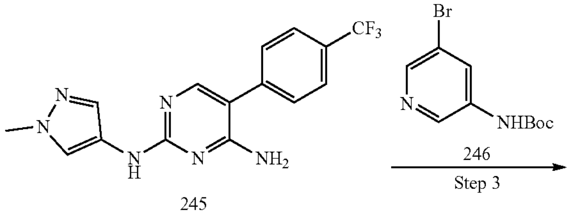

245

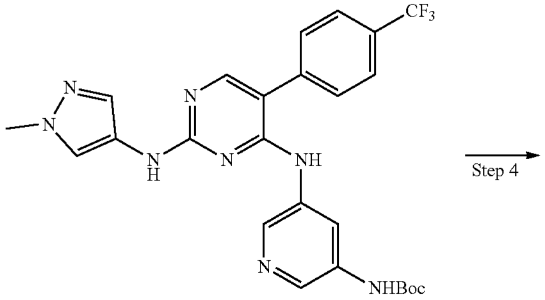

247

-continued

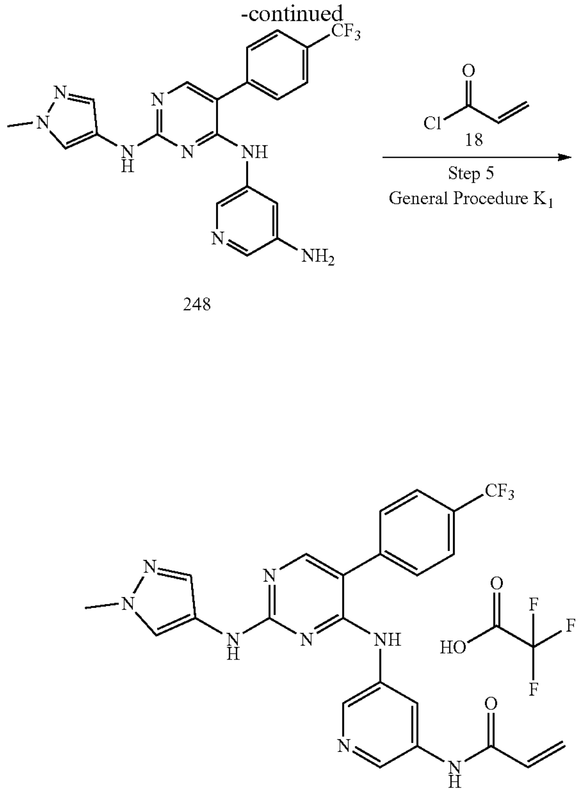

248

Compound 195

Step 1: Synthesis of 5-bromo-N2-(1-methyl-1H-pyrazol-4-yl)pyrimidine-2,4-diamine (244)

The title compound was prepared in a manner substantially similar to procedure mentioned in General Procedure H to get desired product (244) as off white solid. LCMS $[M+H]^+$ 269.1.

Step 2: Synthesis of N2-(1-methyl-1H-pyrazol-4-yl)-5-(4-(trifluoromethyl)phenyl)pyrimidine-2,4-diamine (245)

To a stirred solution of 5-bromo-N2-(1-methyl-1H-pyrazol-4-yl)pyrimidine-2,4-diamine (244) (5 g 18.6 mmol) in 1,2-dimethoxyethane (20.0 mL), water (5.00 mL), ethanol (5.00 mL) were added [4-(trifluoromethyl)phenyl]boronic acid (90) (4.23 g, 22.3 mmol), sodium hydrogen carbonate (3.12 g, 37.2 mmol) and purged with nitrogen for 5 minutes. Then added bis(triphenylphosphine)palladium(II) dichloride (0.65 g, 0.93 mmol) and the reaction mixture was heated at 80° C. for 16 hours. The progress of the reaction was monitored by LCMS. The reaction mixture was cooled and concentrated under reduced pressure. The crude product was purified by using combiflash purifier and was eluted with 70-80% ethyl acetate in hexane to get the desired product (245). LCMS $[M+H]^+$ 335.1.

Step 3: Synthesis of tert-butyl (5-((2-((1-methyl-1H-pyrazol-4-yl)amino)-5-(4-(trifluoromethyl)phenyl)pyrimidin-4-yl)amino)pyridin-3-yl)carbamate (247)

To a stirred solution of N2-(1-methyl-1H-pyrazol-4-yl)-5-[4-(trifluoromethyl)phenyl]pyrimidine-2,4-diamine (245) (0.6 g, 1.79 mmol), tert-butyl N-(5-bromopyridin-3-yl)carbamate (246) (0.54 g, 1.97 mmol) and cesium carbonate (1.17 g, 3.59 mmol) in 1,4-dioxane (7.0 mL), nitrogen was purged for 10 minutes. Then added 4,5-Bis(diphenylphosphino)-9,9-dimethylxanthene (0.026 g, 0.045 mmol), tris (dibenzylideneacetone)dipalladium (0) (0.082 g, 0.089 mmol) and the reaction mixture was heated at 110° C. for 12 hours. The reaction mixture was cooled, quenched with saturated sodium bicarbonate solution (40.0 mL) and extracted with dichloromethane (3×30 mL). The combined organic layer was dried over anhydrous sodium sulfate and evaporated under reduced pressure. The crude product was purified by silica gel column chromatography using ethyl acetate in hexane as eluent to afford tert-butyl N-[5-({2-[(1-methyl-1H-pyrazol-4-yl)amino]-5-[4-(trifluoromethyl)phenyl]pyrimidin-4-yl}amino)pyridin-3-yl]carbamate (247) (0.71 g, Yield: 75%) as yellow solid. LCMS $[M+H]^+$ 527.

Step 4: Synthesis of N4-(5-aminopyridin-3-yl)-N2-(1-methyl-1H-pyrazol-4-yl)-5-(4-(trifluoromethyl)phenyl)pyrimidine-2,4-diamine (248)

To a stirred solution of tert-butyl N-[5-({2-[(1-methyl-1H-pyrazol-4-yl)amino]-5-[4-(trifluoromethyl)phenyl]pyrimidin-4-yl}amino)pyridin-3-yl]carbamate (247) (0.4 g, 0.76 mmol) in dichloromethane (5.0 mL) was added trifluoroacetic acid (2.0 mL) at 0° C. and resulting reaction mixture was stirred at room temperature for 1.5 hours. Progress of the reaction was monitored by TLC. The reaction mixture was evaporated under vacuum to get N4-(5-aminopyridin-3-yl)-N2-(1-methyl-1H-pyrazol-4-yl)-5-[4-(trifluoromethyl)phenyl]pyrimidine-2,4-diamine (248) (0.34 g, crude) as yellow gum. LCMS $[M+H]^+$ 427.2.

Step 5: Synthesis of N-(5-((2-((1-methyl-1H-pyrazol-4-yl)amino)-5-(4-(trifluoromethyl)phenyl)pyrimidin-4-yl)amino)pyridin-3-yl)acrylamide (Compound 195)

The title compound was prepared in a manner substantially similar to procedure mentioned in General Procedure $K_1$ to get desired product (Compound 270) as white solid. 1H NMR (400 MHz, DMSO-d6): δ 10.56 (s, 1H), 9.98 (bs, 1H), 9.54 (bs, 1H), 8.64 (s, 2H), 8.43 (s, 1H), 8.03 (bs, 1H), 7.74-7.86 (m, 4H), 7.31-7.40 (m, 3H), 6.40-6.47 (m, 1H), 6.28 (d, J=8.0 Hz, 1H), 5.82 (d, J=10.4 Hz, 1H), 3.74 (s, 3H); LCMS $[M+H]^+$ 481.3.

TABLE 13

| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 194 | 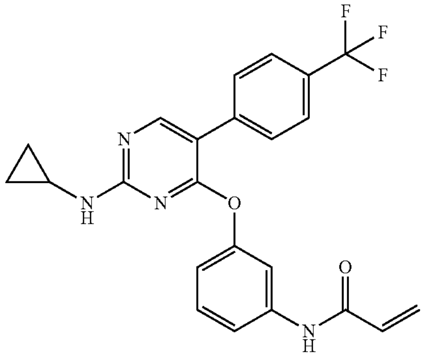 [SMILES: C=CC(=O)Nc1cccc(Oc2nc(NC3CC3)ncc2-c2ccc(C(F)(F)F)cc2)c1] | $K_1$ | 441.2 | δ 10.23 (s, 1H), 8.44 (s, 1H), 7.58-7.84 (m, 4H), 7.42-7.57 (m, 3H), 7.32-7.36 (m, 1H), 6.95 (bs, 1H), 6.36-6.43 (m, 1H), 6.23 (dd, J = 17.2, 1.6 Hz, 1H), 5.76 (dd, J = 10.0, 1.6 Hz, 1H), 2.48-2.65 (m, 1H), 0.41-0.56 (m, 4H). |
| 196 | 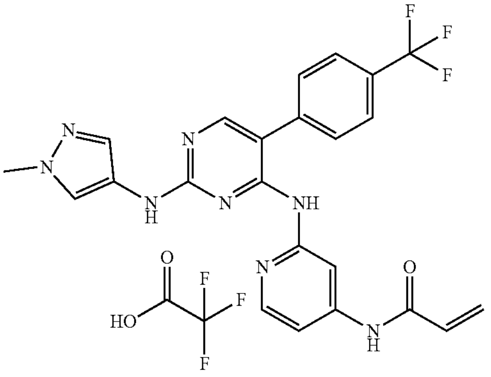 | K | 481.2 | δ 11.16 (bs, 1H), 10.47 (bs, 1H), 9.75 (bs, 1H), 8.31 (bs, 3H), 8.99-7.91 (m, 1H), 7.87-7.86 (m, 2H), 7.74 (d, J = 8.0 Hz, 2H), 7.56-7.55 (m, 1H), 7.37-7.35 (m, 1H), 6.51-6.36 (m, 2H), 5.96 (d, J = 9.2 Hz, 2H), 3.87 (s, 3H |
| 197 | 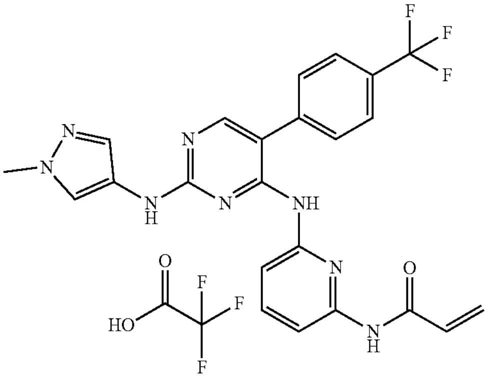 | K | 481.5 | δ 10.2 (s, 1H), 9.20 (s, 1H), 8.09 (s, 1H), 7.78-8.00 (m, 9H), 7.49 (s, 1H), 7.22-6.97 (m, 1H), 6.59-6.52 (m, 1H), 6.32-6.27 (m, 1H), 5.78-5.75 (m, 1H), 3.7 (s, 3H). |

Scheme 55: Synthesis of N-[5-fluoro-4-({2-[(1-methyl-1H-pyrazol-4-yl) amino]-5-[4-(trifluoromethyl)phenyl]pyrimidin-4-yl}amino)pyridin-2-yl] prop-2-enamide; trifluoroacetic acid (Compound 198)

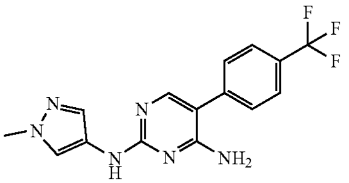

245

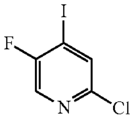

249

Step 1

-continued

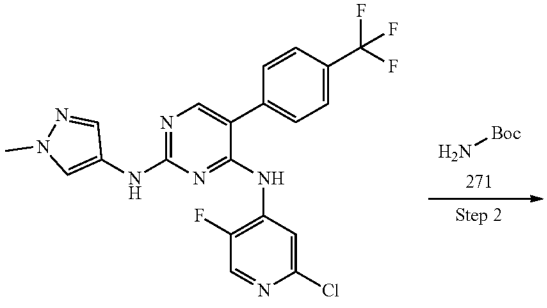

250

-continued

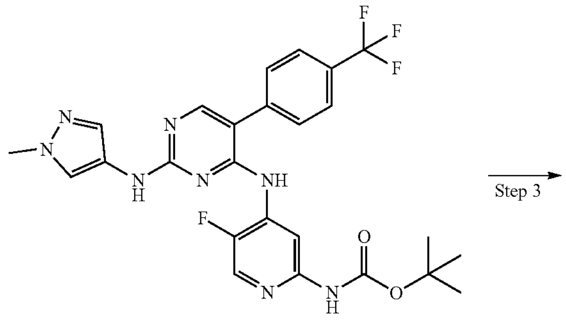

252

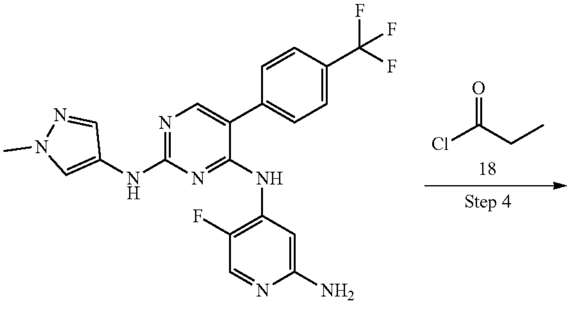

253

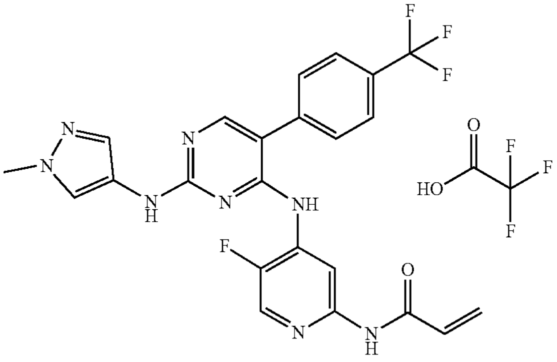

Compound 198

Step 1: Synthesis of N4-(2-chloro-5-fluoropyridin-4-yl)-N2-(1-methyl-1H-pyrazol-4-yl)-5-[4-(trifluoromethyl)phenyl]pyrimidine-2,4-diamine (250)

To a stirred solution of N2-(1-methyl-1H-pyrazol-4-yl)-5-[4-(trifluoromethyl)phenyl]pyrimidine-2,4-diamine (265) (1.00 g, 2.99 mmol) in 1,4-dioxane (25 mL) were added 2-chloro-5-fluoro-4-iodopyridine (269) (0.77 g, 2.99 mmol) and cesium carbonate (1.95 g, 5.98 mmol) and the reaction mixture was degassed with nitrogen for 10 minutes. Then added 4,5-bis(diphenylphosphino)-9,9-dimethylxanthene (0.17 g, 0.299 mmol) and Tris(dibenzylideneacetone)dipalladium(0) (0.274 g, 0.299 mmol) and the reaction mixture was heated at 90° C. for 16 hours in a seal tube. Reaction was monitored by TLC and LCMS. The reaction mixture was filtered through celite and the filtrate was concentrated. The crude product was purified using combiflash purifier with 2% methanol in dichloromethane as solvent to get desired product (250) as off white solid (1.00 g, 67.03%). LCMS $[M+H]^+$ 464.1.

Step 2: Synthesis of tert-butyl N-[5-fluoro-4-({2-[(1-methyl-1H-pyrazol-4-yl)amino]-5-[4-(trifluoromethyl)phenyl]pyrimidin-4-yl}amino)pyridin-2-yl]carbamate (252)

To a stirred solution of N4-(2-chloro-5-fluoropyridin-4-yl)-N2-(1-methyl-1H-pyrazol-4-yl)-5-[4-(trifluoromethyl)phenyl]pyrimidine-2,4-diamine (270) (1.00 g, 2.16 mmol) in 1,4-dioxane (20 ml) were added tert-butyl carbamate (271) (0.379 g, 3.23 mmol), cesium carbonate (1.40 g, 4.31 mmol) and degassed with nitrogen for 10 minutes. Then added 4,5-bis(diphenylphosphino)-9,9-dimethylxanthene (0.125 g, 0.216 mmol) and tris(dibenzylideneacetone)dipalladium(0) (0.197 g, 0.216 mmol) and the reaction mixture was heated to 90° C. for 16 hours in a seal tube. Reaction was monitored by LCMS. The reaction mixture was filtered through celite bed and the filtrate was concentrated. The crude product was purified using combiflash purifier with 40% ethyl acetate in heptane as a solvent to get desired product (252) as solid (0.55 g, crude). LCMS $[M+H]^+$ 545.2.

Step 3: tert-butyl N-[5-fluoro-4-({2-[(1-methyl-1H-pyrazol-4-yl)amino]-5-[4-(trifluoromethyl)phenyl]pyrimidin-4-yl}amino)pyridin-2-yl]carbamate (253)

To a stirred solution of tert-butyl N-[5-fluoro-4-({2-[(1-methyl-1H-pyrazol-4-yl)amino]-5-[4-(trifluoromethyl)phenyl]pyrimidin-4-yl}amino)pyridin-2-yl]carbamate (272) (0.55 g, 1.01 mmol) in dichloromethane (3 mL) at 0° C. was added trifluoroacetic acid (1 mL) and the reaction mixture was stirred for 2 hours at room temperature. Reaction was monitored by LCMS and TLC. The reaction mixture was concentrated under reduced pressure. The residue was triturated with ether and pentane to get desired product (253) as brown solid (0.3 g, crude). LCMS $[M+H]^+$ 445.2.

Step 4: Synthesis of N-[5-fluoro-4-({2-[(1-methyl-1H-pyrazol-4-yl)amino]-5-[4-(trifluoromethyl)phenyl]pyrimidin-4-yl}amino)pyridin-2-yl]prop-2-enamide; trifluoroacetic acid (Compound 198)

The title compound was prepared in a manner substantially similar to procedure mentioned in General Procedure K to get desired product (Compound 198) as white solid. $^1H$ NMR (400 MHz, DMSO-d6): δ 10.77 (s, 1H), 9.56 (s, 1H), 9.17 (s, 1H), 8.35-8.28 (m, 2H), 8.14 (s, 1H), 7.83-7.74 (m, 2H), 7.72-7.57 (m, 2H), 7.30-6.98 (m, 3H), 6.62-6.55 (m, 1H), 6.29-6.25 (m, 1H), 5.78-5.77 (m, 1H), 3.65 (s, 3H); LCMS $[M+H]^+$ 499.2.

Scheme 56: Synthesis of N-(2-{[2-(dimethylamino)ethyl](methyl)amino}-5-({2-[(1-methyl-1H-pyrazol-4-yl)amino]-5-[4-(trifluoromethyl)phenyl]pyrimidin-4-yl}amino)prop-2-enamide (Compound 274).

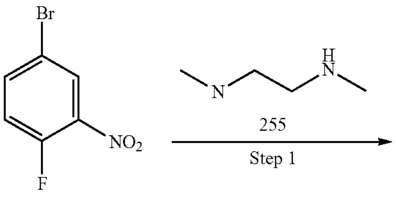

254

-continued

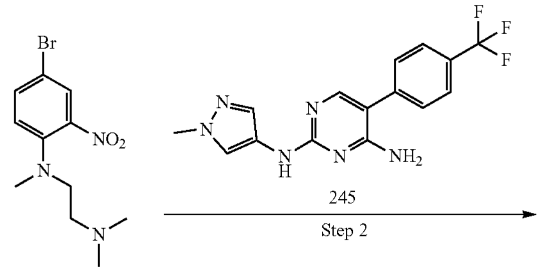

256

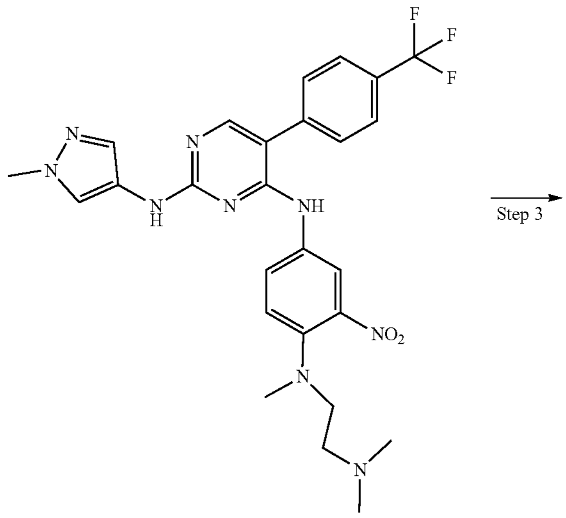

257

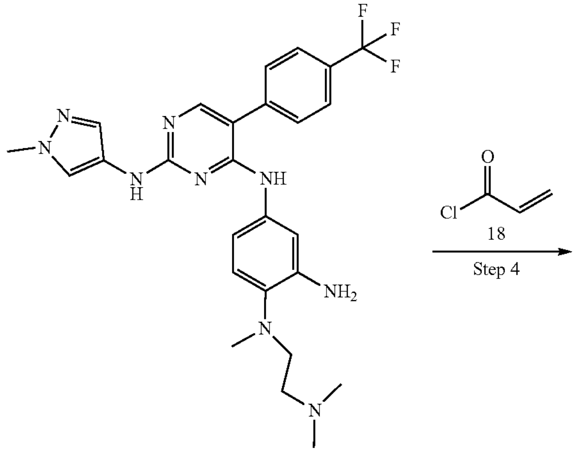

258

-continued

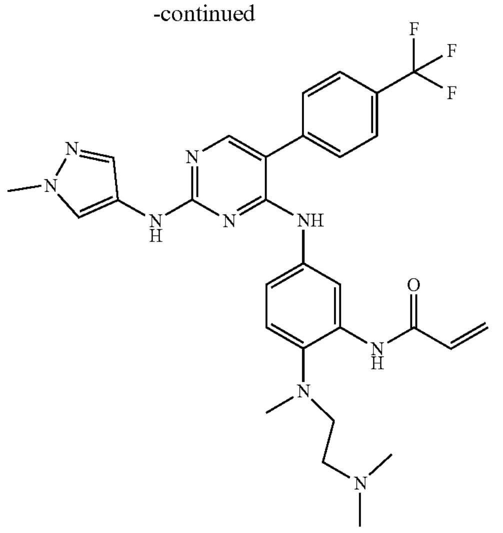

Compound 199

Step 1: Synthesis of 4-bromo-N-[2-(dimethylamino)ethyl]-N-methyl-2-nitroaniline (256)

To a stirred solution of 4-bromo-1-fluoro-2-nitrobenzene (274) (1.50 g, 6.82 mmol) in acetonitrile (15.00 mL) were added potassium carbonate (1.88 g, 13.6 mmol) and [2-(dimethylamino)ethyl](methyl)amine (275) (0.69 g, 6.82 mmol). The reaction mass stirred for 16 hours at 90° C. in a seal tube. Progress of the reaction monitored by TLC & LCMS. The reaction mixture was cooled, diluted with water (100 mL) and extracted with ethyl acetate (100 mL×2). The combined organic layer was washed with brine (30 mL), dried over anhydrous sodium sulphate and evaporated under reduced pressure to get the desired product (256) as yellow liquid (1.8 g, 87.37%).

Step 2: Synthesis of N4-(4-{[2-(dimethyl amino)ethyl](methyl)amino}-3-nitrophenyl)-N2-(1-methyl-1H-pyrazol-4-yl)-5-[4-(trifluoromethyl)phenyl]pyrimidine-2,4-diamine (257)

To a stirred solution of N2-(1-methyl-1H-pyrazol-4-yl)-5-[4-(trifluoromethyl)phenyl]pyrimidine-2,4-diamine (265) (0.6 g, 1.79 mmol) in toluene (15 mL) were added 4-bromo-N-[2-(dimethylamino)ethyl]-N-methyl-2-nitroaniline (276) (0.65 g, 2.15 mmol) and cesium carbonate (1.17 g, 3.59 mmol). The reaction mixture was degassed with nitrogen for 10 minutes then added 4,5-bis(diphenylphosphino)-9,9-dimethylxanthene (0.104 g, 0.18 mmol) and tris(dibenzylideneacetone)dipalladium(0) (0.164 g, 0.18 mmol) and the reaction mixture was heated at 100° C. for 16 hours. Reaction was monitored by TLC & LCMS. The reaction mixture was filtered through celite bed and the filtrate was concentrated. The crude product was purified by using combiflash purifier with 3% methanol in dichloromethane as eluent to get desired product (257) as orange solid (0.65 g, 65.19%). LCMS $[M+H]^+$ 556.4.

Step 3: Synthesis of N1-[2-(dimethylamino)ethyl]-N1-methyl-N4-{2-[(1-methyl-1H-pyrazol-4-yl)amino]-5-[4-(trifluoromethyl)phenyl]pyrimidin-4-yl}benzene-1,2,4-triamine (258)

The title compound was prepared in a manner substantially similar to procedure mentioned in General Procedure $L_1$ to get desired product (258) as brown solid (0.41 g, crude). LCMS $[M+H]^+$ 526.3.

Step 4: Synthesis of N-(2-{[2-(dimethylamino)ethyl](methyl)amino}-5-({2-[(1-methyl-1H-pyrazol-4-yl)amino]-5-[4-(trifluoromethyl)phenyl]pyrimidin-4-yl}amino)phenyl)prop-2-enamide (Compound 199)

The title compound was prepared in a manner substantially similar to procedure mentioned in General Procedure K to get desired product (Compound 199) as white solid (0.034 g, 12.33%). 1H NMR (400 MHz, DMSO-d6) δ 10.21 (s, 1H), 9.19 (s, 1H), 8.53 (s, 1H), 8.28 (s, 1H), 7.95 (s, 1H), 7.75-7.73 (m, 2H), 7.67-7.65 (m, 2H), 7.35-7.21 (m, 4H), 6.39-6.32 (m, 1H), 6.21-6.16 (m, 1H), 5.75 (d, J=8.4 Hz, 1H), 3.61 (s, 3H), 2.80-2.77 (m, 2H), 2.65 (s, 3H), 2.34-2.26 (m, 2H), 2.17 (s, 6H); LCMS $[M-H]^-$ 578.2.

Scheme 57: Synthesis of N-(4-((2-((1-methyl-1H-pyrazol-4-yl)amino)-5-(4-(trifluoromethyl)phenyl)pyrimidin-4-yl)-amino)pyridin-2-yl)acrylamide (Compound 2000)

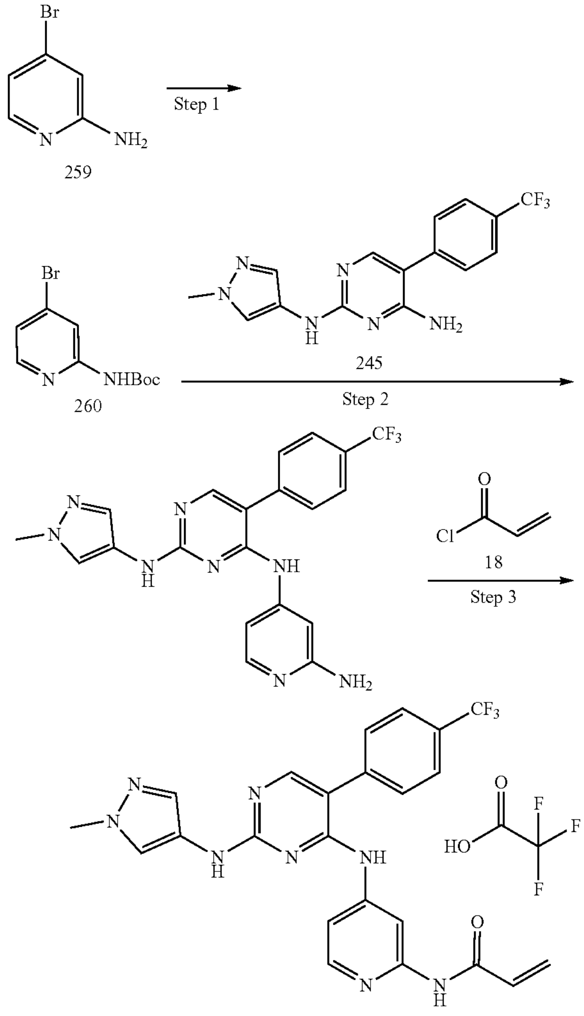

Compound 200

Step 1: Synthesis of tert-butyl N-(4-bromopyridin-2-yl)carbamate (260)

To a stirred solution of 4-bromopyridin-2-amine (279) (2.00 g, 11.6 mmol) in N,N-dimethylformamide (20.0 mL) were added triethylamine (2.42 mL, 17.3 mmol), N,N-dimethylpyridin-4-amine (0.14 g, 1.16 mmol) and di-tert-butyl dicarbonate (3.21 mL, 14.0 mmol) and the reaction was stirred at 90° C. for 4 hours. After completion of starting material (as monitored by TLC), water (25 mL) was added and was extracted with ethyl acetate (3×50 mL). The combined organic layer was washed with brine (25 mL), dried over anhydrous sodium sulfate and concentrated under reduced pressure. The crude product was purified by column chromatography and was eluted with 30% ethyl acetate in hexane to afford tert-butyl N-(4-bromopyridin-2-yl)carbamate (280) (2.50 g, 9.15 mmol). LCMS $[M+H]^+$ 216.8 (carbamic acid mass)

Step 2: Synthesis of N4-(2-aminopyridin-4-yl)-N2-(1-methyl-1H-pyrazol-4-yl)-5-(4-(trifluoromethyl)phenyl)pyrimidine-2,4-diamine (261)

To a stirred solution of N2-(1-methyl-1H-pyrazol-4-yl)-5-[4-(trifluoromethyl)phenyl]pyrimidine-2,4-diamine (245) (0.5 g, 1.50 mmol)) in 1,4-dioxane (5.0 mL) was added tert-butyl N-(4-bromopyridin-2-yl)carbamate (260) (0.61 g, 2.24 mmol), cesium carbonate (1.22 g, 3.74 mmol) and the reaction mixture was purged in nitrogen for 10 minutes. Then added rac-BINAP (0.186 g, 0.299 mmol) and palladium acetate (0.033 g, 0.150 mmol) and the reaction mixture was heated at 110° C. for 16 hours. The progress of the reaction was monitored by TLC and LCMS. To the reaction mixture water was added and was extracted with ethyl acetate (3×100 mL). The combined organic layer was dried over anhydrous sodium sulfate and evaporated under reduced pressure. The crude product was purified by using combiflash purifier using 10% methanol in dichloromethane as eluent to afford N4-(2-aminopyridin-4-yl)-N2-(1-methyl-1H-pyrazol-4-yl)-5-[4-(trifluoromethyl)phenyl]pyrimidine-2,4-diamine (261) (0.2 g, 0.469 mmol). LCMS $[M+H]^+$ 427.1

Step 3: Synthesis of N-(4-((2-((1-methyl-1H-pyrazol-4-yl)amino)-5-(4-(trifluoromethyl)phenyl)pyrimidin-4-yl)amino)pyridin-2-yl)acrylamide (Compound 200)

The title compound was prepared in a manner substantially similar to procedure mentioned in General Procedure K to get desired product (Compound 200) as white solid. $^1H$ NMR (400 MHz, DMSO-d6): δ 11.11 (bs, 2H), 9.60 (bs, 2H), 8.22-8.16 (m, 2H), 7.97 (s, 1H), 7.80 (d, J=8.4 Hz, 2H), 7.69 (d, J=8.0 Hz, 2H), 7.40 (bs, 2H), 7.20-6.90 (m, 1H), 6.57-6.53 (m, 1H), 6.50-6.34 (m, 1H), 5.86 (d, J=9.6 Hz, 1H), 3.88 (s, 3H). LCMS $[M+H]^+$ 481.2

TABLE 14
| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 201 | 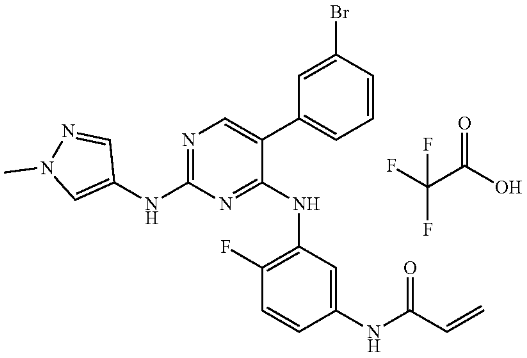 | K | 508.1 | δ 10.27 (s, 1H), 9.77 (bs, 1H), 9.15 (bs, 1H), 7.95 (s, 1H), 7.89 (s, 1H), 7.70 (s, 1H), 7.64-7.62 (m, 2H), 7.53-7.44 (m, 3H), 7.34-7.08 (m, 3H), 6.45-6.41 (m, 1H), 6.23 (d, J = 17.2 Hz, 1H), 5.74 (d, J = 10.0 Hz, 1H), 3.56 (s, 3H). |
| 202 | 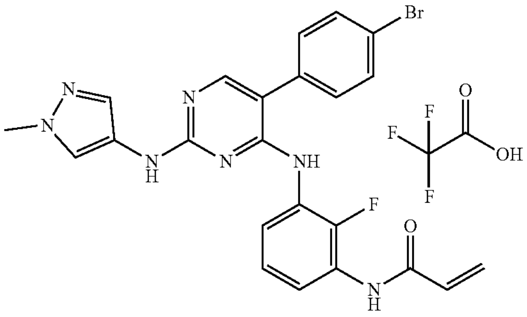 | $K_2$ | 508.0 | δ 10.01 (s, 1H), 8.06 (bs, 1H), 7.94-7.88 (bs, 2H), 7.73-7.70 (m, 3H), 7.50-7.46 (m, 2H), 7.24 (bs, 3H), 7.08-6.95 (m, 2H), 6.67-6.60 (m, 1H), 6.31-6.26 (m, 1H), 5.80-5.77 (m, 1H), 3.65 (s, 3H). |
| 203 | 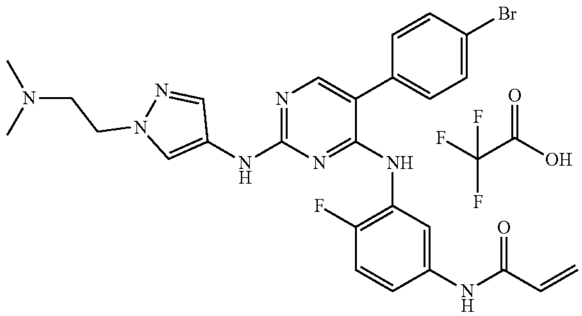 | $K_2$ | 565.2 | δ 10.23 (bs, 1H), 9.28 (bs, 1H), 8.95 (bs, 1H), 7.93 (s, 1H), 7.67-7.65 (m, 5H), 7.45-7.32 (m, 5H), 6.42-6.36 (m, 1H), 6.25-6.21 (m, 1H), 5.75 (d, J = 11.6 Hz, 1H), 4.21 (bs, 2H), 3.47-3.41 (m, 2H), 2.75 (s, 6H). |
| 204 | 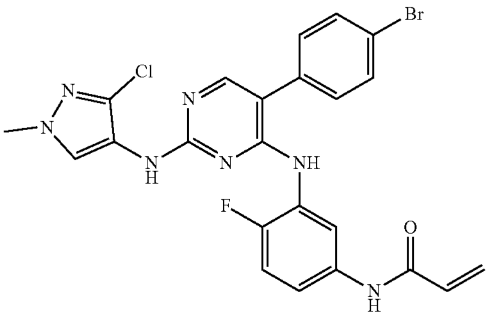 [SMILES: C=CC(=O)Nc1ccc(F)c(Nc2nc(Nc3cn(C)nc3Cl)ncc2-c2ccc(Br)cc2)c1] | K | 542.0 | δ 10.15 (s, 1H), 8.35 (bs, 2H), 7.91 (s, 1H), 7.75 (s, 1H), 7.63 (d, J = 8.0 Hz, 2H), 7.53-7.51 (m, 1H), 7.42 (d, J = 8.4 Hz, 2H), 7.27-7.22 (m, 2H), 6.42-6.36 (m, 1H), 6.25-6.20 (m, 1H), 5.75-5.72 (m, 1H), 3.56 (s, 3H). |

TABLE 14-continued

| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 205 | 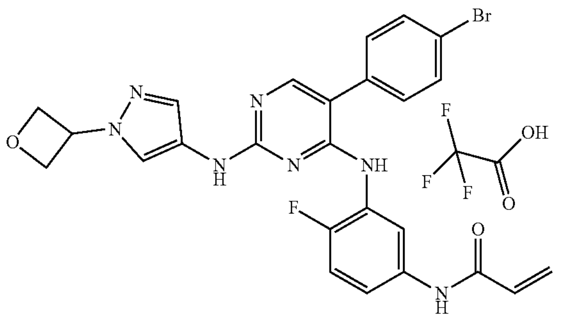 | $K_2$ | 550.0 | δ 10.26 (s, 1H), 9.72 (s, 1H), 8.99 (s, 1H), 7.94 (s, 1H), 7.83 (d, J = 5.2 Hz, 1H), 7.69 (d, J = 8.4 Hz, 2H), 7.57 (s, 1H), 7.47 (d, J = 8.4 Hz, 3H), 7.33-6.90 (m, 3H), 6.45-6.38 (m, 1H), 6.28-6.23 (m, 1H), 5.77 (dd, J = 10.0 Hz, 1.6 Hz, 1H), 5.16 (bs, 1H), 4.82-4.73 (m, 4H) |
| 206 | 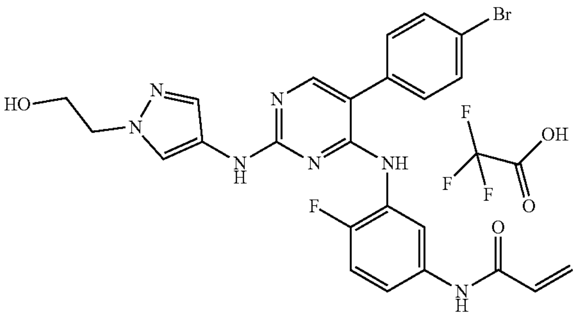 | $K_2$ | 538.0 | δ 10.17 (s, 1H), 9.72 (bs, 1H), 9.08 (bs, 1H), 7.85-7.76 (m, 2H), 7.64-7.62 (m, 2H), 7.46 (bs, 1H), 7.40 (d, J = 8.4 Hz, 2H), 7.25-6.93 (m, 5H), 6.37-6.30 (m, 1H), 6.19-6.15 (m, 1H), 5.70-5.67 (m, 1H), 3.80 (bs, 1H), 3.51 (bs, 3H) |
| 207 | 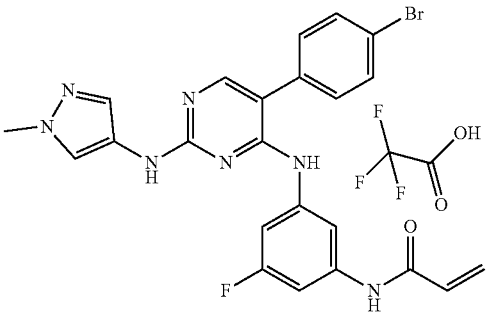 | $K_2$ | 508.1 | δ 10.35 (s, 1H), 9.88 (bs, 1H), 9.32 (bs, 2H), 7.94 (s, 1H), 7.70 (d, J = 8.4 Hz, 2H), 7.55 (bs, 2H), 7.49-7.41 (m, 4H), 7.15 (bs, 1H), 6.45-6.39 (m, 1H), 6.29-6.25 (m, 1H), 5.81-5.78 (m, 1H), 3.66 (bs, 3H merged with DMSO peak). |
| 208 | 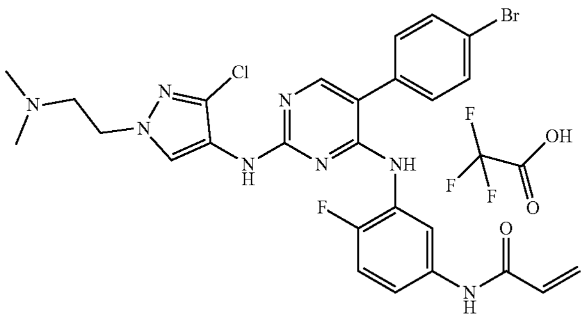 | $K_2$ | 597.1 [M − H]$^+$ | δ 10.20 (s, 1H), 9.72 (bs, 2H), 7.93 (bs, 1H), 7.67-7.65 (m, 3H), 7.54 (bs, 1H), 7.43 (d, J = 8.4 Hz, 2H), 7.30-7.28 (m, 1H), 7.19-7.06 (m, 2H), 6.42-6.35 (m, 1H), 6.25-6.21 (m, 1H), 5.76 (d, J = 10.4 Hz, 1H), 4.24 (bs, 4H), 2.78 (s, 6H). |

Scheme 58: Synthesis of N-(3-(2-((1-methyl-1H-pyrazol-4-yl)amino)-7-(trifluoromethyl)-9H-pyrimido[4,5-b]indol-9-yl)phenyl)acrylamide (Compound 209)

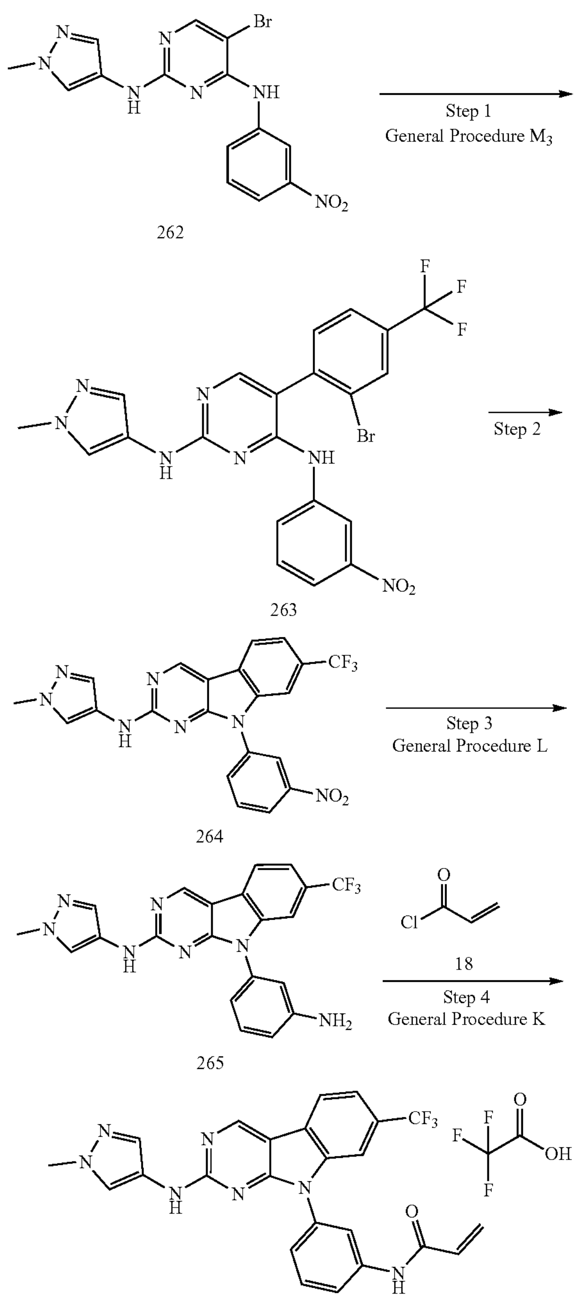

262, 263, 264, 265, Compound 209

Step 1: Synthesis of 5-[2-bromo-4-(trifluoromethyl)phenyl]-N2-(1-methyl-1H-pyrazol-4-yl)-N4-(3-nitrophenyl)pyrimidine-2,4-diamine (263)

The title compound was prepared in a manner substantially similar to procedure mentioned in General Procedure $M_3$ to get desired product (263) as yellow solid. LCMS $[M+H]^+$ 534.2

Step 2: 1-methyl-N-[9-(3-nitrophenyl)-7-(trifluoromethyl)-9H-pyrimido[4,5-b]indol-2-yl]-1H-pyrazol-4-amine (264)

To a stirred solution of 5-[2-bromo-4-(trifluoromethyl)phenyl]-N2-(1-methyl-1H-pyrazol-4-yl)-N4-(3-nitrophenyl)pyrimidine-2,4-diamine (301) (0.4 g, 0.74 mmol) in 1,4-dioxane (20 mL) was added cesium carbonate (0.73 g, 2.25 mmol) and purged with argon for 10 minutes. Then added tris(dibenzylideneacetone)dipalladium(0) (0.06 g, 0.07 mmol) and 4,5-bis(diphenylphosphino)-9,9-dimethylxanthene (0.04 g, 0.07 mmol) and the reaction mixture was heated at 110° C. for 16 hours. The reaction mixture was poured into water (70 ml) and extracted with ethyl acetate (2×40 mL). The combined organic layer was washed with brine (20 mL), dried over anhydrous sodium sulfate, filtered and concentrated under reduced pressure. The crude material was purified by flash column chromatography using 70% ethyl acetate in hexane as the eluent to afford 1-methyl-N-[9-(3-nitrophenyl)-7-(trifluoromethyl)-9H-pyrimido[4,5-b]indol-2-yl]-1H-pyrazol-4-amine (264) as yellow solid (0.1 g, 29%). LCMS $[M+H]^+$ 454.1

Step 3: Synthesis of 1-methyl-N-[9-(3-nitrophenyl)-7-(trifluoromethyl)-9H-pyrimido[4,5-b]indol-2-yl]-1H-pyrazol-4-amine (265)

The title compound was prepared in a manner substantially similar to procedure mentioned in General Procedure L to get desired product (265) as white solid. LCMS $[M+H]^+$ 423.9

Step 4: Synthesis of 1-methyl-N-[9-(3-nitrophenyl)-7-(trifluoromethyl)-9H-pyrimido[4,5-b]indol-2-yl]-1H-pyrazol-4-amine (Compound 209)

The title compound was prepared in a manner substantially similar to procedure mentioned in General Procedure K to get desired product (Compound 209) as yellow solid. $^1H$ NMR (400 MHz, DMSO-d6): δ 10.51 (s, 1H), 9.92 (s, 1H), 9.32 (s, 1H), 8.34 (d, J=8.0 Hz, 1H), 8.22 (bs, 1H), 7.88-7.83 (m, 2H), 7.69-7.54 (m, 4H), 7.45 (s, 2H), 6.52-6.46 (m, 1H), 6.32-6.27 (m, 1H), 5.82-5.79 (m, 1H), 3.69 (s, 3H); LCMS $[M+H]^+$ 478.2

Scheme 59: Synthesis of N-(4-fluoro-3-((2-((1-methyl-1H-pyrazol-4-yl)amino)-5-(4-(trifluoromethyl)phenyl)pyridin-4-yl)amino)phenyl)acrylamide (Compound 308)

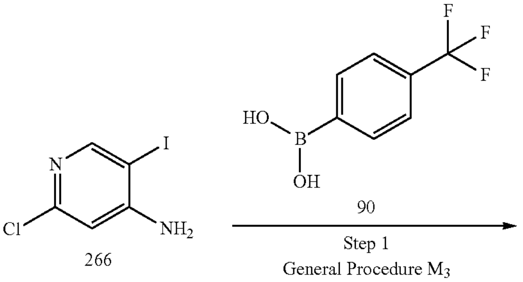

266

-continued

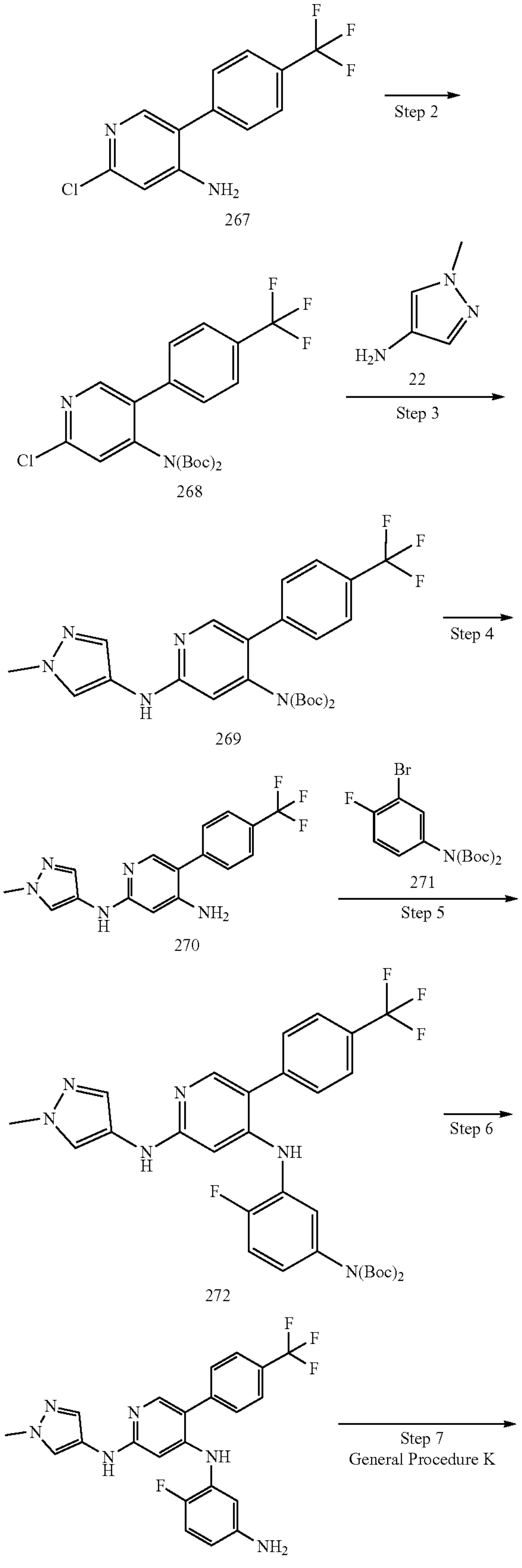

267
268
269
270
272
273

-continued

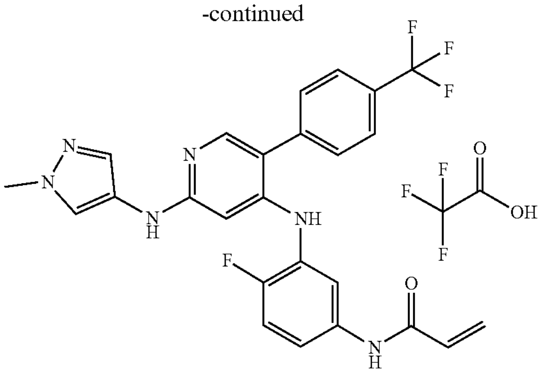

Compound 210

Step 1: Synthesis of 2-chloro-5-[4-(trifluoromethyl) phenyl]pyridin-4-amine (267)

The title compound was prepared in a manner substantially similar to procedure mentioned in General Procedure $M_3$ to get desired product (267) as white solid. LCMS $[M+H]^+$ 272.8

Step 2: Synthesis of tert-butyl N-[(tert-butoxy)carbonyl]-N-{2-chloro-5-[4-(trifluoromethyl)phenyl] pyridin-4-yl}carbamate (268)

To a solution of 2-chloro-5-[4-(trifluoromethyl)phenyl] pyridin-4-amine (267) (2.00 g, 7.34 mmol) in tetrahydrofuran (30.0 mL) was added ditertbutyl dicarbonate (0.978 g, 4.48 mmol), N,N-dimethylpyridin-4-amine (0.896 g, 7.34 mmol), triethylamine (2.84 mL, 20.3 mmol) at room temperature and the reaction mixture was heated at 65° C. for 8 hours. The reaction progress was monitored by LCMS and TLC. The reaction mixture was cooled to room temperature, diluted with water (25 mL) and extracted with ethyl acetate (2×35 mL). The combined organic layer was washed with saturated ammonium chloride solution (2×15 mL), brine, dried over anhydrous sodium sulfate and evaporated under reduced pressure. The crude product was purified by column chromatography using combiflash purifier and eluted with 7% ethyl acetate in hexane to give tert-butyl N-[(tert-butoxy)carbonyl]-N-{2-chloro-5-[4-(trifluoromethyl)phenyl]pyridin-4-yl}carbamate (268) (1.40 g, 72%). LCMS $[M+H]^+$ 473.1.

Step 3: Synthesis of tert-butyl N-[(tert-butoxy)carbonyl]-N-{2-[(1-methyl-1H-pyrazol-4-yl)amino]-5-[4-(trifluoromethyl)phenyl]pyridin-4-yl}carbamate (269)

To a solution of tert-butyl N-[(tert-butoxy)carbonyl]-N-{2-chloro-5-[4-(trifluoromethyl)phenyl]pyridin-4-yl}carbamate (268) (1.50 g, 3.17 mmol), 1-methyl-1H-pyrazol-4-amine (22) (0.308 g, 3.17 mmol), cesium carbonate (3.10 g, 9.52 mmol), 4,5-bis(diphenylphosphino)-9,9-dimethylxanthene (0.091 g, 0.159 mmol) in 1,4-dioxane (25.0 mL) was purged with argon for 15 minutes. Then added palladium (II) acetate (0.071 g, 0.317 mmol) and the reaction mixture was heated at 106° C. for 12 hours. The reaction was monitored by LCMS. The reaction mixture was cooled, filtered through celite. The filtrate was diluted with water (30 mL) and extracted with dichloromethane (3×10 mL). The combined organic layer was dried over anhydrous sodium sulfate, filtered, and concentrated under reduced pressure to afford tert-butyl N-[(tert-butoxy)carbonyl]-N-{2-[(1-methyl-1H-pyrazol-4-yl)amino]-5-[4-(trifluoromethyl)phenyl]pyridin-4-yl}carbamate (269) (1.25 g, 2.34 mmol). LCMS $[M-H]^-$ 534.2

Step 4: Synthesis of N2-(1-methyl-1H-pyrazol-4-yl)-5-[4-(trifluoromethyl)phenyl]pyridine-2,4-diamine (270)

To a stirred solution of tert-butyl N-[(tert-butoxy)carbonyl]-N-{2-[(1-methyl-1H-pyrazol-4-yl)amino]-5-[4-(trifluoromethyl)phenyl]pyridin-4-yl}carbamate (269) (1.25 g, 2.34 mmol) in dichloromethane (20.0 mL) was added hydrochloric acid in dioxane (5.00 mL, 144 mmol, 4N) at 0° C. and the reaction mixture was stirred at room temperature for 1 hour. The progress of the reaction was monitored by LCMS. The reaction mixture was concentrated under reduced pressure and the residue was washed with ether and dried to afford N2-(1-methyl-1H-pyrazol-4-yl)-5-[4-(trifluoromethyl)phenyl]pyridine-2,4-diamine (270) (0.8 g, 1.66 mmol). LCMS $[M+H]^+$ 334.1

Step 5: Synthesis of tert-butyl N-[(tert-butoxy)carbonyl]-N-[4-fluoro-3-({2-[(1-methyl-1H-pyrazol-4-yl)amino]-5-[4-(trifluoromethyl)phenyl]pyridin-4-yl}amino)phenyl]carbamate (272)

To a stirred solution of N2-(1-methyl-1H-pyrazol-4-yl)-5-[4-(trifluoromethyl)phenyl]pyridine-2,4-diamine (270) (0.5 g, 1.50 mmol) in 1,4-dioxane (10.0 mL) was added tert-butyl N-(3-bromo-4-fluorophenyl)-N-[(tert-butoxy)carbonyl]carbamate (271) (0.585 g, 1.50 mmol), cesium carbonate (0.977 g, 3.00 mmol), 4,5-bis(diphenylphosphino)-9,9-dimethylxanthene (0.021 g, 0.037 mmol) and the reaction mixture was purged with argon for 10 minutes. Then added tris(dibenzylideneacetone)dipalladium(0) (0.068 g, 0.075 mmol) and the reaction mixture was heated at 110° C. for 12 hours. The reaction was monitored by TLC. The reaction mixture was cooled, filtered through celite bed and the filtrate was concentrated under reduce pressure. The residue was diluted with water (20 mL) and extracted with dichloromethane (3×20 mL). The combined organic layer was washed with water (10 mL), brine (10 mL), dried over anhydrous sodium sulfate and evaporated under reduced pressure. The crude product was purified by using combi-flash purifier and was eluted with 10% methanol in dichloromethane to afford tert-butyl N-[(tert-butoxy)carbonyl]-N-[4-fluoro-3-({2-[(1-methyl-1H-pyrazol-4-yl)amino]-5-[4-(trifluoromethyl)phenyl]pyridin-4-yl}amino)phenyl] carbamate (272) (0.350 g, 0.545 mmol). LCMS $[M+H]^+$ 443.3

Step 6: Synthesis of N4-(5-amino-2-fluorophenyl)-N2-(1-methyl-1H-pyrazol-4-yl)-5-[4-(trifluoromethyl)phenyl]pyridine-2,4-diamine (273)

To a stirred solution of tert-butyl N-[(tert-butoxy)carbonyl]-N-[4-fluoro-3-({2-[(1-methyl-1H-pyrazol-4-yl)amino]-5-[4-(trifluoromethyl)phenyl]pyridin-4-yl}amino)phenyl]carbamate (310) (0.3 g, 0.467 mmol) in dichloromethane (10.0 mL) was added trifluoroacetic acid (3.00 mL, 39.2 mmol) at 0° C. and the reaction mixture was stirred for 3 hours at room temperature. The progress of the reaction was monitored by LCMS. After completion of starting material reaction mass was concentrated under reduced pressure and was washed with to afford N4-(5-amino-2-fluorophenyl)-N2-(1-methyl-1H-pyrazol-4-yl)-5-[4-(trifluoromethyl)phenyl]pyridine-2,4-diamine (273) (0.15 g, 0.237 mmol). LCMS $[M+H]^+$ 443.2

Step 7: Synthesis of N-[4-fluoro-3-({2-[(1-methyl-1H-pyrazol-4-yl)amino]-5-[4-(trifluoromethyl)phenyl]pyridin-4-yl}amino)phenyl]prop-2-enamide (Compound 210)

The title compound was prepared in a manner substantially similar to procedure mentioned in General Procedure K to get desired product (Compound 210) as white solid. $^1H$ NMR (400 MHz, DMSO-d6): δ 12.4 (bs, 1H), 10.29 (bs, 1H), 9.34 (bs, 1H), 8.65 (bs, 1H), 7.86-7.84 (m, 4H), 7.68-7.66 (m, 2H), 7.55 (s, 1H), 7.44 (bs, 2H), 7.36-7.31 (m, 1H), 6.42-6.36 (m, 1H), 6.26-6.22 (m, 1H), 5.89 (s, 1H), 5.77 (d, J=10.8 Hz, 1H), 3.80 (s, 3H); LCMS $[M+H]^+$ 497.3

Scheme 60: Synthesis of N-(4-fluoro-3-((2-((3-methylisothiazol-5-yl)amino)-5-(4-(trifluoromethyl)phenyl)pyrimidin-4-yl)amino)phenyl)acrylamide (Compound 211)

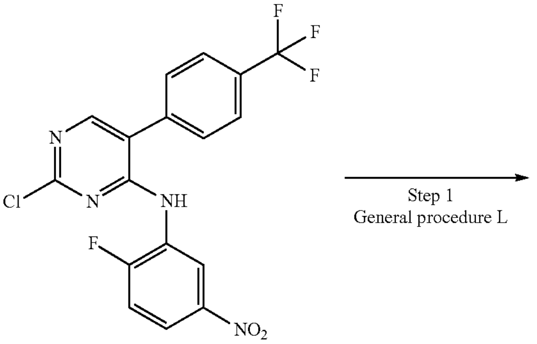

91

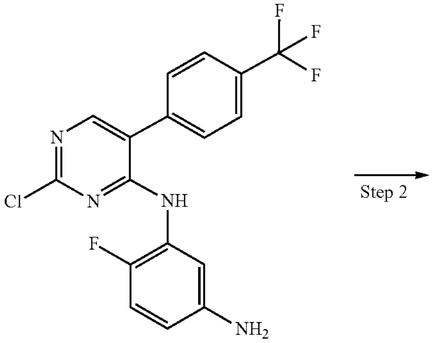

274

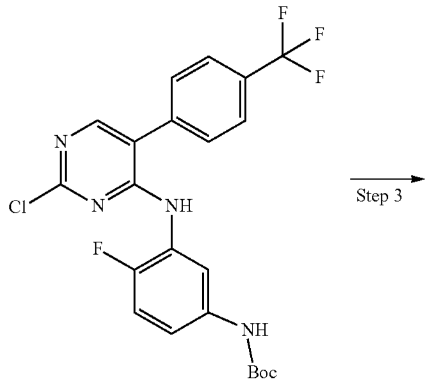

275

-continued

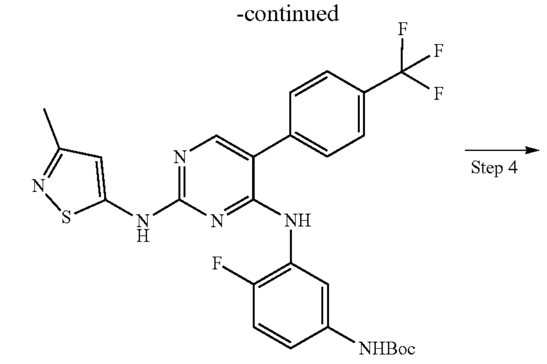

276

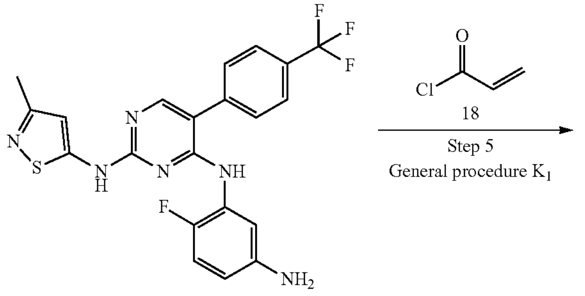

277

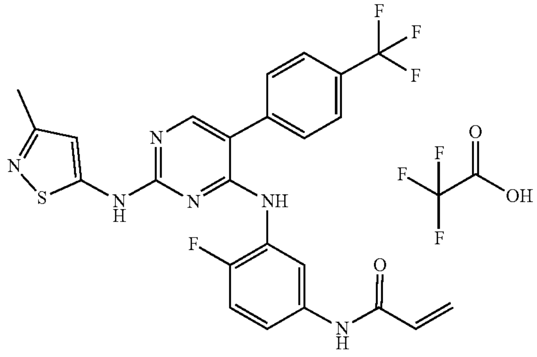

Compound 211

Step 1: Synthesis of N1-{2-chloro-5-[4-(trifluoromethyl)phenyl]pyrimidin-4-yl}-6-fluorobenzene-1,3-diamine (274)

The title compound was prepared in a manner substantially similar to procedure mentioned in General Procedure L to get desired product (274) as white solid. LCMS [M+H]f 383.0

Step 2: Synthesis of tert-butyl N-[3-({2-chloro-5-[4-(trifluoromethyl)phenyl]pyrimidin-4-yl}amino)-4-fluorophenyl]carbamate (275)

To a stirred solution of N1-{2-chloro-5-[4-(trifluoromethyl)phenyl]pyrimidin-4-yl}-6-fluorobenzene-1,3-diamine (274) (1.50 g, 3.92 mmol) in tetrahydrofuran (20.0 mL) were added di-tert-butyl dicarbonate (2.25 mL, 9.80 mmol), sodium hydrogen carbonate (1.65 g, 19.6 mmol) in water (10.0 mL) and the reaction mixture was stirred at room temperature for 12 hours. The reaction mixture was diluted with water (20 mL) and extracted with ethyl acetate (3×20 mL). The combined organic layer was dried over sodium sulfate and concentrated under reduced pressure to afford tert-butyl N-[3-({2-chloro-5-[4-(trifluoromethyl)phenyl]pyrimidin-4-yl}amino)-4-fluorophenyl]carbamate (275) (1.50 g, 2.70 mmol). LCMS $[M-H]^-$ 482.8

Step 3: Synthesis of tert-butyl N-[4-fluoro-3-({2-[(3-methyl-1,2-thiazol-5-yl)amino]-5-[4-(trifluoromethyl)phenyl]pyrimidin-4-yl}amino)phenyl]carbamate (276)

To a stirred solution of tert-butyl N-[3-({2-chloro-5-[4-(trifluoromethyl)phenyl]pyrimidin-4-yl}amino)-4-fluorophenyl]carbamate (275) (0.5 g, 1.04 mmol) in 1,4-dioxane (12.0 mL) was added 3-methyl-1,2-thiazol-5-amine hydrochloride (0.118 g, 1.04 mmol), cesium carbonate (0.675 g, 2.07 mmol) and the reaction mixture was purged with argon for 10 minutes. Then added tris(dibenzylideneacetone)dipalladium(0) (0.094 g, 0.104 mmol), 4,5-bis(diphenylphosphino)-9,9-dimethylxanthene (0.059 g, 0.104 mmol) and the reaction mixture was heated at 105° C. for 8 hours. The reaction mixture was filtered through celite bed, the filtrate was diluted with water (25 mL) and extracted with ethyl acetate (3×20 mL). The combined organic layer was dried over anhydrous sodium sulfate and concentrated under reduced pressure to give tert-butyl N-[4-fluoro-3-({2-[(3-methyl-1,2-thiazol-5-yl)amino]-5-[4-(trifluoromethyl)phenyl]pyrimidin-4-yl}amino)phenyl]carbamate (276) (0.7 g, 0.937 mmol). LCMS $[M+H]^+$ 560.9

Step 4: Synthesis of N4-(5-amino-2-fluorophenyl)-N2-(3-methyl-1,2-thiazol-5-yl)-5-[4-(trifluoromethyl)phenyl]pyrimidine-2,4-diamine (277)

To a stirred solution of tert-butyl N-[4-fluoro-3-({2-[(3-methyl-1,2-thiazol-5-yl)amino]-5-[4-(trifluoromethyl)phenyl]pyrimidin-4-yl}amino)phenyl]carbamate (276) (0.68 g, 1.21 mmol) in dichloromethane (10.0 mL) was added hydrochloric acid in dioxane (6.00 mL, 173 mmol, 4N) at 0° C. and the reaction mixture was stirred for 5 hours at room temperature. The progress of the reaction was monitored by LCMS. The reaction mixture was concentrated under reduced pressure. The crude product was washed with pentane and dried to afford N4-(5-amino-2-fluorophenyl)-N2-(3-methyl-1,2-thiazol-5-yl)-5-[4-(trifluoromethyl)phenyl]pyrimidine-2,4-diamine (278) (0.5 g, 0.76 mmol). LCMS $[M+H]^+$ 461.1

Step 5: Synthesis of N-[4-fluoro-3-({2-[(3-methyl-1,2-thiazol-5-yl)amino]-5-[4-(trifluoromethyl)phenyl]pyrimidin-4-yl}amino)phenyl]prop-2-enamide (Compound 211)

The title compound was prepared in a manner substantially similar to procedure mentioned in General Procedure K to get desired product (Compound 211) as off white solid. $^1H$ NMR (400 MHz, DMSO-d6): δ 11.04 (s, 1H), 10.20 (s, 1H), 8.76 (s, 1H), 8.12 (s, 1H), 7.84 (d, J=7.2 Hz, 3H), 7.75 (d, J=8.4 Hz, 3H), 7.52 (d, J=8.4 Hz, 1H), 7.27-7.20 (m, 1H), 6.55 (bs, 1H), 6.45-6.38 (m, 1H), 6.24 (dd, J=14.0 Hz, 1H), 2.20 (s, 3H). LCMS $[M+H]^+$ 515.1.

TABLE 15
The following compounds were prepared using the procedures described above:
| Cmpd. No. | Structure | General Procedure | LCMS [M + H] | $^1$H-NMR (400 MHz, DMSO-$d_6$) |
|---|---|---|---|---|
| 212 | 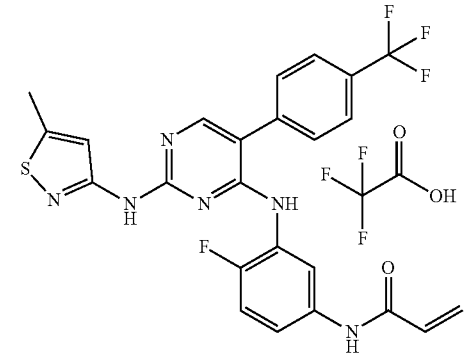 | $K_1$ | 515.2 | δ 10.60 (bs, 1H), 10.23 (s, 1H), 9.07 (bs, 1H), 8.07 (s, 1H), 7.89-7.76 (m, 6H), 7.59-7.57 (m, 1H), 7.32 (t, J = 9.4 Hz, 1H), 7.02 (s, 1H), 6.44-6.38 (m, 1H), 6.25 (dd, J = 16.8 Hz, 2.0 Hz, 1H), 5.76 (dd, J = 12.0 Hz, 1.6 Hz, 1H), 2.38 (s, 3H) |
| 213 | 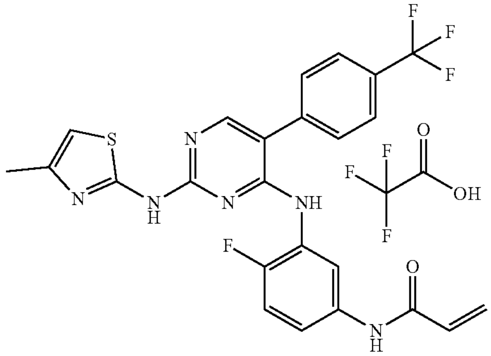 | $K_1$ | 515.1 | δ 13.2 (s, 1H), 10.21 (s, 1H), 9.44 (s, 1H), 8.11 (s, 1H), 7.90-7.80 (m, 6H), 7.54 (t, J = 8.0 Hz, 1H), 7.28 (t, J = 9.6 Hz, 1H), 6.44-6.23 (m, 3H), 5.74 (dd, J = 10.0 Hz, 1H), 2.17 (s, 3H). |
| 214 | 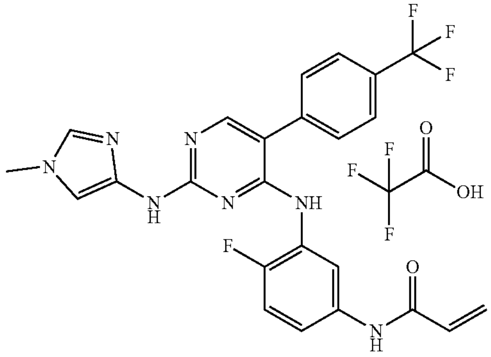 | $K_1$ | 498.2 | δ 10.24-10.10 (m, 2H), 9.03 (s, 1H), 8.24 (s, 1H), 8.04 (s, 1H), 7.85-7.71 (m, 5H), 7.52-7.50 (m, 1H), 7.30 (t, J = 9.4 Hz, 1H), 6.30 (bs, 2H), 6.42-6.35 (m, 1H), 6.23 (dd, J = 17.2 Hz, 2.0 Hz, 1H), 5.75 (dd, J = 10.4 Hz, 2.0 Hz, 1H), 3.59 (s, 3H). |
| 215 | 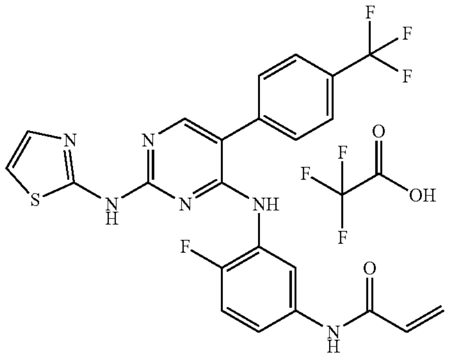 | $K_1$ | 501.1 | δ 13.1 (bs, 1H), 11.2 (bs, 1H), 10.22 (s, 1H), 9.30 (bs, 2H), 8.11 (s, 1H), 7.76-7.88 (m, 4H), 7.52-7.54 (m, 1H), 7.25-7.41 (m, 2H), 6.86 (d, J = 4.0 Hz, 1H), 6.35-6.42 (m, 1H), 6.21-6.25 (m, 1H), 5.73-5.76 (m, 1H) |

Scheme 61: Synthesis of N-(3-((2-((1-(3-(dimethylamino)propyl)-1H-pyrazol-4-yl)amino)-5-(4-(trifluoromethyl)phenyl)pyrimidin-4-yl)amino)-4-fluorophenyl)acrylamide (Compound 216)
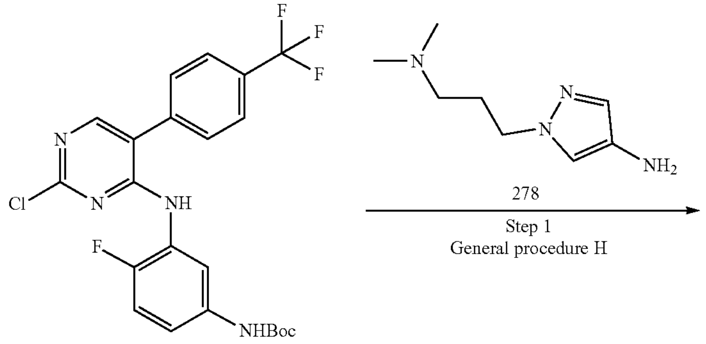
275
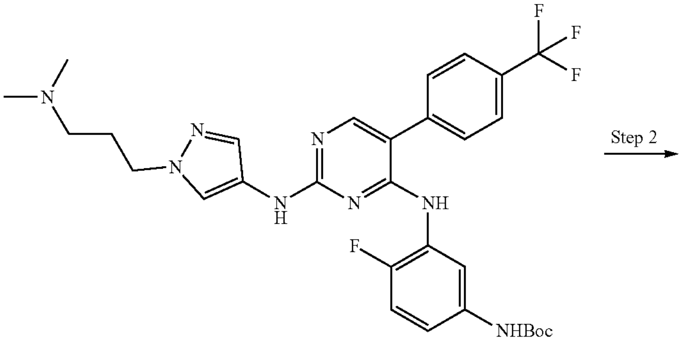
279
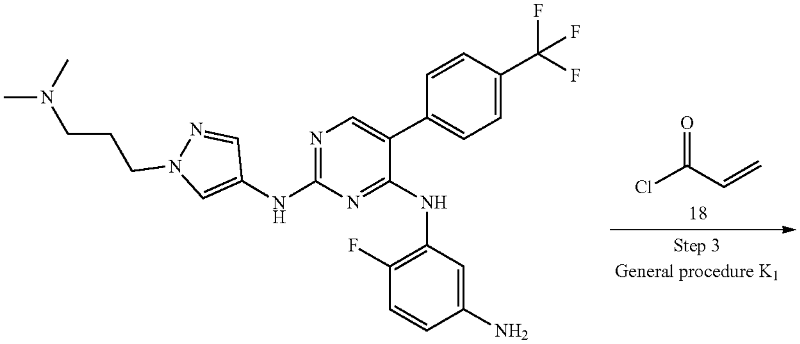
280
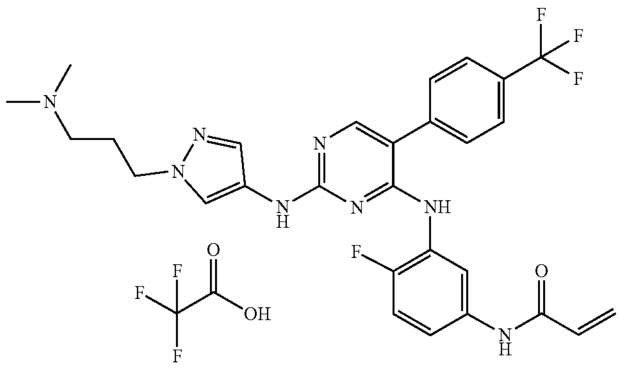
Compound 216

Step 1: Synthesis of tert-butyl N-(3-{[2-({1-[3-(dimethylamino) propyl]-1H-pyrazol-4-yl}amino)-5-[4-(trifluoromethyl) phenyl] pyrimidin-4-yl] amino}-4-fluorophenyl) carbamate (279)

The title compound was prepared in a manner substantially similar to procedure mentioned in General Procedure H to get desired product (279) as brown solid. LCMS $[M+H]^+$ 615.4

Step 2: Synthesis of N4-(5-amino-2-fluorophenyl)-N2-{1-[3-(dimethylamino) propyl]-1H-pyrazol-4-yl}-5-[4-(trifluoromethyl) phenyl] pyrimidine-2,4-diamine (280)

To a stirred solution of tert-butyl N-(3-{[2-({1-[3-(dimethylamino) propyl]-1H-pyrazol-4-yl} amino)-5-[4-(trifluoromethyl) phenyl] pyrimidin-4-yl] amino}-4-fluorophenyl) carbamate (279) (0.5 g, 0.8 mmol) in dichloromethane (15.0 mL) was added hydrochloric acid in dioxane (2.00 mL, 4N) and stirred for 1 hour at room temperature. Progress of the reaction was monitored by LCMS. The reaction mixture was concentrated under reduced pressure. The crude product was washed with ether and dried to afford N4-(5-amino-2-fluorophenyl)-N2-{1-[3-(dimethylamino) propyl]-1H-pyrazol-4-yl}-5-[4-(trifluoromethyl) phenyl] pyrimidine-2,4-diamine (280) (0.4 g, 95%) as a brown color solid. LCMS $[M+H]^+$ 515.5

Step 3: Synthesis of N-(3-{[2-({1-[3-(dimethylamino) propyl]-1H-pyrazol-4-yl} amino)-5-[4-(trifluoromethyl) phenyl] pyrimidin-4-yl] amino}-4-fluorophenyl) prop-2-enamide (Compound 216)

The title compound was prepared in a manner substantially similar to procedure mentioned in General Procedure $K_1$ to get desired product (Compound 216) as off white solid. $^1H$ NMR (400 MHz, DMSO-$d_6$): δ 10.33 (s, 1H), 9.46 (s, 1H), 8.03 (s, 1H), 7.93-7.91 (m, 1H), 7.85-7.83 (m, 1H), 7.74-7.32 (m, 2H), 7.66 (bs, 2H), 7.48 (s, 1H), 7.36-7.10 (m, 4H), 6.43-6.37 (m, 1H), 6.26-6.31 (m, 1H), 5.76 (d, J=12.0 Hz, 1H), 3.87 (s, 2H), 3.01 (s, 2H), 2.73-2.65 (m, 6H), 1.95 (s, 2H); LCMS $[M+H]^+$ 567.2

TABLE 16

The following compounds were prepared using the procedures described above:

| Cmpd. No. | Structure | General Procedure | LCMS [M + H] | $^1H$-NMR (400 MHz, DMSO-$d_6$) |
|---|---|---|---|---|
| 217 | 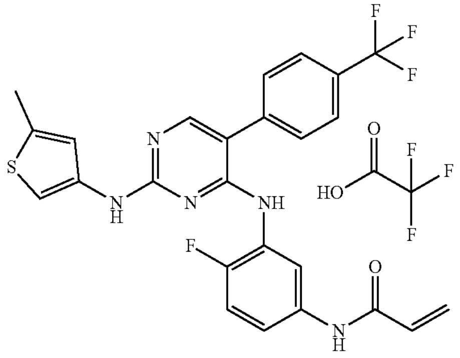 | $K_1$ | 514.2 | δ 10.20 (s, 1H), 9.77 (bs, 1H), 8.85 (bs, 1H), 8.01 (s, 1H), 7.83-7.78 (m, 2H), 7.73 (d, J = 8.0 Hz, 2H), 7.62-7.49 (m, 3H), 7.26-7.21 (m, 2H), 6.73 (s, 1H), 6.42-6.35 (m, 1H), 6.22 (dd, J = 16.8 Hz, 1H), 5.73 (dd, J = 10.0 Hz, 1H), 2.27 (s, 3H). |
| 218 | 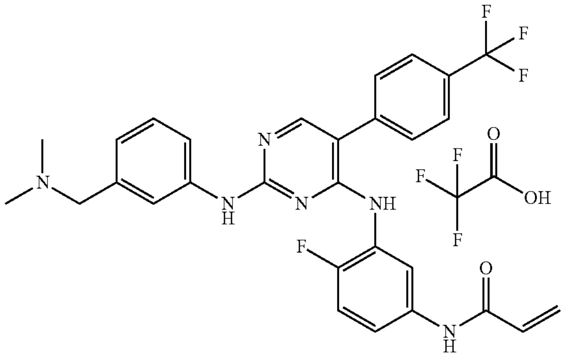 | $K_1$ | 549.2 [M − H] | 10.22 (s, 1H), 9.68 (s, 1H), 9.59 (bs, 1H) 8.80 (s, 1H), 8.09 (s, 1H), 7.86-7.74 (m, 5H), 7.68-7.65 (m, 1H), 7.56-7.50 (m, 2H), 7.31-7.15 (m, 2H), 7.01-6.97 (m, 1H), 6.44-6.22 (m, 1H), 6.27-5.78 (m, 1H), 5.77-5.74 (m, 1H), 4.24 (s, 2H), 2.63 (s, 6H) |

TABLE 16-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 219 | 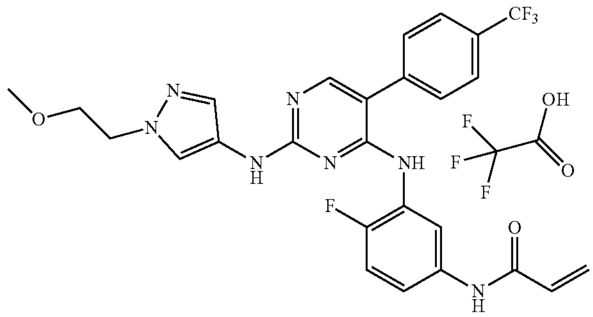 | $K_2$ | 542.2 | δ 10.28 (s, 1H), 9.99 (bs, 1H), 9.31 (bs, 1H), 8.00 (s, 1H), 7.85 (d, J = 8.4 Hz, 3H), 7.74 (d, J = 7.6 Hz, 2H), 7.56 (s, 1H), 7.32 (s, 2H), 7.22 (s, 1H), 7.07 (s, 1H), 6.36-6.42 (m, 1H), 6.23 (dd, J = 19.2 Hz, 2.4 Hz, 1H), 5.75 (dd, J = 11.6 Hz, 1.6 Hz, 1H), 3.93 (s, 2H), 3.47 (s, 2H), 3.12 (s, 3H). |
| 220 | 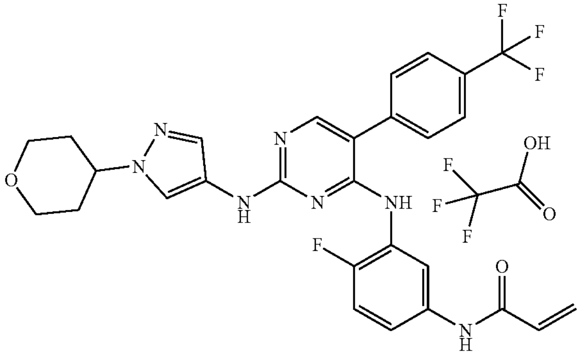 | $K_2$ | 568.5 | δ 10.30 (s, 1H), 9.85 (bs, 1H), 9.25 (bs, 1H), 8.01 (s, 1H), 7.86 (d, J = 8.0 Hz, 3H), 7.76 (d, J = 8.0 Hz, 2H), 7.63 (s, 1H), 7.37-7.33 (m, 1H), 7.29-7.22 (m, 3H), 6.45-6.39 (m, 1H), 6.28-6.23 (m, 1H), 5.78-5.75 (m, 1H), 3.93-3.90 (m, 3H), 3.45-3.39 (m, 2H), 1.69 (bs, 4H). |
| 221 | 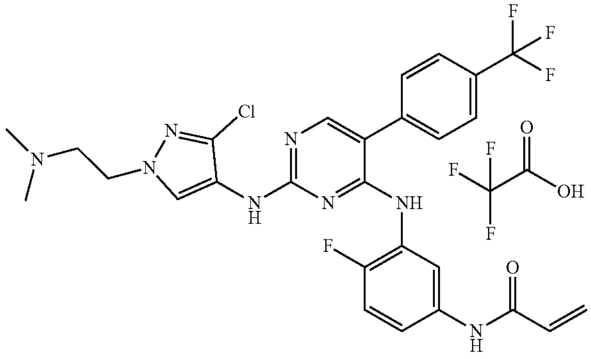 | K | 589.2 | δ 10.22 (s, 1H), 9.39 (bs, 1H), 8.91 (bs, 1H), 8.0 (s, 1H), 7.92 (d, J = 7.2 Hz, 1H), 7.83 (d, J = 8.0 Hz, 2H), 7.71 (d, J = 8.4 Hz, 2H), 7.59-7.32 (m, 2H), 7.28-6.90 (m, 2H), 6.43-6.38 (m, 1H), 6.26-6.21 (m, 1H), 5.77-5.74 (m, 1H), 4.24 (s, 2H), 3.44 (s, 2H), 2.79 (s, 6H). |

Scheme 62: Synthesis of N-(4-fluoro-3-((2-((1-methyl-1H-pyrazol-4-yl)amino)-5-morpholinopyrimidin-4-yl)amino)phenyl)acrylamide (Compound 222)

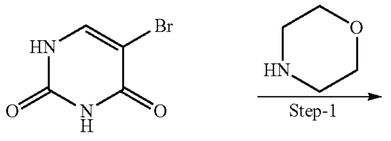

281

-continued

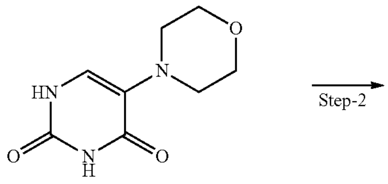

282

-continued

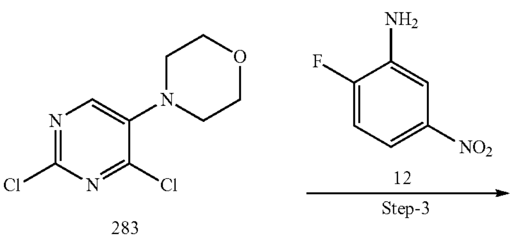

283

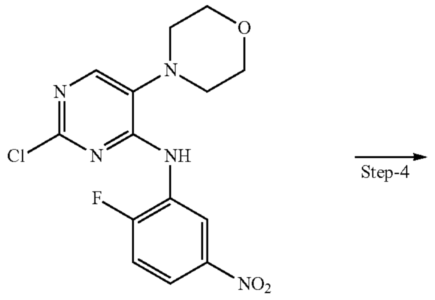

284

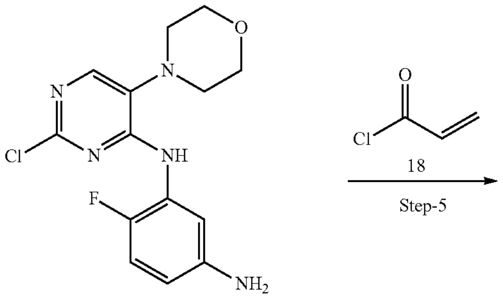

285

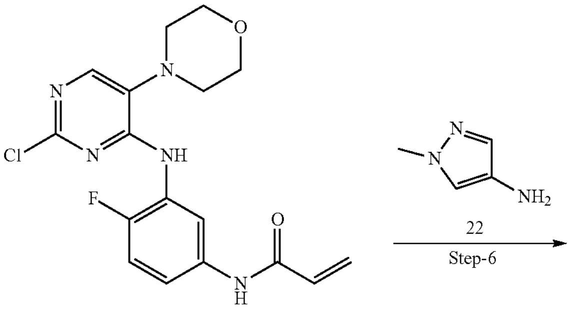

286

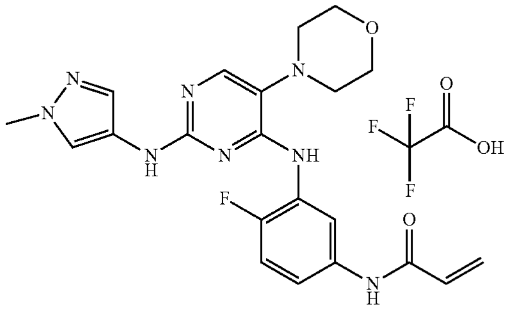

Compound 222

Step 1: Synthesis of 5-morpholinopyrimidine-2,4(1H,3H)-dione (282)

A sealed tube was charged with 5-bromopyrimidine-2,4(1H,3H)-dione (281) (25.0 g, 131 mmol) and morpholine (50 mL) under nitrogen atmosphere and the resultant reaction mixture was heated at 130° C. for 30-minutes. The reaction was monitored by TLC, after completion of reaction, the reaction mixture was quenched with ice cold water, obtained solid was filtered, washed with water and dried to afford 5-morpholinopyrimidine-2,4(1H,3H)-dione 3 as an off white solid (282) (25.0 g, Yield: 96.86%), LCMS $[M+H]^+$ 197.97

Step 2: Synthesis of 4-(2,4-dichloropyrimidin-5-yl)morpholine (283)

To a stirred solution of 5-morpholinopyrimidine-2,4(1H,3H)-dione (282) (25.0 g, 131 mmol) in $POCl_3$ (175 mL) under nitrogen atmosphere. Anhydrous dimethylformamide (5.0 mL) was added dropwise in to the reaction mixture. The resultant reaction mixture was heated at reflux 110° C. for 36 hours. The resultant reaction mixture was monitored by TLC, after completion of reaction, $POCl_3$ was evaporated under reduced pressure, then an ice cold water was added and neutralized with saturated sodium bi carbonate, extracted with ethyl acetate, washed with water, brine and dried over anhydrous sodium sulfate, filtered and concentrated to afford 4-(2,4-dichloropyrimidin-5-yl) morpholine (283) as brown sticky solid (10.0 g, Yield: 33.68%). $^1H$ NMR (400 MHz, DMSO-d6): δ 8.52 (s, 1H), 3.71-3.74 (m, 4H), 3.10-3.20 (m, 4H).

Step 3: Synthesis of 2-chloro-N-(2-fluoro-5-nitrophenyl)-5-morpholinopyrimidin-4-amine (284)

To an ice cold solution of 2-fluoro-5-nitroaniline (12) (1.60 g, 10.3 mmol) in N,N-dimethylformamide (9.00 mL) and methanesulfinylmethane (1.00 mL) was added sodium hydride (0.92 g, 38.4 mmol), followed by portion wise addition of 4-(2,4-dichloropyrimidin-5-yl)morpholine (283) (3.00 g, 12.8 mmol) and stirred at 0° C. for 15 min. After completion of reaction (TLC monitoring), reaction mass was diluted with water (100 mL) and extracted with ethyl acetate (3×100 mL). The combined organic layer was washed with brine solution, dried over anhydrous sodium sulphate, filtered and concentrated. Crude was purified by flash chromatography using 10% ethyl acetate in hexane as an eluent, desired fractions were concentrated to dryness to afford 2-chloro-N-(2-fluoro-5-nitrophenyl)-5-morpholinopyrimidin-4-amine (284) (0.6 g, Yield: 10.34%). LCMS $[M+H]^+$ 353.98

Step 4: Synthesis of N1-(2-chloro-5-morpholinopyrimidin-4-yl)-6-fluorobenzene-1,3-diamine (285)

To a solution of 2-chloro-N-(2-fluoro-5-nitrophenyl)-5-(morpholin-4-yl)pyrimidin-4-amine (284) (0.60 g, 1.70 mmol) in ethanol (5.00 mL)_& water (5.00 mL) were added iron (0.947 g, 17.0 mmol) and ammonium chloride (0.90 g, 17.0 mmol). The reaction mixture was heated to 50° C. for 7 hours. After completion of reaction (TLC monitoring), the reaction mixture was allowed to cool to room temperature. The mixture was filtered through a celite bed, washed with ethyl acetate (3×150 mL). The filtrate was washed with water, brine, dried over anhydrous sodium sulphate, filtered and evaporated under reduced pressure. The crude was purified by flash chromatography using 5% methanol in dichloromethane as eluent, desired fractions were concentrated to dryness to afford N1-[2-chloro-5-(morpholin-4-yl)pyrimidin-4-yl]-6-fluorobenzene-1,3-diamine (285) (0.5 g, Yield: 62.3%) as an off white solid. LCMS $[M+H]^+$ 324.04

Step 5: Synthesis of N-(3-((2-chloro-5-morpholino-pyrimidin-4-yl)amino)-4-fluorophenyl)acrylamide (286)

To a solution of N1-[2-chloro-5-(morpholin-4-yl)pyrimidin-4-yl]-6-fluorobenzene-1,3-diamine (285) (0.50 g, 1.54 mmol), triethylamine (1.12 mL, 7.72 mmol) in dichloromethane (7.00 mL) and tetrahydrofuran (7.00 mL)_at −78° C. was added prop-2-enoyl chloride (18) (0.168 g, 1.85 mmol) and stirred for 30 minutes at same temperature. After completion, the reaction mixture was diluted with water (50 mL) and extracted with dichloromethane (25 mL×3). The combined organic layer was washed with water (20 mL), brine (20 mL), dried over anhydrous sodium sulphate and concentrated to afford N-(3-((2-chloro-5-morpholinopyrimidin-4-yl)amino)-4-fluorophenyl)acrylamide (286) as an off white solid LCMS $[M-H]^-$ 376.00

Step 6: Synthesis of N-(4-fluoro-3-((2-((1-methyl-1H-pyrazol-4-yl)amino)-5-morpholinopyrimidin-4-yl)amino)phenyl)acrylamide (Compound 222)

To a stirred solution of N-(3-((2-chloro-5-morpholinopyrimidin-4-yl)amino)-4-fluorophenyl)acrylamide (286) (0.3 g, 0.79 mmol), 1-methyl-1H-pyrazol-4-amine (22) (0.092 g, 0.95 mmol) in butan-2-ol (5.00 mL) was added potassium carbonate (0.546 g, 3.95 mmol). The reaction mixture was purged with nitrogen for 20 minutes, added dicyclohexyl[2',4',6'-tris(propan-2-yl)-[1,1'-biphenyl]-2-yl]phosphane (0.046 g, 0.079 mmol) and tris(1,5-diphenylpenta-1,4-dien-3-one) dipalladium (0.072 g, 0.079 mmol) and stirred at 100° C. for 16 hours. After completion of reaction (TLC monitoring), the reaction mixture was diluted with water (20 mL) and extracted with ethyl acetate (10 mL×3). The combined organic layer was washed with brine (10 mL), dried over anhydrous sodium sulphate and concentrated under reduced pressure. The crude product was purified by prep HPLC to afford N-(4-fluoro-3-((2-((1-methyl-1H-pyrazol-4-yl)amino)-5-morpholinopyrimidin-4-yl)amino)phenyl)acrylamide (Compound 320) (52 mg, Yield: 11.84%) as an off white solid. $^1$H NMR (400 MHz, DMSO-d6): δ 10.11 (s, 1H), 9.60-9.80 (m, 2H), 8.20 (d, J=5.2 Hz, 1H), 7.78 (bs, 1H), 7.32-7.50 (m, 4H), 6.62-6.69 (m, 2H), 6.24-6.28 (m, 1H), 5.80 (d, J=10.0 Hz, 1H), 3.79-3.83 (m, 4H), 3.67 (bs, 3H), and 2.86-2.88 (m, 4H). LCMS $[M+H]^+$ 439.03

Scheme 63: Synthesis of N-(3-((2-((1-methyl-1H-pyrazol-4-yl)amino)-5-(4-methylpiperzine-1-yl)pyrimidin-4-yl)oxy)phenyl)acrylamide (Compound 223)

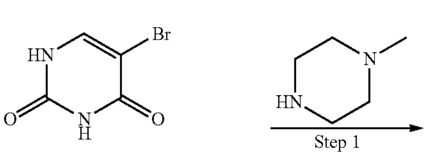

281

-continued

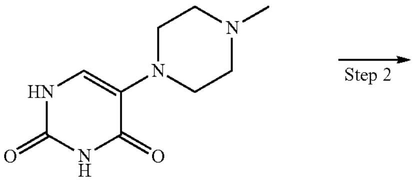

282

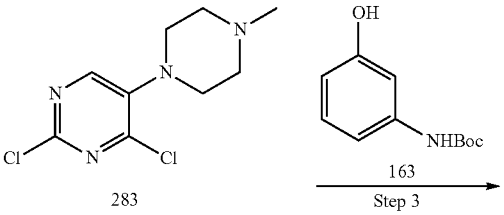

283

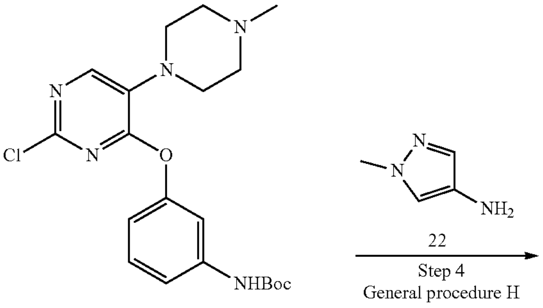

284

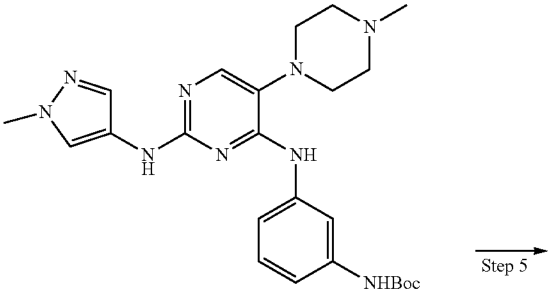

285

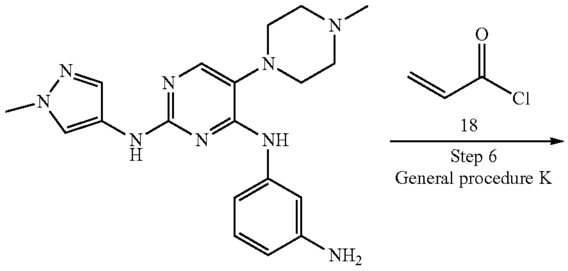

286

-continued

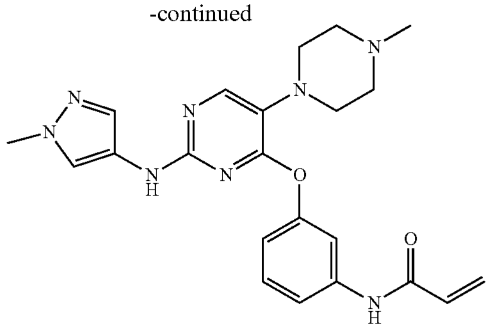

Compound 223

Step 1: Synthesis of 5-(4-methylpiperazin-1-yl)pyrimidine-2,4(1H,3H)-dione (282)

1-methylpiperazine (11.7 mL, 105 mmol) was heated to 100° C. and was added 5-bromo-1,2,3,4-tetrahydropyrimidine-2,4-dione (281) (5.00 g, 26.2 mmol) and the reaction mixture was heated at 130° C. for 15 min. Then the reaction mixture was cooled to room temperature, added methanol (100 mL) and stirred at room temperature for 15 h. The solids were filtered, washed with methanol (50 mL), ether (50 mL) and dried to get the desired product (326) as off white solid (5.0 g, crude). LCMS $[M+H]^+$ 211.1

Step 2: Synthesis of 2,4-dichloro-5-(4-methylpiperazin-1-yl)pyrimidine (283)

To a stirred solution of 5-(4-methylpiperazin-1-yl)-1,2,3,4-tetrahydropyrimidine-2,4-dione (282) (3.00 g, 14.3 mmol) in phosphoryl trichloride (20.0 mL) was heated at 100° C. for 15 h. Then the reaction mixture was cooled and evaporated. The residue was diluted with cold water (20 mL) and was basified with saturated sodium bicarbonate solution and was extracted with ethyl acetate (30 mL×3). The combined organic layer was washed with brine (20 mL), dried over anhydrous sodium sulfate and evaporated to get the desired product (283) as off white solid (1 g, crude). LCMS $[M+H]^+$ 246.8

Step 3: Synthesis of tert-butyl (3-((2-chloro-5-(4-methylpiperazin-1-yl)pyrimidin-4-yl)oxy)phenyl) carbamate (284)

To a stirred solution of 2,4-dichloro-5-(4-methylpiperazin-1-yl)pyrimidine (283) (0.91 g, 3.68 mmol) and tert-butyl N-(3-hydroxyphenyl)carbamate (163) (0.85 g, 4.05 mmol) in N,N-dimethylformamide (10.0 mL) was added potassium carbonate (1.53 g, 11.0 mmol) and the reaction mixture was stirred at room temperature for 15 h. The reaction mixture was quenched with water (20 mL) and extracted with ethyl acetate (20 mL×3). The combined organic layer was washed with water (25 mL), brine (25 mL), dried over anhydrous sulfate and evaporated. The crude product was purified by column chromatography using combiflash purifier and was eluted with 10% methanol in dichloromethane to get the desired product (284) as off white solid (1 g, 64%). LCMS $[M+H]^+$ 420.3

Step 4: Synthesis of tert-butyl (3-((2-((1-methyl-1H-pyrazol-4-yl)amino)-5-(4-methylpiperazin-1-yl)pyrimidin-4-yl)oxy)phenyl)carbamate (285)

Title compound was prepared in a manner substantially similar to procedure mentioned in General procedure H, to get tert-butyl (3-((2-((1-methyl-1H-pyrazol-4-yl)amino)-5-(4-methylpiperazin-1-yl)pyrimidin-4-yl)oxy)phenyl)carbamate (285) (0.42 g, Yield: 74%). LCMS $[M+H]^+$ 481.3

Step 5: Synthesis of 4-(3-aminophenoxy)-N-(1-methyl-1H-pyrazol-4-yl)-5-(4-methylpiperazin-1-yl) pyrimidin-2-amine (286)

To a stirred solution of tert-butyl N-[3-({2-[(1-methyl-1H-pyrazol-4-yl)amino]-5-(4-methylpiperazin-1-yl)pyrimidin-4-yl}oxy)phenyl]carbamate (285) (0.425 g, 0.884 mmol) in dichloromethane (5.00 mL) was added hydrochloric acid in dioxane (2.00 mL, 4N) and the reaction mixture was stirred at room temperature for 2 h. The reaction mixture was evaporated to dryness. The residue was washed with ether and dried to get the desired product (330) as off white solid (0.45 g, crude). LCMS $[M+H]^+$ 380.9

Step 6: Synthesis of N-(3-((2-((1-methyl-1H-pyrazol-4-yl)amino)-5-(4-methylpiperazin-1-yl)pyrimidin-4-yl)oxy)phenyl)acrylamide (Compound 223)

Title compound was prepared in a manner substantially similar to procedure mentioned in General procedure K, to get N-(3-((2-((1-methyl-1H-pyrazol-4-yl)amino)-5-(4-methylpiperazin-1-yl)pyrimidin-4-yl)oxy)phenyl)acrylamide (Compound 223) (110 mg, Yield: 21%) as white solid. $^1H$ NMR (400 MHz, DMSO-d6): δ 10.32 (s, 1H), 9.14 (bs, 1H), 8.04 (s, 1H), 7.63-7.45 (m, 2H), 7.49-7.45 (m, 1H), 7.13 (bs, 1H), 6.98-6.96 (m, 2H), 6.46-6.39 (m, 1H), 6.28-6.23 (m, 1H), 5.79-5.76 (m, 1H), 3.55 (bs, 3H), 3.07 (bs, 4H), 2.55 (bs, 4H), 2.27 (bs, 3H); LCMS: $[M+H]^+$ 435.3

Scheme 64: Synthesis of N-(3-((2-((1-methyl-1H-pyrazol-4-yl)-6-(methylamino)-5-(4-(trifluoromethyl)phenyl)pyrimidin-4-yl)amino)phenyl)acrylamide (Compound 224)

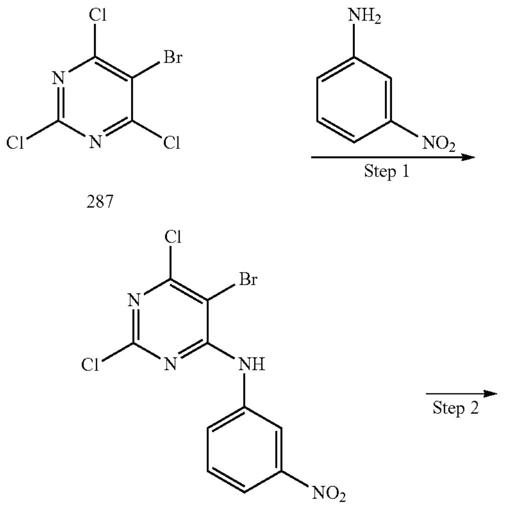

287

288

-continued

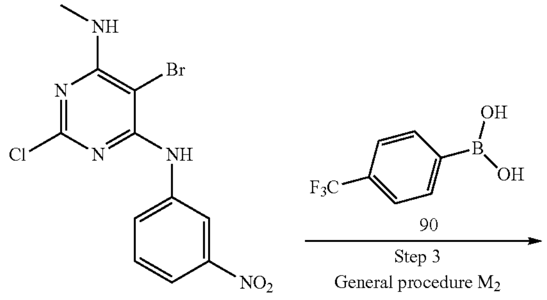

289

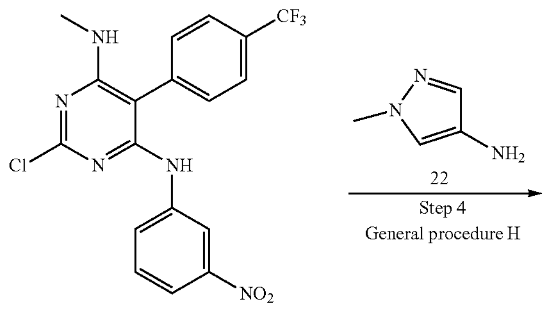

290

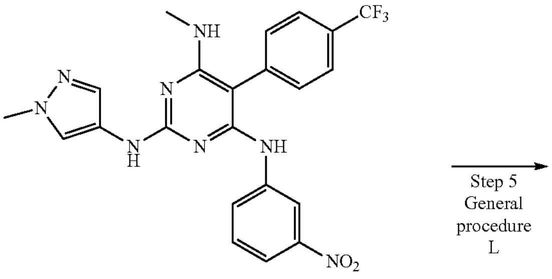

292

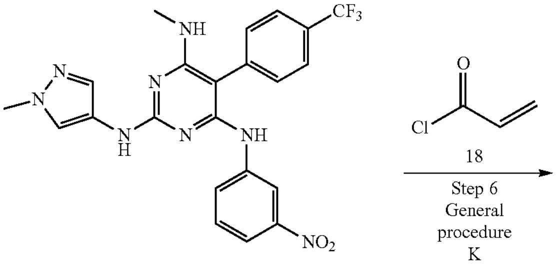

293

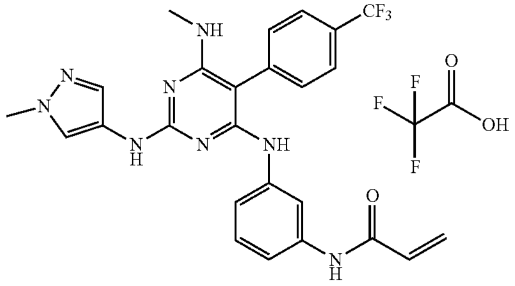

Compound 224

Step 1: Synthesis of 5-bromo-2,6-dichloro-N-(3-nitrophenyl) pyrimidin-4-amine (288)

To a stirred solution of 5-bromo-2,4,6-trichloropyrimidine (287)(3.00 g, 11.4 mmol) in propan-2-ol (30.0 mL) was added N,N-diisopropylethylamine (4.82 mL, 34.3 mmol), 3-nitroaniline (1.26 g, 9.15 mmol) at room temperature and the reaction mixture was at 100° C. for 15 hours. The progress of the reaction was monitored by TLC. The reaction mixture was cooled to room temperature, the precipitated solid was filtered and dried to afford 5-bromo-2,6-dichloro-N-(3-nitrophenyl)pyrimidin-4-amine (288) (2.50 g, 60%). LCMS $[M+H]^+$ 362.9

Step 2: Synthesis of 5-bromo-2-chloro-N4-methyl-N6-(3-nitrophenyl) pyrimidine-4,6-diamine (289)

To a suspension of 5-bromo-2,6-dichloro-N-(3-nitrophenyl) pyrimidin-4-amine (288) (2.50 g, 6.87 mmol) in methanol (50.00 mL) was added methanamine (17.2 mL, 34.3 mmol) drop wise at 0° C. and the reaction mixture was stirred for 3 hours at room temperature. After completion of reaction (TLC monitoring), the reaction mixture was concentrated under reduced pressure to afford 5-bromo-2-chloro-N4-methyl-N6-(3-nitrophenyl) pyrimidine-4,6-diamine (289) (1.3 g, 53%) as yellow solid. LCMS $[M+H]^+$ 358.0

Step 3: Synthesis of 2-chloro-N4-methyl-N6-(3-nitrophenyl)-5-[4-(trifluoromethyl) phenyl]pyrimidine-4,6-diamine (290)

Title compound was prepared in a manner substantially similar to procedure mentioned in General procedure M2, to get 2-chloro-N4-methyl-N6-(3-nitrophenyl)-5-[4-(trifluoromethyl) phenyl] pyrimidine-4,6-diamine (290) (0.35 g, Yield: 30%). LCMS $[M+H]^+$ 423.8

Step 4: Synthesis of N4-methyl-N2-(1-methyl-1H-pyrazol-4-yl)-N6-(3-nitrophenyl)-5-(4-(trifluoromethyl)phenyl)pyrimidine-2,4,6-triamine (292)

Title compound was prepared in a manner substantially similar to procedure mentioned in General procedure H, to get N4-methyl-N2-(1-methyl-1H-pyrazol-4-yl)-N6-(3-nitrophenyl)-5-(4-(trifluoromethyl)phenyl)pyrimidine-2,4,6-triamine (292). LCMS $[M+H]^+$ 485.5

Step 5: Synthesis of N4-(3-aminophenyl)-N6-methyl-N2-(1-methyl-1H-pyrazol-4-yl)-5-[4-(trifluoromethyl) phenyl] pyrimidine-2,4,6-triamine (293)

Title compound was prepared in a manner substantially similar to procedure mentioned in General procedure L, to get N4-(3-aminophenyl)-N6-methyl-N2-(1-methyl-1H-pyrazol-4-yl)-5-[4-(trifluoromethyl) phenyl] pyrimidine-2,4,6-triamine (293). LCMS $[M+H]^+$ 455.4

Step 6: Synthesis of (N-[3-({2-[(1-methyl-1H-pyrazol-4-yl) amino]-6-(methyl amino)-5-[4-(trifluoromethyl) phenyl] pyrimidin-4-yl} amino) phenyl] prop-2-enamide (Compound 224)

Title compound was prepared in a manner substantially similar to procedure mentioned in General procedure K, to get N-[3-({2-[(1-methyl-1H-pyrazol-4-yl) amino]-6-(methyl amino)-5-[4-(trifluoromethyl) phenyl] pyrimidin-4- yl} amino) phenyl] prop-2-enamide (Compound 224) as off white solid. $^1$H NMR (400 MHz, DMSO-$d_6$): δ 10.12 (s, 1H), 9.10 (s, 2H), (d, J=8.0 Hz, 2H), 7.62-7.25 (m, 8H), 7.01-6.93 (m, 2H), 6.43-6.37 (m, 1H), 6.23-6.19 (m, 1H), 5.72 (d, J=10.4 Hz, 1H), 3.73 (s, 3H), 2.79 (s, 3H); LCMS $[M+H]^+$ 509.3

Scheme 65: Synthesis of N-(4-fluoro-3-((2-isoxazol-4-ylamino)-5-(4-(trifluoromethyl)phenyl)pyrimidin-4-yl)amino)phenyl)acrylamide (Compound 225)

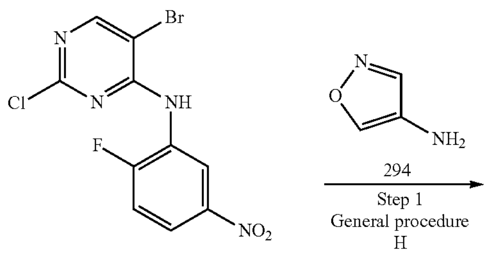

89

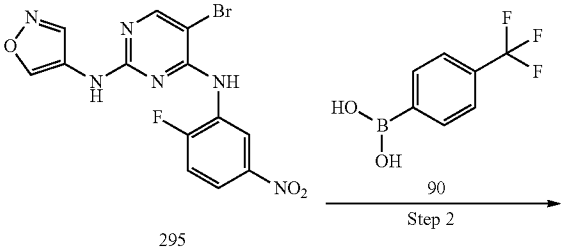

295

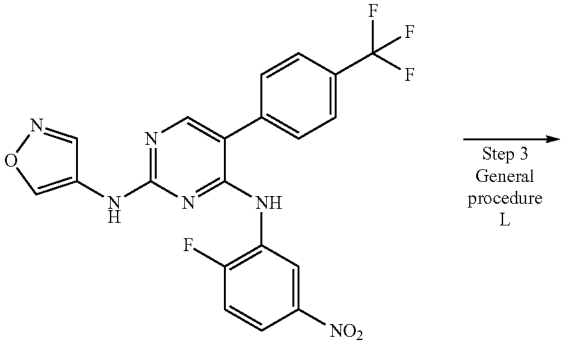

296

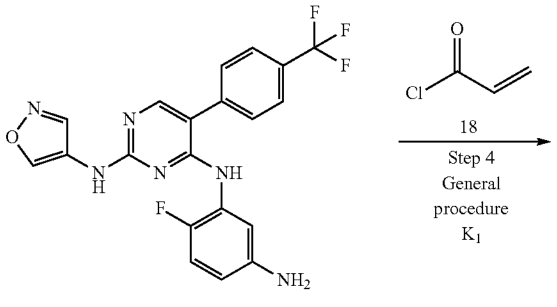

297

-continued

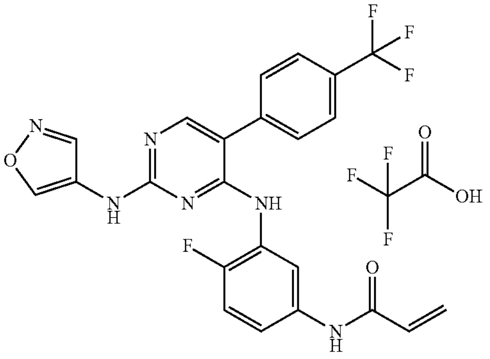

Compound 225

Step 1: Synthesis of 5-bromo-N4-(2-fluoro-5-nitrophenyl)-N2-(1,2-oxazol-4-yl) pyrimidine-2,4-diamine (295)

Title compound was prepared in a manner substantially similar to procedure mentioned in General procedure H, to get the desired compound (295). LCMS $[M+H]^+$ 394.1

Step 2: Synthesis of N4-(2-fluoro-5-nitrophenyl)-N2-(1,2-oxazol-4-yl)-5-[4-(trifluoromethyl)phenyl] pyrimidine-2,4-diamine (296)

To a stirred solution of 5-bromo-N4-(2-fluoro-5-nitrophenyl)-N2-(1,2-oxazol-4-yl)pyrimidine-2,4-diamine (295) (1.50 g, 3.80 mmol), [4-(trifluoromethyl)phenyl]boronic acid (90) (1.08 g, 5.69 mmol), potassium phosphate tribasic (1.61 g, 7.59 mmol) in 1,4-dioxane (2.00 mL) and water (3 mL) was purged with nitrogen for 15 minutes. Then added XPhos Pd G2 (0.3 g, 0.38 mmol) and the reaction mixture was heated at 100° C. for 16 hours. The progress of the reaction was monitored by TLC and LCMS. The reaction mixture was diluted with water (50 mL) and extracted with ethyl acetate (2×100 mL). The combined organic layer was washed with brine (10 mL), dried over anhydrous sodium sulphate and evaporated under reduced pressure. The crude product was purified by column chromatography using combiflash purifier and was eluted with 30% ethyl acetate in hexane to afford N4-(2-fluoro-5-nitrophenyl)-N2-(1,2-oxazol-4-yl)-5-[4-(trifluoromethyl)phenyl]pyrimidine-2,4-diamine (296) (0.9 g, 1.96 mmol). LCMS $[M+H]^+$ 461

Step 3: Synthesis of N4-(5-amino-2-fluorophenyl)-N2-(1,2-oxazol-4-yl)-5-[4-(trifluoromethyl)phenyl] pyrimidine-2,4-diamine (297)

Title compound was prepared in a manner substantially similar to procedure mentioned in General procedure L, to get the desired compound (297). LCMS $[M+H]^+$ 431.0

Step 4: Synthesis of N-[4-fluoro-3-({2-[(1,2-oxazol-4-yl)amino]-5-[4-(trifluoromethyl)phenyl]pyrimidin-4-yl}amino)phenyl]prop-2-enamide (Compound 225)

Title compound was prepared in a manner substantially similar to procedure mentioned in General procedure $K_1$, to get the desired compound (Compound 225) as pale yellow solid. $^1$H NMR (400 MHz, DMSO-d6): δ 10.2 (s, 1H), 9.61

(s, 1H), 8.86 (s, 1H), 8.41 (s, 1H), 8.15 (s, 2H), 7.08-7.72 (m, 6H), 7.47-7.7.50 (m, 1H), 7.23-7.7.28 (m, 1H), 6.35-6.42 (m, 1H), 6.20 (d, J=4.0 Hz, 1H), 5.73 (d, J=4.0 Hz, 1H); LCMS $[M+H]^+$ 485.1

Scheme 66: Synthesis of N-[4-fluoro-3-({2-[(1-methyl-1H-pyrazol-4-yl)amino]5-(1-methyl-2,5-dihydro-1H-pyrrol-3-yl)pyrimidin-4-yl}amino)phenyl]prop-2-enamide (Compound 324) and N-[4-fluoro-3-({2-[(1-methyl-1H-pyrazol-4-yl)amino]-5-(1-methylpyrrolidin-3-yl)pyrimidin-4-yl}amino)phenyl]prop-2-enamide (Compound 325)

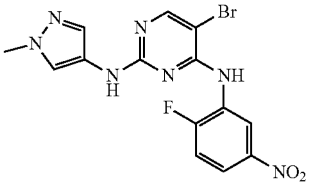

137

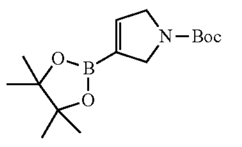

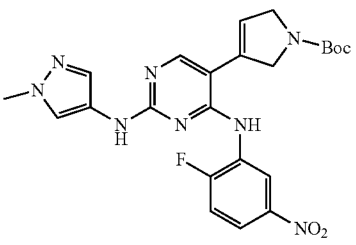

229

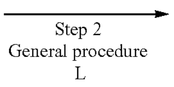

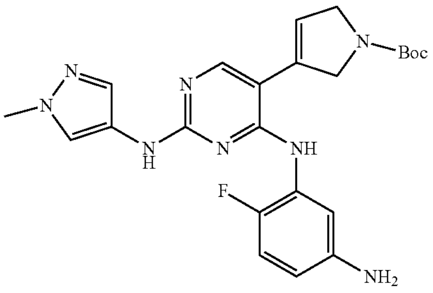

+

300

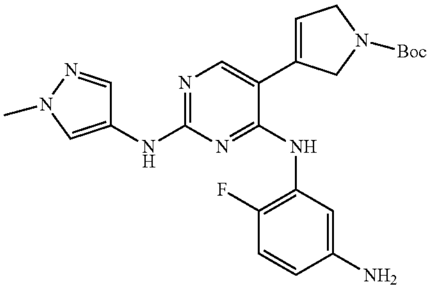

301

-continued

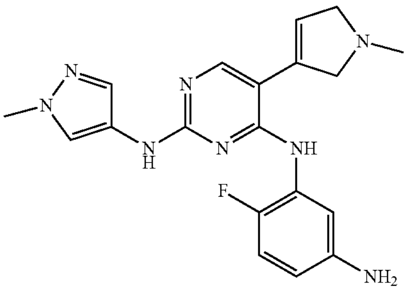

+

302

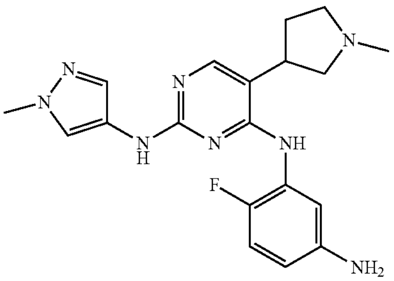

303

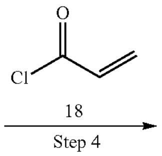

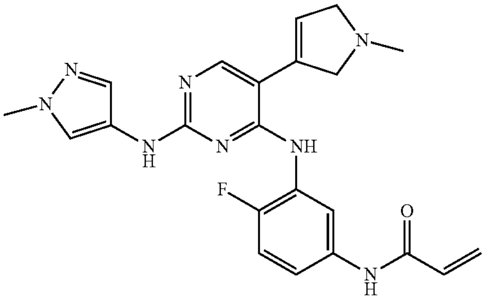

+

Compound 226

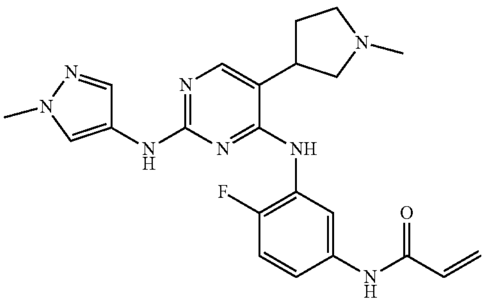

Compound 227

Step 1: Synthesis of tert-butyl 3-{4-[(2-fluoro-5-nitrophenyl)amino]-2-[(1-methyl-1H-pyrazol-4-yl)amino]pyrimidin-5-yl}-2,5-dihydro-1H-pyrrole-1-carboxylate (299)

The title compound was prepared in a manner substantially similar to procedure mentioned in General Procedure $M_1$ to get desired product (299) as brown solid. LCMS $[M+H]^+$ 497.2

Step 2: Synthesis of tert-butyl 3-{4-[(5-amino-2-fluorophenyl)amino]-2-[(1-methyl-1H-pyrazol-4-yl)amino]pyrimidin-5-yl}-2,5-dihydro-1H-pyrrole-1-carboxylate (300) and tert-butyl 3-{4-[(5-amino-2-fluorophenyl)amino]-2-[(1-methyl-1H-pyrazol-4-yl)amino]pyrimidin-5-yl}pyrrolidine-1-carboxylate (301)

The title compound was prepared in a manner substantially similar to procedure mentioned in General Procedure L to get desired products (300 and 301) as brown solid. The mixture of products was directly taken for next step. LCMS $[M+H]^+$ 467.4

Step 3: N4-(5-amino-2-fluorophenyl)-N2-(1-methyl-1H-pyrazol-4-yl)-5-(1-methyl-2,5-dihydro-1H-pyrrol-3-yl)pyrimidine-2,4-diamine (302) and N4-(5-amino-2-fluorophenyl)-N2-(1-methyl-1H-pyrazol-4-yl)-5-(1-methylpyrrolidin-3-yl)pyrimidine-2,4-diamine (303)

To a stirred solution of tert-butyl 3-{4-[(5-amino-2-fluorophenyl)amino]-2-[(1-methyl-1H-pyrazol-4-yl)amino]pyrimidin-5-yl}pyrrolidine-1-carboxylate (343 and 344) (0.3 g, 0.321 mmol) in tetrahydrofuran (5 mL) was added lithium aluminum hydride (1.93 mL, 1.93 mmol) at 0° C. and the reaction mixture was heated at 80° C. for 16 hours. Progress of the reaction was monitored by LCMS. The reaction mixture was cooled to room temperature, quenched with ammonium chloride solution (25 mL) and extracted with dichloromethane (50 mL×2). The combined organic layer was washed with brine (20 mL), dried over anhydrous sodium sulfate and evaporated under reduced pressure to get the desired product as a mixture of two compounds (302 and 303) (0.28 g, crude). The crude product was proceeded to next step. LCMS $[M+H]^+$ 383.2 & 381.2

Step 4: Synthesis of N-[4-fluoro-3-({2-[(1-methyl-1H-pyrazol-4-yl)amino]-5-(1-methyl-2,5-dihydro-1H-pyrrol-3-yl)pyrimidin-4-yl}amino)phenyl]prop-2-enamide (Compound 226) and N-[4-fluoro-3-({2-[(1-methyl-1H-pyrazol-4-yl)amino]-5-(1-methylpyrrolidin-3-yl)pyrimidin-4-yl}amino)phenyl]prop-2-enamide (Compound 227)

The title compound was prepared in a manner substantially similar to procedure mentioned in General Procedure $K_1$ to get desired products (Compound 226 and Compound 227).

Analytical data of Compound 226: $^1H$ NMR (400 MHz, DMSO-d6): δ 10.22 (s, 1H), 9.12 (s, 1H), 8.10 (s, 1H), 7.90 (s, 1H), 7.81 (d, J=4.0 Hz, 1H), 7.62 (s, 1H), 7.33-7.28 (m, 1H), 7.15-6.9 (m, 2H), 6.46-6.39 (m, 1H), 6.28-6.23 (m, 1H), 6.08 (s, 1H), 5.78-5.75 (m, 1H), 3.75 (s, 2H), 3.58-3.54 (m, 5H), 2.45 (s, 3H). LCMS $[M+H]^+$ 435.3

Analytical data of Compound 227: $^1H$ NMR (400 MHz, DMSO-d6): δ 11.01 (s, 1H), 10.14 (s, 1H), 8.74 (s, 1H), 8.10 (s, 1H), 7.80 (s, 1H), 7.60-7.49 (m, 2H), 7.28-7.23 (m, 2H), 6.46-6.39 (m, 1H), 6.27-6.22 (m, 1H), 5.77-5.74 (m, 1H), 3.58 (s, 3H), 3.40-3.36 (m, 2H), 3.14 (t, J=8 Hz, 1H), 2.92-2.89 (m, 1H), 2.37 (s, 3H), 2.34 (s, 1H), 2.33-2.07 (m, 1H), 1.84-1.80 (m, 1H). LCMS $[M+H]^+$ 4

Scheme 67: Synthesis of N-(4-fluoro-3-(methyl(2-((1-methyl-1H-pyrazol-4-yl)amino)-5-(4-(trifluormethyl)phenyl)pyrimidin-4-yl)amino)phenyl)acrylamide (Compound 228)

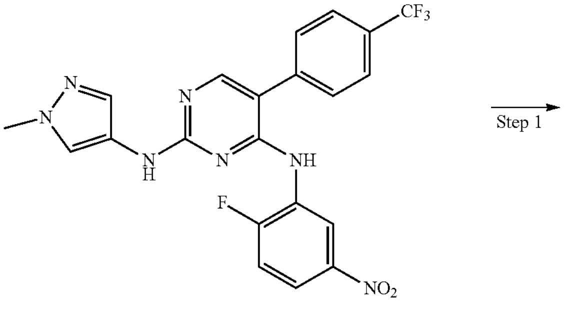

92

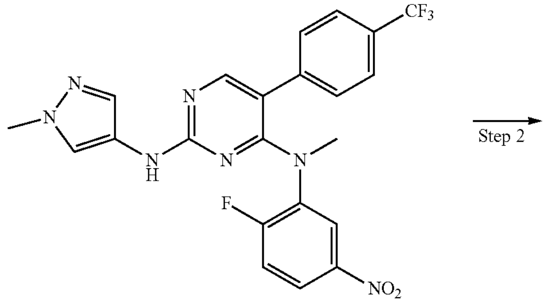

304

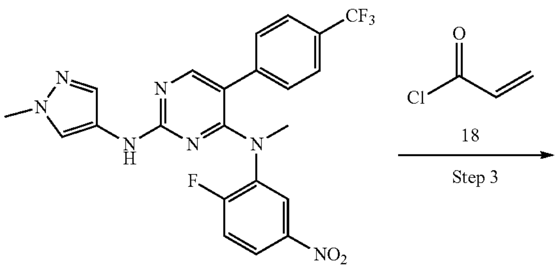

305

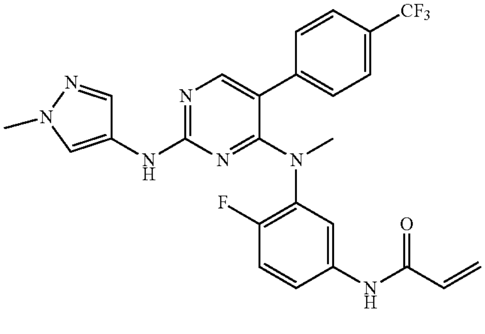

Compound 228

Step 1: Synthesis of N4-(2-fluoro-5-nitrophenyl)-N4-methyl-N2-(1-methyl-1H-pyrazol-4-yl)-5-(4-(trifluoromethyl)phenyl)pyrimidine-2,4-diamine (304)

To a stirred solution of N4-(2-fluoro-5-nitrophenyl)-N2-(1-methyl-1H-pyrazol-4-yl)-5-[4-(trifluoromethyl)phenyl]

pyrimidine-2,4-diamine (92) (2.80 g, 5.91 mmol) in N,N-dimethylformamide (25.0 mL) was added dipotassium carbonate (1.225 g, 8.86 mmol) followed by addition of iodomethane (0.36 mL, 5.91 mmol) drop wise at 0° C. and the reaction mixture was allowed to stirred at room temperature for 16 hours. After completion of reaction (TLC monitoring), reaction mass was diluted with water (50 mL) and extracted with ethyl acetate. The combined organic layer was washed with water, brine, dried over anhydrous sodium sulphate, filtered and concentrated under reduced pressure. The crude was purified flash chromatography eluted with 40% ethyl acetate in hexane to get the N4-(2-fluoro-5-nitrophenyl)-N4-methyl-N2-(1-methyl-1H-pyrazol-4-yl)-5-[4-(trifluoromethyl)phenyl]pyrimidine-2,4-diamine (347) (0.9 g, Yield: 31.25%) as light yellow solid. LCMS $[M+H]^+$ 487.99

Step 2: Synthesis of N4-(5-amino-2-fluorophenyl)-N4-methyl-N2-(1-methyl-1H-pyrazol-4-yl)-5-(4-(trifluoromethyl)phenyl)pyrimidine-2,4-diamine (305)

To a stirred solution of N4-(2-fluoro-5-nitrophenyl)-N4-methyl-N2-(1-methyl-1H-pyrazol-4-yl)-5-[4-(trifluoromethyl)phenyl]pyrimidine-2,4-diamine (347) (0.9 g, 1.85 mmol) in water (8.00 mL) and ethanol (8.00 mL) was added iron (1.03 g, 18.5 mmol) and ammonium chloride (0.988 g, 18.5 mmol). The resulting reaction mixture was heated at 75° C. for 8 hours. After completion of reaction (TLC monitoring), cooled the reaction mass and passed through celite bed, washed with ethyl acetate. The combined filtrates were washed with water, brine, dried over anhydrous sodium sulphate, filtered and concentrated under reduced pressure. The crude was purified by flash chromatography, elution with 5% methanol in dichloromethane to get N4-(5-amino-2-fluorophenyl)-N4-methyl-N2-(1-methyl-1H-pyrazol-4-yl)-5-[4-(trifluoromethyl)phenyl]pyrimidine-2,4-diamine (348) as light brown solid (0.8 g, Yield: 85.24%) LCMS $[M+H]^+$ 458.05

Step 3: Synthesis of N-(4-fluoro-3-(methyl(2-((1-methyl-1H-pyrazol-4-yl)amino)-5-(4-(trifluoromethyl)phenyl)pyrimidin-4-yl)amino)phenyl)acrylamide (Compound 228)

Title compound was prepared in a manner substantially similar to procedure mentioned in General procedure K, to get the desired compound (Compound 228) as an off white solid. $^1$H NMR (400 MHz, DMSO-d6): δ 10.01 (s, 1H), 9.41 (s, 1H), 9.33 (s, 1H), 7.99 (s, 1H), 7.62-7.63 (m, 1H), 7.40-7.48 (m, 4H), 7.26 (m, 1H), 7.16 (m, 1H), 6.87 (m, 1H), 6.30-6.37 (m, 1H), 6.16-6.24 (m, 1H), 5.74 (d, J=9.6 Hz, 1H), 3.85 (s, 3H), 3.30 (s, 3H), LCMS: $[M+H]^+$ 511.98

Scheme 68: Synthesis of N-(4-fluoro-3-((2-((1-methyl-1H-pyrazol-4-yl)amino-5-(thiazol-5-yl)pyrimidin-4-yl)amino)phenyl)acrylamide (Compound 230)

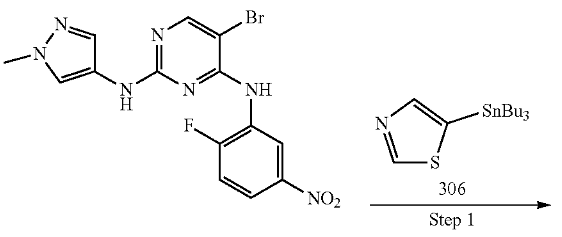

137

-continued

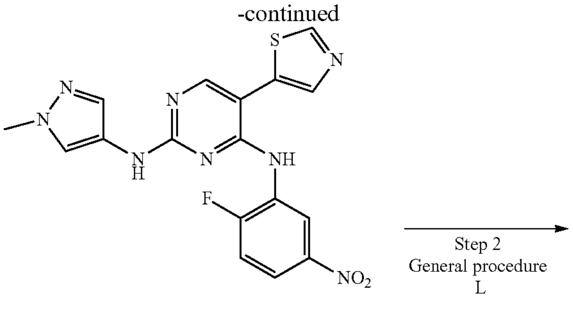

307

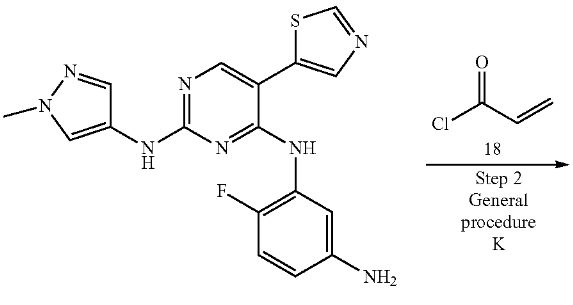

308

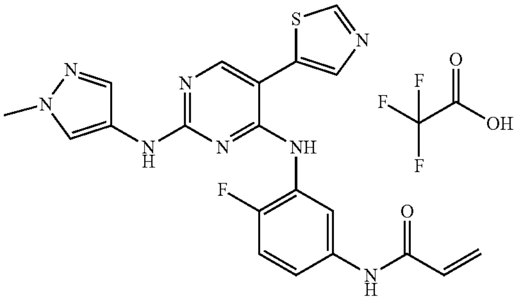

Compound 230

Step 1: Synthesis of N4-(2-fluoro-5-nitrophenyl)-N2-(1-methyl-1H-pyrazol-4-yl)-5-(thiazol-5-yl) pyrimidine-2,4-diamine (307)

To a solution of 5-bromo-N4-(2-fluoro-5-nitrophenyl)-N2-(1-methyl-1H-pyrazol-4-yl)pyrimidine-2,4-diamine (137) (0.4 g, 0.98 mmol) in toluene (8 mL) was added 5-(tributylstannyl)thiazole (349) (0.440 g, 1.18 mmol) and reaction mixture was purged with argon for 15-minutes, added tetrakis(triphenylphosphine)palladium(0) (0.057 g, 0.049 mmol) and the reaction mixture was heated at 100° C. for 16 hours. After completion of reaction mixture (TLC monitoring), the reaction mixture was cooled to room temperature, diluted with water (20 mL) and extracted with ethyl acetate (20 mL×3). The combined organic layer was washed with brine (20 mL), dried over anhydrous sodium sulphate concentrated under reduced pressure. The crude product was purified by flash chromatography eluted with 50% ethyl acetate in hexane to get N4-(2-fluoro-5-nitrophenyl)-N2-(1-methyl-1H-pyrazol-4-yl)-5-(thiazol-5-yl) pyrimidine-2,4-diamine (350) (0.25 g, Yield: 47%), LCMS $[M+H]^+$ 412.97.

Step 2: Synthesis of N4-(5-amino-2-fluorophenyl)-N2-(1-methyl-1H-pyrazol-4-yl)-5-(thiazol-5-yl)pyrimidine-2,4-diamine (308)

The title compound was prepared in a manner substantially similar to procedure mentioned in General Procedure L to get desired product (308) as brown solid. LCMS $[M+H]^+$ 382.99

Step 3: Synthesis of N-(4-fluoro-3-((2-((1-methyl-1H-pyrazol-4-yl)amino)-5-(thiazol-5-yl)pyrimidin-4-yl)amino)phenyl)acrylamide (Compound 230)

The title compound was prepared in a manner substantially similar to procedure mentioned in General Procedure K to get desired product (Compound 230) as off white solid. $^1$H NMR (400 MHz, DMSO-d6): δ 10.33 (s, 1H), 9.96 (s, 1H), 9.24 (s, 2H), 8.06-8.08 (m, 3H), 7.84 (s, 1H), 7.59 (s, 1H), 7.35-7.38 (m, 1H), 7.20 (s, 1H), 7.11 (s, 1H), 6.38-6.44 (m, 1H), 6.22-6.27 (m, 1H), 5.75 (d, J=10.4 Hz, 1H), 3.56 (s, 3H); LCMS $[M+H]^+$ 437.15

Scheme 69: Synthesis of N-(4-fluoro-3-((2-((1-methyl-1H-pyrazol-4-yl)amino)-6-(trifluoromethyl)quinazolin-4-yl)amino)phenyl)acrylamide (Compound 231):

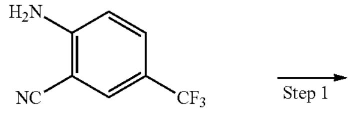

309

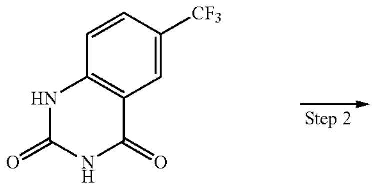

310

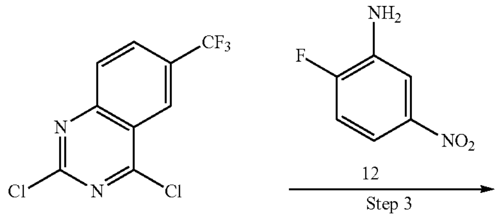

311

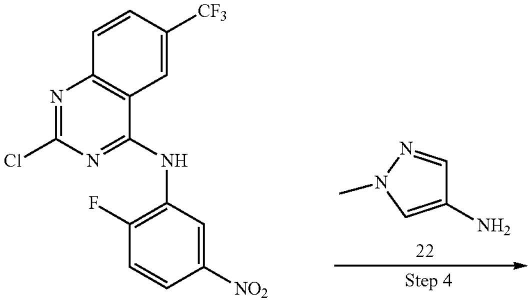

312

-continued

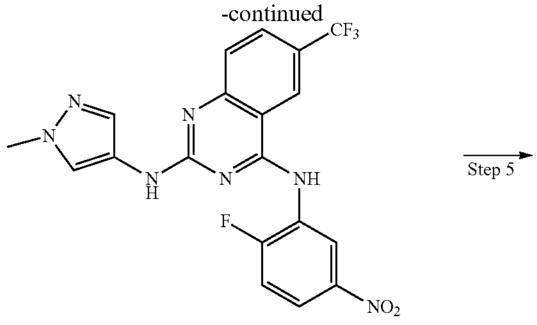

313

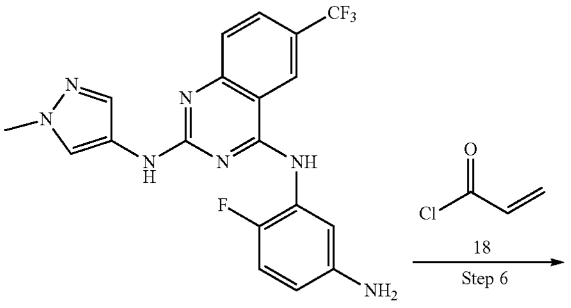

314

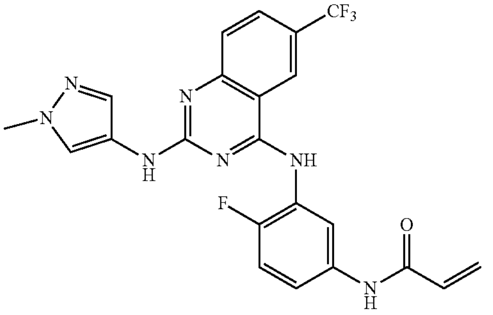

Compound 231

Step 1: Synthesis of 6-(trifluoromethyl)quinazoline-2,4(1H,3H)-dione (310)

To a solution of 2-amino-5-(trifluoromethyl)benzonitrile (309) (10.0 g, 53.7 mmol) in dimethylformamide (100 mL) was added DBU (24.5 g, 161 mmol) under $C_{02}$ atmosphere. The reaction mixture was heated at 100° C. for 16 hours. After completion of reaction (TLC monitoring), the reaction mixture was diluted with water (200 mL), precipitated solid was filtered and washed with cold water (200 mL) and dried under vacuum to get 6-(trifluoromethyl)-1,2,3,4-tetrahydroquinazoline-2,4-dione (310) (12.0 g, Yield: 97.08%) ._LCMS $[M-H]^-$ 228.91

Step 2: Synthesis of 2,4-dichloro-6-(trifluoromethyl)quinazoline (311)

To an ice-cold solution of 6-(trifluoromethyl)-1,2,3,4-tetrahydroquinazoline-2,4-dione (310) (5.00 g, 21.7 mmol) in phosphorus oxychloride (41.6 g, 272 mmol) was added phosphorus pentachloride (22.6 g, 109 mmol). The resultant reaction mixture was heated at 100° C. for 16 hours. After completion of reaction (TLC monitoring), the reaction mixture was concentrated under reduced pressure. The residue was diluted with cold water (100 mL) and extracted with dichloromethane (100 mL×2). The combined organic layer was washed with brine (100 mL), dried over anhydrous sodium sulphate concentrated under reduced pressure. The crude product was purified by using combiflash purifier and was eluted with 1% ethyl acetate in hexane to get 2,4-dichloro-6-(trifluoromethyl)quinazoline (311) (2.2 g, Yield: 37.92%). $^1$H-NMR (400 MHz, $CDCl_3$): δ 8.29 (s, 1H), 8.137-8.09 (m, 1H), 7.78-7.37 (m, 1H).

Step 3: Synthesis of 2-chloro-N-(2-fluoro-5-nitrophenyl)-6-(trifluoromethyl)quinazolin-4-amine (312)

To a solution of 2,4-dichloro-6-(trifluoromethyl)quinazoline (311) (1.50 g, 5.62 mmol) in propan-2-ol (15.0 mL) was added 2-fluoro-5-nitroaniline (12) (0.877 g, 5.62 mmol) at room temperature and the reaction mixture was heated at 100° C. for 16 hours. After completion of reaction (TLC monitoring) the reaction mixture was concentrated under reduced pressure. The crude product was purified by combiflash purifier and was eluted with 40% ethyl acetate in hexane to get the desired product 2-chloro-N-(2-fluoro-5-nitrophenyl)-6-(trifluoromethyl)quinazolin-4-amine (312) (1.2 g, Yield: 55%), LCMS [M+H]$^+$ 386.88.

Step 4: Synthesis of N4-(2-fluoro-5-nitrophenyl)-N2-(1-methyl-1H-pyrazol-4-yl)-6-(trifluoromethyl) quinazoline-2,4-diamine (313)

To a stirred solution of 1-methyl-1H-pyrazol-4-amine (22) (0.362 g, 3.73 mmol), 4-chloro-N-(2-fluoro-5-nitrophenyl)-6-(trifluoromethyl)quinazolin-2-amine (312) (1.2 g, 3.1 mmol) in propan-2-ol (40.0 mL) was added trifluoroacetic acid (1.3 mL, 15.5 mmol) and the reaction mixture was heated at 100° C. for 16 hours. After completion of reaction (monitored by TLC), the reaction mixture was concentrated under reduced pressure. The residue was diluted with water (100 mL) and extracted with dichloromethane (100 mL×2). The combined organic layer was washed with sat. $NaHCO_3$ solution (100 mL), brine (100 mL), dried over anhydrous sodium sulphate and concentrated under reduced pressure. The crude product was purified by combiflash purifier and was eluted with 40% ethyl acetate in hexane to get N4-(2-fluoro-5-nitrophenyl)-N2-(1-methyl-1H-pyrazol-4-yl)-6-(trifluoromethyl)quinazoline-2,4-diamine (313) (1.0 g, Yield: 76%). LCMS [M+H]$^+$ 447.96

Step 5: Synthesis of N4-(5-amino-2-fluorophenyl)-N2-(1-methyl-1H-pyrazol-4-yl)-6-(trifluoromethyl) quinazoline-2,4-diamine (314)

The title compound was prepared in a manner substantially similar to procedure mentioned in General Procedure L to get desired product (314) as brown solid. LCMS [M+H]$^+$ 418.01

Step 6: Synthesis of N-(4-fluoro-3-((2-((1-methyl-1H-pyrazol-4-yl)amino)-6-(trifluoromethyl)quinazolin-4-yl)amino)phenyl)acrylamide (Compound 231)

The title compound was prepared in a manner substantially similar to procedure mentioned in General Procedure K to get desired product (Compound 231) as off white solid. $^1$H NMR (400 MHz, DMSO-d6): δ 10.27 (bs, 1H), 9.87 (bs, 1H), 9.47 (bs, 1H), 8.72 (s, 1H), 7.86 (bs, 2H), 7.31-7.69 (m, 4H), 7.07-7.13 (m, 1H), 6.40-6.46 (m, 1H), 6.24-6.29 (m, 1H), 5.76 (d, J=10.0 Hz, 1H), 3.53 (s, 3H); LCMS [M+H]$^+$ 471.94

Scheme 70: Synthesis of N-(4-fluoro-3-((2-(pyridin-3-ylamino)-5-(4-(trifluoromethyl)phenyl)pyrimidin-4-yl)amino)phenyl)acrylamide (Compound 232)

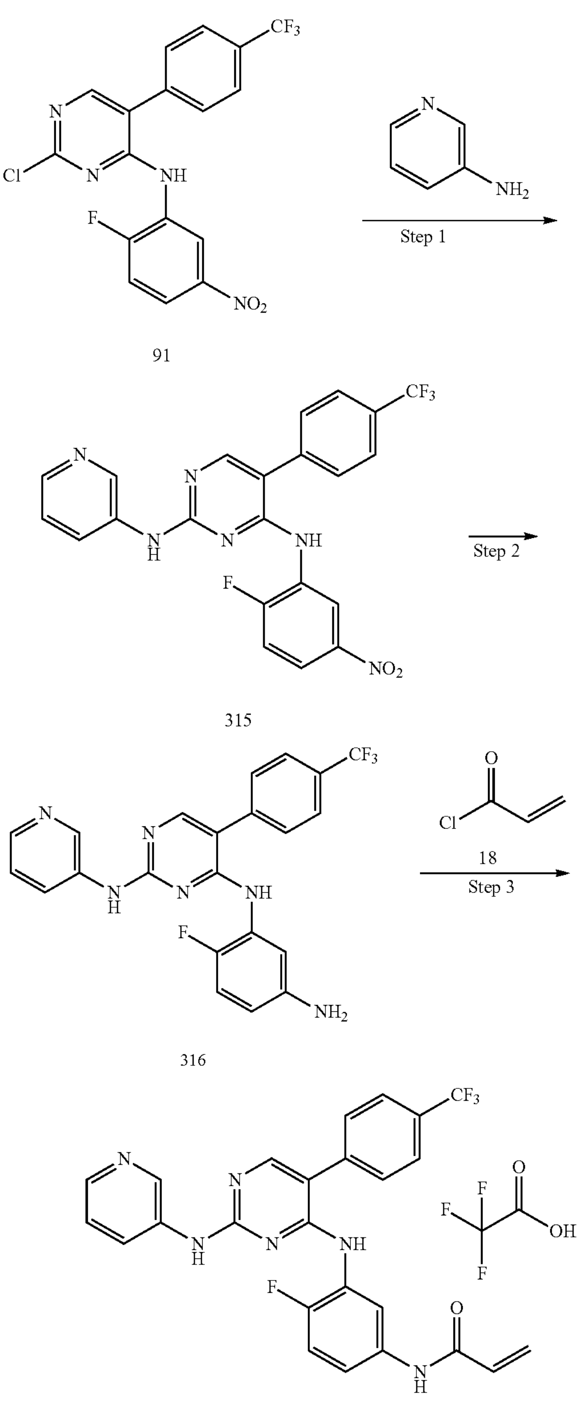

Step 1: Synthesis of N4-(2-fluoro-5-nitrophenyl)-N2-(pyridin-3-yl)-5-[4-(trifluoromethyl)phenyl]pyrimidine-2,4-diamine (315)

To a stirred solution of 2-chloro-N-(2-fluoro-5-nitrophenyl)-5-[4-(trifluoromethyl)phenyl]pyrimidin-4-amine (91) (0.50 g, 1.21 mmol) in butan-2-ol (5.00 mL) was added pyridin-3-amine (0.137 g, 1.45 mmol), potassium carbonate (0.837 g, 6.06 mmol) and the reaction mixture was purged with nitrogen for 10 minutes. Then added tris(dibenzylideneacetone)dipalladium(0) (0.11 g, 0.121 mmol) and stirred at 100° C. for 16 hours. After completion of reaction (TLC monitoring), the reaction mixture was diluted with water (50 mL) and extracted with ethyl acetate (3×150 mL). The combined organic layer was washed with brine (25 mL), dried over anhydrous sodium sulphate, filtered and concentrated under reduced pressure. The crude product was purified by flash chromatography using 5% methanol in dichloromethane as eluent to afford N4-(2-fluoro-5-nitrophenyl)-N2-(pyridin-3-yl)-5-[4-(trifluoromethyl)phenyl]pyrimidine-2,4-diamine (315) (0.2 g, 28%) as off white solid. LCMS $[M+H]^+$ 470.97

Step 2: Synthesis of N4-(5-amino-2-fluorophenyl)-N2-(pyridin-3-yl)-5-[4-(trifluoromethyl)phenyl]pyrimidine-2,4-diamine (316)

The title compound was prepared in a manner substantially similar to procedure mentioned in General Procedure L to get desired product (316) as brown solid. LCMS $[M+H]^+$ 440.96

Step 3: Synthesis of N-(4-fluoro-3-((2-(pyridin-3-ylamino)-5-(4-(trifluoromethyl)phenyl)pyrimidin-4-yl)amino)phenyl)acrylamide (Compound 232)

The title compound was prepared in a manner substantially similar to procedure mentioned in General Procedure K, to afford the desired compound (Compound 232), after prep-HPLC purification as off white solid. $^1H$ NMR (400 MHz, DMSO-d6): δ 10.21 (s, 1H), 10.07 (s, 1H), 8.89 (s, 1H), 8.84 (s, 1H), 8.36-8.42 (m, 1H), 8.28 (d, J=5.20 Hz, 1H), 8.14 (s, 1H), 7.84-7.86 (m, 2H), 7.74-7.80 (m, 3H), 7.48-7.53 (m, 3H), 7.27-7.31 (m, 1H), 6.36-6.43 (m, 1H), 6.20-6.25 (m, 1H), 5.76 (d, J=10.0 Hz, 1H). LCMS $[M+H]^+$ 494.97

Scheme 71: Synthesis of N-[3-({2-[(3-chloro-1-methyl-1H-pyrazol-4-yl)amino]-5-[4-(trifluoromethyl)phenyl]pyrimidin-4-yl}oxy)phenyl]prop-2-enamide (Compound 233)

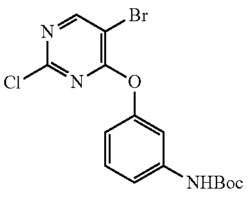

234

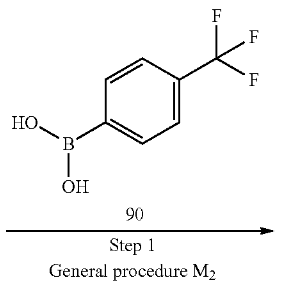

-continued

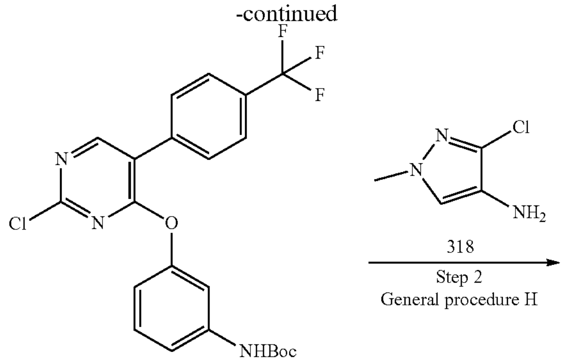

317

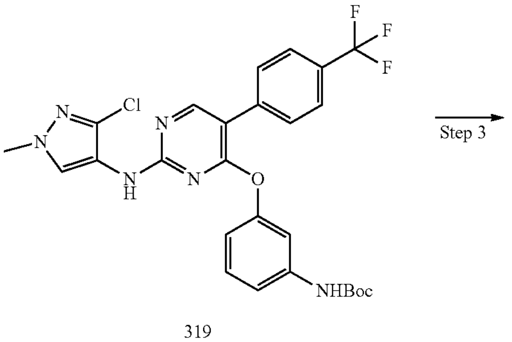

319

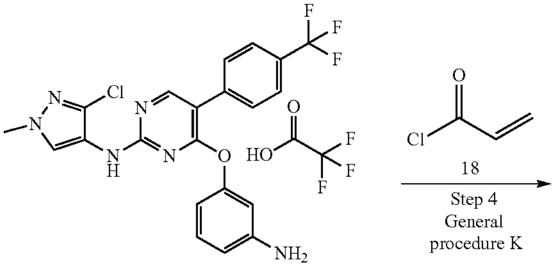

320

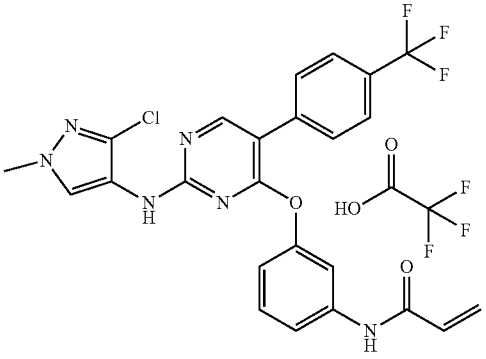

Compound 233

Step 1: Synthesis of tert-butyl (3-((2-chloro-5-(4-(trifluoromethyl)phenyl)pyrimidin-4-yl)oxy)phenyl) carbamate (317)

The title compound was prepared in a manner substantially similar to procedure mentioned in General Procedure $M_2$, to afford the desired compound (317) as yellow solid. LCMS $[M+H]^+$ 466.1

Step 2: Synthesis of tert-butyl N-[3-({2-[(3-chloro-1-methyl-1H-pyrazol-4-yl) amino]-5-[4-(trifluoromethyl) phenyl] pyrimidin-4-yl} oxy) phenyl] carbamate (319)

The title compound was prepared in a manner substantially similar to procedure mentioned in General Procedure H, to afford the desired compound (319) as red solid. LCMS $[M+H]^+$ 561.2

Step 3: Synthesis of 4-(3-aminophenoxy)-N-(3-chloro-1-methyl-1H-pyrazol-4-yl)-5-[4-(trifluoromethyl) phenyl] pyrimidin-2-amine (320)

The title compound was prepared in a manner substantially similar to procedure mentioned in General Procedure I, to afford the desired compound (320) as yellow gummy material. LCMS $[M+H]^+$ 461.1

Step 4: Synthesis of N-[3-({2-[(3-chloro-1-methyl-1H-pyrazol-4-yl) amino]-5-[4-(trifluoromethyl) phenyl] pyrimidin-4-yl} oxy) phenyl] prop-2-enamide (Compound 233)

The title compound was prepared in a manner substantially similar to procedure mentioned in General Procedure K, to afford the desired compound (Compound 233) as off white solid. $^1$H NMR (400 MHz, DMSO-d6) δ 10.33 (s, 1H), 9.37 (bs, 1H), 8.52 (bs, 1H), 7.96-7.79 (m, 5H), 7.65 (s, 1H), 7.55-7.45 (m, 2H), 7.02 (d, J=8.0 Hz, 2H), 6.44-6.37 (m, 1H), 6.24 (dd, J=17.2 Hz, 1.6 Hz, 1H), 5.76 (dd, J=10.0 Hz, 2.0 Hz, 1H), 3.51 (bs, 3H). LCMS $[M+H]^+$ 515.1.

TABLE 17

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 229 | 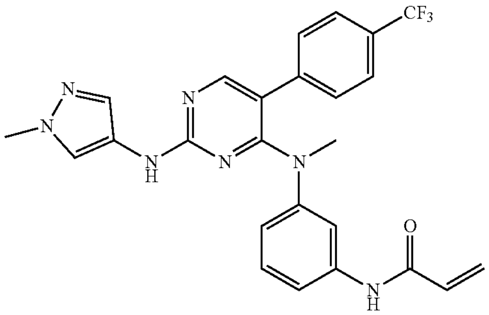 [SMILES: C=CC(=O)Nc1cccc(N(C)c2nc(Nc3cnn(C)c3)ncc2-c2ccc(C(F)(F)F)cc2)c1] | K | 494.18 | δ 9.90 (s, 1H), 9.38 (s, 1H), 7.98 (s, 1H), 7.70-7.72 (m, 1H), 7.50 (s, 1H), 7.24-7.36 (m, 5H), 7.06 (bs, 1H), 6.97-7.00 (m, 1H), 6.68 (bs, 1H), 6.31-6.43 (m, 1H), 6.19-6.25 (m, 1H), 5.74 (d, J = 11.2 Hz, 1H), 3.77 (s, 3H), 3.41 (s, 3H) |
| 234 | 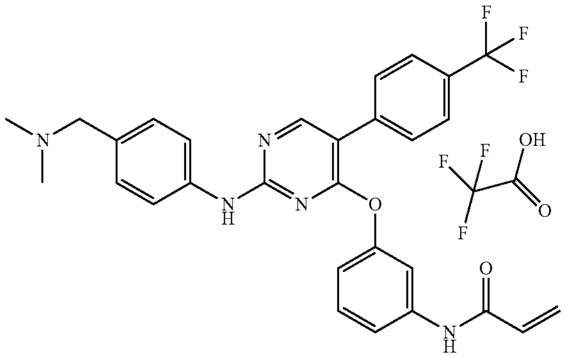 | J | 534.17 | δ 10.34 (s, 1H), 9.99 (bs, 1H), 9.64 (bs, 1H), 8.64 (s, 1H), 7.86-7.97 (m, 2H), 7.60-7.78 (m, 2H), 7.44-7.66 (m, 4H), 6.99-7.25 (m, 5H), 6.40-6.47 (m, 1H), 6.24 (dd, J = 18.8 Hz, 1.6 Hz, 1H), 4.13 (s, 2H), 2.79 (s, 6H). |
| 235 | 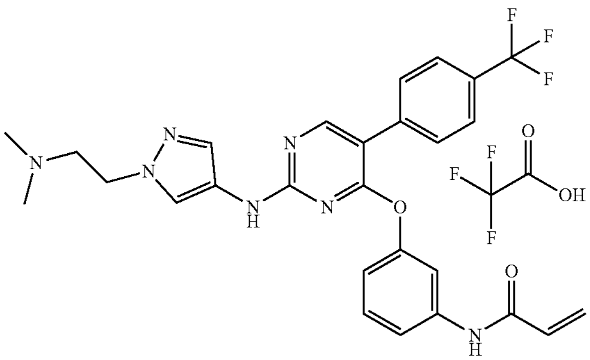 | K | 538.2 | At 90° C., δ 9.98 (s, 1H), 9.44 (bs, 1H), 8.52 (bs, 1H), 7.91 (d, J = 8.0 Hz, 2H), 7.79 (d, J = 8.0 Hz, 2H), 7.63-7.52 (m, 2H), 7.48-7.45 (m, 3H), 7.03-6.90 (m, 2H), 6.47-6.40 (m, 1H), 6.29-6.25 (m, 1H), 5.76 (d, J = 12.0 Hz, 1H), 4.32-4.29 (m, 2H), 3.49-3.46 (m, 2H), 2.81 (s, 6H). |

TABLE 17-continued

The following compounds were prepared using the procedures described above:

| Cmpd. No. | Structure | General Procedure | LCMS [M + H] | $^1$H-NMR (400 MHz, DMSO-$d_6$) |
| --- | --- | --- | --- | --- |
| 236 | 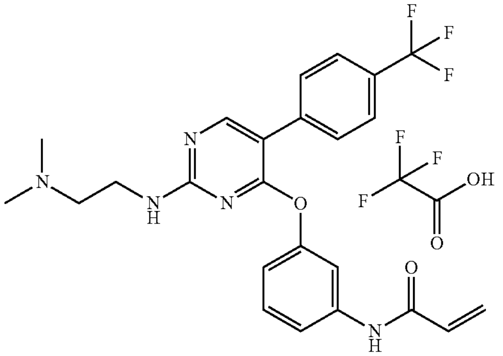 | J | 472.2 | δ 8.45 (d, J = 9.2 Hz, 1H), 7.78-7.90 (m, 5H), 7.09-7.22 (m, 1H), 6.41-6.63 (m, 4H), 5.98-6.05 (m, 1H), 5.54-5.64 (m, 1H), 4.07 (s, 2H), 3.42-3.63 (m, 3H), 3.03-3.17 (m, 3H), 2.86 (s, 2H). 2 NH protons were merging in moisture peak. |
| 237 | 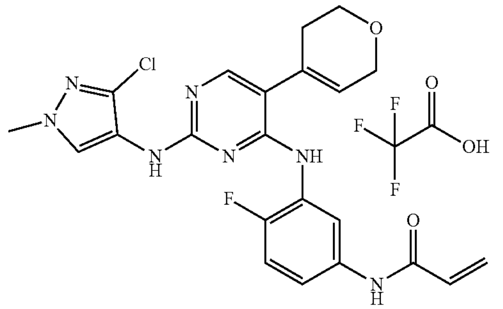 | $K_2$ | 470.2 | δ 10.30 (s, 1H), 9.32 (bs, 1H), 7.90-7.85 (m, 2H), 7.60-7.57 (m, 1H), 7.35-6.93 (m, 2H), 6.46-6.40 (m, 1H), 6.27 (dd, J = 16.8 Hz, 1.6 Hz, 1H), 6.46-6.40 (m, 1H), 6.27 (dd, J = 16.8 Hz, 1.6 Hz, 1H), 6.02 (s, 1H), 5.70 (dd, J = 10.0 Hz, 2.0 Hz, 1H), 4.20 (m, 2H), 3.87-3.78 (m, 2H), 3.63 (bs, 3H), 2.30 (m, 2H). |
| 238 | 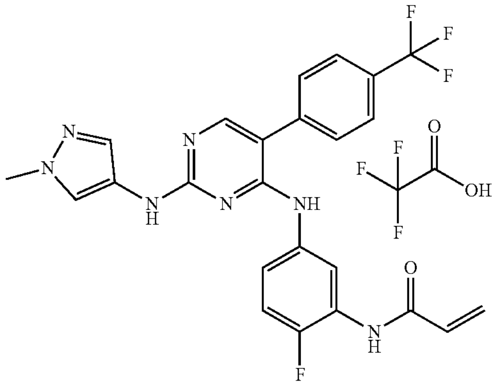 | $K_2$ | 498.2 | δ 10.03 (s, 1H), 9.88 (bs, 1H), 9.35 (bs, 1H), 8.11 (s, 1H), 7.94-7.92 (m, 1H), 7.84-7.82 (m, 3H), 7.73 (d, J = 8.0 Hz, 2H), 7.33 (bs, 3H), 7.10 (bs, 1H), 6.63-6.59 (m, 1H), 6.25-6.20 (m, 1H), 5.76 (d, J = 12.0 Hz, 1H), 3.62 (s, 3H) |
| 239 | 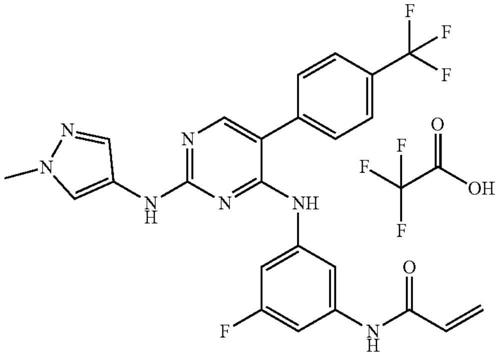 | $K_2$ | 498.1 | δ 10.35 (s, 1H), 9.87 (bs, 1H), 9.30 (bs, 1H), 8.02 (s, 1H), 7.85 (d, J = 8.4 Hz, 2H), 7.73 (d, J = 7.6 Hz, 2H), 7.54 (bs, 2H), 7.41 (bs, 2H), 7.15-6.90 (m, 2H), 6.45-6.39 (m, 1H), 6.29-6.24 (m, 1H), 5.81-5.78 (m, 1H), 3.67 (s, 3H). |

Scheme 72: Synthesis of N-(4-fluoro-3-((2-((1-(2-hydroxy-2-methylpropyl)-1H-pyrazol-4-yl)amino)-5-(4-(trifluoromethyl)phenyl)pyrimidin-4-yl)amino)phenyl)acrylamide (Compound 240)

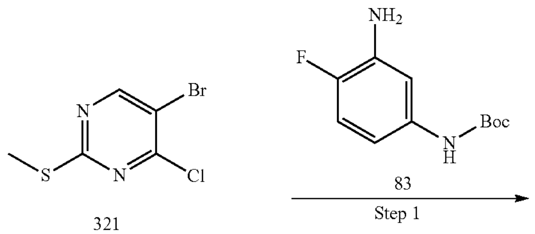

321

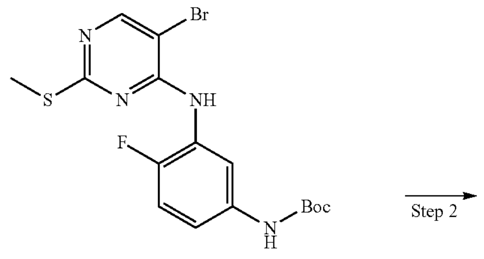

322

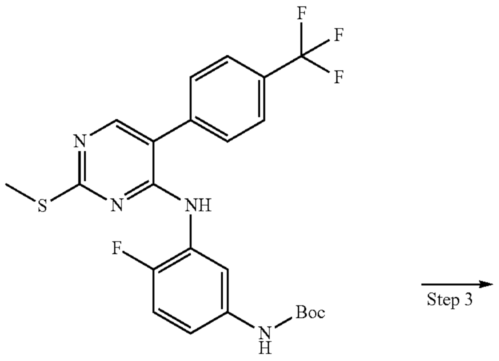

323

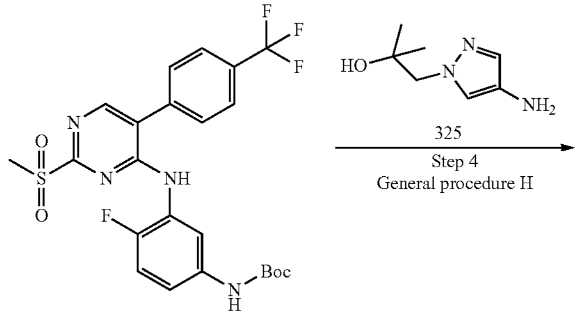

324

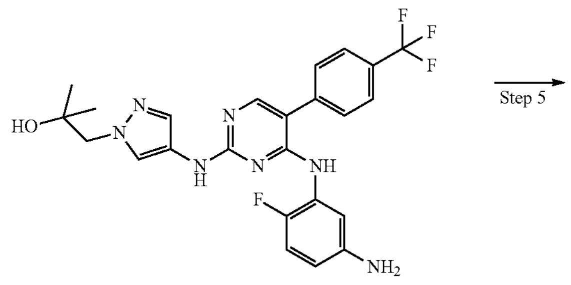

327

-continued

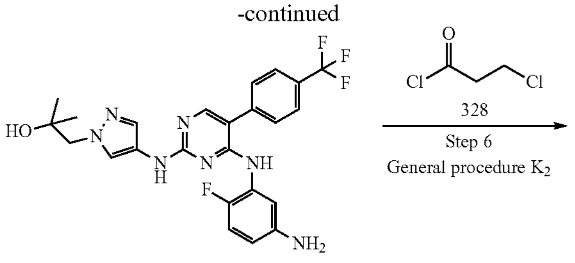

327

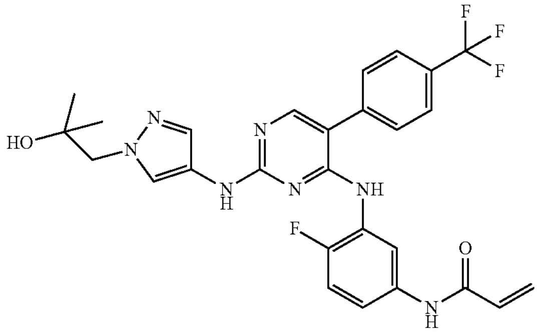

Compound 240

Step 1: Synthesis of tert-butyl (3-((5-bromo-2-(methylthio)pyrimidin-4-yl)amino)-4-fluorophenyl) carbamate (322)

To a stirred solution of tert-butyl N-(3-amino-4-fluorophenyl)carbamate (83) (9.45 g, 41.8 mmol) in tetrahydrofuran (300 mL) at 0° C. sodium hydride (8.35 g, 209 mmol) was added in a portion wise and stirred for 30 minutes. Then added 5-bromo-4-chloro-2-(methylsulfanyl)pyrimidine (321) (10.0 g, 41.8 mmol) and the reaction mixture was stirred at room temperature for 16 hours. The reaction was monitored by TLC and LCMS. Then the reaction mixture was quenched with ice cold water (300 mL) and extracted with ethyl acetate (100 mL×2). The combined organic layer was washed with brine (50 mL), dried over anhydrous sodium sulfate and concentrated. The crude product was washed with 10% diethyl ether in pentane (150 ml) and dried to get desired product (322) as pale brown solid (12.0 g, 67%). LCMS $[M+H]^+$ 429.1

Step 2: Synthesis of tert-butyl (4-fluoro-3-((2-(methylthio)-5-(4-(trifluoromethyl)phenyl)pyrimidin-4-yl)amino)phenyl)carbamate (323)

The title compound was prepared in a manner substantially similar to procedure mentioned in General Procedure $M_2$, to afford the desired compound (323) as off white solid. LCMS $[M+H]^+$ 495.1

Step 3: Synthesis of tert-butyl (4-fluoro-3-((2-(methylsulfonyl)-5-(4-(trifluoromethyl)phenyl)pyrimidin-4-yl)amino)phenyl)carbamate (324)

To a stirred solution of tert-butyl N-(4-fluoro-3-{[2-(methylsulfanyl)-5-[4-(trifluoromethyl)phenyl]pyrimidin-4-yl]amino}phenyl)carbamate (323) (1.20 g, 2.43 mmol) in dichloromethane (100 mL) at 0° C. was added 3-chlorobenzene-1-carboperoxoic acid (1.67 g, 9.71 mmol) in portion wise and the reaction mixture was stirred at 0° C. for 30 min. Progress of the reaction monitored by TLC and LCMS. The reaction mixture was filtered and the filtrate was quenched with sodium bicarbonate solution (100 mL) and extracted with dichloromethane (20 mL×3). The combined organic layer washed with brine (25 mL), dried over anhydrous sodium sulfate and evaporated under reduced pressure. The crude product was washed with diethyl ether (50 mL) and dried to get the title compound (324) as brown solid (0.6 g, crude). LCMS $[M+H]^+$ 527.0

Step 4: Synthesis of tert-butyl (4-fluoro-3-((2-((1-(2-hydroxy-2-methylpropyl)-1H-pyrazol-4-yl)amino)-5-(4-(trifluoromethyl)phenyl)pyrimidin-4-yl)amino)phenyl)carbamate (326)

The title compound was prepared in a manner substantially similar to procedure mentioned in General Procedure H, to afford the desired compound (326) as off white solid. LCMS $[M+H]^+$ 602.2

Step 5: Synthesis of 1-(4-((4-((5-amino-2-fluorophenyl)amino)-5-(4-(trifluoromethyl)phenyl)pyrimidin-2-yl)amino)-1H-pyrazol-1-yl)-2-methylpropan-2-ol (327)

To stirred solution of tert-butyl N-{4-fluoro-3-[(2-{[1-(2-hydroxy-2-methylpropyl)-1H-pyrazol-4-yl]amino}-5-[4-(trifluoromethyl)phenyl]pyrimidin-4-yl)amino]phenyl}carbamate (326) (0.15 g, 0.249 mmol) in dichloromethane (5.00 mL) was added hydrochloric acid in 1,4-dioxane (1.0 mL, 4M) and the reaction was stirred at room temperature for 4 hours. Progress of the reaction was monitored by TLC and LC-MS. The reaction mixture was evaporated to get 1-[4-({4-[(5-amino-2-fluorophenyl)amino]-5-[4-(trifluoromethyl)phenyl]pyrimidin-2-yl}amino)-1H-pyrazol-1-yl]-2-methylpropan-2-ol (327) (0.15 g, crude). LCMS $[M+H]^+$ 502.2

Step 6: Synthesis of N-(4-fluoro-3-((2-((1-(2-hydroxy-2-methylpropyl)-1H-pyrazol-4-yl)amino)-5-(4-(trifluoromethyl)phenyl)pyrimidin-4-yl)amino)phenyl)acrylamide (Compound 240)

The title compound was prepared in a manner substantially similar to procedure mentioned in General Procedure $K_2$, to afford the desired compound (Compound 240) as white solid. $^1H$ NMR (400 MHz, DMSO-d6): δ 10.18 (s, 1H), 9.22 (bs, 1H), 8.74 (bs, 1H), 8.00 (s, 1H), 7.81-7.71 (m, 5H), 7.55 (bs, 1H), 7.26 (s, 3H), 6.44-6.38 (m, 1H), 6.26-6.22 (m, 1H), 5.76-5.73 (m, 1H), 4.49 (s, 1H), 3.71 (s, 2H), 0.96 (s, 6H). LCMS $[M+H]^+$ 556.2

Scheme 73: Synthesis of N-{4-fluoro-3-[(2-{[1-($^2H_3$)methyl-1H-pyrazol-4-yl]amino}-5-[4-(trifluoromethyl)phenyl]pyrimidin-4-yl)amino]phenyl}prop-2-enamide (Compound 242)

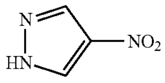

9

Step 4

-continued

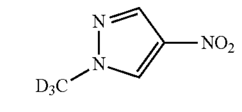

329

Step 2
General procedure $L_1$

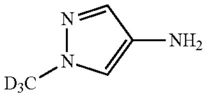

330

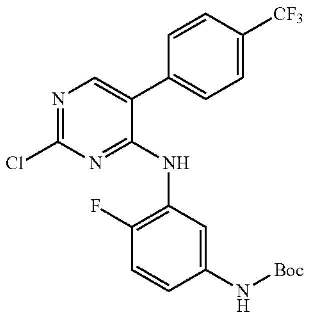

275

Step 3
General procedure H

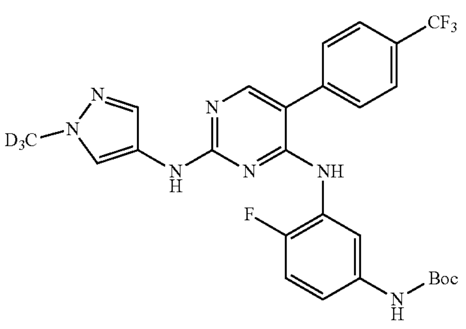

331

Step 4

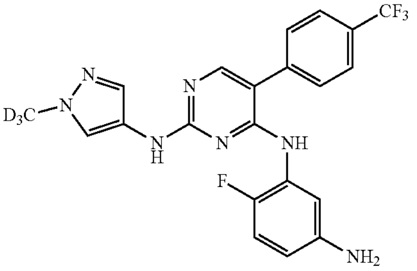

332

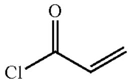

18

Step 4
General procedure $K_1$

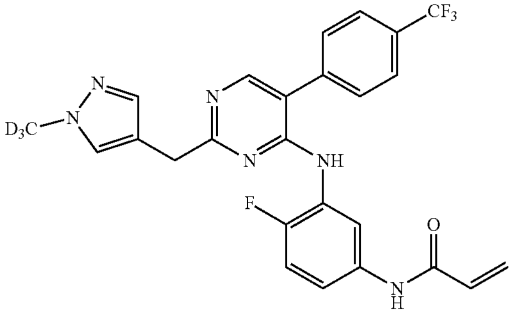

Compound 242

Step 1: Synthesis of 1-($^2H_3$)methyl-4-nitro-1H-pyrazole (329)

To a stirred solution of 4-nitro-1H-pyrazole (9) (0.2 g, 1.77 mmol) in tetrahydrofuran (5 mL) at 0° C. was added sodium hydride (0.1 g, 2.65 mmol) in portion wise and stirred for 30 minutes. Then added iodo ($^2H_3$)methane (0.122 mL, 1.95 mmol) and the reaction mass stirred for 3.5 hours at room temperature. Progress of the reaction monitored by TLC and LCMS. The reaction was quenched with water (20 mL) and extracted with ethyl acetate (20 mL×2). The combined organic layer was washed with brine (20 mL), dried over anhydrous sodium sulfate and concentrated to get the desired product (329) as yellow solid (0.23 g, 99%). LCMS $[M+H]^+$ 131.0

Step 2: Synthesis of 1-($^2H_3$)methyl-1H-pyrazol-4-amine (330)

The title compound was prepared in a manner substantially similar to procedure mentioned in General Procedure L, to afford the desired compound (330) as brown solid. The crude product was directly taken for next step Step 3: tert-butyl N-{4-fluoro-3-[(2-{[1-($^2H_3$)methyl-1H-pyrazol-4-yl]amino}-5-[4-(trifluoromethyl)phenyl]pyrimidin-4-yl)amino]phenyl}carbamate (331)

The title compound was prepared in a manner substantially similar to procedure mentioned in General Procedure H, to afford the desired compound (331) as off white solid. LCMS $[M+H]^+$ 547.2.

Step 4: N4-(5-amino-2-fluorophenyl)-N2-[1-($^2H_3$)methyl-1H-pyrazol-4-yl]-5-[4-(trifluoromethyl)phenyl]pyrimidine-2,4-diamine (332)

The title compound was prepared in a manner substantially similar to procedure mentioned in General Procedure I, to afford the desired compound (332) as brown solid. LCMS $[M+H]^+$ 447.3

Step 5: N-{4-fluoro-3-[(2-{[1-($^2H_3$)methyl-1H-pyrazol-4-yl]amino}-5-[4-(trifluoromethyl)phenyl]pyrimidin-4-yl)amino]phenyl}prop-2-enamide (Compound 242)

The title compound was prepared in a manner substantially similar to procedure mentioned in General Procedure $K_1$, to afford the desired compound (Compound 242) as white solid. $^1H$ NMR (400 MHz, DMSO-d6): δ 10.21 (s, 1H), 9.22 (bs, 1H), 8.51 (bs, 1H), 7.99 (s, 1H), 7.82-7.72 (m, 5H), 7.58 (bs, 1H), 7.18-7.10 (m, 3H), 6.45-6.38 (m, 1H), 6.27-6.22 (m, 1H), 5.77-5.74 (m, 1H). LCMS $[M+H]^+$ 501.2

Scheme 74: Synthesis of N-(3-{[5-(2-cyclopropylethynyl)-2-[(1-methyl-1H-pyrazol-4-yl)amino]pyrimidin-4-yl]amino}-4-fluorophenyl)prop-2-enamide (Compound 244)

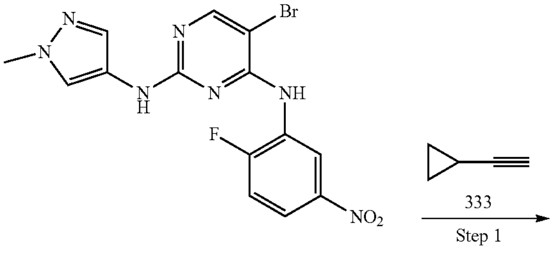

137

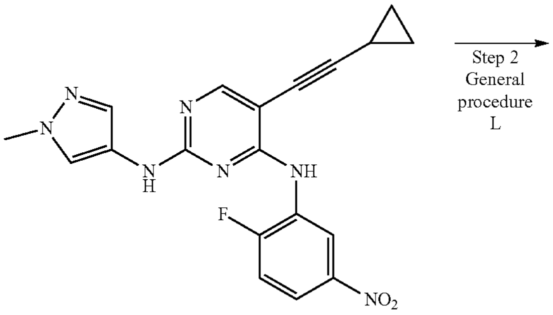

334

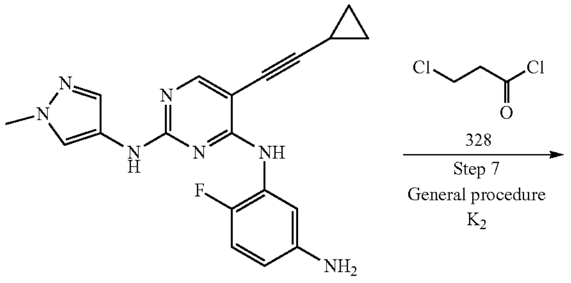

335

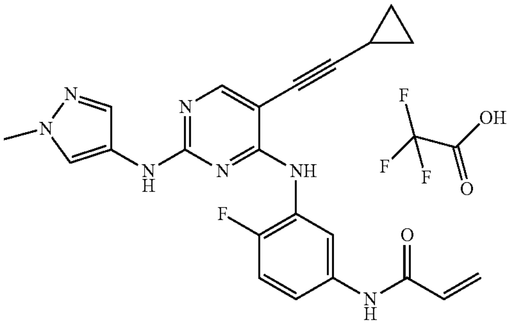

Compound 244

Step 1: Preparation of 5-(2-cyclopropylethynyl)-N4-(2-fluoro-5-nitrophenyl)-N2-(1-methyl-1H-pyrazol-4-yl)pyrimidine-2,4-diamine (334)

To a stirred solution of 5-bromo-N4-(2-fluoro-5-nitrophenyl)-N2-(1-methyl-1H-pyrazol-4-yl)pyrimidine-2,4-diamine (137) (0.3 g, 0.735 mmol), triethylamine (0.2 mL, 1.47 mmol) in N,N-dimethylformamide (10.0 mL) was purged with nitrogen for 10 minutes, added bis(triphenylphosphine)palladium(II) dichloride (51.6 mg, 0.073 mmol) and ethynylcyclopropane (333) (0.102 g, 1.54 mmol). The reaction mixture was heated at 100° C. for 16 hours in a sealed tube. Reaction was monitored by LCMS and TLC. The reaction mixture was diluted with water (20 mL) and extracted with ethyl acetate (2×20 mL). The combined organic layer was washed with brine (20 mL), dried over anhydrous sodium sulphate, and evaporated under reduced pressure. The crude product was purified by column chromatography using combiflash purifier and was eluted with 65% ethyl acetate in hexane to get 5-(2-cyclopropylethynyl)-N4-(2-fluoro-5-nitrophenyl)-N2-(1-methyl-1H-pyrazol-4-yl)pyrimidine-2,4-diamine (334) (0.25 g, 636 μmol) as gummy brown solid. LCMS $[M+H]^+$ 394.4

Step 2: Preparation of N4-(5-amino-2-fluorophenyl)-5-(2-cyclopropylethynyl)-N2-(1-methyl-1H-pyrazol-4-yl)pyrimidine-2,4-diamine (335)

The title compound was prepared in a manner substantially similar to procedure mentioned in General Procedure L, to afford the desired compound (335) as red solid. LCMS $[M+H]^+$ 364.4

Step 3: Preparation of N-(3-{[5-(2-cyclopropylethynyl)-2-[(1-methyl-1H-pyrazol-4-yl)amino]pyrimidin-4-yl]amino}-4-fluorophenyl)prop-2-enamide (Compound 244)

The title compound was prepared in a manner substantially similar to procedure mentioned in General Procedure $K_2$, to afford the desired compound (Compound 244) as red solid. $^1$H NMR (400 MHz, DMSO-d6): δ 10.48 (s, 1H), 9.59 (bs, 1H), 8.62 (bs, 1H), 8.08-8.06 (m, 1H), 7.83-7.80 (m, 3H), 7.57-7.39 (m, 1H), 7.30-6.90 (m, 1H), 6.46-6.42 (m, 1H), 6.31-6.27 (m, 2H), 5.82-5.80 (m, 1H), 3.70 (s, 3H), 1.67-1.63 (m, 1H), 0.88-0.83 (m, 2H), 0.79-0.70 (m, 2H). LCMS $[M+H]^+$ 418.2

Scheme 75: Synthesis of N-[3-({2-[(3-chloro-1-methyl-1H-pyrazol-4-yl)amino]-5-[4-(trifluoromethyl)phenyl]pyrimidin-4-yl}amino)4-fluorophenyl]prop-2-enamide (Compound 245)

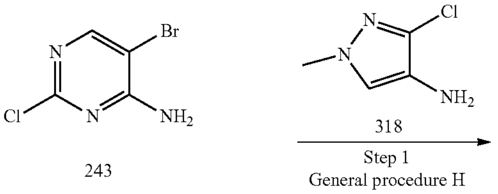

243

318

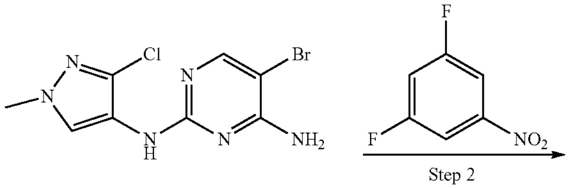

337

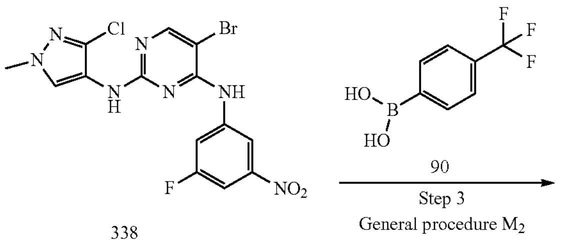

338

90

-continued

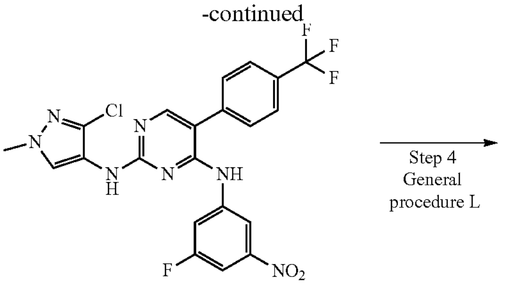

339

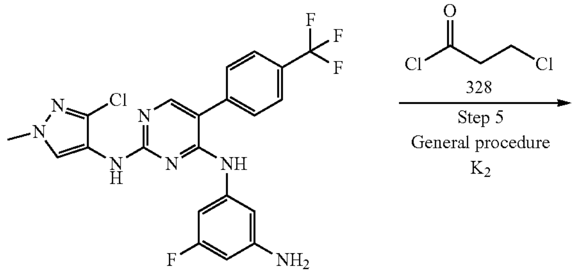

340

328

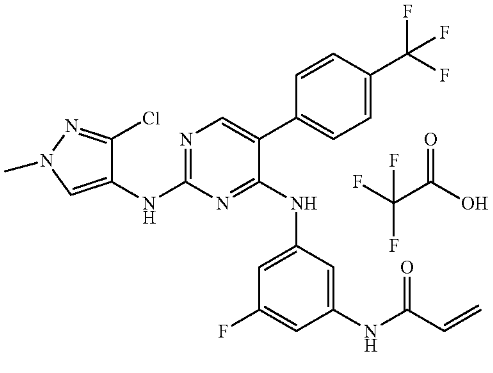

Compound 245

Step 1: Synthesis of 5-bromo-N2-(3-chloro-1-methyl-1H-pyrazol-4-yl)pyrimidine-2,4-diamine (337)

The title compound was prepared in a manner substantially similar to procedure mentioned in General Procedure H, to afford the desired compound (337) as off white solid. LCMS $[M+H]^+$ 302.6

Step 2: Synthesis of 5-bromo-N2-(3-chloro-1-methyl-1H-pyrazol-4-yl)-N4-(3-fluoro-5-nitrophenyl)pyrimidine-2,4-diamine (338)

To a stirred solution of 5-bromo-N2-(3-chloro-1-methyl-1H-pyrazol-4-yl)pyrimidine-2,4-diamine (337) (0.6 g, 1.98 mmol) in N,N-dimethylformamide (5.00 mL), were added 1,3-difluoro-5-nitrobenzene (0.377 g, 2.37 mmol), potassium carbonate (1.37 g, 9.88 mmol) and stirred at 100° C. for 16 hours. The progress of the reaction was monitored by LCMS. After 16 h reaction mixture was diluted with water (20 mL) and extracted with ethyl acetate (3×20 mL). The combined organic layer was washed with brine (60 mL), dried over anhydrous sodium sulfate and evaporated under the vacuum. The crude product was purified by column purification using combiflash purifier and was eluted with 50% ethyl acetate in hexane to get 5-bromo-N2-(3-chloro-1-methyl-1H-pyrazol-4-yl)-N4-(3-fluoro-5-nitrophenyl)pyrimidine-2,4-diamine (338) (0.2 g, 0.452 mmol) as pale yellow solid. LCMS $[M+H]^+$ 466.4

Step 3: Synthesis of N4-(5-amino-2-fluorophenyl)-N2-(3-chloro-1-methyl-1H-pyrazol-4-yl)-5-[4-(trifluoromethyl)phenyl]pyrimidine-2,4-diamine (339)

The title compound was prepared in a manner substantially similar to procedure mentioned in General Procedure $M_2$, to afford the desired compound (339) as off white solid. LCMS $[M+H]^+$ 508.4

Step 4: Preparation Of N4-(5-amino-2-fluorophenyl)-N2-(3-chloro-1-methyl-1H-pyrazol-4-yl)-5-[4-(trifluoromethyl)phenyl]pyrimidine-2,4-diamine (340)

The title compound was prepared in a manner substantially similar to procedure mentioned in General Procedure L, to afford the desired compound (340) as pale yellow solid. LCMS $[M+H]^+$ 478.4

Step 5: Preparation Of N-[3-({2-[(3-chloro-1-methyl-1H-pyrazol-4-yl)amino]-5-[4-(trifluoromethyl)phenyl]pyrimidin-4-yl}amino)-4-fluorophenyl]prop-2-enamide (Compound 245)

The title compound was prepared in a manner substantially similar to procedure mentioned in General Procedure $K_2$, to afford the desired compound (Compound 245) as pale yellow solid. $^1H$ NMR (400 MHz, DMSO-d6): δ 10.26 (s, 1H), 9.10 (bs, 2H), 8.01 (bs, 1H), 7.85-7.83 (m, 3H), 7.73-7.70 (m, 2H), 7.50 (bs, 1H), 7.34-7.32 (m, 3H), 6.45-6.38 (m, 1H), 6.29-6.24 (m, 1H), 5.80-5.77 (m, 1H), 3.74 (s, 3H). LCMS $[M+H]^+$ 532.2

Scheme 76: Synthesis of N-(3-((2-((1-2-cyanopropan-2-yl)-1H-pyrazol-4-yl)amino)-5-(4-(trifluoromethyl)phenyl)pyrmidin-4-yl)amino)4-fluorophenyl)acrylamide (Compound 347)

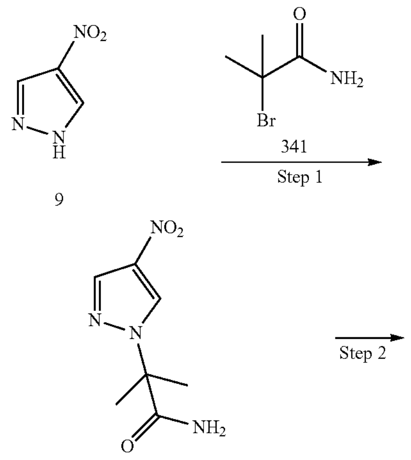

9 341 342

-continued

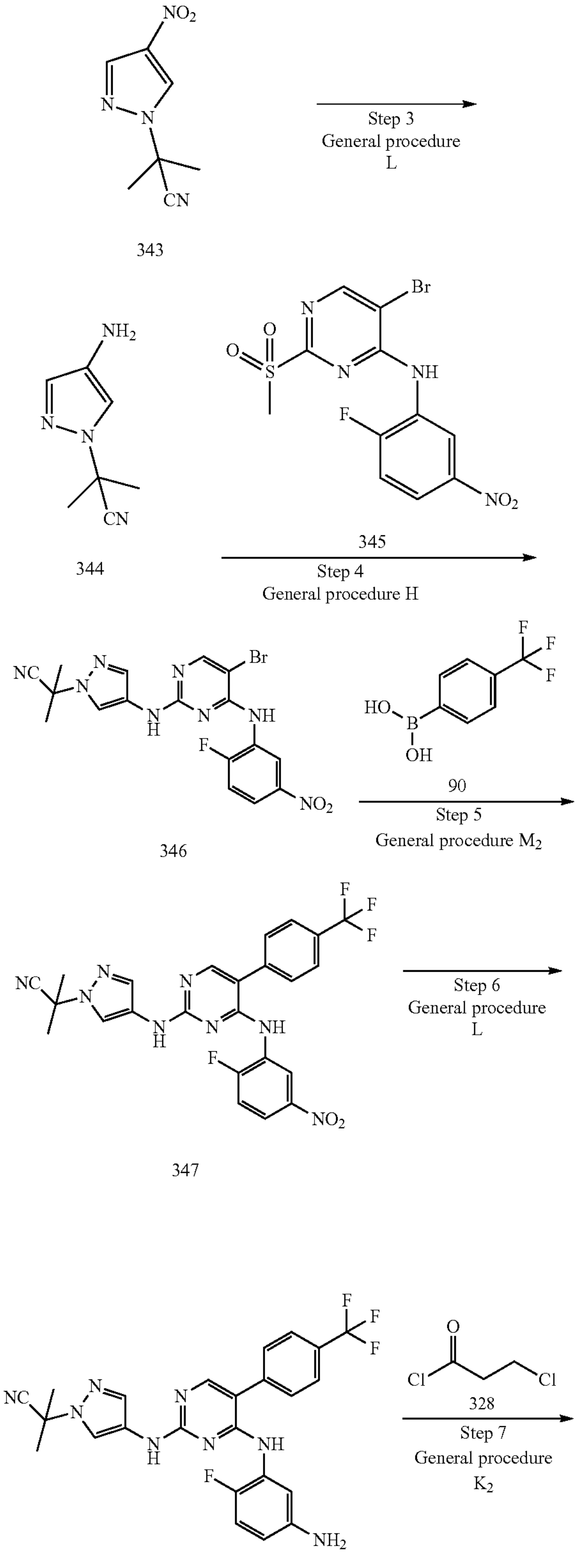

343 344 345 346 90 347 348 328

-continued

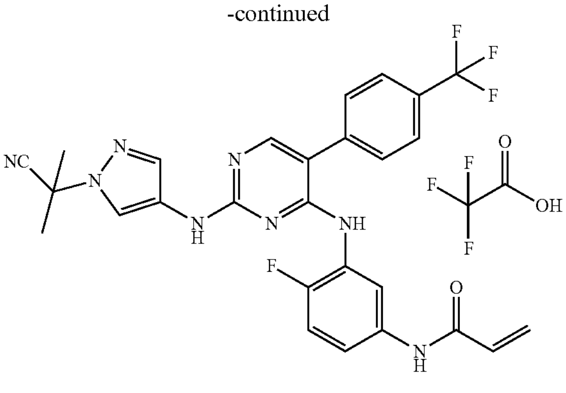

Compound 246

Step 1: Synthesis of 2-methyl-2-(4-nitro-1H-pyrazol-1-yl)propanamide (342)

To a stirred solution of 4-nitro-1H-pyrazole (9) (2.00 g, 17.7 mmol) and 2-bromo-2-methylpropanamide (341) (3.23 g, 19.5 mmol) in N,N-dimethylformamide (15.0 mL) was added potassium carbonate (2.69 g, 19.5 mmol) and the reaction mixture was heated at 60° C. for 20 hours. The reaction mixture was cooled, diluted with 1N sodium hydroxide solution (50 mL) and extracted with ethyl acetate (20 mL×3). The combined organic layer was washed with water (50 mL), brine (50 mL), dried over anhydrous sodium sulfate and evaporated. The residue was washed with ether (50 mL) and dried to get the title compound (342) as white solid (2.4 g, 68%). LCMS $[M+H]^+$ 199.1

Step 2: Synthesis of 2-methyl-2-(4-nitro-1H-pyrazol-1-yl)propanenitrile (343)

To a stirred solution of 2-methyl-2-(4-nitro-1H-pyrazol-1-yl)propanamide (342) (0.5 g, 2.52 mmol) in phosphoryl trichloride (7.00 mL) was heated at 90° C. for 2 hours. The reaction mixture was cooled and evaporated. The residue was diluted with cold water (10 mL) and extracted with ethyl acetate (10 mL×3). The combined organic layer was washed with brine (10 mL), dried over anhydrous sodium sulfate and evaporated. The crude product was purified by column chromatography using combiflash purifier and was eluted with 30% ethyl acetate in hexane to get the title compound (343) as colourless liquid (0.42 g, 85%). $^1$H NMR (400 MHz, $CDCl_3$): δ 8.45 (s, 1H), 8.19 (s, 1H), 2.06 (s, 6H).

Step 3: Synthesis of 2-(4-amino-1H-pyrazol-1-yl)-2-methylpropanenitrile (344)

The title compound was prepared in a manner substantially similar to procedure mentioned in General Procedure L, to afford the desired compound (344) as brown solid. LCMS $[M+H]^+$ 151.1

Step 4: Synthesis of 2-(4-((5-bromo-4-((2-fluoro-5-nitrophenyl)amino)pyrimidin-2-yl)amino)-1H-pyrazol-1-yl)-2-methylpropanenitrile (346)

The title compound was prepared in a manner substantially similar to procedure mentioned in General Procedure H, to afford the desired compound (346) as off white solid. LCMS $[M+H]^+$ 461.0

Step 5: Synthesis of 2-(4-((4-((2-fluoro-5-nitrophenyl)amino)-5-(4-(trifluoromethyl)phenyl)pyrimidin-2-yl)amino)-1H-pyrazol-1-yl)-2-methylpropanenitrile (347)

The title compound was prepared in a manner substantially similar to procedure mentioned in General Procedure $M_1$, to afford the desired compound (347) as off white solid. LCMS $[M+H]^+$ 527.1

Step 6: Synthesis of 2-(4-((4-((5-amino-2-fluorophenyl)amino)-5-(4-(trifluoromethyl)phenyl)pyrimidin-2-yl)amino)-1H-pyrazol-1-yl)-2-methylpropanenitrile (348)

The title compound was prepared in a manner substantially similar to procedure mentioned in General Procedure L, to afford the desired compound (348) as brown solid. LCMS $[M+H]^+$ 497.2

Step 7: Synthesis of N-(3-((2-((1-(2-cyanopropan-2-yl)-1H-pyrazol-4-yl)amino)-5-(4-(trifluoromethyl)phenyl)pyrimidin-4-yl)amino)-4-fluorophenyl)acrylamide (Compound 246)

The title compound was prepared in a manner substantially similar to procedure mentioned in General Procedure $K_2$, to afford the desired compound (Compound 246) as off white solid. $^1$H NMR (400 MHz, DMSO-d6): δ 10.22 (s, 1H), 9.75 (bs, 1H), 8.97 (bs, 1H), 8.00 (s, 1H), 7.83-7.70 (m, 5H), 7.49 (bs, 4H), 7.28-7.23 (m, 1H), 6.41-6.34 (m, 1H), 6.24-6.19 (m, 1H), 5.74-5.71 (m, 1H), 1.72 (s, 6H); LCMS $[M+H]^+$ 551.2

Scheme 77: Synthesis of N-[4-fluoro-3-({2-[(1-methyl-1H-pyrazol-4-yl) amino]-5-[4-(trifluoromethyl) phenyl] pyrimidin-4-yl} amino) phenyl] (3,3-$^2H_2$) prop-2-enamide (Compound 247)

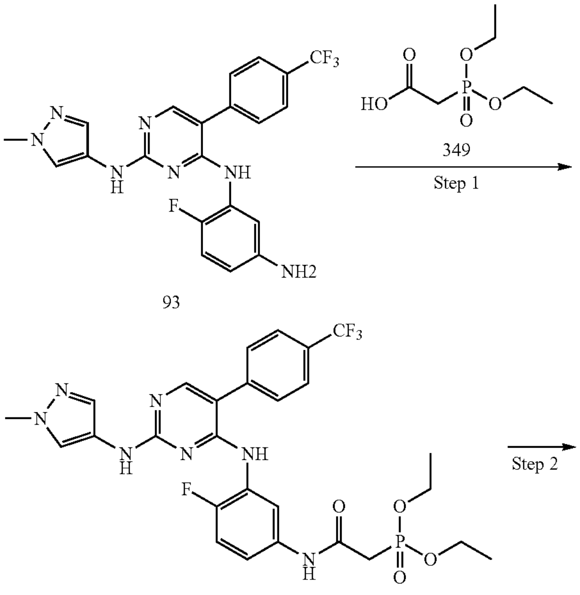

93

349

350

-continued

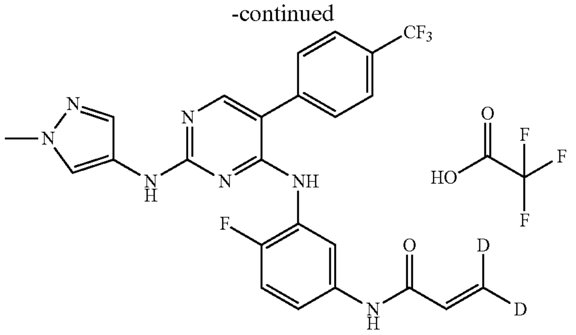

Compound 247

Step 1: Synthesis of diethyl ({[4-fluoro-3-({2-[(1-methyl-1H-pyrazol-4-yl) amino]-5-[4-(trifluoromethyl) phenyl] pyrimidin-4-yl} amino) phenyl] carbamoyl} methyl) phosphonate (350)

To a solution of N4-(5-amino-2-fluorophenyl)-N2-(1-methyl-1H-pyrazol-4-yl)-5-[4-(trifluoromethyl) phenyl] pyrimidine-2,4-diamine (93) (0.5 g, 1.13 mmol) in tetrahydrofuran (5.00 mL) was added N,N-diisopropylethylamine (0.189 g, 1.47 mmol), 2-(diethoxyphosphoryl) acetic acid (349) (0.243 g, 1.24 mmol) followed by HATU (0.557 g, 1.47 mmol) and stirred at room temperature for 4 hours. The reaction was monitored by LCMS and TLC. The reaction mixture was diluted with water (20 mL) and extracted with ethyl acetate (2×10 mL). The combined organic layer was washed with brine (20 mL), dried over anhydrous sodium sulphate, filtered and evaporated under reduced pressure to give diethyl ({[4-fluoro-3-({2-[(1-methyl-1H-pyrazol-4-yl) amino]-5-[4-(trifluoromethyl) phenyl] pyrimidin-4-yl} amino) phenyl] carbamoyl}methyl) phosphonate (350) (0.52 g, 74%). LCMS $[M+H]^+$ 621.5

Step 2: Synthesis of N-[4-fluoro-3-({2-[(1-methyl-1H-pyrazol-4-yl) amino]-5-[4-(trifluoromethyl) phenyl] pyrimidin-4-yl} amino) phenyl] (3,3-2H2) prop-2-enamide (Compound 247)

To a solution of diethyl ({[4-fluoro-3-({2-[(1-methyl-1H-pyrazol-4-yl) amino]-5-[4-(trifluoromethyl) phenyl] pyrimidin-4-yl} amino) phenyl] carbamoyl} methyl) phosphonate (350) (0.5 g, 0.804 mmol) in tetrahydrofuran (4.00 mL), water (0.8 mL) was added lithium hydroxide (0.023 g, 0.965 mmol) followed by potassium hydroxide (0.099 g, 1.77 mmol) and paraformaldehyde-d2 (0.0077 g, 0.241 mmol) and stirred at room temperature for 4 hours. Reaction was monitored by LCMS and TLC. The reaction mixture was diluted with water (10 mL) and extracted with ethyl acetate (2×20 mL). The combined organic layer was dried over anhydrous sodium sulphate and evaporated under reduced pressure. The crude product was purified by preparative HPLC to afford N-[4-fluoro-3-({2-[(1-methyl-1H-pyrazol-4-yl) amino]-5-[4-(trifluoromethyl) phenyl] pyrimidin-4-yl} amino) phenyl] (3,3-$^2$H2) prop-2-enamide (Compound 247) (30.0 mg, 7%) as a white solid. $^1$H NMR (400 MHz, DMSO-d6): δ 10.29 (s, 1H), 9.97 (bs, 1H), 9.30 (bs, 1H), 8.00 (s, 1H), 7.86-7.84 (m, 3H), 7.73-7.73 (m, 2H), 7.56 (s, 1H), 7.35 (s, 1H), 7.20-7.10 (m, 3H), 6.38 (s, 1H), 3.55 (s, 3H); LCMS $[M+H]^+$ 500.5

TABLE 18

The following compounds were prepared using the procedures described above:

| Cmpd. No. | Structure | LCMS [M + H] | $^1$H-NMR (400 MHz, DMSO-$d_6$) |
|---|---|---|---|
| 243 | 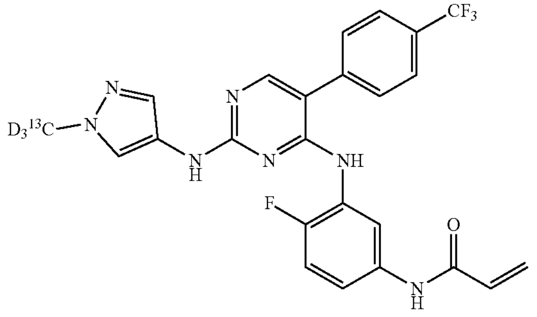 | 502.2 | δ 10.29 (s, 1H), 10.01 (bs, 1H), 9.34 (bs, 1H), 8.00 (bs, 1H), 7.86-7.73 (m, 5H), 7.56 (bs, 1H), 7.35-7.10 (m, 3H), 6.43-6.36 (m, 1H), 6.25-6.20 (m, 1H), 5.76-5.73 (m, 1H). |
| 241 | 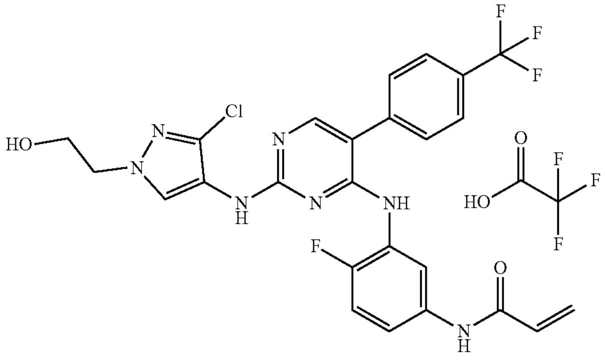 [SMILES: C=CC(=O)Nc1ccc(F)c(Nc2nc(Nc3cn(CCO)nc3Cl)ncc2-c2ccc(C(F)(F)F)cc2)c1 ; O=C(O)C(F)(F)F] | 562.1 | δ 10.19 (s, 1H), 9.01-8.93 (m, 2H), 8.00 (s, 1H), 7.86-7.84 (m, 4H), 7.75-7.73 (m, 2H), 7.53-7.51 (m, 1H), 7.30-7.26 (m, 3H), 6.38-6.45 (m, 1H), 6.25 (dd, J = 17.2.0 Hz, 1.8 Hz, 1H), 5.76 (dd, J = 10.0 Hz, 1.8 Hz, 1H), 3.89 (bs, 2H), 3.62 (bs, 2H). |

TABLE 18-continued

The following compounds were prepared using the procedures described above:

| Cmpd. No. | Structure | LCMS [M + H] | $^1$H-NMR (400 MHz, DMSO-$d_6$) |
|---|---|---|---|
| 248 | 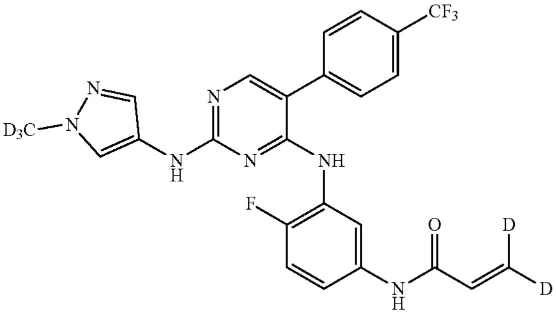 [SMILES: [2H]C([2H])=CC(=O)Nc1ccc(F)c(Nc2nc(Nc3cnn(C([2H])([2H])[2H])c3)ncc2-c2ccc(C(F)(F)F)cc2)c1] | 503.2 | δ 10.21 (s, 1H), 9.30 (bs, 1H), 8.60 (bs, 1H), 7.99 (s, 1H), 7.82-7.80 (m, 2H), 7.88-7.72 (m, 3H), 7.58 (s, 1H), 7.35-7.30 (m, 1H), 7.20-7.19 (m, 1H), 7.10-7.08 (m, 1H), 6.40 (s, 1H). |
| 249 | 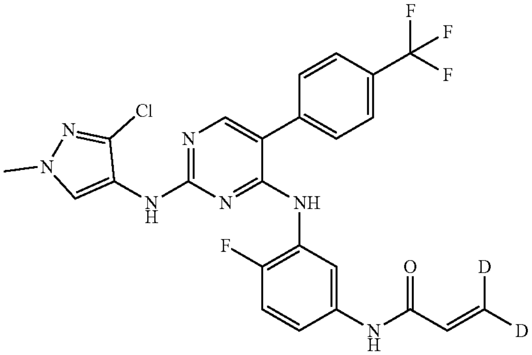 [SMILES: [2H]C([2H])=CC(=O)Nc1ccc(F)c(Nc2nc(Nc3cn(C)nc3Cl)ncc2-c2ccc(C(F)(F)F)cc2)c1] | 534.1 | δ 10.16 (s, 1H), 8.49 (bs, 1H), 8.01 (s, 1H), 7.82-7.71 (m, 5H), 7.55-7.53 (m, 2H), 7.29-7.25 (m, 2H), 6.40 (s, 1H), 3.59 (s, 3H). |
| 250 | 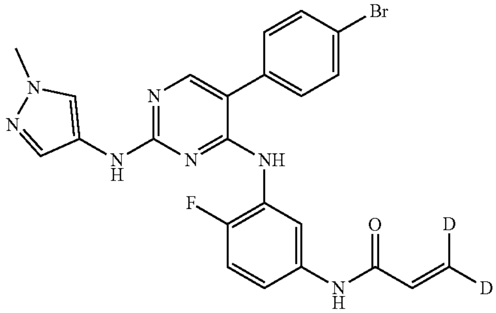 [SMILES: [2H]C([2H])=CC(=O)Nc1ccc(F)c(Nc2nc(Nc3cnn(C)c3)ncc2-c2ccc(Br)cc2)c1] | 510.1 | δ 10.20 (s, 1H), 9.17 (bs, 1H), 8.37 (bs, 1H), 7.89 (s, 1H), 7.74-7.72 (m, 1H), 7.63 (d, J = 8.8 Hz, 2H), 7.55 (bs, 1H), 7.43 (d, J = 8.4 Hz, 2H), 7.27 (bs, 1H), 7.14-7.07 (m, 2H), 6.38 (s, 1H), 3.52 (s, 3H) |

Scheme 78: Synthesis of N-(4-fluoro-3-((2-((1-methyl-1H-pyrazol-4-yl)amino)-5-(4-(trifluoromethyl)phenyl)pyrimidin-4-yl)amino)phenyl)buta-2,3-dienamide (Compound 251)

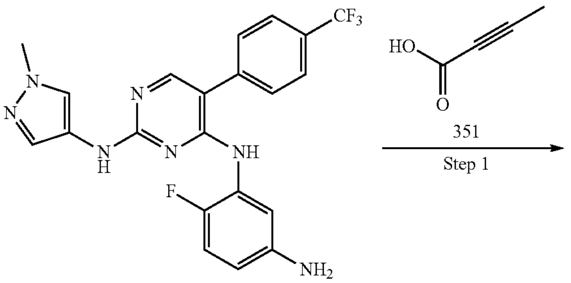

93

-continued

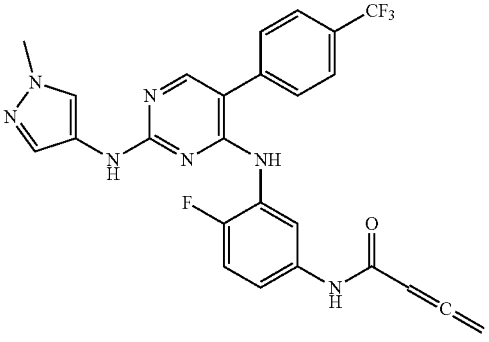

Compound 251

Step 1: Synthesis of N-(4-fluoro-3-((2-((1-methyl-1H-pyrazol-4-yl)amino)-5-(4-(trifluoromethyl)phenyl)pyrimidin-4-yl)amino)phenyl)buta-2,3-dienamide (Compound 251)

To a stirred solution of N4-(5-amino-2-fluorophenyl)-N2-(1-methyl-1H-pyrazol-4-yl)-5-[4-(trifluoromethyl)phenyl] pyrimidine-2,4-diamine (93) (0.2 g, 0.451 mmol) and but-2-ynoic acid (0.045 g, 0.541 mmol) in dichloromethane (4.00 mL) was added triethylamine (0.157 mL, 1.13 mmol) followed by addition of 2-chloro-1-methylpyridin-1-ium iodide (351) (0.138 g, 0.541 mmol) at room temperature. The reaction mixture was stirred at room temperature 1 hour. The progress of reaction was monitored by LCMS and TLC. The reaction mixture was quenched with water (30.0 mL) and extracted with dichloromethane (3×25 mL). The combined organic layer was dried over anhydrous sodium sulfate, and evaporated under reduced pressure. The crude product was purified by Prep HPLC to get N-[4-fluoro-3-({2-[(1-methyl-1H-pyrazol-4-yl)amino]-5-[4-(trifluoromethyl)phenyl]pyrimidin-4-yl}amino)phenyl]buta-2,3-dienamide (Compound 251) (20.0 mg, 9%) as off white solid. $^{1}H$ NMR (400 MHz, DMSO-d6): δ 10.07 (s, 1H), 9.24 (bs, 1H), 8.52 (bs, 1H), 7.96 (s, 1H), 7.65-7.79 (m, 5H), 7.50 (bs, 1H), 7.26 (bs, 1H), 7.13 (bs, 1H), 7.05 (bs, 1H), 5.92 (t, J=6.8 Hz, 1H), 5.40 (d, J=6.0 Hz, 2H), 3.53 (s, 3H). LCMS $[M+H]^+$ 510.2

Scheme 79: Synthesis of 2-chloro-N-[4-fluoro-3-({2-[(1-methyl-1H-pyrazol-4-yl)amino]-5-[4-(trifluoromethyl)phenyl)pyrimidin-4-yl} amino)phenyl)acetamide 2,2,2-trifluoroacetic acid (Compound 252)

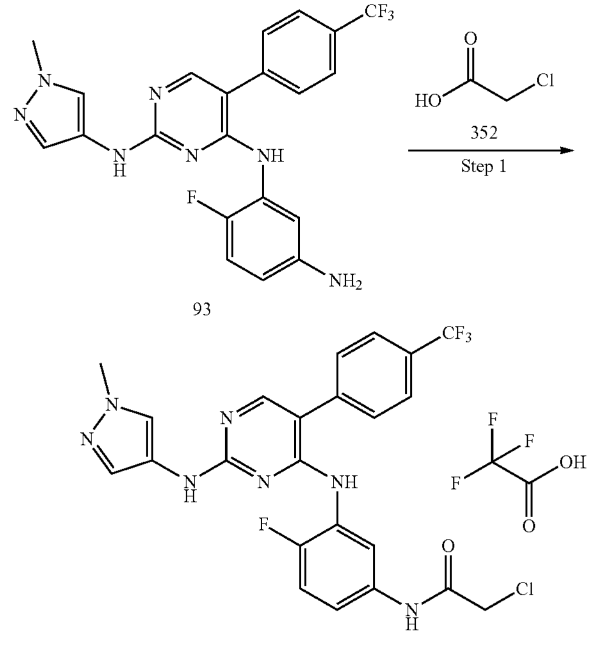

93

Compound 252

Step 1: Synthesis of 2-chloro-N-[4-fluoro-3-({2-[(1-methyl-1H-pyrazol-4-yl)amino]-5-[4-(trifluoromethyl)phenyl]pyrimidin-4-yl}amino)phenyl]acetamide (Compound 252)

To a stirred solution of N4-(5-amino-2-fluorophenyl)-N2-(1-methyl-1H-pyrazol-4-yl)-5-[4-(trifluoromethyl)phenyl] pyrimidine-2,4-diamine (93) (0.2 g, 0.451 mmol) in tetrahydrofuran (4.00 mL) and water (0.4 mL) were added triethylamine (0.189 mL, 1.35 mmol), 2-chloroacetyl chloride (352) (0.043 mL, 0.541 mmol) and stirred at 0° C. for 10 min. The progress of the reaction was monitored by LCMS. The reaction mixture was quenched with water (10 mL) and was extracted with dichloromethane (3×10 mL). The combined organic layer was dried over anhydrous sodium sulfate and evaporated under vacuum. The crude product was purified by preparative HPLC to afford 2-chloro-N-[4-fluoro-3-({2-[(1-methyl-1H-pyrazol-4-yl) amino]-5-[4-(trifluoromethyl)phenyl]pyrimidin-4-yl}amino)phenyl]acetamide (Compound 252) (0.2 g, 0.385 mmol) as off white solid. $^{1}H$ NMR (400 MHz, DMSO-d6): δ 10.43 (s, 1H), 9.89 (bs, 1H), 9.24 (bs, 1H), 7.99 (s, 1H), 7.84 (d, J=8.4 Hz, 2H), 7.73 (d, J=8.0 Hz, 3H), 7.49 (bs, 2H), 7.35 (bs, 1H), 7.70 (s, 1H), 6.94 (s, 1H), 4.23 (s, 2H), 3.57 (s, 3H). LCMS $[M+H]^+$ 520.1

Scheme 80: Synthesis of N-[4-fluoro-3-({2-[(1-methyl-1H-pyrazol-4-yl) amino]-5-[4-(trifluoromethyl) phenyl] pyrimidin-4-yl} amino) phenyl] ethene-1-sulfonamide (Compound 253)

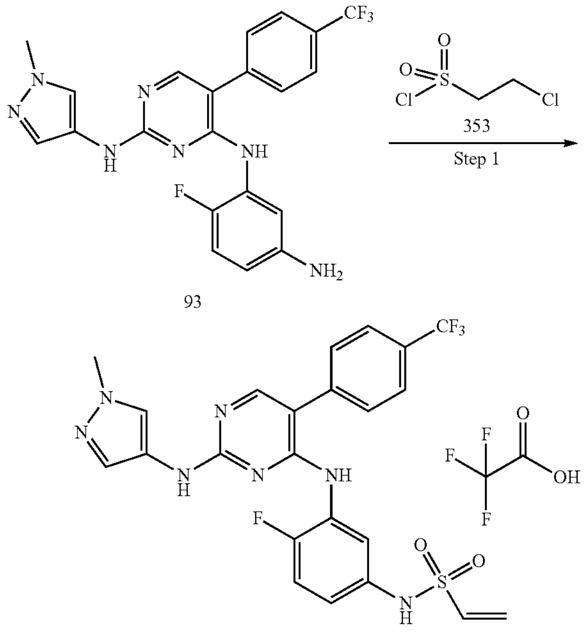

93

Compound 253

Step 1: Synthesis of N-[4-fluoro-3-({2-[(1-methyl-1H-pyrazol-4-yl) amino]-5-[4-(trifluoromethyl) phenyl] pyrimidin-4-yl} amino) phenyl] ethene-1-sulfonamide (Compound 253)

To a stirred solution of N-[4-fluoro-3-({2-[(1-methyl-1H-pyrazol-4-yl) amino]-5-[4-(trifluoromethyl) phenyl] pyrimidin-4-yl} amino) phenyl] ethene-1-sulfonamide (93) (0.5 g, 1.06 mmol) in dichloromethane (10.0 mL) was added triethylamine (0.321 g, 3.17 mmol) followed by 2-chloroethane-1-sulfonyl chloride (353) (0.207 g, 1.27 mmol) at room temperature and stirred for 6 hours. The progress of the reaction was monitored by TLC. The reaction mixture was diluted with water (25 mL) and extracted with dichloromethane (50 mL×2). The combined organic layer was washed with brine (10 mL), dried over anhydrous sodium sulfate and evaporated under reduced pressure. The crude product was purified by Preparative HPLC to afford N-[4-fluoro-3-({2-[(1-methyl-1H-pyrazol-4-yl) amino]-5-[4-(trifluoromethyl) phenyl]pyrimidin-4-yl} amino) phenyl] ethene-1-sulfonamide (Compound 253) (0.20 g, 35%) as a white solid. $^1$H NMR (400 MHz, DMSO-d6): δ 10.10 (bs, 2H), 9.33 (bs, 1H), 8.01 (bs, 1H), 7.85 (d, J=8.0 Hz, 2H), 7.73 (d, J=8.0 Hz, 2H), 7.34 (s, 1H), 7.14-7.08 (m, 3H), 7.04-7.02 (m, 2H), 6.70-6.70 (m, 1H), 6.06-6.01 (m, 1H), 5.99-5.93 (m, 1H), 3.59 (s, 3H). LCMS $[M+H]^+$ 534.3

Scheme 81: Synthesis of N-[4-fluoro-3-({2-[(1-methyl-1H-pyrazol-4-yl) amino)-5-[4-(trifluoromethyl) phenyl] pyrimidin-4-yl} amino) phenyl] prop-2-ynamide (Compound 357)

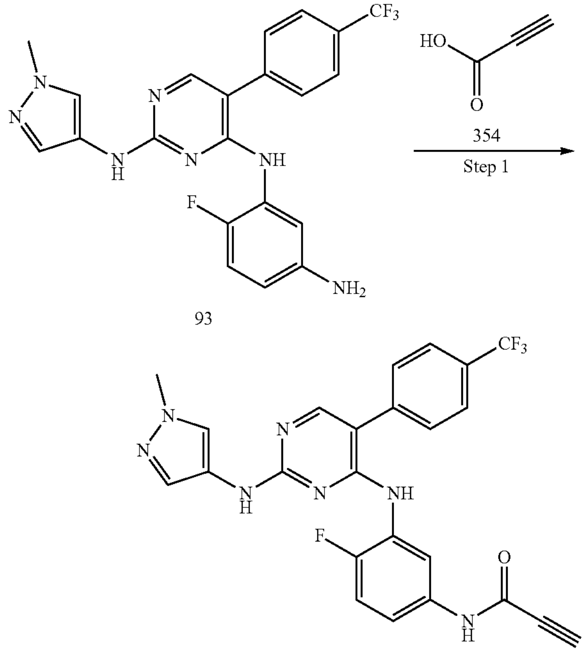

93

Compound 254

Step 1: Synthesis of N-[4-fluoro-3-({2-[(1-methyl-1H-pyrazol-4-yl) amino]-5-[4-(trifluoromethyl) phenyl] pyrimidin-4-yl} amino) phenyl] prop-2-ynamide (Compound 254)

To a stirred solution of N4-(5-amino-2-fluorophenyl)-N2-(1-methyl-1H-pyrazol-4-yl)-5-[4-(trifluoromethyl) phenyl] pyrimidine-2,4-diamine (93) (0.25 g, 0.564 mmol) in dichloromethane (20.0 mL) was added prop-2-ynoic acid (354) (0.045 mL, 0.73 mmol) followed by N,N'-dicyclohexylmethanediimine (0.151 g, 0.733 mmol), N,N-dimethylpyridin-4-amine (0.006 g, 0.056 mmol) at 0° C. and the reaction mixture was stirred for 16 hours at room temperature. The reaction mixture was filtered and the filtrate was concentrated under reduced pressure. The crude product was purified by preparative HPLC to afford the title compound (Compound 254) as off white solid (0.035 g, 12%). $^1$H NMR (400 MHz, DMSO-d6): δ 10.90 (s, 1H), 9.25 (bs, 1H), 8.55 (bs, 1H), 8.00 (s, 1H), 7.81 (d, J=8.4 Hz, 2H), 7.73-7.67 (m, 3H), 7.51 (bs, 1H), 7.31 (bs, 1H), 7.15 (bs, 1H), 7.06 (bs, 1H), 4.43 (s, 1H), 3.57 (s, 3H). LCMS $[M+H]^+$ 496.4

Scheme 82: Synthesis of N-(4-fluoro-3-((2-((1-methyl-1H-pyrazol-4-yl) amino)-5-(tetrahydro-2H-pyran-4-yl)pyrimidin-4-yl)amino)phenyl) acrylamide (Compound 255)

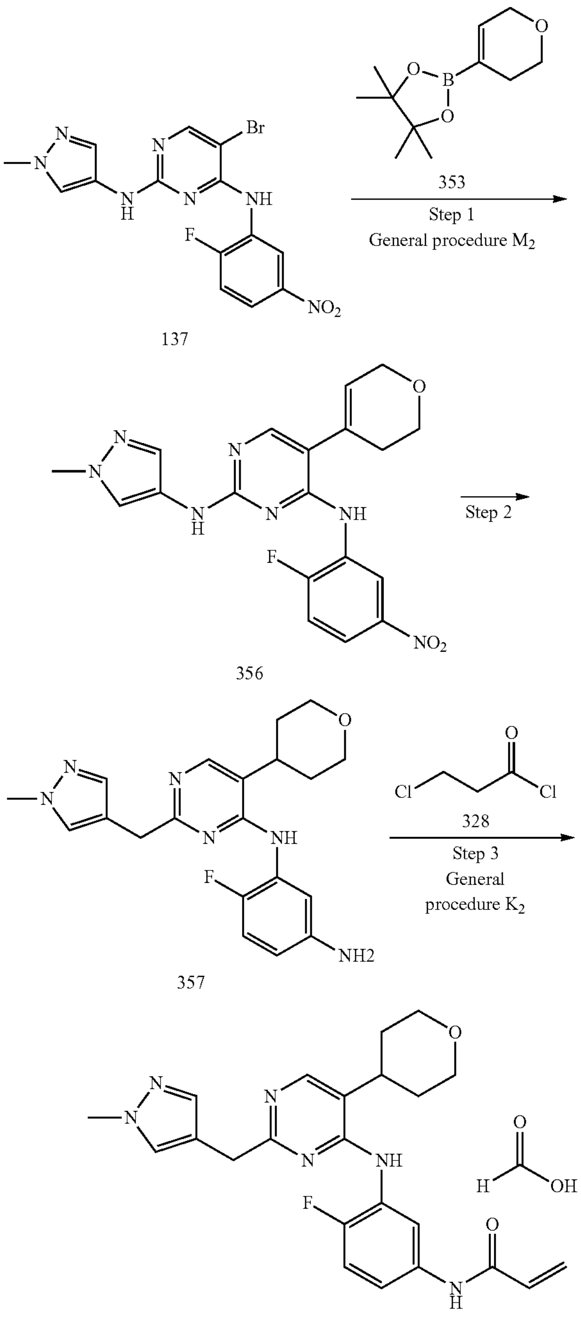

137

356

357

Compound 255

Step 1: Synthesis of 5-(3,6-dihydro-2H-pyran-4-yl)-N4-(2-fluoro-5-nitrophenyl)-N2-(1-methyl-1H-pyrazol-4-yl)pyrimidine-2,4-diamine (356)

The title compound was prepared in a manner substantially similar to procedure mentioned in General Procedure $M_2$, to afford the desired compound (356) as brown solid. LCMS $[M+H]^+$ 412.0

Step 2: Synthesis of N4-(5-amino-2-fluorophenyl)-N2-(1-methyl-1H-pyrazol-4-yl)-5-(tetrahydro-2H-pyran-4-yl)pyrimidine-2,4-diamine (357)

To a stirred solution of 5-(3,6-dihydro-2H-pyran-4-yl)-N4-(2-fluoro-5-nitrophenyl)-N2-(1-methyl-1H-pyrazol-4-yl)pyrimidine-2,4-diamine (356) (0.4 g, 0.972 mmol) in methanol (20.0 mL) and tetrahydrofuran (20.0 mL) was added palladium on carbon (0.8 g, 7.52 mmol, 10% w/w) and the reaction mixture was hydrogenated in a par shaker at 80° C. with 80 torr hydrogen pressure for 14 hours. The progress of the reaction was monitored by TLC and LCMS. After the reaction completion, the reaction mixture was filtered through celite and the filtrate was concentrated under vacuum to get desired product (357) as pale yellow liquid. (0.4 g, crude). LCMS $[M+H]^+$ 384.2

Step 3: Synthesis of N-(4-fluoro-3-((2-((1-methyl-1H-pyrazol-4-yl)amino)-5-(tetrahydro-2H-pyran-4-yl)pyrimidin-4-yl)amino)phenyl)acrylamide (Compound 255)

The title compound was prepared in a manner substantially similar to procedure mentioned in General Procedure $K_2$, to afford the desired compound (Compound 255) as white solid. $^1H$ NMR (400 MHz, DMSO-d6): δ 10.24 (s, 1H), 8.78 (bs, 1H), 8.44 (bs, 1H), 8.17 (s, 1H), 7.84 (s, 1H), 7.75-7.74 (m, 1H), 7.57 (bs, 1H), 7.33-7.16 (m, 2H), 7.11 (bs, 2H), 6.42-6.36 (m, 1H), 6.25-6.21 (m, 1H), 5.75-5.72 (m, 1H), 3.95-3.91 (m, 2H), 3.50-3.44 (m, 2H), 3.33 (bs, 3H merged with DMSO peak), 2.95-2.90 (m, 1H), 1.77-1.66 (m, 2H), 1.64-1.60 (m, 2H); LCMS $[M+H]^+$ 438.2

Scheme 83: Synthesis of N-(3-((5-bromo-2-((1-methyl-1H-pyrazol-4-yl)amino)pyrimidin-4-yl)amino)-4-fluorophenyl)acrylamide (Compound 359)

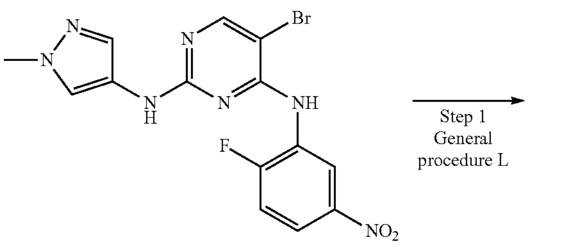

137

-continued

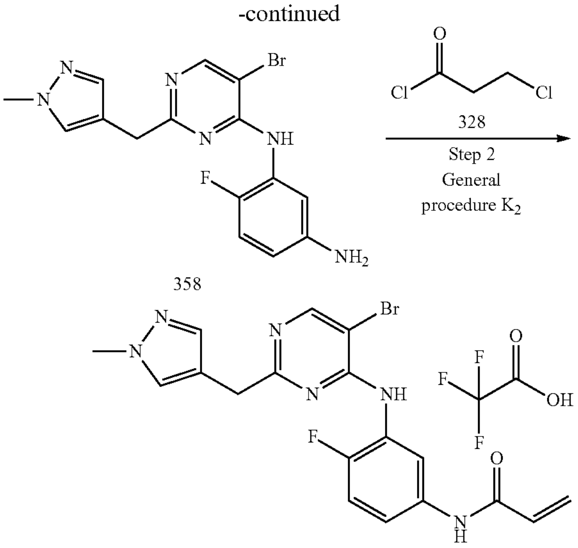

358

Compound 256

Step 1: Synthesis of N4-(5-amino-2-fluorophenyl)-5-bromo-N2-(1-methyl-1H-pyrazol-4-yl)pyrimidine-2,4-diamine (408)

The title compound was prepared in a manner substantially similar to procedure mentioned in General Procedure L, to afford the desired compound (358) as brown solid. LCMS $[M+H]^+$ 378.1

Step 2: Synthesis of N-(3-((5-bromo-2-((1-methyl-1H-pyrazol-4-yl)amino)pyrimidin-4-yl)amino)-4-fluorophenyl)acrylamide (Compound 256)

The title compound was prepared in a manner substantially similar to procedure mentioned in General Procedure $K_2$, to afford the desired compound (Compound 256) as white solid. $^1H$ NMR (400 MHz, DMSO-d6): δ 10.29 (s, 1H), 9.42 (bs, 1H), 8.95 (bs, 1H), 8.16 (s, 1H), 7.81-7.79 (m, 1H), 7.67 (bs, 1H), 7.36 (bs, 2H), 7.22-7.01 (m, 2H), 6.46-6.39 (m, 1H), 6.29-6.24 (m, 1H), 5.79-5.76 (m, 1H), 3.45 (bs, 3H merged with DMSO peak); LCMS $[M+H]^+$ 432.1

TABLE 19

The following compounds were prepared using the procedures described above:

| Cmpd. No. | Structure | General Procedure | LCMS [M + H] | $^1H$-NMR (400 MHz, DMSO-$d_6$) |
|---|---|---|---|---|
| 258 | 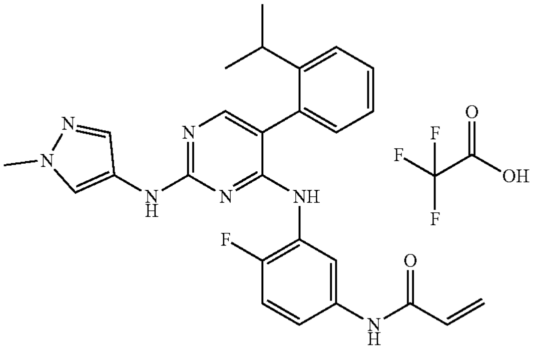 | $K_2$ | 472.3 | δ 10.29 (s, 1H), 9.12 (bs, 1H), 7.87 (bs, 1H), 7.80 (d, J = 4.8 Hz, 1H), 7.60 (bs, 1H), 7.49 (d, J = 2.8 Hz, 3H), 7.36-7.28 (m, 5H), 7.10 (bs, 1H), 6.44-6.37 (m, 1H), 6.25 (dd, J = 17.2 Hz, J = 2.0 Hz, 1H), 5.77 (dd, J = 10.4 Hz, J = 2.0 Hz, 1H), 3.60 (bs, 3H), 2.92-2.85 (m, 1H), 1.28 (d, J = 6.8 Hz, 3H), 1.12 (d, J = 6.8 Hz, 3H). |

TABLE 19-continued

| Cmpd. No. | Structure | General Procedure | LCMS [M + H] | $^1$H-NMR (400 MHz, DMSO-$d_6$) |
|---|---|---|---|---|
| The following compounds were prepared using the procedures described above: | | | | |
| 259 | 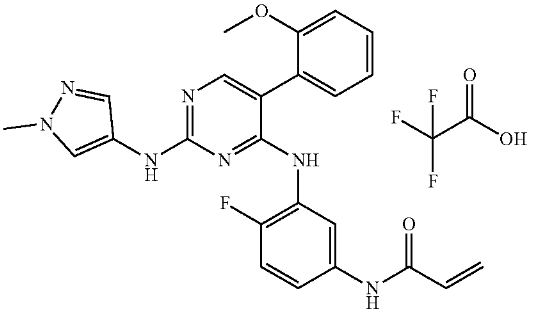 | $K_2$ | 460.2 | δ 10.31 (s, 1H), 10.19 (bs, 1H), 9.09 (bs, 1H), 7.85 (dd, J = 7.2 Hz, J = 2.4 Hz, 2H), 7.61 (bs, 1H), 7.50-7.46 (m, 2H), 7.35 (d, J = 4.0 Hz, 2H), 7.27 (bs, 1H), 7.16 (d, J = 8.0 Hz, 2H), 7.13-7.10 (m, 1H), 6.46-6.39 (m, 1H), 6.25 (dd, J = 16.0 Hz, J = 1.6 Hz, 1H), 5.77 (dd, J = 12.0 Hz, J = 4.0 Hz, 1H), 3.85 (s, 3H), 3.61 (bs, 3H). |
| 260 | 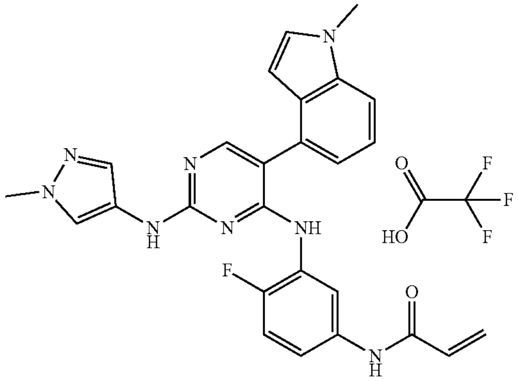 | $K_2$ | 483.2 | δ 10.26 (s, 1H), 10.03 (bs, 1H), 9.07 (bs, 1H), 7.95 (bs, 1H), 7.76 (d, J = 4.8 Hz, 1H), 7.56-7.54 (m, 2H), 7.42 (d, J = 3.2 Hz, 1H), 7.31-7.27 (m, 4H), 7.14-6.95 (m, 2H), 6.41-6.34 (m, 2H), 6.24-6.19 (m, 1H), 5.75-5.72 (m, 1H), 3.82 (bs, 3H), 3.58 (bs, 3H). |

Scheme 84: Synthesis of N-(3-{[5-(2,5-dihydrofuran-3-yl)-2-[(1-methyl-1H-pyrazol-4-yl)amino] pyrimidin-4-yl] amino}-4-fluorophenyl) prop-2-enamide (Compound 261)

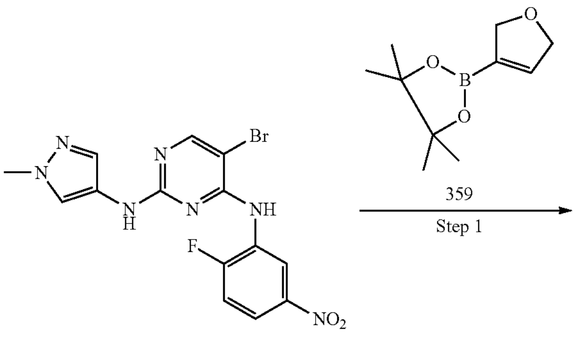

137

-continued

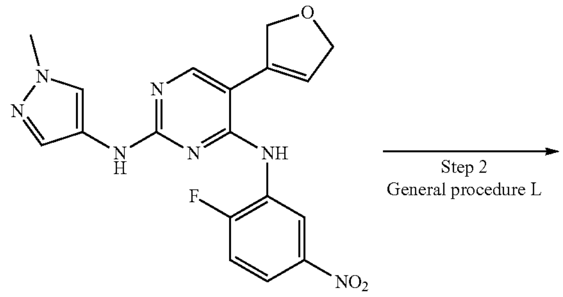

360

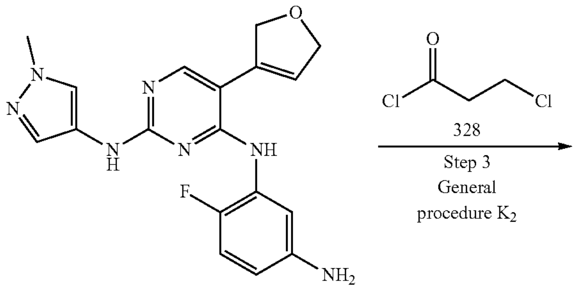

361

-continued

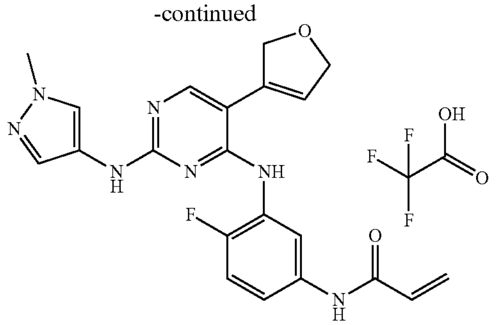

Compound 261

Step 1: Synthesis of 5-(2,5-dihydrofuran-3-yl)-N4-(2-fluoro-5-nitrophenyl)-N2-(1-methyl-1H-pyrazol-4-yl) pyrimidine-2,4-diamine (360)

To a stirred solution of 5-bromo-N4-(2-fluoro-5-nitrophenyl)-N2-(1-methyl-1H-pyrazol-4-yl)pyrimidine-2,4-diamine (137) (0.25 g, 0.61 mmol) in 1,4-dioxane (2.4 mL), water (0.6 mL) was added 2-(2,5-dihydrofuran-3-yl)-4,4,5,5-tetramethyl-1,3,2-dioxaborolane (359 (0.12 g, 0.61 mmol), potassium carbonate (0.25 g, 1.84 mmol) and [2-Dicyclohexylphosphineo-2[1],4[1],6[1]-triisopropylbiphenyl] (0.058 g, 0.122 mmol). Then the reaction mixture was purged with nitrogen for 5 minutes, added tris(dibenzylideneacetone)dipalladium(0) (0.056 g, 0.061 mmol) and the reaction mixture was heated at 100° C. for 16 hours. The progress of the reaction was monitored by TLC. Then the reaction mixture was cooled to room temperature, diluted with water (20 mL) and extracted with ethyl acetate (2×25 mL). The combined organic layer was washed with water (10 mL), brine (10 mL), dried over anhydrous sodium sulfate and evaporated. The crude product was purified by column chromatography by using combiflash purifier and the product was eluted with 10% methanol in dichloromethane to afford the title compound as off white solid (360) (0.2 g, 82%). LCMS $[M+H]^+$ 398.2.

Step 2: Synthesis of N4-(5-amino-2-fluorophenyl)-5-(2,5-dihydrofuran-3-yl)-N2-(1-methyl-1H-pyrazol-4-yl) pyrimidine-2,4-diamine (361)

The title compound was prepared in a manner substantially similar to procedure mentioned in General Procedure L, to afford the desired compound (361) as pale yellow solid. LCMS $[M+H]^+$ 368.2.

Step 3: Synthesis of N-(3-{[5-(2,5-dihydrofuran-3-yl)-2-[(1-methyl-1H-pyrazol-4-yl) amino]pyrimidin-4-yl] amino}-4-fluorophenyl) prop-2-enamide (Compound 261)

The title compound was prepared in a manner substantially similar to procedure mentioned in General Procedure $K_2$, to afford the desired compound (Compound 261) as off white solid.

$^1$H NMR (400 MHz, DMSO-d6): δ 10.34 (s, 1H), 10.19 (bs, 1H), 9.33 (s, 1H), 7.94-7.90 (m, 2H), 7.63 (s, 1H), 7.39 (s, 1H), 7.20-7.08 (m, 3H), 6.47-6.38 (m, 2H), 6.29-6.24 (m, 1H), 5.79-5.76 (m, 1H), 4.86 (d, J=4.0 Hz, 2H), 4.79 (d, J=4.0 Hz, 2H), 3.58 (bs, 3H); LCMS $[M+H]^+$ 422.1.

TABLE 20

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 262 | 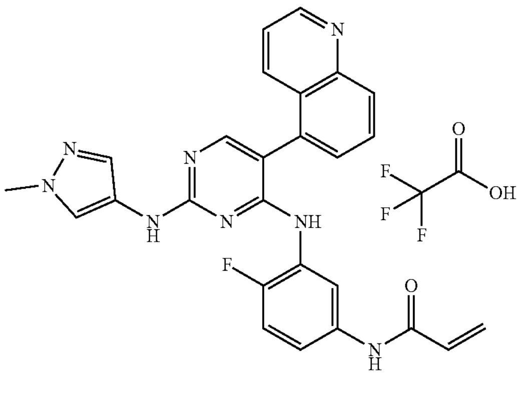 | $K_2$ | 481.1 | δ 10.25 (s, 1H), 10.13 (bs, 1H), 9.09 (bs, 1H), 9.01 (d, J = 4.0 Hz, 1H), 8.31 (d, J = 8.0 Hz, 1H), 8.18 (d, J = 8.4 Hz, 1H), 8.03 (s, 1H), 7.93 (t, J = 8.0 Hz, 1H), 7.73 (t, J = 6.8 Hz, 2H), 7.65-7.62 (m, 1H), 7.55 (s, 1H), 7.32-7.10 (m, 4H), 6.42-6.35 (m, 1H), 6.26-6.21 (m, 1H), 5.77-5.74 (m, 1H), 3.61 (s, 3H). |

TABLE 20-continued

| Cmpd. No. | Structure | General Procedure | LCMS [M + H] | $^1$H-NMR (400 MHz, DMSO-$d_6$) |
|---|---|---|---|---|
| The following compounds were prepared using the procedures described above: | | | | |
| 263 | 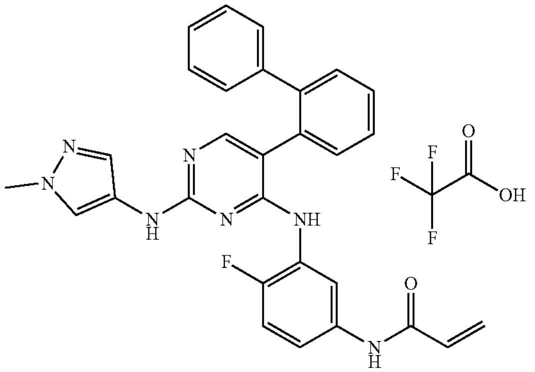 | $K_2$ | 506.2 | δ 10.24 (s, 1H), 9.91 (bs, 1H), 9.12 (bs, 1H), 7.72 (bs, 1H), 7.59-7.50 (m, 7H), 7.47-7.20 (m, 6H), 7.16 (bs, 1H), 7.10 (bs, 1H), 6.42-6.35 (m, 1H), 6.26-6.22 (m, 1H), 5.77-5.74 (m, 1H), 3.35 (bs, 3H). |
| 264 | 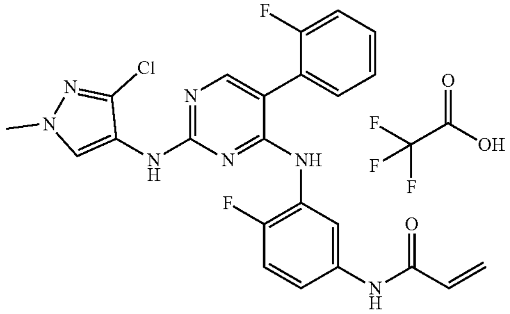 | $K_2$ | 482.2 | δ 10.24 (s, 1H), 9.15 (bs, 2H), 7.95 (bs, 2H), 7.78 (d, J = 5.2 Hz, 1H), 7.51-7.47 (m, 3H), 7.35-7.19 (m, 4H), 6.42-6.35 (m, 1H), 6.25-6.21 (m, 1H), 5.76 (d, J = 11.6 Hz, 1H), 3.55 (bs, 3H merged with DMSO peak). |
| 265 | 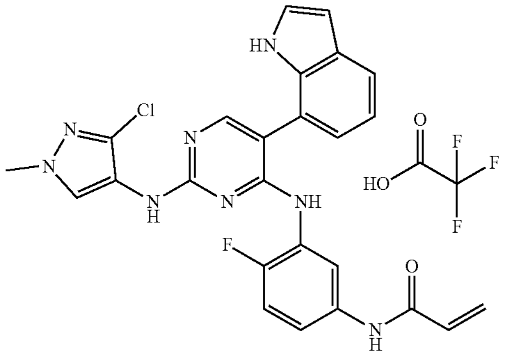 | $K_2$ | 469.2 | δ 11.19 (s, 1H), 10.31 (bs, 2H), 9.16 (bs, 1H), 8.00 (bs, 1H), 7.91-7.89 (m, 1H), 7.69-7.67 (m, 1H), 7.57 (bs, 1H), 7.41-6.99 (m, 7H), 6.57-6.56 (m, 1H), 6.45-6.39 (m, 1H), 6.28-6.23 (m, 1H), 5.77 (dd, J = 10.0 Hz, 2.0 Hz, 1H), 3.61 (s, 3H). |

Scheme 85: Synthesis of N-[4-fluoro-3-({2-[(1-methyl-1H-pyrazol-4-yl) amino]-5-(oxolan-3-yl) pyrimidin-4-yl} amino) phenyl] prop-2-enamide (Compound 266)

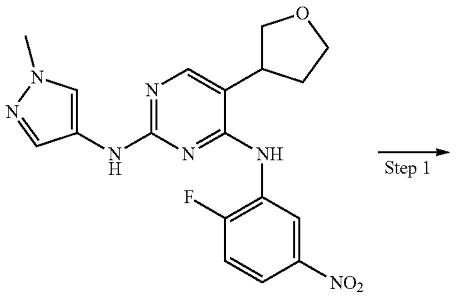

362

-continued

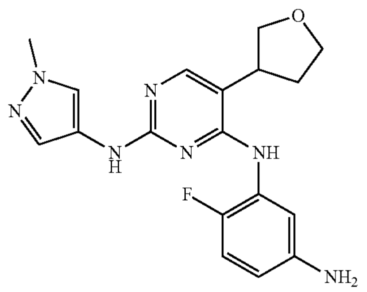

363

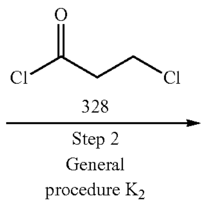

-continued

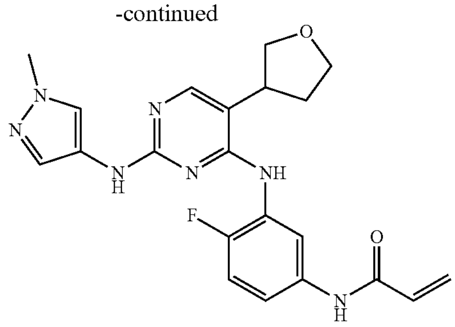

Compound 266

Step 1: Synthesis of N4-(5-amino-2-fluorophenyl)-N2-(1-methyl-1H-pyrazol-4-yl)-5-(oxolan-3-yl) pyrimidine-2,4-diamine (363)

To a stirred solution of 5-(2,5-dihydrofuran-3-yl)-N4-(2-fluoro-5-nitrophenyl)-N2-(1-methyl-1H-pyrazol-4-yl) pyrimidine-2,4-diamine (362) (0.15 g, 0.377 mmol) in methanol (10 mL), tetrahydrofuran (10 mL) was added palladium on carbon (0.1 g, 10% w/w). The reaction mixture was hydrogenated at 80° C. for 14 hours at 100 torr hydrogen pressure. The progress of the reaction was monitored by TLC and LCMS. After the reaction completion, the mixture was filtered through celite and washed with methanol (50 mL). The filtrate was concentrated under vacuum to get desired product N4-(5-amino-2-fluorophenyl)-N2-(1-methyl-1H-pyrazol-4-yl)-5-(oxolan-3-yl) pyrimidine-2,4-diamine (363) (0.14 g, 100) as pale yellow liquid. LCMS $[M+H]^+$ 370.2.

Step 2: Synthesis of N-{4-fluoro-3-([2-[(1-methyl-1H-pyrazol-4-yl) amino]-5-(oxolan-3-yl) pyrimidin-4-yl} amino) phenyl] prop-2-enamide (compound 266)

The title compound was prepared in a manner substantially similar to procedure mentioned in General Procedure $K_2$, to afford the desired compound (Compound 266) as off white solid.

$^1H$ NMR (400 MHz, DMSO-d6): δ 10.25 (s, 1H), 8.87 (bs, 1H), 8.46 (s, 1H), 7.91 (s, 1H), 7.80 (dd, J=6.8 Hz, J=2.4 Hz, 1H), 7.63-7.61 (s, 1H), 7.33-7.28 (m, 1H), 7.14 (s, 2H), 6.45-6.39 (m, 1H), 6.28-6.23 (m, 1H), 5.78-5.75 (m, 1H), 4.03-4.00 (m, 1H), 3.97-3.91 (m, 1H), 3.82-3.77 (m, 1H), 3.68-3.64 (m, 1H), 3.54-3.44 (m, 4H), 2.36-2.28 (m, 1H), 1.99-1.91 (in, 1H). LCMS $[M+H]^+$ 424.2.

TABLE 21

The following compounds were prepared using the procedures described above:

| Cmpd. No. | Structure | General Procedure | LCMS [M + H] | $^1H$-NMR (400 MHz, DMSO-$d_6$) |
|---|---|---|---|---|
| 267 | 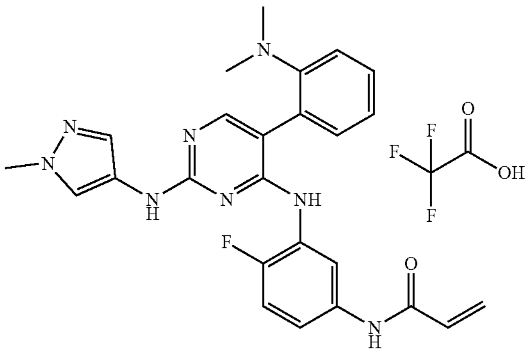 | $K_2$ | 473.3 | δ 9.96 (m, 1H), 9.55 (m, 2H), 8.03 (s, 2H), 7.90-7.89 (m, 1H), 7.54 (s, 1H), 7.42 (s, 1H), 7.32-7.14 (m, 5H), 6.93 (s, 1H), 6.42-6.36 (m, 1H), 6.23 (dd, J = 18.8 Hz, J = 16.8 Hz, 1H), 5.75 (dd, J = 12.0 Hz, J = 10.0 Hz, 1H), 3.49 (bs, 3H), 2.68-2.65 (m, 6H). |
| 268 | 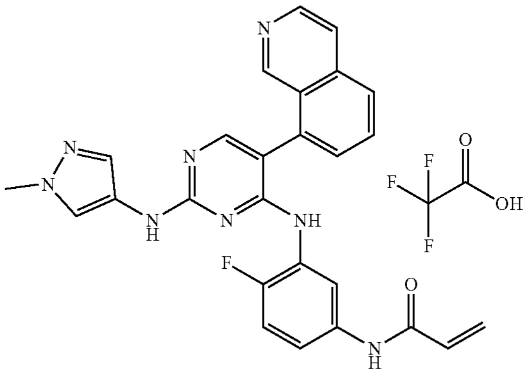 | $K_2$ | 481.2 | δ 10.35 (s, 1H), 10.11 (bs, 1H), 9.37 (s, 1H), 9.08 (bs, 1H), 8.66 (d, J = 19.6 Hz, 1H), 8.23-8.19 (m, 2H), 8.08-8.04 (m, 3H), 7.85 (d, J = 6.8 Hz, 1H), 7.76 (bs, 1H), 7.54 (bs, 1H), 7.37-7.29 (m, 2H), 7.22 (s, 1H), 6.42-6.35 (m, 1H), 6.26-6.21 (m, 1H), 5.76 (dd, J = 10.4 Hz, J = 2.0 Hz, 1H), 3.60 (s, 3H). |

Scheme 86: Synthesis of N-(4-fluoro-3-((2-((1-methyl-1H-pyrazol-4-yl)amino)-5-(piperidin-1-yl)pyrimidin-4-yl)amino)phenyl) acrylamide (Compound 383)

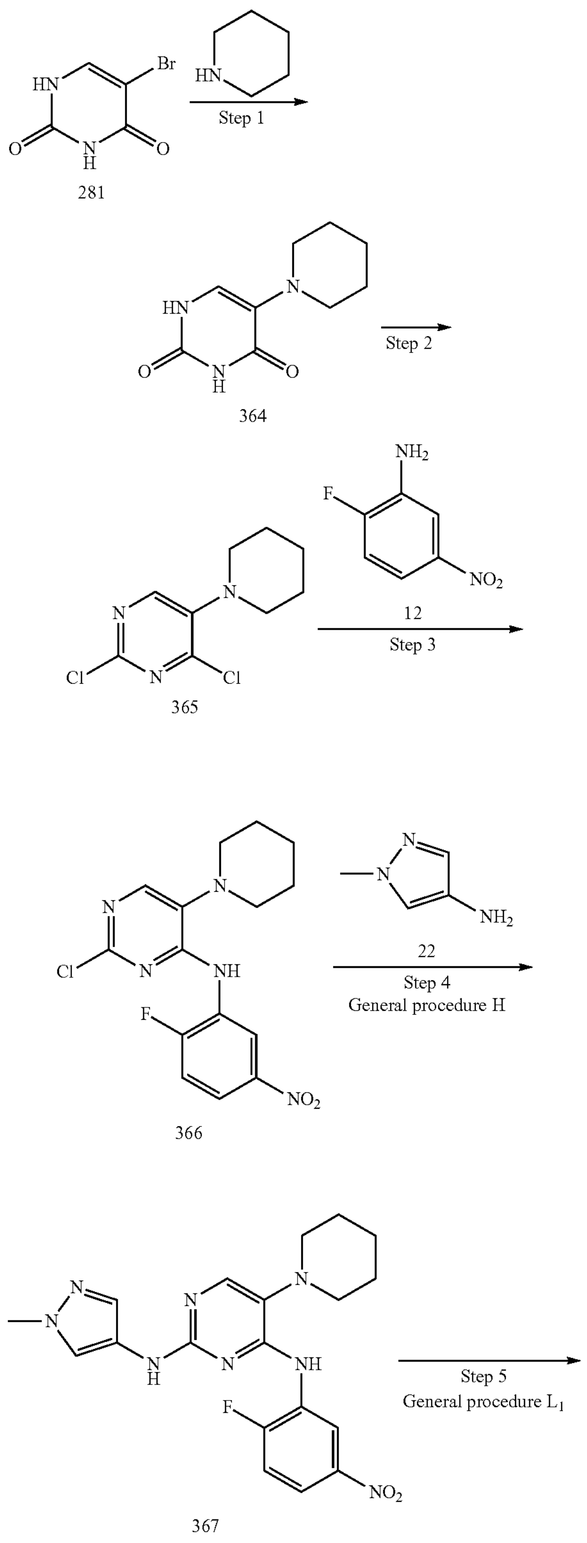

-continued

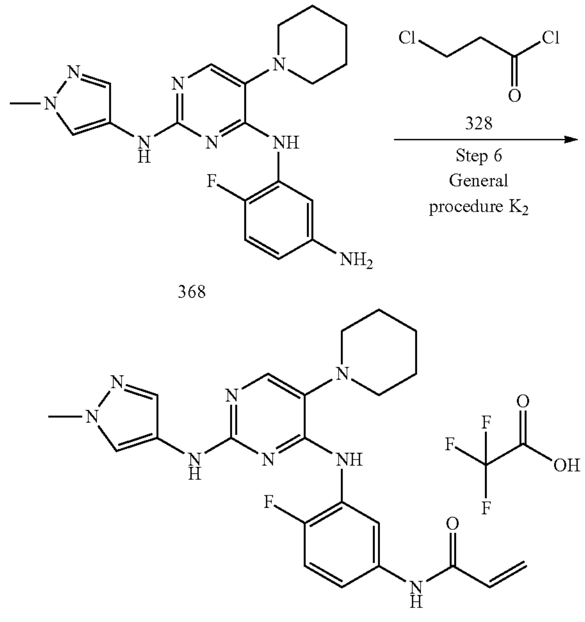

Compound 269

Step 1: Synthesis of 5-(piperidin-1-yl)pyrimidine-2,4(1H,3H)-dione (415)

A mixture of 5-bromo-1,2,3,4-tetrahydropyrimidine-2,4-dione (281) (3.00 g, 15.7 mmol) in piperidine (6.22 mL, 62.8 mmol) was heated at 110° C. for 15 minutes. Then the reaction mixture was cooled to room temperature, added methanol (25 mL) and stirred at room temperature for 30 minutes. The solids were filtered, washed with methanol (50 mL) and dried to get the desired product (364) as white solid (2.9 g, crude). LCMS $[M+H]^+$ 196.2.

Step 2: Synthesis of 2,4-dichloro-5-(piperidin-1-yl)pyrimidine (365)

To a stirred solution of 5-(piperidin-1-yl)-1,2,3,4-tetrahydropyrimidine-2,4-dione (364) (0.5 g, 2.56 mmol) in phosphoroyl trichloride (5 mL) was added triethylamine (0.714 mL, 5.12 mmol) and the reaction mixture was heated at 110° C. for 15 hours. Then the reaction mixture was cooled and evaporated. The residue was diluted with cold water (20 mL) and was extracted with ethyl acetate (30 mL×3). The combined organic layer was washed with brine (20 mL), dried over anhydrous sodium sulfate and evaporated under reduced pressure. The crude product was purified by column chromatography by using combiflash purifier and was eluted with 25% ethyl acetate in hexane to get the desired product (365) as colourless liquid (0.53 g, 89%). LCMS $[M+H]^+$ 231.9.

Step 3: Synthesis of 2-chloro-N-(2-fluoro-5-nitrophenyl)-5-(piperidin-1-yl)pyrimidin-4-amine (366)

To a stirred solution of 2-fluoro-5-nitroaniline (12) (0.336 g, 2.15 mmol) in N,N-dimethylformamide (10 mL) at 0° C. was added sodium hydride (0.172 g, 4.31 mmol, 60% in mineral oil) and the reaction mixture was stirred at same temperature for 30 min. Then a solution of 2,4-dichloro-5-(piperidin-1-yl)pyrimidine (365) (0.5 g, 2.15 mmol) in N,N- dimethylformamide (1 mL) was added and the reaction mixture was stirred at room temperature for 15 hours. The reaction mixture was diluted with water (50 mL) and extracted with ethyl acetate (25 mL×3). The combined organic layer was washed with water (50 mL), brine (50 mL), dried over anhydrous sulfate and evaporated. The crude product was purified by using combiflash purifier and was eluted with 20% ethyl acetate in hexane to get the desired product (366) as yellow solid (0.1 g, 13%). LCMS $[M+H]^+$ 352.1.

Step 4: Synthesis of N4-(2-fluoro-5-nitrophenyl)-N2-(1-methyl-1H-pyrazol-4-yl)-5-(piperidin-1-yl) pyrimidine-2,4-diamine (367)

The title compound was prepared in a manner substantially similar to procedure mentioned in General Procedure H, to afford the desired compound (367) as brown solid. LCMS $[M+H]^+$ 413.2.

Step 5: Synthesis of N4-(5-amino-2-fluorophenyl)-N2-(1-methyl-1H-pyrazol-4-yl)-5-(piperidin-1-yl) pyrimidine-2,4-diamine (368)

The title compound was prepared in a manner substantially similar to procedure mentioned in General Procedure L1, to afford the desired compound (368) as brown solid. LCMS $[M+H]^+$ 383.2.

Step 6: Synthesis of N-(4-fluoro-3-((2-((1-methyl-1H-pyrazol-4-yl)amino)-5-(piperidin-1-yl)pyrimidin-4-yl)amino)phenyl)acrylamide (Compound 269)

The title compound was prepared in a manner substantially similar to procedure mentioned in General Procedure $K_2$, to afford the desired compound (Compound 269) as off white solid.

$^1$H NMR (400 MHz, DMSO-d6): δ 10.33 (s, 1H), 9.85 (bs, 1H), 9.49 (s, 1H), 8.01 (d, J=5.2 Hz, 1H), 7.73 (bs, 1H), 7.61-7.59 (m, 1H), 7.42-7.37 (m, 2H), 7.28-7.21 (m, 2H), 6.46-6.40 (m, 1H), 6.29-6.24 (m, 1H), 5.79 (dd, J=10.0 Hz, J=2.0 Hz, 1H), 3.64 (s, 3H), 2.84 (bs, 4H), 1.74 (bs, 4H), 1.54 (bs, 2H). LCMS $[M+H]^+$ 437.3.

TABLE 22

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 270 | 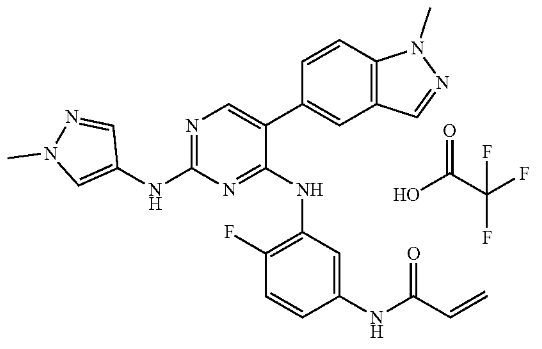 | $K_2$ | 484.2 | δ 10.32 (bs, 1H), 10.20 (bs, 1H), 9.44 (s, 1H), 8.16 (s, 1H), 7.97-7.80 (m, 4H), 7.59 (bs, 1H), 7.52-7.49 (m, 1H), 6.90-7.38 (m, 4H), 6.45-6.38 (m, 1H), 6.28-6.23 (m, 1H), 5.75 (dd, J = 10.0 Hz, J = 1.6 Hz, 1H), 4.11 (s, 3H), 3.61 (bs, 3H, merged with DMSO water peak). |
| 271 | 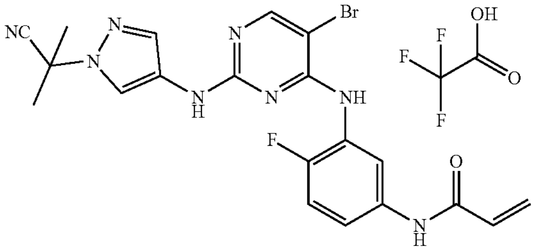 | $K_2$ | 486.1 | δ 10.29 (s, 1H), 9.62 (bs, 1H), 8.97 (bs, 1H), 8.27-8.17 (m, 1H), 7.82-7.81 (m, 1H), 7.63 (s, 1H), 7.53-6.91 (m, 3H), 6.45-6.38 (m, 2H), 6.28-6.24 (m, 1H), 5.78-5.75 (m, 1H), 1.72 (bs, 6H). |

TABLE 22-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 272 | 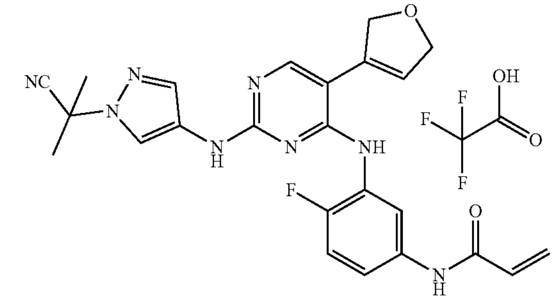 | $K_2$ | 475.3 | δ 10.29 (s, 1H), 9.84 (bs, 1H), 8.94 (bs, 1H), 8.00 (s, 1H), 7.95-7.88 (m, 1H), 7.57 (bs, 1H), 7.43 (bs, 2H), 7.34-7.29 (m, 2H), 6.49-6.41 (m, 1H), 6.28-6.23 (m, 2H), 5.78-5.75 (m, 1H), 4.91-4.83 (m, 2H), 4.78-4.77 (m, 2H), 1.75 (bs, 6H). |
| 273 | 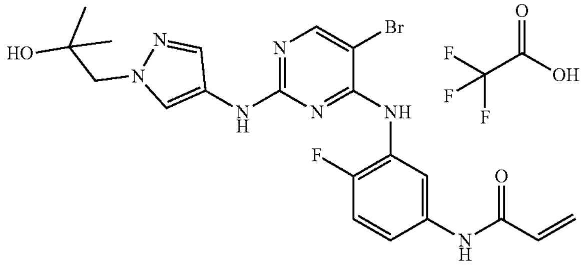 [SMILES: C=CC(=O)Nc1ccc(F)c(Nc2nc(Nc3cnn(CC(C)(C)O)c3)ncc2Br)c1 ; O=C(O)C(F)(F)F] | $K_2$ | 491.1 | δ 10.26 (s, 1H), 9.41 (bs, 1H), 8.91 (bs, 1H), 8.17 (s, 1H), 7.81-7.78 (m, 1H), 7.65 (bs, 1H), 7.34-7.30 (m, 1H), 7.21-6.95 (m, 3H), 6.45-6.39 (m, 1H), 6.28-6.23 (m, 1H), 5.78-5.75 (m, 1H), 3.70 (bs, 3H), 0.94 (s, 6H). |
| 274 | 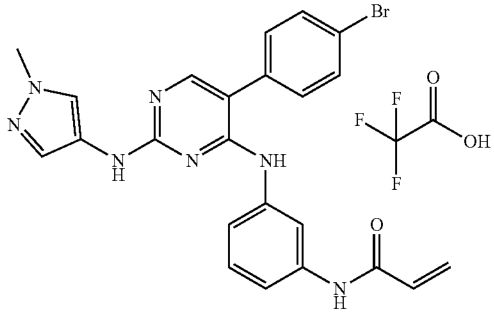 | $K_2$ | 490.1 | δ 11.21 (bs, 1H), 8.05 (bs, 2H), 7.76 (d, J = 8.0 Hz, 2H), 7.67 (d, J = 13.6 Hz, 3H), 7.53 (s, 1H), 7.38-7.28 (m, 5H), 6.89 (d, J = 8.0 Hz, 1H), 6.54-6.50 (m, 2H), 5.87-5.84 (m, 1H), 3.90-3.88 (m, 3H). |

Scheme 87: Synthesis of N-(3-((5-chloro-4-((1-methyl-1H-pyrazol-4-yl)amino)pyrimidin-2-yl)amino)phenyl)acrylamide (Compound 275)

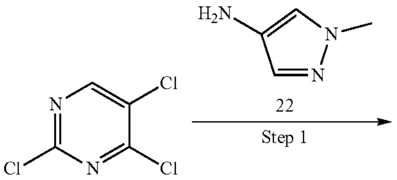

13

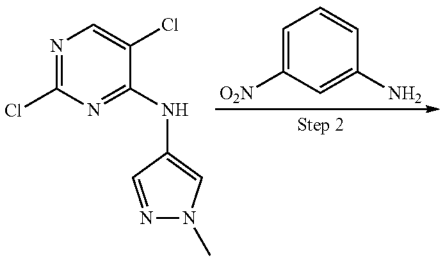

369

-continued

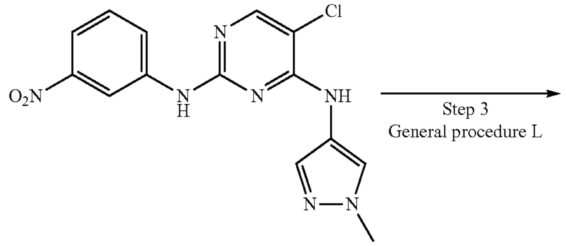

370

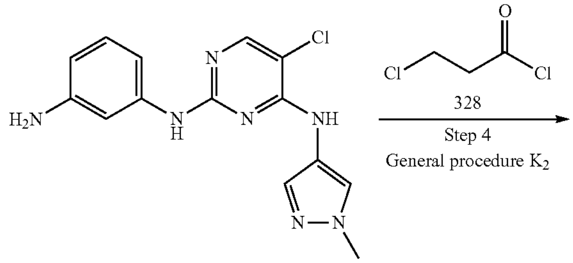

371

-continued

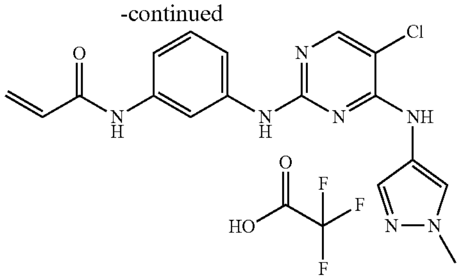

Compound 275

Step 1: Synthesis of 5-bromo-2-chloro-N-(2-fluoro-3-nitrophenyl)pyrimidin-4-amine (369)

To a solution of 2,4,5-trichloropyrimidine (13) (0.50 g, 2.73 mmol) in N,N-dimethylformamide (10 mL) were added potassium carbonate (0.94 g, 6.81 mmol) and 1-methyl-1H-pyrazol-4-amine (22) (0.265 g, 2.73 mmol). Then the reaction mixture was heated at 100° C. for 3 hours. After completion of reaction (TLC and LCMS monitoring), reaction mixture was cooled to room temperature. The reaction mixture was added to the ice-cooled water (50 mL) and stirred for 10 minutes. The precipitated solid was filtered, dried and used for the further steps without any purification. LCMS $[M+H]^+$ 244.0.

Step 2: Synthesis of 5-chloro-N4-(1-methyl-1H-pyrazol-4-yl)-N2-(3-nitrophenyl)pyrimidine-2,4-diamine (370)

To a solution of 2,5-dichloro-N-(1-methyl-1H-pyrazol-4-yl)pyrimidin-4-amine (420) (0.25 g, 1.02 mmol) in isopropanol (10 mL) were added 3-nitroaniline (0.141 g, 1.02 mmol) and trifluoroacetic acid (0.078 mL). Then the reaction mixture was heated at 100° C. for 12 hours. After 12 hours, (TLC monitoring) reaction mixture was cooled to room temperature and the precipitated solid was filtered and washed with ice-cold isopropanol (5 mL). Solid was dried and used for the further steps without any purification. LCMS $[M+H]^+$ 346.1.

Step 3: Synthesis of N2-(3-aminophenyl)-5-chloro-N4-(1-methyl-1H-pyrazol-4-yl)pyrimidine-2,4-diamine (371)

The title compound was prepared in a manner substantially similar to procedure mentioned in General Procedure L, to afford the desired compound (371) as brown solid. LCMS $[M+H]^+$ 316.1.

Step 4: Synthesis of N-(3-((5-chloro-4-((1-methyl-1H-pyrazol-4-yl)amino)pyrimidin-2-yl)amino)phenyl)acrylamide (Compound 275)

The title compound was prepared in a manner substantially similar to procedure mentioned in General Procedure $K_2$, to afford the desired compound (Compound 275) as off white solid.

$^1H$ NMR (400 MHz, DMSO-d6): δ 10.11 (s, 1H), 9.46 (bs, 1H), 9.29 (bs, 1H), 8.11 (s, 1H), 8.06 (s, 1H), 7.92 (s, 1H), 7.70 (s, 1H), 7.36-7.32 (m, 2H), 7.26-6.90 (m, 2H), 6.49-6.42 (m, 1H), 6.26-6.21 (m, 1H), 5.75-5.72 (m, 1H), 3.75 (s, 3H). LCMS $[M+H]^+$ 370.1.

TABLE 23

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 276 | 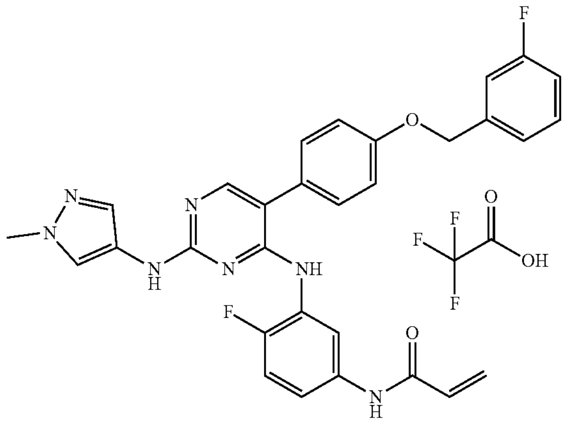 | $K_2$ | 554.2 | δ 10.28 (s, 1H), 9.95 (bs, 1H), 9.28 (bs, 1H), 7.87-7.85 (m, 2H), 7.58 (bs, 1H), 7.49-7.44 (m, 3H), 7.37-7.26 (m, 4H), 7.21-7.09 (m, 5H), 6.45-6.38 (m, 1H), 6.25 (dd, J = 1.6 Hz, J = 16.8 Hz, 1H), 5.77 (dd, J = 2.0 Hz, J = 10.0 Hz, 1H), 5.21 (s, 2H), 3.60 (bs, 3H). |

TABLE 23-continued

| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 277 | 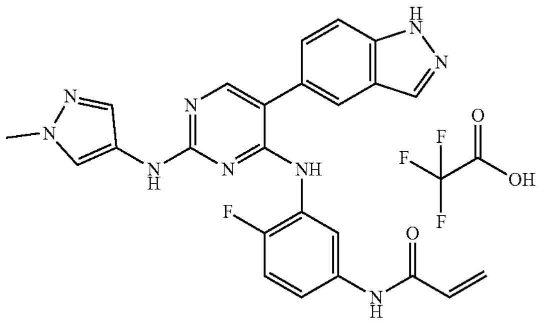 | $K_2$ | 470.2 | δ 13.20 (bs, 1H), 10.27 (s, 1H), 9.93 (bs, 1H), 9.31 (bs, 1H), 8.18 (s, 1H), 7.92-7.85 (m, 3H), 7.70-7.50 (m, 2H), 7.49-6.90 (m, 5H), 6.44-6.38 (m, 1H), 6.25 (dd, J = 16.8 Hz, J = 2.0 Hz, 1H), 5.77 (dd, J = 10 Hz, J = 1.6 Hz, 1H), 3.61 (s, 3H). |

TABLE 39

| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 278 | 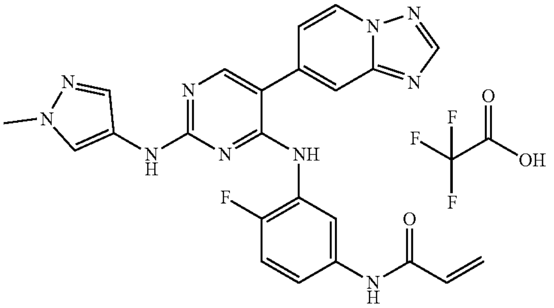 | $K_2$ | 471.2 | δ 10.32 (s, 1H), 10.21 (bs, 1H), 9.53 (bs, 1H), 9.06 (dd, J = 7.2 Hz, 1H), 8.57 (s, 1H), 8.13 (bs, 1H), 8.01 (s, 1H), 7.88 (bs, 1H), 7.56 (bs, 1H), 7.38-6.95 (m, 4H), 6.43-6.36 (m, 1H), 6.25-6.21 (m, 2H), 5.7 (dd, J = 12.0 Hz, J = 4.0 Hz, 1H), 3.57 (bs, 3H). |
| 279 | 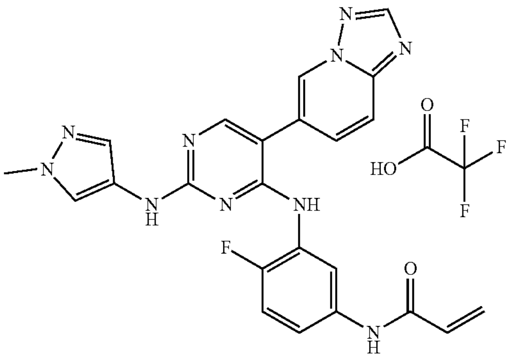 | $K_2$ | 471.2 | δ 10.30 (s, 1H), 9.43 (bs, 2H), 9.13 (s, 1H), 8.57 (s, 1H), 8.07 (s, 1H), 7.95 (d, J = 9.2 Hz, 1H), 7.88 (s, 1H), 7.71 (d, J = 9.2 Hz, 1H), 7.54 (s, 1H), 7.36 (s, 1H), 7.23-7.17 (m, 3H), 6.42-6.36 (m, 1H), 6.23 (dd, J = 17.2 Hz, J = 1.2 Hz, 1H), 5.75 (dd, J = 10.0 Hz, J = 1.6 Hz, 1H), 3.57 (s, 3H). |

Scheme 88: Synthesis of N-[3-({5-fluoro-2-[(1-methyl-1H-pyrazol-4-yl)amino]pyrimidin-4-yl}amino)phenyl]prop-2-enamide (Compound 280)

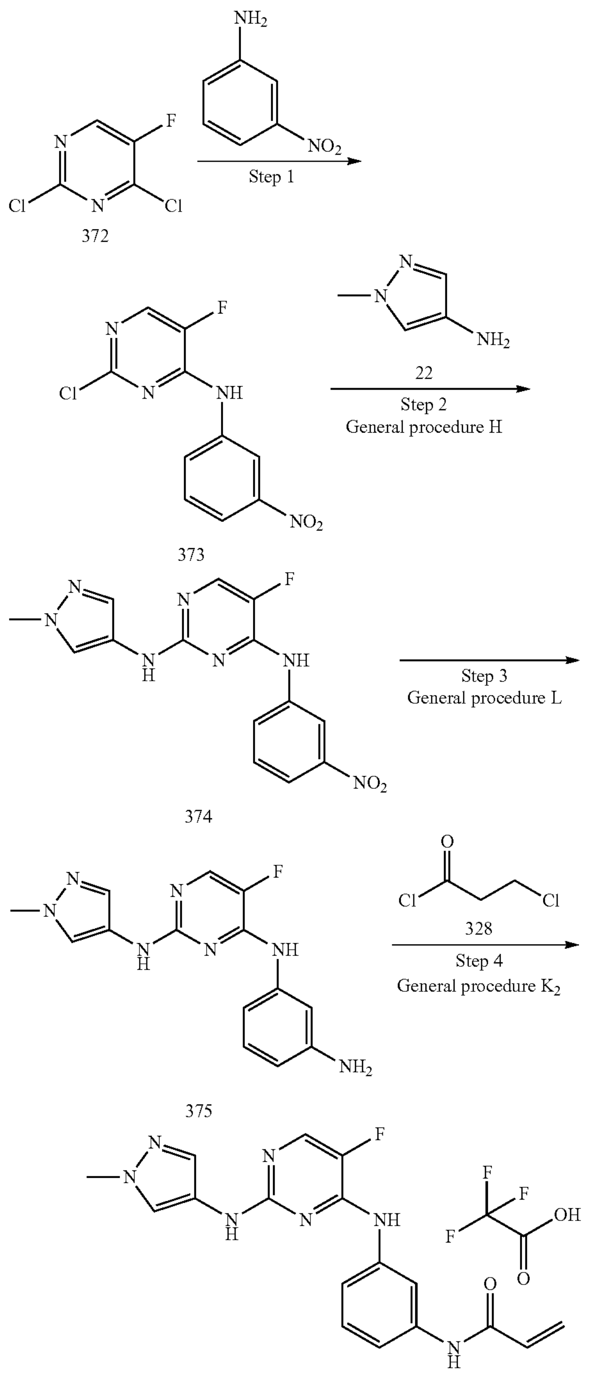

Compound 280

Step 1: Synthesis of 2-chloro-5-fluoro-N-(3-nitrophenyl)pyrimidin-4-amine (373)

To a stirred solution of 2,4-dichloro-5-fluoropyrimidine (372) (1 g, 5.99 mmol), 3-nitroaniline (0.91 g, 6.59 mmol) in isopropanol (10 mL) was added N,N-diisopropylethylamine (2.33 g, 18 mmol) and the reaction mixture was stirred at 100° C. for 12 hours. The reaction was monitored by TLC and LCMS. Then the reaction mixture was cooled to room temperature, the precipitated solid was filtered, washed with hexane and dried to get 2-chloro-5-fluoro-N-(3-nitrophenyl)pyrimidin-4-amine (373) (1.25 g, 78%) as pale yellow solid. LCMS $[M+H]^+$ 269.1.

Step 2: Synthesis of 2-chloro-5-fluoro-N-(3-nitrophenyl)pyrimidin-4-amine (374)

The title compound was prepared in a manner substantially similar to procedure mentioned in General Procedure H, to afford the desired compound (374) as pale yellow solid. LCMS $[M+H]^+$ 330.2.

Step 3: Synthesis of N4-(3-aminophenyl)-5-fluoro-N2-(1-methyl-1H-pyrazol-4-yl)pyrimidine-2,4-diamine (375)

The title compound was prepared in a manner substantially similar to procedure mentioned in General Procedure L, to afford the desired compound (375) as pale yellow solid. LCMS $[M+H]^+$ 300.2.

Step 4: Synthesis of N-[3-({5-fluoro-2-[(1-methyl-1H-pyrazol-4-yl)amino]pyrimidin-4-yl}amino)phenyl]prop-2-enamide (Compound 280)

The title compound was prepared in a manner substantially similar to procedure mentioned in General Procedure $K_2$, to afford the desired compound (Compound 280) as off white solid.

$^1$H NMR (400 MHz, DMSO-d6): δ 10.27 (m, 2H), 8.20 (bs, 1H), 7.94 (s, 1H), 7.73-7.34 (m, 6H), 6.64-6.49 (s, 1H), 6.42-6.23 (m, 1H), 6.07-6.03 (m, 1H), 5.77-5.74 (m, 1H), 2.83 (s, 3H); LCMS $[M+H]^+$ 354.2.

Scheme 89: Synthesis of N-[3-bromo-5-({5-chloro-2-[(1-methyl-1H-pyrazol-4-yl)amino]pyrimidin-4-yl}amino)phenyl]prop-2-enamide (Compound 283)

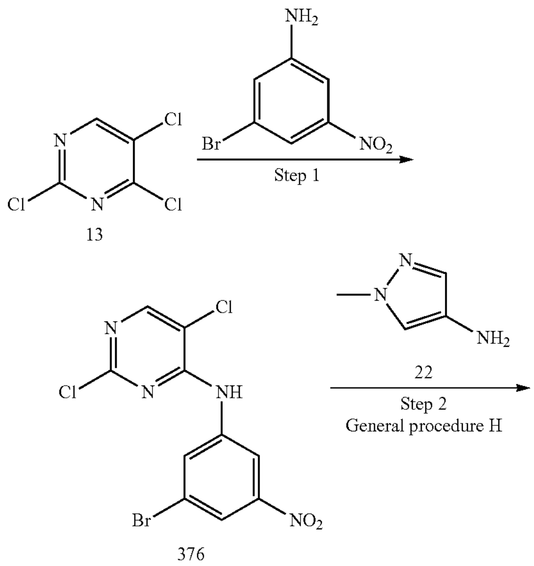

-continued

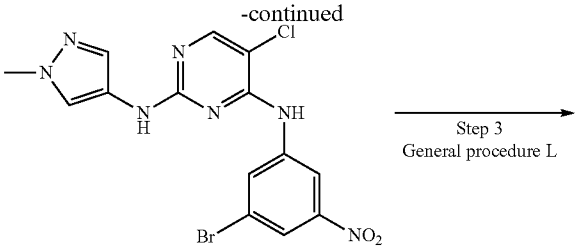

377

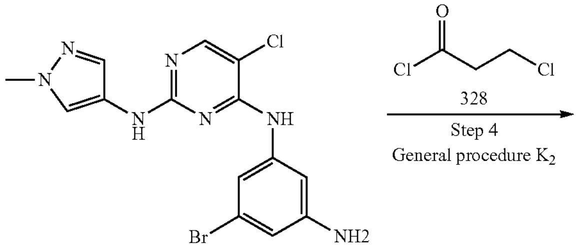

378

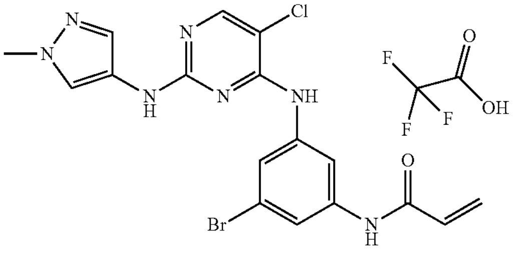

Compound 283

Step 1: Synthesis of N-(3-bromo-5-nitrophenyl)-2,5-dichloropyrimidin-4-amine (376)

To a stirred solution of 2,4,5-trichloropyrimidine (13) (0.5 g, 2.73 mmol), 3-bromo-5-nitroaniline (0.651 g, 3.0 mmol) in dimethylformamide (5.0 mL), was added potassium carbonate (0.94 g, 6.81 mmol) at room temperature and the reaction mixture was heated at 110° C. for 12 hours. Progress of the reaction was monitored by TLC and LCMS. The reaction mixture was diluted with water (30.0 mL) and extracted with ethyl acetate (2×30 mL). The combined organic layer was dried over anhydrous sodium sulphate, filtered and concentrated under reduced pressure. The crude product was purified by silica gel column chromatography and was eluted with 75% heptane in ethyl acetate to give N-(3-bromo-5-nitrophenyl)-2,5-dichloropyrimidin-4-amine (0.6 g, 62%)-1,3,2-dioxaborolan-2-yl)aniline (376) as yellow solid (0.8 g, 33%). LCMS $[M+H]^+$ 364.9.

Step 2: Synthesis of N4-(3-bromo-5-nitrophenyl)-5-chloro-N2-(1-methyl-1H-pyrazol-4-yl)pyrimidine-2,4-diamine (377)

The title compound was prepared in a manner substantially similar to procedure mentioned in General Procedure H, to afford the desired compound (377) as pale yellow solid. LCMS $[M+H]^+$ 424.

Step 3: Synthesis of N4-(3-amino-5-bromophenyl)-5-chloro-N2-(1-methyl-1H-pyrazol-4-yl)pyrimidine-2,4-diamine (378)

The title compound was prepared in a manner substantially similar to procedure mentioned in General Procedure L, to afford the desired compound (378) as pale yellow solid. LCMS $[M+H]^+$ 394.2.

Step 4: Synthesis of N-[3-bromo-5-({5-chloro-2-[(1-methyl-1H-pyrazol-4-yl)amino]pyrimidin-4-yl}amino)phenyl]prop-2-enamide (Compound 283)

The title compound was prepared in a manner substantially similar to procedure mentioned in General Procedure $K_2$, to afford the desired compound (Compound 283) as off white solid. $^1$H NMR (400 MHz, DMSO-d6): δ 10.33 (s, 1H), 9.35 (bs, 1H), 9.12 (bs, 1H), 8.17-8.07 (m, 1H), 7.86-7.78 (m, 2H), 7.49-7.31 (m, 4H), 6.44-6.39 (m, 1H), 6.35-6.26 (m, 1H), 5.81-5.78 (m, 1H), 3.65 (s, 3H); LCMS $[M+H]^+$ 448.1.

TABLE 24

The following compounds were prepared using the procedures described above:

| Cmpd No. | Structure | General Procedure | LCMS [M + H] | $^1$H-NMR (400 MHz, DMSO-$d_6$) |
|---|---|---|---|---|
| 284 | 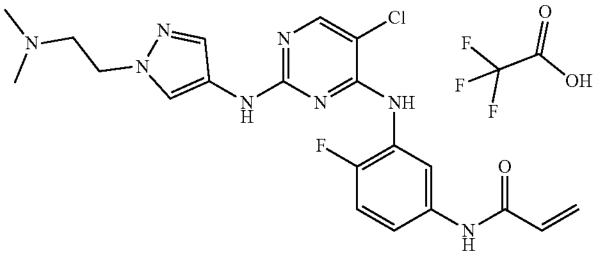 | $K_2$ | 445.2 | δ 10.27 (s, 1H), 9.25 (bs, 1H), 8.89 (bs, 1H), 8.04 (s, 1H), 7.75-7.66 (m, 2H), 7.32 (s, 2H), 7.19-7.03 (m, 2H), 6.43-6.36 (m, 1 H), 6.26 (m, 1H), 5.76-5.73 (m, 1H), 3.81 (s, 2H), 2.48 (bs, 2H), 2.08 (bs, 6H). |

TABLE 24-continued

The following compounds were prepared using the procedures described above:

| Cmpd No. | Structure | General Procedure | LCMS [M + H] | $^1$H-NMR (400 MHz, DMSO-$d_6$) |
|---|---|---|---|---|
| 287 | 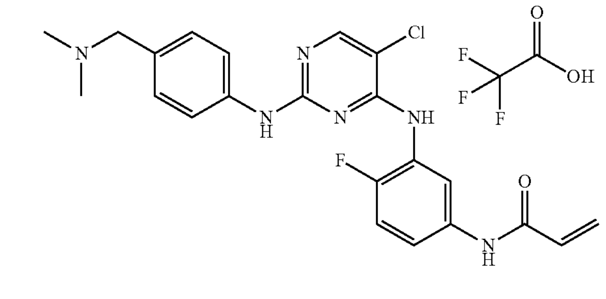 | $K_2$ | 441.2 | δ 10.23 (s, 1H), 9.50 (s, 1H), 9.34 (bs, 1H), 9.06 (bs, 1H), 8.15 (s, 1H), 7.69-7.63 (m, 1H), 7.52 (d, J = 8.4 Hz, 2H), 7.29-6.85 (m, 4H), 6.42-6.36 (m, 1H), 6.26-6.22 (m, 1H), 5.77-5.74 (m, 1H), 4.09 (d, J = 5.2 Hz, 2H), 2.65 (s, 6H). |
| 288 | 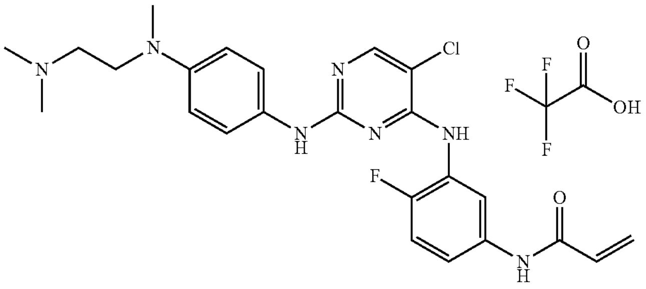 | $K_2$ | 484.2 | $CD_3OD$ δ 8.04 (s, 1H), 7.81 (bs, 1H), 7.69 (bs, 1H), 7.26-7.21 (m, 4H), 7.73 (d, J = 12.0 Hz, 1H), 6.43-6.34 (m, 2H), 5.81-5.79 (m, 1H), 3.61-3.55 (m, 2H), 3.31-3.30 (m, 2H), 2.94-2.79 (m, 9H). |

Scheme 90: Synthesis of N-[3-bromo-5-({2-[(1-methyl-1H-pyrazol-4-yl)amino]-5-[4-(trifluoromethyl)phenyl]pyrimidin-4-yl}amino)phenyl]prop-2-enamide TFA salt (Compound 290)

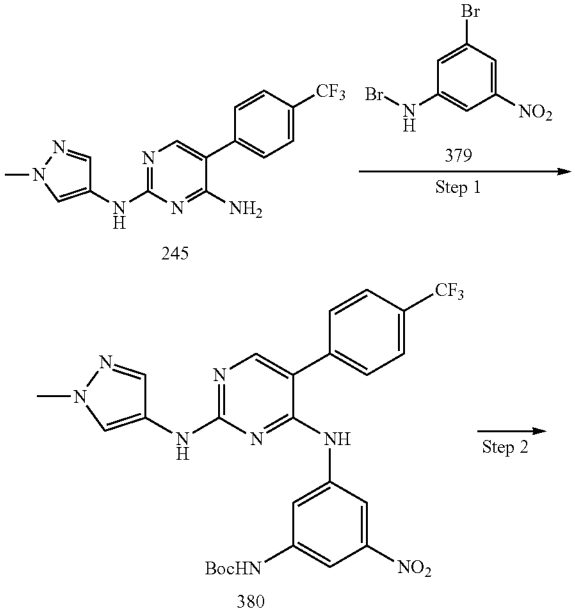

-continued

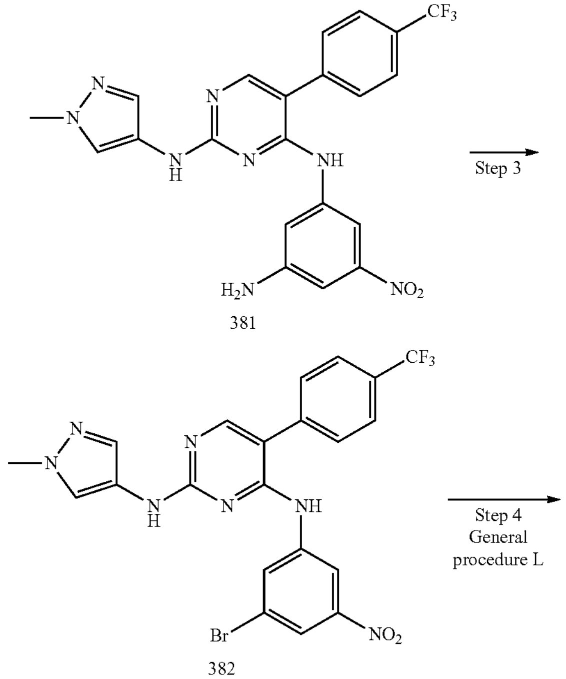

-continued

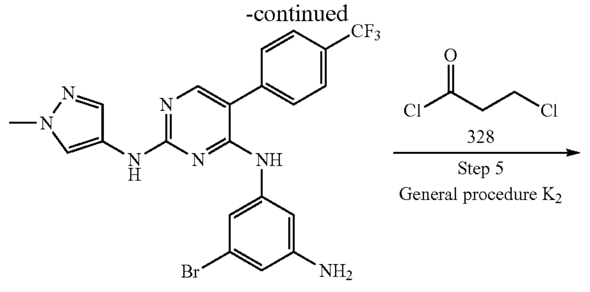

383

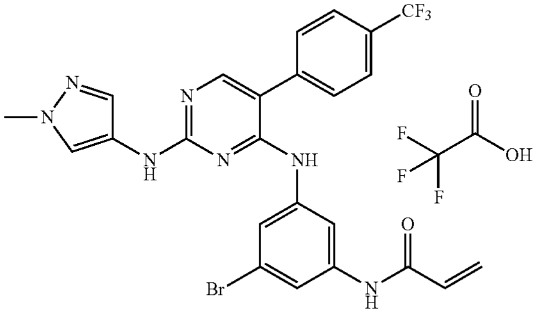

Compound 290

Step 1: Synthesis of tert-butyl N-[3-({2-[(1-methyl-1H-pyrazol-4-yl)amino]-5-[4-(trifluoromethyl)phenyl]pyrimidin-4-yl}amino)-5-nitrophenyl]carbamate (380)

To a stirred solution of N2-(1-methyl-1H-pyrazol-4-yl)-5-[4-(trifluoromethyl)phenyl]pyrimidine-2,4-diamine (245) (1 g, 2.99 mmol) in 1,4-dioxane (20 mL) were added tert-butyl N-(3-bromo-5-nitrophenyl)carbamate (379) (1.42 g, 4.49 mmol), cesium carbonate (2.92 g, 8.97 mmol). The reaction mixture was purged with argon for 10 minutes then added tris(1,5-diphenylpenta-1,4-dien-3-one) dipalladium (0.137 g, 0.150 mmol), [5-(diphenylphosphanyl)-9,9-dimethyl-9H-xanthen-4-yl]diphenylphosphane (0.086 g, 0.150 mmol) and the reaction mixture was heated at 105° C. for 12 hours. Then the reaction mixture was cooled, filtered through celite. The filtrate was diluted with water (10 mL) and extracted with dichloromethane (10 mL×2). The combined organic layer was washed with saturated ammonium chloride solution (10 mL), dried over anhydrous sodium sulfate and evaporated to get tert-butyl N-[3-({2-[(1-methyl-1H-pyrazol-4-yl)amino]-5-[4-(trifluoromethyl)phenyl]pyrimidin-4-yl}amino)-5-nitrophenyl]carbamate (380) as brown solid (1 g, 46%). LCMS $[M+H]^+$ 571.1.

Step 2: Synthesis of N4-(3-amino-5-nitrophenyl)-N2-(1-methyl-1H-pyrazol-4-yl)-5-[4-(trifluoromethyl)phenyl]pyrimidine-2,4-diamine (381)

To a stirred solution of tert-butyl N-[3-({2-[(1-methyl-1H-pyrazol-4-yl)amino]-5-[4-(trifluoromethyl)phenyl]pyrimidin-4-yl}amino)-5-nitrophenyl]carbamate (380) (0.980 g, 1.72 mmol) in dichloromethane (10 mL), HCl in dioxane (10 mL) was slowly added dropwise at room temperature and stirred for 6 hours. The reaction was monitored by LCMS and TLC. Then the reaction mixture was concentrated under reduced pressure. The crude product was washed with ether to obtain N4-(3-amino-5-nitrophenyl)-N2-(1-methyl-1H-pyrazol-4-yl)-5-[4-(trifluoromethyl)phenyl]pyrimidine-2,4-diamine (381) (0.8 g, 69%). LCMS $[M+H]^+$ 471.0

Step 3: Synthesis of N4-(3-bromo-5-nitrophenyl)-N2-(1-methyl-1H-pyrazol-4-yl)-5-[4-(trifluoromethyl)phenyl]pyrimidine-2,4-diamine (382)

To a stirred solution of N4-(3-amino-5-nitrophenyl)-N2-(1-methyl-1H-pyrazol-4-yl)-5-[4-(trifluoromethyl)phenyl]pyrimidine-2,4-diamine (381) (0.8 g, 1.7 mmol) in dichloromethane (10 mL), water (10 mL) was added bromotrichloromethane (4.19 mL, 42.5 mmol), sodium nitrite (0.587 g, 8.5 mmol) and acetic acid (2.92 mL, 51 mmol). The reaction mixture was stirred at room temperature for 3 hours. The reaction mixture was diluted with water (10 mL) and extracted with dichloromethane (20 mL×2). The combined organic layer was dried over anhydrous sodium sulfate, filtered and concentrated under reduced pressure. The crude material was washed with ether to give N4-(3-bromo-5-nitrophenyl)-N2-(1-methyl-1H-pyrazol-4-yl)-5-[4-(trifluoromethyl)phenyl]pyrimidine-2,4-diamine (382) (0.8 g, 62%). LCMS $[M+H]^+$ 536.0.

Step 4: Synthesis of N4-(3-amino-5-bromophenyl)-N2-(1-methyl-1H-pyrazol-4-yl)-5-[4-(trifluoromethyl)phenyl]pyrimidine-2,4-diamine (383)

The title compound was prepared in a manner substantially similar to procedure mentioned in General Procedure L, to afford the desired compound (383) as brown solid. LCMS $[M+H]^+$ 506.0.

Step 5: Synthesis of N-[3-bromo-5-({2-[(1-methyl-1H-pyrazol-4-yl)amino]-5-[4-(trifluoromethyl)phenyl]pyrimidin-4-yl}amino)phenyl]prop-2-enamide TFA salt (Compound 290)

The title compound was prepared in a manner substantially similar to procedure mentioned in General Procedure $K_2$, to afford the desired compound (Compound 2290) as off white solid. $^1H$ NMR (400 MHz, DMSO-d6): δ 10.30 (s, 1H), 9.70 (bs, 1H), 9.13 (bs, 1H), 8.22 (bs, 1H), 8.02 (s, 1H), 7.84-7.72 (m, 6H), 7.47-7.38 (m, 3H), 6.45-6.38 (m, 1H), 6.29-6.24 (m, 1H), 5.81-5.78 (m, 1H), 3.68 (bs, 3H). LCMS $[M+H]^+$ 560.1.

TABLE 25
| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 291 | 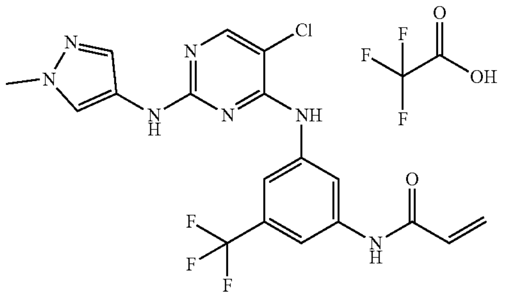 [SMILES: C=CC(=O)Nc1cc(Nc2nc(Nc3cnn(C)c3)ncc2Cl)cc(C(F)(F)F)c1 ; O=C(O)C(F)(F)F] | $K_2$ | 438.2 | δ 10.49 (s, 1H), 9.50-9.10 (m, 2H), 8.20-7.98 (m, 3H), 7.56 (s, 1H), 7.45-6.90 (m, 3H), 6.46-6.39 (m, 1H), 6.30-6.26 (m, 1H), 5.82-5.79 (m, 1H), 3.55 (bs, 3H). |
| 292 | 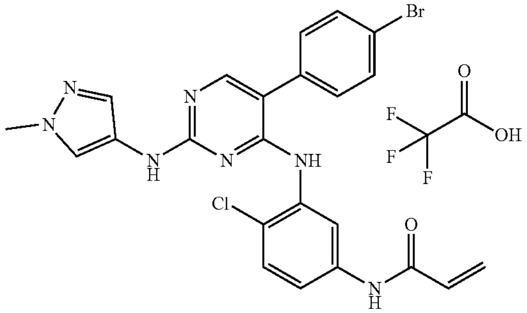 | $K_2$ | 525.1 | δ 10.38 (s, 1H), 9.93 (bs, 1H), 9.34 (bs, 1H), 7.93-7.88 (m, 2H), 7.71-7.47 (m, 7H), 7.17 (bs, 1H), 7.07 (bs, 1H), 6.43-6.39 (m, 1H), 6.24-6.21 (m, 1H), 5.78-5.75 (m, 1H), 3.53 (bs, 3H). |
| 293 | 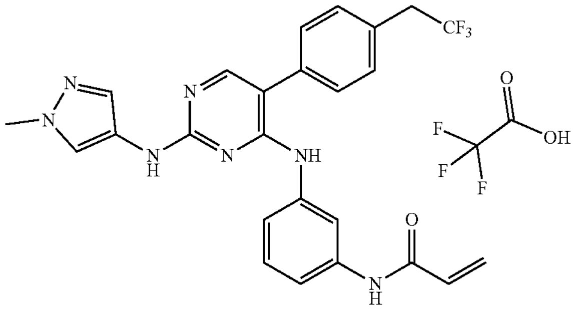 | $K_2$ | 493.0 | δ 10.43 (bs, 1H), 10.28 (s, 1H), 9.77 (bs, 1H), 7.92-7.87 (m, 2H), 7.58-7.40 (m, 6H), 7.34-7.25 (m, 3H), 7.17 (bs, 1H), 6.48-6.41 (m, 1H), 6.27-6.23 (m, 1H), 5.78-5.75 (m, 1H), 3.79-3.70 (m, 2H), 3.62 (bs, 3H). |
| 294 | 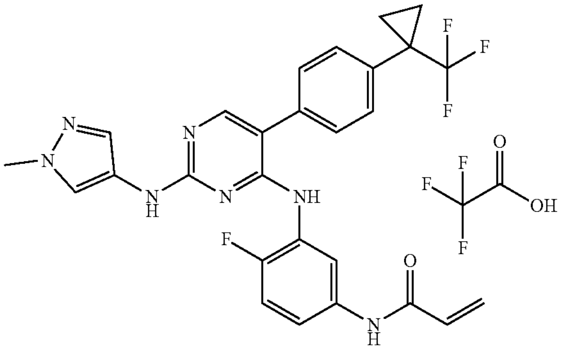 | $K_2$ | 538.2 | δ 10.28 (s, 1H), 9.95 (bs, 1H), 9.31 (bs, 1H), 7.93-7.92 (m, 2H), 7.59-7.52 (m, 4H), 7.40-7.00 (m, 5H), 6.43-6.36 (m, 1H), 6.25-6.21 (m, 1H), 5.76-5.73 (m, 1H), 3.56 (bs, 3H), 1.40-1.37 (m, 2H), 1.21-1.12 (m, 2H). |

TABLE 25-continued
| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 295 | 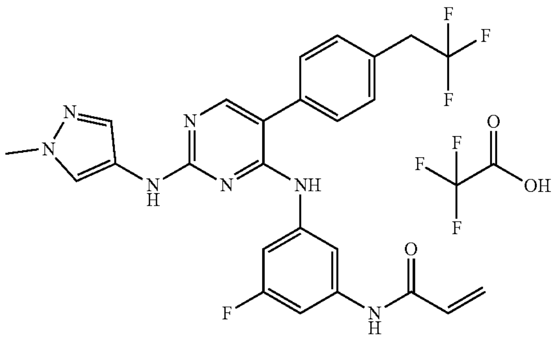 | $K_2$ | 512.2 | δ 10.26 (s, 1H), 9.21 (bs, 1H), 8.50 (bs, 1H), 7.99 (s, 1H), 7.66 (bs, 1H), 7.54-7.37 (m, 8H), 6.45-6.38 (m, 2H), 6.28-6.24 (m, 1H), 5.79-5.76 (m, 1H), 3.74-3.66 (m, 5H). |
| 296 | 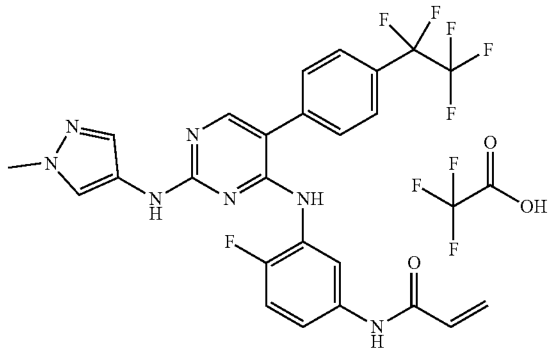 | $K_2$ | 548.1 | δ 10.27 (s, 1H), 9.84 (bs, 1H), 9.22 (bs, 1H), 8.08 (bs, 1H), 7.81-7.75 (m, 5H), 7.55 (bs, 1H), 7.33-7.06 (m, 3H), 6.93 (bs, 1H), 6.42-6.36 (m, 1H), 6.25-6.20 (m, 1H), 5.74 (d, J = 12.0 Hz, 1H), 3.56 (m, 3H). |
| 297 | 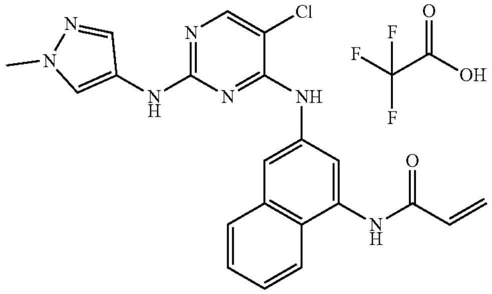 | $K_2$ | 420.2 | δ 10.18 (s, 1H), 9.34 (bs, 2H), 8.14-8.07 (m, 4H), 7.90 (bs, 1H), 7.59-7.53 (m, 3H), 7.29 (bs, 2H), 6.78-6.71 (m, 1H), 6.33-6.29 (m, 1H), 5.84-5.81 (m, 1H), 3.63 (s, 3H). |
| 298 | 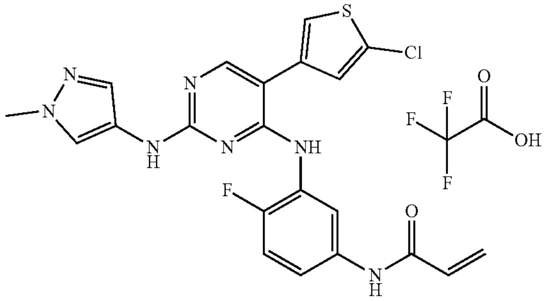 | $K_2$ | 470.1 | δ 10.32 (s, 1H), 10.16 (bs, 1H), 9.39 (bs, 1H), 8.03 (bs, 1H), 7.90-7.89 (m, 1H), 7.66-7.60 (m, 2H), 7.37-7.34 (m, 2H), 7.29-7.12 (m, 3H), 6.46-6.39 (m, 1H), 6.28-6.24 (m, 1H), 5.79-5.76 (m, 1H), 3.59 (s, 3H). |

TABLE 25-continued
| The following compounds were prepared using the procedures described above: | | | | |
|---|---|---|---|---|
| Cmpd. No. | Structure | General Procedure | LCMS [M + H] | $^1$H-NMR (400 MHz, DMSO-$d_6$) |
| 299 | 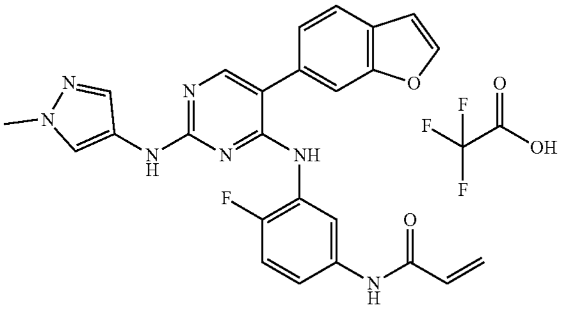 | $K_2$ | 470.2 | δ 10.29 (s, 1H), 10.02 (bs, 1H), 9.39 (bs, 1H), 8.09-7.78 (m, 5H), 7.58 (bs, 1H), 7.40-7.36 (m, 2H), 7.27-7.17 (m, 2H), 7.06-7.05 (m, 2H), 6.45-6.38 (m, 1H), 6.28-6.23 (m, 1H), 5.78-5.75 (m, 1H), 3.60 (s, 3H). |
| 300 | 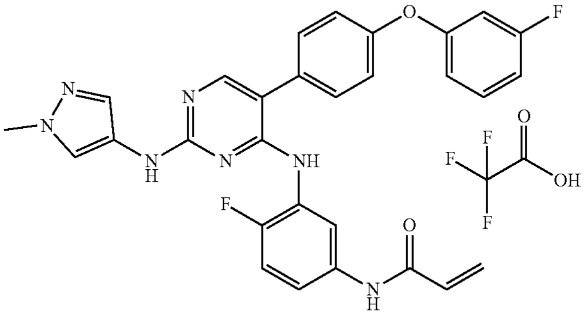 | $K_2$ | 540.2 | δ 10.32 (s, 1H), 10.17 (bs, 1H), 9.49 (bs, 1H), 7.93-7.88 (m, 2H), 7.62-7.56 (m, 3H), 7.54-7.38 (m, 2H), 7.22-7.12 (m, 3H), 7.02 (s, 1H), 7.01-6.97 (m, 2H), 6.92-6.89 (m, 2H), 6.43-6.36 (m, 1H), 6.26-6.21 (m, 1H), 5.77-5.74 (m, 1H), 3.57 (bs, 3H). |
| 301 | 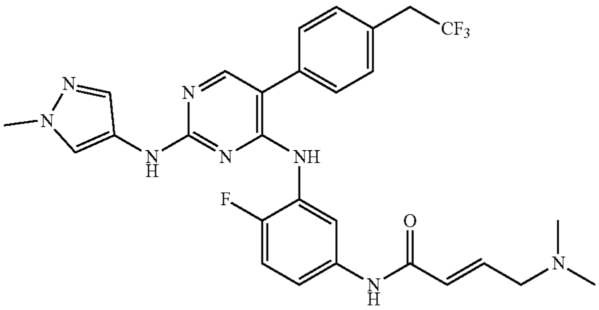 | $K_2$ | 569.4 | δ 10.10 (s, 1H), 9.11 (bs, 1H), 8.27 (bs, 1H), 7.94 (s, 1H), 7.78-7.77 (m, 1H), 7.58 (s, 1H), 7.53-7.51 (m, 2H), 7.47-7.45 (m, 2H), 7.28-7.19 (m, 3H), 6.76-6.69 (m, 1H), 6.27-6.23 (m, 1H), 3.74-3.63 (m, 2H), 3.56 (bs, 3H), 3.06-3.05 (m, 2H), 2.22-2.12 (m, 6H). |
| 302 | 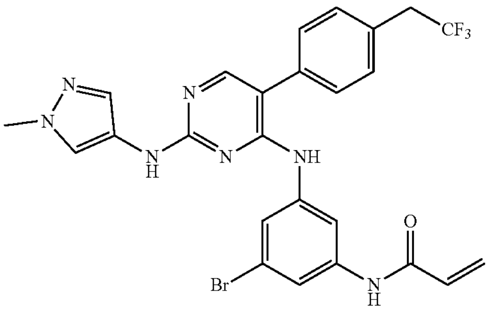 [SMILES: C=CC(=O)Nc1cc(Br)cc(Nc2nc(Nc3cnn(C)c3)ncc2-c2ccc(CC(F)(F)F)cc2)c1] | $K_2$ | 572.2 | δ 10.32 (s, 1H), 9.87 (bs, 1H), 9.28 (bs, 1H), 7.93 (s, 1H), 7.77-7.71 (m, 2H), 7.66-7.35 (m, 7H), 7.21-6.95 (m, 1H), 6.42-6.38 (m, 1H), 6.26-6.22 (m, 1H), 5.79-5.76 (m, 1H), 3.74-3.66 (m, 5H). |

TABLE 25-continued

The following compounds were prepared using the procedures described above:

| Cmpd. No. | Structure | General Procedure | LCMS [M + H] | $^1$H-NMR (400 MHz, DMSO-$d_6$) |
|---|---|---|---|---|
| 303 | 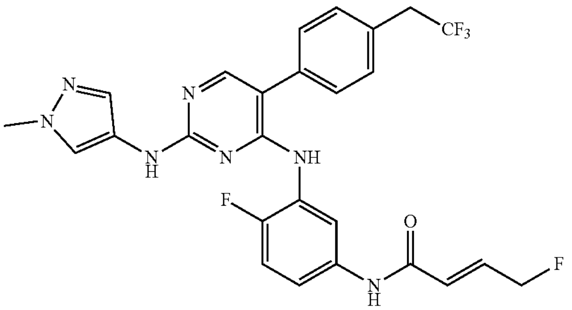 [SMILES: Cn1cc(Nc2ncc(-c3ccc(CC(F)(F)F)cc3)c(Nc3cc(NC(=O)/C=C/CF)ccc3F)n2)cn1] | J | 544.3 | δ 10.22 (s, 1H), 9.14 (s, 1H), 8.30 (s, 1H), 7.91 (s, 1H), 7.68 (s, 1H), 7.60 (s, 1H), 7.51-7.42 (dd, J = 8.4 Hz, J = 28.8 Hz, 1H), 6.89 (m, 6H), 6.34 (s, 1H), 6.32 (d, J = 15.6 Hz, 1H), 5.21 (s, 1H), 5.09 (s, 1H), 3.66 (m, 2H), 3.53 (bs, 3 H). |
| 304 | 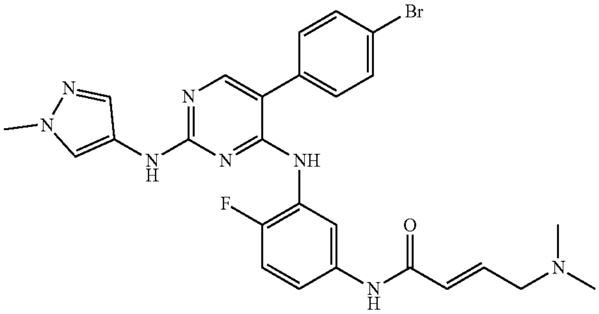 | J | 565.0 | δ 10.53 (s, 1H), 10.37 (bs, 1H), 10.07 (bs, 1H), 9.39 (bs, 1H), 7.99 (bs, 1H), 7.84-7.83 (m, 1H), 7.73-7.64 (m, 3H), 7.49-7.38 (m, 3H), 7.27-7.02 (m, 2H), 6.78-6.71 (m, 1H), 6.48-6.40 (m, 1H), 4.18-4.16 (s, 2H), 3.95 (bs, 3H), 3.10 (s, 6H). |
| 305 | 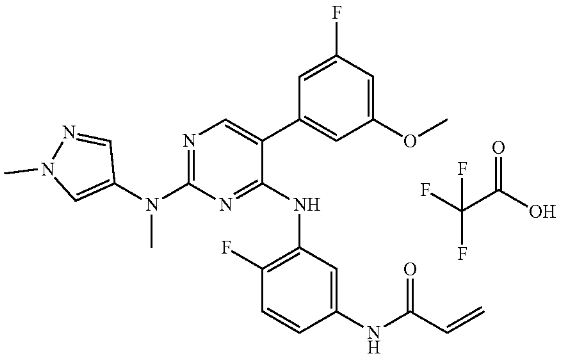 | $K_2$ | 492.3 | δ 10.25 (s, 1H), 8.87 (s, 1H), 7.94 (bs, 2H), 7.62 (bs, 1H), 7.49 (d, J = 13.2 Hz, 2H), 7.31-7.26 (m, 1H), 6.92-6.87 (m, 4H), 6.46-6.39 (m, 1H), 6.25 (dd, J = 16.8 Hz, J = 1.6 Hz, 1H), 5.76 (dd, J = 10.0 Hz, J = 1.6 Hz, 1H), 4.01 (s, 6H), 3.17 (s, 3H). |

Example 2: Cellular Proliferation (Alamar Blue) Assays

Cell Line Details:

1. EGFR(D770_N771insSVD) expressing Ba/F3 stable cell line
2. EGFR (A767_dupASV) expressing Ba/F3 stable cell line
3. A431 cells
4. EGFR (H773insNPH) expressing Ba/F3 stable cell line
5. HER2 (A775_G776insYVMA) expressing Ba/F3 stable cell line Assay Procedure:

1. Seed cells at 5000 for A431 and 15,000 cells for Ba/F3 in 100 μL/well in complete media (for A431: DMEM with 100% FBS and for Ba/F3 cells: RPMI with 10% FBS) in 96-well tissue culture plate. Leave outer wells without cells for background measurements. Incubate at 37 degree Celsius in 500 $CO_2$ humidified incubator for 16-18 hours.
2. Add 0.025 ml of 5× concentration compound dilution or DMSO control. Final compound concentration range is 10-0.0005 μM prepared in 3-fold serial dilutions. Incubate for 72 hr at 37 degree Celsius in 500 $CO_2$ humidified incubator.
3. Add 0.0125 ml Alamar Blue™ reagent to each well with multi-channel pipette and tap gently on each side of the plate to mix. Incubate for 3 hours at 37 degree Celsius in 5% $CO_2$ humidified incubator.
4. Read plates on fluorescence reader (Tecan Spark Control, Device: Spark, Serial #: 1801006040) at 540 nm excitation, 590 nm emission wavelength.
5. Data analysis was performed using XLfit 5.5.0.5.

Table 26 shows the activity of compounds of the present disclosure in the EGFR and HER2 cellular proliferation assays.

TABLE 26
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 1 | 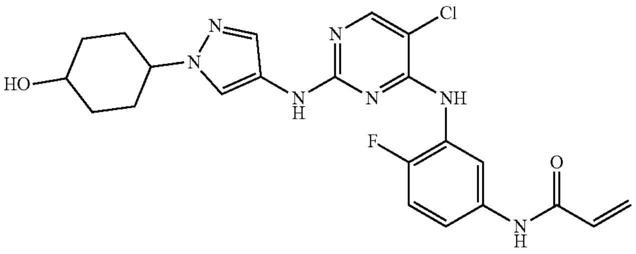 [SMILES: C=CC(=O)Nc1ccc(F)c(Nc2nc(Nc3cnn(C4CCC(O)CC4)c3)ncc2Cl)c1] | 3920 | 930 | 1032 | 796 | ND |
| 2 | 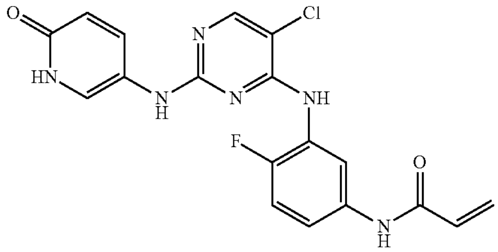 [SMILES: C=CC(=O)Nc1ccc(F)c(Nc2nc(Nc3ccc(=O)[nH]c3)ncc2Cl)c1] | >10000 | >10000 | 9244 | ND | ND |
| 3 | 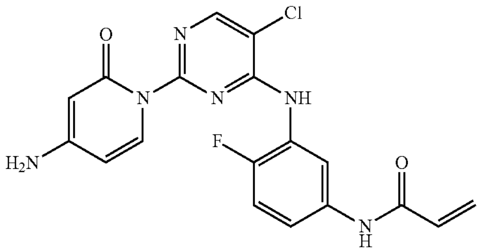 [SMILES: C=CC(=O)Nc1ccc(F)c(Nc2nc(-n3ccc(N)cc3=O)ncc2Cl)c1] | >10000 | >10000 | >10000 | ND | ND |
| 4 | 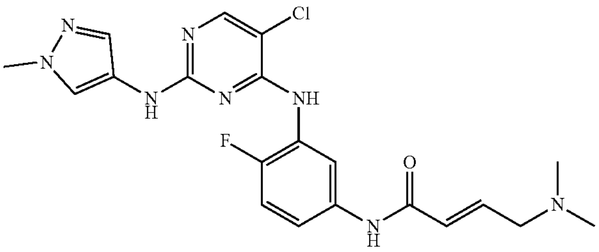 | 6589 | 1755 | 2999 | ND | ND |
| 5 | 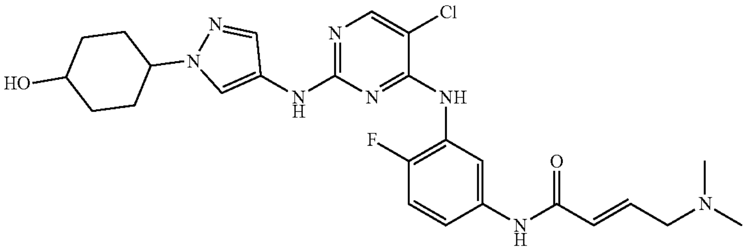 [SMILES: CN(C)C/C=C/C(=O)Nc1ccc(F)c(Nc2nc(Nc3cnn(C4CCC(O)CC4)c3)ncc2Cl)c1] | >10000 | 7379 | 5583 | ND | 4278 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 6 | 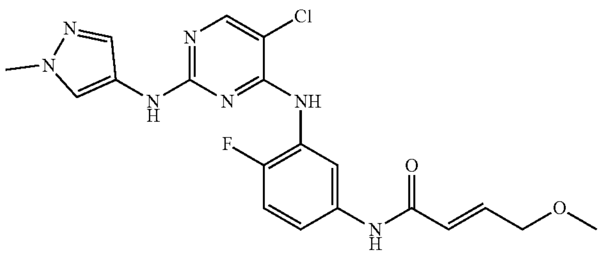 | >10000 | >10000 | >10000 | ND | 9014 |
| 7 | 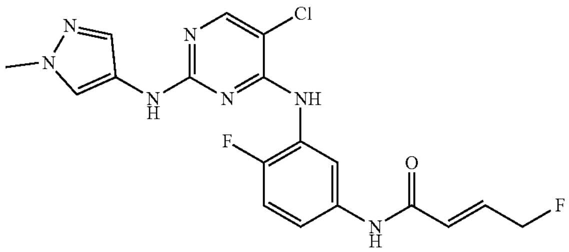 [SMILES: Cn1cc(Nc2ncc(Cl)c(Nc3cc(NC(=O)/C=C/CF)ccc3F)n2)cn1] | 8728 | 995 | 3272 | ND | 3222 |
| 8 | 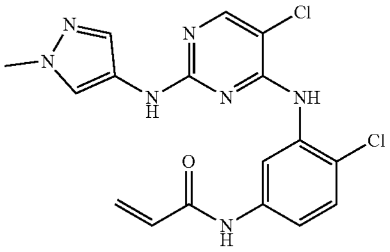 [SMILES: C=CC(=O)Nc1ccc(Cl)c(Nc2nc(Nc3cnn(C)c3)ncc2Cl)c1] | 8585 | 7580 | 7454 | ND | 4991 |
| 9 | 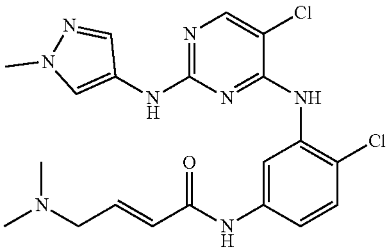 [SMILES: CN(C)C/C=C/C(=O)Nc1ccc(Cl)c(Nc2nc(Nc3cnn(C)c3)ncc2Cl)c1] | 8025 | >10000 | 9480 | ND | 7486 |
| 10 | 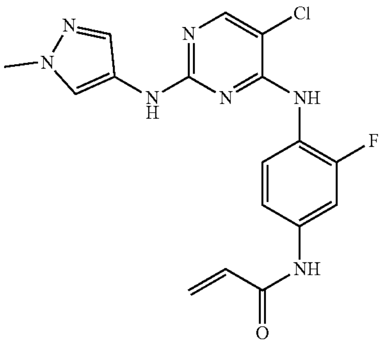 [SMILES: C=CC(=O)Nc1ccc(Nc2nc(Nc3cnn(C)c3)ncc2Cl)c(F)c1] | 3009 | >10000 | >10000 | ND | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 11 | 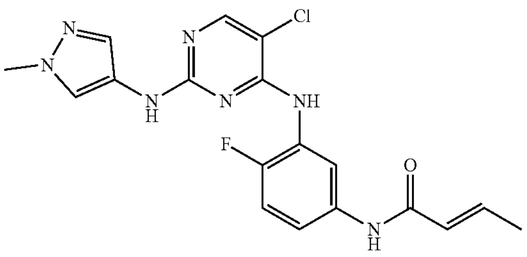 [SMILES: C/C=C/C(=O)Nc1ccc(F)c(Nc2nc(Nc3cnn(C)c3)ncc2Cl)c1] | >10000 | >10000 | >10000 | ND | 4720 |
| 12 | 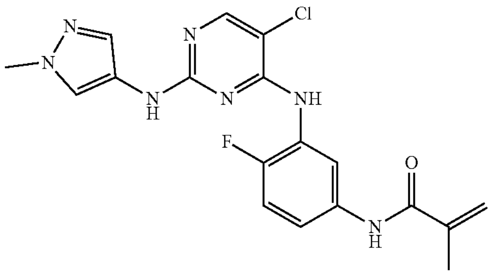 [SMILES: C=C(C)C(=O)Nc1ccc(F)c(Nc2nc(Nc3cnn(C)c3)ncc2Cl)c1] | >10000 | >10000 | >10000 | ND | 7031 |
| 13 | 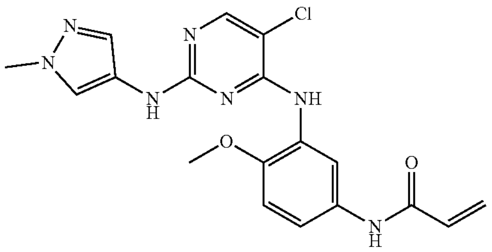 [SMILES: C=CC(=O)Nc1ccc(OC)c(Nc2nc(Nc3cnn(C)c3)ncc2Cl)c1] | >10000 | >10000 | >10000 | ND | >10000 |
| 14 | 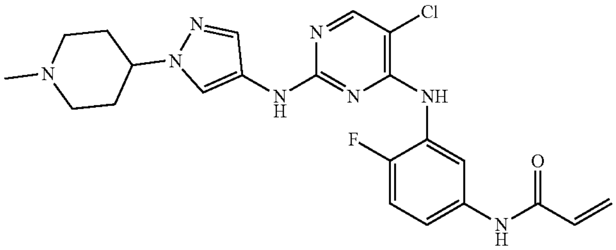 [SMILES: C=CC(=O)Nc1ccc(F)c(Nc2nc(Nc3cnn(C4CCN(C)CC4)c3)ncc2Cl)c1] | 1827 | 170 | 320 | 192 | 756 |
| 15 | 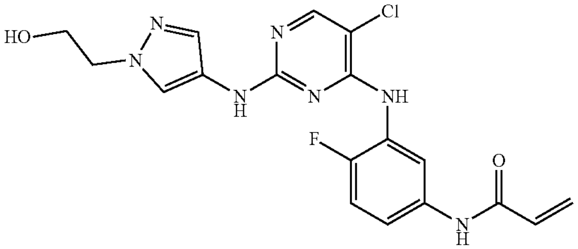 [SMILES: C=CC(=O)Nc1ccc(F)c(Nc2nc(Nc3cnn(CCO)c3)ncc2Cl)c1] | 4221 | 371 | 373 | ND | 543 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 16 | 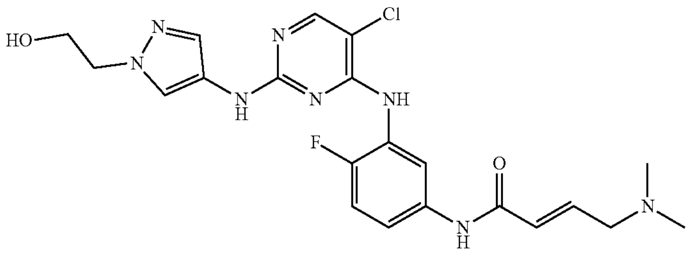 [SMILES: CN(C)C/C=C/C(=O)Nc1ccc(F)c(Nc2nc(Nc3cnn(CCO)c3)ncc2Cl)c1] | 9041 | 8841 | 9055 | ND | 1704 |
| 17 | 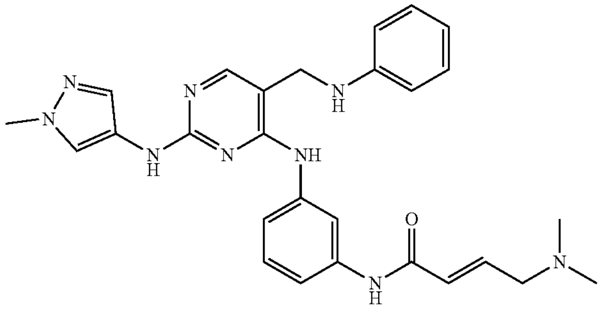 | 7742 | 1020 | 1527 | ND | 1881 |
| 18 | 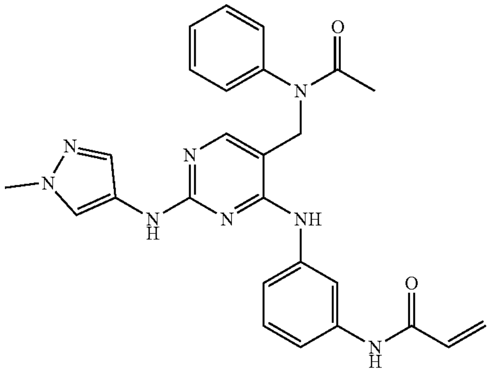 [SMILES: C=CC(=O)Nc1cccc(Nc2nc(Nc3cnn(C)c3)ncc2CN(C(C)=O)c2ccccc2)c1] | >10000 | 7157 | >10000 | ND | >10000 |
| 19 | 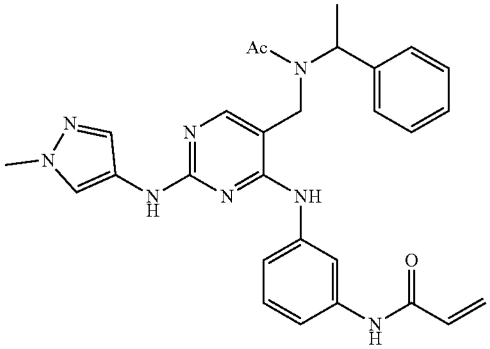 [SMILES: C=CC(=O)Nc1cccc(Nc2nc(Nc3cnn(C)c3)ncc2CN(C(C)=O)C(C)c2ccccc2)c1] | >10000 | >10000 | >10000 | ND | >10000 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 20 | 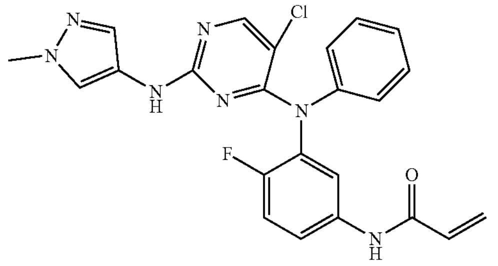 [SMILES: C=CC(=O)Nc1ccc(F)c(N(c2ccccc2)c2nc(Nc3cnn(C)c3)ncc2Cl)c1] | >10000 | ND | 2411 | ND | ND |
| 21 | 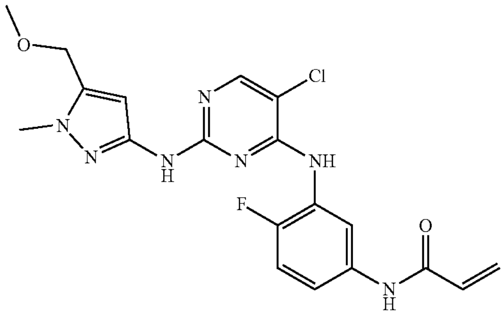 [SMILES: C=CC(=O)Nc1ccc(F)c(Nc2nc(Nc3cc(COC)n(C)n3)ncc2Cl)c1] | >10000 | ND | 4757 | ND | ND |
| 22 | 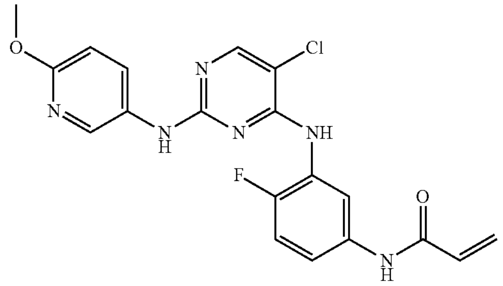 [SMILES: C=CC(=O)Nc1ccc(F)c(Nc2nc(Nc3ccc(OC)nc3)ncc2Cl)c1] | 7104 | 3000 | 7954 | 4738 | ND |
| 23 | 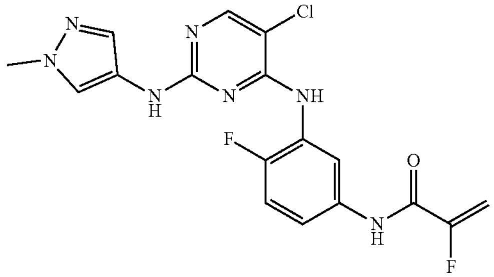 [SMILES: C=C(F)C(=O)Nc1ccc(F)c(Nc2nc(Nc3cnn(C)c3)ncc2Cl)c1] | >10000 | 9918 | >10000 | 4473 | ND |
| 24 | 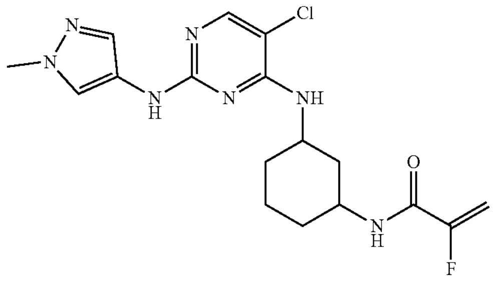 [SMILES: C=C(F)C(=O)NC1CCCC(Nc2nc(Nc3cnn(C)c3)ncc2Cl)C1] | >10000 | >10000 | >10000 | 4126 | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 25 | 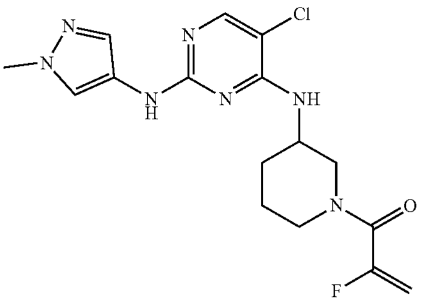 [SMILES: C=C(F)C(=O)N1CCCC(Nc2nc(Nc3cnn(C)c3)ncc2Cl)C1] | >10000 | >10000 | >10000 | >10000 | ND |
| 26 | 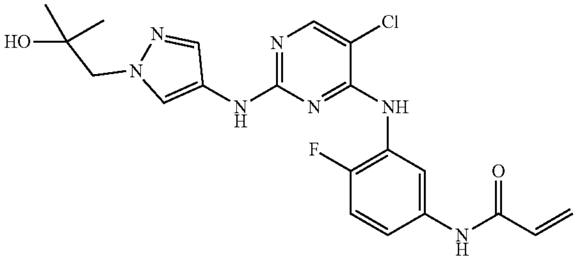 [SMILES: C=CC(=O)Nc1ccc(F)c(Nc2nc(Nc3cnn(CC(C)(C)O)c3)ncc2Cl)c1] | 7407 | 2453 | 4857 | 2092 | ND |
| 27 | 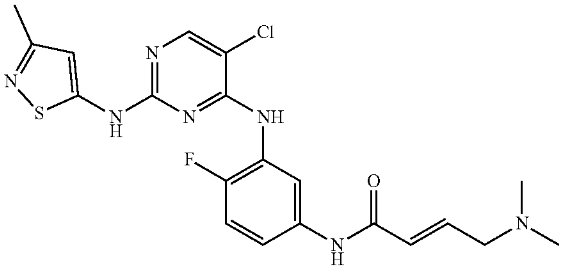 [SMILES: Cc1cc(Nc2ncc(Cl)c(Nc3cc(NC(=O)/C=C/CN(C)C)ccc3F)n2)sn1] | >10000 | 1987 | 2617 | ND | ND |
| 28 | 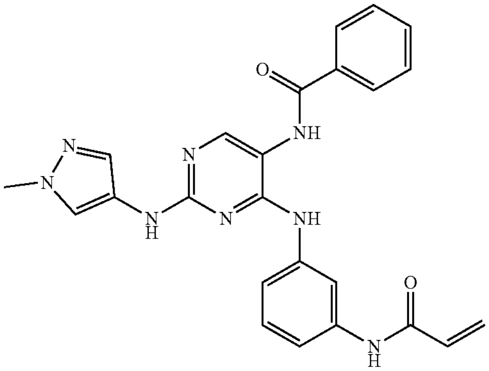 [SMILES: C=CC(=O)Nc1cccc(Nc2nc(Nc3cnn(C)c3)ncc2NC(=O)c2ccccc2)c1] | >10000 | 2240 | 3128 | 3005 | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 29 | 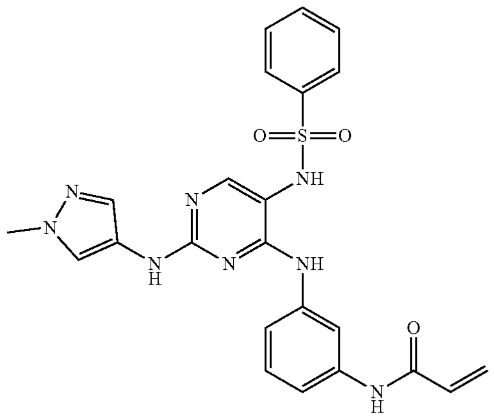 [SMILES: C=CC(=O)Nc1cccc(Nc2nc(Nc3cnn(C)c3)ncc2NS(=O)(=O)c2ccccc2)c1] | >10000 | >10000 | >10000 | ND | >10000 |
| 30 | 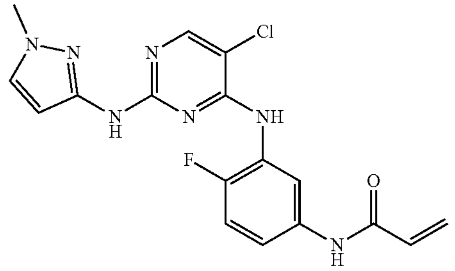 [SMILES: C=CC(=O)Nc1ccc(F)c(Nc2nc(Nc3ccn(C)n3)ncc2Cl)c1] | >10000 | 9626 | >10000 | ND | 2641 |
| 31 | 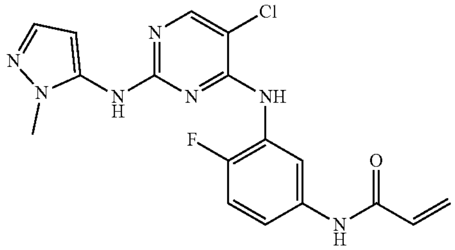 [SMILES: C=CC(=O)Nc1ccc(F)c(Nc2nc(Nc3ccnn3C)ncc2Cl)c1] | 9802 | 9872 | 9961 | ND | 5183 |
| 32 | 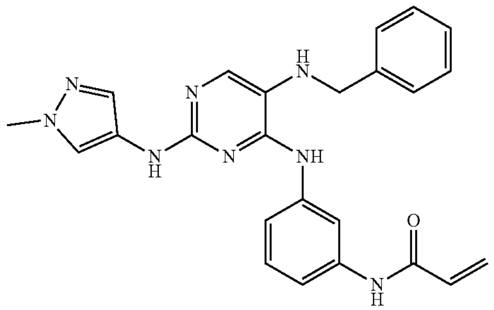 [SMILES: C=CC(=O)Nc1cccc(Nc2nc(Nc3cnn(C)c3)ncc2NCc2ccccc2)c1] | >10000 | 885 | 824 | ND | 1610 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 33 | 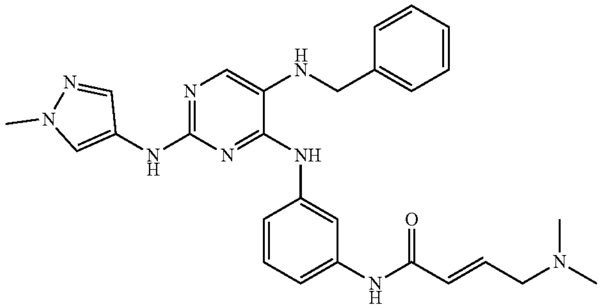 | 4011 | 4067 | 2979 | ND | 3027 |
| 34 | 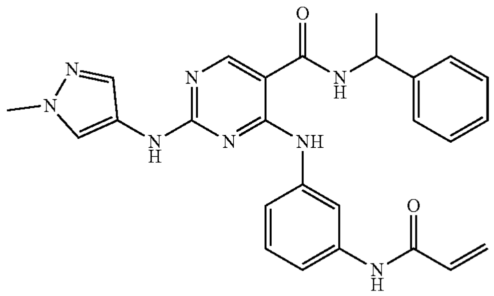 [SMILES: C=CC(=O)Nc1cccc(Nc2nc(Nc3cnn(C)c3)ncc2C(=O)NC(C)c2ccccc2)c1] | >10000 | 9314 | 9517 | >10000 | ND |
| 35 | 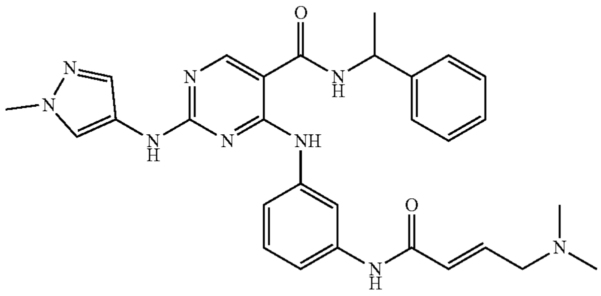 | >10000 | >10000 | >10000 | ND | >10000 |
| 36 | 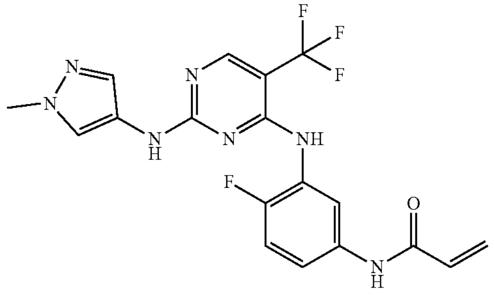 [SMILES: C=CC(=O)Nc1ccc(F)c(Nc2nc(Nc3cnn(C)c3)ncc2C(F)(F)F)c1] | 8150 | 332 | 357 | ND | 416 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 37 | 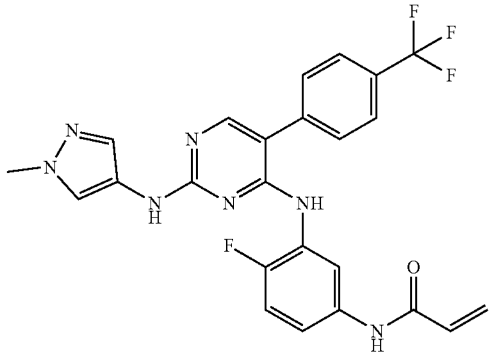 [SMILES: C=CC(=O)Nc1ccc(F)c(Nc2nc(Nc3cnn(C)c3)ncc2-c2ccc(C(F)(F)F)cc2)c1] | 185 | 73 | 34 | 85 | 974 |
| 38 | 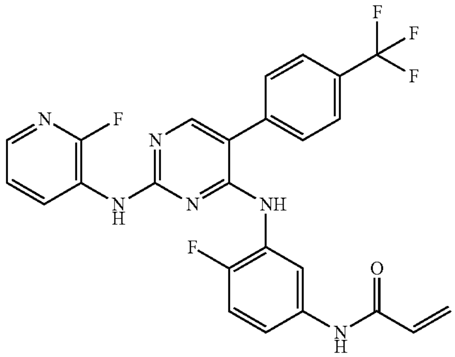 [SMILES: C=CC(=O)Nc1ccc(F)c(Nc2nc(Nc3cccnc3F)ncc2-c2ccc(C(F)(F)F)cc2)c1] | 1356 | 947 | 360 | ND | ND |
| 39 | 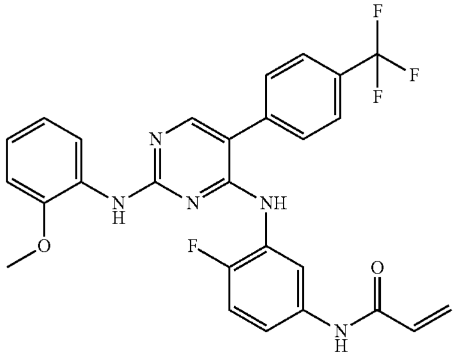 [SMILES: C=CC(=O)Nc1ccc(F)c(Nc2nc(Nc3ccccc3OC)ncc2-c2ccc(C(F)(F)F)cc2)c1] | 2925 | 8294 | 3040 | ND | ND |
| 40 | 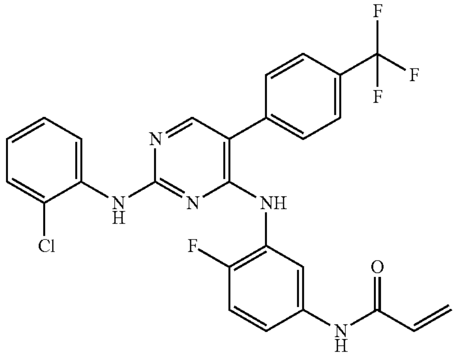 [SMILES: C=CC(=O)Nc1ccc(F)c(Nc2nc(Nc3ccccc3Cl)ncc2-c2ccc(C(F)(F)F)cc2)c1] | 3834 | >10000 | >10000 | ND | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 41 | 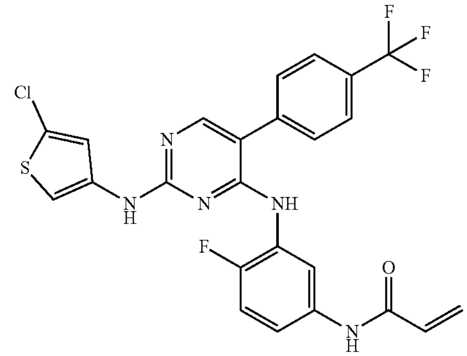 [SMILES: C=CC(=O)Nc1ccc(F)c(Nc2nc(Nc3csc(Cl)c3)ncc2-c2ccc(C(F)(F)F)cc2)c1] | 7330 | >10000 | 1661 | ND | ND |
| 42 | 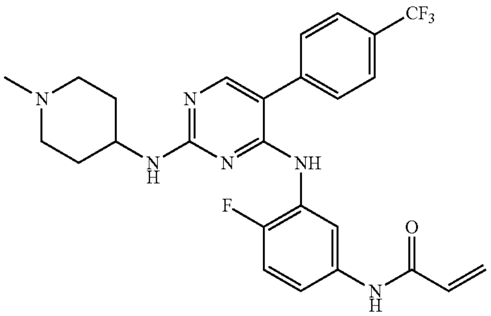 [SMILES: C=CC(=O)Nc1ccc(F)c(Nc2nc(NC3CCN(C)CC3)ncc2-c2ccc(C(F)(F)F)cc2)c1] | 8993 | >10000 | >10000 | ND | ND |
| 43 | 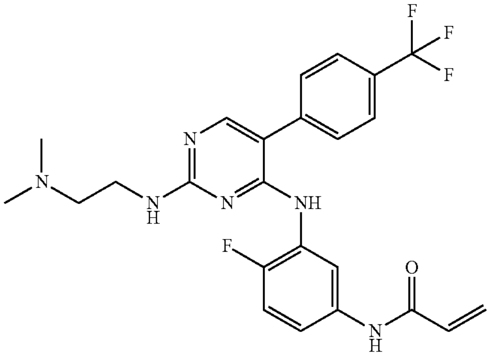 [SMILES: C=CC(=O)Nc1ccc(F)c(Nc2nc(NCCN(C)C)ncc2-c2ccc(C(F)(F)F)cc2)c1] | 3674 | >10000 | >10000 | ND | ND |
| 44 | 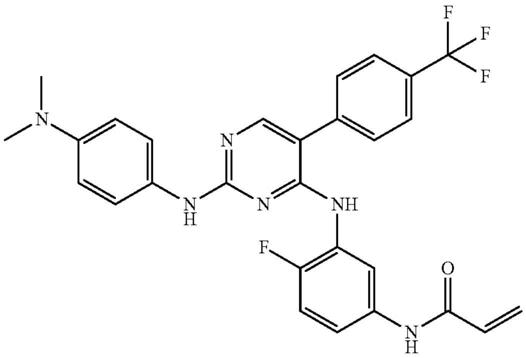 [SMILES: C=CC(=O)Nc1ccc(F)c(Nc2nc(Nc3ccc(N(C)C)cc3)ncc2-c2ccc(C(F)(F)F)cc2)c1] | 484 | >10000 | >10000 | ND | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 45 | 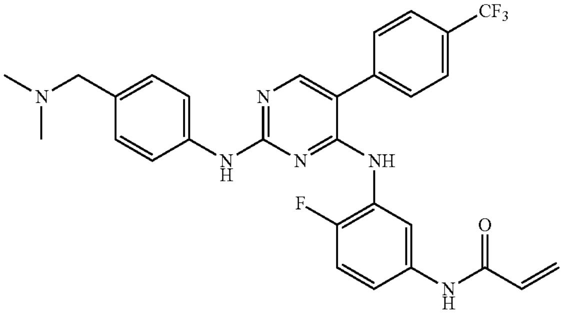 [SMILES: C=CC(=O)Nc1ccc(F)c(Nc2nc(Nc3ccc(CN(C)C)cc3)ncc2-c2ccc(C(F)(F)F)cc2)c1] | 27 | 238 | 105 | 149 | 134 |
| 46 | 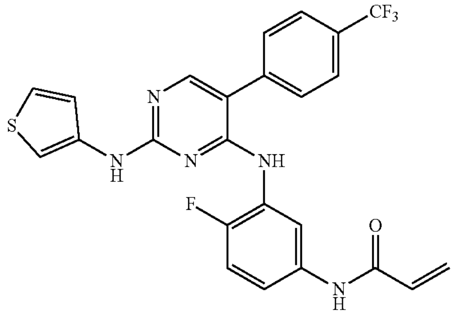 [SMILES: C=CC(=O)Nc1ccc(F)c(Nc2nc(Nc3ccsc3)ncc2-c2ccc(C(F)(F)F)cc2)c1] | 523 | 2737 | 973 | ND | ND |
| 47 | 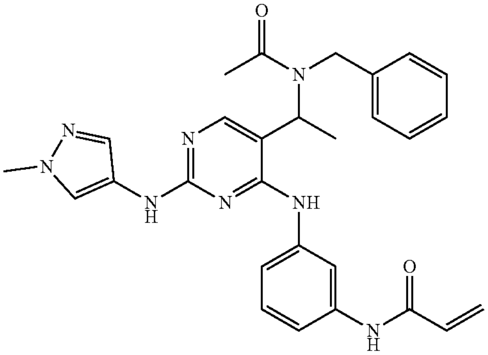 [SMILES: C=CC(=O)Nc1cccc(Nc2nc(Nc3cnn(C)c3)ncc2C(C)N(Cc2ccccc2)C(C)=O)c1] | >10000 | 7076 | 8846 | ND | >10000 |
| 48 | 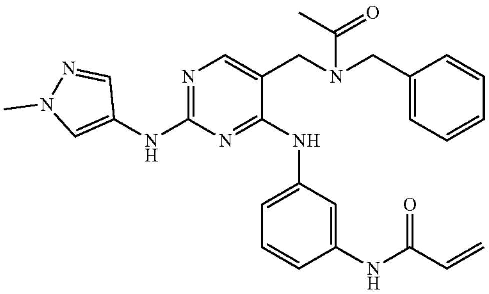 [SMILES: C=CC(=O)Nc1cccc(Nc2nc(Nc3cnn(C)c3)ncc2CN(Cc2ccccc2)C(C)=O)c1] | >10000 | >10000 | 8798 | ND | >10000 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 49 | 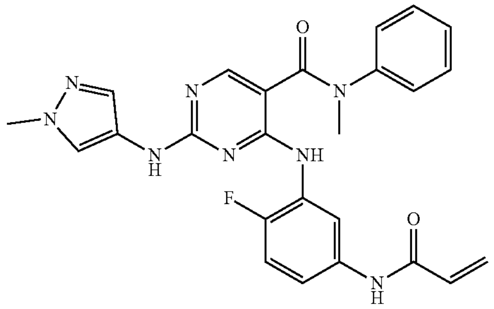 [SMILES: C=CC(=O)Nc1ccc(F)c(Nc2nc(Nc3cnn(C)c3)ncc2C(=O)N(C)c2ccccc2)c1] | >10000 | 3293 | 8621 | ND | ND |
| 50 | 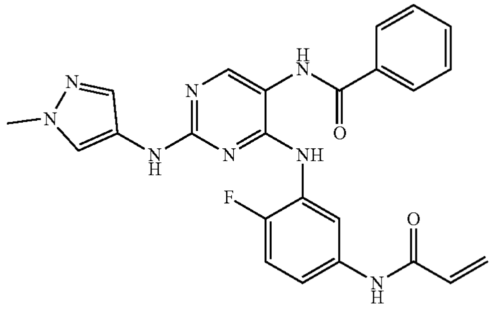 [SMILES: C=CC(=O)Nc1ccc(F)c(Nc2nc(Nc3cnn(C)c3)ncc2NC(=O)c2ccccc2)c1] | >10000 | 1469 | 1727 | ND | 8622 |
| 51 | 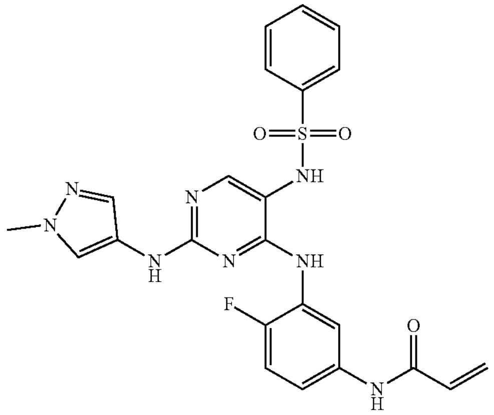 [SMILES: C=CC(=O)Nc1ccc(F)c(Nc2nc(Nc3cnn(C)c3)ncc2NS(=O)(=O)c2ccccc2)c1] | >10000 | >10000 | >10000 | ND | >10000 |
| 52 | 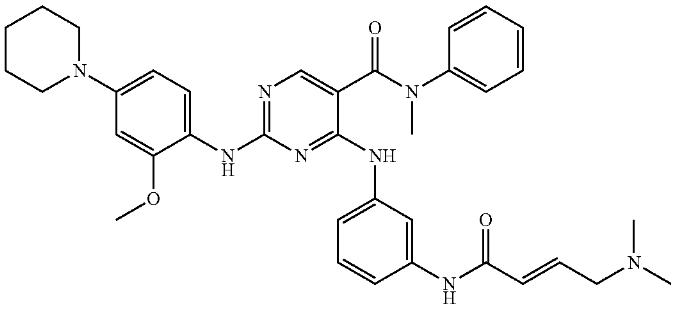 [SMILES: COc1cc(N2CCCCC2)ccc1Nc1ncc(C(=O)N(C)c2ccccc2)c(Nc2cccc(NC(=O)/C=C/CN(C)C)c2)n1] | 6562 | 982 | 3265 | >10000 | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 53 | 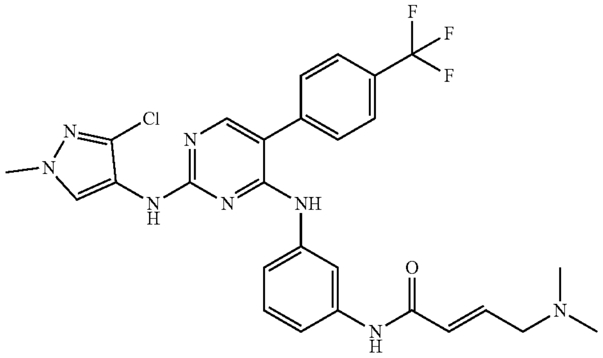 | 7295 | 1022 | 873 | 1890 | ND |
| 54 | 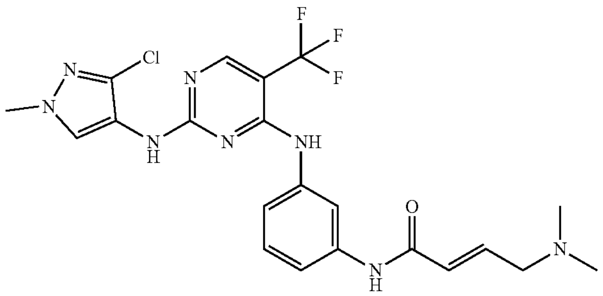 | 4533 | 1041 | 296 | 380 | ND |
| 55 | 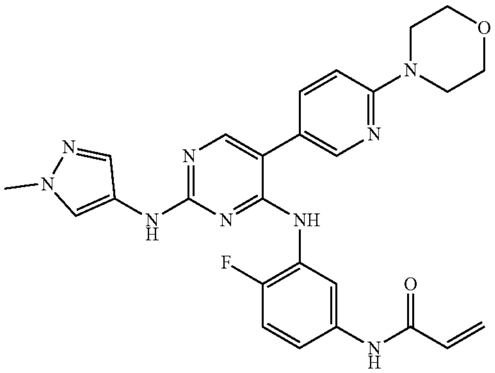 [SMILES: C=CC(=O)Nc1ccc(F)c(Nc2nc(Nc3cnn(C)c3)ncc2-c2ccc(N3CCOCC3)nc2)c1] | >10000 | 492 | 945 | ND | 1869 |
| 56 | 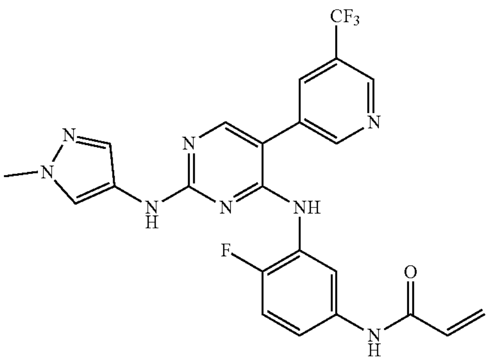 | 34 | 33 | 33 | 41 | 92 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 57 | 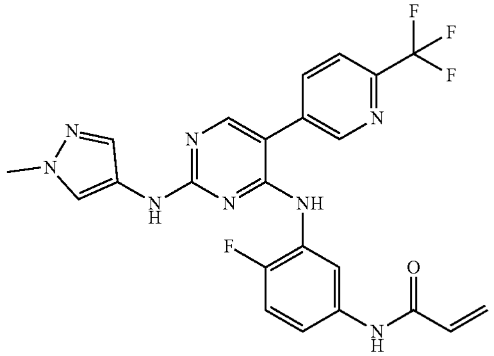 [SMILES: C=CC(=O)Nc1ccc(F)c(Nc2nc(Nc3cnn(C)c3)ncc2-c2ccc(C(F)(F)F)nc2)c1] | 1944 | 71 | 44 | 82 | 177 |
| 58 | 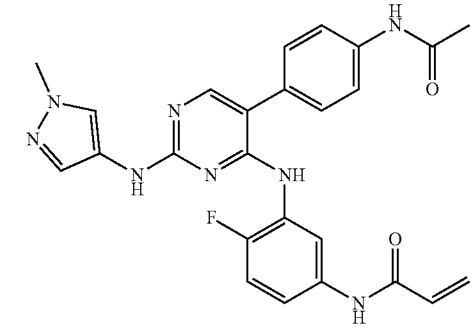 [SMILES: C=CC(=O)Nc1ccc(F)c(Nc2nc(Nc3cnn(C)c3)ncc2-c2ccc(NC(C)=O)cc2)c1] | >10000 | 2659 | 2888 | ND | ND |
| 59 | 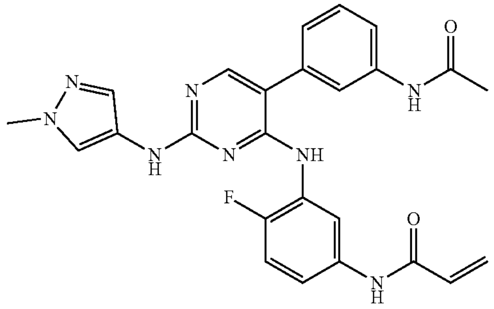 [SMILES: C=CC(=O)Nc1ccc(F)c(Nc2nc(Nc3cnn(C)c3)ncc2-c2cccc(NC(C)=O)c2)c1] | >10000 | >10000 | >10000 | ND | 10000 |
| 60 | 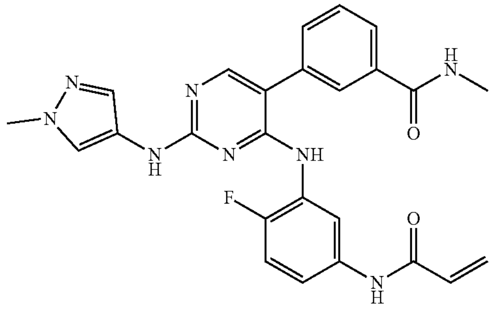 | >10000 | 7651 | 7941 | ND | 6577 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 61 | 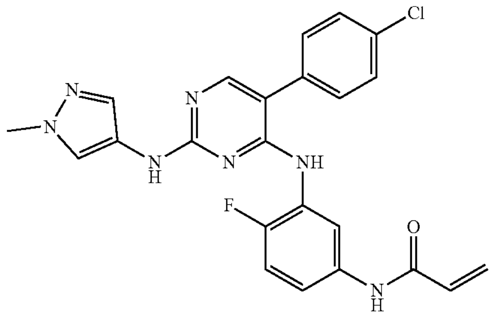 | 261 | 99 | 56 | 91 | 219 |
| 62 | 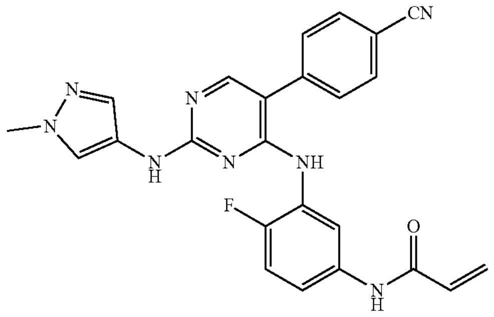 [SMILES: C=CC(=O)Nc1ccc(F)c(Nc2nc(Nc3cnn(C)c3)ncc2-c2ccc(C#N)cc2)c1] | >10000 | 307 | 323 | ND | 2586 |
| 63 | 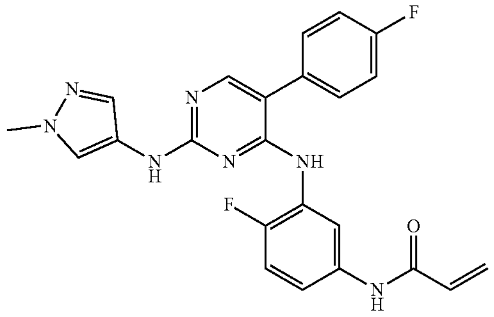 [SMILES: C=CC(=O)Nc1ccc(F)c(Nc2nc(Nc3cnn(C)c3)ncc2-c2ccc(F)cc2)c1] | 1276 | 102 | 60 | 116 | 344 |
| 64 | 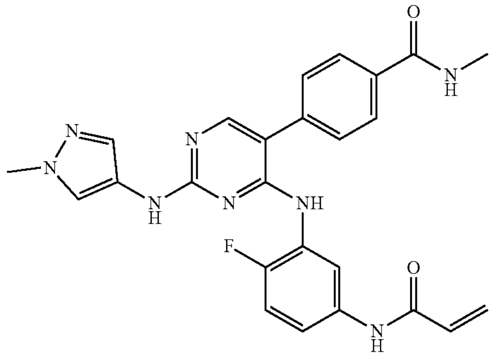 | >10000 | 2998 | 7866 | ND | ND |

TABLE 26-continued
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| | Cellular proliferation data. | | | | | |
| 65 | 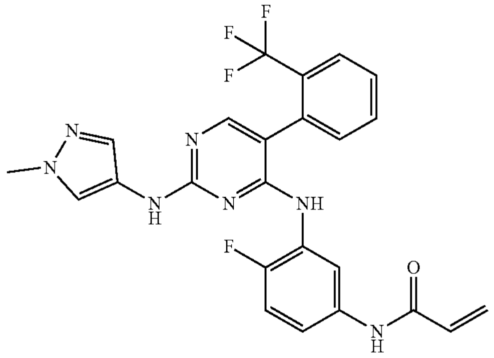 [SMILES: C=CC(=O)Nc1ccc(F)c(Nc2nc(Nc3cnn(C)c3)ncc2-c2ccccc2C(F)(F)F)c1] | 1936 | 2743 | 1004 | ND | ND |
| 66 | 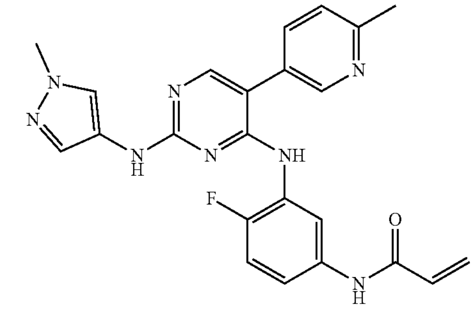 [SMILES: C=CC(=O)Nc1ccc(F)c(Nc2nc(Nc3cnn(C)c3)ncc2-c2ccc(C)nc2)c1] | 138 | 35 | 33 | 73 | 50 |
| 67 | 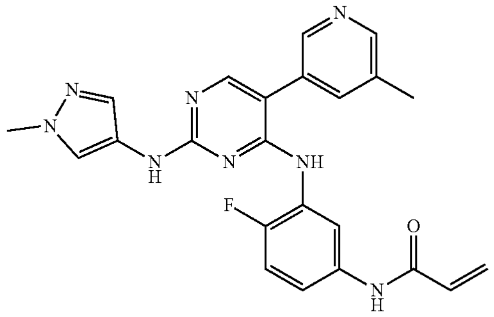 [SMILES: C=CC(=O)Nc1ccc(F)c(Nc2nc(Nc3cnn(C)c3)ncc2-c2cncc(C)c2)c1] | 120 | 36 | 30 | 41 | 26 |
| 68 | 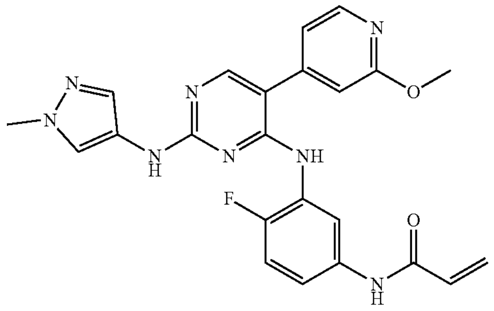 [SMILES: C=CC(=O)Nc1ccc(F)c(Nc2nc(Nc3cnn(C)c3)ncc2-c2ccnc(OC)c2)c1] | 223 | 108 | 101 | 107 | 128 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 69 | 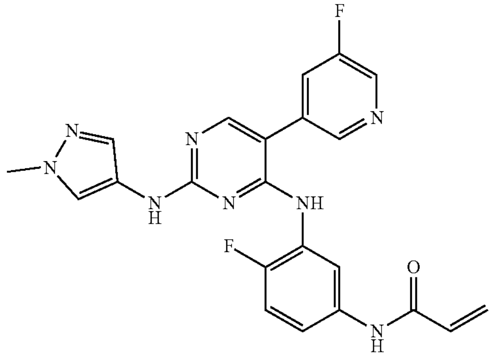 [SMILES: C=CC(=O)Nc1ccc(F)c(Nc2nc(Nc3cnn(C)c3)ncc2-c2cncc(F)c2)c1] | 65 | 14 | 11 | 21 | 19 |
| 70 | 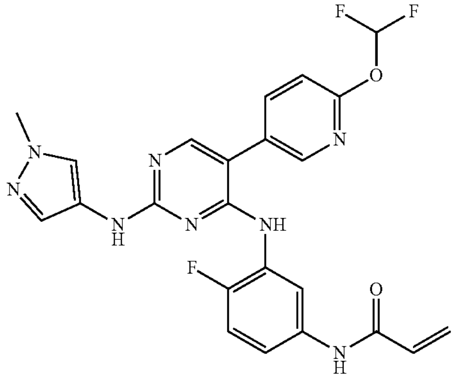 [SMILES: C=CC(=O)Nc1ccc(F)c(Nc2nc(Nc3cnn(C)c3)ncc2-c2ccc(OC(F)F)nc2)c1] | 77 | 36 | 35 | 88 | 123 |
| 71 | 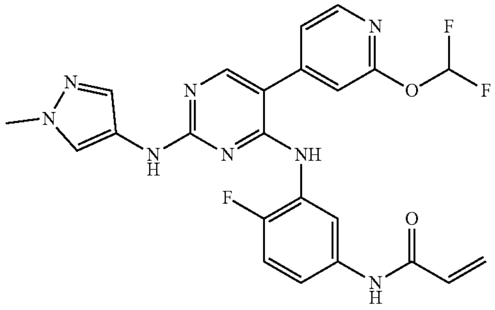 [SMILES: C=CC(=O)Nc1ccc(F)c(Nc2nc(Nc3cnn(C)c3)ncc2-c2ccnc(OC(F)F)c2)c1] | 150 | 107 | 107 | 103 | 226 |
| 72 | 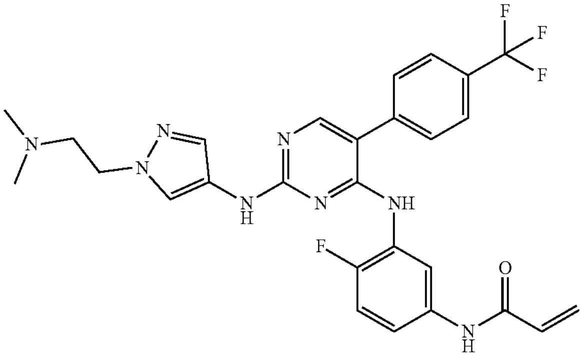 [SMILES: C=CC(=O)Nc1ccc(F)c(Nc2nc(Nc3cnn(CCN(C)C)c3)ncc2-c2ccc(C(F)(F)F)cc2)c1] | 80 | 108 | 99 | 95 | 129 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 73 | 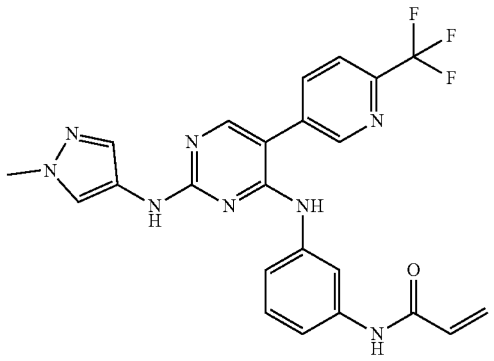 [SMILES: C=CC(=O)Nc1cccc(Nc2nc(Nc3cnn(C)c3)ncc2-c2ccc(C(F)(F)F)nc2)c1] | 252 | 45 | 39 | 100 | 113 |
| 74 | 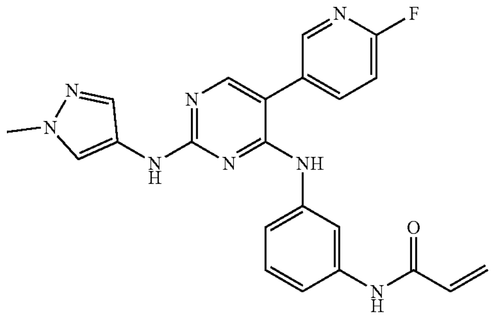 [SMILES: C=CC(=O)Nc1cccc(Nc2nc(Nc3cnn(C)c3)ncc2-c2ccc(F)nc2)c1] | 236 | 38 | 36 | 43 | 70 |
| 75 | 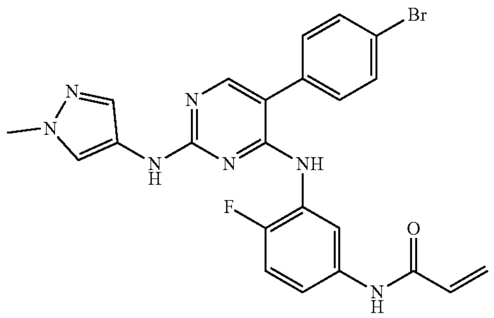 | 37 | 74 | 35 | 43 | 100 |
| 76 | 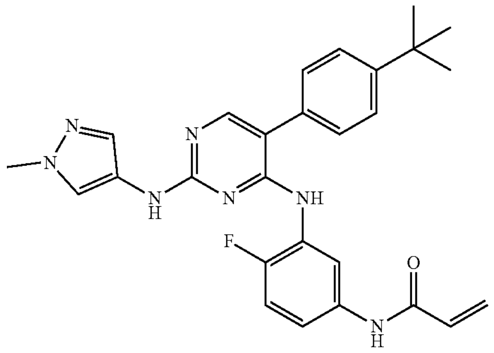 [SMILES: C=CC(=O)Nc1ccc(F)c(Nc2nc(Nc3cnn(C)c3)ncc2-c2ccc(C(C)(C)C)cc2)c1] | 156 | 308 | 265 | ND | 3148 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 77 | 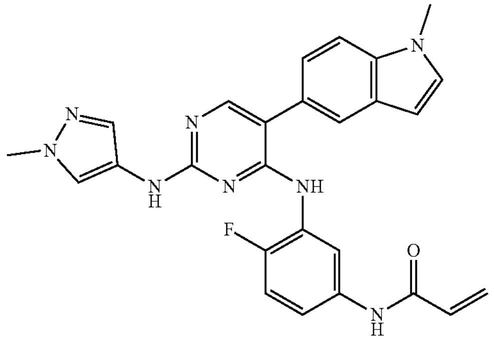 [SMILES: C=CC(=O)Nc1ccc(F)c(Nc2nc(Nc3cnn(C)c3)ncc2-c2ccc3c(ccn3C)c2)c1] | 1033 | 774 | 299 | ND | 2748 |
| 78 | 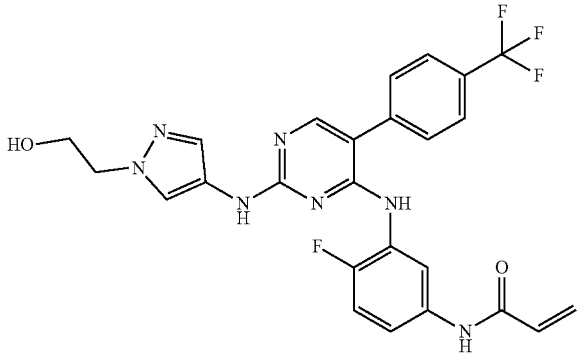 [SMILES: C=CC(=O)Nc1ccc(F)c(Nc2nc(Nc3cnn(CCO)c3)ncc2-c2ccc(C(F)(F)F)cc2)c1] | >10000 | 93 | 84 | 53 | 266 |
| 79 | 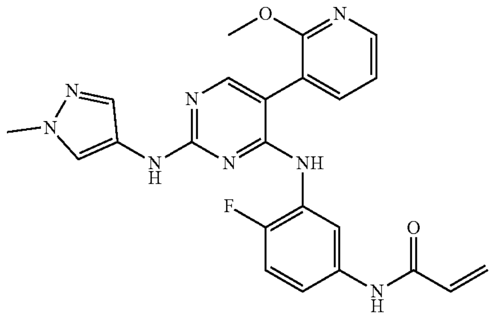 [SMILES: C=CC(=O)Nc1ccc(F)c(Nc2nc(Nc3cnn(C)c3)ncc2-c2cccnc2OC)c1] | >10000 | 887 | 934 | ND | 896 |
| 80 | 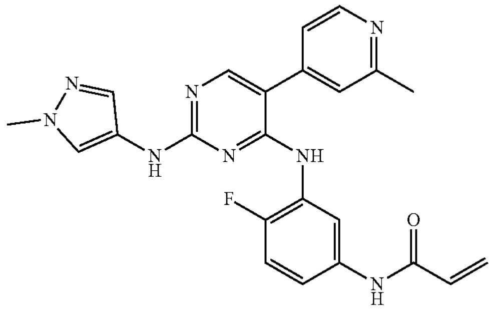 [SMILES: C=CC(=O)Nc1ccc(F)c(Nc2nc(Nc3cnn(C)c3)ncc2-c2ccnc(C)c2)c1] | 82 | 751 | 256 | ND | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 81 | 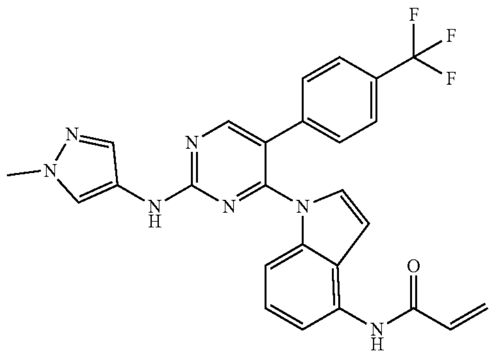 [SMILES: C=CC(=O)Nc1cccc2c1ccn2-c1nc(Nc2cnn(C)c2)ncc1-c1ccc(C(F)(F)F)cc1] | ND | >10000 | >10000 | ND | ND |
| 82 | 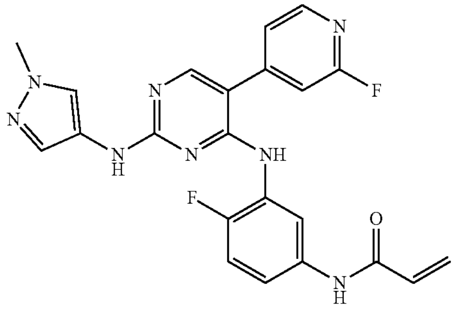 [SMILES: C=CC(=O)Nc1ccc(F)c(Nc2nc(Nc3cnn(C)c3)ncc2-c2ccnc(F)c2)c1] | 590 | 103 | 38 | 57 | 226 |
| 83 | 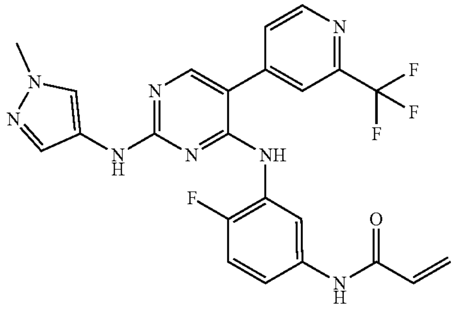 [SMILES: C=CC(=O)Nc1ccc(F)c(Nc2nc(Nc3cnn(C)c3)ncc2-c2ccnc(C(F)(F)F)c2)c1] | 53 | 88 | 61 | 51 | 255 |
| 84 | 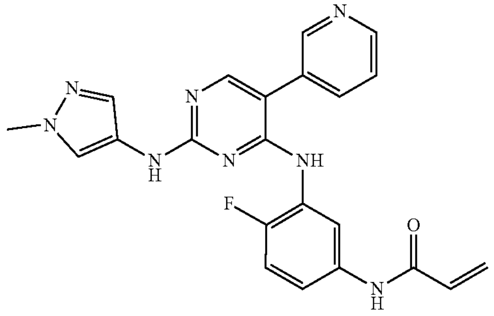 [SMILES: C=CC(=O)Nc1ccc(F)c(Nc2nc(Nc3cnn(C)c3)ncc2-c2cccnc2)c1] | 191 | 83 | 64 | 50 | 119 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 85 | 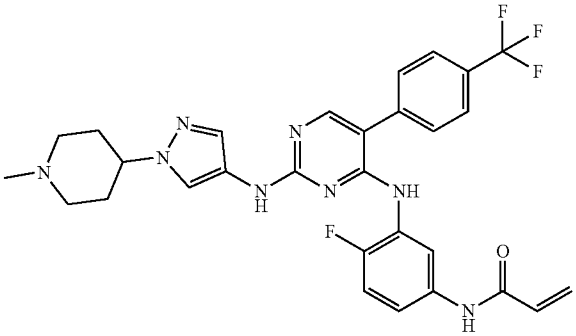 [SMILES: C=CC(=O)Nc1ccc(F)c(Nc2nc(Nc3cnn(C4CCN(C)CC4)c3)ncc2-c2ccc(C(F)(F)F)cc2)c1] | 5439 | 249 | 109 | 119 | 378 |
| 86 | 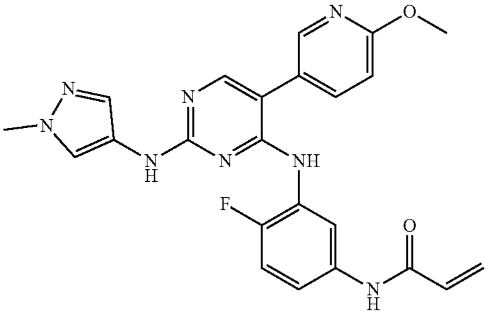 [SMILES: C=CC(=O)Nc1ccc(F)c(Nc2nc(Nc3cnn(C)c3)ncc2-c2ccc(OC)nc2)c1] | 49 | 39 | 36 | 33 | 185 |
| 87 | 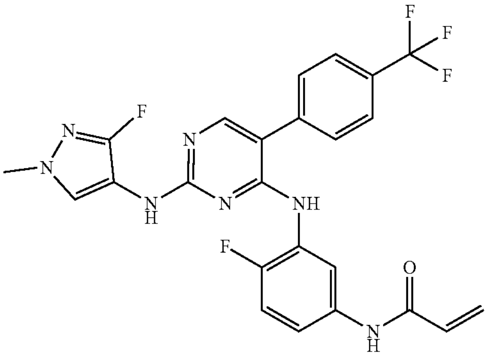 [SMILES: C=CC(=O)Nc1ccc(F)c(Nc2nc(Nc3cn(C)nc3F)ncc2-c2ccc(C(F)(F)F)cc2)c1] | 97 | 239 | 171 | 234 | 413 |
| 88 | 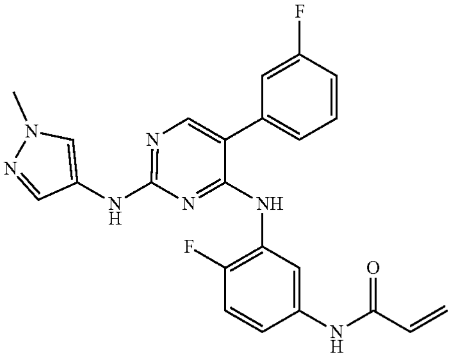 [SMILES: C=CC(=O)Nc1ccc(F)c(Nc2nc(Nc3cnn(C)c3)ncc2-c2cccc(F)c2)c1] | 929 | 48 | 35 | 49 | 198 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 89 | 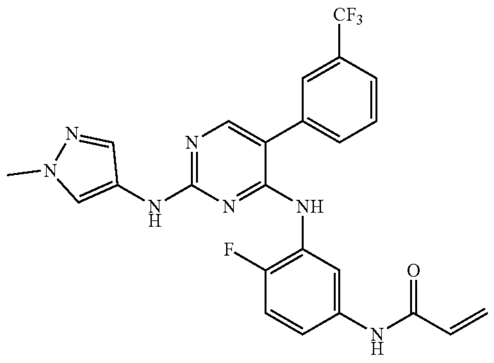 [SMILES: C=CC(=O)Nc1ccc(F)c(Nc2nc(Nc3cnn(C)c3)ncc2-c2cccc(C(F)(F)F)c2)c1] | 84 | 106 | 101 | 58 | 665 |
| 90 | 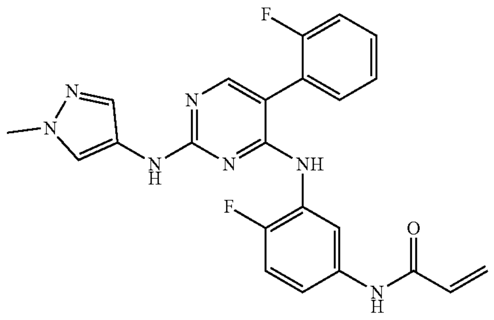 [SMILES: C=CC(=O)Nc1ccc(F)c(Nc2nc(Nc3cnn(C)c3)ncc2-c2ccccc2F)c1] | 320 | 237 | 103 | 103 | 358 |
| 91 | 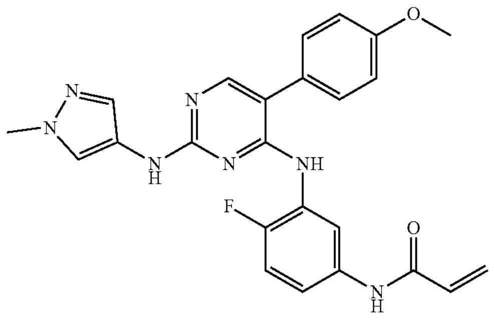 [SMILES: C=CC(=O)Nc1ccc(F)c(Nc2nc(Nc3cnn(C)c3)ncc2-c2ccc(OC)cc2)c1] | 950 | 108 | 62 | 91 | 479 |
| 92 | 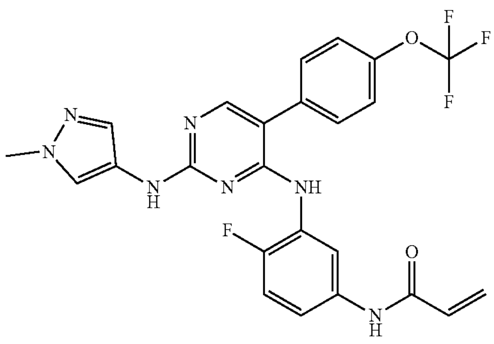 [SMILES: C=CC(=O)Nc1ccc(F)c(Nc2nc(Nc3cnn(C)c3)ncc2-c2ccc(OC(F)(F)F)cc2)c1] | 133 | 75 | 102 | 89 | 612 |

TABLE 26-continued
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| Cellular proliferation data. | | | | | | |
| 93 | 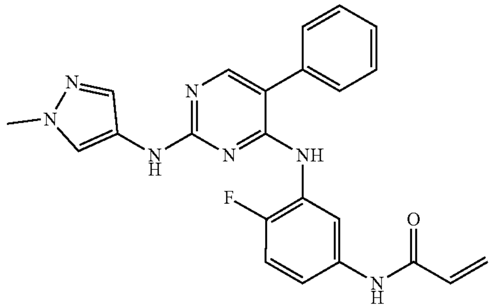 [SMILES: C=CC(=O)Nc1ccc(F)c(Nc2nc(Nc3cnn(C)c3)ncc2-c2ccccc2)c1] | >10000 | 315 | 121 | 148 | 465 |
| 94 | 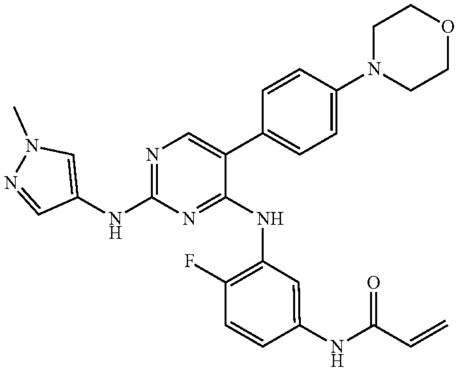 [SMILES: C=CC(=O)Nc1ccc(F)c(Nc2nc(Nc3cnn(C)c3)ncc2-c2ccc(N3CCOCC3)cc2)c1] | >10000 | 109 | 542 | 448 | 1269 |
| 95 | 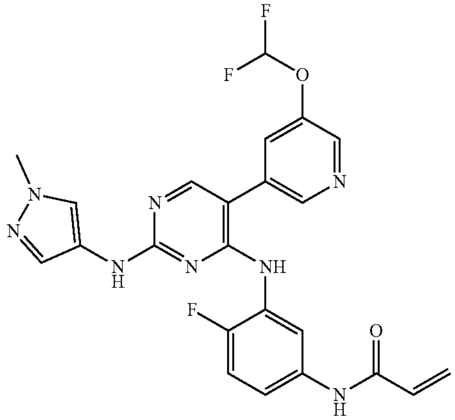 [SMILES: C=CC(=O)Nc1ccc(F)c(Nc2nc(Nc3cnn(C)c3)ncc2-c2cncc(OC(F)F)c2)c1] | 102 | 27 | 38 | 45 | 101 |
| 96 | 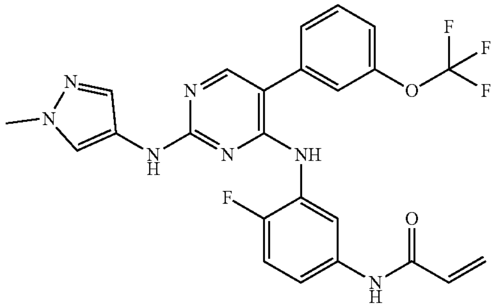 [SMILES: C=CC(=O)Nc1ccc(F)c(Nc2nc(Nc3cnn(C)c3)ncc2-c2cccc(OC(F)(F)F)c2)c1] | 1075 | 790 | 345 | ND | 7727 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 97 | 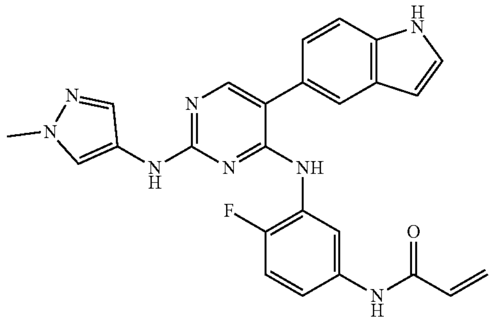 [SMILES: C=CC(=O)Nc1ccc(F)c(Nc2nc(Nc3cnn(C)c3)ncc2-c2ccc3[nH]ccc3c2)c1] | 586 | 862 | 546 | ND | 403 |
| 98 | 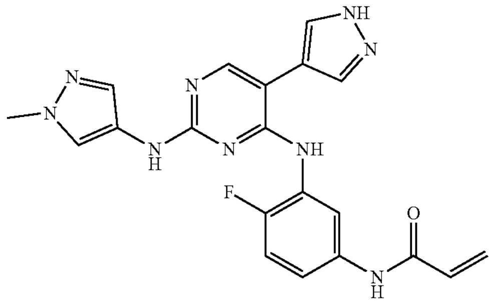 [SMILES: C=CC(=O)Nc1ccc(F)c(Nc2nc(Nc3cnn(C)c3)ncc2-c2cn[nH]c2)c1] | >10000 | 942 | 671 | ND | ND |
| 99 | 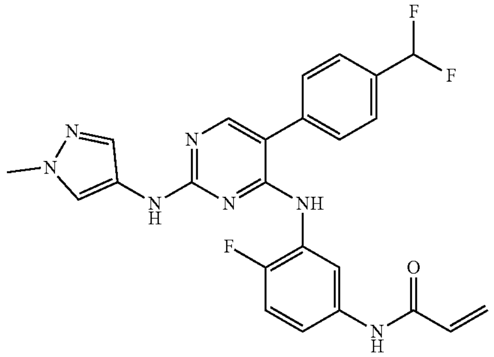 [SMILES: C=CC(=O)Nc1ccc(F)c(Nc2nc(Nc3cnn(C)c3)ncc2-c2ccc(C(F)F)cc2)c1] | 67 | 96 | 37 | 75 | 171 |
| 100 | 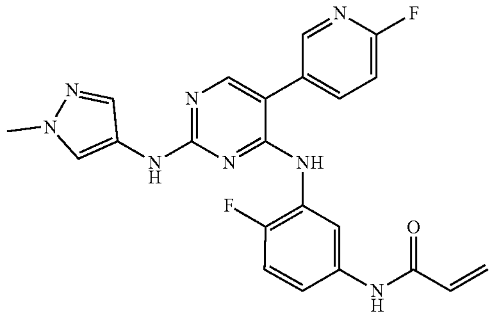 [SMILES: C=CC(=O)Nc1ccc(F)c(Nc2nc(Nc3cnn(C)c3)ncc2-c2ccc(F)nc2)c1] | 472 | 72 | 38 | 53 | 203 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 101 | 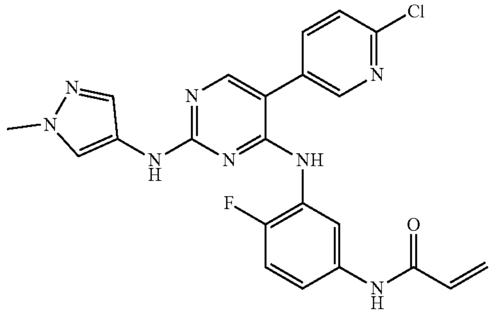 | 56 | 13 | 12 | 30 | 35 |
| 102 | 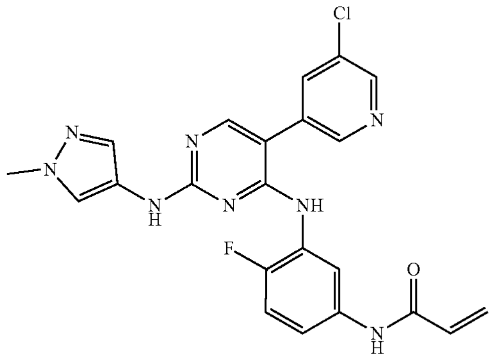 [SMILES: C=CC(=O)Nc1ccc(F)c(Nc2nc(Nc3cnn(C)c3)ncc2-c2cncc(Cl)c2)c1] | 168 | 31 | 35 | 48 | 35 |
| 103 | 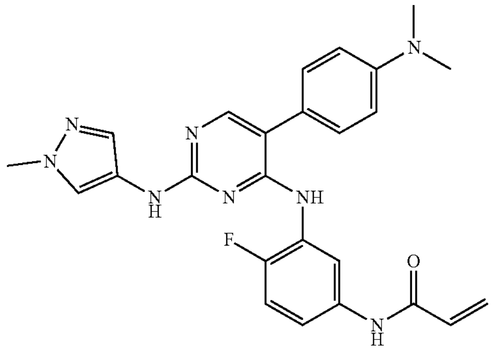 [SMILES: C=CC(=O)Nc1ccc(F)c(Nc2nc(Nc3cnn(C)c3)ncc2-c2ccc(N(C)C)cc2)c1] | 493 | 287 | 157 | 281 | 461 |
| 104 | 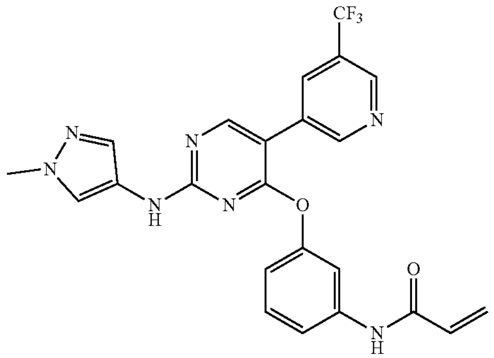 [SMILES: C=CC(=O)Nc1cccc(Oc2nc(Nc3cnn(C)c3)ncc2-c2cncc(C(F)(F)F)c2)c1] | 1117 | 104 | 107 | 101 | 115 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| --- | --- | --- | --- | --- | --- | --- |
| 105 | 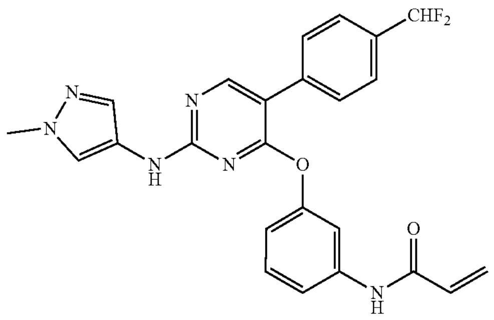 [SMILES: C=CC(=O)Nc1cccc(Oc2nc(Nc3cnn(C)c3)ncc2-c2ccc(C(F)F)cc2)c1] | 171 | 49 | 37 | 75 | 105 |
| 106 | 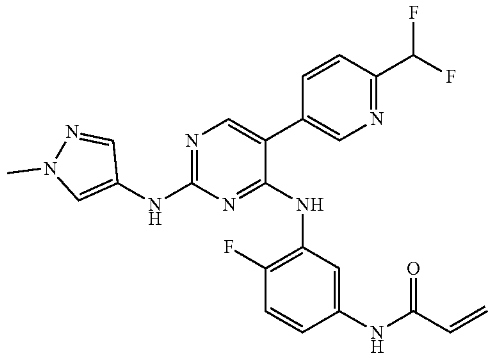 [SMILES: C=CC(=O)Nc1ccc(F)c(Nc2nc(Nc3cnn(C)c3)ncc2-c2ccc(C(F)F)nc2)c1] | 94 | 35 | 16 | 25 | 38 |
| 107 | 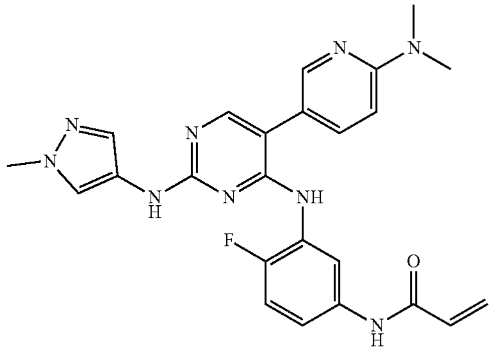 [SMILES: C=CC(=O)Nc1ccc(F)c(Nc2nc(Nc3cnn(C)c3)ncc2-c2ccc(N(C)C)nc2)c1] | ND | >10000 | >10000 | ND | ND |
| 108 | 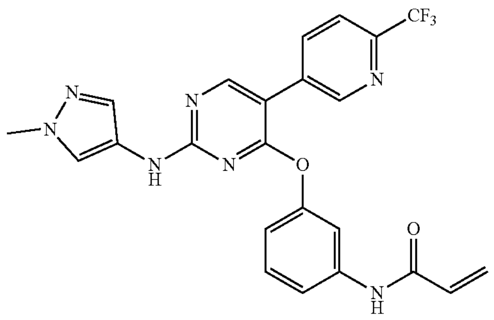 | 341 | 56 | 104 | 294 | 300 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 109 | 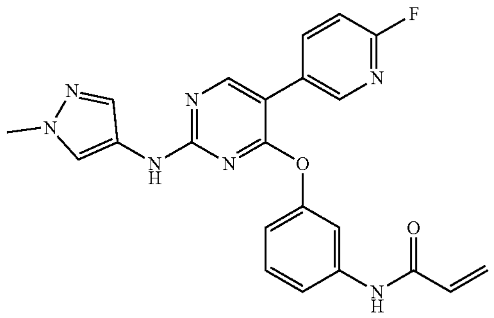 | 613 | 53 | 100 | 112 | 344 |
| 110 | 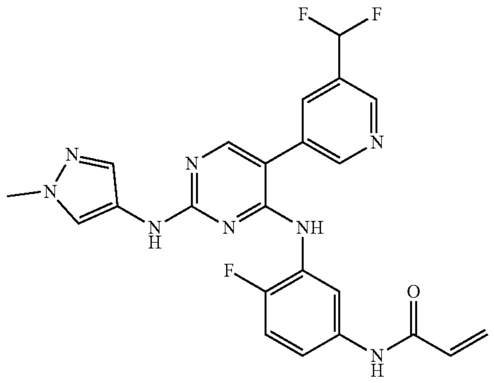 [SMILES: C=CC(=O)Nc1ccc(F)c(Nc2nc(Nc3cnn(C)c3)ncc2-c2cncc(C(F)F)c2)c1] | 309 | 33 | 34 | 34 | 30 |
| 111 | 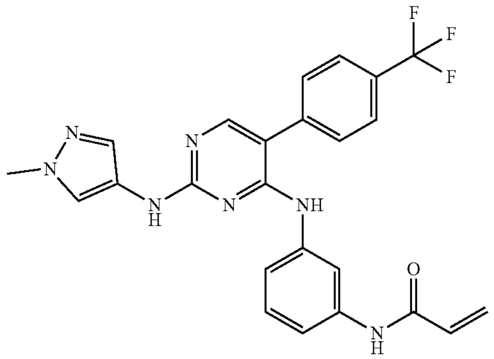 | 27 | 41 | 48 | 103 | 138 |
| 112 | 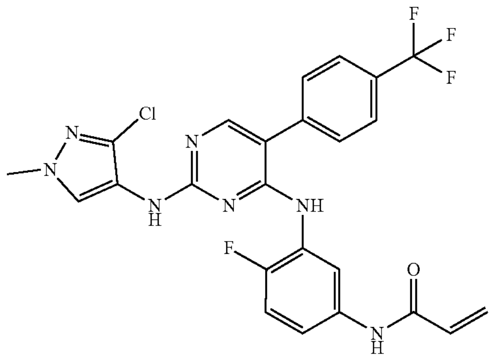 [SMILES: C=CC(=O)Nc1ccc(F)c(Nc2nc(Nc3cn(C)nc3Cl)ncc2-c2ccc(C(F)(F)F)cc2)c1] | 88 | 80 | 93 | 138 | 288 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 113 | 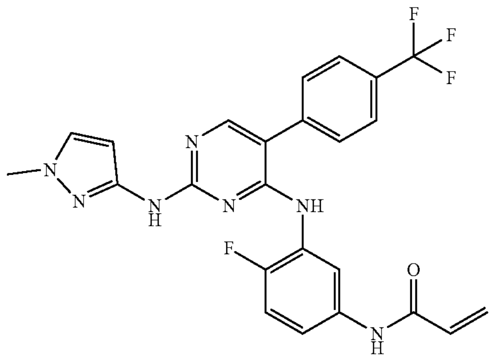 [SMILES: C=CC(=O)Nc1ccc(F)c(Nc2nc(Nc3ccn(C)n3)ncc2-c2ccc(C(F)(F)F)cc2)c1] | 201 | 263 | 317 | ND | ND |
| 114 | 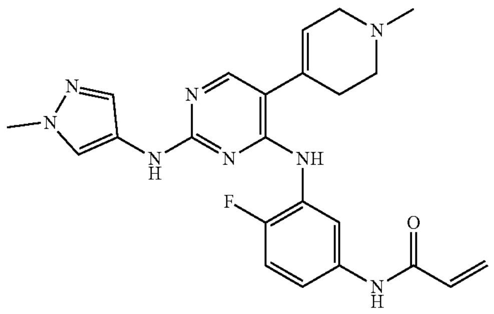 [SMILES: C=CC(=O)Nc1ccc(F)c(Nc2nc(Nc3cnn(C)c3)ncc2C2=CCN(C)CC2)c1] | 816 | 964 | 1838 | ND | ND |
| 115 | 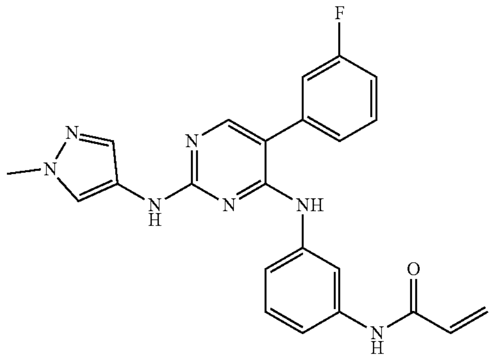 [SMILES: C=CC(=O)Nc1cccc(Nc2nc(Nc3cnn(C)c3)ncc2-c2cccc(F)c2)c1] | 100 | 39 | 16 | 30 | 25 |
| 116 | 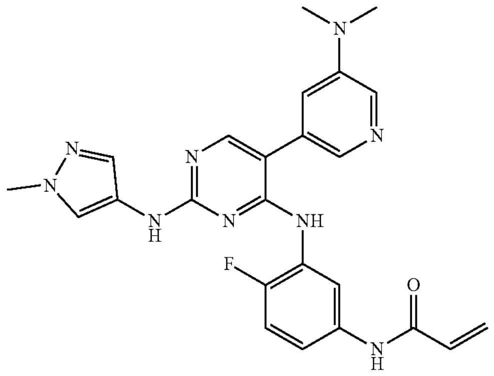 [SMILES: C=CC(=O)Nc1ccc(F)c(Nc2nc(Nc3cnn(C)c3)ncc2-c2cncc(N(C)C)c2)c1] | 108 | 94 | 108 | 136 | 251 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 117 | 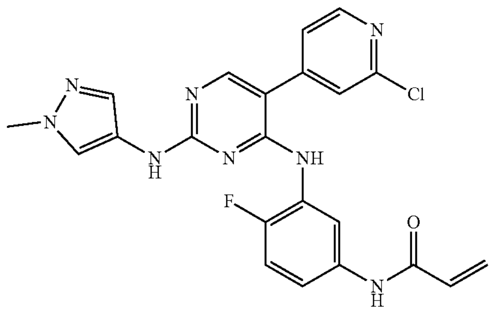 | 85 | 57 | 86 | 107 | 160 |
| 118 | 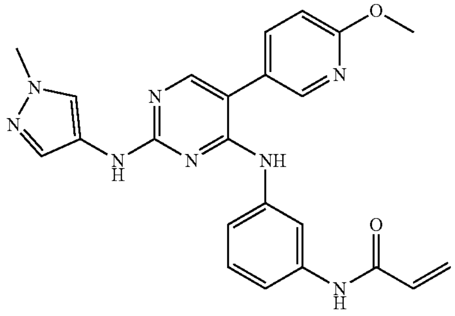 [SMILES: C=CC(=O)Nc1cccc(Nc2nc(Nc3cnn(C)c3)ncc2-c2ccc(OC)nc2)c1] | 163 | 36 | 33 | 29 | 57 |
| 119 | 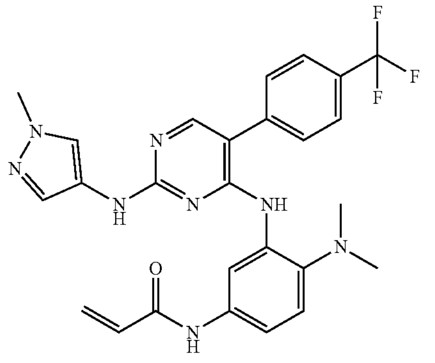 [SMILES: C=CC(=O)Nc1ccc(N(C)C)c(Nc2nc(Nc3cnn(C)c3)ncc2-c2ccc(C(F)(F)F)cc2)c1] | >10000 | >10000 | >10000 | ND | ND |
| 120 | 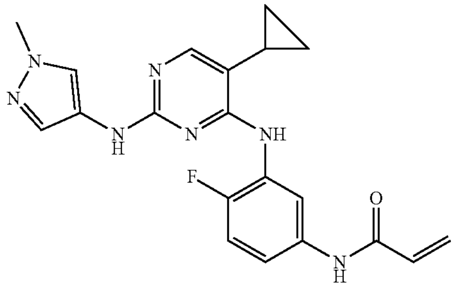 [SMILES: C=CC(=O)Nc1ccc(F)c(Nc2nc(Nc3cnn(C)c3)ncc2C2CC2)c1] | 3801 | 875 | 967 | ND | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 121 | 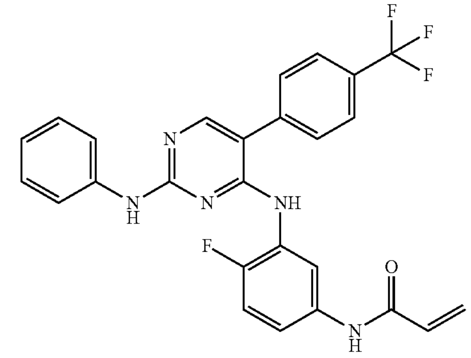 [SMILES: C=CC(=O)Nc1ccc(F)c(Nc2nc(Nc3ccccc3)ncc2-c2ccc(C(F)(F)F)cc2)c1] | 1275 | >10000 | 2871 | ND | ND |
| 122 | 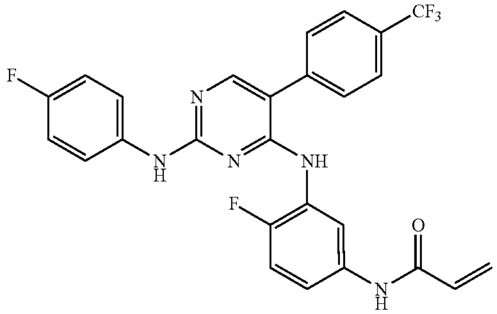 [SMILES: C=CC(=O)Nc1ccc(F)c(Nc2nc(Nc3ccc(F)cc3)ncc2-c2ccc(C(F)(F)F)cc2)c1] | 3693 | >10000 | 1993 | ND | ND |
| 123 | 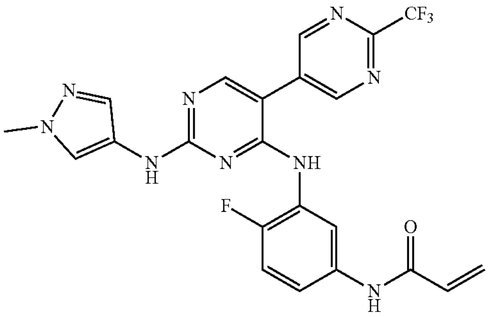 [SMILES: C=CC(=O)Nc1ccc(F)c(Nc2nc(Nc3cnn(C)c3)ncc2-c2cnc(C(F)(F)F)nc2)c1] | ND | 16 | 24 | 30 | 35 |
| 124 | 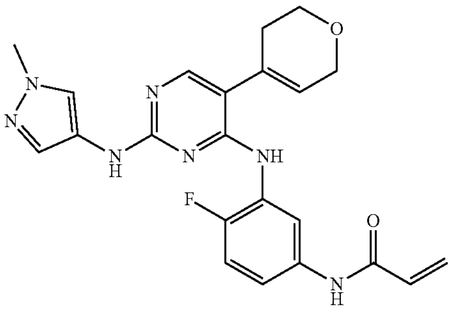 [SMILES: C=CC(=O)Nc1ccc(F)c(Nc2nc(Nc3cnn(C)c3)ncc2C2=CCOCC2)c1] | 1530 | 284 | 328 | ND | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 125 | 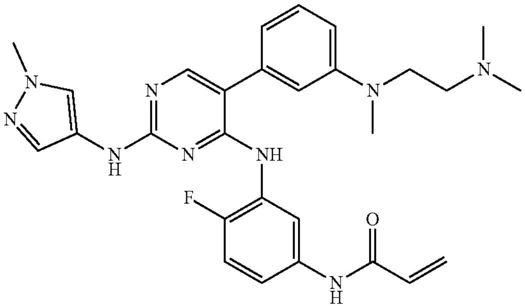 [SMILES: C=CC(=O)Nc1ccc(F)c(Nc2nc(Nc3cnn(C)c3)ncc2-c2cccc(N(C)CCN(C)C)c2)c1] | >10000 | >10000 | >10000 | >10000 | ND |
| 136 | 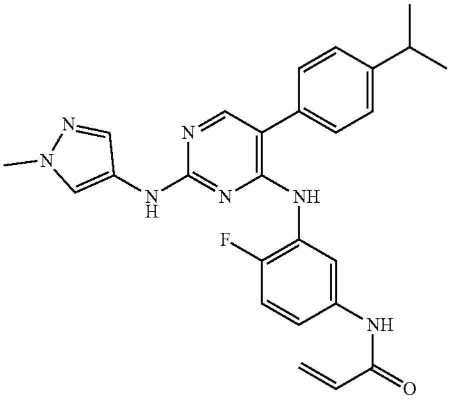 [SMILES: C=CC(=O)Nc1ccc(F)c(Nc2nc(Nc3cnn(C)c3)ncc2-c2ccc(C(C)C)cc2)c1] | 40 | 299 | 106 | ND | 412 |
| 127 | 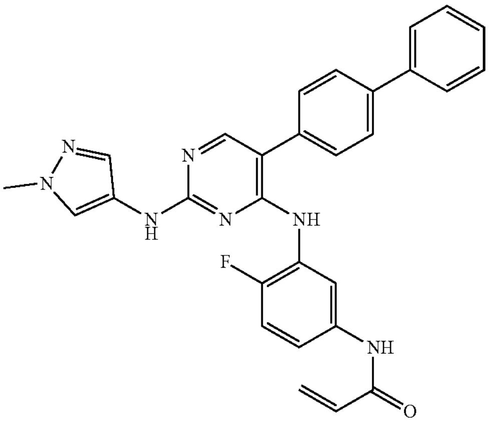 [SMILES: C=CC(=O)Nc1ccc(F)c(Nc2nc(Nc3cnn(C)c3)ncc2-c2ccc(-c3ccccc3)cc2)c1] | 258 | 565 | 971 | ND | 5280 |
| 128 | 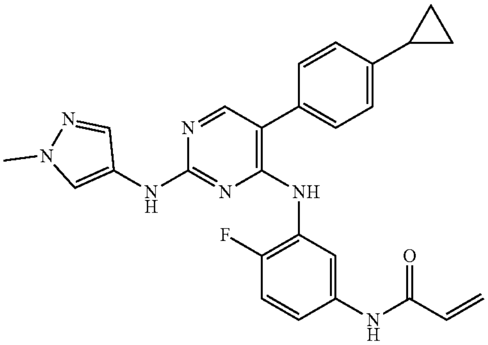 [SMILES: C=CC(=O)Nc1ccc(F)c(Nc2nc(Nc3cnn(C)c3)ncc2-c2ccc(C3CC3)cc2)c1] | 64 | 114 | 101 | ND | 654 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 129 | 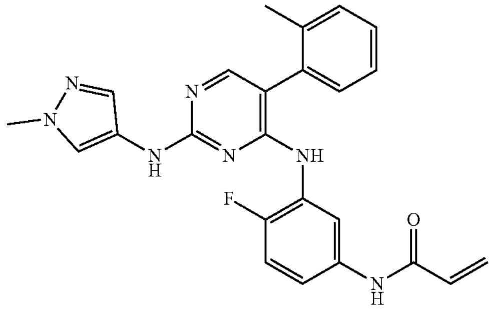 [SMILES: C=CC(=O)Nc1ccc(F)c(Nc2nc(Nc3cnn(C)c3)ncc2-c2ccccc2C)c1] | ND | ND | ND | ND | 2144 |
| 130 | 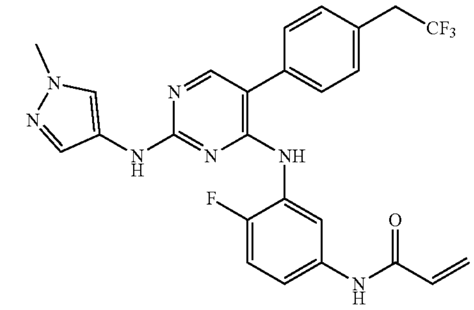 [SMILES: C=CC(=O)Nc1ccc(F)c(Nc2nc(Nc3cnn(C)c3)ncc2-c2ccc(CC(F)(F)F)cc2)c1] | 8 | 27 | 26 | ND | 83 |
| 131 | 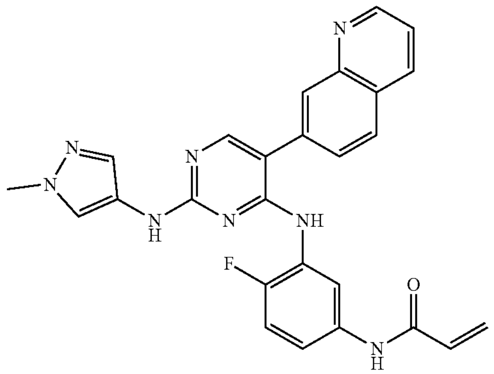 [SMILES: C=CC(=O)Nc1ccc(F)c(Nc2nc(Nc3cnn(C)c3)ncc2-c2ccc3cccnc3c2)c1] | 365 | 758 | 202 | ND | 348 |
| 132 | 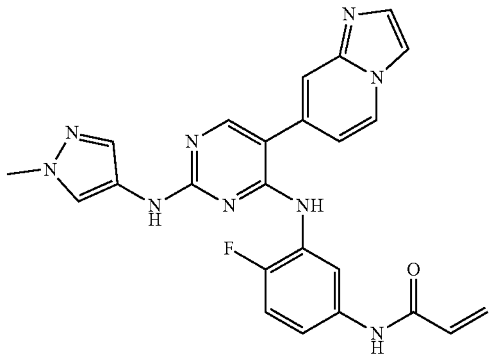 [SMILES: C=CC(=O)Nc1ccc(F)c(Nc2nc(Nc3cnn(C)c3)ncc2-c2ccn3ccnc3c2)c1] | 504 | 368 | 203 | ND | 150.5 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 133 | 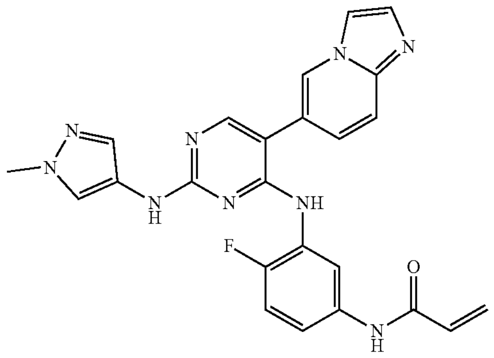 | 158 | 388 | 294 | 323 | ND |
| 134 | 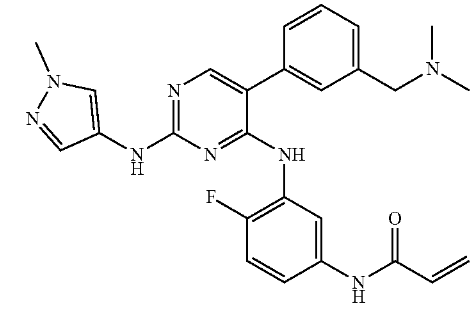 [SMILES: C=CC(=O)Nc1ccc(F)c(Nc2nc(Nc3cnn(C)c3)ncc2-c2cccc(CN(C)C)c2)c1] | 3277 | 8415 | >10000 | ND | ND |
| 135 | 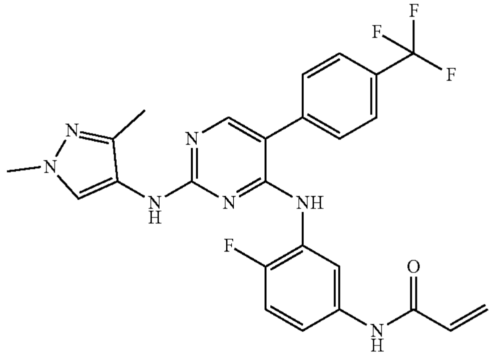 [SMILES: C=CC(=O)Nc1ccc(F)c(Nc2nc(Nc3cn(C)nc3C)ncc2-c2ccc(C(F)(F)F)cc2)c1] | 94 | 257 | 120 | 235 | 413 |
| 136 | 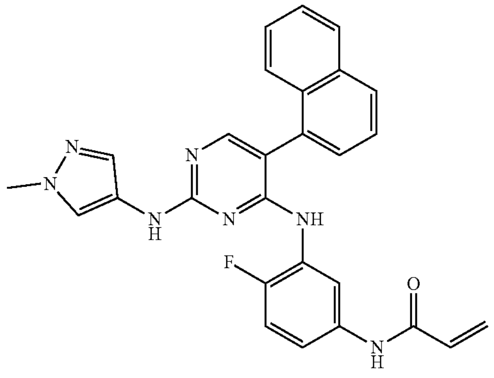 | ND | ND | ND | ND | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 137 | 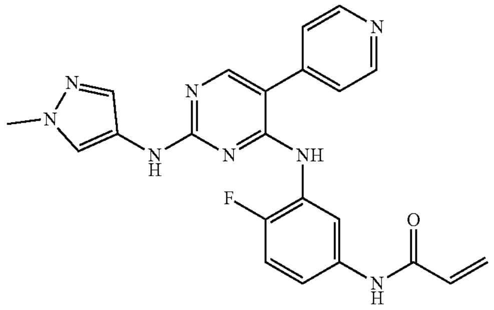 [SMILES: C=CC(=O)Nc1ccc(F)c(Nc2nc(Nc3cnn(C)c3)ncc2-c2ccncc2)c1] | >10000 | 325 | 254 | ND | 751 |
| 138 | 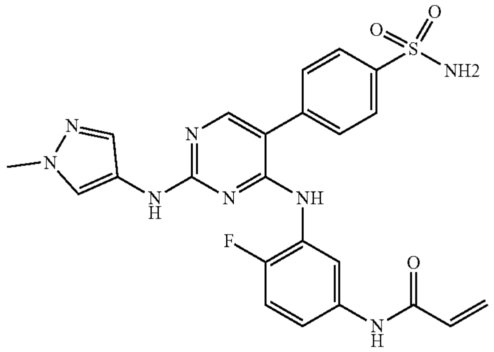 [SMILES: C=CC(=O)Nc1ccc(F)c(Nc2nc(Nc3cnn(C)c3)ncc2-c2ccc(S(N)(=O)=O)cc2)c1] | >10000 | 2880 | 3139 | ND | ND |
| 139 | 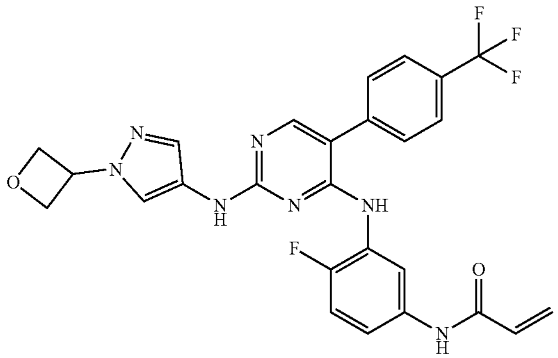 [SMILES: C=CC(=O)Nc1ccc(F)c(Nc2nc(Nc3cnn(C4COC4)c3)ncc2-c2ccc(C(F)(F)F)cc2)c1] | >10000 | 125 | 116 | 148 | 690 |
| 140 | 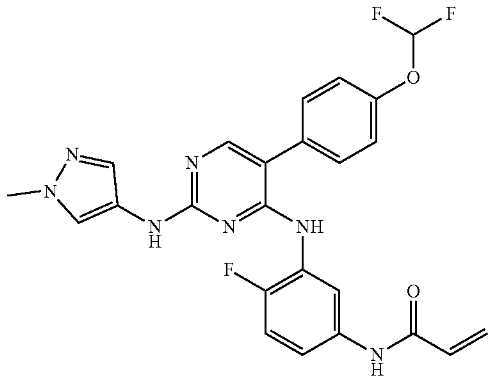 [SMILES: C=CC(=O)Nc1ccc(F)c(Nc2nc(Nc3cnn(C)c3)ncc2-c2ccc(OC(F)F)cc2)c1] | 22 | 34 | 32 | 58 | 269 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 141 | 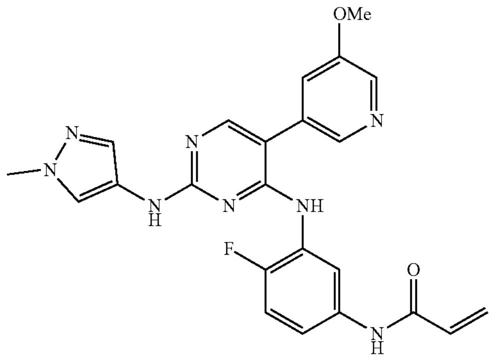 [SMILES: C=CC(=O)Nc1ccc(F)c(Nc2nc(Nc3cnn(C)c3)ncc2-c2cncc(OC)c2)c1] | 141 | 100 | 101 | 49 | 201 |
| 142 | 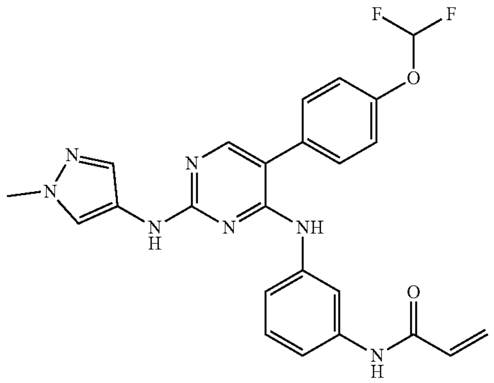 [SMILES: C=CC(=O)Nc1cccc(Nc2nc(Nc3cnn(C)c3)ncc2-c2ccc(OC(F)F)cc2)c1] | 169 | 34 | 16 | 24 | 50 |
| 143 | 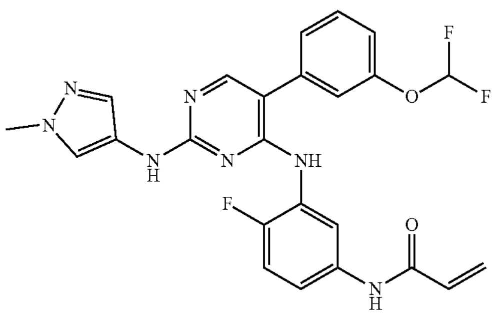 [SMILES: C=CC(=O)Nc1ccc(F)c(Nc2nc(Nc3cnn(C)c3)ncc2-c2cccc(OC(F)F)c2)c1] | 235 | 300 | 276 | ND | ND |
| 144 | 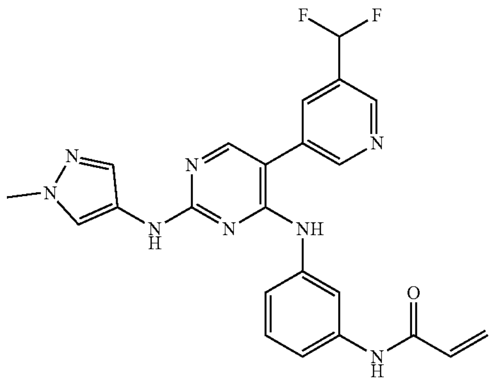 [SMILES: C=CC(=O)Nc1cccc(Nc2nc(Nc3cnn(C)c3)ncc2-c2cncc(C(F)F)c2)c1] | 122 | 70 | 37 | 101 | 38 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 145 | 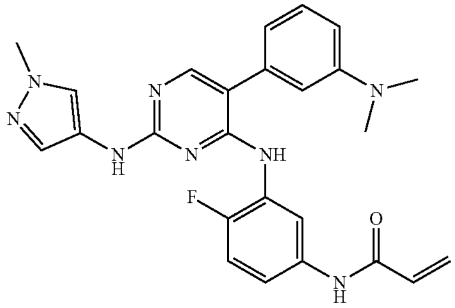 [SMILES: C=CC(=O)Nc1ccc(F)c(Nc2nc(Nc3cnn(C)c3)ncc2-c2cccc(N(C)C)c2)c1] | 3984 | 2016 | 911 | ND | ND |
| 146 | 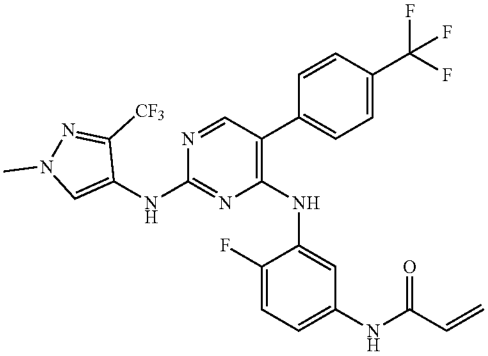 [SMILES: C=CC(=O)Nc1ccc(F)c(Nc2nc(Nc3cn(C)nc3C(F)(F)F)ncc2-c2ccc(C(F)(F)F)cc2)c1] | 274 | 279 | 342 | ND | 6132 |
| 147 | 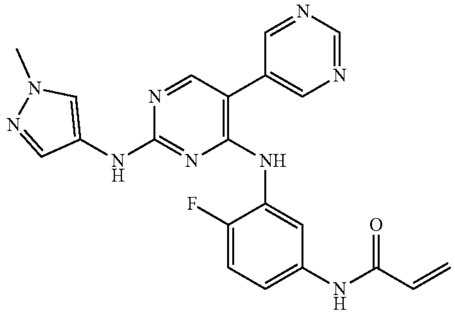 [SMILES: C=CC(=O)Nc1ccc(F)c(Nc2nc(Nc3cnn(C)c3)ncc2-c2cncnc2)c1] | 466 | 101 | 105 | 68 | 100 |
| 148 | 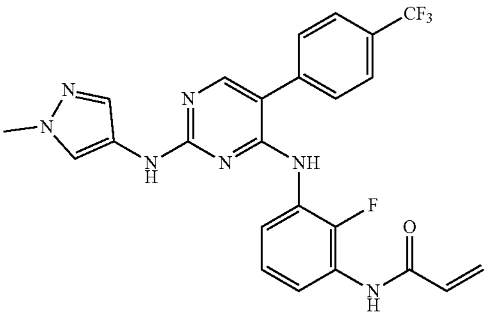 [SMILES: C=CC(=O)Nc1cccc(Nc2nc(Nc3cnn(C)c3)ncc2-c2ccc(C(F)(F)F)cc2)c1F] | 83 | 56 | 33 | ND | 349 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| --- | --- | --- | --- | --- | --- | --- |
| 149 | 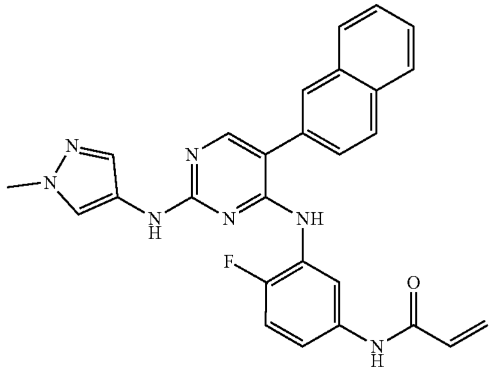 [SMILES: C=CC(=O)Nc1ccc(F)c(Nc2nc(Nc3cnn(C)c3)ncc2-c2ccc3ccccc3c2)c1] | 469 | 747 | 308 | ND | 501 |
| 150 | 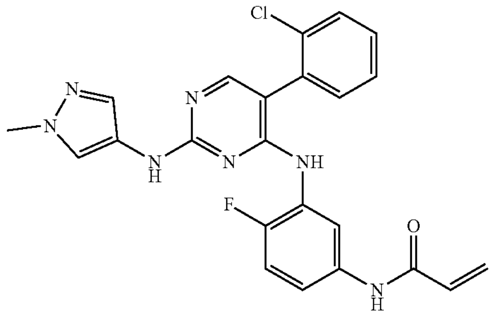 [SMILES: C=CC(=O)Nc1ccc(F)c(Nc2nc(Nc3cnn(C)c3)ncc2-c2ccccc2Cl)c1] | ND | ND | ND | ND | 1807 |
| 151 | 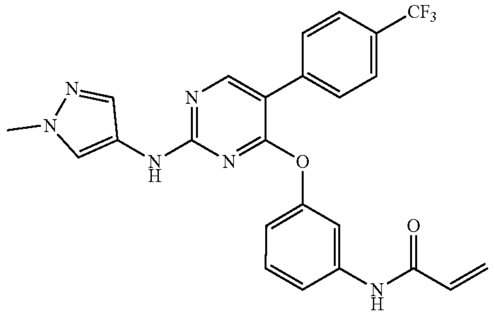 [SMILES: C=CC(=O)Nc1cccc(Oc2nc(Nc3cnn(C)c3)ncc2-c2ccc(C(F)(F)F)cc2)c1] | 375 | 129 | 105 | 226 | 354 |
| 152 | 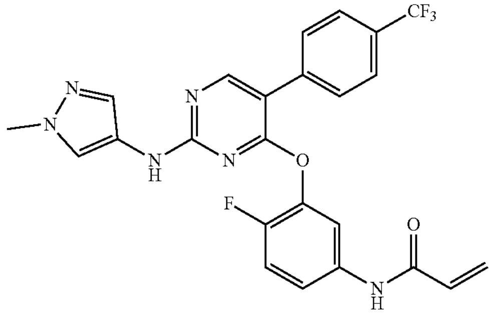 [SMILES: C=CC(=O)Nc1ccc(F)c(Oc2nc(Nc3cnn(C)c3)ncc2-c2ccc(C(F)(F)F)cc2)c1] | 3498 | 300 | 173 | 407 | 651 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 153 | 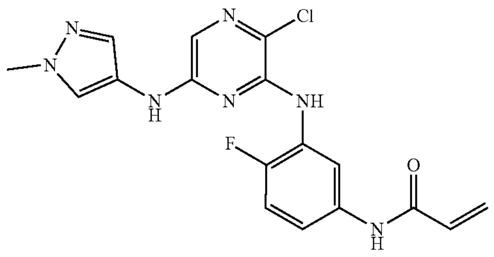 [SMILES: C=CC(=O)Nc1ccc(F)c(Nc2nc(Nc3cnn(C)c3)cnc2Cl)c1] | >10000 | >10000 | >10000 | ND | ND |
| 154 | 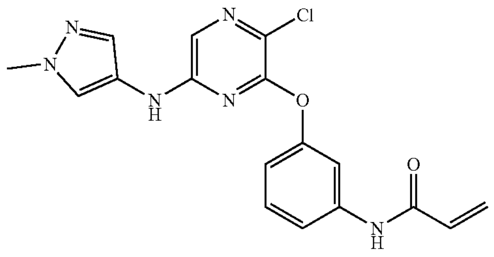 [SMILES: C=CC(=O)Nc1cccc(Oc2nc(Nc3cnn(C)c3)cnc2Cl)c1] | >10000 | >10000 | >10000 | ND | ND |
| 155 | 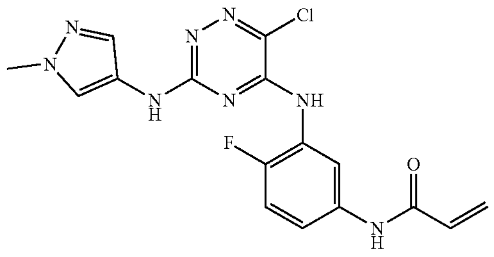 [SMILES: C=CC(=O)Nc1ccc(F)c(Nc2nc(Nc3cnn(C)c3)nnc2Cl)c1] | 6463 | 2477 | 1410 | ND | ND |
| 156 | 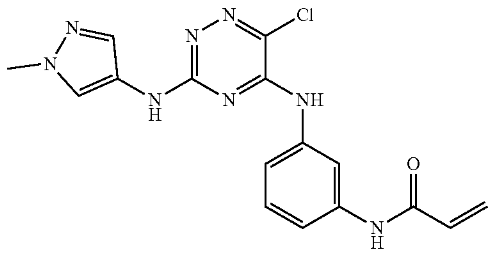 [SMILES: C=CC(=O)Nc1cccc(Nc2nc(Nc3cnn(C)c3)nnc2Cl)c1] | 8022 | 2445 | 1893 | ND | 1516 |
| 157 | 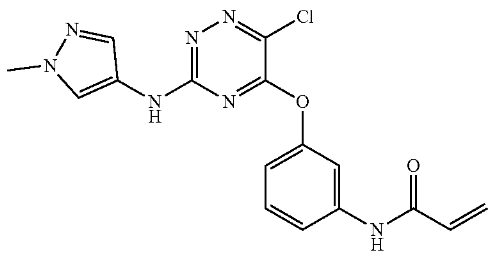 [SMILES: C=CC(=O)Nc1cccc(Oc2nc(Nc3cnn(C)c3)nnc2Cl)c1] | >10000 | >10000 | >10000 | ND | 3660 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 158 | 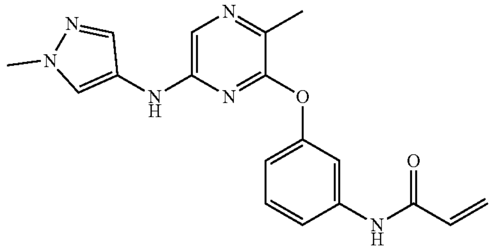 [SMILES: C=CC(=O)Nc1cccc(Oc2nc(Nc3cnn(C)c3)cnc2C)c1] | >10000 | >10000 | >10000 | ND | >10000 |
| 159 | 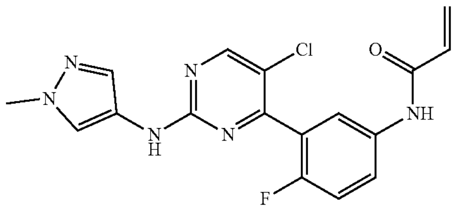 [SMILES: C=CC(=O)Nc1ccc(F)c(-c2nc(Nc3cnn(C)c3)ncc2Cl)c1] | >10000 | 2780 | 9550 | ND | >10000 |
| 160 | 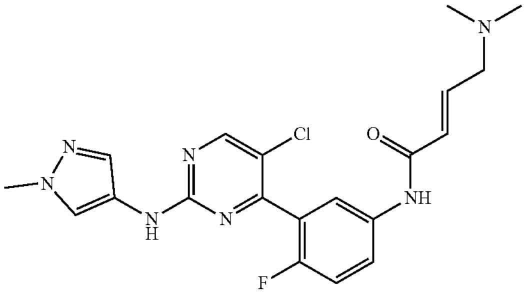 | >10000 | >10000 | >10000 | ND | >10000 |
| 161 | 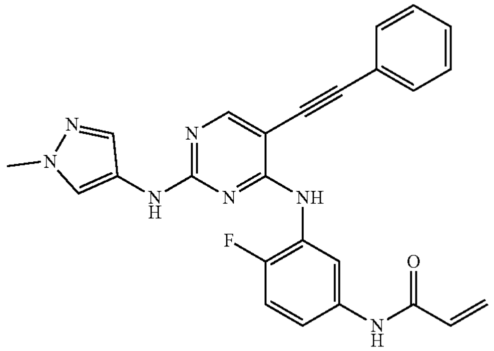 [SMILES: C=CC(=O)Nc1ccc(F)c(Nc2nc(Nc3cnn(C)c3)ncc2C#Cc2ccccc2)c1] | >10000 | 289 | 288 | ND | 897 |
| 162 | 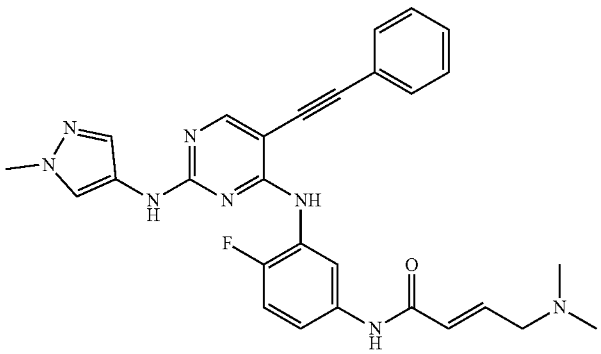 | 2854 | 656 | 1849 | ND | 1879 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 163 | 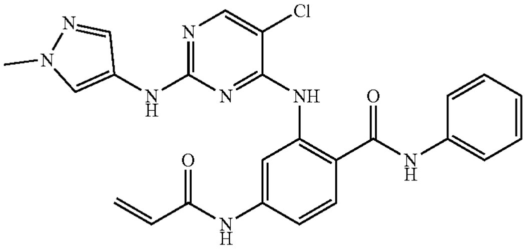 [SMILES: C=CC(=O)Nc1ccc(C(=O)Nc2ccccc2)c(Nc2nc(Nc3cnn(C)c3)ncc2Cl)c1] | 8251 | 9436 | >10000 | ND | ND |
| 164 | 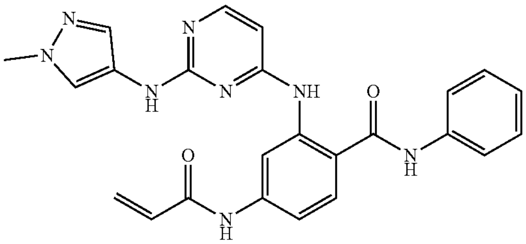 [SMILES: C=CC(=O)Nc1ccc(C(=O)Nc2ccccc2)c(Nc2ccnc(Nc3cnn(C)c3)n2)c1] | >10000 | >10000 | >10000 | ND | 9487 |
| 165 | 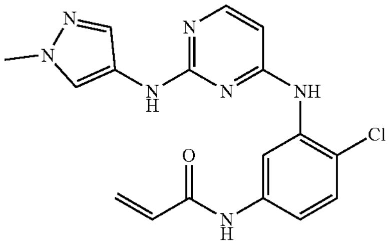 [SMILES: C=CC(=O)Nc1ccc(Cl)c(Nc2ccnc(Nc3cnn(C)c3)n2)c1] | >10000 | >10000 | >10000 | ND | 9931 |
| 166 | 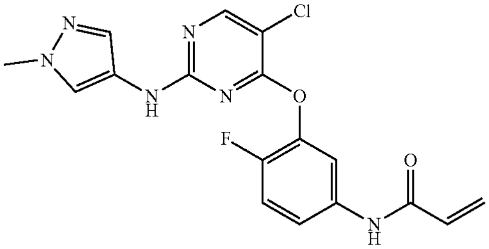 [SMILES: C=CC(=O)Nc1ccc(F)c(Oc2nc(Nc3cnn(C)c3)ncc2Cl)c1] | >10000 | 1251 | 1322 | ND | 1689 |
| 167 | 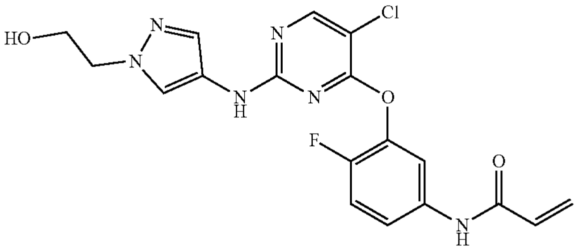 [SMILES: C=CC(=O)Nc1ccc(F)c(Oc2nc(Nc3cnn(CCO)c3)ncc2Cl)c1] | >10000 | 1332 | 2154 | ND | 1754 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 168 | 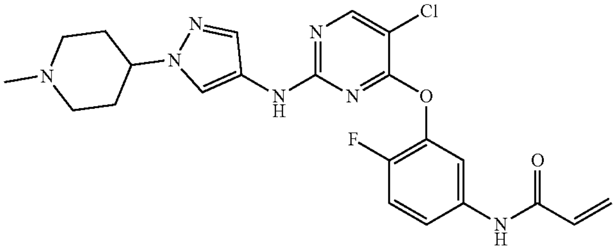 [SMILES: C=CC(=O)Nc1ccc(F)c(Oc2nc(Nc3cnn(C4CCN(C)CC4)c3)ncc2Cl)c1] | >10000 | 904 | 929 | ND | 2255 |
| 169 | 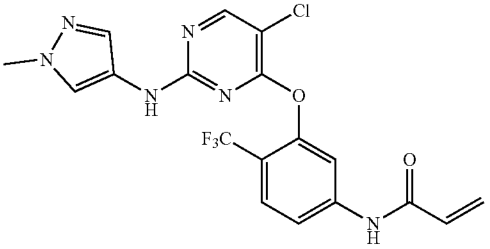 | 9693 | 8950 | >10000 | ND | ND |
| 170 | 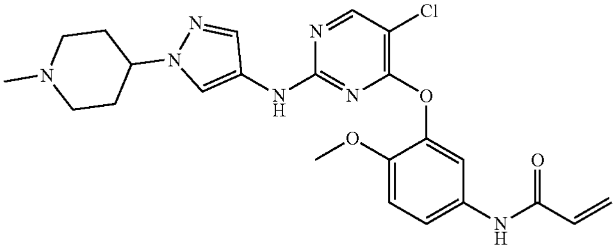 [SMILES: C=CC(=O)Nc1ccc(OC)c(Oc2nc(Nc3cnn(C4CCN(C)CC4)c3)ncc2Cl)c1] | >10000 | >10000 | >10000 | ND | 9710 |
| 171 | 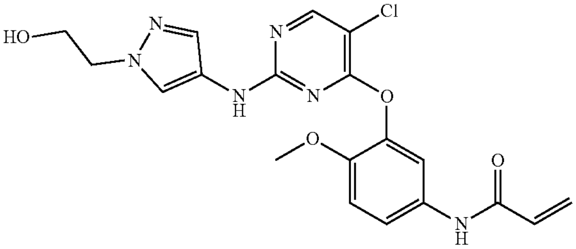 [SMILES: C=CC(=O)Nc1ccc(OC)c(Oc2nc(Nc3cnn(CCO)c3)ncc2Cl)c1] | >10000 | >10000 | >10000 | ND | ND |
| 172 | 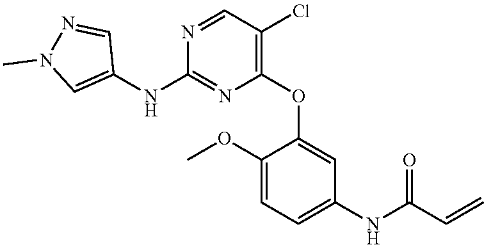 [SMILES: C=CC(=O)Nc1ccc(OC)c(Oc2nc(Nc3cnn(C)c3)ncc2Cl)c1] | >10000 | >10000 | >10000 | ND | >10000 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 173 | 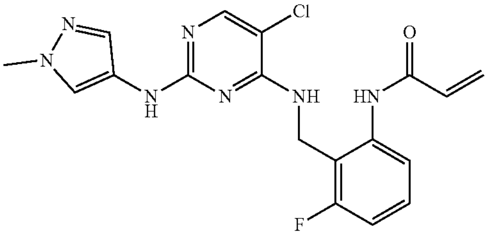 [SMILES: C=CC(=O)Nc1cccc(F)c1CNc1nc(Nc2cnn(C)c2)ncc1Cl] | >10000 | >10000 | 9779 | ND | 2005 |
| 174 | 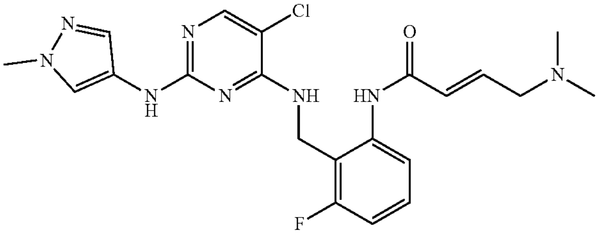 | >10000 | >10000 | >10000 | ND | ND |
| 175 | 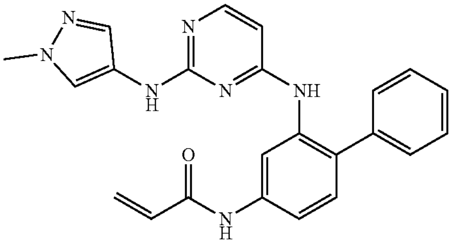 [SMILES: C=CC(=O)Nc1ccc(-c2ccccc2)c(Nc2ccnc(Nc3cnn(C)c3)n2)c1] | >10000 | >10000 | >10000 | ND | >10000 |
| 176 | 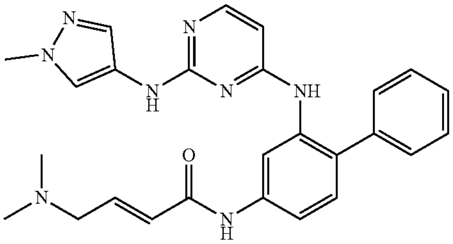 [SMILES: CN(C)C/C=C/C(=O)Nc1ccc(-c2ccccc2)c(Nc2ccnc(Nc3cnn(C)c3)n2)c1] | >10000 | 8021 | >10000 | ND | >10000 |
| 177 | 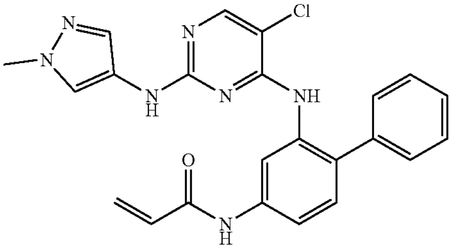 [SMILES: C=CC(=O)Nc1ccc(-c2ccccc2)c(Nc2nc(Nc3cnn(C)c3)ncc2Cl)c1] | >10000 | >10000 | >10000 | ND | >10000 |
| 178 | 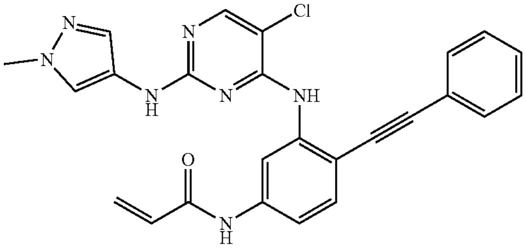 [SMILES: C=CC(=O)Nc1ccc(C#Cc2ccccc2)c(Nc2nc(Nc3cnn(C)c3)ncc2Cl)c1] | 9973 | >10000 | >10000 | ND | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 179 | 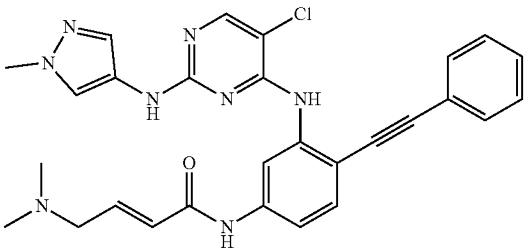 [SMILES: CN(C)C/C=C/C(=O)Nc1ccc(C#Cc2ccccc2)c(Nc2nc(Nc3cnn(C)c3)ncc2Cl)c1] | >10000 | >10000 | >10000 | ND | 4028 |
| 180 | 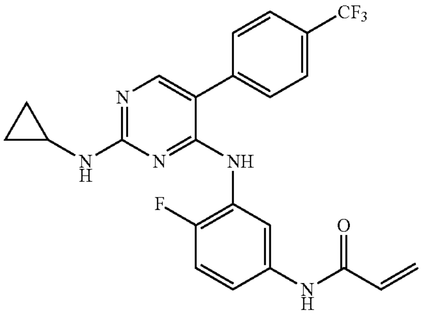 [SMILES: C=CC(=O)Nc1ccc(F)c(Nc2nc(NC3CC3)ncc2-c2ccc(C(F)(F)F)cc2)c1] | >10000 | >10000 | >10000 | ND | ND |
| 181 | 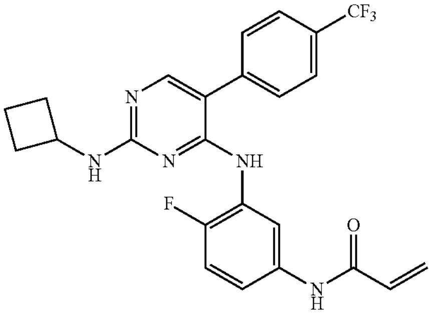 [SMILES: C=CC(=O)Nc1ccc(F)c(Nc2nc(NC3CCC3)ncc2-c2ccc(C(F)(F)F)cc2)c1] | >10000 | >10000 | >10000 | ND | ND |
| 182 | 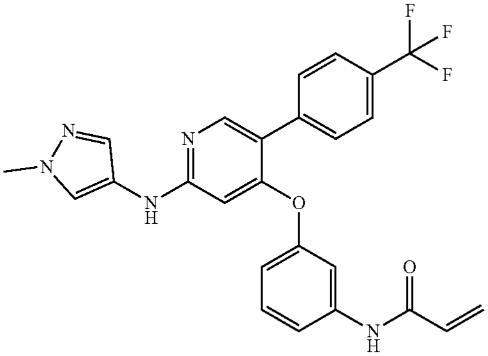 [SMILES: C=CC(=O)Nc1cccc(Oc2cc(Nc3cnn(C)c3)ncc2-c2ccc(C(F)(F)F)cc2)c1] | 6107 | 7469 | 9983 | ND | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 183 | 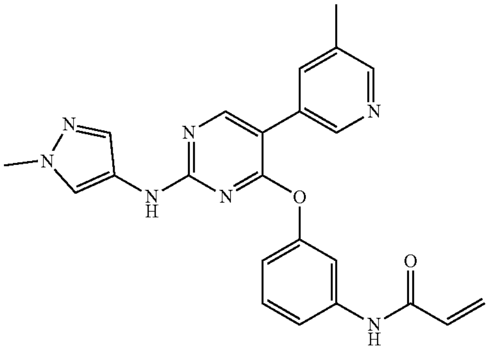 [SMILES: C=CC(=O)Nc1cccc(Oc2nc(Nc3cnn(C)c3)ncc2-c2cncc(C)c2)c1] | 292 | 286 | 320 | ND | ND |
| 184 | 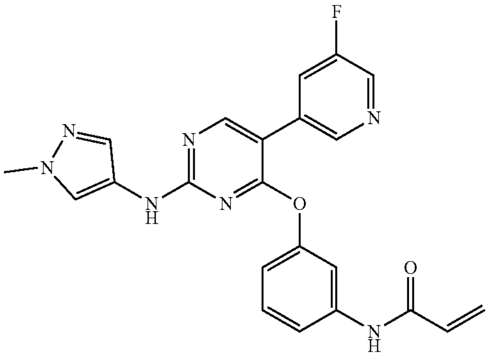 [SMILES: C=CC(=O)Nc1cccc(Oc2nc(Nc3cnn(C)c3)ncc2-c2cncc(F)c2)c1] | 97 | 27 | 37 | 222 | 60 |
| 185 | 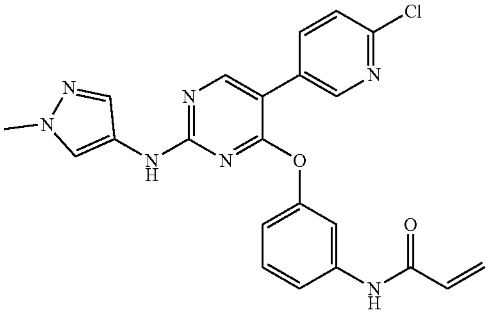 | 522 | 37 | 40 | 97 | 113 |
| 186 | 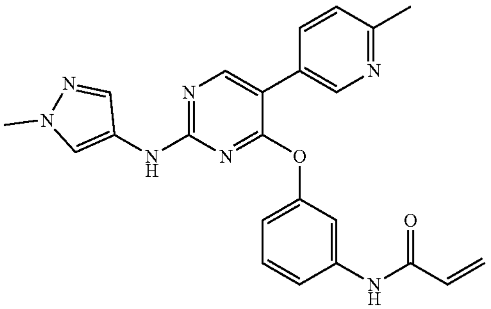 [SMILES: C=CC(=O)Nc1cccc(Oc2nc(Nc3cnn(C)c3)ncc2-c2ccc(C)nc2)c1] | 170 | 90 | 114 | 106 | 175 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 187 | 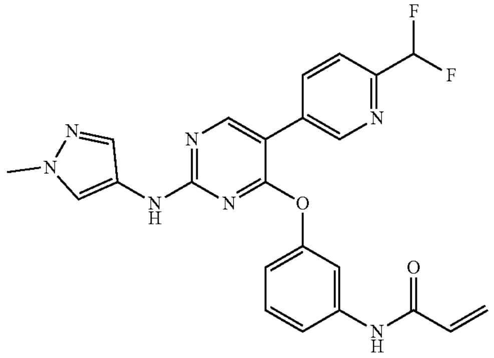 [SMILES: C=CC(=O)Nc1cccc(Oc2nc(Nc3cnn(C)c3)ncc2-c2ccc(C(F)F)nc2)c1] | 281 | 61 | 40 | 99 | 226 |
| 188 | 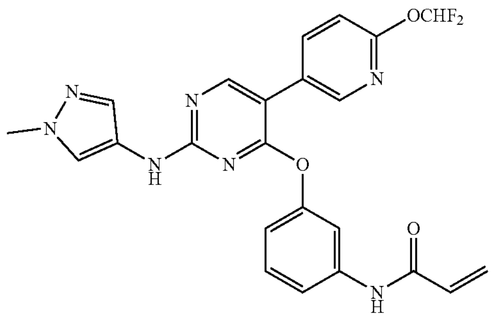 [SMILES: C=CC(=O)Nc1cccc(Oc2nc(Nc3cnn(C)c3)ncc2-c2ccc(OC(F)F)nc2)c1] | 216 | 118 | 108 | 300 | 269 |
| 189 | 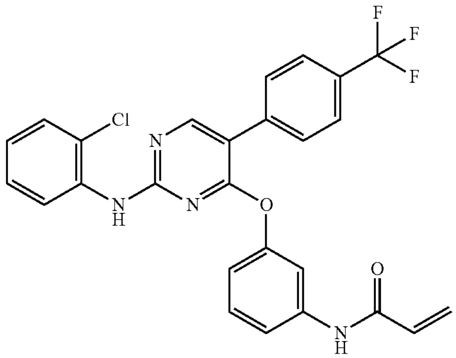 [SMILES: C=CC(=O)Nc1cccc(Oc2nc(Nc3ccccc3Cl)ncc2-c2ccc(C(F)(F)F)cc2)c1] | 8133 | >10000 | >10000 | ND | ND |
| 190 | 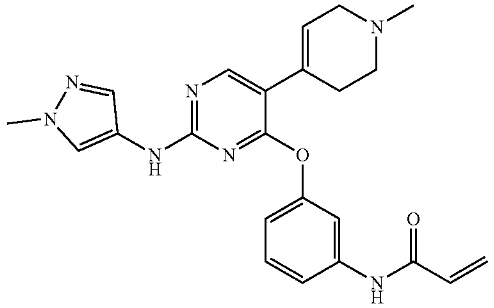 [SMILES: C=CC(=O)Nc1cccc(Oc2nc(Nc3cnn(C)c3)ncc2C2=CCN(C)CC2)c1] | 6756 | 9038 | 8859 | ND | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 191 | 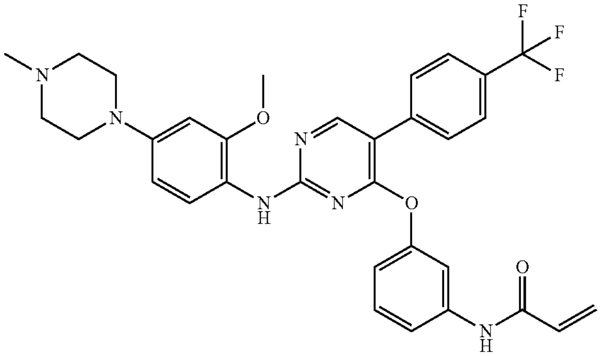 [SMILES: C=CC(=O)Nc1cccc(Oc2nc(Nc3ccc(N4CCN(C)CC4)cc3OC)ncc2-c2ccc(C(F)(F)F)cc2)c1] | 898 | 9650 | >10000 | ND | ND |
| 192 | 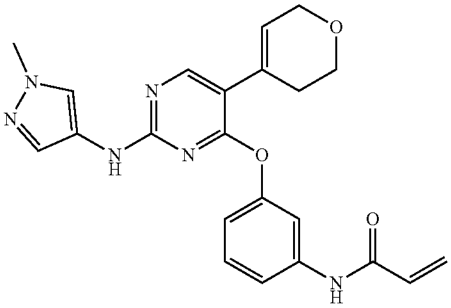 [SMILES: C=CC(=O)Nc1cccc(Oc2nc(Nc3cnn(C)c3)ncc2C2=CCOCC2)c1] | 258 | 241 | 267 | ND | ND |
| 193 | 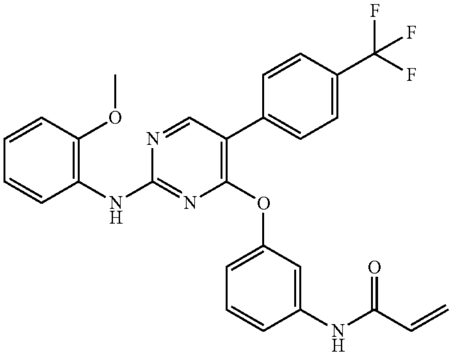 [SMILES: C=CC(=O)Nc1cccc(Oc2nc(Nc3ccccc3OC)ncc2-c2ccc(C(F)(F)F)cc2)c1] | 8755 | >10000 | >10000 | ND | ND |
| 194 | 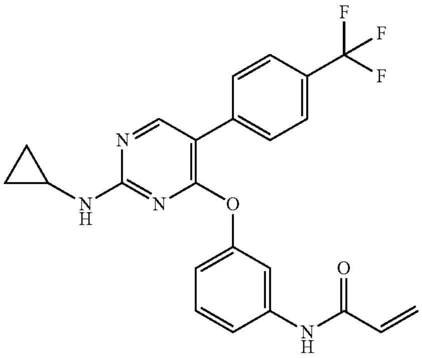 [SMILES: C=CC(=O)Nc1cccc(Oc2nc(NC3CC3)ncc2-c2ccc(C(F)(F)F)cc2)c1] | >10000 | >10000 | >10000 | ND | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 195 | 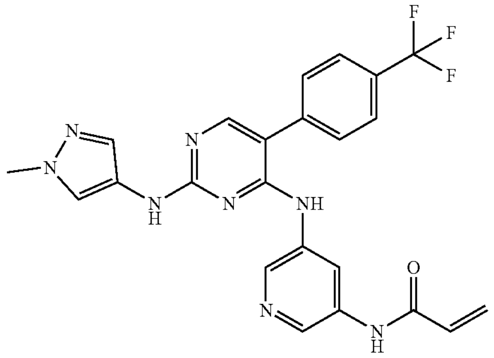 [SMILES: C=CC(=O)Nc1cncc(Nc2nc(Nc3cnn(C)c3)ncc2-c2ccc(C(F)(F)F)cc2)c1] | 524 | 135 | 57 | 180 | 258 |
| 196 | 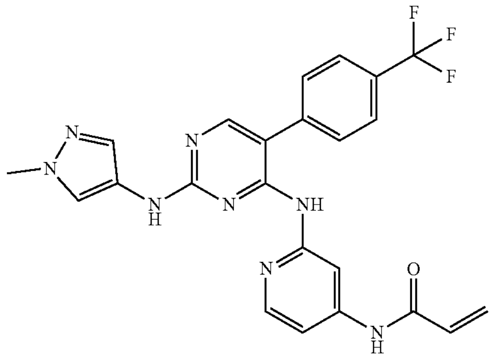 [SMILES: C=CC(=O)Nc1ccnc(Nc2nc(Nc3cnn(C)c3)ncc2-c2ccc(C(F)(F)F)cc2)c1] | 7553 | 8468 | 3215 | ND | ND |
| 197 | 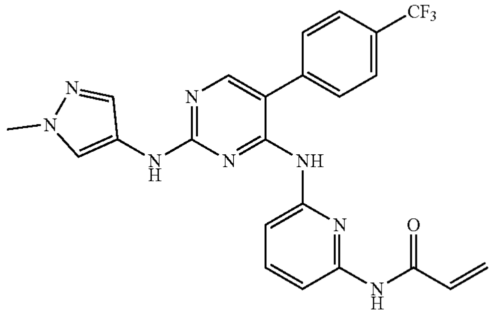 [SMILES: C=CC(=O)Nc1cccc(Nc2nc(Nc3cnn(C)c3)ncc2-c2ccc(C(F)(F)F)cc2)n1] | 373 | 448 | 395 | ND | ND |
| 198 | 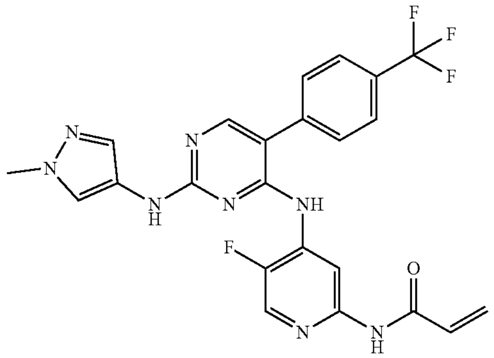 | 2138 | 2639 | 1274 | ND | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 199 | 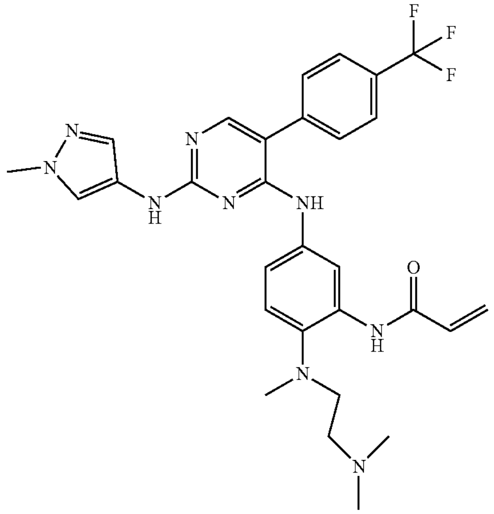 [SMILES: C=CC(=O)Nc1cc(Nc2nc(Nc3cnn(C)c3)ncc2-c2ccc(C(F)(F)F)cc2)ccc1N(C)CCN(C)C] | 716 | 704 | 239 | ND | ND |
| 200 | 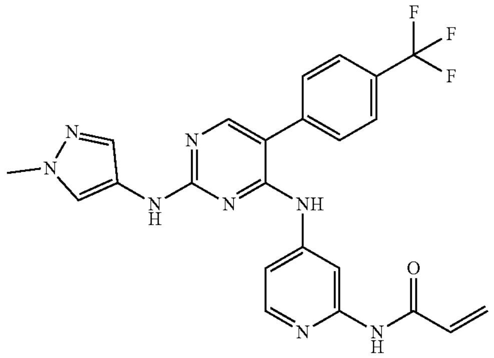 [SMILES: C=CC(=O)Nc1cc(Nc2nc(Nc3cnn(C)c3)ncc2-c2ccc(C(F)(F)F)cc2)ccn1] | 1282 | 2760 | 6023 | ND | ND |
| 201 | 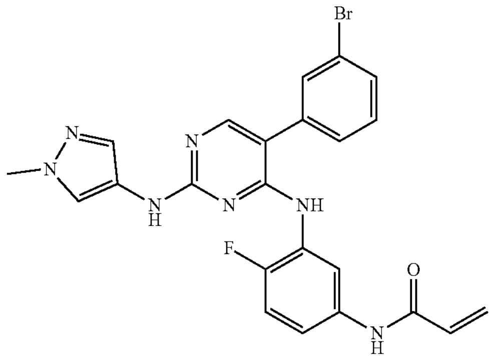 | 1515 | 227 | 270 | ND | 424 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 202 | 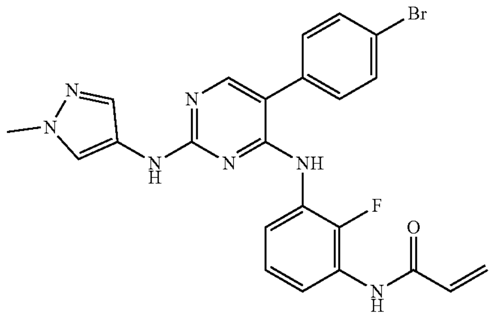 [SMILES: C=CC(=O)Nc1cccc(Nc2nc(Nc3cnn(C)c3)ncc2-c2ccc(Br)cc2)c1F] | 44 | 34 | 35 | ND | 217 |
| 203 | 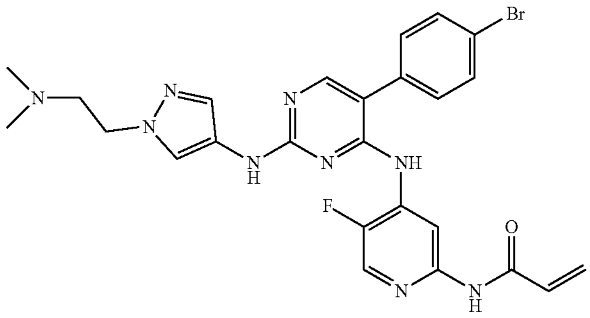 [SMILES: C=CC(=O)Nc1cc(Nc2nc(Nc3cnn(CCN(C)C)c3)ncc2-c2ccc(Br)cc2)c(F)cn1] | 51 | 100 | 69 | 107 | 110 |
| 204 | 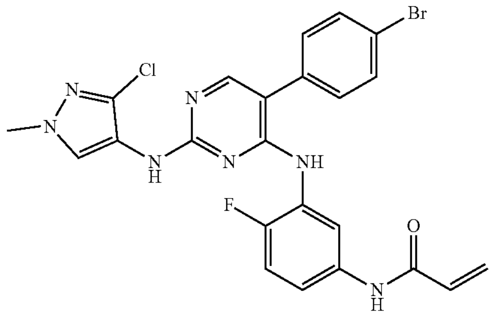 [SMILES: C=CC(=O)Nc1ccc(F)c(Nc2nc(Nc3cn(C)nc3Cl)ncc2-c2ccc(Br)cc2)c1] | 28 | 131 | 93 | ND | 688 |
| 205 | 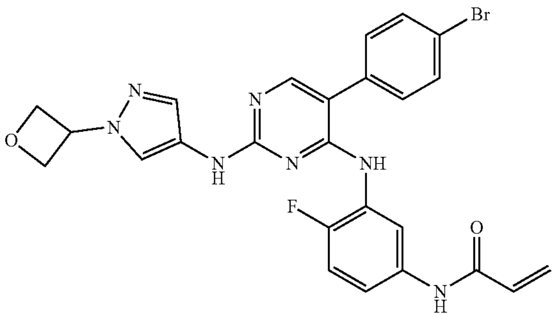 [SMILES: C=CC(=O)Nc1ccc(F)c(Nc2nc(Nc3cnn(C4COC4)c3)ncc2-c2ccc(Br)cc2)c1] | 132 | 73 | 39 | ND | 278 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 206 | 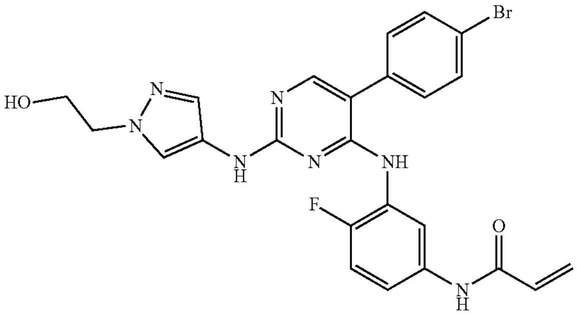 [SMILES: C=CC(=O)Nc1ccc(F)c(Nc2nc(Nc3cnn(CCO)c3)ncc2-c2ccc(Br)cc2)c1] | 36 | 44 | 35 | ND | 120 |
| 207 | 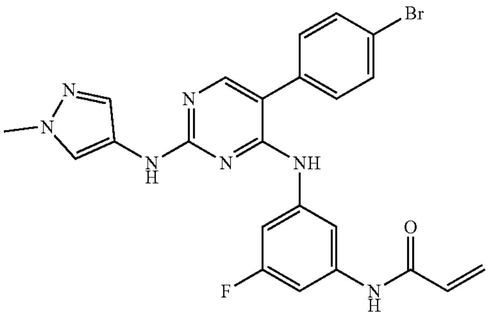 [SMILES: C=CC(=O)Nc1cc(F)cc(Nc2nc(Nc3cnn(C)c3)ncc2-c2ccc(Br)cc2)c1] | 49 | 31 | 32 | ND | ND |
| 208 | 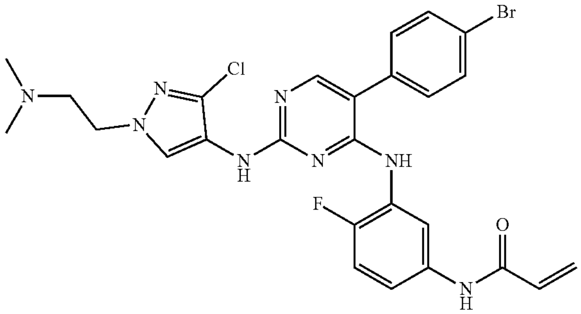 [SMILES: C=CC(=O)Nc1ccc(F)c(Nc2nc(Nc3cn(CCN(C)C)nc3Cl)ncc2-c2ccc(Br)cc2)c1] | 46 | 121 | 76 | ND | 402 |
| 209 | 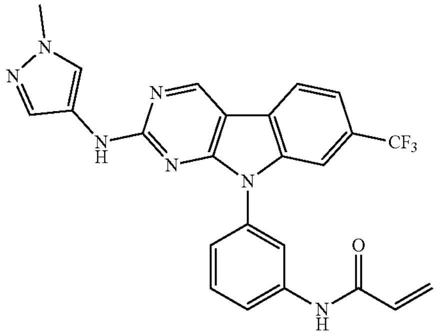 [SMILES: C=CC(=O)Nc1cccc(-n2c3cc(C(F)(F)F)ccc3c3cnc(Nc4cnn(C)c4)nc32)c1] | 5413 | 9859 | 7975 | ND | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 210 | 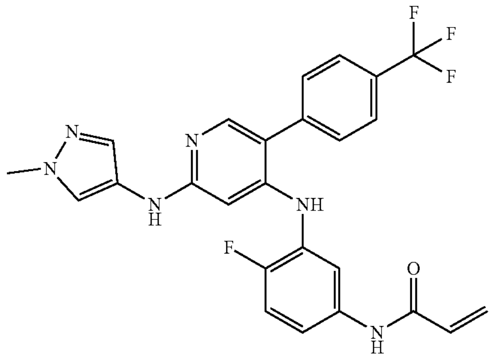 [SMILES: C=CC(=O)Nc1ccc(F)c(Nc2cc(Nc3cnn(C)c3)ncc2-c2ccc(C(F)(F)F)cc2)c1] | 4482 | 2895 | 2841 | ND | 3584 |
| 211 | 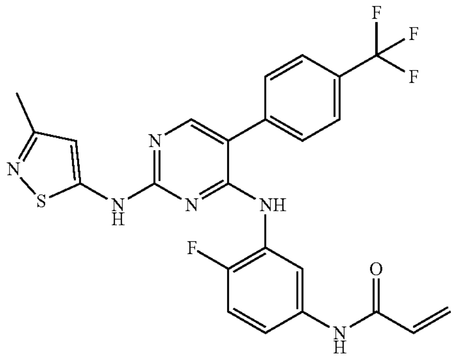 [SMILES: C=CC(=O)Nc1ccc(F)c(Nc2nc(Nc3cc(C)ns3)ncc2-c2ccc(C(F)(F)F)cc2)c1] | 1599 | 667 | 404 | ND | ND |
| 212 | 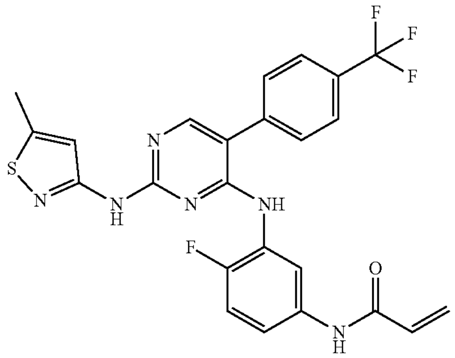 [SMILES: C=CC(=O)Nc1ccc(F)c(Nc2nc(Nc3cc(C)sn3)ncc2-c2ccc(C(F)(F)F)cc2)c1] | >10000 | 1566 | 884 | ND | ND |
| 213 | 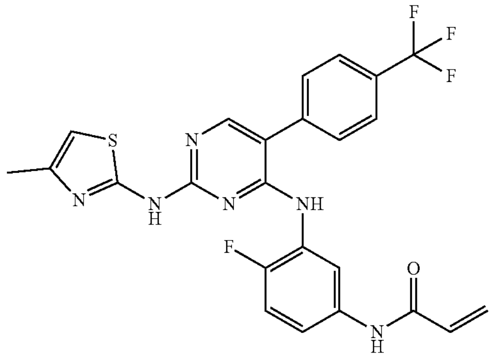 [SMILES: C=CC(=O)Nc1ccc(F)c(Nc2nc(Nc3nc(C)cs3)ncc2-c2ccc(C(F)(F)F)cc2)c1] | 1820 | 3684 | 1292 | ND | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 214 | 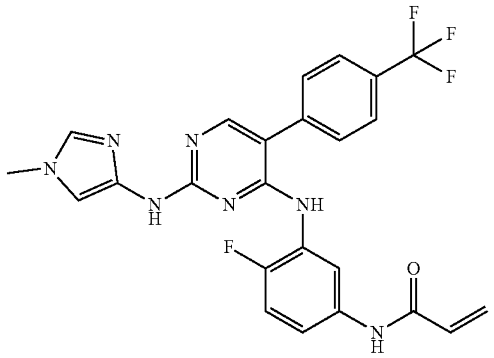 [SMILES: C=CC(=O)Nc1ccc(F)c(Nc2nc(Nc3cn(C)cn3)ncc2-c2ccc(C(F)(F)F)cc2)c1] | >10000 | 543 | 308 | ND | ND |
| 215 | 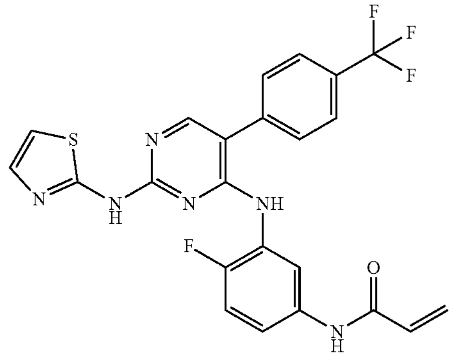 [SMILES: C=CC(=O)Nc1ccc(F)c(Nc2nc(Nc3nccs3)ncc2-c2ccc(C(F)(F)F)cc2)c1] | 2266 | >10000 | 991 | ND | ND |
| 216 | 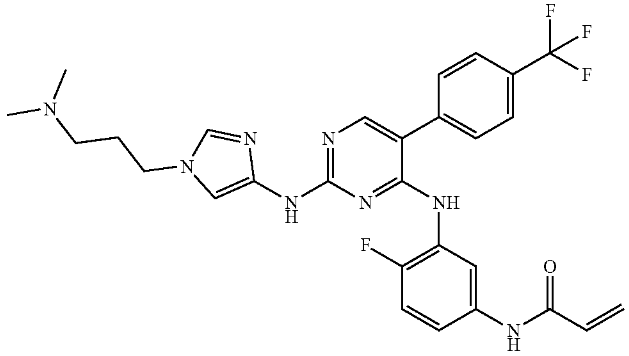 [SMILES: C=CC(=O)Nc1ccc(F)c(Nc2nc(Nc3cn(CCCN(C)C)cn3)ncc2-c2ccc(C(F)(F)F)cc2)c1] | 115 | 335 | 185 | 131 | 233 |
| 217 | 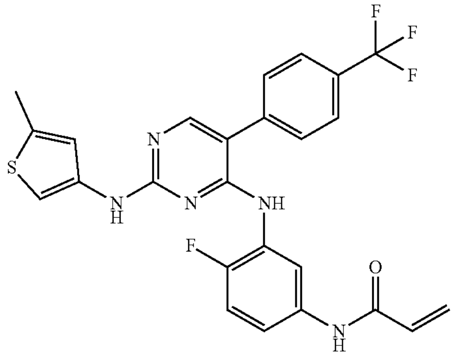 [SMILES: C=CC(=O)Nc1ccc(F)c(Nc2nc(Nc3csc(C)c3)ncc2-c2ccc(C(F)(F)F)cc2)c1] | >10000 | 1130 | 916 | ND | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 218 | 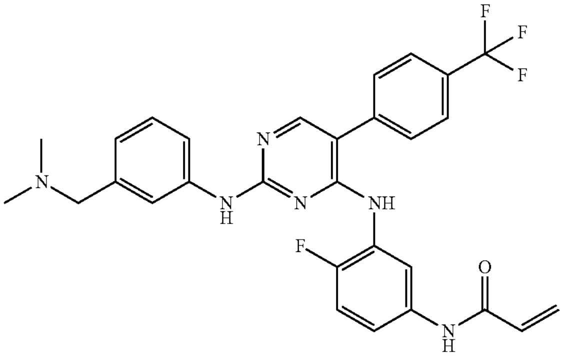 [SMILES: C=CC(=O)Nc1ccc(F)c(Nc2nc(Nc3cccc(CN(C)C)c3)ncc2-c2ccc(C(F)(F)F)cc2)c1] | 1577 | 8466 | 1686 | ND | ND |
| 219 | 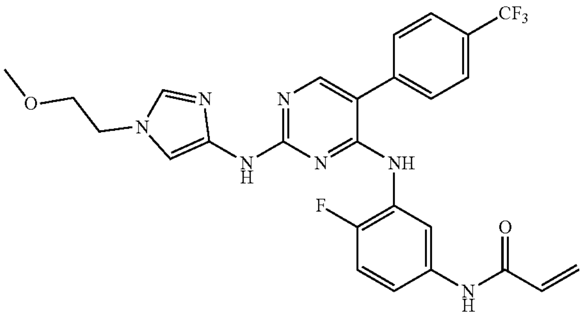 [SMILES: C=CC(=O)Nc1ccc(F)c(Nc2nc(Nc3cn(CCOC)cn3)ncc2-c2ccc(C(F)(F)F)cc2)c1] | 98 | 441 | 113 | ND | ND |
| 220 | 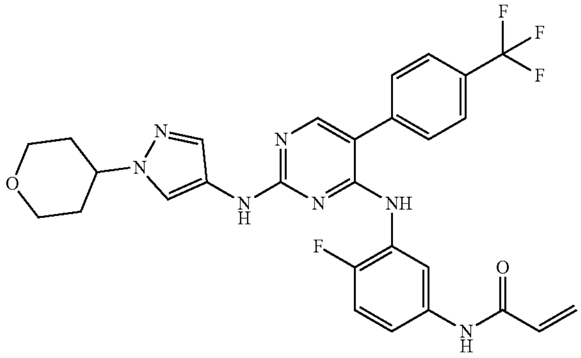 [SMILES: C=CC(=O)Nc1ccc(F)c(Nc2nc(Nc3cnn(C4CCOCC4)c3)ncc2-c2ccc(C(F)(F)F)cc2)c1] | 133 | 211 | 110 | ND | ND |
| 221 | 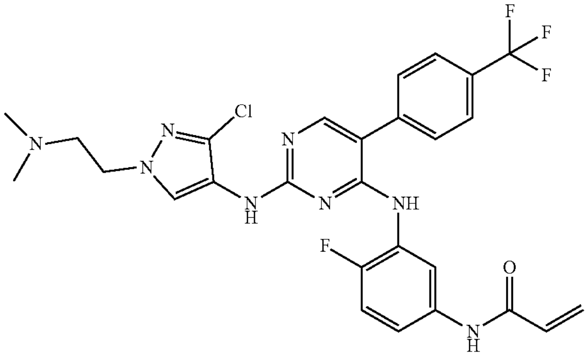 [SMILES: C=CC(=O)Nc1ccc(F)c(Nc2nc(Nc3cn(CCN(C)C)nc3Cl)ncc2-c2ccc(C(F)(F)F)cc2)c1] | 68 | 297 | 123 | 225 | 298 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 222 | 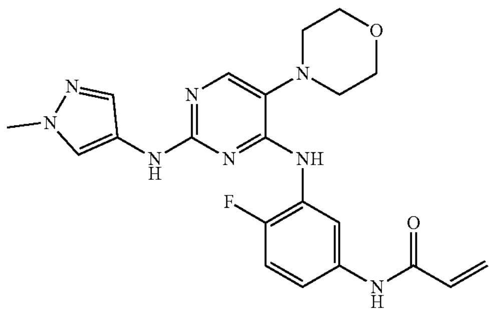 | 8151 | >10000 | >10000 | ND | ND |
| 223 | 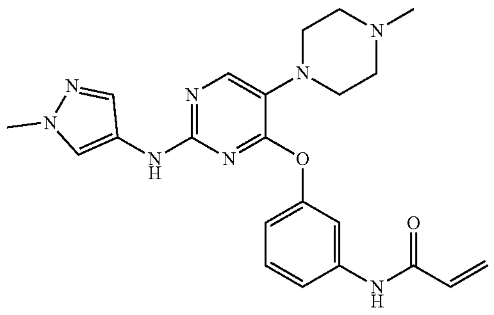 [SMILES: C=CC(=O)Nc1cccc(Oc2nc(Nc3cnn(C)c3)ncc2N2CCN(C)CC2)c1] | 3925 | 9695 | 9028 | ND | ND |
| 224 | 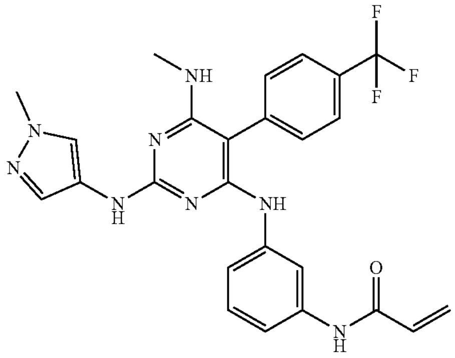 [SMILES: C=CC(=O)Nc1cccc(Nc2nc(Nc3cnn(C)c3)nc(NC)c2-c2ccc(C(F)(F)F)cc2)c1] | >10000 | >10000 | >10000 | ND | ND |
| 225 | 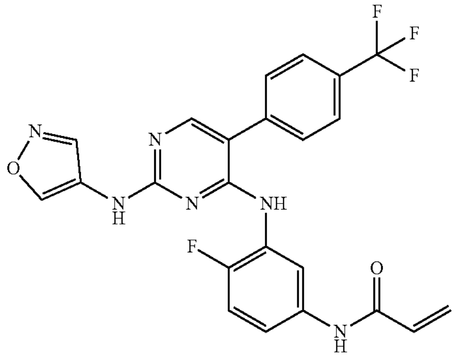 [SMILES: C=CC(=O)Nc1ccc(F)c(Nc2nc(Nc3cnoc3)ncc2-c2ccc(C(F)(F)F)cc2)c1] | 637 | 2686 | 1235 | ND | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 226 | 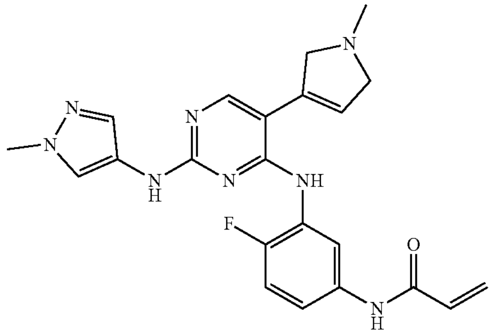 [SMILES: C=CC(=O)Nc1ccc(F)c(Nc2nc(Nc3cnn(C)c3)ncc2C2=CCN(C)C2)c1] | 1779 | 1606 | 793 | ND | ND |
| 227 | 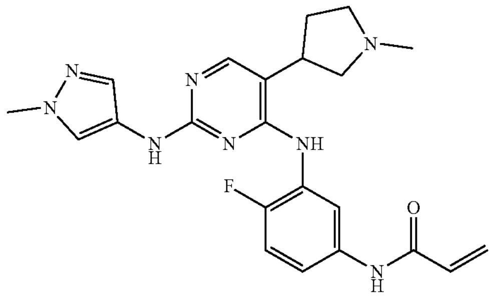 [SMILES: C=CC(=O)Nc1ccc(F)c(Nc2nc(Nc3cnn(C)c3)ncc2C2CCN(C)C2)c1] | 6059 | 7092 | >10000 | ND | ND |
| 228 | 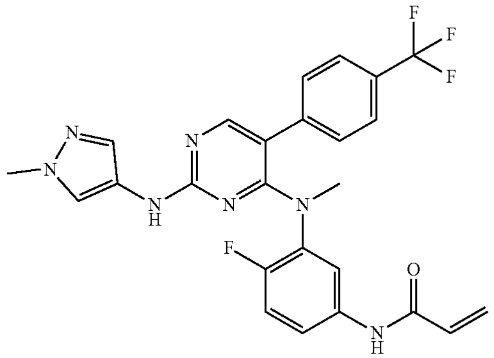 [SMILES: C=CC(=O)Nc1ccc(F)c(N(C)c2nc(Nc3cnn(C)c3)ncc2-c2ccc(C(F)(F)F)cc2)c1] | 4116 | 891 | 952 | ND | 1249 |
| 229 | 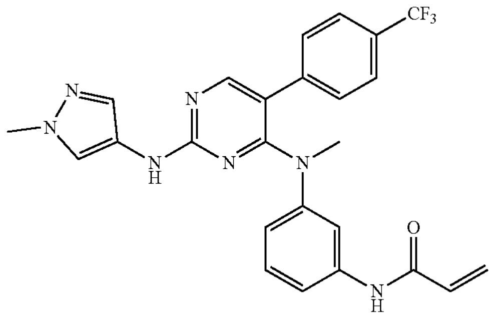 [SMILES: C=CC(=O)Nc1cccc(N(C)c2nc(Nc3cnn(C)c3)ncc2-c2ccc(C(F)(F)F)cc2)c1] | 222 | 426 | 318 | ND | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 230 | 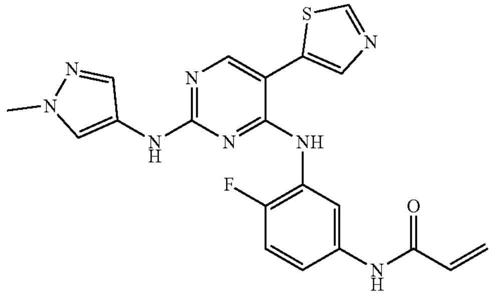 [SMILES: C=CC(=O)Nc1ccc(F)c(Nc2nc(Nc3cnn(C)c3)ncc2-c2cncs2)c1] | 109 | 63 | 63 | 41 | 54 |
| 231 | 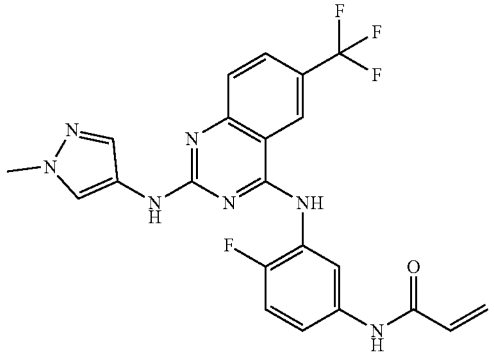 [SMILES: C=CC(=O)Nc1ccc(F)c(Nc2nc(Nc3cnn(C)c3)nc3ccc(C(F)(F)F)cc23)c1] | 4209 | 3899 | 8550 | ND | ND |
| 232 | 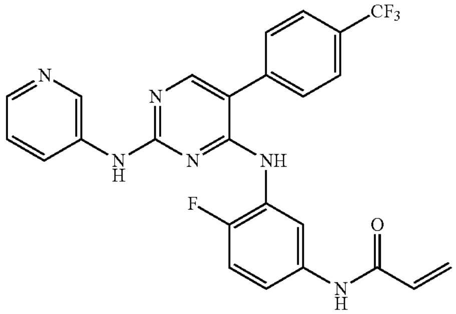 [SMILES: C=CC(=O)Nc1ccc(F)c(Nc2nc(Nc3cccnc3)ncc2-c2ccc(C(F)(F)F)cc2)c1] | 539 | 1126 | 724 | ND | ND |
| 233 | 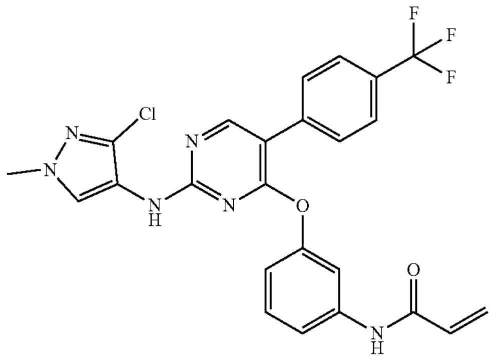 [SMILES: C=CC(=O)Nc1cccc(Oc2nc(Nc3cn(C)nc3Cl)ncc2-c2ccc(C(F)(F)F)cc2)c1] | 262 | 428 | 187 | 385 | 537 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 234 | 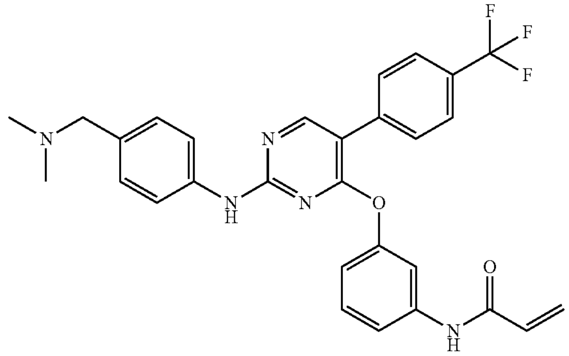 [SMILES: C=CC(=O)Nc1cccc(Oc2nc(Nc3ccc(CN(C)C)cc3)ncc2-c2ccc(C(F)(F)F)cc2)c1] | 1134 | 948 | 383 | ND | ND |
| 235 | 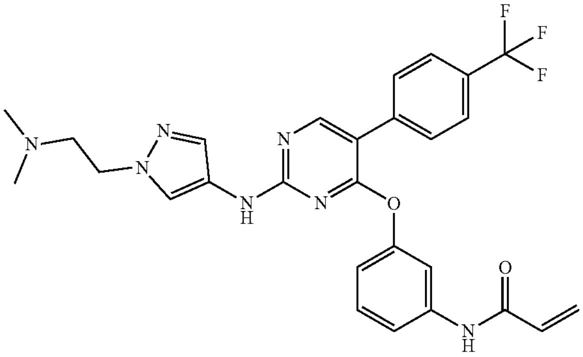 [SMILES: C=CC(=O)Nc1cccc(Oc2nc(Nc3cnn(CCN(C)C)c3)ncc2-c2ccc(C(F)(F)F)cc2)c1] | 1070 | 980 | 619 | ND | ND |
| 236 | 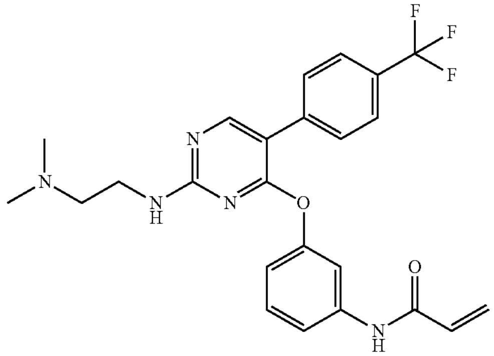 [SMILES: C=CC(=O)Nc1cccc(Oc2nc(NCCN(C)C)ncc2-c2ccc(C(F)(F)F)cc2)c1] | >10000 | >10000 | >10000 | ND | ND |
| 237 | 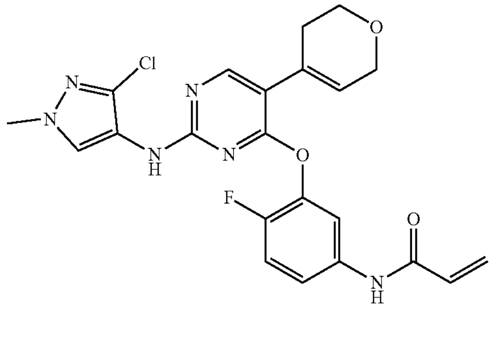 [SMILES: C=CC(=O)Nc1ccc(F)c(Oc2nc(Nc3cn(C)nc3Cl)ncc2C2=CCOCC2)c1] | ND | ND | ND | ND | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 238 | 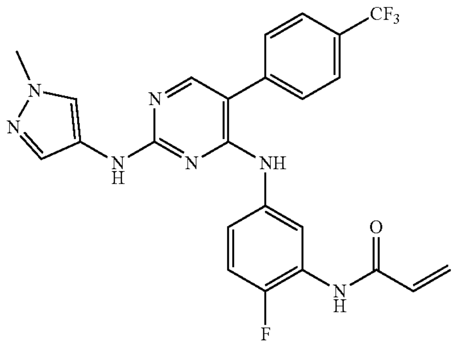 [SMILES: C=CC(=O)Nc1cc(Nc2nc(Nc3cnn(C)c3)ncc2-c2ccc(C(F)(F)F)cc2)ccc1F] | 617 | 90 | 312 | ND | 3011 |
| 239 | 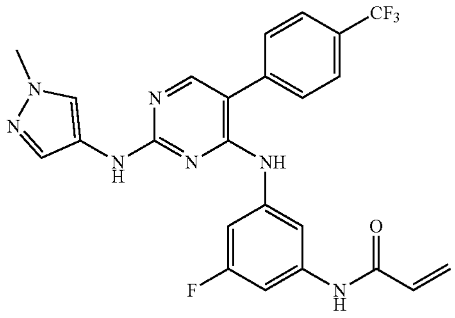 [SMILES: C=CC(=O)Nc1cc(F)cc(Nc2nc(Nc3cnn(C)c3)ncc2-c2ccc(C(F)(F)F)cc2)c1] | 229 | 91 | 36 | ND | 251 |
| 240 | 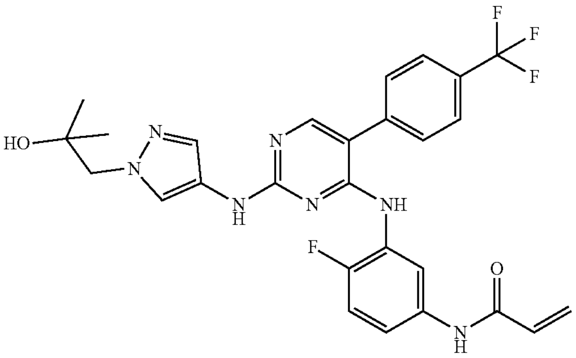 [SMILES: C=CC(=O)Nc1ccc(F)c(Nc2nc(Nc3cnn(CC(C)(C)O)c3)ncc2-c2ccc(C(F)(F)F)cc2)c1] | 441 | 861 | 395 | ND | 2012 |
| 241 | 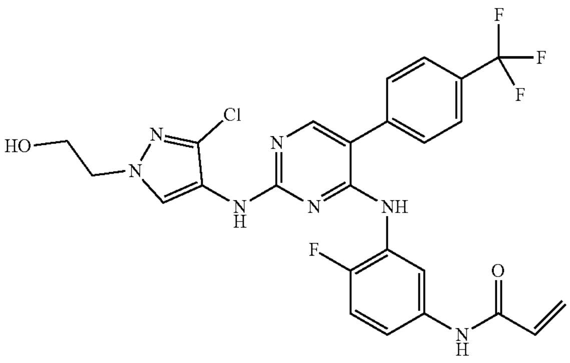 [SMILES: C=CC(=O)Nc1ccc(F)c(Nc2nc(Nc3cn(CCO)nc3Cl)ncc2-c2ccc(C(F)(F)F)cc2)c1] | 105 | 146 | 105 | ND | 343 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 242 | 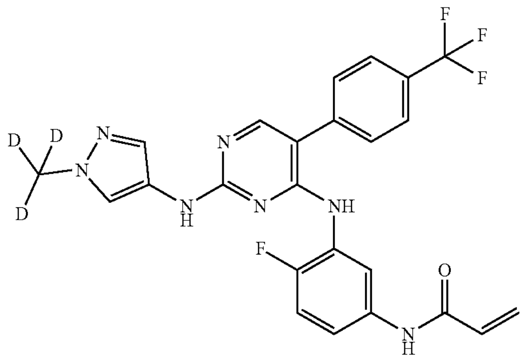 [SMILES: [2H]C([2H])([2H])n1cc(Nc2ncc(-c3ccc(C(F)(F)F)cc3)c(Nc3cc(NC(=O)C=C)ccc3F)n2)cn1] | 129 | 101 | 98 | 101 | 133 |
| 243 | 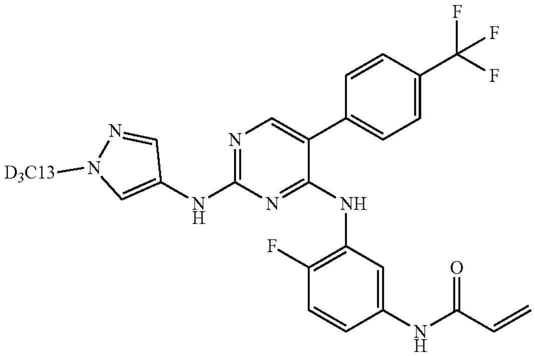 | 2605 | 135 | 88 | 121 | 237 |
| 244 | 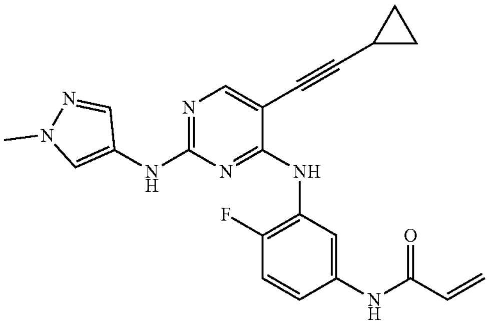 [SMILES: C=CC(=O)Nc1ccc(F)c(Nc2nc(Nc3cnn(C)c3)ncc2C#CC2CC2)c1] | 1806 | 2183 | 1891 | ND | 2254 |
| 245 | 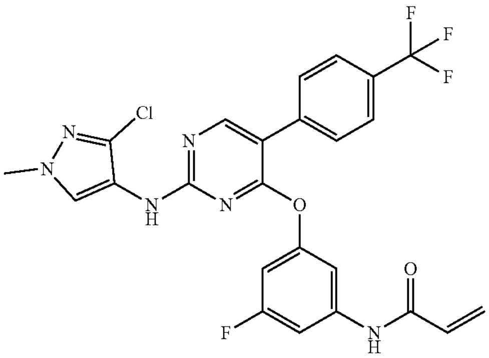 [SMILES: C=CC(=O)Nc1cc(F)cc(Oc2nc(Nc3cn(C)nc3Cl)ncc2-c2ccc(C(F)(F)F)cc2)c1] | 63 | 115 | 91 | ND | 202 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 246 | 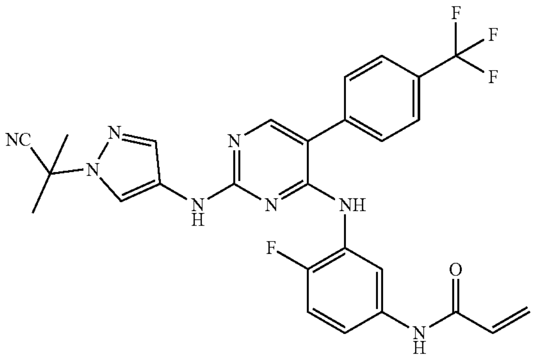 [SMILES: C=CC(=O)Nc1ccc(F)c(Nc2nc(Nc3cnn(C(C)(C)C#N)c3)ncc2-c2ccc(C(F)(F)F)cc2)c1] | 368 | 303 | 299 | ND | 2068 |
| 247 | 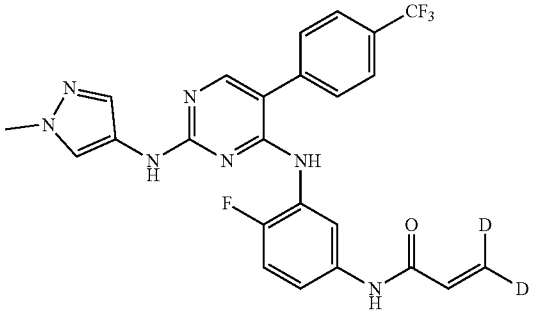 [SMILES: [2H]C([2H])=CC(=O)Nc1ccc(F)c(Nc2nc(Nc3cnn(C)c3)ncc2-c2ccc(C(F)(F)F)cc2)c1] | 3000 | 123 | 86 | 144 | 270 |
| 248 | 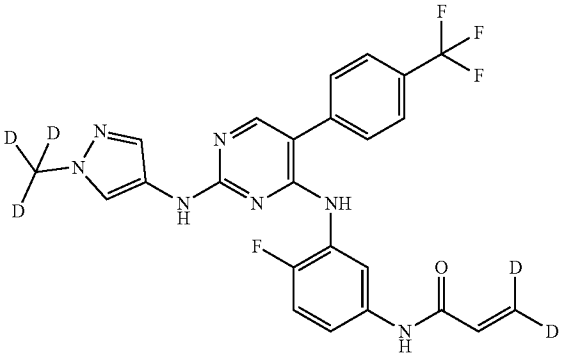 [SMILES: [2H]C([2H])=CC(=O)Nc1ccc(F)c(Nc2nc(Nc3cnn(C([2H])([2H])[2H])c3)ncc2-c2ccc(C(F)(F)F)cc2)c1] | 222 | 143 | 109 | 43 | 250 |
| 249 | 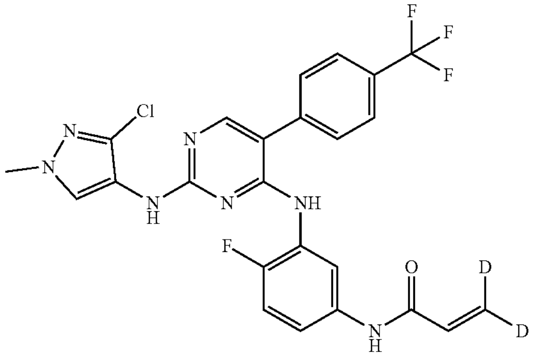 [SMILES: [2H]C([2H])=CC(=O)Nc1ccc(F)c(Nc2nc(Nc3cn(C)nc3Cl)ncc2-c2ccc(C(F)(F)F)cc2)c1] | 123 | 261 | 101 | ND | 1046 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 250 | 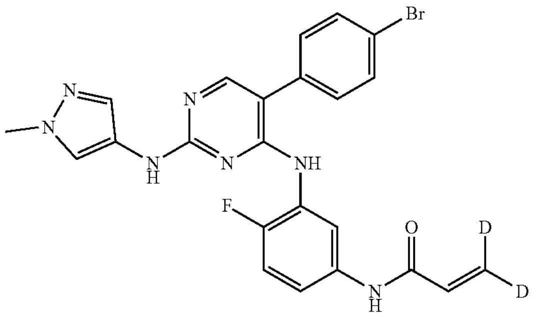 [SMILES: [2H]C([2H])=CC(=O)Nc1ccc(F)c(Nc2nc(Nc3cnn(C)c3)ncc2-c2ccc(Br)cc2)c1] | 65 | 47 | 34 | ND | 204 |
| 251 | 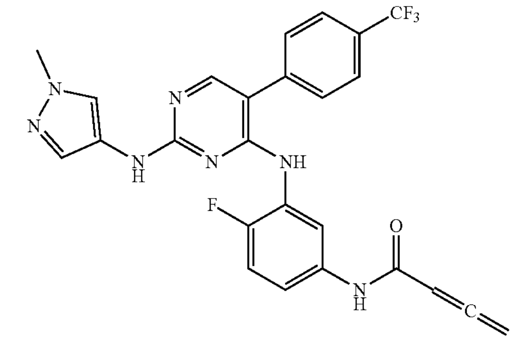 [SMILES: C=C=CC(=O)Nc1ccc(F)c(Nc2nc(Nc3cnn(C)c3)ncc2-c2ccc(C(F)(F)F)cc2)c1] | 9771.5 | 9876 | 9995 | ND | ND |
| 252 | 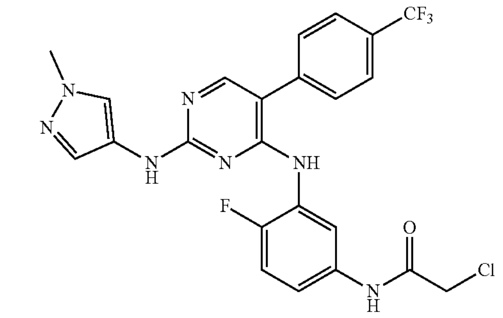 [SMILES: Cn1cc(Nc2ncc(-c3ccc(C(F)(F)F)cc3)c(Nc3cc(NC(=O)CCl)ccc3F)n2)cn1] | 1175 | 5963 | 1420 | 2809 | ND |
| 253 | 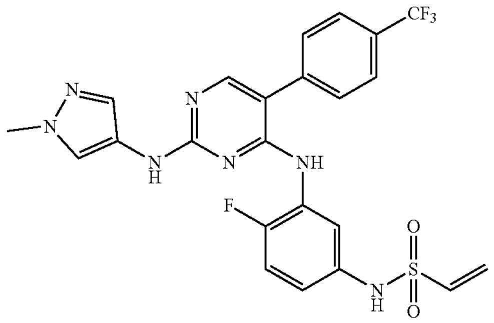 [SMILES: C=CS(=O)(=O)Nc1ccc(F)c(Nc2nc(Nc3cnn(C)c3)ncc2-c2ccc(C(F)(F)F)cc2)c1] | 3981 | 8747 | 8445 | >10000 | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 254 | 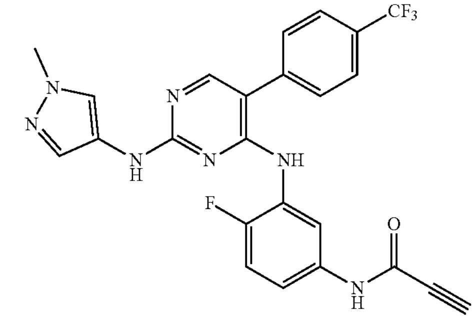 [SMILES: C#CC(=O)Nc1ccc(F)c(Nc2nc(Nc3cnn(C)c3)ncc2-c2ccc(C(F)(F)F)cc2)c1] | 1004 | 9465 | 8457 | ND | 8674 |
| 255 | 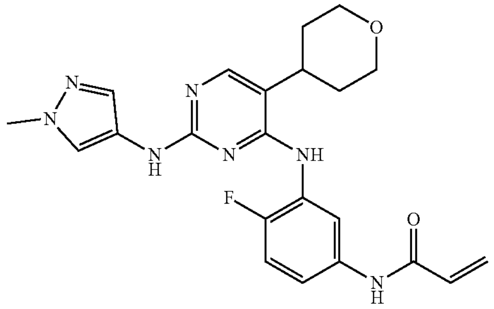 [SMILES: C=CC(=O)Nc1ccc(F)c(Nc2nc(Nc3cnn(C)c3)ncc2C2CCOCC2)c1] | ND | ND | ND | ND | >10000 |
| 256 | 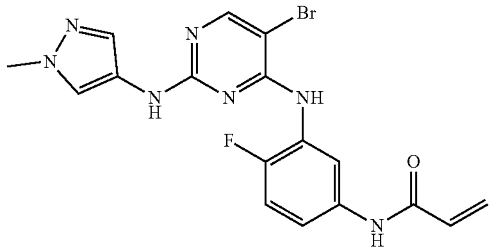 [SMILES: C=CC(=O)Nc1ccc(F)c(Nc2nc(Nc3cnn(C)c3)ncc2Br)c1] | 1024 | 411 | 923 | ND | 755 |
| 257 | 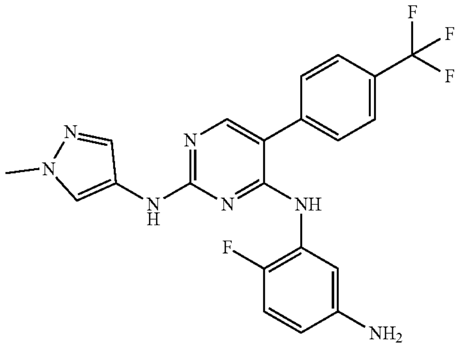 [SMILES: Cn1cc(Nc2ncc(-c3ccc(C(F)(F)F)cc3)c(Nc3cc(N)ccc3F)n2)cn1] | >10000 | >10000 | >10000 | ND | ND |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 258 | 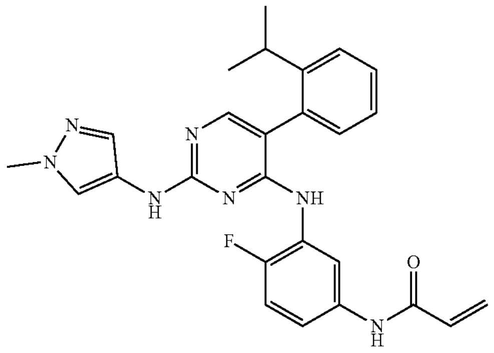 | ND | ND | ND | ND | ND |
| 259 | 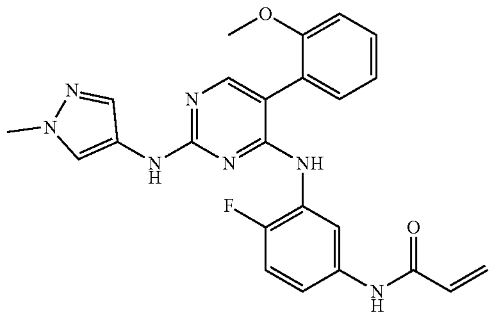 [SMILES: C=CC(=O)Nc1ccc(F)c(Nc2nc(Nc3cnn(C)c3)ncc2-c2ccccc2OC)c1] | ND | ND | ND | ND | ND |
| 260 | 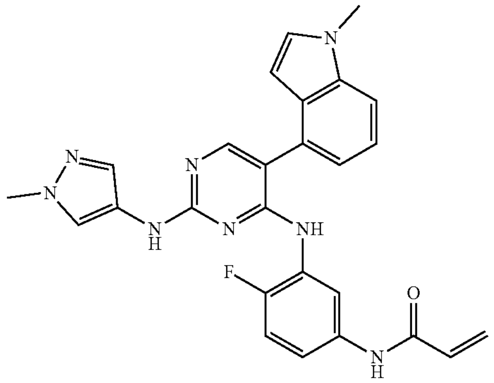 [SMILES: C=CC(=O)Nc1ccc(F)c(Nc2nc(Nc3cnn(C)c3)ncc2-c2cccc3c2ccn3C)c1] | ND | ND | ND | ND | ND |
| 261 | 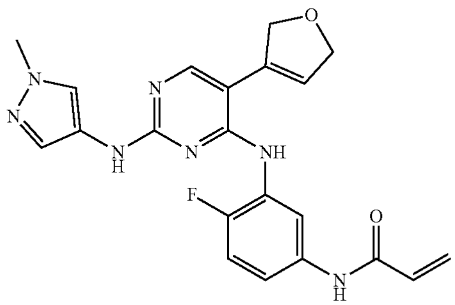 [SMILES: C=CC(=O)Nc1ccc(F)c(Nc2nc(Nc3cnn(C)c3)ncc2C2=CCOC2)c1] | 195 | ND | ND | ND | 222 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 262 | 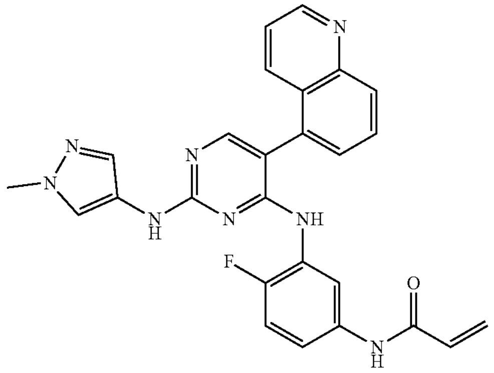 [SMILES: C=CC(=O)Nc1ccc(F)c(Nc2nc(Nc3cnn(C)c3)ncc2-c2cccc3ncccc23)c1] | ND | ND | ND | ND | 4429 |
| 263 | 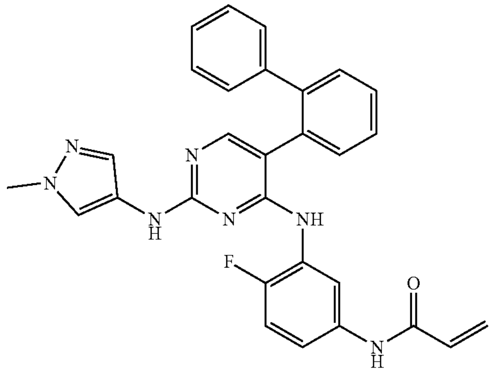 [SMILES: C=CC(=O)Nc1ccc(F)c(Nc2nc(Nc3cnn(C)c3)ncc2-c2ccccc2-c2ccccc2)c1] | 6225 | ND | ND | ND | ND |
| 264 | 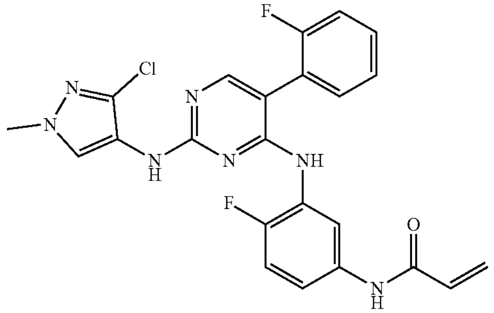 [SMILES: C=CC(=O)Nc1ccc(F)c(Nc2nc(Nc3cn(C)nc3Cl)ncc2-c2ccccc2F)c1] | 145 | ND | ND | ND | 465 |
| 265 | 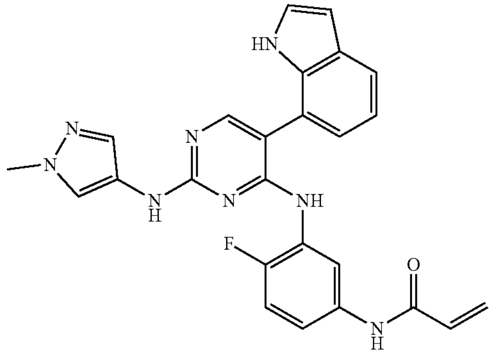 [SMILES: C=CC(=O)Nc1ccc(F)c(Nc2nc(Nc3cnn(C)c3)ncc2-c2cccc3cc[nH]c23)c1] | 4890 | ND | ND | ND | ND |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 266 | 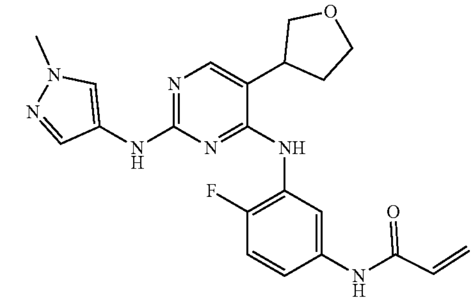 [SMILES: C=CC(=O)Nc1ccc(F)c(Nc2nc(Nc3cnn(C)c3)ncc2C2CCOC2)c1] | 768 | ND | ND | ND | 1379 |
| 267 | 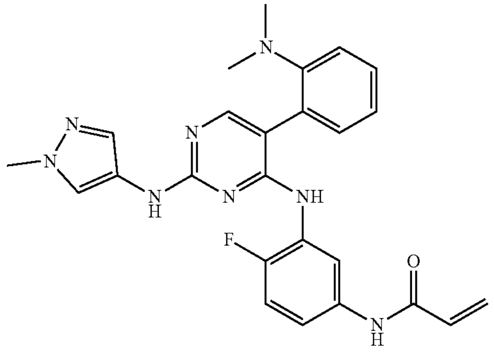 | 5804 | ND | ND | ND | >10000 |
| 268 | 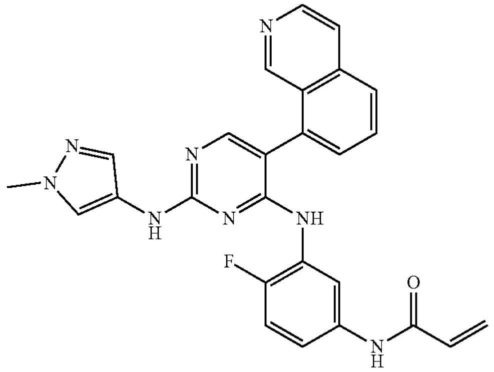 [SMILES: C=CC(=O)Nc1ccc(F)c(Nc2nc(Nc3cnn(C)c3)ncc2-c2cccc3ccncc23)c1] | 3439 | ND | ND | ND | >10000 |
| 269 | 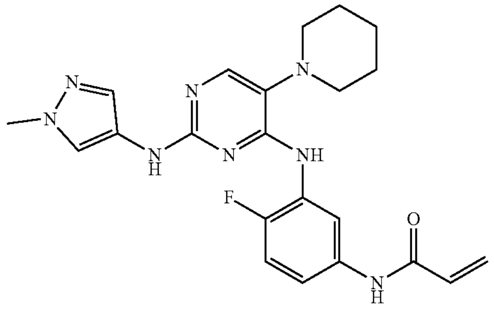 [SMILES: C=CC(=O)Nc1ccc(F)c(Nc2nc(Nc3cnn(C)c3)ncc2N2CCCCC2)c1] | 5608 | ND | ND | ND | >10000 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 270 | 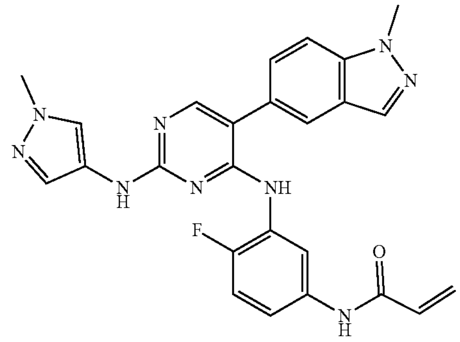 [SMILES: C=CC(=O)Nc1ccc(F)c(Nc2nc(Nc3cnn(C)c3)ncc2-c2ccc3c(cnn3C)c2)c1] | 190 | ND | ND | ND | 985 |
| 271 | 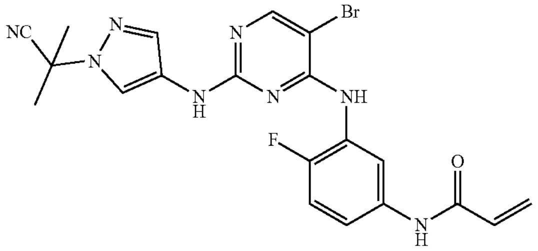 [SMILES: C=CC(=O)Nc1ccc(F)c(Nc2nc(Nc3cnn(C(C)(C)C#N)c3)ncc2Br)c1] | 2962 | ND | ND | ND | 2159 |
| 272 | 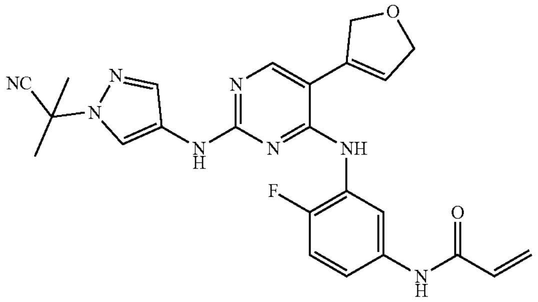 [SMILES: C=CC(=O)Nc1ccc(F)c(Nc2nc(Nc3cnn(C(C)(C)C#N)c3)ncc2C2=CCOC2)c1] | 1011 | ND | ND | ND | 602 |
| 273 | 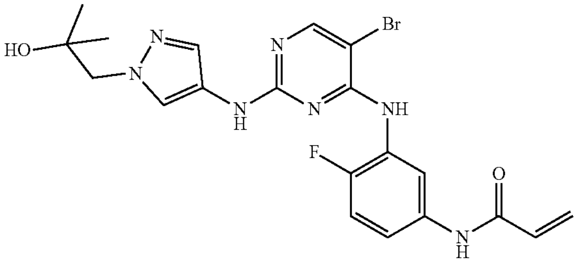 [SMILES: C=CC(=O)Nc1ccc(F)c(Nc2nc(Nc3cnn(CC(C)(C)O)c3)ncc2Br)c1] | 3930 | ND | ND | ND | 2628 |
| 274 | 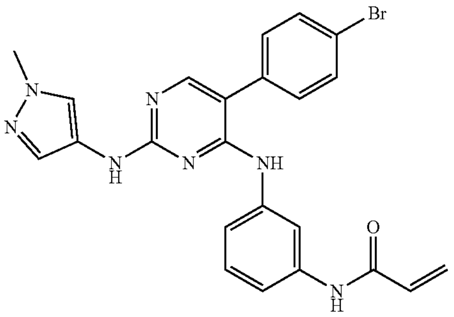 [SMILES: C=CC(=O)Nc1cccc(Nc2nc(Nc3cnn(C)c3)ncc2-c2ccc(Br)cc2)c1] | 22 | 33 | 29 | ND | 120 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 275 | 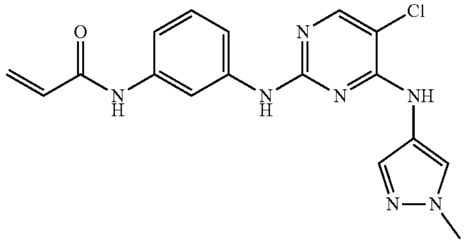 [SMILES: C=CC(=O)Nc1cccc(Nc2ncc(Cl)c(Nc3cnn(C)c3)n2)c1] | 1434 | ND | ND | ND | 3046 |
| 276 | 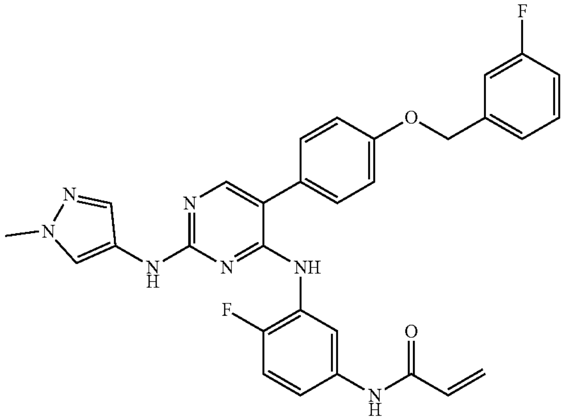 [SMILES: C=CC(=O)Nc1ccc(F)c(Nc2nc(Nc3cnn(C)c3)ncc2-c2ccc(OCc3cccc(F)c3)cc2)c1] | 278 | ND | ND | ND | 861 |
| 277 | 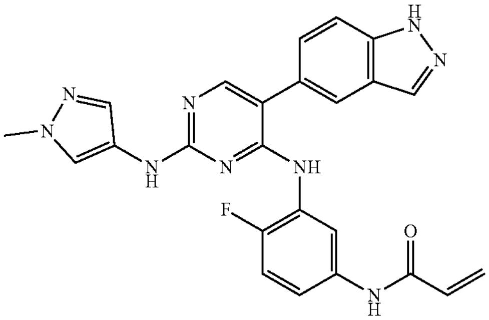 [SMILES: C=CC(=O)Nc1ccc(F)c(Nc2nc(Nc3cnn(C)c3)ncc2-c2ccc3[nH]ncc3c2)c1] | 293 | ND | ND | ND | 645 |
| 278 | 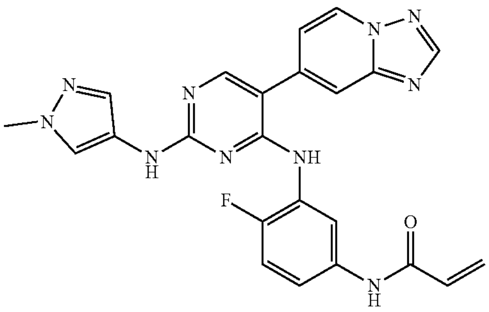 [SMILES: C=CC(=O)Nc1ccc(F)c(Nc2nc(Nc3cnn(C)c3)ncc2-c2ccn3ncnc3c2)c1] | 73 | ND | ND | ND | 444 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 279 | 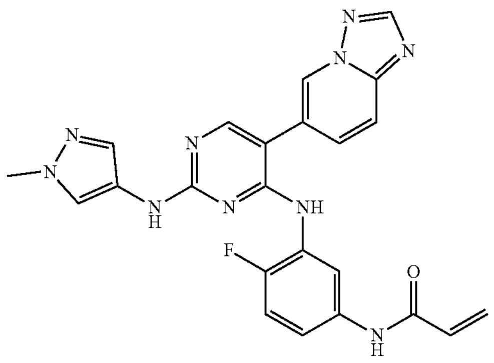 [SMILES: C=CC(=O)Nc1ccc(F)c(Nc2nc(Nc3cnn(C)c3)ncc2-c2ccc3ncnn3c2)c1] | 93 | 328 | 149 | ND | 471 |
| 280 | 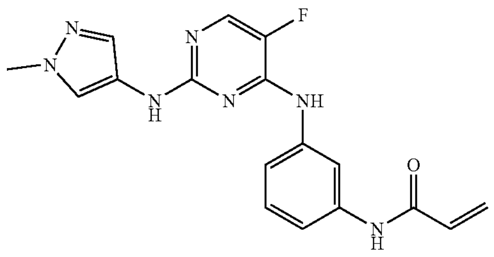 [SMILES: C=CC(=O)Nc1cccc(Nc2nc(Nc3cnn(C)c3)ncc2F)c1] | 520 | ND | ND | ND | 5155 |
| 281 | 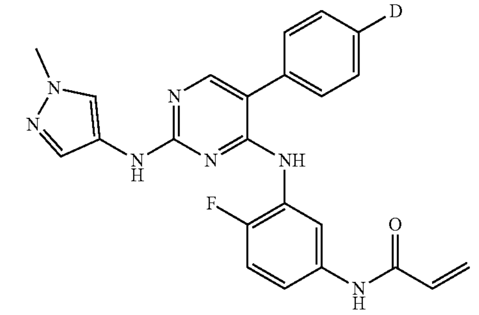 [SMILES: [2H]c1ccc(-c2cnc(Nc3cnn(C)c3)nc2Nc2cc(NC(=O)C=C)ccc2F)cc1] | ND | ND | ND | ND | ND |
| 282 | 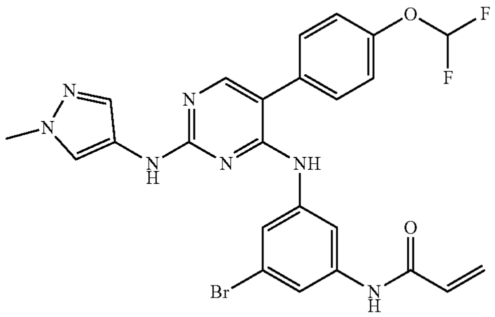 [SMILES: C=CC(=O)Nc1cc(Br)cc(Nc2nc(Nc3cnn(C)c3)ncc2-c2ccc(OC(F)F)cc2)c1] | ND | ND | ND | ND | ND |
| 283 | 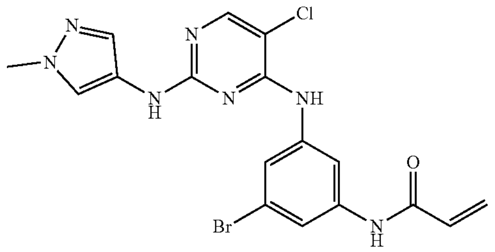 [SMILES: C=CC(=O)Nc1cc(Br)cc(Nc2nc(Nc3cnn(C)c3)ncc2Cl)c1] | 617 | ND | ND | ND | 1485 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 284 | 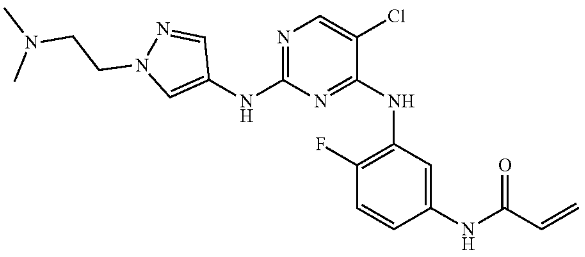 [SMILES: C=CC(=O)Nc1ccc(F)c(Nc2nc(Nc3cnn(CCN(C)C)c3)ncc2Cl)c1] | 536 | ND | ND | ND | 874 |
| 285 | 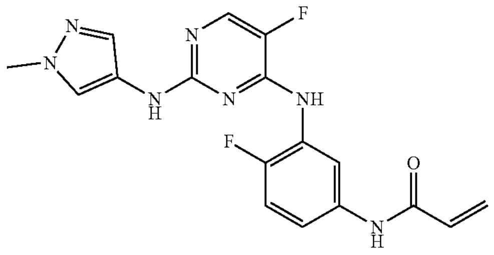 [SMILES: C=CC(=O)Nc1ccc(F)c(Nc2nc(Nc3cnn(C)c3)ncc2F)c1] | ND | ND | ND | ND | ND |
| 286 | 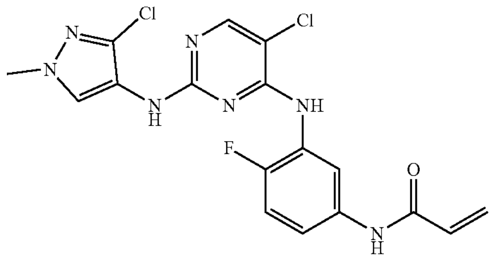 [SMILES: C=CC(=O)Nc1ccc(F)c(Nc2nc(Nc3cn(C)nc3Cl)ncc2Cl)c1] | ND | ND | ND | ND | ND |
| 287 | 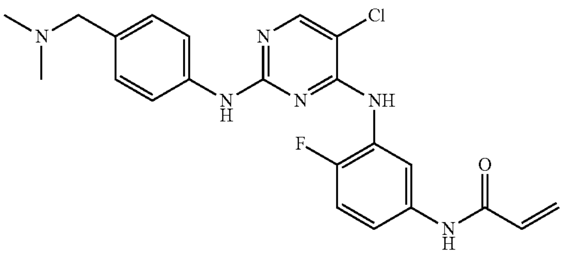 [SMILES: C=CC(=O)Nc1ccc(F)c(Nc2nc(Nc3ccc(CN(C)C)cc3)ncc2Cl)c1] | 473 | ND | ND | ND | 764 |
| 288 | 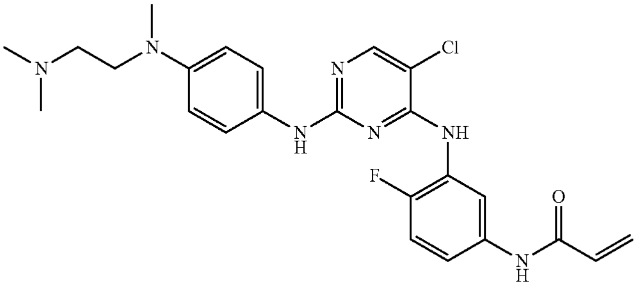 [SMILES: C=CC(=O)Nc1ccc(F)c(Nc2nc(Nc3ccc(N(C)CCN(C)C)cc3)ncc2Cl)c1] | 4913 | ND | ND | ND | 3044 |

TABLE 26-continued
| Cellular proliferation data. | | | | | | |
|---|---|---|---|---|---|---|
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
| 289 | 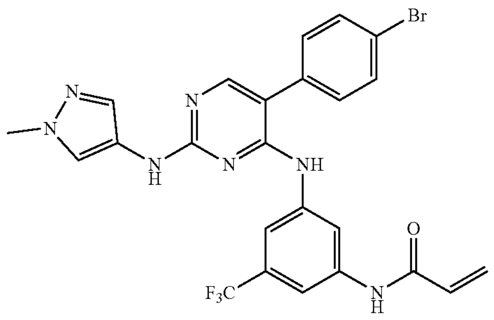 [SMILES: C=CC(=O)Nc1cc(Nc2nc(Nc3cnn(C)c3)ncc2-c2ccc(Br)cc2)cc(C(F)(F)F)c1] | ND | ND | ND | ND | ND |
| 290 | 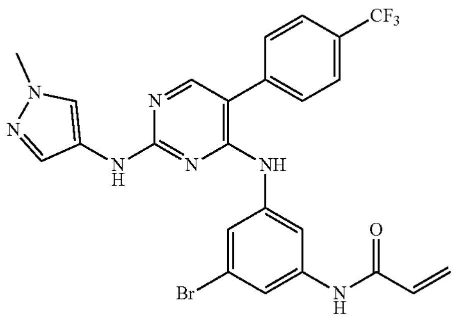 [SMILES: C=CC(=O)Nc1cc(Br)cc(Nc2nc(Nc3cnn(C)c3)ncc2-c2ccc(C(F)(F)F)cc2)c1] | >9785 | ND | ND | ND | 2923 |
| 291 | 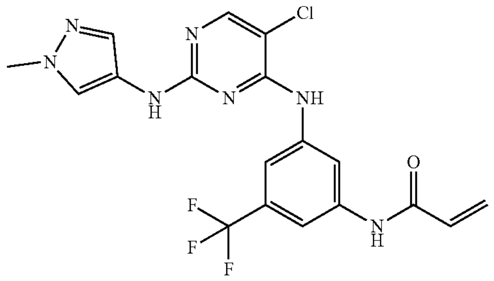 [SMILES: C=CC(=O)Nc1cc(Nc2nc(Nc3cnn(C)c3)ncc2Cl)cc(C(F)(F)F)c1] | >10000 | ND | ND | ND | 1836 |
| 292 | 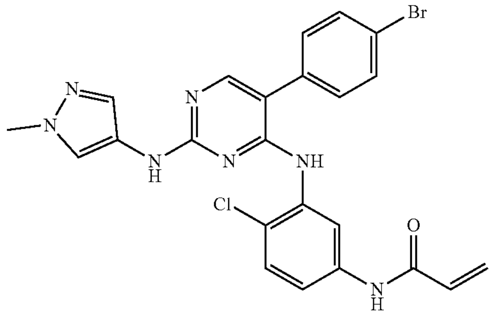 [SMILES: C=CC(=O)Nc1ccc(Cl)c(Nc2nc(Nc3cnn(C)c3)ncc2-c2ccc(Br)cc2)c1] | 1024 | ND | ND | ND | 8827 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 293 | 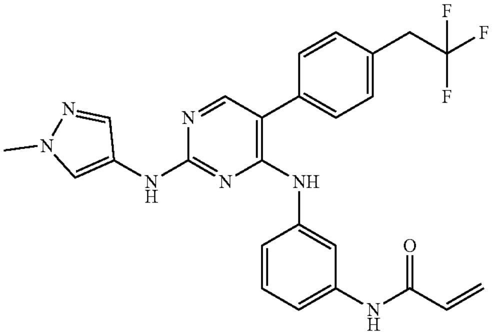 [SMILES: C=CC(=O)Nc1cccc(Nc2nc(Nc3cnn(C)c3)ncc2-c2ccc(CC(F)(F)F)cc2)c1] | 4 | 28 | 21 | ND | 110 |
| 294 | 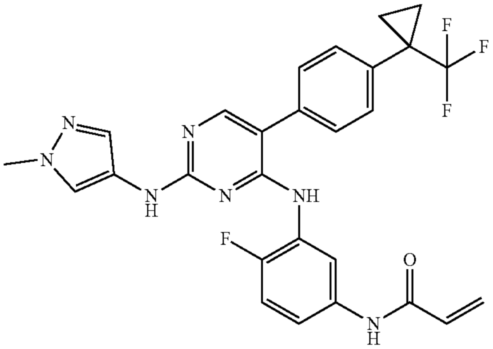 [SMILES: C=CC(=O)Nc1ccc(F)c(Nc2nc(Nc3cnn(C)c3)ncc2-c2ccc(C3(C(F)(F)F)CC3)cc2)c1] | 45 | 80 | 100 | ND | 803 |
| 295 | 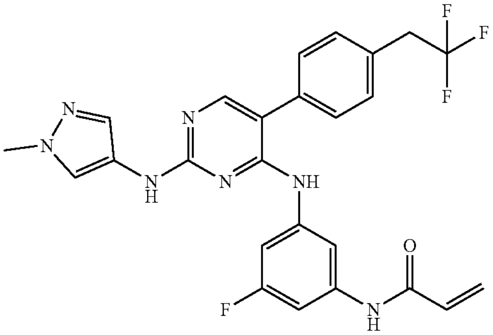 [SMILES: C=CC(=O)Nc1cc(F)cc(Nc2nc(Nc3cnn(C)c3)ncc2-c2ccc(CC(F)(F)F)cc2)c1] | 6 | 38 | 34 | ND | 210 |
| 296 | 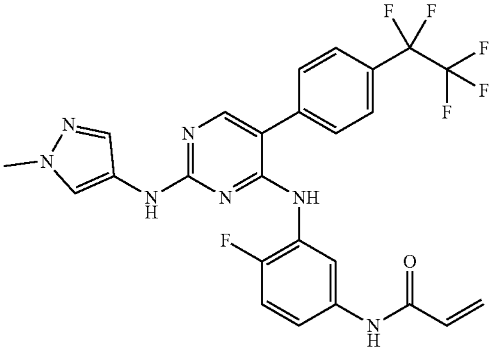 [SMILES: C=CC(=O)Nc1ccc(F)c(Nc2nc(Nc3cnn(C)c3)ncc2-c2ccc(C(F)(F)C(F)(F)F)cc2)c1] | 32 | 106 | 84 | ND | 971 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 297 | 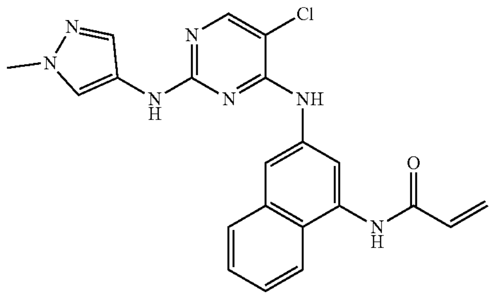 [SMILES: C=CC(=O)Nc1cc(Nc2nc(Nc3cnn(C)c3)ncc2Cl)cc2ccccc12] | 7786 | ND | ND | ND | >10000 |
| 298 | 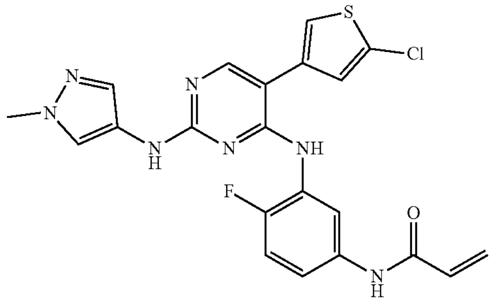 [SMILES: C=CC(=O)Nc1ccc(F)c(Nc2nc(Nc3cnn(C)c3)ncc2-c2csc(Cl)c2)c1] | 120 | 128 | 99 | ND | 402 |
| 299 | 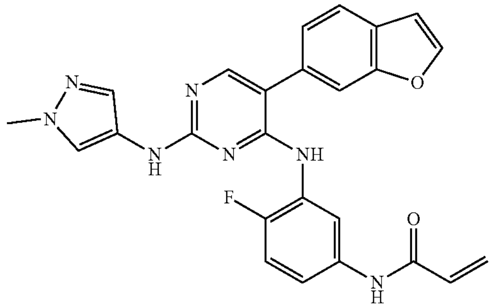 [SMILES: C=CC(=O)Nc1ccc(F)c(Nc2nc(Nc3cnn(C)c3)ncc2-c2ccc3ccoc3c2)c1] | 173 | 257 | 99 | ND | 339 |
| 300 | 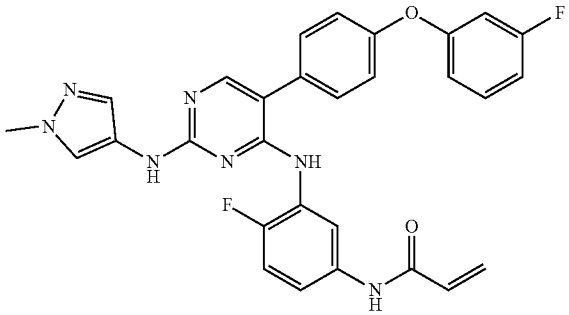 [SMILES: C=CC(=O)Nc1ccc(F)c(Nc2nc(Nc3cnn(C)c3)ncc2-c2ccc(Oc3cccc(F)c3)cc2)c1] | 229 | 289 | 1156 | ND | 9739 |

TABLE 26-continued
Cellular proliferation data.
| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 301 | 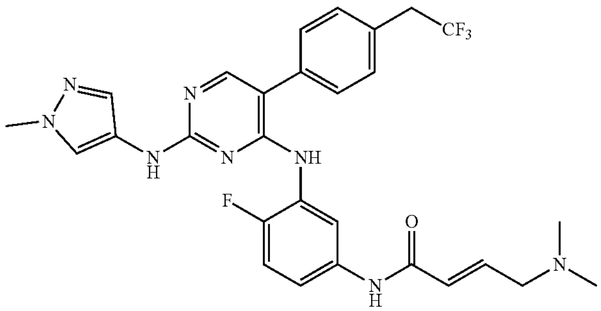 | 16 | 68 | 193 | ND | 187 |
| 302 | 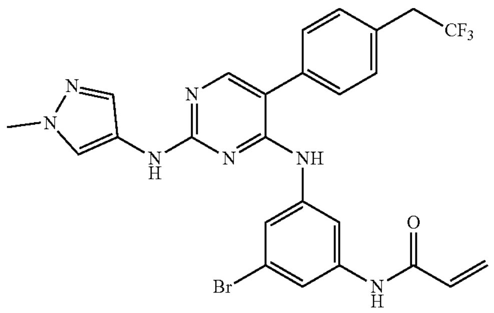 [SMILES: C=CC(=O)Nc1cc(Br)cc(Nc2nc(Nc3cnn(C)c3)ncc2-c2ccc(CC(F)(F)F)cc2)c1] | 12 | 67 | 99 | ND | 653 |
| 303 | 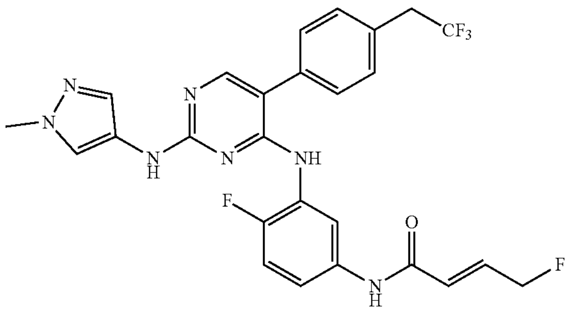 [SMILES: Cn1cc(Nc2ncc(-c3ccc(CC(F)(F)F)cc3)c(Nc3cc(NC(=O)/C=C/CF)ccc3F)n2)cn1] | 20 | 248 | 111 | ND | ND |
| 304 | 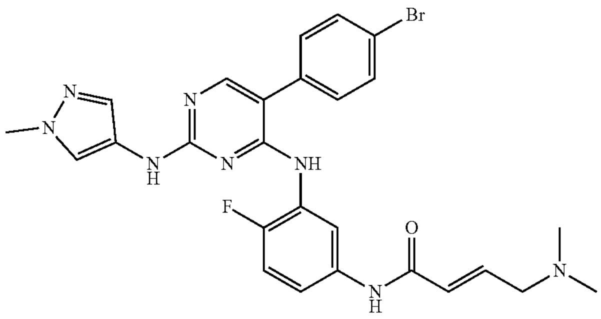 | 790 | 969 | 1520 | ND | ND |

TABLE 26-continued

Cellular proliferation data.

| Cmpd No. | Structure | A431 $IC_{50}$ (nM) | A767 $IC_{50}$ (nM) | D770 $IC_{50}$ (nM) | NPH $IC_{50}$ (nM) | YVMA $IC_{50}$ (nM) |
|---|---|---|---|---|---|---|
| 305 | 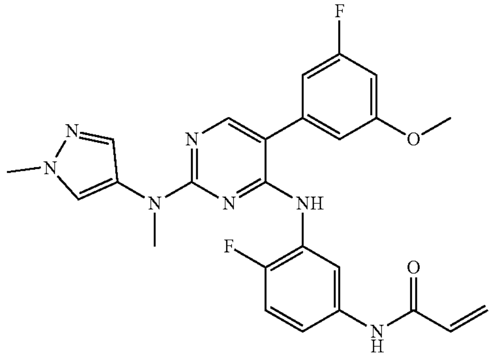 [SMILES: C=CC(=O)Nc1ccc(F)c(Nc2nc(N(C)c3cnn(C)c3)ncc2-c2cc(F)cc(OC)c2)c1] | >10000 | >10000 | >10000 | ND | ND |

ND: Not determined

What is claimed is:

1. A compound of Formula I:

Formula I

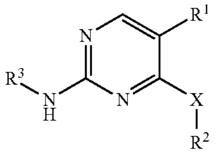

or a pharmaceutically acceptable salt or stereoisomer thereof, wherein:

$R^1$ is —$(C(R^4)_2)R^5$;

X is —NH;

n is 0;

$R^5$ is phenyl substituted with 0 or 1 $R^{5'}$;

$R^2$ is phenyl substituted with at least one $R^7$ and 0, 1, or 2 $R^8$; and $R^3$ is pyrazolyl substituted with 0, 1, 2, or 3 $R^{12}$;

each $R^{5'}$ is independently alkyl, haloalkyl, heterocycloalkyl, halo, hydroxy, or alkoxy;

$R^7$ is

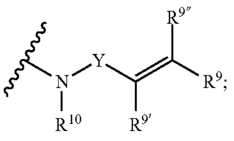

$R^8$ is fluoro;

Y is —C(=O)—;

$R^9$, $R^{9'}$, and $R^{9''}$ are hydrogen;

$R^{10}$ is hydrogen; and each $R^{12}$ is independently methyl, iso-propyl, tert-butyl, hydroxyethyl, methoxyethyl, trifluoromethyl, trifluoroethyl, chloro, cyano, morpholinyl, or cyclopropyl.

2. The compound of claim 1, wherein each $R^{5'}$ is independently methyl, ethyl, tert-butyl, pyrrolidinyl, piperidinyl, piperazinyl, morpholinyl, fluoro, chloro, hydroxy, methoxy, ethoxy, fluoromethyl, difluoromethyl, or trifluoromethyl.

3. The compound of claim 2, wherein each $R^{5'}$ is independently methyl, morpholinyl, fluoro, chloro, methoxy, fluoromethyl, difluoromethyl, or trifluoromethyl.

4. The compound of claim 3, wherein $R^2$ is substituted with 1 or 2 $R^8$.

5. The compound of claim 3, wherein $R^2$ is substituted with 0 $R^8$.

6. The compound of claim 4, wherein $R^3$ is unsubstituted.

7. The compound of claim 4, wherein $R^3$ is substituted with at least 1 $R^{12}$.

8. The compound of claim 7, wherein $R^3$ is substituted with at least 2 $R^{12}$.

9. The compound of claim 8, wherein each $R^{12}$ is independently methyl, hydroxyethyl, methoxyethyl, trifluoroethyl, or chloro.

10. The compound of claim 9, wherein each $R^{12}$ is independently methyl or chloro.

11. The compound of claim 3, wherein $R^{5'}$ is fluoromethyl, difluoromethyl, or trifluoromethyl.

12. The compound of claim 10, wherein $R^{12}$ is methyl.

13. The compound of claim 1, wherein the compound is of Formula I-A, Formula I-B, Formula I-C, Formula I-D, Formula I-E, Formula I-F, or Formula I-G:

Formula I-A

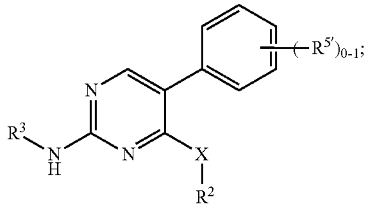

Formula I-B

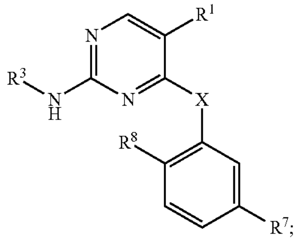

-continued
Formula I-C
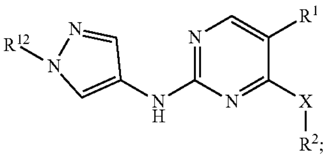
Formula I-D
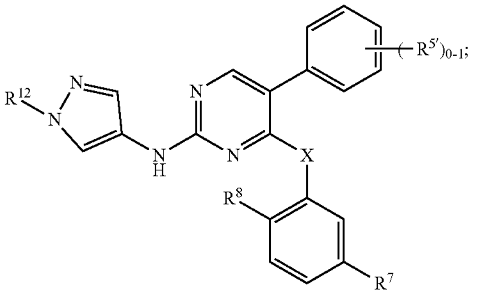
Formula I-E
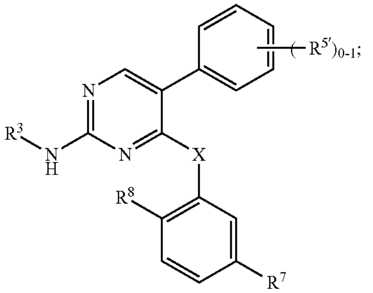
Formula I-F
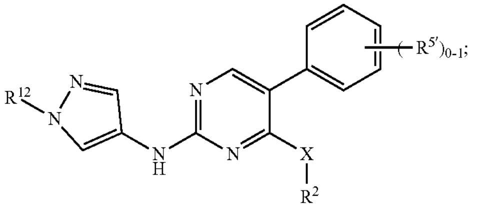
Formula I-G
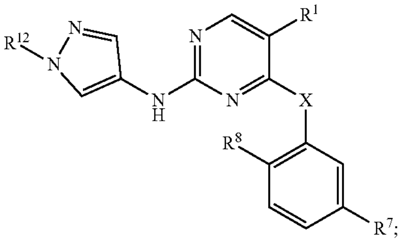
or a pharmaceutically acceptable salt or stereoisomer thereof.
14. The compound of claim 1, wherein the compound is selected from:
37
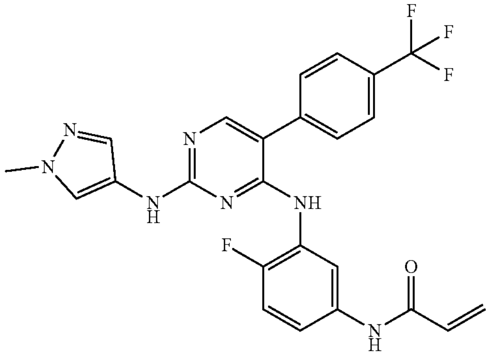
61
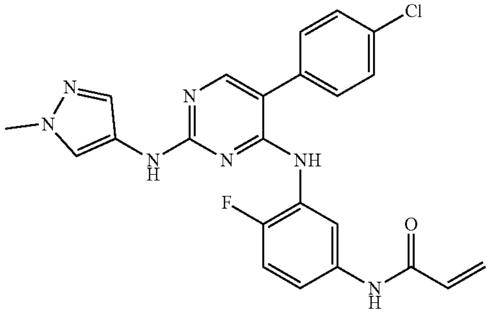
63
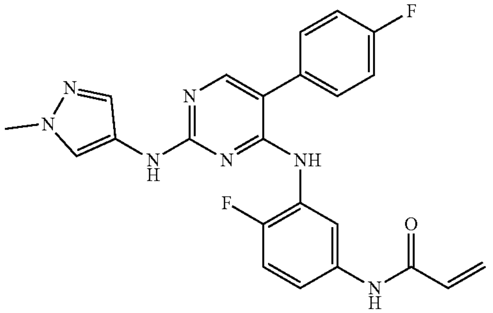
65
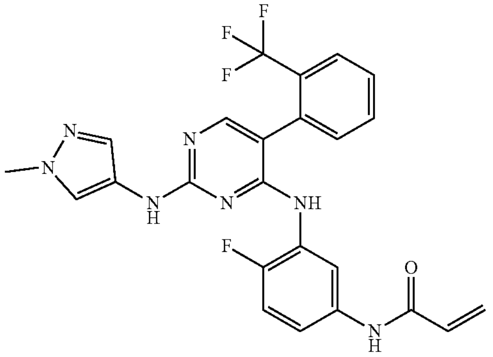

-continued
75
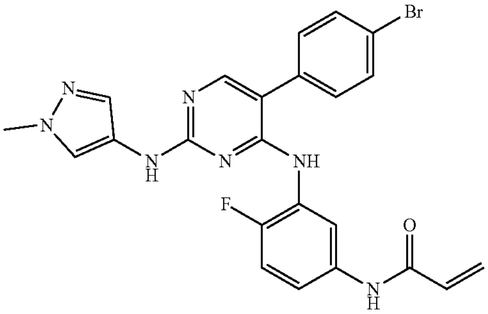
76
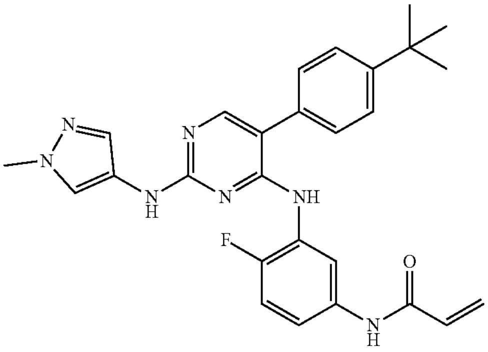
78
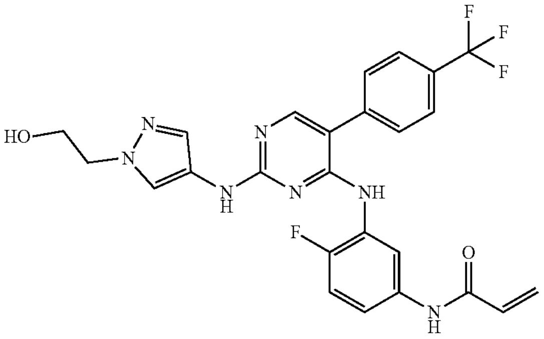
88
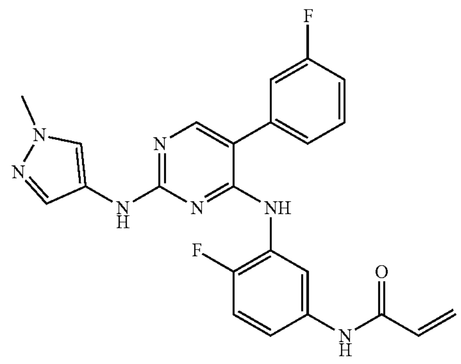
-continued
89
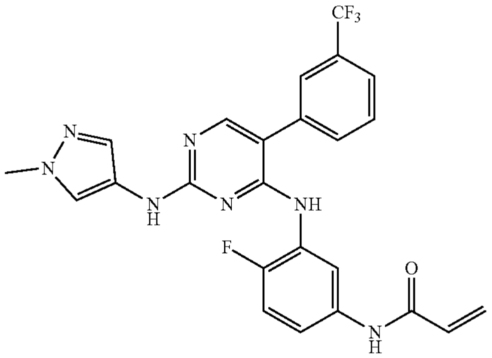
90
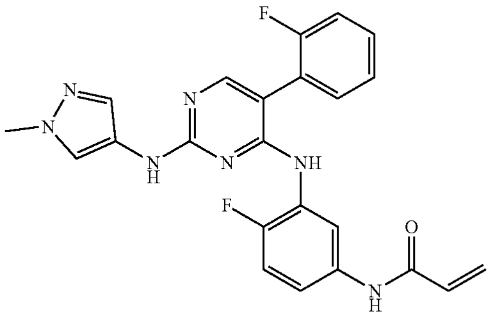
91
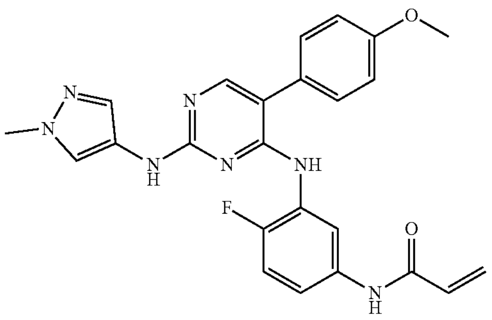
93
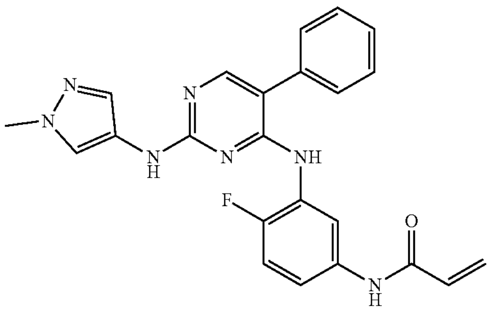

-continued
94
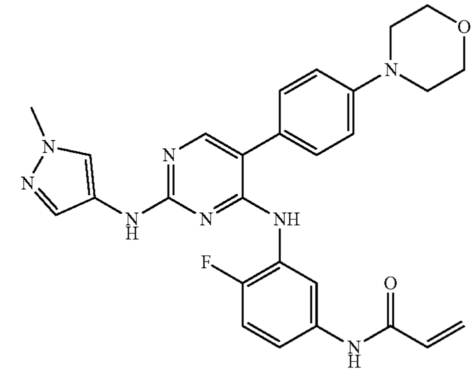
99
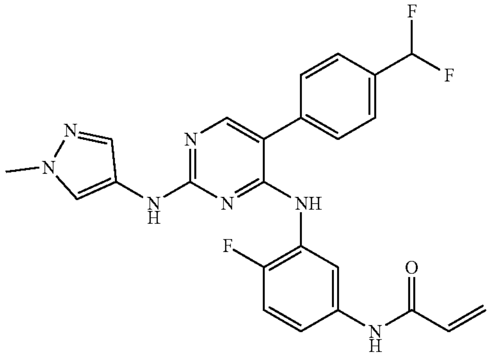
111
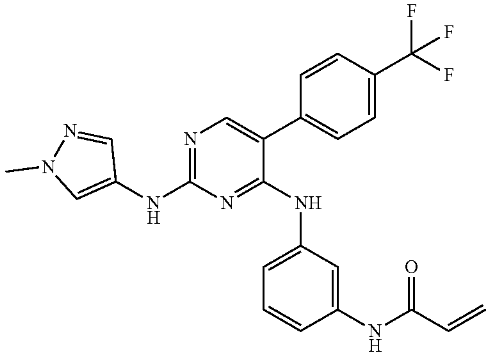
112
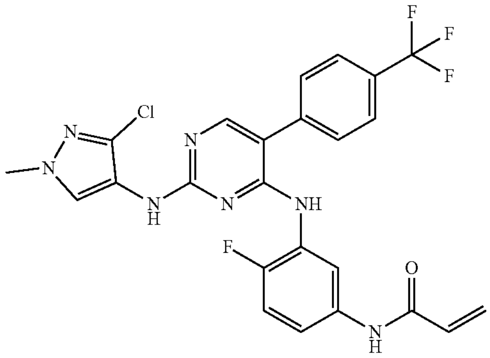
-continued
113
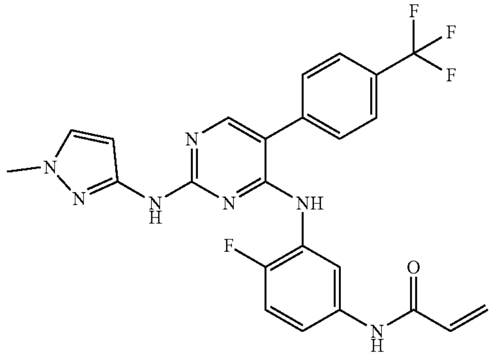
115
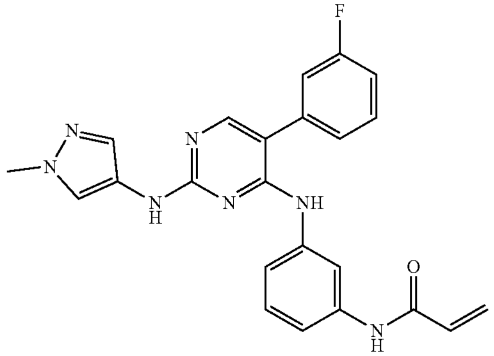
126
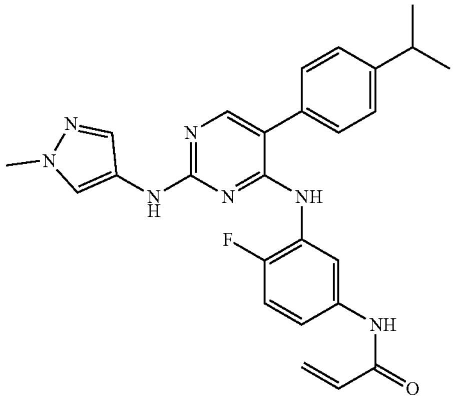
130
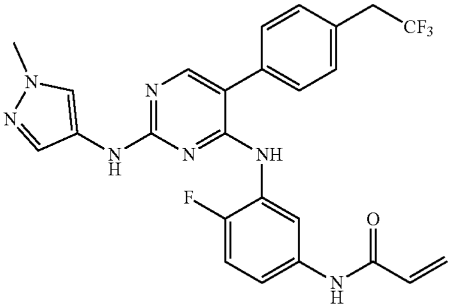

-continued
135
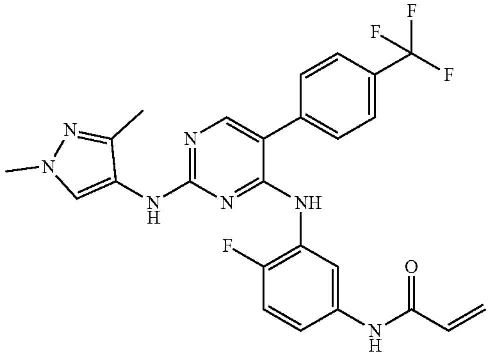
146
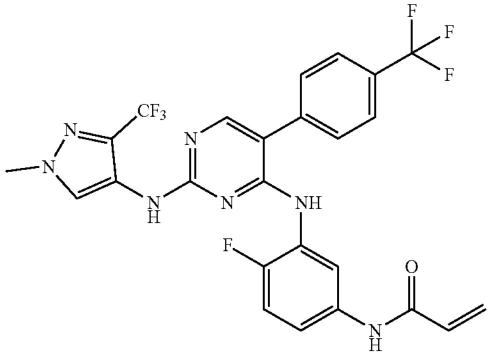
148
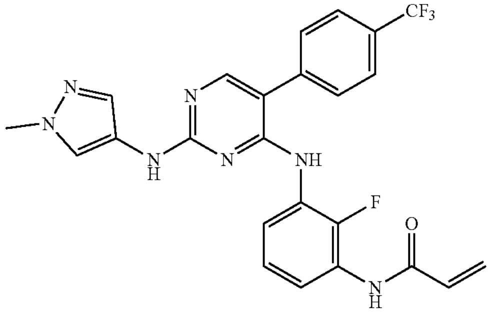
201
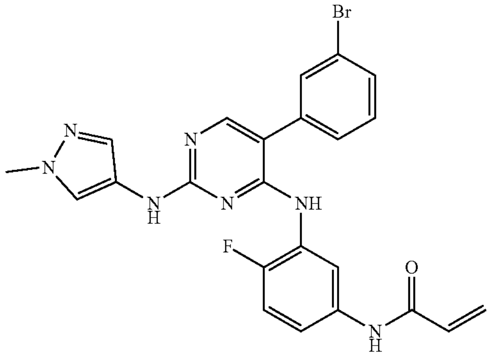
-continued
202
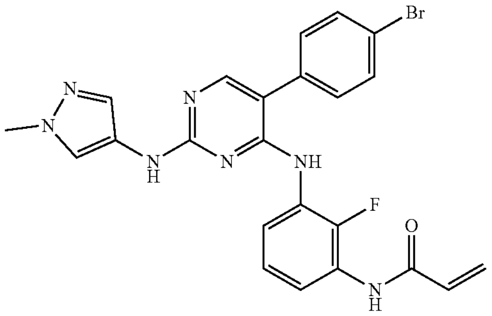
204
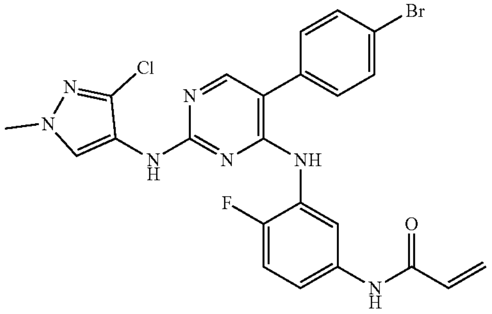
206
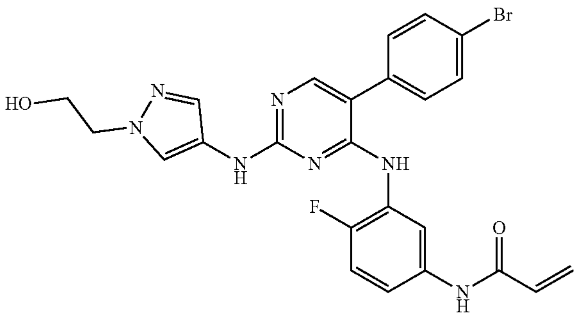
207
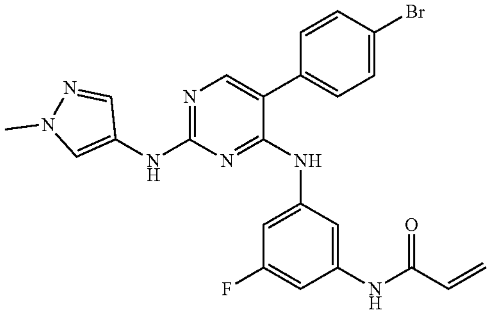

-continued
219
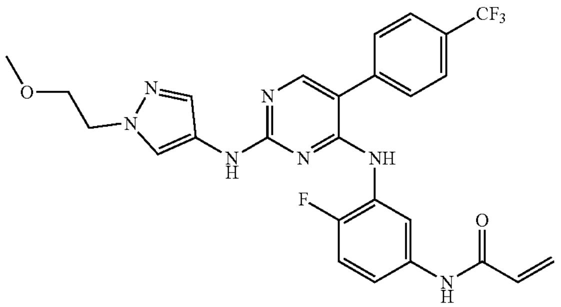
238
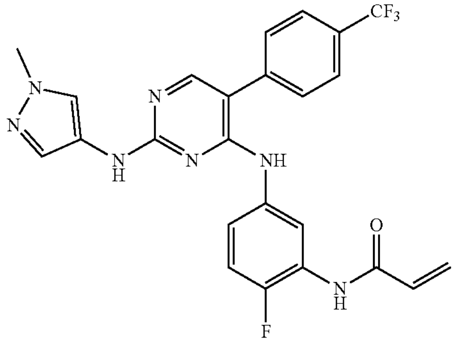
239
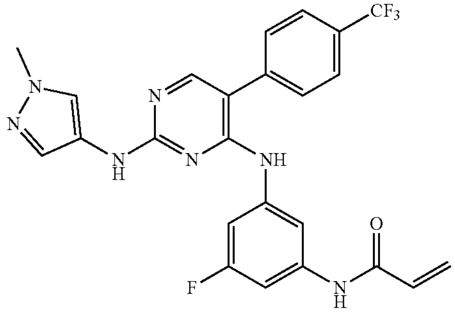
241
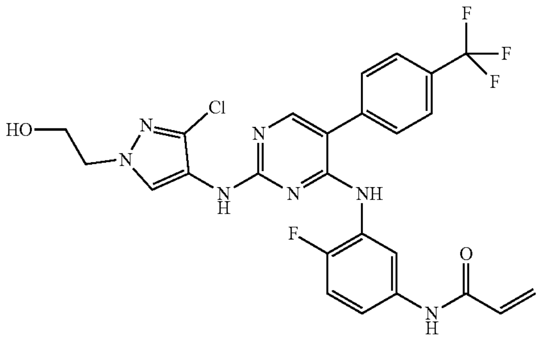
245
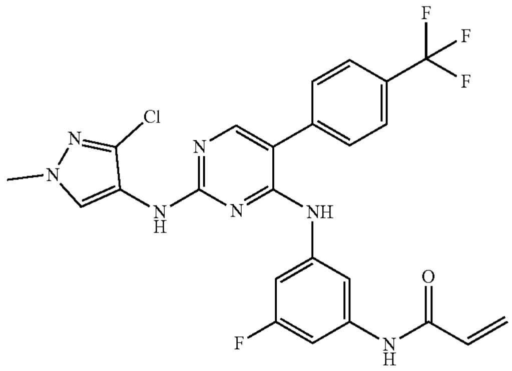
274
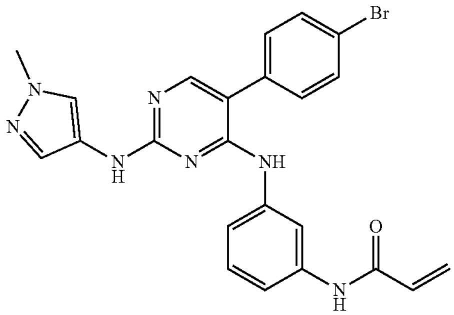
293
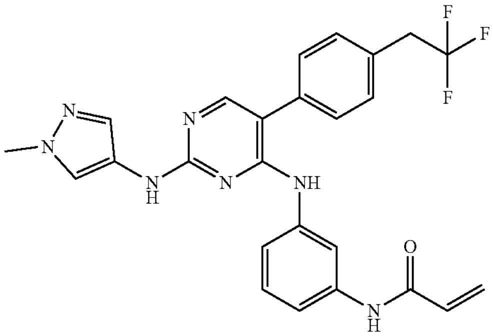
295
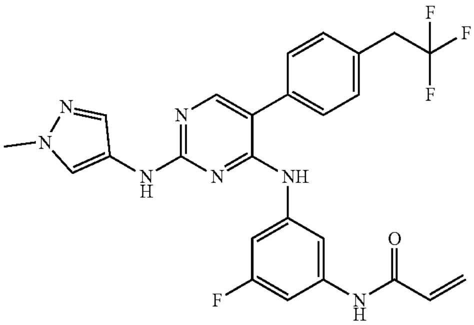
and -continued

296

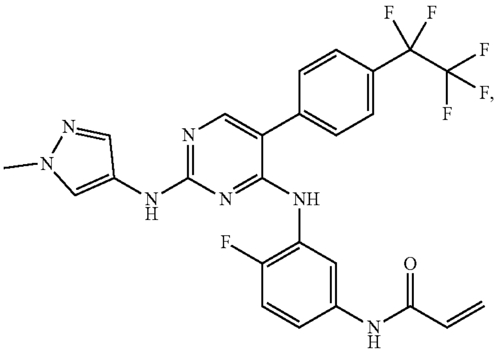

or a pharmaceutically acceptable salt or stereoisomer thereof.

15. A pharmaceutical composition comprising a compound of claim 1, or a pharmaceutically acceptable salt or stereoisomer thereof, and a pharmaceutically acceptable carrier.

16. A method of treating cancer in a subject in need thereof, comprising administering to the subject a therapeutically effective amount of a compound of claim 1, or a pharmaceutically acceptable salt or stereoisomer thereof, wherein the cancer comprises an EGFR mutation.

17. The method of claim 16, wherein the cancer is bladder cancer, prostate cancer, breast cancer, cervical cancer, colorectal cancer, endometrial cancer, gastric cancer, glioblastoma, head and neck cancer, lung cancer, or non-small cell lung cancer.

18. The method of claim 16, wherein the EGFR mutation comprises a substitution in exon 18, a deletion in exon 19, a substitution in exon 20, an insertion in exon 20, a mutation in the extracellular domain, or a substitution in exon 21.

19. The method of claim 18, wherein the EGFR mutation is selected from del19/T790M EGFR, L858R/T790M EGFR, L858R EGFR, L861Q EGFR, G719X EGFR, 763insFQEA EGFR, 767insTLA EGFR, 769insASV EGFR, 769insGE EGFR, 770insSVD EGFR, 770insNPG EGFR, 770insGT EGFR, 770insGF EGFR, 770insG EGFR, 771insH EGFR, 771insN EGFR, 772insNP EGFR, 773insNPH EGFR, 773insH EGFR, 773insPH EGFR, EGFRvii, EGFRviii, A767_dupASV EGFR, 773insAH EGFR, M766_A767insAI EGFR, and any combination thereof.

20. The compound of claim 14, wherein the compound is:

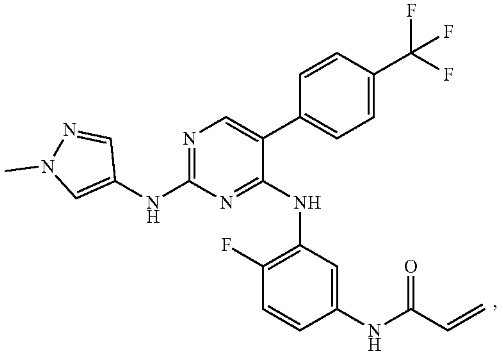 [SMILES: C=CC(=O)Nc1ccc(F)c(Nc2nc(Nc3cnn(C)c3)ncc2-c2ccc(C(F)(F)F)cc2)c1]

or a pharmaceutically acceptable salt or stereoisomer thereof.

* * * * *